US006797475B2

(12) United States Patent
Barnes et al.

(10) Patent No.: US 6,797,475 B2
(45) Date of Patent: Sep. 28, 2004

(54) DETECTION OF POLYMORPHISMS IN THE HUMAN 5-LIPOXYGENASE GENE

(75) Inventors: Glenn Barnes, Haverhill, MA (US); Joanne Meyer, Marlborough, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 85 days.

(21) Appl. No.: 10/071,411

(22) Filed: Feb. 7, 2002

(65) Prior Publication Data

US 2004/0170974 A1 Sep. 2, 2004

Related U.S. Application Data

(60) Provisional application No. 60/267,515, filed on Feb. 8, 2001, and provisional application No. 60/314,248, filed on Aug. 21, 2001.

(51) Int. Cl.[7] .......................... C12Q 1/68; C12P 19/34; C07H 21/04

(52) U.S. Cl. ........................ 435/6; 435/91.1; 435/91.2; 536/23.1; 536/24.3; 536/24.33

(58) Field of Search .................. 435/6, 91.1; 536/23.1, 536/24.32, 24.3, 24.33

(56) References Cited

U.S. PATENT DOCUMENTS 5,750,565 A 5/1998 Cai et al.
6,090,547 A 7/2000 Drazen et al.

FOREIGN PATENT DOCUMENTS

WO WO 97/42347 * 11/1997

OTHER PUBLICATIONS

Balcarek, J.M. et al. "Isolation and characterization of a cDNA clone encoding rat 5–lipoxygenase." *The Journal of Biological Chemistry* 263(27):13937–41 (1988).

Barnard, D.F. et al. "An evaluation of the Coulter VCS differential counter." *Clin. lab. Haernat.* 11(3):255–66 (1989).

Cyrus, T. et al. "Disruption of the 12/15–lipoxygenase gene diminishes artherosclerosis in apo–E–deficient mice." *The Journal of Clinical Investigation* 103(11):1597–1604 (1999).

Dixon, R.A.F. et al. "Cloning of the cDNA for human 5–lipoxygenase." *Proc. Natl. Acad. Sci. USA* 85(2):416–20 (1988).

Dwyer, J.H. et al. "Arachidonate 5–lipoxygenase promoter genotype, dietary arachidonic acid, and atherosclerosis." *The New England Journal of Medicine* 350(1):29–37 (2004).

Foresi, A. et al. "Eosinophils, mast cells, and basophils in induced sputum from patients with seasonal allergic rhinitis and perennial asthma: relationship to methacholine responsiveness." *J. Allergy Clin. Immunol.* 100(1):58–64 (1997).

Funk, C.D. et al. "Characterization of the human 5–lipoxygenase gene." *Proc. Natl. Acad. Sci. USA* 86(8):2587–91 (1989).

George, J. et al. "12/15–Lipoxygenase gene disruption attenuates atherogenesis in LDL receptor–deficient mice." *Circulation* 104:1646–50 (2001).

Hoshiko, S. et al. "Characterization of the human 5–lipoxygenase gene promoter." *Proc. Natl. Acad. Sci. USA* 87(23):9073–7 (1990).

In, K.H. et al. "Naturally occurring mutations in the human 5–lipoxygenase gene promoter that modify transcription factor binding and reporter gene transcription." *J. Clin. Invest.* 99(5):1130–7 (1997).

Israel, E. et al. "The effect of inhibition of 5–lipoxygenase by zileuton in mild–to–moderate asthma." *Annals of Internal Medicine* 119(11):1059–66 (1993).

Jatakanon, A. et al. "Changes in sputum eosinophils predict loss of asthma control." *Am. J. Respir. Crit. Care Med.* 161(1):64–72 (2000).

Khachigian, L.M. et al. "Interplay of Sp1 and Egr–1 in the proximal platelet–derived growth factor A–chain promoter in cultured vascular endothelial cells." *The Journal of Biological Chemistry* 270(46):27679–86 (1995).

Li, L. et al. "Positive regulation of human α1 (I) collagen promoter activity by transciption factor Sp1." *Gene* 164(2):229–34 (1995).

Lönnkvist, K. et al. "Eosinophil markers in blood, serum, and urine for monitoring the clinical course in childhood asthma: impact of budesonide treatment and withdrawal." *J. Allergy Clin. Immunol.* 107(5):812–7 (2001).

Matsumoto, T. et al. "Molecular cloning and amino acid sequence of human 5–lipoxygenase." *Proc. Natl. Acad. Sci. USA* 85(1):26–30 (1988).

Matsumoto, T. et al. "Correction to *Proc. Natl. Acad. Sci. USA* 85(1):26–30 (1988)." *Proc. Natl. Acad. Sci. USA* 85(10):3406 (1988).

Moffitt, J.E. et al. "Management of asthma in children." *American Family Physician* 50(5):1039–50, 1053–5 (1994).

O'Byrne, P.M. "Leukotrienes in the pathogenesis of asthma." *Chest* 111(2 Suppl):27S–34S (1997).

(List continued on next page.)

*Primary Examiner*—Cynthia Wilder
(74) *Attorney, Agent, or Firm*—Lahive & Cockfield LLP; DeAnn F. Smith; Lisa M. DiRocco

(57) ABSTRACT

The present invention is based at least in part on the discovery of polymorphisms within the 5-lipoxygenase gene which are included in a haplotype. Accordingly, the invention provides nucleic acid molecules having a nucleotide sequence of an allelic variant of a 5-LO gene. The invention also provides methods for identifying specific alleles of polymorphic regions of a 5-LO gene, methods for determining whether a patient has a more or less severe phenotype of an inflammatory disease or disorder such as asthma, methods for determining whether a patient will be more or less responsive to treatment with 5'LO inhibitors, forensic methods based on detection of polymorphisms within the 5-LO gene, and kits for performing such methods.

10 Claims, 104 Drawing Sheets-

OTHER PUBLICATIONS

Persson, M.G. et al. "Positive end–expiratory pressure ventilation elicits increases in endogenously formed nitric oxide as detected in air exhaled by rabbits." *Anesthesiology* 82(4):969–74 (1995).

Powell, W.S. et al. "Eotaxin and RANTES enhance 5–oxo–6,8,11,14–eicosatetraenoic acid–induced eosinophil chemotaxis." *J. Allergy Clin. Immunol.* 107(2):272–8 (2001).

Samuelsson, B. "Leukotrienes: mediators of immediate hypersensitivity reactions and inflammation." 220(4597):568–75 *Science* (1983).

Samuelsson, B. et al. "Leukotrienes and lipoxins: structures, biosynthesis, and biological effects." *Science* 237(4819):1171–6 (1987).

Silverman, E. et al. "Pharmacogenetics of the 5–lipoxygenase pathway in asthma." *Clinical and Experimental Allergy* 28 Suppl 5:164–70 (1998).

Tang, J–L. et al. "Role of Sp1 in transcriptional activation of human nitric oxide synthase type III gene." *Biochemical and Biophysical Research Communications* 213(2):673–80 (1995).

Ulrik, C.S. "Eosinophils and pulmonary function: an epidemiologic study of adolescents and young adults." *Annals of Allergy, Asthma, & Immunology* 80(6):487–93 (1998).

Urasaki, T. et al. "Pivotal role of 5–lipoxygenase in the activation of human eosinophils: platelet–activating factor and interleukin–5 induce CD69 on eosinophils throught the 5–lipoxygenase pathway." *Journal of Leukocyte Biology* 69(1):105–12 (2001).

Wariishi, S. et al. "A SP1 binding site in the GC–rich region is essential for a core promoter activity of the human endothelial nitric oxide synthase gene." *Biochemical and Biophysical Research Communications* 216(2):729–35 (1995).

* cited by examiner

FIGURE 1

1 ggatccagaa taaccaaaac aatattgaaa aataaagaac agcgttggtg gattaacatt
61 ttccaatttc aaaacttact atagcactgc ggtaatcaag cagtgtggca ctgtatagca
121 tgtacattac agatcagtgg actagaatca atgtccagaa ataaaccgtt atgtttataa
181 tgaattactt tttaataagg tgtcaagaca acgcaatggg aaaagaataa tgaattcaac
241 aaatgatgca tggacaaccg gacatgcaca tgcaacacaa tgaatttgaa ttcttctatc
301 gctccatgca taaaaactaa ctcaaaatgg gtcacggatg taaatgaaaa gctaaaacta
361 taataatcct agaggaaaac ctaggagtaa atctttaaga tgttattgta ggcagtggtt
421 tctcagatag gaccccaaaa tcacaagcga caaaaagaaa ttggacttaa agttaaatac
481 ttttgtgctt caaacatcat caagaaagtg aaaacacaac ccgcagaagc aataaaaatg
541 tctgtaagtc atgtatccga ttagagactt ctatccagga tatataaata atgcaattca
601 atgataaaaa agataaatag cccagttttc caaagagtca agcatctgaa tatacatctc
661 tccaaaaata tacagatatc caacaagcat gtgaaaagat gttcaaagcc atttgccagg
721 tgcacaaacc caagacagta tgaggagatg ctacagggac tctgctgctt cacagacatg
781 aagcgttggt gagaatgtag gcagccgcct ttggggactt cacatccccg ccgccccacg
841 cacggtgagc tagtgtttaa acttagccga gatcaataca cgcgactgtg tgcccgtcag
901 accctgcgct gccggcgggg ctgggagagg cgggcgccag gagtgggcgg gaacctgggg
961 gtcaggcccc agccgcggga agcgcgccca ggagcgcgcg aaaccttctc cacaccccttc
1021 caggcatttg cccgccgcga ttcagagagc cgacccgtga cccctggcct cccctagaca
1081 gccccgcatg tccagatgtg ccgtcccgcc tgcctcccgc gaccactggc catctctggg
1141 cctgggcgcg gttctcggcg cccggcctgc ccccgccagg agccgcaggt ccagccagtg
1201 aagaagcccg cgcctgaagg agcctctgtg ctccagaatc catcctcagt atcagcgctg
1261 gggtggcctc ctccaggaag cccttctgat tctctcatgg gtcgctcttc ctctgcagac
1321 tcccggagca ccccctgctc caagtaccgc aagtggcact gagaacttgg ggagagcaga
1381 ggctgtgcct agatttgtag ggagtccccg cagctccacc ccagggccta caggagcctg
1441 gccttgggcg aagccgaggc aggcaggcag ggcaaagggt ggaagcaatt caggagagaa
1501 cgagtgaacg aatggatgag ggtggcagc cgaggttgcc ccagtcccct ggctgcagga
1561 acagacacct cgctgaggag agacccagga gcgaggcccc tgccccgccc gaggcgaggt
1621 cccgcccagt cggcgccgcg cgtgaagagt gggagagaag tactgcgggg gcgggggcgg
1681 gggcgggggc gggggcgggg gcagccggga gcctggagcc agaccggggc ggggccggga
1741 ccggggccag ggaccagtgg tgggaggagg ctgcggcgct agatgcggac acctggaccg
1801 ccgcgccgag gctcccggcg ctcgctgctc ccgcggcccg cgccatgccc tcctacacgg
1861 tcaccgtggc cactggcagc cagtggttcg ccggcactga cgactacatc tacctcagcc
1921 tcgtgggctc ggcgggctgc agcgagaagc acctgctgga caagcccttc tacaacgact
1981 tcgagcgtgg cgcggtgagc gcgggcgggg cacgggtgga gcgcgggctg aggtgcgtcc
2041 gggacccggt ttggacggca gaggcctggg cgggggcgcc gagggcccgt cggggcggcc
2101 cggacaggac tgggggtgtc caggaccctg tcagggaggg cagaactgcg gtggggcgtg
2161 ccctgggctc ccagtggccg gtgggtacc

FIGURE 2

| | | | | | | |
|---|---|---|---|---|---|---|
| 1 | ttgcacgctn | ctcagccccg | gctgtactat | tggtctacac | gtgccatcgt | ggtttgctgc |
| 61 | acccatcaac | ccatcatcta | cattaggtat | ttctcctaat | gctctctttc | cccttgcccc |
| 121 | ccaccctcta | acacgccctg | ttgtgtgatg | ttgacctccc | tgtgtacatg | tgttgtcatt |
| 181 | gtacaactcc | tgcttatgag | tgacaacatc | tgtctgattt | tctgtcttgt | gttagtttgc |
| 241 | tgagaatgat | ggttcccatc | ttcatccttg | tacctgcaaa | ggacatgaac | tcatccttta |
| 301 | atatggctgc | ttagaatccc | acagtataga | tgtgcctcat | tttctttatc | cagactatca |
| 361 | ttgatgggca | tttgggttgg | atccaagact | ttgctattgt | gaacagtgat | tcaataaaca |
| 421 | tacgagtgca | tgtgtcttta | tggatgaatg | attgataatc | ctttgggcat | atacccacta |
| 481 | atgggattgc | tggacctaat | ggtttgcctg | gatcctgatc | cttgaggaat | caccacactc |
| 541 | tcttacagtg | taaaagtgtc | tctatatata | ctcatcccct | ccagcatctg | ttatttactg |
| 601 | actctttaat | catcaacctt | cttactggag | agagaaggtt | taattaccac | taatgacgag |
| 661 | cctttaatca | aattgttgtt | ggacccttcc | caacttactt | gcgaaggggt | catttgtaaa |
| 721 | cttacgccac | cttttgatgg | ggcagttttt | ctcgtttatc | cgcaaagatc | ctgggggacc |
| 781 | cctttttta | actcttttga | agaccgttat | atctgaacaa | tttctcccat | accgagaggt |
| 841 | ggcgggttac | aacccttgaa | agtttctttt | ttttttggg | gccccttagt | ttcacaaaaa |
| 901 | tcccttcgga | ccaatttgcc | ttttgttgcc | aaggaatttt | tccccctaag | tcactaggaa |
| 961 | tttttcccag | ggcacacagg | tgtagtggcc | ttccccagaa | tttttctcct | gggtatccaa |
| 1021 | tgttataaga | aaaaaaattg | gggaattttt | ttaaacctcc | aataaaattt | tttatagaga |
| 1081 | taaggccggt | ttcatttnnn | nnnnnnnnnn | nnnnnnnnnn | nnnnnnnnnn | nnnnnnnnnn |
| 1141 | nnnnnnnnnn | nnnnnnnnnn | nnnnnnnnnn | nnnnnnnnnn | nnnnnnnnnn | nnnnnnncgc |
| 1201 | ggtcttcagc | ccgtggtgaa | gactgattaa | cagtcataag | aaggtaaagc | tctaagtgac |
| 1261 | ctgtaagaaa | catacagtct | cacacaatta | ggcaaggagt | ccaacttgga | agaaagagtg |
| 1321 | gcatagattc | aaaccctgat | gccacaactt | atgttaaccc | tcctgaggct | caacttctca |
| 1381 | cacatgacag | gagaatctca | tcatgtacct | caattaattg | atatacagat | tatggtaaac |
| 1441 | attcaatgaa | aaagtatgta | aagtttctat | cattctacta | cagttggtat | tcaacaaatg |
| 1501 | ccactttatt | cactttctgt | taagcctgaa | agaagtactg | aatgacatca | acgagtgcaa |
| 1561 | ttcaacaaat | ataatttgag | cactgattac | tcaataagca | ttatgaggaa | ctaaaatatt |
| 1621 | atcagcaaat | gatggctgac | atagaggaaa | tgtgacagag | taggaagatc | cctgtactcc |
| 1681 | ctgtatcaaa | ggactgagat | tcttccactc | aggaccatgt | gtgaccccaa | cagaaagtag |
| 1741 | aaatttacag | aaagatacct | ggcaaaacac | ccaaatagtt | tgaagttaaa | aaatatacct |
| 1801 | ctgaataaca | ccccatggaa | atttttaaag | attataatgt | gaattaaaat | gaaaacatat |
| 1861 | aaccataaca | aaaattgtag | gatacaggaa | aactggtgct | catatagcat | taactgttta |
| 1921 | cattacattt | tagagaatca | acttaattca | attatctaag | tttctatttt | agaaaactat |
| 1981 | gtaaaaaaag | gagagcatat | ttaaaaagta | agcagaagaa | caaaagataa | gcatgacaga |
| 2041 | caatgaaatt | gaaaatggaa | aaatcataga | gaagaatcaa | atgaatcaaa | agtagtttct |
| 2101 | tggaaaagat | caataaataa | aattggttga | tataatttac | tgatattagg | agtgggaaag |
| 2161 | ataatcactg | atcatagatc | catgatgaac | aagcttattt | caataaatta | ataaactcag |
| 2221 | caacttcaac | aaaatggaca | gattacttgg | aagacaccaa | ttaccaaagc | tcaaaaaaag |
| 2281 | agaatctaaa | tagtcctata | tttatgaaaa | aaaaaaacaa | aactgaattt | gtatttaaaa |
| 2341 | actttgccac | aaagaaaatt | ttaggttcag | atgggtttcc | taataaattt | ttcccattta |
| 2401 | gtaagaataa | tatcaattct | acacaaactc | attcaaaaaa | aaaggagaga | gaatacttta |
| 2461 | caacacgttc | tgcaaggtca | gtattaccct | gataccaaaa | caaaggatat | tacataaaaa |
| 2521 | cgacaccaat | atccttcatg | aacatagatt | cttcaccacg | gggctggaag | gatccgnnnn |
| 2581 | nnnnnnnnnn | nnnnnnnnnn | nnnnnnnnnn | nnnnnnnnnn | nnnnnnnnnn | nnnnnnnnnn |
| 2641 | nnnnnnnnnn | nnnnnnnnnn | nnnnnnnnnn | nnnnnnatag | cacgcccttg | agcccctggt |
| 2701 | gaatataaga | gattaggcta | cagcgtgttc | tactccaact | ttatttgctt | tctgagcatc |
| 2761 | taattccact | ttgcaaaatg | gacatttttt | ttccctcttg | agagtcagga | aattaccagg |
| 2821 | tgtgccagga | taatccttag | tatcaactgt | aaaatatcag | tataaaataa | tgagtaagca |
| 2881 | tatttcagtg | ggtgtttata | tgcttttggt | tgcatagcat | gagccaaagg | cagataaaaa |
| 2941 | atgtgggctc | cagatagtga | ctcaatctcc | agaaatcata | atgtcagtta | cacaatgata |
| 3001 | tttctatatt | ggcatcacaa | aataatccac | ttgtcatagg | ataattgctc | tagatgaggg |
| 3061 | catggagctg | tgctgaggaa | tctgccattt | ttctttatcc | agactctgtc | tcataccgac |
| 3121 | cacaggcccc | aatcattgtc | tatcaaaaaa | catgcttgtg | tctcttttgg | cttactatga |
| 3181 | aaggaagcaa | gatcttttcc | tcaagcattt | aagtgttgac | tgtgggctac | ccagtgtgct |
| 3241 | agacactgng | gatcaaattc | tgtgaggtta | aaaatacccc | ataactcact | ggatagaaat |

FIGURE 2 (cont.'d)

3301 tcaaaatgct cgctatgttg attctatgat caacttccaa ggggaccttt ntacctccta
3361 tcttcatcag caagcaacta cattgatttt gtagcccagg atctattccc acgtcaaccg
3421 tgggtttcaa atgtttgctc tagctcaatg gcctcttaag ccactaaccc aatatgttgc
3481 tttttaccag taaaaaagtg catctgggga ataagttggt gtatatttgt ggttcagcca
3541 gcccatagat cgtccagagg accccaggct taggaggaat cctcagattt gagagccact
3601 gtcctgtatg atgcagatag cacagctctt cctgaaaata ggaattcaaa tgaggaaaaa
3661 tgaaaactct cctaattatt ttcttctgcc tctttcattc caagctcatc taattatcat
3721 gctctattgt gaagaatcaa agaaagaact cataaatata ccttttgtgc ctgtattttg
3781 aatgtacgtt gtgcatgtaa gcctttgtgg ttaagcaaat gtcaagaaaa tccctagtcc
3841 cattgcttac agtcaatatg ggcaattcaa agcaaagtat atgcctctaa tatggtttga
3901 aaattctgaa agttcagaaa aaatgttgct acttcagcca tctgatgtta ctggatattg
3961 agaatgagac ctcctctccc tctgctttcc tcatttccat ctcctccttc ctctttctcc
4021 tctctccctc tcctttattc tccttctccc tcctctctct ccatgcttac tcccttcctc
4081 ttctccctct ttcttcttta ttctccttct ccctcctctc tctctctccc cttttttcctc
4141 ccttcctctc ctccctccct ctcctttatt ctccttctcc ctcctctctc tctctccccc
4201 ttttcctata ttcccagatt aggccatttt caaaactggt taaacattcc ccaaaagcat
4261 ttatgacaga gaattgacta ggatctcacc tgaatcacag agcttgccca ttgaacacag
4321 gcaaagatca agccatttc tcttgatgtg atgcttcagc attttatgca tttgaaacaa
4381 attttatgta aaaaaagct tagccctttg gtgacgggga ttccttttct ggatgatctg
4441 ccaaagaatc aagacccaac gtccagctta tcaaattttc tctggacctt tannnnnnnn
4501 nnnnnnnnnn nnnnnnnnnn nnnnnnnnnn nnnnnnnnnn nnnnnnnnnn nnnnnnnnnn
4561 nnnnnnnnnn nnnnnnnnnn nnnnnnnnnn nnccgtggtg aagacttcca cgtgaacttt
4621 aaagtagttt tttccaattc tgtgaagaat gtcattggta gcttgatggg gatggcactg
4681 aagattttct tcatttttat gactgcatag cattccatgg agtatatgta ccacattttc
4741 tttatccaat tcactgttgg tgggcaccta ggtcaattcc atgactttgc tgttgtgaat
4801 agtactgcaa tgaacatgtg agtgcatgtg tctttttgga ggaataattt gttctctttt
4861 ggatatatac ccagtaatgg ggttgctggg ccaaatggta gttctgtttt aagttctttg
4921 agaaatctcc aaactgcttt ccacagaggc tgaactaatt gacattccca ctgccatgca
4981 tgagcattcc cttttctcct cagctccacc aacatctgtt gctttctgac tttttgataa
5041 tagccattct gatgtgtgag atggtagccc attggggttt cttttttttt ttttaagaca
5101 gagtctcact ctgtcaccta ggctgtggca caatgttggc tcgctgcaac ctctgcctcc
5161 tgggttcaag tgattctcct acctcagcct actgagaagc tagggttaca ggcacctgcc
5221 accacaccca gctaattttg gtatttttgg tagagacagg gtttagccat attggcaagg
5281 ctggtctcta actcctgacc tcaggtgacc cacctgcctc ggcttcccaa agtgctggga
5341 ttgcatgcgt tagctaccat gggtggtttt tgacttgcat ttctctgatg attagtaatg
5401 atgatccttt tttcatacat ttgttggcca cttgtatgtc ttcttttgag aagtgtctgt
5461 tcatatcttt tgcccatttt tcaatggggt tgtttttttcc ttgtccagtt gtttaagtta
5521 tttatagatt ctggatatta gtcctttgtt gggtgcataa tttgcaaata ttttatctca
5581 ttctgtaggt tatctattta atctgttgat agtgtctttt cttgtacaga agttgttcag
5641 tttaattagg tctcacttgt caatttctgt ttttgttgta attgcttttg aggacttaat
5701 cataaattct ttcccaaggc ccatgtccag aatggtgttt ctgagatttt cttctaggat
5761 tcttttactt caaggtctta tatttaaatc tttaatccat ctggagttaa tttttgtatg
5821 tggcaaaagt taggtgtctt gttttatttt tctgcatatg gctagtcagc tatcccagga
5881 ccattcattc actagggagt cctttcccca ttgtttactt ttggcaactt tgtcaaagat
5941 tagatggctg taagtgtgca gatttatttc tcagctctct attctgttca actggtgtag
6001 gtatctgttt tcgtactagc accatgctgt tttggttact gtagtcttat tagtatagtt
6061 tgaagccagg taatgtgatg cctctggctt tgttcttttt gcttaggatt gctttttggg
6121 ctctctgttg ttgttgttcc atatgaattt taggacactt ttttccaatt ctataaaaaa
6181 atgacattgg tagtttggta ataatagcat tgaatctgta gatagattgc tttgggcagt
6241 atggccattt taatgatatt gattcttcca atccctgagc atggaatgtt tttccattta
6301 tttgtgtcct ctctgatttc ttttagcagc gttttatagt tctccttgta gagatctttc
6361 acctccttgg ttagctgttt tcctaggtat tttaattttt tgggcctttg taagtgggat
6421 tgcaagcttg aattggttct tagcctgaat gttattggtt tatagaaata ctactaattt
6481 ttgccatcca ttttgtatcc tgaaacgtcc ctgagtcatt tgttaattcc cagaggcttt
6541 gtggagtctt taggttttct atttttagaa tctattcttc ccaaagagaa atactttccc

FIGURE 2 (cont.'d)

```
6601 ctctcttttc ctaatcggac ccctttattt attcctttgc ccaaggcttg gaaagccctt
6661 ccatactttt ttaaaaagaa cgtggaaaaa ggcccctttc ttattctcgt ttaaaggaac
6721 cttccatttt cgctgtcaaa tggnnnnnnn nnnnnnnnnn nnnnnnnnnn nnnnnnnnnn
6781 nnnnnnnnnn nnnnnnnnnn nnnnnnnnnn nnnnnnnnnn nnnnnnnnnn nnnnnnnnnn
6841 nnntttgttg ggaatatccg gtgcttattc ctcttcagga gtttattctt tccaaaaatg
6901 cagcttttca ttcctcctcg tttttctttc tgtgccaaat gcctccagcc tttccatgtt
6961 ggtgcggtaa gctagacatt tttagtttgt agtgattgtt ttcgtttgtg tttgtatgtt
7021 tttgtgccca tagtcacttc tgtaatgttc gtttctgagt ttcctttggg gggattaacc
7081 tgccactgaa gtgtcagctt ccctgtcatg ggactgtcct tggaatgaca ggttttcctt
7141 ccaccatagg atctgccact gtgaaggaga tgatgagagc cccctgatca ccccctgcca
7201 ctgcacagga agcctccact tcgtgcacca ggcctgcctg cagcagtgga tcaagagctc
7261 cgacacgcgc tgctgcgagc tctgcaagta tgagttcatc atggagacca agctgaagcc
7321 actgagaaaa gtacgtggga ggaagggatg cttcaccctt cctgaaacca gtgaccccca
7381 gaaagctggt gtctcagatc atgaggtcat ggcttgcctg cgttcatttc cttaaaaagc
7441 tggggctggt gcttacattt gcattgtaga gattgttgtt tctggtgctg attttcaagt
7501 ccctcttctc aggaagaagc tctttctgac cattcataat ccttctcttc ccttcaaagt
7561 aagactgctt gcttgtcggt gtcagtcctc tggcctttga ctacagactg tttgtgacat
7621 atcttagcac ctaattttat acatattaac tgttgacgtc ctgcttctct gattaggact
7681 gtctgttgga gattagtatc tccccagcac ccagcacagt gtagcataca gtaaatttat
7741 ttgtatacac ccatgataac tatttgctgg atgggagtgt gagtaggtgg atagggaaaa
7801 gaaaggaagc acaaacgttg cgtgatgtgc aactgtcttc agaaaggacc cacaggcatt
7861 gcatgacacg cagctgtctg gaggcccatg tcactgctcc ctctgagagg agctttgtcc
7921 gccacactgg cttcctgttt aaattttgac tgtttcatat atctctctag atgcccagca
7981 caaaaggttt tgtctggaag aataaaaaac tgttcctatc tcagaacatt aatatataaa
8041 ttgcaagata agtcacataa tcaaatacta gccaattaaa tgctaaatgg tgtgctggta
8101 gagcataaca gtcattcaga aaaggaaatg ctcattatga gctagagtgc tggggaagtg
8161 gagcgatggt agcctcatag ggtgtttggg ttttagagca gttcttgaag gatcactagg
8221 atttggaggc agagtgcaag gagtttagag aggtcaggct gtctgtggag taaagcatac
8281 cctagaaagg tgaaggtgaa cattgacagg gtgtcaagct acgtgcgttg taggaagtag
8341 cagggagcat ggggcactga ggcactgact ctgtattata ggtaggaaga ccagggaact
8401 tgctagtgta taaaatccca gcagaaaaca accagattta gagaaggctt gtgcaaactg
8461 cttaaaaaaa tgttttgccc agtagaaacc ttgtaattta ttgggtgcct actctatgct
8521 aatctctcaa catgggaagt ccttgaggct ctattttcaa ctaccctgca tagactcatc
8581 tggaaagagg ctgtgactag ggttggcaaa ggatatgtgc agagtgttta cacattgttc
8641 tttctctcta cctttatgtg ttttctcctg attcggaaac cagtaaatga aaaagaaagt
8701 ctggctattt ggagtaaatt aatgagctcc tagaggagat gggactagca gagtctgctt
8761 gtaccaggaa ctcttagcgt cgatttcgag ctgttgctgc caaagtagca aggaccaaag
8821 agtgagcgtc ttctgccatt caccttcaca atgtagtgtg acccatctgc tagtgtgttg
8881 tggcatcatc aaccctcttc ttccgctcgt ccatgccagt cagcacatca gggagactta
8941 aaacgtagta cctgggtcct gggccaacat actgttttca ttaggactga aatcatagaa
9001 ttctttatca ggccatctta tgtctgcttg caagaataag cagacaaggg gatttttgat
9061 ggtagttctg cattcatctt gatcctggct tcttttcatt gcatagaaag ttggctgcac
9121 ctggtacctg gttgaagcca agtggtttta ggagaacaat acttggggga atgcatctag
9181 tttgggaagg gagaagtggg gtggaaagcc aatcttacct acctacaatg ctctcacccc
9241 accggagccc ttccccagaa gcctgagcct cacactctgt gttgtctttc tagtgggaga
9301 agttgcagat gacgtccagc gagcgcagga agatcatgtg ctcagtgaca ttccacgtca
9361 ttgccatcac atgtgtggtc tggtccttgt atgtgctcat tgaccgtact gctgaggaga
9421 tcaagcaggg gcaggcaaca ggtgagttct caggctggag caagctcagc atgggggccg
9481 ggatagctca caggagtcct ggggtcagag gattttccag ttagccaaaa acgtctgggt
9541 ttccggagga gggacatcag ttaggaggca ctagcctcct ttttggcatt tctttgctg
9601 tggtggtagt ttttgaaacc cagtcaggag agttcatatt ctggagcatg agaatctccg
9661 caaactacat cctataaaag caggaagtag ctggacactg tcttccactc ttctttgact
9721 gagcaacatt ggatgagttg tgaatccatt ggtcagtggt gcaggcttgt ggtccccaga
9781 tacttgaggc tgagggatgg aggattgctg aggctcagga gttcaaggct gtagtgtgcc
9841 atgatcacac ctgtgaatag ccactgcact ccagcgtggg caacatagca agactccatc
```

FIGURE 2 (cont.'d)

```
9901  tcttaaaaaa caacaacaac aacaaaggtc ttcaccaggg atctgcctag gtcagcgagg
9961  tggttcatca agannnnnnn nnnnnnnnn nnnnnnnnnn nnnnnnnnnn nnnnnnnnnn
10021 nnnnnnnnnn nnnnnnnnnn nnnnnnnnnn nnnnnnnnnn nnnnnnnnnn nnnggagtgt
10081 acttcacccc gtggtgaaga tgcggcacag actggcgttt cctacggcgc cttcactgga
10141 aagcgcccct gtggtcctgg ggagagggcg gctccatccg ccacccttcc cggagctgcc
10201 cccgcccatt ctcatgggag gaaatcgcag ggcgtgtgag cccccgaccc ctcgcccccca
10261 cctctgccag gaccggccgc atttctgcac tgtcccgccc cactgggaag gaaactctct
10321 ttctcaattt cctttaatga ggacattgtc ttttcagccc tgccaccccc tgcaatcgtc
10381 ttccaggctg caaacagcga gtggggaggt gaacacatca gcttttcctc cctccacacc
10441 accaggaaat ttcgcaaacc acttggctct cggcggcctg gcctcgccac acctgtgccc
10501 acagtctctc tccgctgcag ccccctgtgc cattctccag gccccacgta cctctgcctg
10561 ggcccagtaa gacctggtca gatggccccc ggctgcaaag ccttcctggg ccccatcaga
10621 gaggacgccc aggtgaagcg aggtcccct gcccaccctg caagcgcagg ggcccttcca
10681 agagtgcagc cctaggccgg tgtgtgatgg tggagacgcg gtcccagagg gcctgaacca
10741 agaatggaga agacaaaggc tgtctttagg gagaaacttc cctgaggggc tgatgtgtgc
10801 gatcccattt taatctcaca accctgggga ggagctgggg ccgggtctca ttgttcattt
10861 gaggacaccg aggctcaggg aacttagacg actttcctag ggtcccccca acccccaccg
10921 gcccagggcc ctctcccagg caccccctcat ccccacacag gctcctctaa gctgcttcct
10981 tgtggtccag ccccccttggc tcagctcctc aaatacaggg acacctcttc tctcccccgc
11041 agaactcaag ggtctccatc cactgtgcca gcacagaggc ggtgctcaga gtggggctaa
11101 gcttactgtc cagcctgctg ggccaggagg ggcagaaggg cccctctcag gattccttcg
11161 ctctgctcct gccaataggc catcactcaa ggggctaatg acaggacgat gtggagaaac
11221 gtgggctgca gcacttctgg ggccaaggc agggtggcg gcactgggga gtacagggga
11281 ggggacctca ctgggccag aggcttctag aagcttctgc aagaagggc ccctcaccca
11341 tgtcttggcc aagaagtggg gagggtgggt gtggcaaagg aaacagctag gtcagagaca
11401 agagatgctc tgcaaagccc tgctggctcc ccacggtgga gcatcctatg catgtaggac
11461 ctgagagatg gcaggggcgg gtgcgtccct atggatgtat ctccatttct gggcagagac
11521 atctgggctc tcacctgcaa ttgagccaac caagaaatta tatttacttt ttagagcgag
11581 cctccaacaa attatacaag cacttgagaa taagccctcc cactgtcttg agagatggag
11641 cccagggagg cagctggaaa gatgctcctg ccctcactca ggagagatgg tggagctggg
11701 agaggaggag gcactccctg ggacccagca gatggacttg actcagcaaa tagatgcaac
11761 catatgtggg gggtggggag gcccagaaag gcattacagg ccagtgttct taatcctggc
11821 tatacactgg aatccaccag tagccctaaa atataactgt gctggacttc ccctggttcc
11881 acagtttgtg cagagtgggc agcatggagt ctgtaacact aaacacacag gattgagaac
11941 catatgtcta ggctgttgtt agccatgatg gggatacatg aaaaggaggt gcacagttac
12001 cttctatacc acaggatagg tgctcattaa accctgttaa aatggactgt gacccagctg
12061 gcactcaggg gcactcaggg gccaggtggg tcacactttc attttaatag gatttaatga
12121 gcacctattc tgtgacagct gctaagatac agaggctcct gagatacaga gatgacaatg
12181 accttcagaa acactgaaca gagataagaa aggcacagtc tggccttcac tccaccatta
12241 attcctccat ccatccatcc atccatctat ccatccatct ctctgtctat acttccatcc
12301 atccaccatc cattcaccat ccacccatca atccatccac ccatctatcc atccatccat
12361 ctcactatct gtcatccatc catccatcca ccatccatga atccatccat ccgtatatca
12421 atttctcatc tatctctcca tccatccccc atccacctct tcttccatcc ttcctccttc
12481 ccttcatcca tccattcatc atccatccct caacccatcc atctgcctgt ccatcggttt
12541 gattgtccat ctgtccagta ttcctccatt ccctccaaac tgggtggcag tactctccac
12601 ctcactacct caccatcctt attattccct ccaaactgtc tctttcacaa gggccttctg
12661 tcctgcctgt cccatcctgg tctgggacct atcccactaa agctacatgg ctttgatcaa
12721 caatcccaat cccagagtag gggaagggaa gtgagcccct aactgccgtg atgtttccag
12781 ggagatggtg gatactgctg cattactaat ccagatgtta ggttttaatt tttctctcca
12841 gtagacccca attgtggtag gagaaaaatg ccccagcttt ggacacaaac agacctggat
12901 tcaaatcctg gttttgccaa tttctgccta aatgacttta ggcaaactcc ttgaccttga
12961 ccccttggag actcagtttc ctcacctaga aatggtcaat aatattattt acctcccagg
13021 atggccatga agcttaaaat agattattgt acccccccaaa acaccgacac aatgtttaga
13081 aataaataat attattttaa gctttgaagt ctggctgggt tctcagcctc gtctacctgc
13141 tgggtgtgca gactcaaagc cagggtccca ccctcataga ctgtcatctg tgggtgtggg
```

FIGURE 2 (cont.'d)

```
13201 gttggcctgg cactagcagg tgctaatgct cctcagagga ttctaggtgt aaaaggaaat
13261 gaaaatcttt ggaccccaat tcactctgcc aaaagggaaa aattaagctg aaagctgagt
13321 gatgcaagaa acgaagatag ctacagataa aaggtgaaaa cctccacagg tagctcttgg
13381 tgttcacctt atcaagtgct gatgtactaa gcgcaagagg aatacataac tgactattcc
13441 cctacctgct cctttctttt tgcaacatgt ggattcagta acgtgaccat gccctccctt
13501 tcttccttcc agcctgttct cctttaaata ttgatgccct taaagacatc ttcggaaaaa
13561 ggcacagtcc accaactgtt cctgtggatt tgtgttcctt ttttccgtgt atgtcttttt
13621 ttttattatt atactttaaa ttctaggata catgtgcaca acgtgcagga ttgttacata
13681 tgtatacatg tgccatgttg gtgtgctgca cccattaact cctaattagg tatatctcct
13741 aatgctatcc ctcccccctc tccccacccc atgacaggcc ctggtgtgtg atgttcccct
13801 tcctgtgtcc aagtgttctc attgttcaat tcccacctat gagtgagaac atgcggtgtt
13861 tggtttttg tccttgcgat agtttgctga gaataatggt ttccagcttc atccatgtcc
13921 ctgcaaagga cattaactca tcctttttta tggctgcata gtattccata gtgcatatgt
13981 gccacatttt cttaatccag tctatcggtg atggacattt gggttggttc caagtctttg
14041 ctattgtgaa tagtgccaca ataaacatac gtgtgcatgt gtctttatag cagcatgatt
14101 tataatcctt tgggtatata cccgataatg ggatggctgg gtcaaatggt atttctagtt
14161 ctagatcctt gaggaatcgt cacactgtct tccacaatgg ttgaactagt ttacagtccc
14221 accaacagtg taaaagtgtt cctacttctc cacatcctct ccagcacctg ttgtttcctg
14281 actttttaat gattgccatt ctaactggtg taagatggta tctcattgtg gttttgattt
14341 gcatttctct gatggccagt gatgatgagc atttcttcat gtgtctattg gctgcatgaa
14401 tgtcttcttt tgagaagtgt ctgctcatat cctttgccca ctttttgatg ggttgtttt
14461 tttcttgtaa gtttgtttga gttgtttgta gattctggat atcagccttt tgtcagctga
14521 gtagattgca aaattttttt cccattctgt aggttgcctg ttcactctga tggtagtttc
14581 ttttgctgtg cagaagctct ttagtttaat tagatcccat ttgtccattt tggcttttgt
14641 tgccattgct tttggtgttt tagacatgaa gtccttgccc atgcctatgt cctgaatggt
14701 attgcctagg ttttcttcta gggtttttat ggttttaggt ctaacattta agtatttaat
14761 ccatcttgaa ttaattttg tataaggtgt aaggaaggga tccagcttca gctttctaca
14821 tatggctagc cagtcttcac ccggggctga aggtaccgct tnnnnnnnnn nnnnnnnnnn
14881 nnnnnnnnnn nnnnnnnnnn nnnnnnnnnn nnnnnnnnnn nnnnnnnnnn nnnnnnnnnn
14941 nnnnnnnnnn nnnnnnnnnn nacaatgaga acacatggac acgggttggg ggggtatcac
15001 acactggggc ctgttgggct atggggggct ggggagggat agcattaggg gaaataccta
15061 atgtagatga caggttgatg ggtgcaacaa accaccatgg cacatgtata tctatgtaac
15121 aaacctgcac attctgcaca tgtaccccag aatttaaagt ataataagaa aaataaaaat
15181 aaataagtta aaagagatta aaaaaataaa agagaacatt tgccacattc agtctttcta
15241 gatggaaaga ggttgctgac atatgataga attagaaaat cacacatctt gtaaattctc
15301 atttgtttaa aaagaaatca tacaaattag atgtttttg gagatgactt tttaaaatag
15361 agtcgttaga tcacctctgt aagggatatg tctatatctg ttcagtgggt taggggacat
15421 ggatctggaa agcctgagaa gaaaaagaag gttctatacc agacttgtga tatttagaca
15481 ttttcatatt ctatccattg ttttgtgtgc attttattcc tcactattgt atatatagtt
15541 gacaatgcta aactttttg tgtattcttt ctatgtgttc cgaatgccta atatatgtca
15601 aaattagcgg tagtaaaata atattttgta aatatctttt tgctaaaatt catatgaaat
15661 gttgttttg gaggggaatg gccaaactac ctgttgagta atactcatcg tgtttgtgtc
15721 ctggttcagg ggaggaggaa ggaggggaaa gtgcagagag ctctatgccg ctgtgtttac
15781 agtgaggcaa gattaaccat tatctcttat gtctgtgcat tttgttttac ttatctgttt
15841 atgtagtgta tataaaggac aaacgagtcc taatttacaa catctagtct ttttagatgt
15901 taaagaggtt gccagtgtat aacaaaagta gagttagtaa actaatatat tttgtatatt
15961 ttgttttaaa attcctagga aagattgtct tcctatcttt gagcattctt gcgcactgag
16021 ttgatggaga tgggagggat tctaagctag gatgttctta tttggaagac tctttcaaat
16081 tataactatg gttacatgta tgcagtttat tcgagactgc tgtgtatata gtggacaaat
16141 taactcctta cttgaaacac ctagtttatc tagatgttta gaagtgcctg atgtacgtta
16201 aatgtagagg taataaaata ccactttgta aatatctttt tgctaaaatt cataggaaat
16261 actgtctttt agaaatttaa ttgttaagcc acctttgtga gcagtatagt actgtctata
16321 cttgttcaat ggtttagagg aggtgggagg gaagaaaaat atgtgactga cttatttcac
16381 taagcctaat gtctttaagt ttcattcatg ttgtggcatg tgtcagaatt tccttccttt
16441 ttaaagctga ataatattgc attgtataga tatattacct tttatttatc catttatcca
```

FIGURE 2 (cont.'d)

```
16501 tcaatagaaa cttgggttgc ttccatattt tagctatcat gaatattgct gccatcaaca
16561 tgttgagttc ctgtattcaa ctctttgggt aatacccaga agtgaaattg ctgaataagt
16621 atggtaattc tctgttaaat ttttgaggag ctgctgattc atacttttac gtataaaata
16681 ttagacctta aatgtattat gtaaaaacac taagtatttt taacattcta gagtaaagaa
16741 ggtgtttctt agcaagacag aaaagctgaa accctcaata gaaaagcctt gttaatgtta
16801 tcacataaaa tattcaaaat ttctgaacac acagacacac acgcactaac gaaaagctat
16861 ttacaacttg tggtagatga agaaataatt tcttaacata gcaagaaccc aggcaaatga
16921 ttaagaaaaa gaataatcat acaaatttaa tacatgtgag aagctgttca gcctttccca
16981 ttaattaaag aagtaaaata taaaacaaaa catataattt ttcacttagc agagatgaaa
17041 taccaaaaca gatgggtata ggtgtggaac atacttcctt ggttgacagt tagccaatat
17101 ctattaaaat cccttgccac agtaatttca gttctagaca tttgtcttat attactgtat
17161 ttattctgtc ctgtaaccat aaattccaca gctgcctagt gatggttcta tatttaaatg
17221 gaatgcttac tctcagtatt gtttttttctt ttgagatgga gtcttgttct gttgccaggc
17281 tggagtgcag tgccatgatc tcagctcact gcaacctcca cctcccaggt tcaagtgatt
17341 ctcctgcctc agcctcccga gtagctagga ctacaggtgt gcaccaccac gcccagctaa
17401 ttttgtatt tttagtagag atggagtttc accttgttgg ccagtatggt ctcgatctct
17461 tgacctcatg atctgcccac cttggcctcc caaagtgctg tgattacagg tgtgagccac
17521 gacacccagc cagtattttt tttttaaac cacagcttct tcattttgag tcatctctaa
17581 atagctgcaa tttactataa cttagggttt acaattttta aaattgtgta tgttaaggta
17641 tccacatgat gtttgatata cttcttttga cataaatata cacaatgaag tgattactac
17701 agccaaataa tgattaccat acccatcatt gctagcgttt agaaagacaa ctgattttta
17761 tgtgctgata ttgtaccctg caaccttact gaatttacta aatctagtag tttttggtg
17821 catcctttgg gattttctat taacagaatc atgccttctg caaatgtaag taatttagct
17881 gcttcttttt aaatatgtat gcctcttatg tctttttctt ggctatgttc ttttctctgg
17941 ctagaacttc tagtacaatg tccagtgtca gtgttgaaaa tgggcatcct tgtgttgttc
18001 ctgattttag gagtaaagct tacagttttt ctacccctga gtatgatttt agttgtgaga
18061 ttttcctata tgccctttat catgctaaga aagttccctt ttattttagt ttgctgattt
18121 tttaaaatta tgaaagggca tttaatttta tcaaatactt ttttctgtgt ctgttgagag
18181 tttggccatt ttttttctat tgaaatggtg tattatggta gctgattttt ggatgtgaaa
18241 ccaaccttgt gtccttggga taaatcccat gtaatcatgg tgtataattc tttctatgta
18301 ttgctggatt tggtttgcta gtattttgtt gggaactttt gtgcccataa gataagaggt
18361 attgatctat ggtttttcttt tcctgtgatg tctttatttg gtttttgtgt cagggaaata
18421 gtggcttcat aaaatgttca agaagtgtac cctcctcatc tttttgttgg aagagtgtga
18481 aaaattggta ttatcaaatg tttagtagaa ttcaccagtg aagccatttg cttttctttt
18541 tgggtagttt ttgattactg attcattctc ttaatttgtt ttaggtctat tcagattgtc
18601 tgtttcttct tgagtcagtc ttggtagttg tgtctttctt gaaatttttt catttcactt
18661 aaattatctt atttgtcagt gtacaattat ttttggtatt cctttataat cctttttatt
18721 tctttaatgt cagtagtaat gtctcttctt ttatttctga ttctatagtt tgagttttct
18781 ctcctctttc cctgatgaaa ctgaagtttt ttccatttta ttgatttttt tcaaacgatc
18841 aaattatttc attaatttgt gctgttatca ttatttcctt ccttctgctt acttaaattt
18901 agtttcatat tttttgtaag tgtcttaagg tagaatttta agttattgat ttaagaactt
18961 tcttaataca agtgtttaca gctgttgata ttactctaat tacttcttta gctgcatcac
19021 aattgttttg gtatgttgtc ttcattatta ttcgtctaaa aatattatct aatttctgtc
19081 ttgatttctt ctttgactca tgaattgttt tagagtggaa atttcatttt aaatttccaa
19141 atatttgtga atttcccaaa tttcccctgt tgttgatttc taattttatt ccattgtggt
19201 taataacata ctttgcatta tttctatcct tcaaatttat tgaggtgtgt tttatggcct
19261 aatatgtggt ctatcttcta gaatgttcca tgctcacttg acatgaatgt atactttgtt
19321 gttgttgtta agtagaatgt tccatagtcc ttgaggtcta tttggtttgt agtattgctc
19381 aagtcctctt tttccttgtt gatccgtcca gttgttctat ccatttttga acgtgtagta
19441 ttgaagtcct tgactatttc tgttgactcg gttgacttgt ctatttcttt ctttctcag
19501 gtctgttttt gtttcattta ttttggtgct tcatatatat aggtgcatat atgttgataa
19561 cagttatatc ttcctaatgg atggattcct ttgtaattac aaaaggccac tctatctcta
19621 gtaacaattt ttgttttaaa gtctatttgt ctgatatcag tgtactgact ccagtgtttt
19681 tgtggttgct gtttgcataa tatatttttc ctgttctttt actttcattc tgtgtcttcg
19741 aatcaaaatt gtgttttctc cagacaatat atacttcatg ttttcttatc caatataaca
```

FIGURE 2 (cont.'d)

```
19801 cctttgcctt ttgattgcat tgtttattcc attcacactg catattatta tttagtggga
19861 tttatgtctg tcattttagt tctttttttgt ttttgtttg agacagaatc ttgctctgtc
19921 acccaggccg gagtgcagtg gcgtgatctc ggctcactgc aagctccaac tcccgggttc
19981 aggccattct cttgcctcag cctcccaagt agctgggact acaggtgccc accaccactc
20041 gtggctaatt ttttgtattt ttagtggaga ctgggtttca ccgtgttagc caagatggtc
20101 tcgatctcct gacctcgtga tctgcccacc tcggcctccc aaagtgttgg gattacaggc
20161 atgagccacc gcacgcccgg attttttgtt ttttatatgt atcatgtctt tgttgttcct
20221 gttttgtctt tacttctttc tatttcattg aattaatatt ttctaatata gtatttaagt
20281 tttattaata attttatcac tgtattttta tttttagtgg tttctctagg attttctgta
20341 tatatcttat cagtatgagt ttcagattca cactagctta attccagtaa tatgtagaaa
20401 tgttactcat gtagaactta attctcttgc tcttttgtgg ttattttatt tatattatat
20461 caattaatgt tacaaagata tacattgttt aaattattat tggtgctatt attagcatac
20521 ataacaccca catattaaaa ttgtatatat tgcatatatg tattatagaa ttgtatatat
20581 tatagggcca atagtatatt gtatacatgt tattttatat aattgttttt aaaatgagtt
20641 aagaaaaaag aaaaatgcat ttctactgtc tattatagaa aaataattac atcatactga
20701 acgtcttcac cnnnnnnnnn nnnnnnnnnn nnnnnnnnnn nnnnnnnnnn nnnnnnnnnn
20761 nnnnnnnnnn nnnnnnnnnn nnnnnnnnnn nnnnnnnnnn nnnnnnnnnn ngctctaata
20821 aatttgcggc cgctaatacg actcactata gggagaggat ccgcggaatt cctaaaagaa
20881 ttgctgagac aaagtatatg tgcctttgtc atcctgaggg cagttgtcat cctgtggagg
20941 tttaccattt gctctcccac cagcaatgta taagcatacc tgcttcccaa cacttccgcc
21001 aacacatatt atttgattaa ttttcttggc tgataatggt atctcattgt agttttaatt
21061 tgtatttctc attgtgagag aaatgaagca tcttttcatg ttttgagagc catctgtgca
21121 tcttttccca ttgtttctgt taagtcattg atttgcagta ctgtaatttg tgatgagttg
21181 taaacatgag ctcttctggc ctcttaacca tccttatcca gcctgtcttc acgttcctcc
21241 ttgcctaaaa acaagctcac tcaaacagat cattcctgtg gccctctccc ttttgaaata
21301 aatcagatgg gcaaatttgc ttttgttagg ggcctgagac ccaaatgttt aaaagtagct
21361 tagctgatga gtgaaaagga ggcccagttg gggttgcac agaaaatgag gggcgtgggt
21421 aatagaggag gctgggcagt aacctggcag aaggcgccag aggccaagga aggtgcgctg
21481 gtgtcctgca gtgagaagga tgtgtgcact atcaactggg taaacacact gctatagctg
21541 ctccagcgac agcaggcact ctcagaaggg aactgagaaa aggggaatgc cagtttctgc
21601 caaggatata tggaaaagtt ttttttcccc gtatgttctt tggcaacctt gttaaaatca
21661 tttaaaatgg tgaatttgat aacaaagcca gccactaaaa gacttggatg tagcaaaaca
21721 aattgtcaaa aagtatttat catttctaag aaataaaata aactgggatt taggcttgga
21781 tagaaatcca gaggtttgtt ttggcataat taattacaac atctgaagaa gggaggattt
21841 ttacaagaat ttttttttt gtagtgagat tgctttatat tccttttcat gactggagag
21901 tctgtcattt ggcaacccgc aaagaacttc aggaacagag ggcctaagtt ttcttgacac
21961 atttggattt ttgcatgatg aacatttgca cttttattag taattgtcga gtcgtgtgtg
22021 gtctgatcct atggagagga gagtgtaggt gtnntctctg gagctagtac ntgcccccgn
22081 gctcacacgt gccacactgc ctgctgcttt cangaaagag caggacggct ggtcctgtcc
22141 catctagtga ggtcctgtcc catctagtaa ggttctgtcc tcagagctcc taagagggga
22201 ttgctggcct ttgattacac tggcttccag aatctgacca tggaaccatt atttgaagct
22261 gtcagcttca ttttgttgtt gatcaggcca gtcttttagg tctttgttgg ttgatagatt
22321 tctctcaggt ctatagcagc aacaaataaa gctctttaaa attattttct tgaccattct
22381 gcctatggat tggttctgac ctttgaaatg tttgctgtcc tttagatcgt gacagaagga
22441 gcctcttctg ggagctgtga agaccccaca gatctcactg gttttcttgc ttttattgga
22501 agagttagca tttgttgaag tttatattta tgtaaaataa caataagtag attttaaaat
22561 ttttctttaa attctgtgat ctaataagaa gagagactct ttctctgtca ttgggaggct
22621 tgatgaggat cggacatacc tgctgagagt atcctgtaat gttttcataa gattggaaat
22681 ggtgaaatga gagcagaaat gtaggcagag gatgccaacg ctgtttccta tttcctaagt
22741 aaaactgagc agggcagaat ctccccagcc ctgccagaac tcccttcctc cttgggtccg
22801 ctgtcactgt catgctggcc ttgacatctg ctacaagtgc acacacatgg ggaaccacac
22861 agggaagtga acacatgtcc tgacgtgtgt gtgtgcctgg tgtggctgct tccttgatcc
22921 aggctttgtt ttgttacgag gctctgccct cctaccttca ggccttgctc ctcatcatgg
22981 gcatgcaagg atggaatcgt taccccagag tacacttttt gacttggatt acttgtagtt
23041 tagtactgga gttcagaact ttaatttccc atcagaaacc tgcctcccgg acccaggaca
```

FIGURE 2 (cont.'d)

```
23101 ctgaccttga ttgggcacga ttttccagat aagaccttac ctcctcccaa cagggtttgc
23161 cttcccttca gaatacagga aagtacacgt ggttccaaga ggaccatgct cttactaaga
23221 taaaagggag gagggtgact aggtactttc ctctgctgcc atcccttgaa ggaagggggc
23281 ttccttcaat gcctcatcag ttccagggag tatgcttgac ccagcaacac agaggaagaa
23341 gtgacctcat agcaatgagg ggcaagcatg tggatattgc tgggtatttc ttcctcaaag
23401 tctacctggg gacaggtgat gaagacgctt acttctctgc aatacaccgt gatcaggctt
23461 tggtcttcat gacacatttt agccttgcct atgtgtgttg aacagagctg gtcatcctca
23521 gaaataaaag aagagagcaa taagtacagg aaggctttca gtcccagaat agtgttagga
23581 ctaaatgtca gagaacaggg ggactgtagg agtttgggga ccttagcatg gataccctct
23641 caatctgctc ccctgtggta taaacagtaa agcccattgt actaaaaggc cttgagtgct
23701 tgtctctggg gcaggtggag ccagtgatgg gtgccccgag aggaggatgc tggagagggg
23761 acagtgtcta aggcagttgg agaaaaagga caatggctta tgcagtcagg cctagaagat
23821 gcaagggatg tcacagcata gtgtccacag gcatccctag atgtctttca ttttgtttca
23881 ggaagaatat tgacaaaggt agtgatggga gggttatttc aaggatgcta ttttcatgtg
23941 tccaagtaaa cttaagattc ctaagaactt tgacctctaa tgcttttaaa gaccgtgtac
24001 ctcatgccca tatgcacatt cagttagaaa ataaatgtag attctttggt gaattcgaag
24061 atgtgctcat ggagtggcac agcgtgatct cagtgtacac atgaagcatg ctgatgagag
24121 cttcttggat cttgtttctt caggtggact tgcattaaag tgctgttgaa tctctgcact
24181 gggagtggga gcagccatgc gatgggtgcc ttaatccgag tgccatcctg gctctctcca
24241 ggctgcttca tttgctgtga ggggtagggg gaggaggagt ttccaggcaa tggccttatc
24301 tgttctggtg gttgaccaag ggtcgggggt cccaaaggtg gagttccagg atgagagtgc
24361 acccttgggg atggtactta gaaagagtgg ggactaggcc tcagccaggg aatggtgggc
24421 cagggtggag ctcctttgta tcaaggagtt agggccaagg gccatgcagg tgggcctgca
24481 gaaggtgggt ggtgatatgg cctttctggt gataacagac tcgtggcact gttttcctgg
24541 ggctgttggg gttgcatgga gcagattctt actcaggctt actgtcttaa ggagggaaga
24601 atgctttttt atgaatacgc ataggtctgt ggggctgtgg agcctgggga atccgaggct
24661 ggcgtgggag tctggggccc tctagcggtg gtggtgcatc ctcagctcag tgccactcac
24721 tgtccctatt tctctctgtc catttctctc ctcactgcag tgcttcctct ccttcctaga
24781 tttttttctc taagtttgac tattcaccac cccagagact ctgttctatc ccatgacctc
24841 ttgctgtact ttctttcaaa tctaaatttt cttgattatt tttcttaatt tacagtttca
24901 agattagatc tgttgggagc attctgtgct ctacctcagc ccctggttga gctatggatt
24961 ggtgtccccc atggtgacgt ggtctggact ccccttttgtg tgaagagctg tggcagggca
25021 gtgaggtttt gtggaactca gggagcatct ggcactatgt atgaggttgt gaggtgggag
25081 agagctctta aatctaccag ccttgttgat cttgggaact aggagagagt gctagggaag
25141 ccagtgccag caggcctgga gcctcatatt tctttggcat ttgtatgata ccttctagta
25201 cttcgttttt tgacttatat atgaactaac tcaatttaga tgcttagaaa ataaacggcc
25261 actggacctg caagagatta gtagtggtgt tccatagcct tagacatttc ttacactttt
25321 atccacagat aagaaaaaaa tagtgatatt tgatttgttt tgccaaggct tagaaggatc
25381 taatatgtgt tactcgttga gcagcgggaa gcagcagaca tttctagggt ttctccctgt
25441 caccattcag gagacagtgc acacaatccc cttggctctt acctgaacac tgaccacagg
25501 tctgtcattg caggctggga gtcctccgtc agcatcagct ccggctccgg tgtcctcctt
25561 ctctcgcact tctatcacgc catccagcca ggacatctgc aggtaacact ctgcttcaga
25621 tgctgccatg atcagtgtgc agccagaaat aagcattagt gtctgtaggt tcttgaattt
25681 ccatttgctt aatcaatctg cctttggtct aaacagttgg cgagttttat gtgtggtttg
25741 ctcaccaagt tacccatgct agtctcattt cttcactatg atgtctattc tcttttaaaa
25801 ttgtttttac tttctgtgct tttatcccac tgttctgcat gcagttccag tgcagtgttt
25861 tctgagtgtt gtcaccacag ttccgtgcag tctgctgttg tctcgaaagc tcctcactgc
25921 cagagttctc tgacacaagg gctcactgtg acagttatct gtaaggacac attacaggcg
25981 tcaaagagaa attcctttgg ttcagaatgg gcccaggcct tgaagcctgc taagaatacc
26041 aaagccagaa gaacactaaa gttctcaagg tccctcaatg atgtgggtga gaaggcgcag
26101 gatacttcag aaagttttgc ctatgtggaa agaacttgtt ctgaagggaa attaatactc
26161 cctcaagata cgtgtctcag aactaacagg tttcatcata aagaaaaaag aaccctgaac
26221 cacaaacctc ttggcaattc caaacattct tgtgtttcat gcctttctgc cggtcgctca
26281 actgcctcag aggtggaagc tggcaagggg ggcaggcccg gcctgctgct ggaagagaag
26341 gcggatggtg aggccacgtc ccgaagccgg caactgctcc agtacctgtt ctcactctcg
```

FIGURE 2 (cont.'d)

```
26401 cacggcttga gcgccagcag cctgcacagg ttccatgagc tggagagctg cgctgctcgc
26461 ctgcacactg ccaagtcctc cagcgggctg gcagggagta tgggcttctg ctctgacgag
26521 atgggagacg acgatgtctt tgaggacagc acatctgcaa aactgaagag tagggttctg
26581 cggcgcgccc tctgctccac ggaaaaggac agcgacctgg attgtccttc tcccttctct
26641 gaaaaattac cccccatatc tcccgtgtcc acgtcagggg atgtctgcag gttggtttgc
26701 caggaagtgc cattctagcc atctctgctc gcatcaggaa cctcctcttg ctttagtatg
26761 tgaagtttca ggaaaatgaa gtaataggaa gttgtaacca gttgtgggtt gatggttttc
26821 tccagaagaa tggagtatca atatcgtttg aaaaacttaa tttttatgat gtgagtccca
26881 agatagtttt acaaatgata aaagaggaag aagctggctg ggcgcagtgg ctcacgcctg
26941 taatcccagc actttgggag gctgaggcgg gtggatcacc tgaggtcagg agtttgagac
27001 cagcttggcc aacgtggcga aaccccgtct ctactaaaaa tacaaaaatt agccgggcgt
27061 ggtggcgggc gcctgtaatc ccagctactc aggaggctga ggcaggagaa ttgcttgaac
27121 ccgggaggcg gaggttgcag tgagccaaga ttgcgccatt gcactccagc ctgggcaaca
27181 agagtgaaac tctgtctaaa aaaaaacaaa acaaaacaaa aaaaaaaaga ggaagaagct
27241 acacatatta aaggccaagc tgactcttct aaactaaaaa taagtagact ttgcataaag
27301 aaactggaag aaagaaacta gtatcttcag ttttccagcc tgatggtcca gattttaagc
27361 attgttgcat ctcccagcct ctttttaac ccttgctccc tacctacccc caaaaggtgt
27421 gtggggactg gctgttctcc agtagctcct tccttccttc tttttaactg aggtgtagcc
27481 acctatgtcc catcctaact ctgtttcccc cctttatctt cccttgtgca gcatccttgt
27541 ctggcctcca taattcactt tttgtcatga ctcttgtgcc ctcctcattc tgacctttct
27601 ccagtctccg ctccttagtg ccagctgtca tcatttctaa catttggatc agagatcccc
27661 tcactaaaac agcctgagag cctggctcct tccaggacga gtgccccaac ctgttctcta
27721 gctgctggaa aagacccctc tgtttcttaa aagcctgtta agttccttca ggctagtagc
27781 tacaccttgt tgcatacttc cttggaaata gagagtgctt tcaaattaat ttctcactta
27841 ttgctattag tggtcccaag aaaaagagat gaaattgcag catcttgtaa tggtgagttt
27901 tttaggtcta ggagagaggt actgtcatct ttgtttactt gctgagagac gacagaaatg
27961 tgtagttgtg gggtatgaag gtaaagtcag tgattatagc taaaaagcaa acgtcattta
28021 aggtcactgg tatttttgga tgttggaatg cagcgcttac catccataca agaacccgct
28081 gggagggcca agaccatccc gtgcgcggcg ggaaccgcga catccgccac tcggatgccc
28141 gctggagcgg gcggagaccc acgcgcgcgc caatgtcccg gcgcgcgggc tgctcaccca
28201 gggcagcggc gtagtcgccg gggcacaag cccgagccgc ccgggcggc gcgcggagaa
28261 ggagcgcaga ccccgtgaac acgccggagg accgtccgcg cggcccgtcg cgccactgcc
28321 tactgccagg ggcggcgggt gacgacaaaa ccctcggtgc gccgcgcctg gcagtccgcg
28381 gcccccgccc ccccagcggc gcgcacccgg gggcgcgggc cgaacccggc aaggtgagag
28441 ggccgtggcg cccgggcgct gaccactatc attctccgcc acacggacga aggcaggagc
28501 accacgggcg gccggcgggc cgcccgctcg ggccaaagag cccgcccgcc agcggannnn
28561 nnnnnnnnnn nnnnnnnnnn nnnnnnnnnn nnnnnnnnnn nnnnnnnnnn nnnnnnnnnn
28621 nnnnnnnnnn nnnnnnnnnn nnnnnnnnnn nnnnnngagg ccgggcgagc gcaggcgggc
28681 ggagagcaga ccacgcggaa gaggccgaga gagaaagcgg ggcacccggc cgggggggtc
28741 atttacaagg gacgctgggc acgaaggagg ctggggcgaa gatgagtcca ggggttgggt
28801 tgagagcgct gcgcagccgg gctgagaaga gaagctgacg agtgactccc gacaagggac
28861 gggggagagg gaacctgggg gcaggcagag gcctaggggg tgggctctga gggcagccac
28921 tcccaccggc cctcccccag ccccgcaggc cagccacatg ccccgtgctc cagacgaccc
28981 agctacatgg atggcagcgt cctgaagggg gatgatcggt agggagtggg tgcggaggct
29041 cacgcctgta atcccagtgt tcggggattc ccgagcggga ggatcgcttg agccggggag
29101 gtggaagctg cagtgatctg cgccactgaa ctcccgcctg ggcggcagag tgagaccctg
29161 tttcaaaagg caccaggggt gtagggaagg agcgatatcc cccaggcaag gaaggctgcg
29221 gaggggccag gccaggagag aagggccctg agctcagtgg acgggcaggg tgcctgtgga
29281 ggaagggagg gacgtagcag caggaggaag ggtgaggacc caggctgggg atcgggagaa
29341 gtgatggcgg aggaaagaga ggccggaaga ggagggggcc tgctggcctg gcactggaaa
29401 gcaaagcgtg ggtttgtata tgggaagaag accacatccc ctcttatcgt catcccaact
29461 cagaaaccat ttggccccaa gtcaccaaag cactcatagg aaccactttt cctgtgacac
29521 aagtaggatt ctcccacttt taacttccca aatgctaccc gaaagcctct gaaatccttg
29581 gaaatttaaa aaataatccc cttctattaa ctgatgccta taaaacatat tgactttcat
29641 taaattttgt tatgaaatca gggatgtgtc ccattgtaaa ataaatttgt ttggaaaatg
```

FIGURE 2 (cont.'d)

```
29701 tagggtggta tcccatctaa aaatcagacg aggctagaaa atttcaattt tatttgctaa
29761 ggtagcatca tgttgttaaa aatgcatcat aaaataagac caagagttaa tacaaagcat
29821 gaagtcatgt ttccctcaaa aaaatgattt gttctgtagt caaattaatt tggaaaacat
29881 tgcaaactct tcagcagtgg ttctcaaagt atagcttgcg tcagaatccc ctggggccct
29941 tgctaaaatc tggatggcta cactccccgc ctagagtggg ttaaactcag tgcccactgg
30001 caggaaactg aaacttggct gaagtcaccg aggaggcctt ccccgttaaa cctctggctg
30061 gcgacagctt ggtttcctcg ccgctgcttc tgagtaattc tggcacgcag ttcctcctag
30121 ccacctgctg tacctggaag gggccagcc ctcctcagca ggctttgctc ctgccctgca
30181 cagcacaact gtggcgtaaa aatggaaaa gctggtagca gaaggaaaga gcagggagac
30241 agaggttagg tgaacctcaa tggcctcatt aaagcaaatt gagaaagaga gtttccttcc
30301 cagtgaggcg ggacagtgca gaaatgcggc ccgtcctggg agaagtaggg gcgaggggtg
30361 gggggctcac cgggcacatg gccaacagct ggtgcccagc ctgggccaca gtttggcaca
30421 ggagaaagct gaagatgcag gagaaagcta ggtcactgcc cctaggccag gtgatcaagg
30481 tggctgttac ctgcctgtgt ggccttgaaa aagcctggtg ccctctctgg cttgcagggt
30541 ccttcttttt acaaaagcgg gtcttcgaag ccctgaatat tccagttatc tgtaaggata
30601 tagaaatatt ttgcctctag atgacatgta aatatgttcc tcctaactcc acttcttcct
30661 acatctgtgg cttcttctga gaactaccag acccaccctg ttttcagagt aaacctcctg
30721 ttttgaggtc aaacagaccc agctgggtaa ttggtgactc actcctggtt cctccaaaga
30781 acaggggcaa gggaccaccc gggacctcag gtgccccagc acaggacctc tttctggggc
30841 accctctggc actgggccat cttcaggccc tacagggctc tcggggcctg cgtaggcctc
30901 tcatctccca gaaataagtt cttttcccca cccagactga caccagatgc tacagtgagg
30961 tttacccctc cagcttgaca agcattccta gcccagaaca ctcagctgac gaggggtgct
31021 gggggaggaa ggaggcagca aggctgaaag aagcttctct gggtattcca gtgcctggct
31081 gctggtcgta gccatggtga gaccacagca gcctccctgg aagcaagcac ctgtgtaaaa
31141 gcccctcctt ccccacaagg ggctggatcc aagtgaagaa ggtaccagaa ggactggaag
31201 atgatgctgg tattattcga cagctccagg gtgctgtagc actgagcacc tactgtatgc
31261 agcccatcac aaagccagcc acactgccca ggctgtgcca tggcaacttc cagcagtaca
31321 ccctctcggt cacctgcagg ctccttgttc atcctgacac atgaggagaa aaagacagta
31381 ctcacaaagg cctctagcct tgtggcccca ggaccctctc ctgagcatca tggcctccta
31441 ggagacccag ggtagccagg acaaaggaga gaagcatttg ctaagctaag aaaggatgga
31501 aggggattgc tgttctgcct ggatgcaccc ctagacctgg cagggcaggc aggagagacc
31561 cccagtgtct cttgcttatc ctaggagttc ccccctgtgg ttgctccagt ttgctgcctt
31621 catgcatgtt cacagggtga ttcccctgag acaacagagc tggatgtca ccaagccctg
31681 tgtcccatca gccaggctct ccccagcctc catcctctca ttctgctgga tcaggaggat
31741 gtggggaggt ccctgactcc ccagctttcc ccatgacaag gtgtgtgtct acagctcaga
31801 cccagccatg ctccacctga gaagtgggtc caggcagagc actgggtcct ggccacctag
31861 ggctgcctcc tcaggggtgg gcaggaaggg gagccactgg aggagtgccc cgggcacagt
31921 cccctgcacc aggtgaggtc acctcttagt ccatgaggcg atgctgcatg agcccctctg
31981 gacactagaa ggcctgggct caatgctgag taaagtgcag gcatgactgt gccctcagca
32041 tgcatagggc agcaggcata gattcataca cgtgagtttg cacttaagct gcagtaagag
32101 ctacagagga aatgaacaga gacagcatca ctccagtgag ccctccagat acaccccatg
32161 tgcgcagtaa gagaatggca tagtctattg ggacagccac atcaaaatac cacagaccag
32221 atggcttaaa cggcagatat ttgtctctca caggtccgga ggctagaagt ccaagattag
32281 ggtgccagcc aatccacttg ctggtgaggg ccctcttccc agcttgcaga tgtctctgtg
32341 ttcccacagc atggtcacgt ggcagagaga gggggacagg gcatgaataa gccctcggtg
32401 ccttcctctt cttacgagga tgctaatccc atcacgggta ccccaccctc gtgacctcgt
32461 ctaaccctaa tcacctccca aaggccccat ctcctaatgc catcacactg gggtcaggg
32521 cttcaacaca tgaatttggg gagcacaatt tagtccacag cagaaaagaa aggggcacag
32581 agcattccag cctgaaggaa acagatgtgc aaaggcccaa ggcaaaggcc tgagctctga
32641 ggggcaacca gagtcaaggc tgaagagtgg gcagtgattg agcactgacg gtggagaggc
32701 aacaggctat cttgttaatc tcagtctttt gtgtgccaga gagagaaact gaggcacagt
32761 gtgtcatggt gaacactggg cagcactccc acgctcctgt cctgcactct gcagggttat
32821 ggaggaagcc tgggaagtct ctcccctctt ttccaccttt cctggaccca tcccacaccc
32881 tgcctcctcc aggaagccct ggggattgct catacactca catctcactc cttagtacct
32941 gcagcctgca ttctgaattt agcaagctct ggccttgggt ttctatttc ttgtcctgtg
```

FIGURE 2 (cont.'d)

```
33001 cagtgagcat ttggaaactt ctcctcagca ccaaacacgg agccatttag cagaaaatac
33061 atgagttttc aagtcaattg aactgttcat cgccccaaaa gccaggcaac acggtagagc
33121 agctggatct ctgttcgtag aagctttctc agggactggc ccaccgagtg ggggactgca
33181 agtgcccgat gagtgaatga atgaacacat gtgtgaatgg aattcaaggc actgcaggct
33241 attctggagg gtactggcct gtctcttcga caggtgaggt gcagtagaac agcatcccgt
33301 atagatgcca gtttctgacc tggttctgaa aagccagtca cctacctctg cagagctgcc
33361 tggaggggc gggggttgtg aggacccctg agagcttggt gtgaaggggc tctgcagagg
33421 gaggcatggc tagtgtgcgc aaggtgacct ctctcctggt ctgcaggatg gagaacctgt
33481 tcatcaaccg cttcatgcac atgttccagt cttcttggaa tgacttcgcc gactttgaga
33541 aaatctttgt caagatcagc aacactattt ctggtgagtg tgcctctggg ggcccaagtg
33601 gtgctgggga caggggatgc tgctctcctg tctgatactt gccgggaaat tgacaagggc
33661 cttcctgcct gctgcagcat gggggcctcg ctgccaccat gccaccctgg acagcacccc
33721 ctacactcca caccttttac catcactgtg gtcacccttg tgcccagagg tttctcctcc
33781 tcagatattc aagctcgagc accctcaacc tcatttcact atcaaaagtc tcaaaagtat
33841 cagaactttt tcttggcaca aatcaatcat ttgtgcttct gaacagagca aaggcagaac
33901 ttggcttgtg ttttaggtat ttacacaaaa gcaactttgg gttcctttgg actaggatgt
33961 gtttgatgag agcactagct tcatagtggc cagtcatggc atgggaagga cgttaggaag
34021 gcaggaatgg ctggacaaga agaggtgctg aaatcaggac atggggaacc aaacttggca
34081 aactgccccc agggactctc ctccacgccc tccttcttcc atcctggaca ctccatgctg
34141 ggctgaagga cctgagtgct ccaggaggct tctgagccac gaagggccag ctcaggtatg
34201 atgagttggt gccacagcct gacccagtga tgggcagggg gcagcagttg gagctgtgcc
34261 catccaggga gcactcggga gaggagacca agcagggact ctgctcttag gtgaggtcag
34321 gagggccatg gccctggctg ccctctactc agagctcagg gtgggcctcg cttttctcct
34381 ggtagagcgg gtcatgaatc actggcagga agacctgatg tttggctacc agttcctgaa
34441 tggctgcaac cctgtgttga tccggcgctg cacagagctg cccgagaagc tcccggtgac
34501 cacggagatg gtagagtgca gcctggagcg gcagctcagc ttggagcagg aggtccaggt
34561 aggggttgat gggctgggga agtggccaag gtcacagtct gtcaggtgga agccagttcc
34621 tcctggccag tgctcatagg ccaccaagac gctaactgca ggcccatctg gcctacagca
34681 gccgcttcct tttcctggca gcagtgtcag ccagggtcct gggcattatg cagactgtct
34741 tgtgcaacat cagaggagga attgcgggga atgtttctcc atgatgctcg agtctgggaa
34801 cataatgtca atattttcac tatcagtatc aataattaca ggagctaccc ttgattaggg
34861 gcctgtggtg ggacaggcat tgtgacaggt gctttacaca caaggtcatc agttgtcacc
34921 caccttgcaa aggggagaac actggagaaa gaagcagacc ttgtgtgaca atacacaagg
34981 ggcacgagga gaacccaaca gaatggttga ttttctcgtt agaaatgctg ctgcccatgc
35041 tcctgtcgca ccctcctccc caccctcacc tgcagactca gctgcctccg gctgcaaggc
35101 tgacctagtc ttgagacaga agaagttcaa accaactcca cctggatctg gtggggctca
35161 gcaacaggcg ctggcccatc agcctgcctc ttccccatgg atccagcgtg atggggcctc
35221 ctgccaccca ggccctgctg cctatcccca ggtgtccagg tggcctctgc tgcttccagt
35281 cttttgagct cagcttaccc tgaggcccta gttggagagg gatggttggt gccctttaga
35341 gataaaccta cagccccagt acctggccca cctgaatcta gagggccacc cacccagctg
35401 aagtccctgg gcaagtctcc tgccccagtg caggcagtgt ttcctaacct cctcctcctc
35461 ctgcacccaa ccaggcccag aacacttcct ggtcatgtga acagctgaca gttacaatcc
35521 cccacacact gagagagcat ctgtgttcct gagtggactg aattgctaga tgtagtaaca
35581 ttgatttggt ggctataggt ttcaaacttc aagtcagaga tcatagaact ttaagccata
35641 tagaatccta gaattggaag actctgagca gccatctctg cacccagcag ccaaggagtg
35701 gccatcctca gcacctggca gggcatcagc ctcccactgg gagtcccggc cacctccagg
35761 gcacgtgggt tatgagtcac ctttcctttg agctgaccca cccctcactg actagactct
35821 taaacacaca ctgccccgtc taatacacac cagcatgatt cttaatcccc acagtcattc
35881 acgctgccca tctggcagca ccttaatgat ctacagcaag cttgtggcct actaaaaacg
35941 cctccattgt tttttaaaat gtgcagttat tttccggatc atgaatagag aaattgtatc
36001 cctgttgttg gtattgattc agtgttccag ctcaagtttg agttcttaga ctttatattt
36061 ggattctttg gtttcaaatc acaaaaatca actccatctg gtttaatcca agaactctat
36121 tggctcaggc aacagtaaaa agcaatgcta actcatttgg gaccagggct cagatcatcc
36181 cctgcactgt ctctctctcg ctccatgtct caatcctctg cctctggtga tttttttcctt
36241 aggagggttt ccttatgtgg aggtaaaaaa tgatcaccgg cagcttcaga tttaccttcc
```

FIGURE 2 (cont.'d)

36301 accagcttag caaacaccac ccactcccag caagaaagac cctgtttccc aatgctccca
36361 gcagatgtct taggccatcc tcgggcctca ctgattctgt gagccagtgc ccacggccag
36421 gagaatggaa tacactgacc tagaggggac agggactcta gacaggcaaa aactccactg
36481 tcagaagcag aatcctaaaa tgtcagaact gaaaggtagg cccgcccctc gttttccaga
36541 aatatgaaag ggaggcttgg gataacagag aaatgctgca ggcattggcc ccaaatctca
36601 ggcctcctat tcccagtatc accttcacca gcctgggtgg tctcaagatt ggattagcag
36661 ccattccttc tgggtagagt ctgatggtca cttcagctct caaagtccag ctatccagcc
36721 atagtcctag aaggcaagac atcactgtgc ccgaccaacc caagggtctc cacctgcccc
36781 cctcaacaca aggtgccctg agtgcctccg cggggatagt ccccgtcccc acccctgctt
36841 cccccgccca tcgcgacaga tgctcagagc tcatccctgg tgtcacacca cataaaggag
36901 gagggcggtg gccaggctcc gagctcctgc cgtcctgggt gggtggcttc tgtcctgcgt
36961 gccgccgggc agcccggggg tcctgcgcgc gggcgcggtc ggtggagctg caggggggcg
37021 ctctgggatg tctccaggca gagtagatac tgacccctcc gcagccggga ccctcaccct
37081 ttccttcatc actcaggaaa cagaaaaggc ttcagaagga gcggccatgc cccggcccta
37141 agcgctgcgt tcccggccca gcaggcctac cctgcacctg gcgttcctag gggcccctct
37201 gcgggaccca ctgcgcggct cgcagcggcc gcccgcctcc cacttcaccg gcacgctcgt
37261 tgcgtgtcga ggtgtgttga ctcctacagc aaagggcacg gatccgcggg tcagcaagcc
37321 cgacgaattt acaccaatga cccgccgtgt cgccagtctc agaccagggc acaacacgcc
37381 aaccctgcag accaccccca cctccccagc cactgcagac ccttccccct ctgcttctgc
37441 agcacctgtc ccgaaacacg ctcattcccg cccccgcaga ccttccctac ctcctggaga
37501 ccccccctcaa cccctgtaga gtcccctgcc cgtgcagaat cccctccccc ttcccccgca
37561 gccccccctac cccacccggc ggacagcccc gctcgcttcc tgttcttctc ccaagggaga
37621 cccctgtcct ggctctgact ggggttgagt tcgccagttt tgacttatgt gtagagtctt
37681 caccacgggc tggaagtacg gtnnnnnnnn nnnnnnnnnn nnnnnnnnnn nnnnnnnnnn
37741 nnnnnnnnnn nnnnnnnnnn nnnnnnnnnn nnnnnnnnnn nnnnnnnnnn nnnnnnnnnn
37801 nngagcgtac ttcagcccgg gtgaagattc cttacacctt atacaaaaat taattcaagt
37861 tggattaaag acttacatgt cagacctaaa accataaaat ccttagaaga aaacctaggc
37921 aataccattc aggacatagg catgggcaag gacttcatgt ctgaaacacc aaaagcaatg
37981 ggaacaaaag ccaaaataga caaatgggat ctaattaaac taaagagctt ctgcacagca
38041 aaagaaacta ccatcagagt gaacaggcaa cccacagaat gggagaaaat ttttgcacct
38101 actcatctga caaagggcta atatccagaa tctacaatga actcaaacaa atttacaagc
38161 aaaaaacaaa caaccccatc aaaaagtagg caaaggatat gaacagacac ttctcaaaag
38221 aagacattta tgcagccaaa aaacacatga aaaaatgctc atcatcactg gccatcagag
38281 aaatgcaaat caaaaccaca gtgagatgcc atctcacacc agttagaatg gcgatcatta
38341 aaaagtcagg aaacaacagg tgctggagag gatgtggaga aataggaaca cttttacact
38401 gttggtggga ctgtaaacta gttcaaccat tgtggaagtc agtgtggcaa ttcctcaagg
38461 atctagaact agaaatacca tttgacccag caatcccatt actgggtata tacccaaagg
38521 actataaatc atgctgctat aaagacacat gcacacgtag gtttattgtg gcactattcc
38581 caagagcaaa gacttggaac caacccaaat ttccaacaat gatagactgg attaagaaaa
38641 tgtggcacat atacaccatg gaatactatg cagccataaa aaatgatgag ttcatgtcct
38701 ttgtagggac atggatgaag ctggaaacta tcattctcag caaactattg caaggacaaa
38761 aaaccaaaca cctcatgttc tcactcatag gtgggaattg aacaatgaga acacatggac
38821 acaggaaggg gaacatcaca cactggcgcac tgttgtgggg tggggggctg ggggagggat
38881 agcattagga gatataccta atgctaaatg acgagttaat gggtgcagca caccaacatg
38941 gcacatgtat acatatgtaa ctgacctgca cgttgtgcac atgtacccta aaacttaaag
39001 tataataata aaaaaaaata aataaaaata aaaaataaaa gaaaatgaag aaaatcatgt
39061 catttgcagc aacatggatt tggctagagg accttatcct aggcaaacaa atacagaaac
39121 agaaaatcaa ataccacata ttctcactca taaggggggag gtaaacactg ggtactgatg
39181 gacataaaga tagcaacaat agacactggg gactattggg gtggtgaagg agggaaggga
39241 gaaagtgttg aaaaactgtt gagtactatt ctcagtatct gggtaatggg accattcata
39301 ccccaaacct caacatcaca caatataccc aggttacaaa cttgcacaag tgccctctga
39361 atctaaaata aaagttgaaa aagcaaaaat aaaacagtaa acaacaacaa caacaaaaca
39421 gcaaaaccct caataaatac ataaataaaa atataaataa atgtctttgc cagagctttt
39481 tgttttttgt gtggctttga gttagtatct ggggtcacgt tgcttttaag ctgtttgcta
39541 tcaactgcat cctatctaat atttcttttt cttaatagta aaccactcaa tttttgtgag

FIGURE 2 (cont.'d)

```
39601 gagatattac attgtggttt tgatttacat ttctctaatg atttcctttc cagtttggat
39661 gctgagcatt ttttcttatg ttttttgccc attcatatat aattttaaaa gaaatgtcta
39721 ttcaaatcct tttgccattt taaaatcata ttatttttaa atattgtgtt gtagaaatta
39781 tttatatatt ctggatatta actctttatc agatatataa tttactaata ttttcttcca
39841 tccacaagtt tttttaaca ttgttatgtc ctttaatgca taaaagtttt aaaaagtttg
39901 atgtagtccc aattgtctat tttttctttt gttgtctgta cttttggtgt catattaaaa
39961 aataattgcc atatcccctt attctaagag ttttatagtt ttagatcttc catttaagtt
40021 ttaaatccat tttgagttaa ttcttgtata tggcataaga caaagtttca acttcactct
40081 ttcatgtgtg gatatccaag tttcccaaca ctgtttgttg aagagaatgt tcttccctca
40141 ttgagcggat ctggaatgct gtaaatatta tttgaccata tatgtggagt tttcttttaa
40201 tgggttcttt attctattcc attggtctat atgtctctct ttaagccagt gtcatgctgt
40261 tttaattact gtagtcttgt aacatgtttt gagatcacgg agcatgagac cttcaactca
40321 gttagttttc aagattgtct agtcagagta tatatgaata tttagataaa tttttctctt
40381 ttttcaaaaa atgcagctta gatttgata gggattacat ataatttgta gactgctttg
40441 ggttctattg acttttcaaa ttaatacata atgttgtaca gatttgggga atacatctga
40501 tattttggag atcttaacat taaatcttcc aatccatgaa taccaatgtc tttacattta
40561 tttgtgactt ctttcagtac tgttttgtag ttttcagtgt acaagccttt tatttccctg
40621 gctaagttta ttcctaagta ttttactatt tttgatggta ttgtaattaa attattttct
40681 taattacctt tggattgttt atagttaatt tatagaaagg caactgattt ttgtgtgtcg
40741 attttggatc ctgcaacttt ccagaatttg tttaatagtt ccaacagttt tctggatttt
40801 atgcatatat gcatctaaca gttttctaga ttttatgcag gagtctagga ttttatgcat
40861 ataggatcaa gtcatctgtg agcagagata attttacttt tttcttttat tctttggatg
40921 tcttttcttg cttaattttt ttttcctaat tggtctgctt ggaaattcaa atactatatt
40981 gaatagaagc gaagagacag agtatacttg tcttgttcct aatccagaag aaaagtttga
41041 atcttttacc attgagtgta agtttacctg tggatttttc atatatggcc tttattatgt
41101 tattttcctt ctattcctag tttgctgagt gttttcgtga taaaaggtgt taaattttgt
41161 taaacatttt ttctacatca atataaatga tcatgctgtt ttgtccttta ttctattact
41221 atagtgtatt acattgattt ttgcatgttg tattattctt tttttttgag atgaaatctc
41281 attctgtcat tctggctgga gtgcagtggc atgacctcag ctcactgcaa catttgcctc
41341 ctgggttcaa gggattctcc tgtctcagcc tcccaaagtg ctgggattac aggcatgagc
41401 cagcacaccc tgccacatgt tctatcattc ttgcattcca ggaataaagc caacctgatc
41461 atcacaaata ttggtctgta gttttctttt catgtaatgt ctttgtttga ctttgaaatc
41521 agggtaatac tggcctcata taatgagctt tgaagtgttt tttatattca tttttgtaaa
41581 tgactttgag aaacattggt tctaattctt ccttaaatgt ttggtagtca tccggttctg
41641 ggctgttgtt tgtttggagg tttttgaacc agtttaatct ccttcgtagt tataagtctg
41701 ttcgtttttt ctacttcttc atgattcact cttattaggt tgtatatttc tagaaattta
41761 tgcacttcta aattatccaa tttgttgaca tataattaac tgttgatggt attttcttat
41821 aatcctttg atttctatgg catgggttct aatgttctct tttttatttc tgatttatta
41881 gttgaatctt ttttccttag ttaatctagc taagcatttg ttaattttgt tggtgttttc
41941 aaaaaccacc tcttagtttt gttgattttt ttctattgtt tttatattct atatttcatt
42001 tatctctgat ttaatctaat ctttaggatt ttcctccttc tgctagcttt gggtgtagtt
42061 ttttttctct cctagtttcc tgaggtataa agttaggttg ttgatttgca aactttcttc
42121 tacttctttt ttttttttc ttaagttgtg gagatggggt cttgctttgt tgcccaggct
42181 ggtctcaaat tcctggcctc cagaagttct cctccctcag cctgtcaaag tgctgggatt
42241 gcaggcatga cccaccatgc ctagccactt tcttcctttt ataatgcaca tatttatagc
42301 tataaaattc tctgttagca ctgcttctgc tgcatcttac acattttggt acattgtatt
42361 tttattttcc tttatctcaa gatattttct aacttccctt gtgatttctt ttttgaccca
42421 ttgcttgttg aaaactgtgt tgtttaattt tcacatattt gtgaattttt tgttttcctt
42481 ctgctactga tgtctagttt tatgtcattt tcatcaaaat agatattttg tataatttca
42541 atcttttaaa atttgttaca agttttttg tggtataaca tgtgatttat ctttgggaat
42601 attccatgta aacttgagaa aaatactatt ctgattttat tgggtggaat gttctgcaca
42661 tgtttgttag cactatttat agtgttgttc aagtactgta tttccttatc gattttctgt
42721 cttgttgttc tagccattat tgtaagtgag gaattgaagt cgcctaccat tattatgctg
42781 tttatgtttc ctctctgatc tgtcaatgtt tgcttcagat atttaggagc tctggtatta
42841 gaggtatata tatttgtaat tgttatatct ttctgctgaa ttgacttttt gttatataat
```

FIGURE 2 (cont.'d)

```
42901 atccattttt ttgtcttgtg actatttttg actttaagtc tattttgttg gatagtagta
42961 tagtcacttc tgcttgcttt tatttaccat ttgcatggca tttacttttc cttttttca
43021 ttttaagcat atttgtttct tagacctaaa tgacaggata aagttggatc ctttttacaa
43081 atccattttc cagtctatat cttttgattc aggagtttaa tccatttaca tttaaagtaa
43141 ttactgatag ggaaggacct acacttgcca ttttgttgtt tcctgtatgt tttgtaaatt
43201 ttgtttttta ttccttctct tactgacctc ttttgggttt tgtcgatttt tttttgtggt
43261 gacattttga ttcccttcct gtttcctttt gtgtgtattc tatagatttt tttatggtta
43321 ccataagaat tataaaaaac atcttaaagt gttaacaagc tattttaaac tgttaagaga
43381 ataacttcga ctgtgtacaa aaactatttc ttcaaagctc ctaccctcac cttaggttac
43441 ttatgtcaca agttacatct tcatatgtaa tgtattcatt aacacagttt tatagttatt
43501 tttaagcttt tgtcttgtaa attctataca agaattaaaa gtgcatttat gtaccaaaac
43561 tgcatagtac agtctctata tatgtccata tatttatctt tactggagag ctttatattt
43621 tcataagact tcatgttact atttagcatc cttttgtttc aacttgcaag atactacagc
43681 aggtccagtg gtaatgaact ccccagtttt tgttcatcct ggaaaggctg atttttcctt
43741 tatgtttgaa ggatggtttt gctggatata atatttttgg ttgaaatttt cttttctttc
43801 agctctttga atatattatc cccctgcctt ctggcctgca aggtttctgt tgataaatcc
43861 actgataatt ttataaaggc ttccttttac atgacaagtt actttctttt gctgcttca
43921 agattgtctc tttgtctttg acttttgaga gtttgattat agtgtgtctc actgtgagtc
43981 tctgggtttt ctttaacatt ttttttttgt tcatatcttc tgatgatgaa ttcctttaac
44041 ttttatattt gtgaaatgtt ttttcttcat tttcagaagg tatttttagt gagtgtaaaa
44101 ttctacattg acagtttttt tctttcagta ctgtttagtg tttctctact gtcttcttgc
44161 ttgtactgat tgtatagaaa ctctgctgta attcttatct ttgtgtcttt gtacttaatg
44221 tgccttttta ctctgcctgt ttttaagatt ttatttttat tattgatttt gatcatgtgg
44281 cttggtgtga gtttcttcat atttattgtg cttggggttc attgagctta ttaagtctgt
44341 aggtttatat ttttcattac atttagaaaa attgtagcca ttattcattc aaattttttt
44401 ctgttcttct cccatttctc atgcccttat ggggtctaat tatatgtata ttaggctatt
44461 tgaggttgtc ttacagctca cttacagttc ttatgtttat ttttccactt ctatttcatt
44521 tgggcaggtt tattatactt ttccctaatt tgctaatttt tttgcaatgt ctaatccact
44581 gttaatctca tccaatgtat tattaatttc agacattgta gttttcatct ctagaaattg
44641 ttcatctttt tatatcttct ttgtctctat ttgatatgct aagtcttttc tctagcttct
44701 tgagcatatg aaatatagtt atgacaacta ttttatttta ttacaacttt taccttaggt
44761 tcagaggtac atgtgcaggt ttgttatgta ggtaaactcg tgtcacagga gtttgtttat
44821 tatttcatca ctcaggtact aagcctagta cccaatagtt gtttttctgt tcctctccct
44881 tctcctaccc tccaacttca agtaggcccc agtgtttatt gttcctctct ttgtatcact
44941 actattttaa tgtctctact agttctctta ttttgtcat ttctgagttg attttatttt
45001 tctcactatg gccatattct cctacttctt tgaatatctg gtatgcaaat tatacctagt
45061 atggatatta tatcaagacc ctgtcgcaat atggatacct aaaagaaaat aacaatgttt
45121 accagtttgc tctaagcctt tcttagctct tttgcttgtt tctcaagaac aagcacagag
45181 ggtggagctc aaccaagact gaagttaaag atgtagaaag attgagatgg gaagtaatta
45241 agttgaggag ctctgataca atggtatttc tctttttaat catgtaagat gcaagcccaa
45301 gataatatgt tgggaaagtt gaaggcgaat gtcttgagaa atatgaaatg cacccaaggc
45361 tatggctggg tgatagaaat aactaaaaag ttttaaaagg attgttttat agctggtcct
45421 tgctgaggtt aggggatagg cctggaaaaa ttgagcagtg gtattgccca ggcaggactc
45481 ctcatgacat tctccagatc cctaagtttt tccaagtttc caagcatttc cttggccagc
45541 aagtcatctc gcagcacaga tcctactctc tttcagtcag tcattccaca actctacaaa
45601 gcatttttct ccatcaaatg ggaacttttg gggttctgca taatttttca gggttccacc
45661 acttttgact ctttctggat accttgtaag gatattataa ctctttaatt catgtccttg
45721 attttctctt ttaactttta atactgttca ttgcctgttt acctctttca ccctcttctt
45781 ttcacttccg ccctctttct tgtgtaagta tataatcatc cttttttct tcctcgaatc
45841 tcagttctcg ggagtaacat atacaattca ttcttacttc cagtctttta ttcctaagtt
45901 ccttatctct agttctcttg catatttgtg gcaattatta gttttttcc aaaaatccat
45961 tctccctttt tcctgtacat gtatctttcc agcttgacca catttcccag cttccctggc
46021 agctaggtga agcaatgtaa ctaaactttt gcctgtaaaa tatgagcaga agttatgtgc
46081 acaatatctg cctcacttgc ttaaaataaa ttgtattatt tgagctttct atattgtccc
46141 tttttacaac taaaatgtag aggttatggc aactttttatg gtaaagagaa tcatcacgta
```

FIGURE 2 (cont.'d)

```
46201 ggagatcaag aatcattgat ttgagaggaa cctaaatcct ttaatgactt agtggagcaa
46261 gactgcccca tcagtctgga agctacccca caacttatgt atatcttcag attgttgagc
46321 aaaagagaaa aaatgaagcc actatatatt taggtctctt catgttaaca gtttagcttt
46381 taacctaaca cacatttatt cctgaatggt agcatattat taacatcaca ggaagggaat
46441 tccttgttca tggatctttt attttgttga aataaaggta atctgcttgg gcttaatact
46501 gccaaggcag aattttttgg aataattatt tctatagatg acccattcat aatgacaact
46561 aacatggttt ctaaaatgga ttcatgtacg tcatcttatt tagtccccgc aaaaattctg
46621 aaggtaggta taattattcc cattctatat attgaaaaat tgggattcag agagactacg
46681 gacttataca agtttctgca gctatttaag aaacagagta aagtctcaaa gccattaatg
46741 aactgtttag tttagtgctg cttagtaaaa ttagaactgt ttgaagtgcg ttttaatagt
46801 aaacccatcg atatttagtc agctctctgc ttgctaacta atatggaaga aaaaacatac
46861 atctacgtac atcctgaatt gggagaaggg aaataaaata ttgccaatcc cctttcctgt
46921 attaggtact gtgataaggc gataaggctt ttcattatta taaatgagtc ctggagaggt
46981 taagcgcagt cacccaaagt cacatgacca gtaactttca gagattttac cccaggtctg
47041 gaaagactct gaagcccatg ttattgcctc cagagcctgg tggagaaccc ctgaatggga
47101 cagagactca gcagacagag tggtcctttc cttccaggga gtcagggaag gtttggtagg
47161 ggagatagag ttagatctgg gtgggatttg gatgaaatga gatcaagcag ggataaataa
47221 gatccaagct gtttatgagg gacagggaga ggccagctct gttagaaaga gtggtttata
47281 cagagaagca tggaaacatt tgctccatgc ctcgccttcc atggatagca gtccagaaat
47341 gctacttgcc tgcctgacag tctttctcca gtccccaggt gtggacacgt tctgagcacc
47401 tgagcctggg tctgccctga cccagattct gtgagctggg acagagaatg tgtcctgctg
47461 tccctcctcc cccacttggg cccacaccct tttctacaca tttggattag aaatctgaat
47521 tggcctttct gtgaacccca atgacaggca agtccccagt aaagaagcac ttaatttaat
47581 tgctccttca gggtccactt agagtaatag ttgtgaacag ctctccctag tgtctcccac
47641 aggcagtgac aaatgttgct aaagataagt cacaaattct tggcaaggcc atcttaaata
47701 tgggaaggaa accttgttca gtcctgaaca gtcctgttca gactgatctt atcacaggtt
47761 gcacactgcc tcaatgtcac catgtttcta ccctcagttg tgcttggcag agagaggaca
47821 gctatacata aagtctgttc actctacaaa ggtgaaatca ttttttttaa ggtaattatg
47881 attgttctga ggatggtgat tgagtgacat ttaaaaaatg ggaaaagttc tactcataac
47941 tctgtctgct taatttgctt atataaaaga cttaatggtt tttgttgagt tgatccagag
48001 tcagtaacat ttgaatatgt gttattacca tttgatcagt aacaaaacaa cagggtaagt
48061 gggatgccaa atgtggctga gagtttaggg tttacattcc acaccccagc cttaaatacg
48121 tttgtataaa ttattggttg atttttcttt ttcatggctt ttctttgaca tttgatgggg
48181 ctggatttat ggaggcaacc aacaaattac acagcaatga attctggact gtagtcccac
48241 agccttgagc ctagatacta gctgtgtcac taatactctg tgtgaccagg gtaagttatt
48301 tagatacatt tatgactttc caaatcaata ggttggacaa agttatcttc aaaatgtctt
48361 tcagatttga ccctgaacat atgcgattct ggcatgttct gatttttagt tttctgttct
48421 tgaagcatgt ctacaataga aatgcctacc ttcatataca ataaaaggac attagattaa
48481 tatggtgtct gtgaaaatca ttgaacagct ttagagataa aaataatgaa atgagtcaag
48541 ttctccatta ttaattaaat cttttaaatt ttctgtttat gaaactatga acaataaatt
48601 ggaacaaaga tataatctca ctacaagtaa attgtatttt atgtaaaata taatttgtct
48661 ttagaaaata ctcaatgaaa ttaccttttt aatttcagag attttgagga ctattattgt
48721 tatttcttta aagtgataaa tgtaatccaa gatgcctttt ttcccccttc agaagcttga
48781 gtgcccaagg gtttgataaa tgtggaaaat aaccgctgtt cgaatatcct gttggcctgc
48841 tggtgagatg tcatcgtgtt gtctgaatgc agtatgtgtt taaacttgcc atttattacc
48901 tgaaattgtg ttattttgcc tcataccctt agtaatactc ttgtaatgct ggctgagaat
48961 tgaagcaaat gccctatgaa actcaaggga gcaaggtctt tgttattttt cagaagaaat
49021 gactggctga ggctgtaaag aaatcttgtg gtcattctca tggaaagagg attggagccc
49081 cgattctttg atctcattat tgaccagttg attgagaaga ctgtcctcct gtccccaccc
49141 aatcacaata agtgggtaat tacctgaggg ctaatttgct ccttgaatgt gaatacattt
49201 gtggaaattt ccttgtgctc agcacctgtt caaaacatcc atttgtattg cagagctatt
49261 gtttttctaa tctcattgtg gagctaagag agagattgtg tttaaggttt ccttcgtaat
49321 aggttttctt gctccaggaa ggatgcgtga cagactctgc acactgctgc ttggtaggtg
49381 ttcagtgatg gatgcgtttt ccatctccca ggtacagctg cagctgtgct gactctggtg
49441 cgtttgtaat atgcactgtg gagtgcacca tgatttcatg atggctggag aaatctggtg
```

FIGURE 2 (cont.'d)

```
49501 gctagaattc tagggaggag gacatgagtc ggaagtgcag aaacctcaca ctgggacatt
49561 gatggagaaa atccaattct gtccctggag ttaaagagga gtcactcact gggccatcat
49621 aagagcaaat aaagttacag ttatttcttc agatccacaa ctcaaactca gcgaaagtaa
49681 ttattcactc tttttgtccc aaacaataat gaaatcagct aaagcatatt gtatttatta
49741 cttccactca agttattgag ctgttctgac accttgttgc tgggaagata cacagatgga
49801 acaccatcat ttccattgat tctgatcata ccccacgcta atatagcctt attgctctga
49861 gtcataggga ttttatgctt gcctattcaa aaaacagttt ttaccttatt aaaaggtgat
49921 atgacctgag ctggagatga tgtttggtca ttttgtgtaa accttttaat attttagtgg
49981 taaatacatt tcttgaatct tgacaaaaac ataattaaaa tgaacatatt taaaatggac
50041 atcttccaaa tgttcatttt taaaacaaac atcttccaaa tgttcatttt taaaatgaat
50101 atcttcgtta actttttttt ttttttttga gacggagtct cgctctgtca cccaggctgg
50161 agtgcagtgg cgcgatctcg gctcactgca agctccgcct cccgggttca cgccattctc
50221 ctgcctcagc ctccagagta gctaggacta caggcgcccg ccaccacgcc cggctaattt
50281 ttgtattttt agtagagacg gggtttcacc gtgttagcca ggaaggtctc gatctcctga
50341 ccttctgatc caccctccac ggcctcccaa agtgctggga ttacaggcgt gagtcaccac
50401 gcccagcctc ttccttaact tttaatgaat aaagagttga aagggaaaaa ccaaatgtgc
50461 actatgctga ttttatcttg agctgtacag aatgtgcagt aacttaagaa tataagtcat
50521 tctgctgtta ttcatactag cctattcttt agcattattt aaacacacat atttgagtgt
50581 ctacacactg cctgctaggc aggggggctgg gtgccaagaa gggatgtcca gagataaacg
50641 ggcatatgtg ttaatctttt agggcacagt ccagtaacct gatcaaggag tgacgtgtat
50701 tgtgtactag gatagaagtc agtatcagag gaaacacaaa ggaaagagtg gtactttctc
50761 cccagggaag ggatgctcag aaagaggggg ctgattatgt ccctggttca tgagaaaaag
50821 ggcattcctg gctcagggag tgggaagaac aaaaccaaga aatcctggaa tggcttggtg
50881 catcagccag tctgtgagtg cagggcatgg ctggagttct ggctttaaga tgagtgggaa
50941 gaaaggctgg agaggaggtg gatccaggaa aagttgctgg gagcatttat tcttttggca
51001 atgggaagcc atggaagaac tgttgtaagg aggattctgt gtgatacatc tgccttttag
51061 agaggtcatt ttatagaaaa agtagaaaat acagaccagc aaaaatttaa aaagtgaaaa
51121 caatcactgt tcaagctctg gtctagcact caccagtgtt tttcctacag gtgcatatac
51181 aaacatgctt ttacatttta tttttatttt aaatttttca ctatcctcaa tatcagtgga
51241 aacaaatctg ctttttttaat tttttttttta aaaatgagat cctattgtac acattatttt
51301 aaattttttt tcattctttc cttttttttaa aattaaaaca attttttttg agacagtctc
51361 actctgtcgc ccaggctaga gtgcagcatc gtggtctcag ctcaccgaaa ccttgcctcc
51421 caggttcaag cgattctcct gcctcagcct tccaagtagc tgggattaca gacatccacc
51481 accaccgtgt caggttaatt tttgtatttt tagtagagaa tggggtttca ccattttgga
51541 caggctggtc ttgaattccg cggatccttc tatagtgtca cctaaatgtc gacggccagg
51601 cnnnnnnnnn nnnnnnnnnn nnnnnnnnnn nnnnnnnnnn nnnnnnnnnn nnnnnnnnnn
51661 nnnnnnnnnn nnnnnnnnnn nnnnnnnnnn nnnnnnnnnn nagcgtattc gcccgtggtg
51721 aagatcgtag tagagtctac cacctcggcc gtgaacctgg ctcagggggc gcagccgggg
51781 tgggcgaccc agccaggtct gcggagcggt gcccggcggc aaccccctca cggacgctgg
51841 gactccccca ccccgtcccc attcagcgct agcggtggag gggccaggcc cgccccaggt
51901 agtcaggcag gggtcccggc tcctccccca ggaccaccgc cccgcgggcg ctcacgtcct
51961 gatggcttcc cacaccagga gcccgtcgtc ccggtagaag tagtagggga tgtcttcttt
52021 gctctccatg ccccgggcct tgatggcctc gggaaagcac agggaggcat aggtcaggtc
52081 cttcatggcc ctctgcacca tctgcacgtg cccaccgccc cctgtggcgt tggcctggag
52141 tgggaggtag agtgccctga gcgggtggct cctcccacag ctgtccagac ccatccctga
52201 ggaaatgtgc caggggaggc gaggaggcca ggcaggcaga ggtgcaagcc cttgtcctgt
52261 gagatggggg agggatgttt aacgcagaga atgacaaggg cagccgggtg gagaggtgct
52321 agggaggagc ctcccgccca atccaatgca agggactgaa ccgtggggct gcagagtaca
52381 agagggaagg gtgcgctccc agccacagga gggcagcagg cgtgggcagg tgtgtggggg
52441 accccagcac cagcgggcct gggctgtgaa gtctgctcta gtgctgagca cacgaccctc
52501 agtcattgct ctcagtgacc ctcagtttcc aggacccatg caactctgtt gagggcctgt
52561 tgtgtgctca ggtgagggct ggagagaccc acaaggaggg atcctggtcc tgatcccgat
52621 cccggcttct gagtgatgca gacacactca caagctcact ggcacatatg tgtgtccacg
52681 tgcacacaca cacatgcaaa tacacccagg gggctgggct gtcggtgcca cagaggtttt
52741 gaagaaggac ttgggtgctg gggtgccaga gattggtcca cggtgggcat tcagcccaag
```

FIGURE 2 (cont.'d)

```
52801 caggaccaac cagagctgcc ccccagcact ttctgtttag atgcggctgg gagataatgg
52861 ccacatgaga acctgaggtg gagctactat gatgagctcc tgtgccctct cccatggggg
52921 cctgtctgca gcaggagagt gtgatgccaa cacaggtgaa agagacagaa agagggagcc
52981 agtgtgcatg caccctgggg cattgcttga gtccctggat ccatttctgg ctgaggcccc
53041 cgaccctcta ttgtgtccag gtatttgaga taaggcatgt cttgtccagc tgcagctggt
53101 ttgagttggg ttttgtcatt tgcagcccaa acagtgtctc aacttcagtg gtcatctggc
53161 ctggtcacta atgggctggg gaaaggagga aggttggggc aagggcccat gtgagagtcc
53221 aagcttggta aggctacaga gggctcaaaa cgaggtgggg tgctacctga gggatgcgag
53281 ggctgggcag ggcctggagt ccccgatgca ggagacagtg ggttgggagg gttgggaccc
53341 gggaagcaga gtgctgggga ggtccaggtc agggtggcag gggtgtggca gattaagagg
53401 cagacacagg ttcctggtgc gtaggaggtc agggggccat aaggagtgtg ttccagaggg
53461 gggtctacac ccaggtccca gaggctggga gaggggaggg gtgggaggag gggaccagga
53521 gccatcagtg agaaggaaga cctggtggtg cgcctggagg agtgctcctg gctgaatggc
53581 acgggctgga gacatcagga ggatgctgga gccagtgctc tgagcagact ccagccttca
53641 cccttccagg cctcctgaaa gggtgtctag atctcagata gggagtgaag gcggccaggc
53701 tgggctcttc caggcaacaa gtagggtagg agggcaccca ccttgtcaaa gaggccacac
53761 tcgcagatga gctgctcacg ggccttggtg ttgattgcaa tggtgaatct cacgtgtgcc
53821 accagcagct ggggagggga gaggaggagg cctcagaggg ggcccagtca ggtgacctgg
53881 tgcctcaggg acccgcagct cccccaccca ggcctgccct ataggatgat gctgggcgca
53941 gggaggaagt gaaggctggg tgctgatctt tctgctgaat aagtgctgga ggcctgcacc
54001 cctctgatgc ttactaagca tgataatgat tcagagggtc ctggccagca cttgtacaat
54061 gcttacctct ttgctccctg agttcactgt cttaatctga ccatcattct gtaaggcagc
54121 tgtactattt gacctgtttt actggtgagg aaactgaggc acatgggtac ttttagcatg
54181 cagtcacccc agcagccaat gcttgtagga ttcgagaaca gggacggaga gtgatggcag
54241 gggcggccat cagcatcagc cgaggatcac catgaactca tttgcctttt ccaactctac
54301 tggctggcca gcgaggcccg tgtgtcaggc ccatgcccca gccgcgtgtc ctggggaaca
54361 gcaggctcct agctgttttc ttcctttagg ggcattactg actctgagaa catctctcca
54421 gggctccctt tctgccaccc actcccagcc acaggtcccc ctgtgggatg tcagtgatcc
54481 ctcccactcc acatctcaga tgccctccca tagcaggtgg ggcggtagct ggctgtacct
54541 tgaaaatggg gtgcacagca ggcagctggc ggtacattgc aatgccaaaa acctcagaca
54601 ccagatgtgt tcgcagaagg tgggtgatgg tctggtggac gtggaagtca ctggaacgca
54661 cccagatttt ggccaaaagc cagtcgtatt ttgcatccga agggaggaaa atagggttct
54721 catctcccgg gatttggttg agctgataca ttgggggaaa ggaaacacac tgctatattt
54781 cacttcagag tatagttgtt ggagaacttc gcctcttggg aagttccaga agtatctgaa
54841 tttctttaac agtgactttg gaatcagaag agcctggagg gggtaaaggg ccctgcggtg
54901 gtatttcctg tcccagccat attacttaca acctgcatga ctctggatga cacactgggc
54961 tttctaagct ccggcttcag catctgtcat gtggggacag tgatcgctcg gctcacagtt
55021 actcaggagc tggcagcatg gaaggagcgg gcaggccgaa ggcccagcag cggaggggga
55081 ggatcgctgt ccccctcttc cctccttgcc ctgctccctc ttctactgcc tctccttggt
55141 ctctcatact ttcctccctc tcctcttccc tgaaatgctg gagctcccca gggtctgcca
55201 tggtgctcct gtcttctttt cttgccctaa gtcagctcct cctgtttaaa ggcttggggc
55261 cctcctggta ctgagcctcc cagatcaggg tctgcagctt gagctctgcc tggagcccac
55321 acctgtggcc aggcacctcc tgtagcagag gctggacctg tcttcccttt ccagtttcca
55381 ctccacactg ggacaaggtg agttttttc ttttccaaaa tgcaaatcat gtcatgttaa
55441 ctgcctcctc aatcacctct taatgccaga aaataaaatc cccaagctct gtggtgacct
55501 ggttgctgat gcctctgtac acacagcctc actttcgtgc ccccacacca gcacccagcc
55561 ccaggtccct ccatgccagc agccctgcac gttgcccccct tattgagagc ccagcacagc
55621 ctcagcaccc gacagtgagt tctcacggga gccggcagca ggtgctggca ttgcccattt
55681 ttacatgaag acatggggta ttggaggggt tgacagaaag aatgaggtgg gtggcagggc
55741 tgcagccaag agcggccagg aaggggcatg gccagacttt aggtgctggg aaagaccagt
55801 gtcactgcag cacagtggtc atggctgggg agggagaact gtcccagagc acacagctgt
55861 gtcacttgct ataagtattg tggaaggtgg ggtccttggg cgtctctccc tcgaaaacag
55921 tgctgtccaa tagacatata atgctacccc acacatggaa ttgtatatat tcaggaagcc
55981 atattaataa aaataaaagg aaacaggtga aatgccggtg aataatataa ttttatttta
56041 cccaatatat ccagaatatt atcacttcaa catgaaacca atctaaaact attaaatgag
```

FIGURE 2 (cont.'d)

56101 atatttcaca ttccccacct ccttattcta agtcttaaaa atcaggtgtg aactttgcac
56161 ttgcagcagg ttttggtttg gacgagccaa atcccaagtg ctccagagcc ctggtggcca
56221 gtggctccac cctggtcaga gagaccccag aagcctcagc actccctgag gaccaaggag
56281 gggggaggga ggagggagag cagagtgtga cttgcacatt aggcgtgcct gtctgtttat
56341 acttgagatt agttggctgc ttttaaatac cagacagttt cacataaaaa tttgaatgac
56401 ctggttttct tgaaaaatta gaaggtctca gaactctgca cccaggttct cacagaacta
56461 cgctcttgtc ccttttacag agtcccagct ctcagggtcc ccactgccac acccgtttgc
56521 atgagatgcc tgggccactg atacctgatc tgtgccctag aatgctgggc tgcctggcat
56581 gctctgagac actttctgac atgtccccac atgctctgac atgttcctga tggctctggg
56641 acactgacat gttcctgatg gctctgggac actgacatgt tcctgacatc ctctggggcc
56701 gaggagcccc cctgttgtgt gctaggggct ttacccatgc tatctcactt aatcctcact
56761 ttgaccctgc aaggcagata ttccttgctg tacccatttt acatgggggg aaactgaggc
56821 tccagctggt ttagcagctc tcccaagtca cacagtaggt aaagagctca gccggcaaca
56881 tgatattgaa caggcaaaaa ttggaagcaa tccccctaaa aactggaaca agacaaggat
56941 gtccactctc acccctccta ttcaatagag tactggaagt cctagtcaga gcaattaggc
57001 aagagaaaga aataaaagcg atccaaatga aaaaaaaaaa aagaggaagt caaattatct
57061 ttgttcatcc atgatatgat tctataccta gaaaaccctg aagattcctc caaaagactc
57121 ctagacttga taaacaactt cagtaaagtc tcaatgttat aagtaaaatg cttgtttaga
57181 aacagaatgc ttgttcctcg gtactgcaag gaaaaatcag catttagaca aaaagttttt
57241 ttagcaagcc aattttactt tctgcagaaa gggtgctcct cgcagatgga acaatggcga
57301 gagcacacct gaataatgga gagaagcaat ttttattcct tacgcagctt gtccctgcta
57361 ccgtgtcctg tctccattgg ctggagccaa acctcacagt ctaaactaaa acccgactgg
57421 ctaataactt aaaacttttc taaataggta aaagcagtgg aaagacaaag gaaaagagga
57481 agttgcttat gaaaggactt agaaaagtaa taacatttcc aaataaggaa ggggcatggg
57541 ctgcaagctg ggacatgcct gtgagcacgt ccagcacaaa tatcttggtt aaagtacaag
57601 gacatagaat gtactcattc ccttatatct aacagctaca tatgataggg cttaacaaaa
57661 agttattagc acaaagcgaa aaggcttaaa aaaagttagt ctttagaaaa aactattatt
57721 tctaacacat aatttactcc ttaacaaaaa aaaaactttt gactttctac actcaagata
57781 caaaatcagt gtacaaaaat cagtagcatt tctttttatt tgagacggag tctcactatc
57841 acccaggctg gagtgcagtg gtgtgatcgc agctcactgc aacctccgcc tcccaggttc
57901 aagcaattct cctgcctcag cctcccaagt agctgggatt acaggcaggt gttaccacac
57961 ctggctaatt tttgtatttt taattgagac ggggtttcac catgttggtc aggctggtct
58021 caaactcctg acctcaggtg atctgcccac ctcggcctcc caaagtgctg ggattacagg
58081 cgtgagccac tgtgcctggc ctaaaaatca gtagcatttc tatgcaccaa caatgttcag
58141 gttcaggctg agaaccatat caggaacgtg gtgatctcag ttacaatagt cccccataca
58201 caaaataaaa taccaaagaa tgtatccagc caaggaggtg aaagagctct acagagagaa
58261 ctataaaaca ctgatgaaag aaatcataga tgacacaaaa aaatggaaaa acatcccagc
58321 taatgggttg gaagaaagca atctacagat acaacacaat tcctatcaaa ttatcaacat
58381 catttttcac agaattagaa aaaaaaatcc taaaattcat atggaaccaa aaaatagccg
58441 aatagccaaa gcaatcctag gcaaaaatac aaagctggag gcatcacatt acctgacttc
58501 aaactatact acaagactac agtaacaaaa acagcatggt atactggtac aaaaataggc
58561 acagagatca atggaacaga acagagaacc cagaaataaa gccatatacc tgcaaccaac
58621 tgatttttga caaaatcaac aaaaataaac aataaggaaa ggacatccta ttcaataaat
58681 agtgttggaa aaactggcta cctatatgca gaagaatgac gctgggcccc tacctctcac
58741 catatacaaa aattacctct agatggatta cagacttaaa tgtaagactt caaactttaa
58801 acattctaga agaaaaccta ggaaaaaatc ttatggacat ttcctaggca aagaatttat
58861 gactagacct caaaggcata tgcaacaaaa acaaaaattg acaaatgaga cttaatcaaa
58921 ttaaagagct tctgcacagc aaaacaaact atcaacaaag taaacagaca acctacagaa
58981 tgagagaaaa tatttgcaac tatgcatcca caaacgacta atacccagaa tctatgagga
59041 acttaagaaa aaacaccacc attaaaaagt gggcaaagga caggaacaga cacttctcaa
59101 aagaagacat acaagtggcc aacaaacata tgaaaaaatg cccaacatca ctaatcatca
59161 gagaaatgca aattaaaacc acaaagggat accagtcaga atggctatta ttaaaaagta
59221 aaaaaatgac agatgttggc aggatgcaga caaaagggaa tgcttacaca ctgttggtgg
59281 cagtgtaaat tacttccatc cctgtggaaa gcagtttgga gattttgcaa agaactgcaa
59341 atagaattac cagttgaccc aacaacccca ttactgtgta cctacccaaa ggaaaagaaa

FIGURE 2 (cont.'d)

```
59401 ttgttttacc aaaaggacat aggcacacat atgtttattg cagcactgtt cacaatatca
59461 aaatcatgta atcaacctag gtgcccatca atagtggcac cagataaaga aaatgtgata
59521 catgtactcc aaggaatact acatagccat aaaaaagaat gaaatcgtgt tctttgcagc
59581 aacatggatg cagcttagga ttggcactta agccataatc ttaagtgaat taacccagaa
59641 acagaaaatc gaatactgca tgttcttatt tataagtggg agctaagcat tgtgtacaca
59701 tgggcataaa agtgggaaca aaagacactg gggactccag gaaggggagg gagggaggaa
59761 agggttgaaa aactgggtat tgggtactat gctcagtatt tgagtgatgg gttcaataga
59821 agcctaaccc cagcattatg caatataacc atgtaacaaa cctgcacatg tacctgaatc
59881 taaaatttta tatattaaaa aaaaaaaaac tgttctgacc agtaaaaaaa gagctgaatg
59941 aggatgggcc cagtgctctg cctatttcag cccatcactc tcccttctgc ttctcttcac
60001 ctcccggcct gaccgggcct cacctgccca tctccttgag ctcttgtacc actgagctgg
60061 gccttcccca acccatcctt cacatcctcc cactcctgtc caggattttg gcctgccatg
60121 ggatgccaga acttgccctg agcaatttgt gtttcttaaa tttgtttttt gggtaaggaa
60181 gtagctttgc gtttctgatt agaaaagaat atgtgcttat cgtaaaaaga aatctgagtc
60241 atgacaggag agcctgagaa agaaaacatc atctcatctt ccagcgccca gggataacca
60301 ccaaattctg ggagcctcc tttcataggt ctttgcatgt gtgcacattt atctgtccaa
60361 ttttccatca actgaatatg attataatca acatctgtct ctttgttttg ctcacctgtc
60421 ccccactggg ccatcactgt gttcctacct ggtgacactg cgtccttgtg tccccatgct
60481 ggcacagtag gcctgctgca tccttgcatt cattttacat aagtgagacc atgcccattg
60541 ccttagcagt ttgaaggagc tatttgtata cgacagatat gtatccttta tcggtccctt
60601 gtgtcttgtt tttccactgt taactcattg tggagacccc tccaggtcag ctggaaggga
60661 accaaagcat tcctttcaaa gacgcctcaa cattttatgg tgaggacatg gaagggctca
60721 ctcactcaat cctcttctgc cttcagactg ttttcaattt ttttccccat cacaaactat
60781 gctcctgttg ctacccacac acatttgtgc tttcatttct gctgagtggc tgctagcgaa
60841 ggctgagcct tgggggtttg ggtatgtttt cgagtagaca gtgcctgccc tactgttcct
60901 cagacagttt cactctcctg gtgcacacct gttcagtgct actggctgtc agaacactta
60961 aacaataaag tcccctccag tgctcctcca attgagacgg ggcaggggcc tcctcttagg
61021 gcactgtagc cccccagccc cgcaacaggg catggaaatg aaggaaaatc ccgagttcct
61081 tgaagggaag ttccaggcac ctagctagcc ctgagaaata aatgagcaac ttgacaaaca
61141 agagggtaac agcagcctaa aacaacagcc aaggaagcca gagtcctggg ctgtttggtt
61201 ccctctggaa actaaagaga acccctgaac atgtgtctct gagttgtttt tcagaaaccc
61261 agacccccac caaaccgatc cactggcaca gagacctcag ataagacgga actgaggact
61321 gaactctgag caggctcttt gttctaaatt tcttcctggg gggcctgggg gaagtcccgc
61381 ccacaagcca cagctaacat tcctttctgg taacccaaat ttttaaatga aacttctctt
61441 ccttaaccaa tttcaaaaca acaaattttt gaatctacct atgacctgga agcccacccc
61501 cacttcaaga tatcccgccc ttttaggcca aaaccaatgt gtaccctcca tgtattgatt
61561 aatgattttg cctgttaact tctgcaattc ctgaaattca ctctgccttt aaaaaccctt
61621 acctgcaagc catcagggag ttccggtctt aagagtgagc tgcccaattc tcctttttttg
61681 gtccccgcaa taaatgcctt gtgttctcgt agattatatc ccaatctcag tgtttggttt
61741 tgctgcactg ggcaagcaga tcccagtcca gctcggtaac acaactgtcc tcgccacgac
61801 agcctcaacc ccaggacccct ctgaccgccc actgcaacat gcacctggta cagcaggcgc
61861 tgtgggatct gctccggtgc tggccgaagc tctgaccttg ctccggtgct ggccgaagct
61921 ctgaccttgg gctgcccagg cccaccagtt atcccgtgaa cactgccagg ctgcaacaac
61981 tcatgagcag agcatggggc tccgtccttg ctggtgtctg ggagttaccc ctttgttttt
62041 ccaaccaggc atgtcagaaa tgatatctca ttgttaactt tcatttgcat ttctctaact
62101 acaggtgaag ttaggagttt ttccatatgc tggttgccca tttacatttc ttcttttgtg
62161 aattgcctat tcatattctc tgctcatttt tccactggag tattggtatt ttcccgtcaa
62221 tgtaaaggag ctacctgtgt atcatagata ggcatctctt agctgtcact tctgttatgg
62281 ttactcaccc taatctctgt tttgcttttt ggctttgttt atggtttatc actcaagttt
62341 taaaacatta cataatcaaa tatgcttagc tttcccctta taacttcttg gtttcctttt
62401 ccttctaaaa gtcttctgag tgtctgcgta attagttttt ctaaattcgt ttactttttt
62461 cattttaatt tttacttcat ctgaattttt tctttttctt ctaagcaact cctctacatg
62521 atgagattta tttttgtaaa tggcatgaca gagcagtcca atttaatttt cttctcatgc
62581 aaaggcagtg tgatagcatc attaaaataa tatccctttt tcactgagtt gaaaaacctc
62641 cattgtgata cactgaattc ctctgtgggg gagtccattt ctggatctta ctctatactg
```

FIGURE 2 (cont.'d)

```
62701 tcccccaatt ctctctgttt tcaagcacag tgtctgctta acagtaacct tacaaatcca
62761 gcaaggaaag tgttccttct gtgttttctt ttactttttt tttttttttt aaagataggg
62821 tcttactctg ttgcccagtg tggagtgcag tggagcgacc atggctcact gcagcctcaa
62881 actcctggac tcaagccatc ctcccacctc agcctcctga gcagttggga ttacaggcat
62941 gcgccaccat acctaatttt ttctattaat tttttttttt tttaagacat gaggtctcac
63001 ttggttgccc tgcctctcta tgtggtttta atttttttca aaaaattttt gactatgcta
63061 gatttctttt tccatatgaa tctttcaatt ttttaattgt tttctctcct ttttagttcc
63121 tcttcaccac caccacaccc ccaccaagaa agataaaaaa ttctggctga aattttactt
63181 ggaagtgcat taagttttta taatagaatt tggtagaact gacattttta cagtttcctc
63241 cccaatatca aatcactgtt aagagttcat tgtatatcct ttaaaataac tttatagttg
63301 gccgggtgcg gtagctcacg cctgtaatgc caacactttg ggaggctgag gcaggcaaat
63361 cacaaggtca ggagttcgag accagcctgg ccaacatggt gaaatgccgt ctctactaaa
63421 aatacaaaaa attagctggg cgtggtggca ggtgcctgta atcccagcta ctcgggaggc
63481 tgaggcagga gaattgcttg aacctgggag gtggaggttg cagtgagccg agatcacgcc
63541 actgcactct agcctgggtg acagtgcgaa actccatctc aaataaataa ataaataaat
63601 aaataaataa ataaataaat aactttatag tttttcctta tatgggcatt atattttatt
63661 gttagtatgg agaaaggcta ttgatttttt tgagaaatat atttatctaa acactttgcc
63721 aaatgaattt attaatctag tagcttttaa aaaaattaga atctcttgtg ttttctaggt
63781 ctaccatagc attaccagaa aagatcatct tccctgttct ttgacaatat gtttattgat
63841 tgttttcctg ttttatcatg tggtatgacc tctaaaataa tgttgaataa aaacagtgat
63901 atcagcattc ttattatttt aatggaaatg gcattagagt tgcacctttt tgatgttagc
63961 tatctttatc atataaagta aggttcctcc tattaatttt tattagttgt ggctattaaa
64021 tgttattaaa ttcccttttta gtgtgaattg atataatcat aaactttatc cttatgggta
64081 taataaatta tggtggtagc tctcttgata ttgaaatatc tggaataaac cctgcttggt
64141 tattacatat agtcatttaa tacactgctg cactcacttc gctaatatca cctttagttt
64201 tcttttaaat ctttatttaa tacttggatt ggtcttcagc cttcttttga agcctgcctg
64261 tatccagttt cagaactaag cttacaccag ctttatatga tcaatttggg gctgataaag
64321 agccctggaa atgtcagctg tctagtggct gggtgagact cagctgctcg ctgtgtaggt
64381 ctgtttccaa tcactatatg gaaattggcc tattttctac aatttcttct aatttatctt
64441 ttcctaggtt tttatccatt tctctaattt ttcaaatttt tgccatatta ctctcattta
64501 aaaaatatgt aatcataatt actgttcttt tttttttta agagacgggg tcttgatatg
64561 ttgctcaggc tagactgctg tggctattca caggtgtgat catagcacac tacagcctca
64621 agtgagcctc ctgcctcagc ctctcaagta gctgggacta cagttgtgta ccaccatggt
64681 gcctggctat aattactctt tttatgattc cttttttatt ccgaatcttg cattttttttt
64741 ttctatctct tttttccat cagcctcatg aggaggttat tattattatt ttttggacct
64801 ttcaaagaac cagatcttgg atttactatc ctctggcttt catttgcttg agtctttata
64861 gtttgcaaag tttccatttt cagaagaaga aagagaccca ggaacattct gtggcttgct
64921 caaggtccca cagcctgcta gcaagtggct gaactggaat ttaagctagg cccctgactc
64981 caggctgctc caagagatct ctgagccaag cttttgaagg caccatcagt ggtgcctggg
65041 atctccgggg atctcccagc aattttgtct tcttttaggt cacctgtccc tttacctgct
65101 gcttcagttt cttaggcaca gggcttctct ctggtaacag acaggaagct cctctgaggc
65161 tacgtgcccc tgggagactg tggggaggct ggaatctaga gtcagatgac ctggcttgaa
65221 tcctagctct gtggctggct gtgggcacct gtgtctcagt tttcttatct gggtaaaatg
65281 atcaacatca atagagccca ctacctagga tggttgtggt gatgattaca caaataaaga
65341 taggttatct aaaaccccag tggtcaaatg tgcttcagaa tccagaattt ttaggatttt
65401 agcagtgggt atacttcatt atgtgccata ccccctccca cccccagtct agggcaacat
65461 actattttac aatcgaacag agcagtattt ctgcagtgat ccacatacat atcacattga
65521 atggaaaaag cctctaaata acctcaccta ttgcttcaaa gaaggtttgt ttacaaacaa
65581 tgaatttgct gcacagtttt gaaatatgca gcagttttca gattttttag atttagaatc
65641 gagggtaagg gattgcggac tgtgcaggtt aacccatagg atagccttgg catgtggctg
65701 gtgcctgacc tatccagctg ctattgtgtc cacagctccc aaggtccagt tcatggacat
65761 tatttgctga atgctcatct gccagtctcc cacggtgtcc tctgcgcagt tcctccctac
65821 tcccagggac ctatgcccag tccagtcctg gccttggccc ctgctgtctg cacaccagct
65881 cccagcctgg cagcaggctg gtgccaggaa caggggggaga caaagccctg tgcccgcctg
65941 cctttcctcc agggtctccc tcttcctcct gcctcatctc cggtggacat aagaactcac
```

FIGURE 2 (cont.'d)

```
66001 atcatcatca aaggtggcat accaggactg gcctggttcc tgaccccaga acccatggtg
66061 cccctcagtg gtcttggtct ccagcttagt ccacagcttc acctgcctgg cccctggcag
66121 caccttgact gggggccctt ggtcagggtg ctggggtgga gagtgcagaa tatgatccca
66181 gggcaggtcc tccacagtgt gcctcgactg gccaggggct tctcaagtgt gccttgggga
66241 gtagaaccct ctccgcccct atggacagcc cacctcaggg cctgcaggaa gccctagtgt
66301 ctttcaagac atagcttcct cagctggagt gtgaatggag ccacccagga gccctggatc
66361 gcagaggact gagctgctca gaaaggtgtg ccccccagca gcctacctgg atggcaatgg
66421 ggacaatctt gttggccagg ttcttataca gcaagcagat gggagcggcc aggaactgga
66481 gtgtgcaggg gtctgttttg ttggcatcga tgccatccag cagctcaaag tccacgatga
66541 aaatgttccc ttgctgcagg aggcagagag atgtgtccaa atcaggctca gcagacggac
66601 caaaaatcag gcctggggaa agagtgatga cctctgggca cccctctccc tttcctgcga
66661 ctcagcggag ctcagaatgt gtacttctct cctctgactc caaggctgat tgattcacat
66721 ggaaggtgtt cacaggttgt ggcagttcgg ggtaagatga aggaatggca gcagctcatt
66781 cggcatttgt ggtgtctgaa acctgcttga ctggcacgaa agatgagaga ccgacccgag
66841 tgtcagttta ctaagaagaa agaggttagg tgaaatagat gtgacgagtt aaatgccaat
66901 cttcaccacg gggctgaagg tccgnnnnnn nnnnnnnnnn nnnnnnnnnn nnnnnnnnnn
66961 nnnnnnnnnn nnnnnnnnnn nnnnnnnnnn nnnnnnnnnn nnnnnnnnnn nnnnnnnnnn
67021 nnnnggggtc ctcagggact gggcctcagc ccgccggtgg ttccacccta ggcttcccca
67081 agtcggtcaa gagccgggag cagctgtcgg agtacctgac cgtggtgatc ttcaccgcct
67141 ccgcccagca cgccgcggtc aacttcggcc aggtaggcag ggccgggccc gctgggcagg
67201 gctcccttct caaggccgct gcctcctccc ccgccccggt tctgcacgcg tactgcaccc
67261 tcggacagcc tcggggcctg gcacgggact tgcaggatgg attctgcccg ctcagccaag
67321 ggcgctggcc gcggggaaag aggatggacg gactgcaggg cccgctggag ttgggggca
67381 cggggaggac ggggcccagg gggcagctgg gcagcagggc ttcgggggtg cccacgcttg
67441 ctggcggtcg tctccgcagt acgactggtg ctcctggatc cccaatgcgc ccccaaccat
67501 gcgagccccg ccaccgactg ccaagggcgt ggtgaccatt gagcagatcg tggacacgct
67561 gcccgaccgc ggccgctcct gctggcatct gggtgcagtg tgggcgctga gccagttcca
67621 ggaaaacgag gtgaagctgg gcagggcggg gcacagcccc aggtcacccc aggttaagcg
67681 gttcctcagc ctcagggctt tgtgactcgg gccccaaggc tcacttggag caaaggaatc
67741 ctgacttcca aggctggaag ggcccagaag gctgcagccg ccaccaggtc ccccggcctc
67801 agcctggaca gagctcaggg tgtgcagggc aggagagcac acagcccagg ctttgctcac
67861 tgtcaccaga gggtcgtgtg tgacgccccc tccccccagc tattgacaaa gttcttgcac
67921 atgtgtttta ccctggtact ccagagggaa tgaccaagag tttcctgggt tccttccgga
67981 cacgtgcatc tcatttaacc taacaactga atccggtgtg tcttcgtgga tgcacccgct
68041 ttggggtagc tcagtactgc atagaatggc cggaccagtc caacctgctc cagactgctg
68101 ggtgtctgag ttgttcccgg ccaatgtgtt ggtccctcac tggacatcct tgtttttgtg
68161 gctttgcaca tgtgttcagt atgaccgcac acattcctag cagacaaatt ccttggtcaa
68221 agaatattga tactgaattg ccctccacaa actaaattca aaatcccatt atcaatagcc
68281 tatgtttctt ggacctttcc agctcagaag ctttgtgatc ttaatccaat acagtatttt
68341 tttaaaatga tatctagctc tgccccgcag acatctgtgt gagaatgcaa ataagcacag
68401 gaccccaaca gggcagccac cccttcaggc tccctggccc gctttctgcc ttcctgggct
68461 ggagaggcca gtgctggccc cagcgcccct gatgggaggt gagagtgctg cgcaggggtg
68521 gcccaagaca gcaggatacc atggctgcaa acaccagcag cccccagctt catctgcatc
68581 atctcgtaac cacttggcag caggcagtta ttttcccact tatccatgaa gccccagccc
68641 tggagccttc cttagagaag caggttggag gcgacgacac ttgccttccc gaggccctct
68701 tgtcaggcag cagagggtga atatggggag gtgaatagat gctccctcct tcatctccca
68761 aacggtggct ggccccttgg gatgagacag gcctgtcagt ttacacgggt agtggattga
68821 cctatgtgtg tgtccatgtc tgggccctca gctgttcctg ggcatgtacc cagaagagca
68881 ttttatcgag aagcctgtga aggaagccat ggcccgattc cgcaagaacc tcgaggccat
68941 tgtcagcgtg attgctgagc gcaacaagaa gaagcagctg ccatattact acttgtcccc
69001 agaccggatt ccgaacagtg tggccatctg agcacactgc cagtctcact gtgggaaggc
69061 cagctgcccc agccagatgg actccagcct gcctggcagg ctgtctggcc aggcctcttg
69121 gcagtcacat ctcttcctcc gaggccagta cctttccatt tattctttga tcttcaggga
69181 actgcataga ttgatcaaag tgtaaacacc atagggaccc attctacaca gagcaggact
69241 gcacagcgtc ctgtccacac ccagctcagc atttccacac caagcagcaa cagcaaatca
```

FIGURE 2 (cont.'d)

69301 cgaccactga tagatgtcta ttcttgttgg agacatggga tgattatttt ctgttctatt
69361 tgtgcttagt ccaattcctt gcacatagta ggtacccaat tcaattacta ttgaatgaat
69421 taagaattgg ttgccataaa aataaatcag ttcatttaaa atgggtcttg ttccatgtgt
69481 tatattccaa tcaccccaaa cagctcactg ccatctccca caccaagaga aaaaaaaagc
69541 catagtcacc gtgattttat caaggcaaaa gcctccccac ccaagtctgg atagaaggtg
69601 ctttttccct caagcagtgt ctactctctt tggaacacat cccaaatgtc accacctctg
69661 ggaaggcatc cttggttcct gtctctaccc tggatttgtc agaacctctg ttcttgcccc
69721 ctctgtggtc tctcccttgg gacaggagcc cctggaagga cagaaaaccc actttattta
69781 tgtctgtgcc ccagggctgg cataaggcac cagcactcag ctgttctctc cttttcctcc
69841 tggaagggca cctagctaat ggatattagg cattgtcttg ggagctgggg gcttattttt
69901 tcctgaggca gggttcttaa catgacataa aaaataaaaa tgggcagggc gcggtggctc
69961 acgcctgtaa tcccagcatt ttgggaggcc aaggtgggag gatcatttga ggtcagaatt
70021 caagaccagc ctggccaaca cggtgaaacc ccatctctac tgaaaataca aaaattagcc
70081 aggcatggta gcaggtacct gtaatcccag ctactcagga ggctgaggca ggaaaattgc
70141 atgaacctgg gagacagagg ttgcagagag tggatatcgc accactgcac tccagcctgg
70201 gcaatagagc gagactctgt ctcaaatagt taataaataa ataaattaaa ttaaataaaa
70261 acgcattctc tttccccagc cccaagtagc agagcccgct ctgagcctgg gcatggtgac
70321 ccattctcct cgtgctcaca tgcccaactc ccagccctcc agcccctggc ttcggaatca
70381 tgtcatcagg gtctcccatg tctctggaag gtgcttccag tgtggcaggc catcagctca
70441 gtgtctgggt aaaggcttct acagggccag catggcatag gggggaggtg tgcatgcgtt
70501 cctgaagcca caaggtcttc tgaggagacc tgactattgg ggtggggact agagactgag
70561 gtccagcccc ttaatgcccc agactccctg ccatccctcg gagaatttcc caccacactt
70621 atgaatgatc ttcgggacag gtgacataaa catacagcta tggtagaggc attcagctcc
70681 atgccactgt gagaatgaac ataccaactt ttaggcaaca aggccatgtg gtcaaggaga
70741 gaggagaaac gaataggagt aggcaggggt ggtgaagcag gtctgacatt ggcaaaagtg
70801 acagagaagg attgggttgg aagggcttca gatggcagag aacctctgaa aaagtctcat
70861 gccagctaat gaagagtcct caaagtcacc atcacagaaa tcttacatct ggcagaaatg
70921 acagcaatag tttggcatga accccacagt ggatccaaac gtgtggcagc tgagatcgtc
70981 agttaattat gttctctgca gctggtcctt ctggttccct ggagctgggt atctgagtag
71041 cacagctcca ctgctaccac aggagaggga gaatcccaaa ttctgtgcat agactgtcta
71101 aacctctgga tgacccctaa gacacatgta cataaggcaa actgcaaaca gcccaattta
71161 ggataaaaca gcctgtctta ctctgtttgt gctgctataa taaaatacct cagactgggt
71221 catttatata gaacagaaat tgattcctca cagttctgga ggctggaagt ctaagaggag
71281 gcactggcag tttcagtgtc tggtaaggga gggatcagtg tctgctccca agaggatgcc
71341 ctctgtgctg tgtcctcacc cagcagaaga gcaaaaaagg gcgaacattc tcaaaagcct
71401 cttttataag gacatcaatc cattcatgag ggcagaaccc tcaagaatta atcatttctc
71461 aaaaggcccc tcctcctaat gccatcacct tggggtttaa gttccaacac atgatttttg
71521 gaaggacaca tacattcaaa tcattgcaca accaaagtga tatttgaact ttcaaatagt
71581 ttgcagtttg agatcaacta agttaattgc ttgcttgaat aaaaacatca cagccgggca
71641 cgatggctca cgcctgtaat tccagcactt tgggaagcca aggtgggcag atcacttgag
71701 gtcaggagtt cgaaaccagc ctgaccaaca tggtgaaacc ccatttctac taaaaataca
71761 aaaattagcc aggcggccgg gcgtggtggc tcatgcctgt aatcccagct ctttgggagg
71821 ccgaggcggg tggatcacaa ggtcaggaga ttgagaccat cctggccaac acagtgaaac
71881 cctgtctcta ctaaaaatgc aaaaattagc tgttgagact actcgggaag ctgaggcagg
71941 agaattgctt gagccgagat cgtgccatcg cactccagcc tgggggacaa gagcaagact
72001 tcgtctcaaa aaaaaaaaaa gaaaagaaat tttctggatt aggataatgt tctatatttg
72061 gataagggtt taggttacct agatagatac atttatcaaa agtcatcaaa tggtacactt
72121 cagatgtacg catgtcactg tatgtaaata ttaccccaaa atcaacaaga accatgagca
72181 aatactgact tctagtgaac gacatgcata ctgaaacttt cgtagtgaag tataattatg
72241 gctgcagttg actctgaaat acataaaaac ctaagttgat gggtgaatac agtgattaat
72301 agatagaaat ctgtggtaaa gcatacggag aaaaatgtta attgtagatt ctagggttta
72361 tatatattct cactatataa ttaaacgttt ttatgtttaa aaatttttat aatgttgaaa
72421 aaccatgaaa tcctacctaa cgcagtaaga caagaaaaag agataaaagg tatatgtact
72481 gggaagtaag aaataaaacc gtctttgtta gcagatgaca tgctcatcta tgtagaaaat
72541 ccaaaagaat ggataaagaa actcctggaa ctaataagtg gttacagtaa ggttgtagga

FIGURE 2 (cont.'d)

```
72601 tacaaggtta atatacaaaa gtcaatcact ctcttattca ccagtaatga acaagtggaa
72661 attgaaattc aaaacaaaat actatttaca ttaatactcc aaaaatacat acttaggttt
72721 aaatctaata aaatacatac aagatcttta tgaggaaaac tgcaaccctg atgacagaaa
72781 tcaaagagaa actaaagaaa tagacataag taaatattcc ccagaaagac tcaatattgt
72841 caagatgtca gttcttcaaa acttgaccta tagattcaat gcaatcctaa tcaaaatctc
72901 agcaagttat gttgtggata ctgacaaact tattcttttt tttttttttt ttttttttga
72961 gacggagttt cgctctgttg cccaggctgg agtgcagtgg cgcgatctcg actcactgca
73021 agctccgcct cccgggttca cgccattctc ctgcctcagc ctcccatgta gctgggacta
73081 caggcacgcg ccaccatgcc cggctaattt ttgtattttt agtagagacg gggtttcacc
73141 gtgttagcca ggatggtctc gatctcctga cctcgtgatc cacccgtctc ggcctcccaa
73201 agtgctggga ttacaggcgt gagccaccgc gcccggccaa cttattctaa aatttagata
73261 gggaagcaaa agacccagaa cagctaacac aacaatatag taggaaaaca acaaatttgg
73321 aaaatggata ctacccaact ccaagactta ctataaagct acagtaatca agatagtgcc
73381 gtattggtga aagaatagac aaatagatca atggaacaga atagagagcc taagaaatag
73441 accttcataa atacagtcaa ctcatccttg acaaagtagc atagacacta caatggagca
73501 aagattgtct tttcaacaag tggtgcagga acaactggat atccacatgc aaaaacaaac
73561 aaacaagcat gaatctagat acagacctta tgctcttcac aaaaattaac tcaaaatgga
73621 ttatagatct aaatgtaaaa ttcaaaacta taaaattccc ataacatagg ataaaatcta
73681 gatgacctag gtatggctat gacttttag acataacacc aaagccatgg tccatgaaag
73741 aaataattgg taagttggac ttaattaaaa ttaaaacctt ccgctctgca aaagaccaca
73801 ctaggagagg gaggaaatat ttacaaagac acatctgata aagaattgtt acttaaatta
73861 tacaaagcct tcttaaactt aacagtaagg aaacaatctg attgaaaaat gggccaaaga
73921 ctttaacaaa caaaagaaga tatacaaatg gcaagtaagt atgtgaaaag aagctgcaca
73981 gctgggggc gtggtggctc acgcctttaa tcccagcact ttgggaggtc aaggcgggca
74041 gatcacctga ggtcaagaga ccagcctgtc caacatggaa aaacctgtct ctactaaaaa
74101 tataaaatta gctaggcatg gtgatgcatg cctgtcatcc cagctacttg ggaagctgag
74161 gcaggagaat cgcttgaacc cggaaggtgg aggttgcagt gagccaagat cgcgccattg
74221 cactccagcc tgggcaacaa gagtaaaact ctgtctcaag aaaaaaaaaa aaaagctgca
74281 cattctatgt tatcagggaa atgcaaattt agaataacgc aataacaaga taccactaca
74341 tacatattag aatggccaaa attgagaaca ctgacagcac caaatgtgga ggaggatgtg
74401 gagcaacagg aactagagag aatgcaaaat ggtatagcca cttaggaaga cagcttggca
74461 gtttcttaca aaactaaata tactcttacc acacaatcca gcaatcacac tccttggtat
74521 ttacttacat cccaacaaaa accctcatat ggatgtctag agcagctttg ttcataattg
74581 tcaaaacttg gaagcaacca aagatgccct tcggtaggtg agtaaataaa taatatccag
74641 acaatggaaa taccattcag tactaaagag aaatgagcta tcaagccatg aaaaggcgtg
74701 gaagaaactg aagtgtgtat cactaaaagt caatctgaaa agggtgcata agtttccaaa
74761 gatatgatat tgcagaaaag gcaaaactgt ggagacagta aaaagattgc caggggctag
74821 ggcagtggga gggatgaata ggcagggcac agaggatttt cagggcaata acactactct
74881 gtatgacact ataatgttgg atacatggcc agatccacag aatgtagaac accaagagtg
74941 aaccttgaac tatggacttt gagtgatgag gatgagtcag tgtaggctca tggattgtaa
75001 taaatgcacc actgtggggg gggggggata ttgataactg gggggctgta catgtgtagg
75061 gacaggagta aatgggaaat ctctactttt gttaccggtg gagggtgtac cgcatttga
75121 acaaaaaatt ggacaaaacg cacaaagcaa ggaaagaatg aagcaacaaa agcagagatt
75181 tattgaaaac gaaagtacac tccacagggt gggagcaggc ctaagcaggt ggctcaaggg
75241 cctgaataca gatttttctg gggtttaaat accctctaga ggtttccatt ggttacttgg
75301 tgtataccct acgcaaatga agaggatgaa gggaggttac aaagttattt acttggtgta
75361 gaaaattagg gtttttccct tttatttagt tgtaggaagc ccttaggtta cctgcctcca
75421 gaccctattc tcctgcctca ttttattcct aattttgttg tgaacctaaa attgctctaa
75481 aaaatgaaat cttttaaaca agaaaataaa cttataaatt gcaaatatgt gtcacttaca
75541 taaaaacaaa gaattagtgt ccctacatca ggaaaaaaac acctataatt caatgtaaaa
75601 atgcaaaaaa gccaagagaa atggccaagc catggaaatt cacagaagta gaaataggca
75661 gtaaataaac aatgctcaat ttcatttatc tgagaaatgg agagtaaaac ttcagtgaca
75721 tacaaaggag taacaatcat tttaggaaca attttaaaaa taacacttgt gatgtggctc
75781 aggaaagatt catattctca ctgtaggaag gtaagtgaat cattttagag gtcagttttg
75841 caacttagaa gatcaaatgc atctaccctt tttctacttc tagaaatgta tcttcagaag
```

FIGURE 2 (cont.'d)

75901 tgcccctccc tccctcacac acccccaagt gtacaaaaat aaatgacatg gatgtggact
75961 gcagccttgt ttctaatacc aaaaatcagt aaacaaccta aaaatctgta tccatgagga
76021 tttaaagaaa tcctgcatga gttagaaaga ataaggtaga tgcctgggtt ctaacataga
76081 aaatatcaaa ctggttgtta gatgaaaaaa gcaagttgca aagtgaggta atgtgtaaat
76141 gcagtaagca aaatacatca tatatatagt actttctatg tatttaccta tatgagcgtg
76201 atgcctccaa ctgcatagct gtggctccgg gagcaggacc ttgtaacaga gcctctgccc
76261 ctgactgtcc tgaggggcct ttccctggga aaggaaccag gtttgatttt cagtctcttt
76321 tgttatcacc atgctgacag ctttgcttgt catatgcctt tccctccgct gtactgattt
76381 taccttacag aagctctcct tagtgcttca tcagacactc cctcttttcc aaagaaaaga
76441 cagccgcatt ccatggtcat ctggttgagc tcgaggtgag ccccagggat catgtgcctc
76501 ccaccaggct gacaccccag tggtgaggag ttgccccttg gctttttcga ggccaagcaa
76561 ctcagaggtg tggcaggatt gcatgtcaca gtggcacttc caaggccctg gagagtgact
76621 caacgcctct gttattaaga tgtcacacag gctgtgcagc aacaactcta gggacaccct
76681 tcacactgac agagttggca agcttttcct ataaaggggc acacagtgaa tactgtaggc
76741 tttgtaggcc atactatctg tcccaacaat tcaactttgc ccactgtagc tgtgaatcaa
76801 ccgtagataa tattaagtga atgtgcactg ctgtttgcta atagtttatt gacaaaaaca
76861 gctgcttttg agcagtttgc taccccgaca gagactgtgg ggagtccctg gtggcagcga
76921 gctacaggca gccagtaccc catcagtgtg gctggttcca tcctctcaag cctgcctgca
76981 cccagacact gtcgagtgtg tcttcagaaa aactcctaaa attccccaaa agcacagtgg
77041 ctccccgaga gccacctccc tcaccttctt acaggggcag gttcctcttc cggttccacc
77101 ctcctcagca cggagctcag gggccatccc cacctcctct tggccgcaag cacagacctt
77161 cccacacagg ctcagcagct ctgcgggcct gtcccccacc tggagctgca ggcctccact
77221 cctggggaca gctgtgacca tggctctgca aagcagcctt gtgcctagct cccaagtcag
77281 ctggcagccc agagtggaac aattctgtgg atcacctctg agacagcagc acatctgggc
77341 aagcctggct tcccacccct cacctcctgc aacctctgac ccttgccatg catgtggtag
77401 ggaagctgca accaggcctc agcactccca gacctgtggg cggtttgctg tctgaggatc
77461 gtggcactgc cttccctcag aggccttgcc agagccaggg gatgcagcgt ggcagagctg
77521 tcactggcaa ccctgctggt ctccctggtg ctttctcagc tgggctgtgg gtcaggacaa
77581 atttctatgg ataaggctgg atcataatct agtgctccat ggtcatgcag cgacagactc
77641 gagtctgcct tctctcaggg tggtgagctc aggtaggaac gggatgtttg aagcaagcac
77701 acctgtgaga aatgcctgtt ttcactccca tcccacacac tcgtccagac actgccagcc
77761 cacccccgac acacgtgtct gagggaggct gaggaaaaca gacacctcca ggagccgcat
77821 actatttcct gatgtgtaag ccagacaacc ctggaaagga ggtcagggaa ccggagtgcc
77881 tgccaacgtc cccagcctcc ctgcagcaaa acactctcat ggcaaaactc ctttttaaag
77941 aaaggcttta ttgctgcaat tagacatccc agtgtatagc acaaaccccc ctgtacagag
78001 aattattcaa gtggtaatac tgagaaacag tgaacacaca caaaagaata caaaactaga
78061 catttagatc actagaaact ttctaaggta agaaaaattt caaatgtgaa gtgcctttta
78121 gaaactacac cacacatgcc agtgtaaatt tggtttaaca atcaatttct ataaacattg
78181 catctaactg tgcactgatc aactgcacaa cttcaacaat tacttccaag acaaagataa
78241 atgcttttat ttccctatgt tttggtcttt ccttgggcta gagacagaag ctgcatgttt
78301 caaaccagat tcaaaaggga aagcacttca aaacagaaag tacttcaatt gtgtatttgc
78361 cttcagccac atccagagac ttgtggatct caccccggttg gtcccagccc ttctccaacc
78421 ctgaagccca cagcaggggt gcagaggcag ccccagatcg tgcagacatc acccgaggct
78481 cccaaactgg cccagctgcc tgaggcctgc atgcctgtgg ccaggtagga cacatgtgca
78541 ggtttgaaaa ctaggcctac aagactgaag agtggactga agcaaaaagg ggagaaacat
78601 tagaggccta cagtaggaag agacctttta tagagttttc aggaaattct cacaataaac
78661 ttgggcacaa agaccaaatt gctgaggcca gaagcctgct tatggtactg tgacttatgg
78721 ggagtagagg ccaaatcaga gagggctggc tggtgatacc ccagaccact tgcctcttcc
78781 ccttccctgg cctacaaata ccaggcctcc tggccctgag acctcattct gggtttctat
78841 atgggtcaac caaatgccat cctttcacta aacccaggtg caaaatgggg ggggaagggg
78901 ggaagctggg gagtacacag cacccaaaag aaccgagaga gcaagttttc caaggctaca
78961 ggaacattgg cagagctggt ggccacacca gatgggagta ccacatcccc accaggcttc
79021 atgcttcact gctagatgca gggggctaga agggtctgat gaatcaggag ctgaactaga
79081 accttcaaga aaagaaaagg caagggggtg gctctgtgcc ccgccaggag aggaaagaag
79141 aatgtgtgtg gattgtccac agtgaggcca gaaacgatga gatggtgtta ggcagaaaag

FIGURE 2 (cont.'d)

```
79201 aagggagagg gcttcccatg agaatctggc tgggcatggg agggatacag ggctcagtta
79261 tcaaggcacc tttgccatag tggggtgcca gctacattgg gtgggatgcc caggggctgt
79321 ccctacctaa gcactttctt gtctacagga agtcttggtg cttttcaagt tcagcataag
79381 gggttccata tgtgaagtgg ggattcacac ttagaaaatc tatcctggtc ttcacctgaa
79441 acactcatct actgctgggt ggcaggaaca agtatacaaa accaggggcc ttgcctgggc
79501 agttcctaag ggacattggc agggctgacc tgggattcag ctcccctgag tggacagtct
79561 gtggttgcct ggggtcccca ggctgagaag gggtatgggt aattgcactt cggggcacag
79621 tgaacacagg cacgggctgg atgtgccctg ggagacagaa aggagaggct gacctattct
79681 caggagctgg ctatggctgg acagtgcctg cccggccaga ggaaggccac agcagagcca
79741 ctccacagac taagacctgt gttgccaagg aatcagacac tggcttggag gagacaggag
79801 gacaaagcct gctgctatta agcccacacc gtagcttaga gatccttcag cctcctggcc
79861 ttcaaaacaa actccagggc ttccactctg aaaggcaaag gaatcacctc gtgtttgctt
79921 catcccctta gcaggatgaa cgaaacgcct aaggcccaaa aagactgagg gcaggacccc
79981 cagcatctcc catctcctcc gtgcaggctg ggtgagagaa tggcctggaa aggaagcatc
80041 tgcgctacat tgtgcttcag gcccccccag caactttccc ggaggtaact atttgcctgg
80101 aaaactagga aactgggttt taaaaacaga attttaagca gactttttag agggacaagg
80161 ccatttgatg gtagtgattt tggttttgtt ttatgaaaat ggtacaggtg gtaatccctg
80221 atgacagaat gcactgagag tggggccaag ggccctgaag gatcctgtct gttcagtctg
80281 gttaaggcga cagctgggcg ggcatgtggc cggggagcag tggcacagcg gaccctggca
80341 gtttgctcac acctggccct cgtcccagag ccagcccacc tgcctcttgg ccctggtagt
80401 gactccacag aacttccccg agcagaagcc tcacagtggg ccagcaccca tcttgcatgc
80461 aagggagaac ctgcatgcag tgcacacacc ccggccaggg tggcacatgg ctgctctttc
80521 aatgtgaagc caacaccaac tggagagatt taactataaa ggaatatttt ttaaatattc
80581 agttttgttg tcattactca cttcctttcc ttccatttcg atctcagaaa ctgttctttt
80641 tcagtgttga caaaaaagaa atgtatgggc caggtctaca aagtaacacc ttgtcataaa
80701 acaggctcaa aagcatagga atcatgcttt aattgccatt tagcatccac taattcccat
80761 gagatctgtg attaaaaaaa aagcctctgg cctgcttgtc ctgtcttaaa agtcatgagt
80821 ctgttttatg aacagaaaga atgccacgct tcttagcata tgtaaggcaa aatggatttt
80881 tgatctctca tgatgtaaag gagatacaaa ggtaaggaag ggaagatttc taagtgagac
80941 tttttttgag tgtcaatccc gctggacaca catattacaa aataaagatt ttcttctgta
81001 aagtgctgtt tgctcagtga atcatgcgcc accacagagc accatggctc cacctgctca
81061 agagcatgga ggaggcagca tcggcagagg gcaggcagga gtctgtgttt ggggggtctgt
81121 ttcaatacca tctcctgggg ttcgccgtga tgcagaggga atcttctcgt catggctaga
81181 cactccccaa tgctctgctc caggctgggg accactgcaa gctggaggcg gctgggtatc
81241 agggcctggg caccccctgct cctcctcttc ccttgggatt ggcattttat tctctcattc
81301 agctcaagac catgggcagg aactctgctg gctccccatg atgtcatcat ggggtcttcc
81361 actttcccac agagctgcca ggcagaggca ggacccaggc atgcctggcc cacaggaagg
81421 ttttctagga gactaaggag ggtttagaaa aagagaagcc actataaata gtcacctgtc
81481 cagtctatgc tattaaagga cataagaaag gtatacaatt ggcagtaaac aatttccttc
81541 agctcttcat ggatgtccag gaaaatgaca acccgcacac aatcagacgt gaatgatttc
81601 tgctccagtg tcttcaggct ctgtgcaaca agaagagttt gtgtcggaat gacagattcc
81661 atatccatgt ttattttcaa agttgggctc tgttagtgga gatttttcaa aaatattctt
81721 tttgcttgtt tctggacagt tttgaacata gatcactcta ttataggcct tgagtctctt
81781 ccacaattgc acatacactt tacactgaac atacataaaa agaagtcctc cggtgaagcc
81841 gatggccaca accaccaatt tagtccaaaa gggccattct aggattcctg gaagggaaaa
81901 actcagccta ttagatttta tttaagatat gtcttcacca cggggctgaa gnnnnnnnnn
81961 nnnnnnnnnn nnnnnnnnnn nnnnnnnnnn nnnnnnnnnn nnnnnnnnnn nnnnnnnnnn
82021 nnnnnnnnnn nnnnnnnnnn nnnnnnnnnn nggcggtgac tgtgacattg aggttcggcg
82081 tcgggggaga gggaaaagga gagggagagg gagagggaga gggagaggga gagggagagg
82141 gagagccata tgtagtttaa agtagttttt ttccaattct gagaagaagg tcattggtag
82201 cttgatgggg atggcaatga ctctataaat taccttgggc agtatggcta ttttcacgat
82261 attgattctt cctacccatg agcatggaat gttcttccat ttgtttgtat cctcttttat
82321 ttccttgagc agtggtttat atttctcctt gaagaggtcc ttcacatccc ttgtaagttg
82381 gattcctagg tattttattc tctttgaagc aattgtgaat gggagttcac tcatgatttg
82441 gctctctgtt tgtctgttat tggtgtataa gaatgcttgt gatttttaca cattgatttt
```

FIGURE 2 (cont.'d)

```
82501 gtatactgag actctgctga agttgcctat cagcttaagg agattttggg ctgagacgat
82561 ggggttttct aggtatacaa tcatgtcatc tgcagacagg gacaatttga cttcctcttt
82621 tcctaatcga atgcccttta tttccttctc ttgcctgatt gccctggcta gaacttccaa
82681 cactatgttg aataggagtg gtgagagagg gcatccctgt cttgtgccag ttttcaaagg
82741 gaatgcttcc agtttttgcc catgatgtat gatattggct gtgggtttgt catagatagc
82801 tcttattatt ttgagataca tctcatcaat acctaattta ttgagagttt ttagcatgaa
82861 gcgttgctga atttgtcaa aggccttttc tgcatctatt gaaataatca tgtggttttt
82921 gtcattggtt ctgtttgtat actgggttac atttattgat ttgtgtacgt tgaaccagcc
82981 cttgcatccc agggatgaag cccacttgat catggtggat aagcttttg atgtgctgct
83041 ggattcgttt gccagtattt attgaggatt tttgcatcga tgttcatcaa ggatattggt
83101 ctaaaatggg tttttgttg ggtctctgcc cagctttggt ctcaggatga tgcctcccct
83161 attaaaagag ggagggagga ttccctcttt ttctattgat tggaatagtt tcagaaggaa
83221 tggtaccagc tcctccttgt acctctggta gaattcggct gtgaatcctt caggtcctgg
83281 actgttttg gttggtaagg tattaattgt tgcctcaatt tcagagcctg ttattggtct
83341 attcagagat tcatcttctt cctggtttag tcttgggagg gtgtatgtat ggaggaattt
83401 ttccatttct tctagatttt ctagtttatt tgcatagagg tgtttataat attctctgat
83461 ggtagtttat atttctgtgg gatcagtggc gatatcccct ttatcatttt ttattgcatc
83521 tatttgattc ttctgtcttt tcttctttat tagtcttgct agcggtctat caattttgtt
83581 gatcttttca aaaaaccagc tcctggattc attgattttc tgaagggttt tttgtgtctc
83641 tatttccttc agttctgctc tgatcttagt tatttcttgc cttctgctag cttttgaatg
83701 tgtttgctct tgcttctcta tttcttttca ttgtgatgtt agggtgtcaa ttttagatct
83761 ttcctgcttt ctcatgcggg catttagtgc tataaatttc cttctacata ttgctttgaa
83821 tatgtcccag agattctggt atgttgtgtg tttgttctca ttggtttcaa agaatatctt
83881 tgtttctgcc ttcatttcat tatgtaccca gtagtcattc aggagcaggt tgttcagttt
83941 ccatgtagtt gagtggtttt gagtgagttt cttagtcctg agttctagtt tgattgcact
84001 gtggtctgag agatagtttg ttacaatttc tgttctttta catttgctga ggagagcttt
84061 acttccaact atgtggtcaa ttttggaata ggtgtggtgt ggtgctaaaa aaaatgtata
84121 ttctgttgat ttggggtgga gagttctgta gatgtctatt aggtccgctt ggtgcagagc
84181 tgagttcaat tcctgggtat ccttgttaac tttctgtctc gttgatctgt ctaatgttga
84241 cagtggggtg ttaaagtctc ccattattat tgtgtgggtg tctaattctc tttgtagatc
84301 tctaaggact tgctttatga atctgggtgc ccctgtactg ggtgcatgta tgtttagtat
84361 agttagctct tcttgttgaa ttgatccctt taccattgtg taatggcctt ctttgtctct
84421 tttgatcttt gttggtttaa agtctgtttt atcagagact aggattgcaa cccctgcctt
84481 tgttttccat ttgcttggta gatcttcctc catcccttta ttttgaacct atgtgtgtct
84541 ctgcatgtga gatgggtttc ctgaatacag cacactgatg ggtcttgact ctttatccag
84601 ttttccagtc tgtgtctttt aactggaaca tttagcccat ttactttaa ggttaatatt
84661 gttatgtgtg aatttgatcc tgtcattatg atgttagctg gttattttgc tagttagttg
84721 atgcagtttc ttcctagcat cgatggtctt tacaatgtgg catgtttttg tggtggctgg
84781 tatgggttgc ccctttccat gtttagtgct tccttcagga gctcttttag ggcaggcctg
84841 gtggtgacaa aatctctcag catttgcttg tctgtaaagg attttatgtc tccttcattt
84901 atgaagctta gtttggttgg atatgaaatt ctgggttgaa aattcttttc tttaagaatg
84961 ttgaatattg gccctcactc tcttctggct tgtagagttt ctgccaagac atgagctgtt
85021 agtctgatgg gcttcccttt gtgggtaacc tgacctttct ctctggctgc tctcaacatt
85081 ttttccttga tttcaacttt ggtgaatctg acaattatgt gtcttggagt tgctcctctc
85141 gaggagtatc tttgtggcat tctctgtagt tcctgaattt gaatgttggg ctgccttgct
85201 agattgggga agttctcctg gataatatcc tgcagagtgt tttccaactt ggttccattc
85261 tccccgtctc tttcaggtac accaattaga tgtagatttg gtcttttcac atagtcccat
85321 gtttcttgga ggctttgttc atttttttt tcttttttctt ctaaacttct cttcatgctt
85381 catttcattg atttgatttt ccatccccaa taccctttct tccagttgat tgaatcagct
85441 actgaggctt gtgcattcat catgtagttc tcatgccatg gttttctgct ccatcaggtc
85501 atttaaggac ttctctgcat tggttattct agttagccat tcatctaatt tttttcaag
85561 gtttttaact gctttgccat gggttcggac ttcctccttt agctcagagt agtttgatca
85621 tctgaagcct tcttctctca actcgtcaaa gtcattctcc atccaggttt gttctgttgc
85681 tggtgaggag ccgtgttcct ttggaggagg agaggcactc tgatttttag agcttccagt
85741 ttttctgctc tgtttgttcc tcatctttgt ggttttatct acctttggtc tttgatgatg
```

FIGURE 2 (cont.'d)

```
85801 gtgacgtaca gatggggttt tggtgtggat gtcctttctg tttgttagtt ttccttctag
85861 aattcaggac cctcagctgc aggtctgttg gagtttactg gaggtccact ccagaccctg
85921 tttgcctggg tatcagcagc agaggctgca gaacagtgga tattggtgaa cagcaaatgt
85981 tgctgcctga tcattcctct ggaagttttg tctgagagga gtacccagcc gtgtgaggtg
86041 tcagtctgcc cctactaggg ggtgcctccc agttaggcta ttcgggggtc agggacccac
86101 ttgaggaggc agtctgccca ttctcagatg tcaagctgtg tgctgggaga accacttctt
86161 tcttcaaagc tgtcagacag ggacatttaa gtctgcagtg gttattgctg tcttttgttt
86221 gtctgtgccc tgcccctgga ggtggagtgt acagaggcat gcaggcctcc ttgagctgtg
86281 gtgggctcca gccagttcaa gcttcccggc tgctttgttt acctactcaa gcctgggcaa
86341 tggcgggcac ccctccccca gcctcgctgc cgccttacag tttggtctca gactgctgtg
86401 ctagcaaaga gtgaggctct gtgggtgtag aaccctccaa gctatgtgtg ggatataatc
86461 tcctggtgtg ctgtttatta agcccattgg aaaagcacaa tattagggca ggagtgaccc
86521 aattttccag gtgccatctg tgaatgcttt ctttgactag gaaagggaat tccctgacct
86581 cttgcccttc ccaggtgagg tgatccctca ccctgctttg ggtcacgcat ggtgtgctac
86641 acccactgtc ctgcaaccac tgtctggcac tccccagtta gatgaacccg gtacctcagt
86701 tggaaatgtg gaaatcacct gtcttttgca tcgctcatgc tgggagctgt agactggaac
86761 tgttcctatt cagccatctt ggctccacgt atatccactg ccacacttct ttagtcataa
86821 agtgagtgcc ttggtcagag gcaatgctgt gtggaatacc atgatggtgg ataaggcatt
86881 ctgtgagtcc atgaatggta gtcttggcag agcattgtgt tcagtttagg caaacccata
86941 tccagagtaa gtgtctgttt cagtgaggac aaacctctgc ccttttcagg atggaagagg
87001 tccagtataa ccaaccttcc accaggtaac agactgatca ccccgaggaa tggtgccata
87061 ttgagggctc agtgttagtc tctgctgctg tcaaattggg cactcagctg tagccatagc
87121 caggccagtt ttggtgagtg gaagtccatg ttgctgagcc catgtataac ctccatccct
87181 gccaccatgg ccactttgtt tatgggccca ttgggtgata acaggggtgg ctggggaaag
87241 aggctgagtg atgtccacag aacaggtcat cttatccact tgattattaa aatcctcctc
87301 tgctgagatc acccattggt gagcactcac atgggatcca aatatcttca caggttttgg
87361 ccactcagag aggtccatcc acatacctct tccccaaatt tctttgtcac caattttcca
87421 atcatgcttc ttccaagtcc ctgaccatcc agccaaacca ttggctacag cccatgaatc
87481 aatatataat cgcacatctg gccatttatc cttccatgaa aagtgcacaa ccaggtgcac
87541 tgcttgaagt tctgcccact gggaagattt cccttcacca ctgcccttca gtgatgtcct
87601 agaaaggggc tgtagtgctg cagctgtcca cttttgggtg gtgcctgcat atcgtgcaga
87661 accatctgtg aaccaggccc tagtcttctc ttcctctgtc aactgatcat agagaactcc
87721 ccatgaggcc atcggtgcag gctggggaag agaaggtggg gtggcagttg tggagaccat
87781 gggcatttga gctacttcct tgtgtaactt acttgtgcct ttaggacctg ctcgagccca
87841 atcacatata tatcacttcc atttgatgat ggaatgctgc tgtgcatgac ccattttatg
87901 gctacatggg tcagaaagca cccagttcat gatagacagt tcagttcaca tggtgacttg
87961 atgacccata atcaaatgtt cagtttccac caaagctcag taacaggcca agagctgtct
88021 ttcaaaagca cagtagttat atgcagaaaa tggcagggcc ttgtttcaaa atttagagg
88081 catctgctgt gattcacctg tgggggcctg ccaaaggctc caaacagcat ccctatctgc
88141 cactgatgcc tcaagcacca ttggatctgc tgagtcatat ggcccaaaca gcagagcagg
88201 ttggacagca gcctggacct gaggcagagc cttatcctgt tctggacccc actcaaaact
88261 ggcagccttt tgagtcactc gataaatggg cctgagtaac acacccaaat gaggaaagtg
88321 ttacctccaa aatccaagta ggcccactac atattgtgcc tttttcttag ttgtaggagg
88381 ggccaaatgc agcaacttat ccttcatctt acaaggagta tcttgacagg ccccacacca
88441 gtggaccccct agaaatgtta ctgaggtaga aggtccctga atttagtca aatttatttc
88501 tcatcctctg gcacacaaac atctcacaaa taagtccagt gtgtttgcta cttcttgctc
88561 actggatccg atcagcataa tgtcatcaat gtaatggacc agtgtgatat cttgcagaag
88621 caaaaagtgg tcaagatctc tccaaataag attatgatgc aaagccagag tttatatact
88681 cttgaggtag gagagtaaag atatattgct agtcttgcca gctgaaggca aattgcttct
88741 agtgggcctt atgaatagga atggagaaaa aggcatttgc caagtcaatg gctgcatacc
88801 aggtaccagg aaatgtgtta atttgctcaa gcaatgaaac cgtatctggt acagcagctg
88861 caattggagt caccacttag ttaagcttat gataatccac tgtcattctc caagatccat
88921 ctgtcttatg cacatgccaa atgggagagt tgaatggggg tgtgatgaaa atcaccaccc
88981 ttgcgccttt caagtccttg atcatggcac taatctctgc aatccctcca gggatgtgat
89041 attgtttttg atttaccatt tttctaggta gaggcagctc taatgccttc catttggcct
```

FIGURE 2 (cont.'d)

```
89101 ttcccaccat aataggcctc accctaccag tcagggagcc aatgtgggtg ttcttccagc
89161 tgctaagtat gtctatgcca attatgcatt ctggcactgg ggaaatgaac acaggatgag
89221 cctggggacc cattggaccc actgtaagtc agacctgagc taaaactcca ttaattacct
89281 cacctccata agctcctgct ttaactggag gaccacaatg acgttttgag tcccttagaa
89341 ttaacgtcag ctcagagcta gtgtcctgta atccccccaaa tgactgataa tttccctttc
89401 cccaatgcac agttaccttg ataaaaggct ggaggtctcc ttgggaaaaa atgggagaaa
89461 gattaacagc ataaattgtt ggtagtgtag tgggctcctt ccttaatggg acccaacttc
89521 ccctttattc aaggggttct gtgtctgtaa actggctcaa gtcaaaaatt gattgagggg
89581 ccatgattct ctatttttat aattcaaagt agtgttttgt ccatttgacc tggaagtttt
89641 ctgcttatat aaattaagta ggaaagaagt aggcatccta acaatttcac ttctgggaac
89701 actgtgatta attagcgaat gccagaactc tacatgagtc agactattct gattgctgct
89761 ttgccactac tgtctgttat ggtagttatg cccaccttgc ctttgatggt tgagtgccac
89821 cacttggcct ctgccacctt gggatccaat tattcccatt gtatttacct ttattagttg
89881 agtgactgtg gttctcacca ttggatctga tatgcagaga attacggggc tcttcaaaga
89941 tgcaggtgct accctcacag atctattttg caaggtattg gtcaagggta tatcttctgg
90001 gcccttccat ctgggatgag taggtctaaa gtgactaatc cactccacca tctcaatctc
90061 tctaagcctt tggatccctt cctctacatt aaaccaagag tgatcagaca tttccagctc
90121 cctcacagtg gccatctttc aatccatatt tcagctaact aagcaaataa attattagaa
90181 cctttttta actccctgag ctgcaatatt aaatgcagag tctctactta gtgggcccaa
90241 atcaacaaat tcagcctgat ccaactctat gttccttcca ccattatccc acacccttaa
90301 tatccattct catgcctgtt ctccagattt ctgtttatat aaattagaaa actcaagtag
90361 ttcttttcaa gtatagtgaa cctcctcatg ggtttcactc tcaacctcac ctcttggggc
90421 ccataaggac tttagtctgg ttataggtct agaagcagac aggggtgttg gggtggctc
90481 ctgaggagaa tcaacattat tttgcctggc aactgctcag ggggggccat cactgttgcc
90541 ttaggcagca cagtgtttat ctccccagac aaatatggaa aggctgatgg cagcatgggt
90601 cagggagagg atgtcaccac tactggggat ggggaagctg ttttttttct ggcaaaaaag
90661 gtttcctgag actttacaaa ctcagtgtcc ccagcttcat cagggtcctc ccacatgtcc
90721 cctttccaag ttgcagggtc ccattctttt ccaaacgatg ccctcacttt aatagtacat
90781 acctggtgag gctgtgcatg caccettcat tggaagtcag ccacttgcac aataagagct
90841 catatccatt ttcccacaat ttcagctctt tctctgcagg agataatact ttcactcagg
90901 gcaatcttag cagatttgag gctcagtatc tgcttctgaa gccaggagtt agaatcccta
90961 agttcatttt ctttcatcac tttgtccatt gaacttagga gaaaccaacc aacttcatta
91021 tgtttccaca tatggtcaaa ggtattattt atagagtcac taaactcctt gcctctcatg
91081 agcgctgaat caggaatgtc aaatgcattt attttgctta actctctaaa cagttcatag
91141 aaaggaacac tgaatcagtg ttctccatac tatcagaagt agagtcctta gcatttttga
91201 gtctaatcat attaaacagc cactccagaa accctaaaac caatgaaaga actgcatcct
91261 taatgttctg ttcctctaga accactcctg gtacaaaaat ctgtgttagg gttctctaga
91321 ggggcagaac taataggata gagatatata agaaggaaag tttattaagt attaactcac
91381 atgatcacaa ggtcccacaa taggatatct gcaagctgag gaacaaggag agccagtcca
91441 agtcctaaac tgaagaactt cgagtctgat gttcaagggc agggagcatc cagtaccaga
91501 gaaagatgta ggctgggaag ctaggccagt ttagtctttt catgtttttc tgccaacttt
91561 tcatattcta gctgcactgg cagctgatta gatggtgccc acccaggtta agcgtgggtc
91621 tgcctttccc agcccactga ctcaaatgtt aatctccttt ggcaacacct tcacagacac
91681 acctaggatc aatactttgc atccttcaat ccaatcaagt tgacactcag tattaaccat
91741 cacagaagca ttatctacta ataccaccat ataaaagatg cggatgttag catagttatc
91801 acactgtttc ctcacacaat ccactaccca tggcttggtt tctatggaca tattattgga
91861 tctgagccag cttattataa tgttttaaat aatattcaag aattgttaca attgcatttt
91921 gaattgttat tatttaaata taggtcaatt tctaaataga ttcttgtcca tagtcagatt
91981 ttacatcatg atttcctcac tcatgacatt taaaagttta tttgttaaat ttagccaata
92041 tatacaagtc tgcatttggg gatgggtaat tgaatgccat ttttaatttt tgggtaatgg
92101 agactttttt tatgttgcct ttatatttga tccataacta ggctatgtag tacatttctg
92161 ggtcaaatct ctattgcttt aaaactttgt ggttttgctt cattatctcc tagtatctac
92221 agttactgaa gtgatacgta caaccagctt tggacatgat gaatgtttta ggctaaagac
92281 ttgggtgttc tttggtcttt ggaagttttc tttaatactc tctttaaatt tgtctgattc
92341 cacttcttgg ttccctttc aggaacacca agtattcaca cagtggatag tcatctgtcc
```

FIGURE 2 (cont.'d)

```
92401 tctacttcta aaattttgtt atttaacaaa atgttataaa agtagaatca catttatgta
92461 accttttttgg attgatgttt tttgctcagc ataatttcct ggcaatccat ccaagttgtt
92521 gcatgcatca atcatccatt cctttacatt gctaagtagt attccatgct atgtatttac
92581 aacagtttgt ttacccattc acctgttgaa aaacatcttg gctgaatcta gttcttagct
92641 attaatatta taaacaaaga tgctataaac atttgtttga cagtttttttg tgtgaagttt
92701 ttatttttct gggataaatg cctgggagtg caattgctgg gtcatatgat agttgtgtgt
92761 ttttctttga gaaactccca aaatttccca gagtggatga agtattttat gtttctatca
92821 gtaatgtatc agtgatccgg tttctacaca tccttaccag catttggtgg tgtcatgatt
92881 tttaatttta gccattctga tagatgagta gtgatagctt attgttgttt caatttgcat
92941 ttccctaaaa cctaataatt ttgaacatct tttcatgtga ttatttgctg tccatgaaat
93001 atctgtggaa acagtgagta gaaggatgct ttccacagtc tgagaaggac agctgggaga
93061 ggtggatgaa gagaggttgg tatatgggta caaaaataca attaagacct ctggtccatg
93121 ctgggcacag tggctcatgc ctgcaatccc agcactttgg gaggccaaag cgggtggatc
93181 acctgaggtc aggagcttaa gaccagcttg gccaacatgg tgaaaccctg tctctactga
93241 acatacaaaa attagccggg catggtggtg cgtgcctgta atcccagcta ctcaggaggc
93301 tgaggtggga gaatcactta aacccgggag gcgaagtttg cagtaagccg aggtcacacc
93361 actgcactcc agcctgggca acagagcact ccagccgggg caacagagca agactctgtc
93421 tcaaaaaaat aaaataaaat aaagtaaaac aaaataaaga gttccaatcc agcagagagt
93481 gtggtgagat ggtgcgggac cagctccctg ggacttctga gcctttgccc tggccagtgg
93541 gggagctgag ccaggatagg ctgtagcctc tgccccgtga caccaggacc cttgtggtgg
93601 ctgccaccag gacccttggg gtgggtgcct gggccttgaa gatgcagcaa gcctcccttc
93661 cccctacacc tcagtgactg agggtggtgg tggcctttcc caggccgcac cctgccgggt
93721 atagacgaag tccccactga gcctggatgc agtgcctttg ggtggtggtg ggagtggcag
93781 gggcagcttg gtgactatcc gggtgtgagg attgggaagg tgctcttggc atgcaggaca
93841 cgggctcagc cacctcttta ggccatggcg ctgccagatc cgggtcctgg tgaccactct
93901 gtcccagctg ggtgagactt acctagtcct gaggacaaca gacaatggcc ttaataggcc
93961 tggaaggtga gtggaggcac agaggaggac agtgtggaac agttagcagg cattgggctg
94021 ttggtcttcc ttctaccaga cctggaagga cctcacattt ggcctatggg aaatgcccgc
94081 cacactttgg gaagatttac tatctgcttc tagaaggctg tgtgtatatt atgaaaaagc
94141 tattctcaac tcacccccaa ccttttaata gataacatct gtggggaggc tgacaagatg
94201 gctgaataga aacagctcag gtgtgcagct cacagtgaga tcaatgcaga aggtgggtga
94261 tttctgcatt tccaactgag gtacccggct catctcattt ggactggtta gacagtgggt
94321 gcagcccatg gagggtgaac tgaggcaggg tggggtgttg cctcacctgg gaagtgcaag
94381 gggtcagaaa actcccctgt tagccaaggg aagctgtaag gagctgtgcc atgaggagtg
94441 gtgcattcca gcccagatac tatgcttttc ccatggtctt tgcaacccac agaccaggag
94501 attccctcca gtgcttatgc caccagggtc ttgggtttca agcacaaaac tgggtggcca
94561 tttgggtaga caccaaggta gctgcaggag tctttttttca taccccaggg atgcctggaa
94621 tgtcagcgag acagaaccat tcactcccct ggaaaggggg ccgaagccag ggaaccaggt
94681 ggtctagctc agtggatccc acccccatgg agcccagcaa gctaagatcc actggcttga
94741 aattcttgct gccagcacag tagtctgaag ttgacctggg atgctggagc ttggtatggg
94801 gaggggcgtc tgccattact gaggcttgag taggcagtgt tcctctcaca gtgtaaacaa
94861 aactgcaagg aagttccaac tgggtggaac acaccacagc gctgccaggc tgctgtagca
94921 agactgcctc tctagattcc tcctgtctgg gcagggcatc tctgaaaaaa aggcagaagc
94981 cccagtcagg gacttataga taaaactccc atctctctgg gacagagcac ctgggggaag
95041 gggcagctgt gggtgcagct tcagcagatt ttaacatccc tgcctgccag ctctgaagag
95101 agcagtggat ctcccagcac agtgtttgag cagactgcca cctcaagtgg gtccctgacc
95161 ccctggcctc ctgaccggga gataccttcc agaagaagcc aacagacacc tcacacaaga
95221 gagctccagc tggcatctgg caggtgcccc tctgggacaa agctttcaga ggaaggaaca
95281 ggcagcaatc tttgctgttc tgcagcctcc actggtgata cccaggcaaa caaggtctga
95341 agtagatgtc cagcacactc cagcagacct gcagcagaga ggcctgactg ttagaagaaa
95401 aactaacaaa cagaaaggaa tagcatcaac atcaacaaaa aggacatcca ctcagaaacc
95461 ccatccaaag gtcaccaaca tcaaacacaa aaggtaggta aatccatgaa gatggggaga
95521 aaccagcaca aaaaggctga aaattccaaa aaccagaatg cctcttcttc tccaaaaaat
95581 cacaacttct caccatcaag ggaacaaaac tggatggaga atgaatttga tgaattggca
95641 gaagtaggct tcaaaggtgg ataataacaa actcctctga gctaaaggag aatgttctaa
```

FIGURE 2 (cont.'d)

```
95701 cccaacgcaa ggaagcaaag aaacttgaaa aaagattaga tgaattgcta actagaataa
95761 cgagtttaga gaagaacata aatgacctga tggagctgaa aaacacagca caagaactta
95821 gtgaagcata cacacatatc aatagctgaa tcgatcaagt ggaagaaagg atatcagaga
95881 ttgaagatca acttgcagaa accctataag ccagaagaga ctaggggcca atattcaaca
95941 ttcttaaaga aaagaatttt caatgctgaa tttcatatcc agccaaacta agcttcataa
96001 gtgaaggaga aataaaattc tttacagaca agcaaatgtg agacattttg tcgtcaccac
96061 gcctgcatta caagagctcc tgaagggagc aataagcatg gaaaggaaaa aatggtgcca
96121 gccactgcaa aaacatgcca aatggtaaag accatcaacg ctatgaagaa actgcatcaa
96181 gtaatgggca aaataaccag ctagcatcat aatgatagga tcaaatttac acataacata
96241 ttaaccttaa atgtaaatgg gctaaatgcc ccaattaaaa gacacagact ggcaacatgg
96301 ataaagagtc aagacccatc agtgtgcagt attcaggaga cccatctcac atgcaaaaac
96361 acacataggc ccaaaataaa gggatggagg aatatttacc aagcaaatgg aaagcaaaaa
96421 acaaacaaac aaacaaacaa acaaacaaac aggggttgca atcatagtct ctgataaaac
96481 agactttaaa ccaacaaaga tcaaaagaga aaaagaaagc cattacatag tggctaagaa
96541 gagctaacta tcctaaatat acatgcaccc aatacaggag cacccagatt cataaggcaa
96601 gttcttaaac acctacaagg agacttagac tcccacacaa taatagtggg agattttaat
96661 accccactgt caatatcaga caggtcaatg agacagaaaa ttaacaagga tatctaggaa
96721 ttgaactcag ctccagacta agcagaccta atagacatct atagaactct ccaccccaaa
96781 tcaacagaat atacattctt ctcagcacca catcgcactt attctaaaat tgaccacata
96841 attggaagta aaacactcct cagcaaatgc agaagaatgg aaatcataac aaacagtctc
96901 tcacaccaca gcgcaattaa attagaattc agaattaaga aactcactca aaacctcaca
96961 cttacatgga aactgaacaa cctgctcctg aatgactgct ggataaataa tgaaatgaag
97021 aaggataaag atgttgtttg aaaacaataa gaataatgta ccagaaactc tgggacatat
97081 ttaaagcagt gtgtagagga aaatttatag cagtaattgc ctacaaaaga acacaggaaa
97141 gatctaaaat cgacacccta acatcacaat taaaagaact agagaagcaa gagcaaacaa
97201 attcaaaagc tagcagaaaa caagagataa ctaagatcag ggcagaactg aaagagatag
97261 agacatgaaa aaccccttaaa aatcaattaa tcgctctccc tctccctctc cctctccctc
97321 tccgtctccc tctccgtctc cctctcccca cggtctccct ctccctctct ttccacggtc
97381 tccctctgat gccgagccga agctggactg tactgctgcc atctcggctc actgcaacct
97441 ccctgcctga ttctcctgcc tcagcctgcc gagtgcctgc gattgcaggt gcgcgccgcc
97501 acgcctgact ggttttctct gcccggccag ccgcccccgtc cgggagggag gtaggaggtc
97561 agcccccccgc ccggccagcc gccccatccg ggaggtgagg ggtgcctctg cccggccgcc
97621 cctactggga agtgaggagc ccctctgccc agccaccacc ccgtctggga ggtgtaccca
97681 acagctcatt gagaaggggc catgatgaca atggcggttt tgtggaatag aaagggggga
97741 aaggtgggga aaagattgag aaatcggatg gttgccgtgt ctgtgtagaa agaagtagac
97801 atgggagact tttcattttg ttctgtacta agaaaaattc ttctgccgtg ggatcctgtg
97861 gatctgtgac cttacccccca accctgtgct ctctgaaaca tgtgctgtgt ccactcatgg
97921 ttaaatggat taagggtggt gcaagatgtg ctttgttaaa cagatgcttg aaggcagcat
97981 gctccttaag agtcatcacc actccctaat ctcaagtacc cagggacaca aacactgcgg
98041 aaggcagcag ggtcctctgc ttgggaaaac cagagacctt tgttcacttg tttatctgct
98101 gaccctccct ccattattgt cctatgaccc tgccaaatcc ccctctgcga gaaacaccca
98161 agaatgatca ataaaaaaat aaataaataa aaataaaaat aaaataaaat aaaataaaaa
98221 aagaaataaa cacaaataaa atgttaaaat tcccattcta cataaaatca tctatagatg
98281 tttttaaata tacaacatga ttatcaagga cttaatctgt accacattct tgtagatgta
98341 aagttaaaat tcttgtaacc atcactctca accctaccct atcttccagc ataaatgaga
98401 ctttcacatg ttttctcttg cccagatgga gacactaact gtaggctttg gaaatgtctt
98461 aaaaaaaaaa aaaaaaaaaa gagagccagg catcttcaaa cagagaaaag ctgtttgaac
98521 acatttatct aagtctatca aaagctatga ttgttagcaa gaggtaacct tgtaatgcca
98581 aggcagaaaa ctgccaccaa accacaaaaa gcttgttcaa ctgctgaacc taaaattaaa
98641 caatttatct ctcattaaaa aaaaaaaatc aattaatcca ggagctggtt tttttttaaa
98701 gatcaacaaa atagatagac cactagccag actaataaag aggaaaagag agaagagtca
98761 aatagacata ataaaaaatg ataaaggaga tatcaccact gatcccacag aaatacaacc
98821 taccatcaga gaatattata aacacctcta tgcaaataaa ccagaaaatc tagaagaaat
98881 ggataaattc ctggacacat acaccctccc aagactaaac caggaagaag tcaaatccct
98941 gaataagcca ataacaaact ctgaaattga ggtggtaatt aatagcctac caaccaaaaa
```

FIGURE 2 (cont.'d)

```
99001 aagtccagga ccagacggat tcacagctga attctaccag aggtacaaaa ggagctggta
99061 ccattccttc tgaaactatt ccaaacaata gaaaaagaga gaatctccct aactcatttt
99121 acgaggccag catcatcctg ataccaaagc ctggcagaga cacaacaaaa aaagaaaatt
99181 tcaggccgaa atccctaatg aatattgatg caaaaatcct cagtaaaatt ctggcaaacc
99241 gaatccagca gcacatcaaa aagcttatcc accatgatca agttggcttc atccctggga
99301 tgcaaggctg gttcaacata tgcaaattaa tgaacgtaat gcatcacata aacagaacca
99361 atgacaaaaa ccatgtgatt atctcaatag atgcagaaaa gaccttcgac aaaattcaac
99421 agcccttcac gctaaaaact ctcaataaac tagatattca tggaacatgt ctcaaaacaa
99481 tcagagctat ttatgagaaa cccacagcag ccaatatcat actgaatggg caaaaactgg
99541 aagcattccc tttgaaaact ggcataagac aaggatgccc tctctcacca ctcctattca
99601 acatagtatt gggagttctg gccagggcaa tcaggcaaca gaaagaaatg aaggatattc
99661 aattaggaaa agaggaagtc aaattgtctc tgtttgcaga tgacatgact gtatatttag
99721 aaaaccccat catctcagcc caaaatctcc ttaagctgat aagcaacttc agcaaagtct
99781 tgggatacaa aatcaatgtg caaaaatcac aagcattcct atacaccaat aacagacaaa
99841 ccgagagcca aatcacgagt gaactcccat tcacagttgc tgcaaagaga ataaaatact
99901 taggaatcca acttacaagg gatgtgaagg acctcttcaa ggagaactac aaatcactgc
99961 tcaatgacat cagagaggac acaaacaaat ggaaaaacat tccatgctca tggataggaa
100021 gaatcaatat cgtgaaaatg gccataatat ccaaagtaat ttatagattg aatgctatcc
100081 ccatcaagct accactgact ttcttcacag aattggaaaa aactacttta aatttcatat
100141 agaaccaaaa aagagcctgc atagccaagc caatcttaag caaaaataac aaagctggag
100201 gcatcacact acctgacttt aaactatact acatggctgc agtaaccaaa acagcatggt
100261 actagtacca aaacagatat atagaccaat ggaacagaac agaggcctca gaaataacac
100321 cacacatcta caactatctg atctttgaca aacctgacaa aaacaagcaa tggggaaagg
100381 attctctact taataaatgg cattgggaaa actggttagc catatgcaga aagctgaaac
100441 tagatccctt ccttccactg tatacaaaaa ttaactcaag atgggctaaa gacttaaatg
100501 taagacctaa aaccataaaa accctaaaag aaaacatagg taataccatt caggacatag
100561 gcatgggcaa agacttcatg actaaaacac aaaaagcaat ggcaacaaaa gccaaaattg
100621 acaaatggga tctaattaaa ctaaggagct tctgcacagc gaaagtaact accatcagag
100681 tgaacaggca accaacagaa tgggagaaca tttttgcaat ctatccatct aacaaagggc
100741 taatatccag aatctacaaa gaacttaaac aaatttacaa gaaaaaacaa acaattccat
100801 caaaaagtgg gtgaaggata agaaaagact cttctcaaaa gaagacattt atgcagtcaa
100861 caagcatagg aaaaaaagct catcatcact ggtcattaga gaagtgcaaa tcaaaaacac
100921 aatgagatac catttcatgc cagttagaat ggccatcatt aaaaagtcaa gaaacaacag
100981 atactagaga gcatgtggag aaataggacc acttttacac tgttggtggg agtggaaatt
101041 agttcaacca ttgtggaaga cagtgtggta ttcctcatct tcaccacggg gtggaggtac
101101 gnnnnnnnnn nnnnnnnnnn nnnnnnnnnn nnnnnnnnnn nnnnnnnnnn nnnnnnnnnn
101161 nnnnnnnnnn nnnnnnnnnn nnnnnnnnnn nnnnnnnnnn nagaaacata gaccctgccc
101221 aacgcatatt cctgaaaggg atggcaaggt tttttaaag gttttatggg tttaggtgta
101281 ctctaaagga ttttaaccct tctaaaatta tttttgtata aaggtgtaag aaagggatcc
101341 aacttcactc ttttacaaat gggaagccag tttttcccgg cccctttttt taaaaaggat
101401 tccctttccc attggttgtt tttttcaagg ttgtcaaaga tcagaaggtt gtagatgtgg
101461 gttggtaatt tttaggggtt tgttttggtc ccattggtcc ataggtcggt tgtggtacca
101521 gggccatgtt gttttggtta ctgtaagcct cgtagtatgg tttgaagtca ggtagcatga
101581 tgcctccagc tctgttcttt tggcttagga ttgtcttggc aatgcgggct ctttttttggg
101641 ttccatatga actttaaagt agtttttccc aattctgtgc agaaagtcat tggtagtttg
101701 atggggatgg cattgatcta taaattacct tgggagtatg gccattttca tgatattgat
101761 tcttcctatc catgagcatg gaatgttctt ccatttgttt gtgtcctctt ttattttgtt
101821 gagcagtggt ttgtagttct ccttgaagag gtccttcaca tcccttgtaa gttggattcc
101881 taggtatttt attctctttg aagcaattgt gaatgggagt tcactcatga tttggctgtc
101941 tgtctgttat tggtatataa gaatgcttgt gatttttgca cattgatttt gtatcctgag
102001 actttgctga agttccttat cagcttaagg agattttggg ctgagacgat ggggttttct
102061 agatataaaa tcatgtcatc tacaaacagg gacaatttga cttcctcttt tcctaattga
102121 atacccttta tttccttctc ctgcctgatt gccctggcca gaacttccaa cactatgttg
102181 aataggagtg gtgagagagg gcatccctgt cttgtgccag ttttcaaagg gaatgcttcc
102241 agtttttgct ccttcagtat gatattggct gtgggtctgt cataaatagc tcttattatt
```

FIGURE 2 (cont.'d)

```
102301 ttgagataca tcccatcaat acctaattta ttgagagttt tcagcatgaa tggttgttga
102361 attttgtcaa aggccttttc tgcatctatt gagataatca tgtgtttttt gtcattggtt
102421 ctgtttatat gctagattac atttattgat ttgcgtatgt tgaaccagcc ttccatccca
102481 gggatgaagc ccacttgatc atggtggata agctttctga tgtactgctg gattcggttt
102541 gccagtattt tattgaggat tttcgcattg atgttcatca gggatattgg tctaaaattc
102601 tctttgtttg ttgtgtgtct gccaggcttt ggtatcggga tgatgctggc ctcatataat
102661 gagttaggga ggattccctc tttttctatt gattggaata gtttcgccaa actgacatga
102721 tttttaaaat tccctatagg gtcaatgtgc agatttaaag atccctacac tcagtagtcc
102781 tgggataggg tcgggggatc catatgttta acaagcagcc tagagtctcc cgatagcctg
102841 ggcaagcttt aaaaagccct gcggacattc ggatgaaaca aaggtgcaca gaacctatat
102901 ctctgccatt tattagctgg gggccttagg caaggaaggt agtcaacctc cgtattcctc
102961 agttcctcaa ctgtaaaatg gggatgatga ctgtggctcc ctcgtggggt tgtgacggag
103021 gaacagggga catatgtcct gggatcagca ctggcaattt ggccattctt accatagcac
103081 ctgccatctt ggtgacagcc tggacacaaa gccttcacac ctttgaagtg gccatagaga
103141 gcatgagata tggatgggga ggaggcattc caactaaaga cccctgcttt gggccaaaaa
103201 cacatgtatg tctggtgtct ggagtcctct ggttatgcct tttttaagat accggttgtc
103261 ctgcaattgt gcgttgagaa tccactctat ggccaacata tcatcaaagc gtttggctca
103321 gctaggctgt tcccccaacc caaggacccc atgaggaaag gagtgagggt tccacccccca
103381 gcaccagcca ctggaggggc tgcccagagt ccctcagttc tcgtaaactt acgctttgga
103441 gtaattcaga acaaagtcca ctcctttttc actatcaaac tggatatcac ggggtaaatc
103501 cttgtggcat ttggcatcga tgctcaaggg gaagccaggg ttccactcca tccatctgag
103561 catgagaaag gagaagaaat tgagttaaat gccagccttt ggtctgcccc ctcagctgag
103621 ggccgcccac actgtcagac gatgttacac agggagattg atgtactcaa aataaagtca
103681 acacatcata ggctgacccct gtgtccagta aggttctggg acctcttcca aagtccagtc
103741 gcaccaactt tgctgtgccc tgagcatcag agtgggaacc ctgagactgg gcttatagtg
103801 gtacaggtgt gcaccactgc ataaaaagtt ctgtaggtag tctagggaga cctcacttac
103861 tagaggtgac attgaacagt agaggcctgc cttgccagtc actggaggta gaaggtatta
103921 aggctgccca gccacgccca acctggacat ccaccattct gccaacttga tcagtgtgtg
103981 ccctggactg cgtgcatgtc ctgcatgtgg catttgggga aatgggacag ttcttctgcc
104041 ttcacaatag gacgacacgg cagcaggtgg cctgggagag ggacccaggc acagatggct
104101 aaaaggcttc cctctctcac ctgctggcca atagcagctt tagagattat tacaatcaaa
104161 acagcttccc caaagacaag ccacggactg catccagtaa acatgctcag atcctgacat
104221 ccttgaaacg tatcccgtgg cattgggcat ttgtgttttt gaaaaatgtt tattttgctt
104281 ttttgtttac ttattgagta aacttaaatt gtgaaaatgt cagaggtgtt tgaaccacag
104341 caactccatc ttgaataggg gctgggtaaa ataaggctga gacctactgg gcagcattcc
104401 caggaggtta ggcattctaa gtcacaggat gagacaggac attgatgcaa gatacagggc
104461 agaaagacct tgctgataaa atgggttgtg gtaaagaagc cggccaaaac ccaacaaaac
104521 taagatggtg atgaaagtga cctctgttca tcctcaccac tcattatatg ctaattataa
104581 tgcattagca tgctaaaaga aactcccacc agtgccatga cagtttacaa atgccatagt
104641 aatgtcagga agttacccta tatggtctaa aaaagggagg aaccttcagt tcctggaatt
104701 gcccacccct ctcctggaaa actcatgaat aatccactca ttgtttagca catgatcacg
104761 aagtgactgt aagtatgctc agtcgagtag cccatgctac tgccttgcct atggagtagc
104821 ctttctttat tgctttactt tcctaataaa cttgctttca ctttatggat tcaccctgaa
104881 ttctttcctg tggaggtcca agaactctct cttggggtct ggatcaggac cccttctgg
104941 taacaaaaac aaaatgaaat cctgttagtt tctttgggga gggagaatga ttttgtgttt
105001 gtttaaaaac cagattttac attttagggt tttagctttt tcatttatat tcctaattct
105061 ccttcctttt aaaattttct tttgagagga aagtaaaata tcgagatttt gggtcttaaa
105121 aaagtcctga gttattttaa tatgatcttg tgctttgact ttccccaaat cccaactgtc
105181 acagtgtcct cttggcccag tagcctctcc ttaggatcac aagaagtgaa cagggaccgg
105241 gtatgatcct tctgacagca aaggcatttt gtcaagtgtt ttctgttatg tggcacctta
105301 catttctcac tgttggttta tttagaatat tctacgtcct cagattttaa gaaaaccttc
105361 catttttgct gtttgtatta atgccaatga tagtatatta acaaggataa aaatgtggac
105421 aagtctacac attttttgtt tgtttgtttt ggaaaatgac tcaaggcatc tccaatatat
105481 atctaaaatt gagccattca gtagcctcac tggtagtaat gatcaattaa ttagctatca
105541 ttagtcatat caatttaaat attactgatg attttctctt tgcctggaca gttcaagggc
```

FIGURE 2 (cont.'d)

```
105601 tctagttaat tttaaaagct cagtggagct agatgttttt cagtatgtaa acaatgagcc
105661 atgcaagggc atctgtgcca gcaaatggca ttaatgtttt cttaagtgaa tagtccactt
105721 ggacggatgt ggaatacttc ttcagcacca aaaagacctt cttgccccat gccctgccct
105781 ggtctatgga gggtggcagc accaatgggc agaaatgccc cacttgtgtg gttagaagat
105841 gatggcctca cagcacatgg agacaggaca gcttgcttgc tagttcacta ctgccccccct
105901 gaaaccaaat gtttatgtcc cttccactgc aggtcactgc tgcttaagag accctgacag
105961 gctgacctgc acaggagccg aaggcctgca tggccacaga cattaactgg tggagatgga
106021 atcccactcc attgaggaag accaagtgga acacccaggc agaaggaaca aagaagtaga
106081 aaggcattta atttattgga aaaaaaatga gagagagaga gaaagagaga gagagaaagc
106141 aagagagaca gagagacaga gagagagaga gagagaaaga gagagagaga aagcaagaga
106201 gacagagaga cagagagaga gagagagaga gagagacaga cagacagaga gatcctaagg
106261 ggatgcagtt agtataattg gagtgtaaaa agactttctg taaccacaaa catgatttct
106321 gaatgaagac ttcaatagag aaacagacaa agagaataat cactgtgaga tgtttggtct
106381 cttgtattaa aagaaaagct ttagacaaat taaatttagc agtttaattg agcaaagaac
106441 aattcaagaa tagggcagcc cctaaaccag agcaggctcc gagtgacttt gatgctgtct
106501 catagttgga taggatttat gggcagaaaa aggaacgtga tgtacagaaa atggaagtga
106561 ggtacagaaa cagccagatt ggtgatggct cagcatttgc cttacttgag cccagtttga
106621 acagctggcc actgtgagtg gctgaagtct ggccgctgtg attggctgag acttggttac
106681 ttgctatgag agtaggtgac agtctgttta cacatccagt taggttacag ttcactatgt
106741 acagagaaac ttttaggctg aatttaaaat atgtaaggag aaaagtttaa gctaaactca
106801 ttaacaccta gaagagagaa ggtgttcatt cgacaactaa ttatggagca cctactatgt
106861 gccaggaagt gctttgtgca aaatagaaga acatgtaacc caaatacagg gtgaaactac
106921 aaagaaatgg aagccataaa tgaaactatg agagacataa accaaaaata aaattctaag
106981 cccctgaact gactgatgga ccctcccctt ggccaagggc attccaaagt taacctgaaa
107041 aattagttca ggccatgata ggaatgggtg gctaaacgtg cctcattgta ctctcctcct
107101 cttggaattc aggcacaact gatcagcatt cacatcaaca cagagatgtt aagcccatta
107161 gaacagactc tttaagattg ataagaaaca tttacaattg attctacctg aagcctgcta
107221 cctggaggct tcatctgcat gataaaaaac tttgtttcca caacccctta tcttaaccta
107281 gacattccaa gtttttagat aataattctt ttaagcagtt gccaatcaga aactctttga
107341 atctgcctat gacctggaag ctcccctccc ccaagttgtc ccacctttcc aaaaccaaac
107401 cactgtccat cttacatgta ttgactgatg tcttatgtct ccctaaaatg cacaaaagca
107461 agctgtaccc caaccacctt gggtgcatgt tctcaggatc tcctggggct gcatcatggg
107521 ccactggtca ctcatatttg gctcagaata agtcttttca aatatttcac agagtgtgac
107581 tcttttcatt aacagacatg aaagccagat acagatgtaa tatgcaagga gtaaaagctc
107641 caaaaggaga gagagtaata tatggagaag tgaaaaaaat caaagaaata aaagaagaac
107701 tcctttaagc tgaaaaatac ttcaatatct taagtctgtg aaaggaaatt aaattttagg
107761 accccaaact catttagcca aagggaaatg tcaagctggg aactgtgtca tgcaaacctg
107821 cctccccctt ttggttccta aataagatgg ctatgatgaa aagctacatg tctccaccat
107881 attttgctca caaggaaatt cctagtgaac cgttaaaatt tcaccatggc aatgcaaatt
107941 gatagcttat ctttacaagt gcagtcaccc accagataca aatgcatatc tgattgttcc
108001 cctgccttac tttatctatg ttctcttatg taaaatgcag actccctgca tttttcctct
108061 gcctcatttg tttatgtcat cttatgttaa aaaaaatgca gattcactga gccagagaaa
108121 ggcatgaata actatttttc cctgccctgc tcttacatga aaattgtgta cttctcaata
108181 tcccgcccct ttccctttaa atttggagcc ctcaaaatca ccttcagaga aaggcatagt
108241 gctgtctccc gggcatgcgt ccttaacttt cgcaaataaa tttcctaaaa tgattgagac
108301 ttgtctcgtc atttttctca atgacaagtc ctaggtgggg gggaaaaaaa aaaaggaaaa
108361 agatacacct aggtatatac tgaatacatt ttaaaatgtc caagagacag gagaaacaga
108421 gacagagaga aggaaagaga tgcagagagt gaacgagaga ggaagaaagt gggggaggga
108481 gggagataga aactctagga aaagaaacaa actatcatta gatttctcct ctgtcattct
108541 gaaaatggga agactgaagt gtatacacac tttttttaga tcgtcatcta agcctctcat
108601 attgtcatca atgagggcag gggaatttgt ttgaggggat gggtaggggg acaggacgac
108661 aagcacagac tcagatctta cactacacat ggaccttctg aggaaattaa ttgaacaagt
108721 tcagctgaac aaaaattaaa ttagaatgaa tcaataaact cctaaataca gcaaagaata
108781 tgcattataa aactacagca aatataatag taaacaaaga aacaaaaata tgagagggat
108841 gttcatcact actaccacta cttgttttgg gaattccaga catggaataa gaaaagaata
```

FIGURE 2 (cont.'d)

108901 tcagtggtgt agataatgga aagtaagaga caaaattatt aacatttaga taatatgagc
108961 acattaacta accagactca ctaacaacaa acaaacaaaa acaagtgatt agaaccaatg
109021 aaagaattca gtaagggacc aacacacagt aaatgtaaga aacaagtaat ttacatttat
109081 cccagcaata tttttgcaaa cagaaaaata tcctactcag aacagcaaat gctaaatgta
109141 gagtagctag aaaggtgaag gacctgcatg aagaaaacta gaaattctat ggaagtacgt
109201 tgacacagga tctagagagg tggaaagaca cgctgtgttc ctggatggaa agactgaatc
109261 tcagtaaaat gccaacacat aacacagtta tgtgaagttc aaagtaattc tcattatgaa
109321 aaacttaaga aagaacagtg agatatgtaa cagacattaa catttattag aaagttatga
109381 taaccaaaag ctggtgctgg ggtctcgagt agaaaaatag gctaacacat aaagtgcgga
109441 aacagaccca gagactatgt atacataata caaaactcgc caacacttat ccagtgcttt
109501 ctatgtgcct actactattc tctgtgtttt catggtttaa cctattatct caaaccccta
109561 aaaggaaggc actgttattt ccctcatttt acagatgagg gaagtgaggc acagacagat
109621 taaacaactt tcacaggact ggagaaagtg ccagtaagtg tgagttgagc ccagacactc
109681 gaatccagag ctcatgactg ccatcctatg ccagcttgta ccgtgggtat catcatccct
109741 gtcatccaag tcaggaggaa agacatcatc cctgtcatcc aagtcaggaa cgaatgctac
109801 cgggagagtt ccacccaggt atgtatgaaa acacgtggca ggagtggggc atggtggcgc
109861 acgcctgtag ccccagctac ttgggaggct gacgtgggaa gatggattga gcctgggtta
109921 gtttgaggca gcagtgaacc atgatcatgc cactgcactc cagcctagga aacagagcaa
109981 gactctgtct caaaaaaaaa aaaaaaggta gatgaatgaa agctctaaac tcaaagggga
110041 aattataaaa gtattagaca aaattacggg ggaagtattt gtgtaacact gggatggaaa
110101 gggttttctt aagcaaagga ggaaacccaa aagttataga tgtaaacaat acatagttaa
110161 taaaataaag aactaaaatc tcctgtggca aaagcaacag aagacaaata ataaatgcta
110221 tacatatgta acaaacggat actatcctga tatagaaaga gctcctttag attaataatt
110281 gaaagaacaa tagggaaaaa aagcttataa ataggcaatg cagtgatgct tattagtggt
110341 caggggagtg cagactaaaa caaccacaag gtcttaggga tttttagact gtcaaacaag
110401 gtcatcgggt actgacaaat gtatggatgg gcaaaagtat cttttcatac acagctggta
110461 ggaccgcaaa ttacgataca attttgtgaa aggatttttg tcggtatttc ttaagatgaa
110521 aaaatgctga tttgttccag caatctgagt tctggaaatg gatctgccat taattaaagc
110581 accagtacat caagatgttt gtacaaggtt ggttctggca gcattgtttg tactgcaata
110641 cccaaaacaa acaaacacat ctacaaatgg gaaatgaact gaacgtcagt gaatagggga
110701 atggctaagt aaattatggt gcattcccag aaggcaagaa atagtagcag tttaagaagg
110761 ggaaaatata tgagatacta tttcacacgc aagaatgaaa acatctgaag atgcgaagtg
110821 ttgatgatgc agggaaacag tgaatctcag aaacagttac tggggtgtct actggcagaa
110881 tgcctttgga aaacaatcag caatatctag aaagcttaaa aacacgtggt ctgcaaccct
110941 gcaactctac ttcttggaat attccctaca gtaactcttc catgagagca cagagagatg
111001 tgtgagaaag ctcactgtcg cttggtttgc aacagctaga aattaaagac agcccgcctg
111061 cccatcagca ggagagcgga cgagcgcatg ggttattcag atactgatat gccatgaaga
111121 agttaactgc atgaaccaca tctatctgtg tcaaccagat cctcttcaat acttagtgat
111181 gagtgaaaag tgcaggtcac ataatgatta gattaaatta tatcgattaa caaacaccta
111241 cactttgcca tttactgctg tgtgtgagtg tgcatgtaac acagacagat gtggtcacag
111301 tgggagagca caagctgtgg gctatgacct gggtctgctt ctccttctcc ctgcgtggct
111361 gagtgagtaa ggagggcctg caagaagcgc cagctttctg acatagtgtg gactattctt
111421 agtcattgct ttacttccaa actctgatct ggaagcctga gaaatcttct gagaaagagg
111481 aactccaaga ttgtgcagac agtgcaaagt tcagtgtttc ctgaacggaa gcaaaggacg
111541 gtttctgaaa aggacagatg agtggaagga ggaagaaaaa aatgattaaa tctaagaaac
111601 ggggaaacga tctcaccaga agccccctgc tgcaagatta tgataatgtt aagtagctcc
111661 cagataattg ggctagtttg tgttatctta gatgagtaga tagcaaagtc taattagagc
111721 cccactaatt catactaaag tgttagtggc ttataacaaa ttaaatgaat tttatgggca
111781 ttttatctta acccagattc acaggccaga agtgctctga gaactggctg caggggcttt
111841 gccataggtg tctgaaacag ggagggaagc caaggaagaa gcatagaaac aacagcccctt
111901 tgggatggga ggcagagctc aagcacaacg tgtgcactgc accaggtatg gaagtctgga
111961 aacacatcat atggtgcctg agctgagagg cttgtgcaca aatactctaa aacaaatcac
112021 acatttataa acccttaaca tgacccacag cacagcaggt tactctccca cacttgatgc
112081 taatggcatg taagttttat ttttgatttt tcaattggga aatagaatat ataaaatatg
112141 tatggatatg tatatatgca cacacacact cacacatgca gaaaaatgta caaaacacct

FIGURE 2 (cont.'d)

```
112201 gtacgaacac catccaggta aaaaatcaga acattgtccg taccctcacc cccacctttc
112261 ccaatcaacc ctccttccat ccccggtaat gaccatcctc ggctttatga taatcatttt
112321 cttgttattg tttaaggttc cgctatgaca cacctcccta aacaatttca ttccaaagtt
112381 atgaattggc cagacacgct cctggcttct ttccttcaac actgcgtcag tgaggtttgt
112441 ccatgttagc agcagtttgt tgattttcct tgcagtgtag aattttcctt gacaatttgt
112501 ctgttctact gtttgttgga cattgagttg ttgccatttt ttggccatca tgagtaatgc
112561 tgttgtgagt atccaggcgc acatgcacac aaatttggat cccactatag gatttctggg
112621 tcatagatta taatgtagct tcagttttat gacatattgc taaattgttt tccacggagg
112681 tcttaccaac ttgtcctcct gccggtggta tatgagtgtt cccagccctc tggatcttct
112741 ttaatactca ggtgttgtca gttgttgaag tgttgcccat ctgcggcgcat atgtgtggta
112801 gtagcagcag ttcactgtga tcttctgatt tccccgagtc ctaatgaagt tgaacacctt
112861 ttgtatactt gctgcttata ttttgtacag taagtactca aacttcttgc ccattttcta
112921 gtgaatgaca ctccccttct taaagatttg taggtccttc acatactagg aataattctc
112981 gtcaatcact ccatgacttg ccttcactct ctcctggtgt ctttcaatga acagagtgtc
113041 cttatcttga gggaggcaaa cttaccaatc ttttcctttg tgtttaatat gttctgagtc
113101 ttgtttgaaa aatcctttta gcttgagacc tggaagaata atcacctgta gtctaaatgt
113161 cttacagttt tgcctttaac ttttaagtct aatcaacccc aagctgagtc tcctgaatgg
113221 caagaggtgg agtctgattt cttctccttc tccttcagcc ctccgtgctg gctggcccct
113281 gtcctcgaga tgcatgtcca gtggcccagt gccacccatc agccgagccc tccgtagcag
113341 acccagtacc cacatacgtg tggctgtttg ttgtttcttt attctgtttc aaggaatgtt
113401 tttgatgaaa agggggatga agctaagaca gttttgaggt ggggcaattg tgttcttggt
113461 gtgggatttc tcaccccttg acagcagtgg gtggctgggc atagggggaag aaggagctac
113521 agggttgagg gatgctgttg caacttagaa aaattaagaa aaatgaagat attgctcagt
113581 tatggcaagt gtttgatgaa acagggaccc atacatggct cgtgaaaact ggttaaagat
113641 tttttttttt tttttttttg agacggagtc tcgctctgtc gcccaggctg gagtgcagtg
113701 gtgcaatctc ggctcactgc aagctccgcc tcccaggttc acgccattct cttgcctcag
113761 cctcccgagc agctgggact acaggcgccc gccaccacgc ccggctaatt ttttgtattt
113821 tttagtagag acggggtttc accgtgttag ccaggatggt ctcgatctcc tgacctggtg
113881 atccacccac ctcagcctcc caaatggtta aagatttttg aggagaaatt tgtcaatgta
113941 tactaataac ttttactatt tggtaatttc atatctgggc atctgtccta ggaaaatact
114001 taataatgta tacaaatttc acatacaagg gttttcactt tgcttataag aatacaaaaa
114061 ttagaaacct cctaaatgtc cagggaagct gggtgtttaa gtgaatgatg aggcatccat
114121 ccaatggaat agtacataga aactagaata atgtttatga tgagattttg aaaatatggg
114181 aaaatgattt ttgctacact gctaaagggc agcaaggagg atgcaaagtg gtatatatag
114241 cacaatccca aattttaaaa agtgaataag acaaagtgaa aacaattaaa catgaatttt
114301 tatgaaaaag ttcataaaat tcataattca tacagaaaat aggtattttt ctggctctat
114361 attattttcc ttcttttact tttttgagtt aaaaaaacaa cccagatata ctacatattc
114421 cttgtaagaa gttcaactat tgagggatat gtagaaaagt atcacaatat tggctcccaa
114481 aggcccctcc acagcccagg taacttcact gtccatgtag aatgattcct tccactttct
114541 tcccttggaa ggaggcacag actcaaatgt ttccaggggc caaagcagga aatgaaatga
114601 aagaaaacct tgatatagac aacagacaag tgtggactgg ggaagcctga agaatatctc
114661 tgtttactca taagtcaata atgatccatc aaacacttgt agaggctgga tacagcccat
114721 cagccaccca tttccagagg agcactctgt aatgtgttat tatcttccaa aaagctttac
114781 tgagatacat ttacatacca ttaaattcac cccttaaaaa tatgctatca aaagatttta
114841 atatatttgc agagttgtat gtgtaaccat cattataacc caattctgaa ataatctcat
114901 ccccagagga cacctcgaac ccattaacat tcactccttg tttcccctcc ccaactccta
114961 gtgctaggca actactcacc tactaacctg actctgtggg tttgcctatt ctggacattt
115021 catacagata gaatcacaca atatggggtc ttccgtaagt gagttttcca tttagcatat
115081 ttttgaagtt cattcagtgt ttggcatcta tctgtagttc atttcttttc ttttcttttc
115141 tttttttgaa atggagtctt gctctgtcac ccaggctgga gtgcagtggc gggatctagg
115201 ctcactgcaa cctccgcctc ccgggttcaa gtgattctcc tgccttagcc tcccaagcag
115261 ctgggattac aggcgtgcac caacatgccc ggctaatttt tgtatttttg tagacatggg
115321 gtttcaccat gttggccagg ttggtctcaa actcctgacc tcaagtgatc tgcccgtctc
115381 aacctcccaa agtgctagga ttacaggtgt gagcctccgc gcttggcatt cattcctttt
115441 tgatgccaaa aaatatccca ttgtatggat aaactatatt ttgtttattc attcctcagt
```

FIGURE 2 (cont.'d)

115501 taatggaatt taggttgttt ctactttttg actattgtga acaatggtgc tataaatatg
115561 tgtgtacaag ttttgtatag acatgtggtt tcaatattct tgggtagagg cctaggagta
115621 gaattgctgg gtcatattgt agctgggttt cagattttga ggaaccacta aactgttttc
115681 tgaagtggct gcatcatctt acattccggt agcagcatca gggttccagt ttctccacat
115741 ccttggcagc acttgttact atctgtcttt tttattctaa ccattttagt ggttagaatt
115801 gtatcttgtg gttttgattt gaaatttcct gatgattaat aatgttgagc atattttcac
115861 gtgcttattg gagattcaca aattttctct ggagaactat ttaattaaat cctttgctaa
115921 tttttaaacg ggtttttttg tacagaatat tttaaaattg agttgtcaga gttctttata
115981 tattctggat acaagtccct tatcagacat atgatttaga tattttctcc attctgtgga
116041 ttgtcttttc actttattga tgatgtcctt tgaagcatag atcttttaca ttttaatgac
116101 atctaacttg tctactttct tttgctgcct gtgctcttgg tgccatatct aagagacttt
116161 gccgaaccca agattatgaa gacttacttg tatgttttct tccaagagtg ttatgttgtt
116221 agcccttact tttagatcta tcatccattt tgaattaatt tttaaattta tctagcagcg
116281 ttattgaaat ataatgcaca tactgtaaaa tttatccatt taaagtgttc aattcaagga
116341 tgtttagtat taatttttac acaatggaca accatcagtt ttagaacatt ttcatccccg
116401 gcaaaaggaa cactgtatcc tttagctgtc actcccatga ccacttcctc attccctgcc
116461 cctaggcaac cagtaatcta ctttatatct gtacagattt ttcttttcca gaaatttcat
116521 ataaaaggaa tcatacaata tatgatcttt tgtgactggt ttctttcact tagcataatg
116581 tttttgagat tcatccatgt tgtaacaagt gtcagtattt cattcttctt tcatggtcaa
116641 attatataga tatactatat tttatccatt catccattaa tggacgtttg ggttgtgtac
116701 actttttgat agttacaggt catgctgcta taatcatgca tgtacaagtt tttgtgtggg
116761 catatgtttc catttctgtt gggaatatgc ttaagagtgg aaatgctgtc atattgtaac
116821 tctctgttga acagtcagga gctagcagac tgtttcccaa gcagctgtgc cattttacat
116881 tcccaccagc agtgtatgag ggttctgatt tctccacatc cttgtcaaca cttgttcttg
116941 tcggattttt ttattctagc catcctagta tcaagtggta tctcattgtg gtgttgattt
117001 gcatttccta gatgactaat gggtccttgg agaaatatct attcagatcc tcactcattt
117061 ttttcatttt ttaattggac tatttgtctt tattgagttg taagagttct ttataaatta
117121 tggatggaag gcccttatca gatatacaat ttgtaaatat ttcttccatt ctgtggttca
117181 tctttttcact ttcttgatgg tgtcctttga aacataaagg tttgtaaatt tgatgacatc
117241 actttatcac tttatctatt tttcttttgt tgctgatgct tttggtgtca tatcaagagt
117301 cctttgtcaa atccaaagtc atgaaggttt actcctgtgt tttcttaaaa gagttttata
117361 gttttagctc ttacatttag gtaggtattt gactcatttt gtgttaattt atgtatatgg
117421 tgtgagctaa ggatccaact tcattctttt gcatgtggct atccagtttt gctaggacca
117481 tttgttgaaa agactattct ttctctgtta aactgtcttg ctgcttctgt caaaaattaa
117541 ttggccataa gtgtaagggc ttatttctgg actctcaagt ctatttcatt gatctatata
117601 tctatcctta tgccgatatc acattgtctt gaatactata gctgtgtagt aattttgata
117661 ttgagaagtg caagtcctcc atctttgttt tctttttatc aagattgttt tggctattct
117721 gggtcccttc catttccata tgaatttgca gaattgacag cttgtcaatt tctgcaaaga
117781 aatcagctag aattttgata agggttgtgt tgaacgtgta cattaatttg tggggtattg
117841 ccattttaac aaaattaagt cctctgattc atgaacatga aatgtctttc aacctattta
117901 gatcttcttt aataatgtta aacaatgttt tgtagtttca ttgtacaagt ctcagactac
117961 tttgttaaat ttattcataa atgtttactg tttttgatgc tattgtaaat tgaacttttt
118021 cttactttta tttcacatag ttggttgtta atgtatagaa aaacaattga ttatcttgta
118081 tcttgcaatc ttggtggttt attagttcta ataatttctt ttggtgaatg ccttcagatt
118141 ttctatatat aagatcatgt tatttgtaaa ttgtggtagt tttacttact gtactccatt
118201 gtgggtgcct ttacttatct ttttattccc taactgagct ggctagaccc tccagtacaa
118261 tgttgaatag aagtagcaaa agtgaacatc tttatcctgt ttctggattc agcctttcat
118321 cattaagtat aatgttaact gtgaattttc ttttttgtg tatgtggggg gacggagtct
118381 tgcttgtcac catgctggag tgcagtggca tgatctcagc tcactgcaac ctccgccttc
118441 tgggttcaag tgattctcct gcctcagcct cctgagtagc tgggactaca ggcgcatgcc
118501 accacacaca gctacttttt gtattttagt atagacgggg tttcaccatg ttggccagga
118561 tggtctcaat ctcttgacat cgtgatccac ccgccttggc ctcccaaagt gctgggatta
118621 caggtgtgaa ccaccacgcc cagcctaatt gtgaattttc aaacctttat caggttgagg
118681 acattttctt caattcctat tttttgagtg ttttatcatg aatgggtgtt ggattttgtc
118741 aaatgccttt tttgtatgtc tattgaaatg attatgtact ttgttttgtt ttgttattta

FIGURE 2 (cont.'d)

```
118801 ctctattgat atggtgaatt caattaattg atttttggat gttaaaccaa ctttgcattc
118861 ctgggctaaa tcccacatgt tcatattgtt taatgccttt tatatacttc tgggttaggt
118921 ttgctagtat ttcgttgaaa atgtttatat ctatattgct aagggatatt ggtttatagt
118981 tttcttgtga tgcctttagt tttggtataa tatgggtatg agacaatgaa ttgggaagtg
119041 ttccttctat ttcttaaaag agtttatgca agatcagtat taattcttta aatgtttgat
119101 agaattagcc agtgaagcta tctgggtctg ggcttctatt tgtgggaaat tttagaatta
119161 gtaattcaat ctctttggtt gtgattgttt tattcagatt aactatttct tcatgagtca
119221 gttttggcag tttgcgtctt tctaggaatt tgcgcatttc atttaactag tttgttggca
119281 tgcaattgtt catagtattc tttttatta atttttaattt ctgtattgat tttccctcat
119341 tttatgagtc tcatttttcc tttttattc atttttaattt ctgtattgat tttctcttat
119401 tgctcatttt aatggtttga atcctctggt cagttggctg aagagttgtc aattttattg
119461 ctgatcatgt atcactttta taattgaatt gttataagaa gacataagaa gtaagaggca
119521 acccctacaa tggagaacat taaggtacac tcaagctttt ctgcccattc ttcctacatg
119581 ccaatatggt tgatccaaag ttattttcat tactctcctc tccatctctt gtctggagtt
119641 gtaggtaagg tgaagtttgg ggattgtgca cccacactgg gagctggtgc cttggtgact
119701 ttccagcagt gacaggccat acactgtgga aagggtttat ttcataccat gctcttgaga
119761 tagaagaaac catggccccg tggccactcg atctgatgtc ataactcacc gatattgttt
119821 ttgccgtgtt tccagttctt tacgtcggtg ttgcttgaga atgtgaattt ggtcatctcg
119881 ggccaacttt gctgtaaaga aagaacaaca tgagaggagc ctgaggaaga acaataacaa
119941 tgcccaatgc caagtgttca ggcttccctc agatgccctg cccatgccga gtgctttatg
120001 tgcatgacct catttgagcc tcagagcact tccccaatta atgatgaaga aactgaggct
120061 tagggaagtt gtgtagcttt gctcttgaac tttacccaag gtcacacacc taattagtga
120121 attttctttt ttttttttta attctacttt aagttctagg atacatgtgc acaacgtgca
120181 ggtttgttac atatgtatac atgtgtcatg ttggtgtgct gcacccatta actcgtcatt
120241 tacattagtt atatctccta atgctatccc tccccttac ccccacccca tgacagacct
120301 tggtgtgtga tgttcccctt cctgtgtcca agtgttctca ttgttcaatt cccacctatg
120361 agtgagaaca tgtagtgttt gtttttttgt ccttgcgata gtttgctgag aagggtgatt
120421 tccagcttca tccatgtccc tacaaaggac atgaattcat ccttttttat ggctgcatag
120481 tattccatgg tgtatatgtg ccacattttc ttaattcagt ctatcattga tggacatttg
120541 ggttggttcc aagtctttgc tattgtgaat agtgctgcaa taaacatacg tgtgcatgtg
120601 tctttatagc agcatgattt ataatccttt gggtatatac ccagtaatgg gatggctggg
120661 tcaaatggta tttctagttc tagatccctg aggaattgcc acagtgtctt ccacaaaggt
120721 tgaactagtt tacagtccca ccaacagtat aaaagtgttc ccatttctcc acaccctctc
120781 cagcacctgt tgtttcctga ctttttaatg attgccattg taactggtgt gagatggtat
120841 atcattatgg ttttgatttg catttctctg atggccagtg atgatgagca ttttttcatg
120901 tgtctgttgg ctgcataaac gtcttctttt gagaagtgtc tgttcatatc cttcgcccac
120961 tttttgatgg ggttgtttgt ttttttcttg taaatttgtt tgagttgttt gtagattctg
121021 gatattagcc ctttgtcaga tgagtagatt gcaaaatttt tttcccattc tgtaggttgc
121081 ctgttcactc tgatggtagt ttcttttgct gtgcagaagc tctttagttt aattagatcc
121141 catttgtcca ttttggcttt tgttgccatt gcttttggtg ttttagacat gaagtccttg
121201 cccatgctta tgtcctgaat ggtattgcct aggttttcct ctagggtttt gatggtttta
121261 ggtctaacat ttaagtcttt aatccacctt gaattaattt ttgtataagg tgtaaggaag
121321 ggatccagct tcagctgtct acctatggct agccagtttt cccagcacca tttattaaat
121381 agggaatcct ttccccattg cttgtttttg tcaggtttgt caaagatcag atggttgtag
121441 atgtgtggtg tcatttctga gggctctgtt ctgttccatt ggtctatatc tctgttttgg
121501 taccagtacc atgctgtttt ggttactgta gccttgtagt atagtttgaa gtcaggtagc
121561 atgatgcctc cagctttgtt cttttggctt aggattgtct tggcaatgcg ggctcttttt
121621 tggttccata tgaactttaa cgtagatttt tccaattctg agaagaaagt cattggtagt
121681 ttgatgggga tgacattgaa tctataaatt accttgggag tatggccatt tttatgatat
121741 tcattcttcc tatccatgag catgggatgt tcttccattt gtttgtgtct tcctttattt
121801 cgttgagcag tgatttgtag ttctccttga agaggtcctt cacatccctt gtaagttgga
121861 ttcttaggta ttttattctc tttgtagcaa ttgtgaatgg gagttcactc ctgatttggc
121921 tctctgtttg tctgttattg gtgtataaga atgcttgtga ttcttgcaca ttgattttgt
121981 atcctgagac tttgctgaag ttgcctatca gctttaagga gatttgggc tgagacaatg
122041 gggttttcta aatatacaat catgtcatct ggaaacaggg acaatttgac ttcctctttt
```

FIGURE 2 (cont.'d)

```
122101 cctaattaaa taccctttat ttctttctcc tgcctgattg ccctggccag aacttccaac
122161 actatgttga ataggagtgg tgagagaggg catccctgtc ttgtgccagt tttcaaaggg
122221 aatgcttcca gtttttgccc attcagtatg atattggttg tgggtttgtc ataaatagct
122281 cttattattt tgagatacgt cccatcaata cctaatttat tgagagtttt tagcatgaat
122341 ggttgttgaa ttttgtcaaa ggccttttct gcatctattg agataatcat gtggtttttg
122401 tctttggttc tgtttatatg ctggattaca tttattgatt tgtgtatgtt gaaccagctt
122461 tgcatcccag ggatgatgcc cacttgatcc tggtggataa gctttttgat gtgctgctgg
122521 attcggtttg ccagtatttt attgaggatt tttgcatcga tgttcatcag ggatattggt
122581 ctaaaattgt tttttttgtg tgtgtatctg ccaggctttg gtatcaggat gatgctggcc
122641 tcataaaatg agttagggag gattccctct ttttctattg attggaatag tttcagaagg
122701 aatggtacca gctcctcctt gtacctctgg tagaattcgg ctgtgaatcc atctggtcct
122761 gaacttttct gggttggtag gctgttaatt attgcctcaa tttcagagcc tgttattggt
122821 ctattcaggg attcaacttc ttcctggttt agtcttggga gggtgtatgt gtcgaggaat
122881 ttatccattt tttctagatt ttctagttaa tttgcttaga gttgtttata gtattctctg
122941 atggtagttt gtatttctgt ggaatccgtg gtgatgtccc ctttatcact ttttattgcg
123001 tctaattgat tcttctcttc tttttttttt cttttttttt aattgatcat tcttgggtgt
123061 ttctcgcaga gggggatttg gcagggtcat aggacaatag tggagggaag gtcagcagat
123121 aaacaagtca acaaaggtct ctggttttcc taggcagagg accctgcggc catccgcagt
123181 gtttgtgtcc ctgggtactt gagattaggg agtggtgatg actcttaagg agcctgctgc
123241 cttcaagcat ctgtttaaca aagcacatct tgcactgccc ttaatccatt taaccctgag
123301 tggacacagc acatgtttca gagagcacag ggttgggggt aaggtcatag atcaacagga
123361 tcccaaggca gaagaatttt tcttagtaca gaacaaaatg aaaagtctcc catgtctacc
123421 tctttctaca cagacacagc aaccatccga tttctcaatc ttttccccac ctttcccccct
123481 tttctattcc acaaaaccac cattgtcatc atggcccgtt ctcaatgagc tgttggctac
123541 acctcccaga tggggtggtg gccaggcaga ggggctcctc acttcccagt aggggtggcc
123601 aggcagaggc acccctcacc tcccggacgg ggcagctggc cgggcggggg gctgaccccc
123661 ccacctccct ctcggacggg gcggctggcc gggcgggggg ctgaacccct cccctcccgg
123721 acggggcggc tggccgggcg gggggctgac cgcccccccac ctccctcccg gacagggtgg
123781 ctgccgggcg gagacgctcc tcacttccca gacggggcgg ctgccgggcg gaggggctcc
123841 tcacttctca gaagggggcgg ctgccgggcg gaggggctcc tcacttctca gatggagggg
123901 ctcctcactt ctcagatggg gcggctgccg ggcggagggt ctcctcactt ctcagacagg
123961 gcggccgggc agaggcgctc ctcacctccc agacagggtg gtggggcagt ggtgctcccc
124021 acatctcaga tgatgggcgg ctgggcagag acgctcctca cttcatccca gacgatgggc
124081 ggccaggcag agacgctcct cacttcctag acaggatggc ggccgggcag agacgctcct
124141 cactttccag actgggcagc caggcagagg ggctccttac atcccagacg atgggtggcc
124201 aggcagagac gctcctcact tcccagacgg ggtggcggcc gggcagaggc tgcaatctcg
124261 gcactttggg aggccaaggc aggcggctgg gaggcggagg ttgtagccga gccgagatca
124321 cgccactgca ccccagcctg ggcaccattg agcactgagt gaatgagact ccgtctgcta
124381 tcccggcacc tctgggaggc cgaggctggc ggatcactcg cggttaggat ctggatatta
124441 gcctgttcta cacagtgaat ctccgtcttt accattttat tatgttatat tagttctgcg
124501 tggtggtgcg cacctgtctc tctcatgcac tcggctatgc tgtagcatga caatccgtca
124561 gtgttgttgt ttcgactctt gagtcgcctc gacactcagt cttggtgctc cttatcatat
124621 ggagatcgtt ggtcgtcgtt tcttgtttgg gttttgcttg tgccttttct gtttattgta
124681 tcgcttatga tcgtgatgtt gtcttagttg cttgttggtc tctagtgtgt tttttgtgtt
124741 gtatcttgtt cttgcgttga gtgggttggg cgttggcccg aggctttctt ttggttctgt
124801 ggtgtctctg acgttttgtt gctctnnnnn nnnnnnnnnn nnnnnnnnnn nnnnnnnnnn
124861 nnnnnnnnnn nnnnnnnnnn nnnnnnnnnn nnnnnnnnnn nnnnnnnnnn nnnnnnnnnn
124921 nnnnntagat ttggacgtta tgttttgagt attttatttg attgggtatg gttagtagta
124981 ttgaggggca tgtgggttaa ttaggttttg tatagattat atttatttta tttattgtat
125041 tttaatgatt agatgttggt tttaacgtga tagatggtgg gtatagatta tagatgtgag
125101 tcggtgagct atatgggata ggtaggttgg gtgtgtcgtg cttctcgcgg cctctctcag
125161 cagtgtgctt cggcctcgag accaccaact caacatcacg tccatctcat ttcgcgctac
125221 gacacactca tgtctgtacg cacgagtgta tcttctcgcg agcgcttctg tctggcgtgc
125281 tgggggggcg tggggggggg gggcggggcg gggggagata ggacgtggaa gaggagagat
125341 ggcagagggg agatggcaga gggagagctg aatcttctct tttcttcttt attagtcttg
```

FIGURE 2 (cont.'d)

```
125401 ctagcagtct atcaattttg ttgatccttt caaaaaatca gctcctggac tcattgattt
125461 tttgaaggga ttttgtgtc tctacctcct tcagttctgc tctgatctta attatttctt
125521 gccttctgct agcttttgaa tgtgtttgct cttgcttctc tagttctttt aactgtgatg
125581 ttagggtgtc aattttagat cttccctgct ttctcttgtg ggcatgtagt gctataaatt
125641 tccctctaca cactgcttta aatgtgtccc agagattctg gtatgttgtg tctttgttct
125701 cattggtttc aaagaaaatc tttatttctg ccttcatttc gttatgtacc cagtagtcat
125761 tcaggtgcag gttgttcagt gtccatgtag ttgagaggtt ttgagtgagt ttcttaatct
125821 tgagttctag tttgattgca ctgtggtctg agagacagtt tgttatggtt tctgttcttt
125881 tacatttgct aaggagtgct ttacttccaa ctatgtggtc aatttcagaa taggtgtgat
125941 gcagtgctga gaagaatgta cattctgttg atttggggtg gagagttctg tagatgtcta
126001 ttagctccgc ttgctggaga gctgagttca attcctggat atccttgtta actttctgtc
126061 tcattgatct gtctaatgtt gacagtgggg tgttaaagtc tctcattatt attgtgtggg
126121 agtctaggtc tctttgtagg tttttaagaa cttgcttaat aaatttgggt gctcctgtat
126181 tgggtgcata tacgtttcgg atagttagct cttcttgttg aattgatccc tttaccatta
126241 tgtaatggcc ttctttgtct ctttgatct ttgttggttt aaagtctgtt ttatcagaga
126301 ctaggattgc aacccctgcc tttgttttcc atttgcttgg tagatcttcc tccaatccct
126361 ttattttgag cttatgtgtg tctccgcaca tgagatgggt ttcctgaata cagcacactg
126421 atgggtcttg actctttatc caatttgcca gtctgtgtct tttaattgga gcatttagcc
126481 catttacatt tatggttaat attgttatgt gtgaatttga tcttgtcttt acgatgttag
126541 atggttattt tgctcattag ttgatgcagt ttcttcctag cattgatggt ctttacaatg
126601 tggcatgttt ttgcagtggc tggtaccagt tgttcatttc catgtttagt gcttccttca
126661 ggagttcttt tagggcaggc ctggtggtga caaaatctct cagcatttgc ttgtctgtaa
126721 aggattttat ttctccttca cttatgaagc ttagtttggc tggatatgaa attctgggtt
126781 gaaaattctt ttctttaaga atgttgaata ttggccccca gtctcttctg gcttgtaggg
126841 tttctgccga gagatcagct gttagtctga tgggcttccc tttgtgggta acctgacctt
126901 tctctctggc tgcccttaac atctttcct tcatttcaac tttggtgaat ctgacaatta
126961 tgtgtctcgg agttgctctt ctcaaggagt atctttgtgg tgttctctgt atttcctgaa
127021 tttgaatgtt ggcctgcctt gctagggtga gcaagttctc ctgcataata tcctgcagag
127081 tgttttccaa cctggttcca ttctccccat cactttcagg tacaccaatc agatgtagat
127141 ttggtctttt cacatagtcc catatttctt ggaggcttcg ttcatttctt tttattcttt
127201 tttctctaaa cttatcttct cgcttcattt cattcatttg atcttcagtc actgataccc
127261 tttcttacag ttgatcgaat cggctactga agcttgtgca ttcgtcacat agttctcgtg
127321 ccatgttttt cagctccatc aggtcattta aggacttctc tacattggtt attctagtta
127381 gccattcgtc taatcttttt tcaaggtttt tagcttttttt tgcgatgggt tccaacttcc
127441 ttctttagct gggagaagtt tgatcatctg aagccttctt ctctcaactc gtcaaagtca
127501 ttctccatcc agctttgttc caccactcgc gaggagctgc cttcctttgg aagggggagag
127561 gcactctgat ttgtagaatg ttcagctttt ctgctctgtt tttccccatc tttgtggttt
127621 tatttacctt tggtctttga tgatggtgac gtacagatgg ggttttggtg gtgtggatgt
127681 cctttctgtt tgttagtttt ccttctaaca gtcaggaccc tcagctgcag gtttgttgat
127741 gtttgctaga ggtccactcc agaccctgtt tgcccgagta tcagcagcag aggctgcaga
127801 acagcgaata ttgctgaaca gcaaatgttg ctgcctgatt gctcctctgg aagctttgtc
127861 tcagaggtgt acctggccat gtggggtgtc agtctgcccc tactggaggg tgcctcccag
127921 ttaggctact ctggggtcag ggagccactt gaggggggcag tctgtccctt ctcagatctc
127981 aaattccatg ttgggtgaac cactagtcac ttcaaagctg tcagacaggg acatttaagt
128041 ctgcagaggt ttctgctgcc ttttgttcgg ctatgacctg cccccagagg tggagtctac
128101 agaggctggc aggccttctg agctgcgatg ggctccaccc agttcgagct tgctggcaat
128161 gagcaaggct ctgtgggcat gggaccctcc gagccagaca tgggatataa tctcctggta
128221 tgctgtttgc taagactgtt ggaaaagtac agtattaggg tgggagtgac ccaattttcc
128281 aggtgctgtc cgtcaccact tcccttggct aggaaaggga attccctgac tccttgcact
128341 tcccaggtga ggtgatgctc acactcaatg ggctgccccc actgttctgc ccccactgtc
128401 caacaatccc cagtgagatg aacccagtgc ctcagttgga aatgcagaaa tcacccatct
128461 tctgcattgc tcatgttggg agctgtagac tggagctgtt cctattcggc catcttggaa
128521 ccagtctgaa ttagtgaatt ttcaacataa aactcaactc ctgtgctctt agccactcac
128581 tttacaaaag ccaaatccag ttcctcatcc tcttgcccac tcactcagca agccttgggg
128641 cccctgcctt tcagtgctta gagaatcatg ttcagatgca agagccaggc ttggttctca
```

FIGURE 2 (cont.'d)

```
128701 ctgggcttgg caggcacagt acatgcctaa ctctggcctg cgtgtgcatt tccacttgag
128761 gtcctaacct tccactcagc ccctcaagac tcttcaggga cctaagggcc cctggtgcag
128821 agctgccttt ttgctccagg agaaaggcat ttcgtggccc ttggtgggta tctttaaatc
128881 actgcagaat agtttactcc tcttctctga aattcttata ctgagcaaaa acgggagttc
128941 actctgggtt ttagtgttgc ctgtgagagc agcagttctc acagctctta tgtttctaag
129001 tccatttcat tgtttcatgg agaaatgtgt gacgatgaca caacccggtt tcctgtcgtg
129061 cctacacaga ggattgagaa tgagctccat tctaaaagag tgcagtgtcc tagatggctt
129121 tagaagagac acatgtgctt ggacttgggc tctgtcactg aagctgtgtg accaagagtt
129181 gccctgaccc cctcacatgt aaaatggaga tgataatgcc tacttctccg ggtcatggtg
129241 tgcatttggg gagagaatgc aggaaagccc tccacacggc gcctggcacg cagtaaatgc
129301 caatggatgg gaacaatgat cattatcatt atgcctatag tcatcactgg cctgagggtt
129361 ctgctcctcc ctctaagcct agctctgaga gcatcttatc tctcagcctg tcctgctgcc
129421 gtctctcact gcaggagttg gagcaggtag caggtagcta agggcggggc tgcttctcag
129481 agcctttaga gcagatgagg tcatatcatg accactcttt aaactattgc ttaaggccaa
129541 gcctgtgaac gcagcccata gagctgtgaa taggggagc ccagatctcc tgaaaacagg
129601 tcctggaata gtttctctag ctctcgtggt aaagcattgt gttttaaaac ttacttttca
129661 acacagatta ttatattttt gtaaaatata ataaaaatta attactagaa aaatgaaatt
129721 ttaaaaaccc aaagatattc aaaatccaag tctttttttt tcttattagg tgcaaaagtc
129781 acaaaattgt tctgttaagt tgctataaaa gtttctaaaa cccctcctct gagtctttgt
129841 attttatttt gtatttattt tatttttatt tttttaaga gacagggtct ccctctgtct
129901 cccaggctag agtgcagtgg catgatcata gctccctgca gccttgaact tcaggactca
129961 agtgattccc caacctcagc ctcctaagta gttgggacta taggcacaca ccaccacacc
130021 tggctaattt tttttttttt tttgagacag agtcttgctc tgttgcccag gctggggtac
130081 agtggcatga tctcagctca ctgcaagctc cacttcccag gttcacgcca ttctcctgcc
130141 tcagcctccc aagtagctgg gactacagtt gcccaccacc acatccagct aatttttgt
130201 atttttagta gagacggggt tttactgtgt tagccaggat ggtctcgatc tcctgacctt
130261 gtgatccacc cgcctcggcc cctagctaat tttcaatttt ttttgtagag atggggtctc
130321 tctacattgc ccaggcttgt gacaaaatcc tagactcaaa caatcctccc gccttagcca
130381 cccaaagtgc tggaactata ggcttcaacc tctgtactga tctaattgca gacctggacg
130441 cagttagttc tcagatgaca ctcaggccac attctgagct gtccacccga cagcacttcc
130501 aggctgagac atcttcatcc ttgagcttgg aactggggtc caaaaaggaa tattaacggg
130561 atacctctgc atcctcccct ggggatgtaa agccagccag gaggggaggc ttgaggccac
130621 agaaggcaag ctgagtatta atggtgacaa taactgttat cattggctat gggggtaatt
130681 ctggaggcac tcaacattca tcatctctta tctaccttaa ggaaccagct aatctcttgg
130741 gcaccttgac tctgaggagc tggatctctt cagtttcact ggtatgaata agtcagtaca
130801 tgcggaattg caacatgcca agtttcaaaa agagaatagt tctgtctccc ctggtcccga
130861 aggtgtttga agaatttatc caatggctga tgaagttctg ggagcacagc aggatgagaa
130921 agcctggact gacggcagaa gagctcagca gggcaggttc caaggactga cacagtgcct
130981 taatgaagct gtcccttcac acagatgctc tggatctgtg gggccacagt aatggccctc
131041 tgacattcat gttcacccaa ggtgtagtgg tgaaatatta gatttaaggg gtgatcatat
131101 ggtgagtaat tgaatcactt gtaggctggc ccccctcatt tccaggttgt tcaagggatt
131161 ggttgttttg ccatgtggtg gattaataat tggccacagc tggacatggt agctcatgac
131221 tgtaatccca gcactttggg aggccgagcc gggtggatca cctgaggtca ggagttccag
131281 actagcctgg ccaacatggc aaaacccttt ctctagtaaa aatacaaaaa ttagccaggc
131341 ttggtggcta cctggagcct gtaaaccaag ctccctagga ggctgaggca ggagaatcgc
131401 ttgaacctgg gaggcagagg ttgcagtggg ctgagatcgt gccactgccc tccagcttgg
131461 gcaatagagt gagactctgt cccaaaataa taataataat aataataata ggccacaaat
131521 tctttgacat tccttccatt gagagatggg ggggtctgca tcccccaccc cacccccgga
131581 gtctgggtgg gctctgtgac tgcttggacc agtagaatat gatggaagtt acagtgtgcc
131641 agtttccagg cccaagcctg aagagattgg cagcttccac tttctgtctc ttagaaaact
131701 tgctcttgga agccagccat catgtaagaa atgcaggcac ccagaggaca ccattctgtg
131761 agaagcctta aagaatgaga ctccatatgg acagagaggc caaggagcct agaggtgcca
131821 gacacatgac agaagaaggc ccagcccccct tcagctgatg ctacatggcc acagatgaac
131881 tgcccagtga agcctttcct aaattcctga cctgcaagag catgaacaaa attaaatggc
131941 tgtttaaagt taccaaggag gttggtttta cagcagtaga gagaatggaa cttgctggac
```

FIGURE 2 (cont.'d)

132001 agcttctcta tgctcaccct ccaacctgtg ctgtccctga aagtgattgg aatgagatgc
132061 ctcaatgggt tttccactgg gaactctgac cagaaaggag ggaatgtgta gaggaaggag
132121 aggccaatca ctccccagaa cctttctact gagggccgca gctcctccaa gggtgctgtc
132181 tccaggatac ttctgcatta ctcccacaac cttccccctc cccctgcatc aggactagtg
132241 gtgctgatgg ccccgcactc tgcatggtcc ctctgcacat gggcccacac ctttgtgatg
132301 cccctttgtt aaaccctcat cctagtgtac catctgtttt ttgccaagat gagctgaagg
132361 gtctgcagga agaagggctt cataaccgag accttgggta gatgtgcagg agggagtttc
132421 agagccagca ttttctaact accagaaaaa gagaagtgcc ctgtccacaa ccttccacat
132481 tctgttgacc acaggaataa atgaactttg tgattttttt tcctgtcatt aggtaggggg
132541 acaaaaatcc tcttaactcc atgttcagaa atattctgga aatttggttt cttaagtcaa
132601 attccacatc agaaacgatg ggatgtggcc tggtagctta agaacagcag gtacagaata
132661 acttttttct cctttgtctc agttttctta gctataaaat gggggtaaca gtcatctctt
132721 cctacctacc ccaccaaact tcgtgaagaa cacactagct acaggaaact tggcaaagag
132781 aaagagtttg acgctgtcat ggcagaagca gtggctttct cttattacgg tggctgcctg
132841 gcctttgaag gcttatcttt ccaggtttaa actgagagca agctgaaggg ttatgactcg
132901 aagtgaggta ggattttgcc aggcacacta ggaggctggg tatgcaaggt ggttcattca
132961 gggagccttg gctgaccttg acgcctgcgt ccgtctctga tgctctgtac caggtcagct
133021 gtgtgtccct aacaaagaat ggcctcctaa ctggggtctg cacatctggg catcttagta
133081 aggggaacag atttgaggtt cttctttctt tcagcgaaag gtgagacttc gggttgaaga
133141 actggtaact gtgatttgca ggcttgtcca tggctcctca gagctggcac ttggggtgct
133201 ccttgtccac cccttccctc cctaggccca catggggcac cctgagcttg cctgagccct
133261 actgtgatct cacggagggc aggctatgaa ctagaaagtg atgccacacc ctggcaacta
133321 gagaagtgcc catccagggg catgtcccat aggtatctgc ctgtatggac cctagttacc
133381 cactgacaaa aagaggggca caaccctccc ctgtagaact gtagcgcaga gtgaggacat
133441 gacgacagtg aggcctgggg ccacccgctc caccctcagg ggcttgtaag aatcccaagg
133501 aaagtcatgc ctcctgcagg tgtgtcgagg cacagggcag agccctccca cttcccgccc
133561 ctgcacagca gtgtcattcc tcctatgact acagtgcttt gaggacagga agaactttcg
133621 gttcttggga agcccggggc agaaggggcc tgagctgctc accgcgtcca tccctcagga
133681 caacctcgac atcgccggtg atccagcggt agcaggggaa ctcgatgtag tccccgtggg
133741 gcgtcttcag cgtgatgtac ttcaggtacc agtcgtcatt cagccagtac ttgcgcttct
133801 cgattctgac cagctggatc tcgcccagtt cctcgtccac agtcacgtcg tatgaatcca
133861 cctgggaagg agaacaggca atcaggccat gcgtggtctc ctgagccttt gttctggagg
133921 tgttaagaat ttgtcacccc aaggtatgct gctgtggcac agggactacg ttgaatgaaa
133981 agcacttaaa aaaacagcag gtgcaagata ctctgacatt cgtgctgttt cttagaagca
134041 ggagatgaaa gtcccctatg aaagatgtcc tcactatacc aaaaggaaag taacactctt
134101 ttcatcaagg ttgggaagtt gaagccaaag gaaatccata caaacagatc ttgtacaatg
134161 aacgcttacc tcccgagtca cttccctgcc cagttacctg ccctagccca agccccttgg
134221 ccttatcaca tctcacgatg attcattcaa tgcagtatct aaggggggatt gactctaact
134281 gcttcttggg gtcttcatct ttttaagagg gctcccatgc cacgtacaac ttgtattaaa
134341 gaaatctgta ggctttcgcc catgaatctg tcttatgccg attctcagac ctagctgaaa
134401 tgggaagagg tggagttttg cctccactac agttcatgga gccaagattc ttcatgaaca
134461 ccttaaatga actcctgaat tcatttaccc aagacattca ctgaaggcct gcccctgaca
134521 aggctcagtg ctacgaccca ggcaggtgaa agaaatggac aaatcctggg ccctgccctt
134581 gaggagagag aatccagtga gccaggatgg tgctgtgctg ctcagagggc aacgcctgct
134641 gactgcactt agctcaggct ggaggatggg gagatgccca ggctcatgcc tgcacctgcg
134701 aggctgtgcc cagtgagggt ccgcagctgc ccccacatgg gatagccttg tgggagacct
134761 ttacaactgg agatgggctt gctgacagtg gatccccaca atgactctgg gagtgcaggg
134821 gagttaccac cccttccaca gatgaagaca gcgaggctca gtgactccca cctctgccac
134881 ttgccagcag agctggagtc acaccccagg tctttccatc atagccactt cctctctttc
134941 cagttttcag tggggataat aagtgagtga aaatggtgag gcttagatac agggagcttg
135001 catggattcg agtcgtcctg ggacatttgc agttcacagc tgcatggtga tgcccagaga
135061 acagtgagac caagcagctc tgctgcacct gtggcattac tggtggcagg gtgaggctag
135121 ccttgcagct agaaggcacc accccaggct gtgtacagcg cagctgccca ggcctctggg
135181 acaaggctgc ttggccccct ccctgccagg ctcctgcttc caggacacag gcggctctga
135241 ggcaacagcc atagcttctg gagggctttt gtctctgcag caatggatgg cagacaggaa

FIGURE 2 (cont.'d)

```
135301 gttgggatga gaggctcagg cattgcatca cgcattctga tgaccagcag gtttggaaag
135361 ccccggactc gatgccctcc aaggcatgtt ctttttattt ttgaggtgga gtctcactgt
135421 gttgctcagg ctggagtgca gtggctcgat ctcggctcac tgcaacctcc acttccaggg
135481 ttcaagtgat tctcctgcct cagtctccca agtagctggg actacaggca cctgccacca
135541 catctggtta agttttgtat tttcagtaga gacagggttt caccatgttg gccaggctgg
135601 tctcaaactc ctgacctcaa gtgatccacc tgcctcggtc tcccaaagtg ctgggattac
135661 aggcatgagc cactgtgcct ggcccctgca aggcactttc taagccagat tcatcaaccc
135721 ttgaacttta tccctggcgg cagaacctag agttctcagc atgatggcaa agtggaaggg
135781 gcgaggggta tcatcctttg tgcgagcgca ggcatcccca ttccatgccc tgcctccaag
135841 ctgccaggag gacccctgga gggcttccta agaggaatgg gaacttgagt gttttccaca
135901 aacctcctgg ctctgaatac cgtgagcagt ttggggtggc tgacgctgag gccagacgct
135961 tgtggtcaga aagcggaagc ttcctccctg tgctctgtag tctaggccag aggccctagg
136021 aacagtttct gatgacagag gagccaggcc catgtggtgg gatgacatgt cttgggtcca
136081 gccacatgtg gaccagcctc ggccccacga caatgcccct cctgcaggga gagtatcagc
136141 ctcatctgcc acctctgaga aagccttcct gccacagctt gtcctcagga gagcagggcc
136201 acacacaagg cctcgcccat catggacagg gtgggcaggt tctgatggga caggagtctc
136261 agcatctcag gggctcgggc ccatctggag gagcagagtg ggggctgagt ggcccaggac
136321 tggatacgcg tcgggcctgc cccacgccag gccctgcatg ccacagggat ttacagaggc
136381 cttagctgca ggttgtgagc caagacagag attcctgatc ccaccgagga gtggggagag
136441 ggcagtgagg ggtagaaggc tcggtgggcc ctggggtctg gagctctgaa ttcacatccc
136501 agcttcaggc aagtagctgg atggcctggg cacattgctt cattctctga agctgtttct
136561 tcatctaccc aaaggagata cccctcactt gcaggaccat tgagaaaatg aaatgacacc
136621 atcctgggtg gcctcctttc tccagaggca caggccaccg gttgtgtgca tcagaaccac
136681 cagtgcccct tcctgaatcc agggggttgc agggcaccag gccccacacc gcctgtgagc
136741 tagcatgggc ccctgcgtca cggccacttc gtgactacat gtgccaatcc gagtaactgg
136801 agcacacatg ggaggaggaa actgaacctg tgacctcaaa ctccttcact caaagcccag
136861 aaggaactcc tgaaaggctg gagacagggc tgtgaggaca gagggagagt gggaggcatt
136921 ctgaatgctg gtggggcagg cagagcaagt ctgtgtgcgg tgaggactga ggggcggcca
136981 ccagaggccc gggcctggtc tgagtgtggc tgctgcaggg gaagtagctt tcctatggct
137041 ctgaggggct ggagagggag gaaggtgtcc ccaggggata gatgacagga aagctggggt
137101 ggggtgggag gagctaacag ggacactctc atgggaggga ggctcccagt accttggact
137161 aagaggggag ggagatggcg tgaggaggca ttccaggact gggcaggtcc cacagggagg
137221 gcccgatgtc tacctggggg tgacgaccca cacgaagaga ctgagcagct tctctgaggg
137281 agtggacagt ggggtgaccc tccagcacac ctgtggtgca gtcacagggg actgggacac
137341 tcctggcccc ctgccctacc tacacctgca ggcacctggt ggagagcccc tgagtttcac
137401 ttggggtgaa atcactaggc agatttacaa ggactccatc tgccatctga cagggacttc
137461 cacagcagga gggggccagg cctgcagtct ggctggtcta tggccagccc agccactttc
137521 ctggtgctgg cttcaagcct gaatatgata agaggtgaac aaggggcaga gggctccagc
137581 cttgacccaa ctcagggagt aaaagacaaa gcttgatggc tgtggttcta acatcccagg
137641 ggccactaat ggaagaatga cagataaagg cctccttcca ggaaaatacc agggtcacat
137701 gtgtcaaact gcaaaatatc ttcggaaggt ttgtggaact acaatggcca ccttcctccc
137761 tcctctctgg gccaagtaca ctgggctgat gctatatttg tctatttgct gtgacacatt
137821 aaattctcag gtgacacact gaattatggt gggcactatc aacagtggac accccccaac
137881 aggccctcag gaagcactgg gcctgggaat ggccgagcga gtgattatcc tgctttacag
137941 atagaaactg aggctcagag agcaatggtg gcctcaagat cagaacctac acctgtgtga
138001 tggccaagcc caggttcctc ccacagttcc ccaaggccac atcttgagaa aagccctgaa
138061 ccggaagcta gaaggcccag ctttgagccc tggtttgtac cctggatgga gtgtaaaggg
138121 gcaatgtgga gtggcatgga aggacaggga aaagcttcat aagagggtat ttcaggcagc
138181 ttttaggggc tgatcagatt tcagagggca gatgagtagg aggatgggca tgggtagcac
138241 atttcagatg tggggaactg ggagggcagg gtccccgggg gattcacacg tgggaggagg
138301 aaggctggac acagtttctg gggacagaag tgggtggcgt ggtggtgcag atgctggaga
138361 gaaacaaggg aaacctgcaa ctcaccggcc tcatttcaca aggggccact ttgctgattt
138421 tgcttgttgc ttttaacttt ttattggata tgtagtttta aagcttttga atatttcggc
138481 aaagagtcag ttggtcagtt ttcatgtgag ctttctatca gcattttagg aaagttttca
138541 tctgtctttc atcagatctc tgctgttgct gggacaggga gacggatctc tctgcggaag
```

FIGURE 2 (cont.'d)

```
138601 caaggatgtg tgccccaccc ccagactacc catcttggag ggggactaat gaggggctgt
138661 gggaggagga agctgtagag cagagaggaa gattgggggc cagacaaaac agagactcgg
138721 gatgagagag ggggaggcta tggggaagag ctgaggaaaa caagggacgg agagagggat
138781 tggggtagtg gatagggaga ccaagggggca gagaaggggg aaaatgtggg acagagagcc
138841 ggagattgag ggagcagaga aggggcctct gagaggtggc tggaagacag agtgtagagg
138901 aaaattcaga gcaaaaaaga agggagagtt gtagggtaga gagcagaaac gggggggcatt
138961 tagggaactg ggagcagggg aaggaagagg aggcagaaga gggggcagaa tgtagggaaa
139021 agatggctca gagggggaga ctgggagatg agagacggat tgagggtcat accaaagaaa
139081 tatttatgct ccactaatat attcccattc acaagaagga ggtattctag aattaatttt
139141 tcatgaatgt aagaatactc actgacttaa gaagcatgaa tcattataac acttttctac
139201 acttgttgaa catattcaag tatcatatat taaacaccac gctattgccc ttagctttct
139261 taaaagtacc agcacagaat gaaatgggcc aactaagatt tctcagaaat cttcagatct
139321 gttacagtta tcgtatccga tctgaattac tttaaattta cagagttaaa gaaataaatc
139381 aacttgttaa atttgcctag acttgggtta gcctctggaa acagggccat tctgtgtagg
139441 atcccggctt tctccagcag acagtgagga gccaaggaag acacaaccgt ttataggata
139501 atcccacctg cgaaggactt gattcccagt cctgactgaa tcactatgcg gaactctgat
139561 gagaataaca agggacctgt gactcacttt atcaaggaaa aaatcagtcc tgtccattat
139621 ttgactgaac tatgccctgg aggaggggggg tgttgacctg ccaataactt ggaaatgatt
139681 aaattgtgtg gaaatacctt tattgttatt gttatcgtta ctactgttaa caatacagat
139741 tttaacactt ttccctgtaa aatgggataa ccttgtcttc tcagcaagta cttcctctag
139801 ggtttctctt ttacctttac ccaaaaagga tgattgtctt tacagatacc aagctgggag
139861 aatgaggaag tagttctggg ctgggcaaga gaaagtgttg agtaactttg catcaacagg
139921 aactttctca aaagctgatt ttttcaagga aactttcagc cttagctggt tccccaccct
139981 gcggtagccc ccaccccaa ccacccccg ccccacccct gacttatagc cctctcaacc
140041 caatggaaat gtgacatgca aatctctcct gaaatttgcc cctgggattc cggctgaggt
140101 gtttaattat aatgtcattt gaatgacttc tcagggtagg ggaagacaga ccgagagagg
140161 gagatagtgg acaaaacagt gccttcactc tttgtccgaa gagcccgcta tggccacgtt
140221 atcatgtccc ctgcaggagg aaagcacaca cggggtgccc gtgctgtgca gtgtgagcac
140281 accaatggcc tgtgcttcta gaaccttatg atgtgtggag gagaatgggg aggaggaagc
140341 acttacaaag gggaagtagc ctgtaccctg tccttctccc ccaggtgtgg ggaatccatg
140401 aaataatgga agtaaatgaa ggtgcgtcag aaatggcaga gggtgccatc accctaaatg
140461 gacgacacat taactccagg gcaccgcagt cctcagggtc agttccccga ctggggcaac
140521 taagcaactg aaggttgctc ttgtactcaa cacctaactc ttcttgaagg gagctcaagc
140581 caggatgcta gtgaacttgg ctgagggcca tgtcgtgcta cagcgagggt atgggctcct
140641 ggataggaat cgagcccatg gagagcttgg aatccagaaa aagagtagtt tttacttact
140701 ttaggctctg cacacctaaa acacaaattt tatccaagag taatcagttg aaacatgaac
140761 ttgccggttg tatttgtcca ttatgagcaa tttcacaagg tttgatcaaa taataaacta
140821 aatggtgaga aggcagcttg gtaaagtcta aatctttttg gtccagttag gagctggggt
140881 ggggtggaag ggaactgata ttccctgcgc acctgcagta tgtctgggac tattaccagt
140941 catttacgga gcgcttcctc tgtgccaggt actggattag gcacttcatt aaaggctcag
141001 tgagaactgc gacctgccca tgctcatgga aaagagtcgt ggggctggaa ttcaggtcca
141061 gatcagcatt aggaactagc ttccaaatgc tgagggctcc ctcgcgtcct cacacctagc
141121 gtggaagtgt tccctggtgt acattctgct gggagggagt gcagcccctc catttaggaa
141181 aagcctctcc tggcctgggt tctgttcctt ccctttaatt tcctctgggg actgtcctga
141241 gaatgtaagc tgcccaggtg ccgtctgagc caccagatgg gcctgggctc acccatgact
141301 catggaccag actgaagcca accctccatt ttcagctggg gaaactgagg cccagacaga
141361 cggtagagtg agctggtggt catgtctgga cagaactcag gcctctggac ccgctgacgt
141421 gcacccttcc ccacggctca cagctggctg ctccgaggtg ccctcagagt tctgtgagca
141481 tgactcatct gcctctccct ccctgtgcga cctgcagaag gagcctaagg aagaggtggc
141541 acaagaaacg cggcccagtg aagggggctc cggagcctcg gagcccagat cttgaagtgg
141601 aggggaaacc ttgggccttc tcctcccagg gaagacgcct tgcaggcggc acgcgggaag
141661 tctccgtttc cgacagggggt cgcggccgcc gcgaggggtc ctggacgctt gcccaccagg
141721 gtacccaccg gccactggga gcccagggca cgccccaccg cagttctgcc ctccctgaca
141781 gggtcctgga cacccccagt cctgtccggg ccgccccgac gggccctcgg cgcccccgcc
141841 caggcctctg ccgtccaaac cgggtcccgg acgcacctca gcccgcgctc cacccgtgcc
```

FIGURE 2 (cont.'d)

```
141901 ccgcccgcgc tcaccgcgcc acgctcgaag tcgttgtaga agggcttgtc cagcaggtgc
141961 ttctcgctgc agcccgccga gcccacgagg ctgaggtaga tgtagtcgtc agtgtcttca
142021 ccacggggtg aagtacggtc cnnnnnnnnn nnnnnnnnnn nnnnnnnnnn nnnnnnnnnn
142081 nnnnnnnnnn nnnnnnnnnn nnnnnnnnnn nnnnnnnnnn nnnnnnnnnn nnnnnnnnnn
142141 ntttttgggt tgttgttgtc tctttgtttt tgcgagcggt ccttccgccc cgtggtgaag
142201 acaagtgggc gcctctgcct ggccatccca tctgggaggt gaggagtgcc tctgcccggc
142261 caccccgtct gggaagtgag gagcgtgtct acccagccac cacgtctggg aggtgaggag
142321 cgcttctgcc tggccgcccc atctgggaag tgaggagcgc ctctatctgg ccaccccttc
142381 tgggaagtga ggagtgcctc tgcccggccg ccaccccgcc tcggaggcga ggagcacctc
142441 tgcccggcca ccaccccatc tgagaggcaa ggaccacctc tgcctggccg ccatcctgtc
142501 tgggaggcga ggagcacctc tgcccagccg ccgcccccacc taggaggtga ggagcgcctc
142561 tggccagccg ccccacctgg gaggcgagga gcgcctctgc ctggccgccc catctgggag
142621 gtgaggagcg cctctgccca gccaccaccc catctgggaa gtgaggagcg tctctgccag
142681 gccgccccgt ctgggaagtg tacccaacag ctccgaagag acagcgacca ttgagaacgg
142741 gccatgatga cgatggcggt tttgtcaaaa agaaaagggg gaaatgtggg gaaaagaaag
142801 agagatcaga ttgttactgt gtctgtgtag aaagaaggtg acataggaga caccattttg
142861 ttctgtacta agaaaaattc ttctgccttg ggatgctgtt aatgtacaac cttacccccca
142921 accccgtgct cgctgaaaca tgtgctgtgt caactcaggg ttaaatggat taagggtggt
142981 gcaagatgtg ctttgttaaa cagatgcttg aaggcagcac gctcattaag agtcatcacc
143041 actccctaat ctcaagtacc cagggacaca aacactgctg aaggctgcag ggacctctgc
143101 ctaggaaaac cagagacctt tgttcacctg tttatctgct gaccttctct ccactattat
143161 actatgactc tgccacatcc ccctctctga gaaacaccca agaatgatca ataaatacta
143221 aaaaaacaaa ttaattaatt aaataaattt catatggaac caaaaaagag cctgcattgc
143281 caagtcaatc ttaagccaaa ggaacaaagc tggaggcatc acactacctg acttcaaact
143341 atactacaag gctacagtaa ccaaaacagc acggtactgg taccaaaaca gaggtataga
143401 ccaatggaac agaacagagc cttcagtaat aatgccacat atgtacaact atctgatctt
143461 tgacaaacct gacaaaaaca agaaatgggg aaaggattcc ctatttcata aatggtgttg
143521 ggaaaactgg ctagccaata aatggtgtag ggaaaactgg ctagccatat gtagaaagct
143581 gaaactggat cccttcctta catcttatac aaaaattaat tcaagatgga ttaaagactt
143641 acatgttaga cctaaaacca taaaaaccct agaagaaaac ctaggcaata ccattcagga
143701 cataggcatg ggcaaggact tcatgcctaa aacaccaaaa gcaatggcaa tgaaagccaa
143761 aattgacaaa tgggatctaa ttaaactaaa gagcttctgc acagcaaaag aaactaccat
143821 cagagtgaac aggcaaccca cagaatggga gaaaattttt gcaatctact catctgacaa
143881 agggctaata tccagactct acaatgaact caaacaaatt tacaagaaaa aaacaaacaa
143941 ccccatcaaa atgtgggcca aggaaaagaa cagacacttc tcaaaagaag gcatttatgc
144001 agccaaaaga cacatgaaaa aatgctcatc atcactggcc atcagagaaa tgcaaatcaa
144061 aaccacaatg agataccatc tcacaccagt tagaatggtg atcgttaaaa agtcaggaaa
144121 caacaggtgc tggagaggat atggagaaat aggaatactt ttacactgtt ggtgggactg
144181 taaactagtt caaccattgt ggaagtcagt gtggcgattc ctcagggatc tagaactaga
144241 aataccattt gacccagcaa tcccattact gggtatatac ccaaagtatt ataaatcatg
144301 ctgctataaa gacacatgca cacatatgtt tattgtggca ctattcacaa gagcaaagac
144361 ttggaaccaa cccaaatgtc caacaatgat agactggatt aagaaaatgt ggcacttata
144421 caccatggaa taccaagcag ccataaaaaa tgatgagttc atgtcctttg tagggacatg
144481 gatgaagcta gaaaccatca ttctcagcaa actattgcaa ggacaaaaaa ccaaacactg
144541 catgttctca ctcataggtg ggaattgaac aatgagaaca catggacaca ggaaggggaa
144601 catcacacac tggagcctgc tgtggggtgg ggggttgggg gagggatagc attaggagat
144661 atacctaatg ctaaatgacg agttaatggg tgcagcacac caacatggca catgtataca
144721 tatgtaacta acctgcatgt tgtgcacatg taccctaaaa cctaaagtat aataataaaa
144781 aaataagctt ataaaatgct tttaatgcta tataacttta taactctgaa agaataatag
144841 atttgtatta tgctgtcagt gagtaggtct attaagtgat aacattaaac acaaatacca
144901 ccatttataa agtatgattt tgatatcatc ggttgtgtat tttcacccca aactctgtag
144961 atagtaactt tgttttctca tttgaccatg ctcaatcttt agagaccatg ctcttctctc
145021 aaaatgactg taggttcatc caagtatgtt tgctacccaa aatcaatgaa acacagtcac
145081 aactatgtct gtctaggaat aaagccagct aattagattc ttattctaag gaacaagaag
145141 agggcaggta agaatttgat tatggcagaa ttctgaccat aatcaataac tgttttctat
```

FIGURE 2 (cont.'d)

```
145201 tttttctcca tgttgtcggg tggttcatac ctgactttca tcatttccaa tgattcctgt
145261 ttgttttgtt tataaatttc aaaatcatca tgaaaagttt cactgaatga aaacctgaaa
145321 attgggaaat aaacattttt ctgcaaaaaa aaaaaaacaa tgaacactga cttctcctat
145381 ttctcaaagt catctcaaag ccatatgagg attaccacaa acttgcaggt gagaaaattc
145441 tttgcaatgt aagaagtgcc atgcaaatta gttgatgcta ttataattag tctcagggat
145501 caaaaatgct tgaaccctaa atctaacact tcaaaggaaa gcattatttt tcattcattt
145561 tacaagttac acctcccttc ttccccacat ctttgtttag aatctggacc ctgaagttag
145621 aggaccaaga ttcaaatccc agcctcatca gtactagcta tgtgatattg ggaatgttac
145681 ttgatccctg cttatcttac tttctgcatt tattaaatgg ggatgagaat aatatctacc
145741 caaataaggt gcccaatgca gtgcccaaca gcatgaagcc caataaaggt tagttaacat
145801 cacatccata attgacacct ttaggtatta gattttcatc atcccagaac atttccttc
145861 tttaagcctt tttctttcta agtggcactt tcttggatac tgattgcact cctcacaaac
145921 ttgaaacgtt caaacacaca agatgccatt taggagacat tggaacttgg gtttccttct
145981 ctgtaaaact gagtaatgac agtcacctcc cagggctgtt gtaagaatga atgagctaga
146041 gtatgtaaaa tatcttagca cagagtgctt aagaaattat tagttccagc caagcgtggt
146101 ggctcacgcc tgtaatccca gcacttaggg aggccaaggc aggcggctca tctggggtca
146161 ggagttcaag accacctggt caacatggtg aaaccccgtc tctactaaaa atacaaaaat
146221 tagccaggcg tggtggcatg tgcatgtaat cccagctact caggaggctg agacaggaga
146281 atcacttgaa cccaggaggt ggaggttgca gtgagccgag atcgtgccat tgcactccag
146341 cctgggcaac aagagtgaaa ctctgtctca aaaaaaaaaa aaaaaaaaag aagaagaaga
146401 agaaagaagg aaagaaagag agagagagaa agaaagaaag aaagaaagaa agaaagaaag
146461 aaagaaagaa aaagaaagaa agaaaagaaa gaaagaagga aagagacaga aagaaagaag
146521 ggaagaaaga aagaaagaaa gaaagaaaga aagaaagaaa gaaagaaaga aagaaagaag
146581 ggaagaaaga aagaaagaaa gaaaaaaaga aagaaagaaa gaaaaagaaa gaaagagaga
146641 aagagaaaga aagaaagaaa gaaaggagag acagaacgaa ggaaagaagg aaggaattat
146701 ttccctttt cccacccacg cctcaccaca aaccttgttg tggggataac atgtaaaagt
146761 gaacaaaact gagaagatca catcgcatat gcactcagcc tctagtggga gacacaggca
146821 ataaacagga aaagttaaaa acagtactag gtagtggtga gtgcaattag cctcccgcag
146881 cataaaggga ggagaataac cagtggctct ttcatgcaga gaatcagggt agacctctgg
146941 ggagagaccc gcactcagac tgggatggaa ttatttattt tatgcgtgtt cagttaggag
147001 tagaggtgct ctgtcgtgat tatctaatct tgggaggaac aatgtcagac gggtttcaag
147061 atgagtatga gaattggtct tccttctgaa aaaacaagaa ttgagttcac actaatcaca
147121 aatacatcaa gcctatttga gtcttgtgtg tgtcatggat tgaagtgtat ctttccactt
147181 agtcaagaag ttccaatgag aagaatgctc cttaacttcc taagtgcaac agagtagttg
147241 aactgagcca tggatggtaa atctacttaa gaaagcacat gccatggaaa gatagcattg
147301 gctgccctgc ctacttctga tggcacagcc ttgcaggaag ggaaagaagc caagaggcaa
147361 aagcctggtc ttgttctgaa aggcacaagg aggtggaaga ttaggggaaa ctcacccaaa
147421 aatgactcag ctctgaactc agactcaaga agccacaata agcaacatga atggaactgg
147481 agggaaataa accaggcgta gaaacacaaa tgttgcatat tcttactcat gtgggaacta
147541 aaaacatgca tttcaaggag aatagaatga tggttatcag agactgggaa cagttgtggg
147601 tggggggtgtt aagagaggtt gcttaatggg tacaaacata tagttagata gaaggtataa
147661 gttctaatgt ttgacagcag agtaggagaa ctatagttaa cagtaatata ttgtatactc
147721 caaaatagct agacaggaag atttgaaatg ttcccaacac atagaaatga caaaagcttg
147781 aggtaatgga taccctaaat atcctgactt gatcattaca cagtctatgc gtgtaacgaa
147841 ataccatatg taccccataa atatgtacaa atattatgta tcaataaaaa tttttaaaaa
147901 gaagctgcaa tcaacatttc atcattatct tttcagcagc atccttacaa agttacagag
147961 acatcttaag atgtatccct cttcctctga atcttcctgg gatagaacaa atgaaaacta
148021 aacaaggagt gggctgggag gagctgtcaa catccatcct aaggaaaagt ctgttagggc
148081 tatgagcttc ctctgtccta gagtagagct gggaaaatag agtcttgaca attgatttct
148141 tattctttct ttctctaaat ccccaatgaa tatgtttttc tttttagtgc tcagtggtag
148201 acagggctta attctgttta gttatgcaaa caggccagaa gaaactgaaa taggctataa
148261 atgtttgaag ctggccaaaa gaagatgtag tcacacaaga taccctctgg aggaaagtga
148321 ctgtcaggaa agtcactttc ctgaccagca aaaggaccag cactattttg tcctgctgaa
148381 gaagtacatt tgtcctgctg ctgtcatggg gacagtggct ccagggcttc ctgtggacat
148441 gccacaagtt ccactccatg agtcaggaga tcatgcggtc agctgggggg aacttagggt
```

FIGURE 2 (cont.'d)

```
148501 tgctctcttg agcttagcct tatgctgcgt gtctgctttg ccaaccacaa aaacgatagt
148561 ttcatagcaa gttgcaggct ccctggaaac ttaacctacc tactaggata catttacagc
148621 tgcttttctc ctggcatcag gctggagatc aagaaataca taaaacatag tccctgccct
148681 cagttagctc agaatatggt gggggaatgg agacagaagc aaatactggt gggacaagtg
148741 acgatgggcc aaaatatggg cttaaacaaa ggttgtggga gctcagaaaa ggagcaactc
148801 actctgcctg aaagagtcat ggagggctcc acggaaaaag caacatttgt gcaggaggag
148861 attagaacac agaggagaag gatagcagca ctccagatga agggaaggaa atgtgccaag
148921 atttcatggg aatgagaaga tgtaaactgc tcaggaaaaa ccatggttga agctcttcac
148981 agtggctgaa gcatggtgtg attgtcagtt ttgcttgtca acttggtcag gctgtagtac
149041 tcaactattc aaccaagcac tgatctaggt attgctgtga aggtatttg tagtcgcaat
149101 taacctctac aatcagttga ctctatttaa aggacattat tctgtactat ctgagtggac
149161 ctgatccact tcatcccaaa ggtaaatgat tctccaacag tgttctcatc tacatctagg
149221 gcttggaaga tgaaggtgaa ggagaatatg gaaaaacaac aagaaaaaag tcaatcaatc
149281 agaacttcca gccctgtgtt tgttagttca ctttatgttc aaccagtatg tctccacttt
149341 tatctgcttc cttgtaagat ttcatctgaa aaagggaatt cactcttcag gtgttggaaa
149401 tcaattatga gagaagcact tacagaatga ctatctgaag agctctgcag acattctcca
149461 gagtaaaaca accataaccg gtgaaaatta aaaacaaaca aaataaaaaa atgttagagt
149521 attggaaatt gttctaaggg ccgacagcaa atgaagaaat ccaagaaagc ctaccaattt
149581 cagtgagagg agtgagagtc tatggtgttg agtctatggt gtttaagttc tgttcatttc
149641 ctccctctcc tgcaatcagt tcagtgaaac agaaaccctg ctccagagat gtgcagccaa
149701 aaagacaggg tgccctttcc cctcagctcc caatctaggg cagactacca gcatttccca
149761 agcccatctc tggctctatg ttgcagaagt tctattccaa gaaagtttga ctgagaatct
149821 gaagcttcct tcttccactc agcctctact attaaggcgt aagttctatc cccagtgcca
149881 cgggccaaga atactgatgc tgaatgtcct tgctccgcta cactcatagg gcagagattc
149941 catgggagga gtgaagtttc cattccagaa aaggcagaaa aacagaaatt actgcccaat
150001 ccagtacccc acccataaag aaggaaagac atctgagaaa agcatgacac tgtccccaaa
150061 accacctgca gagtagtggc agtagaggca gtagggagac tagaggacct gcctagaggg
150121 agaagtaggc cataagaaga aaagtctcta gttctcccta aagggacaaa ctttatttgc
150181 aacagaacat gcggaagttc aagcctaagg gcactgtcaa aaacaatgaa tattttggtg
150241 gtaagcaatt aataggttaa tggcagctta gtgagagcaa caaactaaac cataaaccag
150301 ctagacatat acaataaaaa tccaagaaag agagagccaa gaagggcctt cctgaggtta
150361 aaacaaacat caaagtcttg tctgaaaaac tgctcctgca aaggaagcaa aatatatttg
150421 gatcagactg tggagcaatt tatgccccta aaaagctgtc aaaaccaaaa gagcaattat
150481 ctagcaattg ctggaggtta acagttgggt atgataccaa aagaggcaaa caactgaaca
150541 gatcagagaa agaggcagtc aaagagagca ctgctaaatg cactgtaatt ccaatttgag
150601 agaaaatgtg cccagtgctg tgactccctc aggaacaaca tcagaggcca caaattatgg
150661 tggaaatagg cttcactata tagtctagcc aggcaattaa acaaataaac aattaaacaa
150721 cagtaacata gtgagggggg cagaaatgag tattgcaact agctagaaca tatttttgaa
150781 caaaaaaatt atgagtcaag cagagatatg gaaaagacag agccatacac cagaaaaaag
150841 gtaagcaaga gaaactgcct ttgtgagtgc caagatgtca gacatagcag aaaaaaaacc
150901 tcaaagtaat tattataaat atgttcaaaa actaaaagaa aatgtgctta aaaaataaaa
150961 gatggtatga taatttcttg tcaattcaaa aataccaata atagattaaa aatattttt
151021 caaaagttaa ttaaccaaat ggaaattctg ggtttaaaa gtaaaataac aacaataaga
151081 acattttgct agaggaaatg aacaatagat ttgtaccaga aggaaaaata atcaaataaa
151141 cagggatttc atcaacacca aacctgtctt acaagaaata ctaaagggag ttcaatctga
151201 aagaaagaac attaacaagc aacaggaaat catctgaagg tacaaaactc actgtacctt
151261 cagatgataa taagtcctca aaaaacacag aatattataa cactgtaatt atggtgtgta
151321 agctacttat atcataagta gaaagaggaa aagatgaact gattaaaaaa caattacaac
151381 agcttttcaa gacagtataa taagatatat aaataacaga aagcttaaaa gcatataaat
151441 aaagttaaaa tgtagaggtt ttttagttt tctttttgct tgattgtgta tttatttatg
151501 caatcagtgt tgttttcatc agcataaaat aatgggttat aagatagtat ttgcaagcct
151561 catagtaacc tcaaatttaa aaacatacaa tgtatacaca aaaagtgaag agcaagaaat
151621 taaaacatac caccaaaaaa aatactttca ctaaaaagga gacaggaagt aagaaaagat
151681 gggagagaag atcacaaaac aaccagaaaa taaataacaa aatggcaagc aagtccttat
151741 ttgtcaataa taatattgaa tgtaaatgga ctatactctc cagtaaaaag atacagagtg
```

FIGURE 2 (cont.'d)

```
151801 gttgaatgga ttaaaaaaaa ggacccaatg atctgttacc tacaagaaat aaacttcact
151861 tataacaata cacagactaa aaataaagtc atgggaaatg atacttcacg acaatggaaa
151921 ccaaaaaaga acaggagtag ctataccttt atcagactaa atagatttca agacaaaaat
151981 tgttaagaaa aaccaaataa ggtcattata taatgataaa gagatcagtt aagcaagagg
152041 atgtaacaat tgtaaatata tatgcactca acattggagc acctagataa ataaaacaaa
152101 tattattaga gctaaagaaa gatagacccc ctcccccaaa acaataatag ctgtagattt
152161 caatgctcca ctttcagcat tggacagatc ttccagacag aaaatcagca aggaaacatc
152221 agatgtaatc tgaactatag accaaatggg cctaataagt atttacagaa tatttcatcc
152281 aaaggttaca gaagacacat ttttctcctt agcacataca tcattctcaa gaacaggcca
152341 tatattaggt catgaatcaa gtctcaaaac attcaaaaaa actgaaataa tctcaagcat
152401 cttctttgac cacaatggaa taaaactaga aaccaataac aaggggaatt ttggaaacta
152461 tacaaaaaca tggaaattaa acaatatgtt cctaaatgat aagtgggtca atgaagaaat
152521 tatgaattga attgaaaatt ttctaaaaac aaatgacaat ggaaacataa tgcaccagaa
152581 cctatgggat acaacaaaag cagtaccaag agtgatattt ccagataagg gcctacatca
152641 aaaaggaaga aaaacttcaa gtgaataacc tgatgatgca tcttaaagaa ttaaaaaggc
152701 aagagtaaac caaacccaaa attagtagaa gaaaagaact aataaagatc acagtagaaa
152761 taaataaaat tggacttctg ctccaagatg gcctaataga aacagctcca gtctgcagct
152821 cccagcatga ttggcacaga agatgggtga tttctgcatt tccaactgag gtaccaggtt
152881 catctcattg ggactggttg gacaatggat gcagcccatg gagggtgagg tgaagcaggg
152941 tgaggagtca cctcaccccg gaagcacaag tgattggggg atttcccttt cctagccaag
153001 ggaagccgtg acagactgta cctggaaaat cggttcactc ccacccaaat actgtgcttt
153061 tcccatagtc ttagcaaccg gcagaccagg agattctctc ccaagcctag ctcatcaggt
153121 cccatgccca cggagcctgg ctcactgcta gcacagcaat ctgagatcaa cctgcgaggc
153181 tgcagctggg tgggggagg ggtgtcagcc attgctgagg actgagtagg taaacaaagt
153241 ggccaggaag ctcaaactgg gcagagccca ccgcagctca gcaaggccta ctgcctctat
153301 agattccacc tctgtgggca gggcataact gaacaaaagg cagcagacaa cttctgcaga
153361 tttaaacgtc cctgcctgac agctctgaag agagcagtgg ttgccccagc atggcatctg
153421 agctctgaga acagacagac tgcctcctca agtgggtccc taaactccat gtagcctaac
153481 tgggagacat ctccccatag gggccgacag acacctcata caggtgggtg ccactctggg
153541 acaaagctct cagaggaagg atcaggaagc aatatttgct cttctgcaat atttgctgtt
153601 ctgcagcctc tgctggtgat acccaggcaa acagagtctg gaatggacct ccagcaaact
153661 ccagcagacc tgcagctgag ggacctgact gctagaagga aaactaacaa acaaaaagga
153721 atagcatcaa catcaacaaa aaggacattc acaccaaaac ctcatctgta gtcaccaata
153781 tcaaagacca aaggtagata aaaccacaaa gatggggaga aaccagagca gaaaagctga
153841 aaattctaaa aactgagcac cgcttctcct ccagaggatt gcaactcctc accggcaacg
153901 gaatgaagct gggtggagaa tgactttgac aagttggcag aagtaggctt cagaaggtcg
153961 gtaataacaa actactccaa actaaaggag catgttctaa cccattgcaa ggaagctaaa
154021 aaaccttcaa aaaaggttag acaaatggct aactagaata aacagtgtag agaggaactt
154081 aaatgacctg atggagctga aaaccgtggc atgaggacat catgatgcat gcacaagctt
154141 aaatagctga ttaaatcaag tggaagaaag aatatcagtg actgaagatc aaattaacaa
154201 aataaagcaa gaagataaga ttagagaaaa aagagtaaaa agaaatgaaa agcacctcca
154261 agaaatatgg gactatgtga aaaaaccaaa tctacacttg attggtgtac ctgaaagtga
154321 tggggagaag gaaaccaagt tggaaaacac tcttcagaat actatccagg agaacttccc
154381 caaactagca aggcaggcca acattcaaat tcaagaaata cagagaacac cacaaagata
154441 ttcctcaaga agagcaaccc caagacacat aattgtcagc ttcaccaagg ttgaaatgaa
154501 ggaaaaaaat gttaagggca gccagagaga aacgttgggt taccaacaaa gggaagccca
154561 tcagactaaa agtagctctc tcagcagaca ccctgtaagc cagaagagag taggggtcaa
154621 tattcaacat tcttaaagaa aataattttc aacccagaat ttcatatcca gccaaactaa
154681 gcttcataag tgaaggagaa ataaaatcct ttacagacaa gcaaatgctg agagattttg
154741 tcaccatcag gcctgcctta caagagctcc tgaaggaaac actgaacatg gaaaggaaca
154801 actgttacca gccactgcaa aaacacgcca cattgtaaag accatcgatg acatgaagaa
154861 actgcaacaa ttaactggca aaataagcag ctcacagcat aatgacagga tcaagttcac
154921 acataacaat attaacctta aatgtaaatg ggctaaatgc ctcaattaaa gacacagact
154981 ggcaaattgc atagagtcaa gacccatcag tgtgcggtat tcaggagacc catctcacat
155041 gcaaagacac acatagggat ggaggaagat ccaccaagca aatggaaagc caaaaaaaaa
```

FIGURE 2 (cont.'d)

155101 aaaaaaaaaa aaaaaagcag gggttgcaat cctagtctct gataaaacag agtttaaacc
155161 aacaaagatc caaagagaca aagaaagcca ttacataatg gtaaagggat caatacaaca
155221 agaagaacaa actatcctaa atatatatgc aaccaatatg ggagcaccca gattcataaa
155281 gcaagtctgt agagacgtac aaagagatgt agacttccac acaataataa tgggagactt
155341 taacactcca ctgtcaatat tagacagatc aatgacacag aagggtcaca aagatatcca
155401 ggacttgaat tcagctattc accaagtgga cctaatagac atctacagaa ctctacaccc
155461 caaatcaaca gaatgtacat acttctcagc accacatcat acttattcta aaattgacca
155521 cataattgga agtaaaacac tcctcagcaa atgtaaaaga acagaaatca caacaaactg
155581 tgtctcagac tacagtgcaa acaaattaga actctggatt aataaactca ctcaaaatca
155641 cacaactaca tggaaactga ataacctgct cctgaatgac tactgggtac ataatgaaat
155701 gaaggcagaa ataaagatgt tctttgcaac caataagaac aaagacacaa cataccagat
155761 tctccgggac acatttaaag cagtgtgtac agggaaaatt atagcactaa atgcccacaa
155821 gagaaagcag gaaagaacta aaatcaacaa cctaacatcg caattaaaag aactagagaa
155881 gcaagagcaa acacattcaa aagctagcag aaggcaagaa ataactaaga tcagaacaga
155941 actgaaggag atagagacac aaaaagcact tcaaaaaaat caatgaatcc aggagctggt
156001 ttttaaaaag atcaacaaaa ttaatagacc gctagcaaga ataataaaga aaagagagaa
156061 gaatcaaatt agactcaata aaaaaagata aaggggatat caccactgat cccatagaaa
156121 tacaaactac catcagagaa tactataaac acctctacat aaataaacta gaaaatctag
156181 aagaaggggg aggagccaag atggccaaat aggaacagct ccagtctaca gctcccagcg
156241 tgagtgacac agaagacggg tgatttctgc atttccatct gaggtaccgg gttcatctca
156301 ctagggagtg ccagacagtg ggcacaggtc agtgggtgcg cgcactgtgt gcgagccaat
156361 gcagggtgag gcgttgcctc actcgggatg tgcaaggggt cagagagttc cctttcctag
156421 tcaaagaaag ggtgacaga tggcacctgg aaattcgggt cactcccacc tgaatactgc
156481 acttttccaa cggcttaaa aaacggcgca cctggagagt atatcccgca cctggcttgg
156541 agggtcctat gcccacggag tcttgctgat tgctagcaca gcagtctgag atcaaactgc
156601 aaggcagcgg cgaggctggg ggaggggcgc ctgccattgc ccaggcttgc ttaggtaaac
156661 aaagcagctg ggaacctcaa actgggtgga tcccaccaca gctcaaggag gcctgcctgc
156721 ctctgtaggc tccacctctg gggcagggc acaggcaaac aaaaagacag cagtaaccac
156781 tgcagactta aatgtccctg tctgacagct ttgaagagag cagtggttct cccagcacgc
156841 agctggagat ctgagaacgg gcagactgcc tcctcaagtg ggtccctgac ccctgacccc
156901 cgagcagcct aactgggagg catccccgag cagaggcaga ctgacacctc acacagccgg
156961 gtactccaac agacctgcag ctgagggtcc tgtctgttag aaggaaaact aacaaacaga
157021 aggacatcca caccaaaaac ccatctgtac atcaccatca tcaaagacca aaagtagata
157081 aaaccacaaa gatggggaaa aaacagagca gaaaaactag aaactctaaa aggcaaagcg
157141 cctctcctcc tccaaaggaa tgcagttcct caccaggaat ggaacaaagc tggacggaga
157201 atgactttga cgagctgaga gaagaaggct tcagatgatc aaattactcc gaactacggg
157261 aggacattca aaccaaaggc aaagaagttg aaaacgttca aaaaatttag aagaatgtat
157321 aactagaata accaatacag agaagtgctt aaaggagctg atggagctga aaaccaaggc
157381 tcgagaacta cgtgaagact caggagccga tgcgatcaac tggaagaaag ggtatcagcg
157441 atggaagatg aaatgaatga aatgaagtga gaaggaaagt ttagagaaaa aagaataaaa
157501 agaaatgaac aaagcctcca agaaatatgg gactatgtga aaagaccaaa tctacatctg
157561 attggcgtac ctgaaagtga cggggagaat ggaaccaagt tggaaaacac tctgcaggat
157621 attatccagg agaacttccc caatctagca aggcaggcca acattcagat tcaggaaata
157681 cagagaacgc cacaaagata ctcctcgaga agagcaacac caagacacat aattgtcaga
157741 ttcaccaaag ttgaaatgaa gggaacaatg ttaagggcag ccagagagaa aggtcgggtt
157801 accctcaaag ggaagcccat cagactaaca gcggatctct cggcagaaac tctacaagcc
157861 agaagagagt ggtggccaat attcaacatt cttaaggaaa agaattttca aaccagaatt
157921 tcatatacag ccaaactaag cttcataagt gaaggagaaa taaaatcctt tacagacaag
157981 caaatgctga gaaattttgt caccaccagg cctgccctaa aagagctcct gaaggaagtg
158041 ctaaacatgg aaaggaacaa ccggtaccag ccgctgcaaa atcatgccaa aatgtaaaga
158101 ccatcgaggc taggaagaaa ctgcatcaac taacgagcaa aacaacctgc taacatcata
158161 atgacaggat caaattcaca cataacaata ttaactttac atgtaaatgg actaaatgct
158221 gcaattaaaa gacacagact ggcaaattgc ataaagattc aagacccatc agtgtgctgt
158281 attcaggaaa cccatctcac gggcagagac acacataggc tcaaaataaa gggatggagg
158341 aagacctacc aagcaaatgg aaaacaaaaa aaaggcaggg gttgcaatcc tagtctctga

FIGURE 2 (cont.'d)

```
158401 taaaacagac tttaaaccaa cacagatcaa aagagacaaa gaaggccatt acttaatggt
158461 aaagggatca attcaacaag aagagctaac aatcctaaat atatatgcac ccaatacagg
158521 agcacccaga ttcataaagc aagtcctgag tgacctacaa agagacttag actaccacac
158581 attaataatg ggaaacttta acaccccact gtcaacatta gacagatcaa caagacagaa
158641 agtcaacaag gatacccagg aattgaactc agctctgcac caagcagacc taatagacat
158701 ctacagaact ctccacccca aatcaacaga atatacattt ttttcagcac cacaccatac
158761 ctatttcaaa attgaccaca tacttggaag taaagctctc ctcagcaaat gtaaaagaac
158821 agaaattata acaaactgtc tctctaacca cagtgcaatc aaactacaac tcaggatgaa
158881 gaaactcact caaaactgct caactacatg gaaactgaac aacctgctcc tgaatgacta
158941 ctgggtacac aacgaaatga aggcagaaat aaagatgttc tttgaaacca atgagaacaa
159001 agacacaaca taccagaaat tctgggatgc attcaaagca gtgtgtagag ggaaatttgt
159061 agcactaaat gcccacaaga gaaagcagga aagatccaaa attgacaccc taacatcaca
159121 attaaaagaa ctagaaaagc aagagcaaac acattcaaaa gctagcagaa ggcaagaaat
159181 aactaaaatc agagcagaac tgaaggaaac agagacaaaa aaaacccttc aaaaattaat
159241 gaatccagga gctggttttt tgaaaggatc aacaaaattg atagaccgct agcaagaata
159301 ataaagaaaa aaagagagaa gaatcaaata gatgcaataa aaaatgataa aggggatatc
159361 accaccgatc ccacagaaat aaaaactatc atcagagaat actacaaaca cctctatgca
159421 aataaactag aaaatctaga agaaatggat aaattcctcg acacatacac tctcccaaga
159481 ctaaaccagg aagaagttga atctctgaat agaccaataa caggagctga aattgtggca
159541 ataatcaata gcttaccaac caaaaagagt ccaggaccag atggattcac agccgaattt
159601 taccagaggt acaaggagga actggtacca ttccttctga aactattcca atcaatagaa
159661 aaagagggaa tcctccctaa ctcattttat gaggccagca tcatcctgat accaaagccg
159721 ggcagagaca aaaccaaaaa agaggatttt agaccaatat ccttgaggaa cattgatgcc
159781 aaaatcctca ataaaatact ggcaaaccaa atccagcagc acatcaaaaa gcttatccac
159841 catgatcaag taggcttcat ccctaggatg caaggcttgt tcaacatatg caaatcaata
159901 aatgtaatcc agcatataaa cagaaccaaa gacaaaaacc acatgattat ctcaatagat
159961 gcagaaaagg cctttgacaa aattcaacaa cacttcatgt taaaaactct caataaatta
160021 ggtattgctg ggacgtatct caaaataata agagctatct atgtcaaacc cacagccaat
160081 atcatactga atgggcaaaa actggaagca ttccctttga aaattggcac aagacaggga
160141 tgccctctct caccactcct attcaacata gtgctggaag atctgtccag ggcaatcagg
160201 caggagaagg aaataaaggg tattcaatta ggaaaagagg aagtcaaatt gtccctgttt
160261 gcagatgaca tgattttata tctagaaaac cccattgtct cagcccaaaa cctccttaag
160321 ctgataagca acttcagcaa agtctcagga tacaaaatca atgtacaaaa atcacaagca
160381 ttcttataca ccaacaacag acaaacagag agccaaatca tgagtgaact cccattcaca
160441 attgcttcaa agagaataaa atacctagga atccacctta caagggatgt gaagcacctc
160501 ttcaaggaga actacaaacc actgctcaac gaaataaaag aggatacaaa caaatggaag
160561 aacattccat gctcatgggt aggaagaatc aatattgtga aaatggccat actgcccaag
160621 gtaatttaca gattcaatgc catccccatc aagctaccaa ttactttctt cacataattg
160681 gaaaaaacta ctttaaagtt catatggaac caaaaaagag cccgcatcac caagtcaatc
160741 ctgagccaaa agaacaaggc tggaggcatc acactacctg acttcaagct atactacaag
160801 gctacagtaa ccaaaacagc ttggtactgt taccaaaaca gagatataga tcaatggaac
160861 agaacagagc cctcagaaat aatgctgcat atcgacaact gtctgatctt tgacaaacct
160921 gagaaaaaca agaaatgggg aaaggattcc ctatttaata aatggtgctg ggaaaactgg
160981 ctagccatat gtagaaagat gaaactggat cccttcctta caccttatac aaaaattaat
161041 tcaagatgga ttaaagactt aaatgtcaga cctaaaacca taaaaaccct agaagaaaac
161101 ctaggcatta ccattcagga cataggcatg ggcaaggact tcatgtctaa aacaccaaaa
161161 gcaatggcaa caaaagccaa aattgacaaa tgggatctaa ttaaactaaa gagcttctgc
161221 acagcaaaag aaactaccat cagagtgaat aggcaaccta cagaatggga gaaaattttt
161281 gcaatctact catctgacaa agggctaata ttcagaatct acaaagaact taaacaaatg
161341 ttcaagaaaa aaacaacccc atcaaaaagt gggcaaaata catgaaaaga cacttctcaa
161401 aagaagacat ttatgcagcc aacagacaca tgaaaaaatg ctcatcatca ctggccatca
161461 gagaaatgca aatcaaaacc acaatgagat accatctcac accagttaga atgacgatca
161521 ttaaagtcag gaaacaacag atgctggaga ggacatggag aaataggaat gcttttacac
161581 tgttggtggg ggtgtaaatt agttcaatca ttgttgaaga cagtgtggca attcctcaag
161641 gatctagaac tagaaatacc atttgaccca gcaatcccat tactgggtat ataccgaaaa
```

FIGURE 2 (cont.'d)

```
161701 gattacaaat ggtgcaacta taaagacaca tgcacacgaa tgtttattgt ggcactattc
161761 acaatagcaa agacttctaa caaacccaga tgtccatcaa tgatagactg gattaagaaa
161821 atgtggcaca tatacaccat ggaatactat gcagccataa aaaaggatga gttcatgtcc
161881 ttttcaggga catggatgaa gctggaaacc atcattctca gcaaactatg acaaggacag
161941 aaaaccaaac accgcatgtt ctcactcata gatgggaact gaacaatgag aacacttgga
162001 cacagggcag ggaacatcac acaccagggc ctgttggggg gtggtggact gggggagaga
162061 tagcattagg agaaatacct aatgtaaatg atgagttgat ggatgcagca aaccaacagg
162121 gcacatctat acctatgtaa gaaacctgca ctttgtgcac aggtacccta gaacttgaag
162181 tataataaaa atgaaaaaaa gaaaatgtta ctagcaaatt gtagatgggt atacctaata
162241 taactctgca tgtgcactat gtgtctggat acacatggaa agtattcagg catacacacc
162301 aaattgttaa aataaatccc cttccaacat taggagtggc tggggagcag atggctttca
162361 cttccgcaca ttccatggtg ccagggtaat accacatcac aatagtaaat agcaaaaata
162421 acaaccttaa gtttagattt tcttatctaa attttaattc tgtgaagaag tttccatttc
162481 ccttttcac acaggatagt agaatgcagt ttagaaagag tgagatcact tgttagactg
162541 tacaattttt aagcatcagc gaagtatacc attaaacttc tctatcaatc cattctctaa
162601 acttcccaac ccaaaaaaaa agaaacacat aaaattgaaa tgaagaaaac aatacaaaag
162661 atcaacaaaa atgaaaggtt ggctttttaa agagataaac aaaattgaca aatgtttagc
162721 cagactaaga aaaagagaag gcccaaataa ataaaatcag agatgaaaaa gcagacatta
162781 taactgatac tgcggaaatt caaaggatca ttaatggcta ctatgagcaa ctgtatgcca
162841 aacattggaa aatattgaag aaatagataa attcgtagac acacgcaacc taacaagatt
162901 caaccatgaa gaaattcaaa atctgaacag accaaaaaca agtaacaaga tcaaagccat
162961 aattaaaatt ttcccagcaa agaaaagcct gagacccaat ggcttcactg ctgaattcta
163021 tcaaacattt aaagaactaa taccaatcct actcaaacta ttccaaaaag tagaagagga
163081 gggaatattt ccaaacttat tctatgaggc cattactgct cctatatcaa aaccaaggac
163141 acatcaaaaa aagaaaacta taggccaata tctcacatga atattgatga atcctcaaaa
163201 aatgctagca aactgaattc aacatcacat taaaaatcat tcattatgac caaatgggat
163261 ttatcccagg gatgcaaata tggttcaaca tatacacatc agtcagtgta acatatcata
163321 tcaacagaat gaagaagaaa aaccatatgg tcatgttaat tgatgctgaa aaagtatttg
163381 agagaattaa acatctcttc atgacaaaaa ccctcaaaaa cactggagac agaaggaaca
163441 tacctcaaca caataaacag acatatatga cagactcaca gctagaatca tactaaatgg
163501 ggagaaactg aaagtcattc ctctaagatc tggaacaaga caaggatgct cattttcacc
163561 agtgttagtg gaacatagta ctgaaagtcc tagctagaac agactagaga cagaaataag
163621 gggcatccaa actgggaaga gagaagtcaa attacctttg ttcgcagatg gtatgatctt
163681 ctgtttggaa aaacctagac tccataaaaa aatgattaga actgataaat tcagtaaagt
163741 ttcaggatac aaaattaaca tacaaaaatc agtagcattt ctatatgtca atagcaaaca
163801 atctgaaaat gaaatcaagg aagtaatccc atttcccatt tgcaatagct ataaataaaa
163861 ttaatataat ctcatctctt caataagtgg tgttgggaaa actgcatatc cacatacaaa
163921 agaataaaat tagacccttt taatatacaa aactggaccc aagttaatat acaaaaatta
163981 acttgaaatg aattaaagac ttaaatgtaa gatctgaaac caaaaactcc tagagagaaa
164041 catagggggaa aagctccttg acgttggcct tggcaataat tttttgggat attacaccaa
164101 aagcacagac ttttgaaaaa ataaacaagt aggactacat caaactaaaa agcttctgca
164161 tggcaaaaga aagtcaacaa catgaaaagg caacctacag aatggaggga aatatttgca
164221 aaccatatac ctgatgagaa gttaatatca aaatatagaa aatatataag gaactcacat
164281 atctcaatac caaaaaaata ataacctgtt ttataatggg caaaggacct gaatagacat
164341 tttttcaaag aagacacaca gatggccaac gagtgcagga aaaagcgttc aacatcacta
164401 atcatcaggg aaatgcaaat caaaaccaca atgagatatc actccacacc tgttaggaaa
164461 gctattatga aaaacacaag agacaatgaa tattggcaag ggcatggaga aaaaagaacc
164521 cttgtacact gttggtagaa atgtaaattg caacagcctt tatggaaaat agaatggagg
164581 ttcctcaaaa aataaaaata gaactaccat acaatctagc aattccactt atgagtgtac
164641 atccaaagga atcaaatcac tatgtcaaag agatatctgt acttccttgt ttattgcagc
164701 tttactcaca gtagccaaga taaggaaaaa atctaaatgt ccatcaacgg ataaagaaaa
164761 tgggggggagg ggtgtgcatg tatacataca caatggacta tttttcagcc ataacaaaga
164821 aggaaaccct gccatttgtg acgatatgaa tgaacccaga ggacattatg ttaagtgaaa
164881 taagccagac acagaaatac aaatattgta tgatctcatt tatatgcgaa tctaaaaatt
164941 tcaaacttga agacgaataa gtagaacagt atttatcagg agctagggga tgtggggaag
```

FIGURE 2 (cont.'d)

```
165001 aagcaaaata ttgggcaaag agtataaact ttcagttatg agatgaaggc caggtgcgat
165061 ggctcatgtt ggtaatccca atactttgga aggctgaggc agagggattg cttgagacca
165121 gcctaggcaa gaaagtgaga cctcatctct acaaaaaata aaaataaaag aatcagctgg
165181 gagtggtggc atacacctgt agtcccagct agtcaggagg ctgagggggg aggatcattt
165241 gaaattggaa agtcaaggct gcagtcagcc aagatagtgc cactgcattg cagcctgggt
165301 gacagagcga aaccctgtct caaaaaaaaa aaaaaaaaaa agatgaataa gttctgggga
165361 tcaaatgtac agcatggtga ctatagttta taactgcgtt attacttgaa attggataag
165421 agcagatttt aagcatcccc agcacccccc caacatacac acacacaaat ggtaactata
165481 ggtggtgata gatatgttaa tttgactgtg acaatcagca ttcaatatat acatatatca
165541 aatcatcaca ttttacccct tgaaatagaa actttgattt gtcaatcaaa tattttaaaa
165601 cgaaaataat cataatatta atatagcata caggaaaaaa tttcgtatct cgactgatac
165661 agaaaatttc atgataaaaa cactttaaaa caaaagaaat aaaagggaac tccctcaacc
165721 tgataaatgg catctgtgga aaccccccagc tagcatcaaa cttaatacag aaaggctggg
165781 tgttcacctc ttgaacccagg aacaagacaa agatgcctgc ttttgccact tccatttgac
165841 cttgtactga ggttctggct agggcaatta tccctgaaaa agaaataaaa ggcttccaaa
165901 taaaagaaga agtaaaacta tctctactcg ctcatgacat gatcttgcat atagaaaatg
165961 tgcacatgta cacacacaca aaccattaga actaataaac aagttcagca agtttgcaga
166021 atataaaatg aatgtacaaa aatcaagtgt ttttctatat actagcaatt aacaatctca
166081 aaatgaatta aaattccatt tacaatagta tcaaacataa attatttaga aataaaaagt
166141 gcactgaaaa ctacaaaata ttttgaaata aatcagaaaa gatttaagta aatggatcac
166201 ttgaacctgg gaagcagagg ttgcagtgtg ccgagattgt accactgcac tttagcctgg
166261 gcaacagagg gagactccaa agagtcgaaa agaaaagaaa agatttaaat aagctgaaac
166321 atattctatg gatcagaaga cttaatattg ttaaagtgac aatattcccc aaattgatct
166381 acagcttcaa ctcaacccct atcaaaatcc tagcttgctt tttggctgaa attgacaagc
166441 tgattctata atttatatgg aatctcaaag gatccagaat aaccaaaaca atattgaaaa
166501 ataaagaaca gcgttggtgg attaacattt tccaatttca aaacttacta tagcactgcg
166561 gtaatcaagc agtgtggcac tgtatagcat gtacattaca gatcagtgga ctagaatcaa
166621 tgtccagaaa taaaccgtta tgtttataat gaattacttt ttaataaggt gtcaagacaa
166681 cgcaatggga aaagaataat gaattcaaca aatgatgcat ggacaaccgg acatgcacat
166741 gcaacacaat gaatttgaat tcttctatcg ctccatgcat aaaaactaac tcaaaatggg
166801 tcacggatgt aaatgaaaag ctaaaactat aataatccta gaggaaaacc taggagtaaa
166861 tctttaagat gttattgtag gcagtggttt ctcagatagg accccaaaat cacaagcgac
166921 aaaagaaatt ggacttaaag ttaaatactt ttgtgcttca aacatcatca agaaagtgaa
166981 aacacaaccc gcagaagcaa taaaaatgtc tgtaagtcat gtatccgatt agagacttct
167041 atccaggata tataaataat gcaattcaat gataaaaaag ataaatagcc cagttttcca
167101 aagagtcaag catctgaata tacatctctc caaaaatata cagatatcca acaagcatgt
167161 gaaaagatgt tcaaagccat ttgccaggtg cacaaaccca agacagtatg aggagatgct
167221 acagggactc tgctgcttca cagacatgaa gcgttggtga gaatgtaggc agccgccttt
167281 ggggacttca catccccgcc gccccacgca cggtgagcta gtgtttaaac ttagccgaga
167341 tcaatacacg cgactgtgtg cccgtcagac cctgcgctgc cggcggggct gggagaggcg
167401 ggcgccagga gtgggcggga acctggggggt caggccccag ccgcgggaag ccgcccagga
167461 gcgcgcgaaa ccttctccac acccttccag gcatttgccc gccgcgattc agagagccga
167521 cccgtgaccc ctggcctccc ctagacagcc ccgcatgtcc agatgtgccg tcccgcctgc
167581 ctcccgcgac cactggccat ctctgggcct gggcgcggtc tcggcgcccg cctgccccccg
167641 ccaggagccg caggtccagc cagtgaagaa gcccgcgctg aaggagcctc tgtgctccag
167701 aatccatcct cagtatcagc gctggggtgg cctcctccag gaagcccttc tgattctctc
167761 atgggtcgct cttcctctgc agactcccgg agcacccctg ctccaagtac cgcaagtggc
167821 actgagaact tggggagagc agaggctgtg cctagatttg tagggagtcc ccgcagctcc
167881 accccagggc ctacaggagc ctggccttgg gcgaagccga ggcaggcagg cagggcaaag
167941 ggtggaagca attcaggaga gaacgagtga acgaatggat gaggggtggc agccgaggtt
168001 gccccagtcc cctggctgca ggaacagaca cctcgctgag gagagaccca ggagcgaggc
168061 ccctgccccg cccgaggcga ggtcccgccc agtcggcgcc gcgtgaagag tgggagagaa
168121 tactgcgggg gcgggggcgg gggcgggggc gggggcgggg gccgccggga gcctggagcc
168181 agaccgggcg gggccggcac cgggccaggg acagtggggg aggaggctgc gggctgagcg
168241 accctgaccc cccccagtcc gcgctcgttc cgg
```

FIGURE 3

```
1    gggcgccgag gctccccgcc gctcgctgct ccccggcccg cgccatgccc tcctacacgg
61   tcaccgtggc cactggcagc cagtggttcg ccggcactga cgactacatc tacctcagcc
121  tcgtgggctc ggcgggctgc agcgagaagc acctgctgga caagcccttc tacaacgact
181  tcgagcgtgg cgcggtggat tcatacgacg tgactgtgga cgaggaactg ggcgagatcc
241  agctggtcag aatcgagaag cgcaagtact ggctgaatga cgactggtac ctgaagtaca
301  tcacgctgaa gacgccccac ggggactaca tcgagttccc ctgctaccgc tggatcaccg
361  gcgatgtcga ggttgtcctg agggatggac gcgcaaagtt ggcccgagat gaccaaattc
421  acattctcaa gcaacaccga cgtaaagaac tggaaacacg gcaaaaacaa tatcgatgga
481  tggagtggaa ccctggcttc cccttgagca tcgatgccaa atgccacaag gatttacccc
541  gtgatatcca gtttgatagt gaaaaaggag tggactttgt tctgaattac tccaaagcga
601  tggagaacct gttcatcaac cgcttcatgc acatgttcca gtcttcttgg aatgacttcg
661  ccgactttga gaaaatcttt gtcaagatca gcaacactat ttctgagcgg gtcatgaatc
721  actggcagga agacctgatg tttggctacc agttcctgaa tggctgcaac cctgtgttga
781  tccggcgctg cacagagctg cccgagaagc tcccggtgac cacggagatg gtagagtgca
841  gcctggagcg gcagctcagc ttggagcagg aggtccagca agggaacatt ttcatcgtgg
901  actttgagct gctggatggc atcgatgcca acaaaacaga cccctgcaca ctccagttcc
961  tggccgctcc catctgcttg ctgtataaga acctggccaa caagattgtc cccattgcca
1021 tccagctcaa ccaaatcccg ggagatgaga accctatttt cctcccttcg gatgcaaaat
1081 acgactggct tttggccaaa atctgggtgc gttccagtga cttccacgtc caccagacca
1141 tcacccacct tctgcgaaca catctggtgt ctgaggtttt tggcattgca atgtaccgcc
1201 agctgcctgc tgtgcacccc attttcaagc tgctggtggc acacgtgaga ttcaccattg
1261 caatcaacac caaggcccgt gagcagctca tctgcgagtg tggcctcttt gacaaggcca
1321 acgccacagg gggcggtggg cacgtgcaga tggtgcagag ggccatgaag gacctgacct
1381 atgcctccct gtgctttccc gaggccatca aggcccgggg catggagagc aaagaagaca
1441 tcccctacta cttctaccgg gacgacgggc tcctggtgtg ggaagccatc aggacgttca
1501 cggccgaggt ggtagacatc tactacgagg gcgaccaggt ggtggaggag gacccggagc
1561 tgcaggactt cgtgaacgat gtctacgtgt acggcatgcg gggccgcaag tcctcaggct
1621 tccccaagtc ggtcaagagc cgggagcagc tgtcggagta cctgaccgtg gtgatcttca
1681 ccgcctccgc ccagcacgcc gcggtcaact tcggccagta cgactggtgc tcctggatcc
1741 ccaatgcgcc cccaaccatg cgagccccgc caccgactgc caagggcgtg gtgaccattg
1801 agcagatcgt ggacacgctg cccgaccgcg gccgctcctg ctggcatctg ggtgcagtgt
1861 gggcgctgag ccagttccag gaaaacgagc tgttcctggg catgtaccca gaagagcatt
1921 ttatcgagaa gcctgtgaag gaagccatgg cccgattccg caagaacctc gaggccattg
1981 tcagcgtgat tgctgagcgc aacaagaaga agcagctgcc atattactac ttgtccccag
2041 accggattcc gaacagtgtg gccatctgag cacactgcca gtctcactgt gggaaggcca
2101 gctgccccag ccagatggac tccagcctgc ctggcaggct gtctggccag gcctcttggc
2161 agtcacatct cttcctccga ggccagtacc tttccattta ttctttgatc ttcagggaac
2221 tgcatagatt gtatcaaagt gtaaacacca tagggaccca ttctacacag agcaggactg
2281 cacaggcgtc ctgtccacac ccagctcagc atttccacac caagcagcaa cagcaaatca
2341 cgaccactga tagatgtcta ttcttgttgg agacatggga tgattatttt ctgttctatt
2401 tgtgcttagt ccaattcctt gcacatagta ggtacccaat tcaattacta ttgaatgaat
2461 taagaattgg ttgccataaa aataaatcag ttcattt
```

FIGURE 4

```
   1 ttgcacgctn ctcagccccg gctgtactat tggtctacac gtgccatcgt ggtttgctgc
  61 acccatcaac ccatcatcta cattaggtat ttctcctaat gctctctttc cccttgcccc
 121 ccaccctcta acacgccctg ttgtgtgatg ttgacctccc tgtgtacatg tgttgtcatt
 181 gtacaactcc tgcttatgag tgacaacatc tgtctgattt tctgtcttgt gttagtttgc
 241 tgagaatgat ggttcccatc ttcatccttg tacctgcaaa ggacatgaac tcatccttta
 301 atatggctgc ttagaatccc acagtataga tgtgcctcat tttctttatc cagactatca
 361 ttgatgggca tttgggttgg atccaagact ttgctattgt gaacagtgat tcaataaaca
 421 tacgagtgca tgtgtcttta tggatgaatg attgataatc ctttgggcat atacccacta
 481 atgggattgc tggacctaat ggtttgcctg gatcctgatc cttgaggaat caccacactc
 541 tcttacagtg taaaagtgtc tctatatata ctcatcccct ccagcatctg ttatttactg
 601 actctttaat catcaacctt cttactggag agagaaggtt taattaccac taatgacgag
 661 cctttaatca aattgttgtt ggacccttcc caacttactt gcgaaggggt catttgtaaa
 721 cttacgccac cttttgatgg ggcagttttt ctcgtttatc cgcaaagatc ctgggggacc
 781 ccttttttta actcttttga agaccgttat atctgaacaa tttctcccat accgagaggt
 841 ggcgggttac aacccttgaa agtttctttt ttttttgggg gccccttagt ttcacaaaaa
 901 tcccttcgga ccaatttgcc ttttgttgcc aaggaatttt tccccctaag tcactaggaa
 961 tttttcccag ggcacacagg tgtagtggcc ttccccagaa tttttctcct gggtatccaa
1021 tgttataaga aaaaaaattg gggaattttt ttaaacctcc aataaaattt tttatagaga
1081 taaggccggt ttcatttnnn nnnnnnnnnn nnnnnnnnnn nnnnnnnnnn nnnnnnnnnn
1141 nnnnnnnnnn nnnnnnnnnn nnnnnnnnnn nnnnnnnnnn nnnnnnnnnn nnnnnnncgc
1201 ggtcttcagc ccgtggtgaa gactgattaa cagtcataag aaggtaaagc tctaagtgac
1261 ctgtaagaaa catacagtct cacacaatta ggcaaggagt ccaacttgga agaaagagtg
1321 gcatagattc aaaccctgat gccacaactt atgttaaccc tcctgaggct caacttctca
1381 cacatgacag gagaatctca tcatgtacct caattaattg atatacagat tatggtaaac
1441 attcaatgaa aaagtatgta aagtttctat cattctacta cagttggtat tcaacaaatg
1501 ccactttatt cactttctgt taagcctgaa agaagtactg aatgacatca acgagtgcaa
1561 ttcaacaaat ataatttgag cactgattac tcaataagca ttatgaggaa ctaaaatatt
1621 atcagcaaat gatggctgac atagaggaaa tgtgacagag taggaagatc cctgtactcc
1681 ctgtatcaaa ggactgagat tcttccactc aggaccatgt gtgaccccaa cagaaagtag
1741 aaatttacag aaagatacct ggcaaaacac ccaaatagtt tgaagttaaa aaatatacct
1801 ctgaataaca ccccatggaa atttttaaag attataatgt gaattaaaat gaaaacatat
1861 aaccataaca aaaattgtag gatacaggaa aactggtgct catatagcat taactgttta
1921 cattacattt tagagaatca acttaattca attatctaag tttctatttt agaaaactat
1981 gtaaaaaaag gagagcatat ttaaaaagta agcagaagaa caaaagataa gcatgacaga
2041 caatgaaatt gaaaatggaa aaatcataga gaagaatcaa atgaatcaaa agtagtttct
2101 tggaaaagat caataaataa aattggttga tataatttac tgatattagg agtgggaaag
2161 ataatcactg atcatagatc catgatgaac aagcttattt caataaatta ataaactcag
2221 caacttcaac aaaatggaca gattacttgg aagacaccaa ttaccaaagc tcaaaaaaag
2281 agaatctaaa tagtcctata tttatgaaaa aaaaaaacaa aactgaattt gtatttaaaa
2341 actttgccac aaagaaaatt ttaggttcag atgggtttcc taataaattt ttcccattta
2401 gtaagaataa tatcaattct acacaaactc attcaaaaaa aaaggagaga gaatacttta
2461 caacacgttc tgcaaggtca gtattaccct gataccaaaa caaaggatat tacataaaaa
2521 cgacaccaat atccttcatg aacatagatt cttcaccacg gggctggaag gatccgnnnn
2581 nnnnnnnnnn nnnnnnnnnn nnnnnnnnnn nnnnnnnnnn nnnnnnnnnn nnnnnnnnnn
2641 nnnnnnnnnn nnnnnnnnnn nnnnnnnnnn nnnnnnatag cacgcccttg agcccctggt
2701 gaatataaga gattaggcta cagcgtgttc tactccaact ttatttgctt tctgagcatc
2761 taattccact ttgcaaaatg gacatttttt ttccctcttg agagtcagga aattaccagg
2821 tgtgccagga taatccttag tatcaactgt aaaatatcag tataaaataa tgagtaagca
2881 tatttcagtg ggtgtttata tgcttttggt tgcatagcat gagccaaagg cagataaaaa
2941 atgtgggctc cagatagtga ctcaatctcc agaaatcata atgtcagtta cacaatgata
3001 tttctatatt ggcatcacaa aataatccac ttgtcatagg ataattgctc tagatgaggg
3061 catggagctg tgctgaggaa tctgccattt ttctttatcc agactctgtc tcataccgac
3121 cacaggcccc aatcattgtc tatcaaaaaa catgcttgtg tctcttttgg cttactatga
3181 aaggaagcaa gatcttttcc tcaagcattt aagtgttgac tgtgggctac ccagtgtgct
3241 agacactgng gatcaaattc tgtgaggtta aaaatacccc ataactcact ggatagaaat
```

FIGURE 4 (cont.'d)

3301 tcaaaatgct cgctatgttg attctatgat caacttccaa ggggaccttt ntacctccta
3361 tcttcatcag caagcaacta cattgatttt gtagcccagg atctattccc acgtcaaccg
3421 tgggtttcaa atgtttgctc tagctcaatg gcctcttaag ccactaaccc aatatgttgc
3481 tttttaccag taaaaaagtg catctgggga ataagttggt gtatatttgt ggttcagcca
3541 gcccatagat cgtccagagg accccaggct taggaggaat cctcagattt gagagccact
3601 gtcctgtatg atgcagatag cacagctctt cctgaaaata ggaattcaaa tgaggaaaaa
3661 tgaaaactct cctaattatt ttcttctgcc tctttcattc caagctcatc taattatcat
3721 gctctattgt gaagaatcaa agaaagaact cataaatata ccttttgtgc ctgtattttg
3781 aatgtacgtt gtgcatgtaa gcctttgtgg ttaagcaaat gtcaagaaaa tccctagtcc
3841 cattgcttac agtcaatatg gggcaattca agcaaagtat atgcctctaa tatggtttga
3901 aaattctgaa agttcagaaa aaatgttgct acttcagcca tctgatgtta ctggatattg
3961 agaatgagac ctcctctccc tctgctttcc tcatttccat ctcctccttc ctctttctcc
4021 tctctccctc tcctttattc tccttctccc tcctctctct ccatgcttac tcccttcctc
4081 ttctccctct ttcttcttta ttctccttct ccctcctctc tctctctccc ctttttcctc
4141 ccttcctctc ctccctccct ctcctttatt ctccttctcc ctcctctctc tctctccccc
4201 ttttcctata ttcccagatt aggccatttt caaaactggt taaacattcc ccaaaagcat
4261 ttatgacaga gaattgacta ggatctcacc tgaatcacag agcttgccca ttgaacacag
4321 gcaaagatca agccattttc tcttgatgtg atgcttcagc atttatgcca tttgaaacaa
4381 attttatgta aaaaaaagct tagccctttg gtgacgggga ttcctttcct ggatgatctg
4441 ccaaagaatc aagacccaac gtccagctta tcaaattttc tctggacctt tannnnnnnn
4501 nnnnnnnnnn nnnnnnnnnn nnnnnnnnnn nnnnnnnnnn nnnnnnnnnn nnnnnnnnnn
4561 nnnnnnnnnn nnnnnnnnnn nnnnnnnnnn nnccgtggtg aagacttcca cgtgaacttt
4621 aaagtagttt tttccaattc tgtgaagaat gtcattggta gcttgatggg gatggcactg
4681 aagattttct tcatttttat gactgcatag cattccatgg agtatatgta ccacattttc
4741 tttatccaat tcactgttgg tgggcaccta ggtcaattcc atgactttgc tgttgtgaat
4801 agtactgcaa tgaacatgtg agtgcatgtg tctttttgga ggaataattt gttctctttt
4861 ggatatatac ccagtaatgg ggttgctggg ccaaatggta gttctgtttt aagttctttg
4921 agaaatctcc aaactgcttt ccacagaggc tgaactaatt gacattccca ctgccatgca
4981 tgagcattcc cttttctcct cagctccacc aacatctgtt gctttctgac tttttgataa
5041 tagccattct gatgtgtgag atggtagccc attggggttt cttttttttt ttttaagaca
5101 gagtctcact ctgtcaccta ggctgtggca caatgttggc tcgctgcaac ctctgcctcc
5161 tgggttcaag tgattctcct acctcagcct actgagaagc tagggttaca ggcacctgcc
5221 accacaccca gctaattttg gtatttttgg tagagacagg gtttagccat attggcaagg
5281 ctggtctcta actcctgacc tcaggtgacc cacctgcctc ggcttcccaa agtgctggga
5341 ttgcatgcgt tagctaccat gggtggtttt tgacttgcat ttctctgatg attagtaatg
5401 atgatccttt tttcatacat ttgttggcca cttgtatgtc ttcttttgag aagtgtctgt
5461 tcatatcttt tgcccatttt tcaatggggt tgttttttcc ttgtccagtt gtttaagtta
5521 tttatagatt ctggatatta gtcctttgtt gggtgcataa tttgcaaata ttttatctca
5581 ttctgtaggt tatctattta atctgttgat agtgtctttt cttgtacaga agttgttcag
5641 tttaattagg tctcacttgt caatttctgt ttttgttgta attgcttttg aggacttaat
5701 cataaattct ttcccaaggc ccatgtccag aatggtgttt ctgagatttt cttctaggat
5761 tcttttactt caaggtctta tatttaaatc tttaatccat ctggagttaa tttttgtatg
5821 tggcaaaagt taggtgtctt gttttatttt tctgcatatg gctagtcagc tatcccagga
5881 ccattcattc actagggagt cctttcccca ttgtttactt ttggcaactt tgtcaaagat
5941 tagatggctg taagtgtgca gatttatttc tcagctctct attctgttca actggtgtag
6001 gtatctgttt tcgtactagc accatgctgt tttggttact gtagtcttat tagtatagtt
6061 tgaagccagg taatgtgatg cctctggctt tgttcttttt gcttaggatt gctttttggg
6121 ctctctgttg ttgttgttcc atatgaattt taggacactt ttttccaatt ctataaaaaa
6181 atgacattgg tagtttggta ataatagcat tgaatctgta gatagattgc tttgggcagt
6241 atggccattt taatgatatt gattcttcca atccctgagc atggaatgtt tttccattta
6301 tttgtgtcct ctctgatttc ttttagcagc gttttatagt tctccttgta gagatctttc
6361 acctccttgg ttagctgttt tcctaggtat tttaattttt tgggcctttg taagtgggat
6421 tgcaagcttg aattggttct tagcctgaat gttattggtt tatagaaata ctactaattt
6481 ttgccatcca ttttgtatcc tgaaacgtcc ctgagtcatt tgttaattcc cagaggcttt
6541 gtggagtctt taggttttct atttttagaa tctattcttc ccaaagagaa atactttccc

FIGURE 4 (cont.'d)

```
6601 ctctcttttc ctaatcggac ccctttattt attcctttgc ccaaggcttg gaaagcccctt
6661 ccatactttt ttaaaaagaa cgtggaaaaa ggcccctttc ttattctcgt ttaaaggaac
6721 cttccatttt cgctgtcaaa tggnnnnnnn nnnnnnnnnn nnnnnnnnnn nnnnnnnnnn
6781 nnnnnnnnnn nnnnnnnnnn nnnnnnnnnn nnnnnnnnnn nnnnnnnnnn nnnnnnnnnn
6841 nnntttgttg ggaatatccg gtgcttattc ctcttcagga gttttattct tccaaaaatg
6901 cagcttttca ttcctcctcg tttttctttc tgtgccaaat gcctccagcc tttccatgtt
6961 ggtgcggtaa gctagacatt tttagtttgt agtgattgtt ttcgtttgtg tttgtatgtt
7021 tttgtgccca tagtcacttc tgtaatgttc gtttctgagt ttcctttggg gggattaacc
7081 tgccactgaa gtgtcagctt ccctgtcatg ggactgtcct tggaatgaca ggttttcctt
7141 ccaccatagg atctgccact gtgaaggaga tgatgagagc cccctgatca ccccctgcca
7201 ctgcacagga agcctccact tcgtgcacca ggcctgcctg cagcagtgga tcaagagctc
7261 cgacacgcgc tgctgcgagc tctgcaagta tgagttcatc atggagacca agctgaagcc
7321 actgagaaaa gtacgtggga ggaagggatg cttcaccctt cctgaaacca gtgaccccca
7381 gaaagctggt gtctcagatc atgaggtcat ggcttgcctg cgttcatttc cttaaaaagc
7441 tggggctggt gcttacattt gcattgtaga gattgttgtt tctggtgctg attttcaagt
7501 ccctcttctc aggaagaagc tctttctgac cattcataat ccttcttttc ccttcaaagt
7561 aagactgctt gcttgtcggt gtcagtcctc tggcctttga ctacagactg tttgtgacat
7621 atcttagcac ctaattttat acatattaac tgttgacgtc ctgcttctct gattaggact
7681 gtctgttgga gattagtatc tccccagcac ccagcacagt gtagcataca gtaaatttat
7741 ttgtatacac ccatgataac tatttgctgg atgggagtgt gagtaggtgg atagggaaaa
7801 gaaaggaagc acaaacgttg cgtgatgtgc aactgtcttc agaaaggacc cacaggcatt
7861 gcatgacacg cagctgtctg gaggcccatg tcactgctcc ctctgagagg agctttgtcc
7921 gccacactgg cttcctgttt aaattttgac tgtttcatat atctctctag atgcccagca
7981 caaaaggttt tgtctggaag aataaaaaac tgttcctatc tcagaacatt aatatataaa
8041 ttgcaagata agtcacataa tcaaatacta gccaattaaa tgctaaatgg tgtgctggta
8101 gagcataaca gtcattcaga aaaggaaatg ctcattatga gctagagtgc tggggaagtg
8161 gagcgatggt agcctcatag ggtgtttggg ttttagagca gttcttgaag gatcactagg
8221 atttggaggc agagtgcaag gagtttagag aggtcaggct gtctgtggag taaagcatac
8281 cctagaaagg tgaaggtgaa cattgacagg gtgtcaagct acgtgcgttg taggaagtag
8341 cagggagcat ggggcactga ggcactgact ctgtattata ggtaggaaga ccagggaact
8401 tgctagtgta taaaatccca gcagaaaaca accagattta gagaaggctt gtgcaaactg
8461 cttaaaaaaa tgttttgccc agtagaaacc ttgtaattta ttgggtgcct actctatgct
8521 aatctctcaa catgggaagt ccttgaggct ctattttcaa ctaccctgca tagactcatc
8581 tggaaagagg ctgtgactag ggttggcaaa ggatatgtgc agagtgttta cacattgttc
8641 tttctctcta cctttatgtg ttttctcctg attcggaaac cagtaaatga aaaagaaagt
8701 ctggctattt ggagtaaatt aatgagctcc tagaggagat gggactagca gagtctgctt
8761 gtaccaggaa ctcttagcgt cgatttcgag ctgttgctgc caaagtagca aggaccaaag
8821 agtgagcgtc ttctgccatt caccttcaca atgtagtgtg acccatctgc tagtgtgttg
8881 tggcatcatc aaccctcttc ttccgctcgt ccatgccagt cagcacatca gggagactta
8941 aaacgtagta cctgggtcct gggccaacat actgttttca ttaggactga aatcatagaa
9001 ttctttatca ggccatctta tgtctgcttg caagaataag cagacaaggg gatttttgat
9061 ggtagttctg cattcatctt gatcctggct tcttttcatt gcatagaaag ttggctgcac
9121 ctggtacctg gttgaagcca agtggtttta ggagaacaat acttggggga atgcatctag
9181 tttgggaagg gagaagtggg gtggaaagcc aatcttacct acctacaatg ctctcacccc
9241 accggagccc ttccccagaa gcctgagcct cacactctgt gttgtctttc tagtgggaga
9301 agttgcagat gacgtccagc gagcgcagga agatcatgtg ctcagtgaca ttccacgtca
9361 ttgccatcac atgtgtggtc tggtccttgt atgtgctcat tgaccgtact gctgaggaga
9421 tcaagcaggg gcaggcaaca ggtgagttct caggctggag caagctcagc atgggggccg
9481 ggatagctca caggagtcct ggggtcagag gattttccag ttagccaaaa acgtctgggt
9541 ttccggagga gggacatcag ttaggaggca ctagcctcct ttttggcatt tcttttgctg
9601 tggtggtagt ttttgaaacc cagtcaggag agttcatatt ctggagcatg agaatctccg
9661 caaactacat cctataaaag caggaagtag ctggacactg tcttccactc ttctttgact
9721 gagcaacatt ggatgagttg tgaatccatt ggtcagtggt gcaggcttgt ggtccccaga
9781 tacttgaggc tgagggatgg aggattgctg aggctcagga gttcaaggct gtagtgtgcc
9841 atgatcacac ctgtgaatag ccactgcact ccagcgtggg caacatagca agactccatc
```

FIGURE 4 (cont.'d)

```
9901 tcttaaaaaa caacaacaac aacaaaggtc ttcaccaggg atctgcctag gtcagcgagg
9961 tggttcatca agannnnnnn nnnnnnnnnn nnnnnnnnnn nnnnnnnnnn nnnnnnnnnn
10021 nnnnnnnnnn nnnnnnnnnn nnnnnnnnnn nnnnnnnnnn nnnnnnnnnn nnnggagtgt
10081 acttcacccc gtggtgaaga tgcggcacag actggcgttt cctacggcgc cttcactgga
10141 aagcgcccct gtggtcctgg ggagagggcg gctccatccg ccacccttcc cggagctgcc
10201 cccgcccatt ctcatgggag gaaatcgcag ggcgtgtgag cccccgaccc ctcgccccca
10261 cctctgccag gaccggccgc atttctgcac tgtcccgccc cactgggaag gaaactctct
10321 ttctcaattt cctttaatga ggacattgtc ttttcagccc tgccaccccc tgcaatcgtc
10381 ttccaggctg caaacagcga gtggggaggt gaacacatca gcttttcctc cctccacacc
10441 accaggaaat ttcgcaaacc acttggctct cggcggcctg gcctcgccac acctgtgccc
10501 acagtctctc tccgctgcag ccccctgtgc cattctccag gccccacgta cctctgcctg
10561 ggcccagtaa gacctggtca gatggccccc ggctgcaaag ccttcctggg ccccatcaga
10621 gaggacgccc aggtgaagcg agggtcccct gcccaccctg caagcgcagg ggcccttcca
10681 agagtgcagc cctaggccgg tgtgtgatgg tggagacgcg gtcccagagg gcctgaacca
10741 agaatggaga agacaaaggc tgtctttagg gagaaacttc cctgaggggc tgatgtgtgc
10801 gatcccattt taatctcaca accctgggga ggagctgggg ccgggtctca ttgttcattt
10861 gaggacaccg aggctcaggg aacttagacg actttcctag ggtccccccca accccccaccg
10921 gcccagggcc ctctcccagg cacccctcat ccccacacag gctcctctaa gctgcttcct
10981 tgtggtccag ccccccttggc tcagctcctc aaatacaggg acacctcttc tctcccccgc
11041 agaactcaag ggtctccatc cactgtgcca gcacagaggc ggtgctcaga gtggggctaa
11101 gcttactgtc cagcctgctg ggccaggagg ggcagaaggg cccctctcag gattccttcg
11161 ctctgctcct gccaataggc catcactcaa ggggctaatg acaggacgat gtggagaaac
11221 gtgggctgca gcacttctgg ggccaagggc agggtgggcg gcactgggga gtacagggga
11281 ggggacctca ctggggccag aggcttctag aagcttctgc aagaaggggc ccctcaccca
11341 tgtcttggcc aagaagtggg gagggtgggt gtggcaaagg aaacagctag gtcagagaca
11401 agagatgctc tgcaaagccc tgctggctcc ccacggtgga gcatcctatg catgtaggac
11461 ctgagagatg gcaggggcgg gtgcgtccct atggatgtat ctccatttct gggcagagac
11521 atctgggctc tcacctgcaa ttgagccaac caagaaatta tatttacttt ttagagcgag
11581 cctccaacaa attatacaag cacttgagaa taagccctcc cactgtcttg agagatggag
11641 cccagggagg cagctggaaa gatgctcctg ccctcactca ggagagatgg tggagctggg
11701 agaggaggag gcactccctg ggacccagca gatggacttg actcagcaaa tagatgcaac
11761 catatgtggg gggtggggag gcccagaaag gcattacagg ccagtgttct taatcctggc
11821 tatacactgg aatccaccag tagccctaaa atataactgt gctggacttc ccctggttcc
11881 acagtttgtg cagagtgggc agcatggagt ctgtaacact aaacacacag gattgagaac
11941 catatgtcta ggctgttgtt agccatgatg gggatacatg aaaaggaggt gcacagttac
12001 cttctatacc acaggatagg tgctcattaa accctgttaa aatggactgt gacccagctg
12061 gcactcaggg gcactcaggg gccaggtggg tcacactttc attttaatag gatttaatga
12121 gcacctattc tgtgacagct gctaagatac agaggctcct gagatacaga gatgacaatg
12181 accttcagaa acactgaaca gagataagaa aggcacagtc tggccttcac tccaccatta
12241 attcctccat ccatccatcc atccatctat ccatccatct ctctgtctat acttccatcc
12301 atccaccatc cattcaccat ccacccatca atccatccac ccatctatcc atccatccat
12361 ctcactatct gtcatccatc catccatcca ccatccatga atccatccat ccgtatatca
12421 atttctcatc tatctctcca tccatccccc atccacctct tcttccatcc ttcctccttc
12481 ccttcatcca tccattcatc atccatccct caacccatcc atctgcctgt ccatcggttt
12541 gattgtccat ctgtccagta ttcctccatt ccctccaaac tgggtggcag tactctccac
12601 ctcactacct caccatcctt attattccct ccaaactgtc tctttcacaa gggccttctg
12661 tcctgcctgt cccatcctgg tctgggacct atcccactaa agctacatgg ctttgatcaa
12721 caatcccaat cccagagtag gggaagggaa gtgagcccct aactgccgtg atgtttccag
12781 ggagatggtg gatactgctg cattactaat ccagatgtta ggttttaatt tttctctcca
12841 gtagacccca attgtggtag gagaaaaatg ccccagcttt ggacacaaac agacctggat
12901 tcaaatcctg gttttgccaa tttctgccta aatgacttta ggcaaactcc ttgaccttga
12961 ccccttggag actcagtttc ctcacctaga aatggtcaat aatattattt acctcccagg
13021 atggccatga agcttaaaat agattattgt accccccaaa acaccgacac aatgtttaga
13081 aataaataat attattttaa gctttgaagt ctggctgggt tctcagcctc gtctacctgc
13141 tgggtgtgca gactcaaagc cagggtccca ccctcataga ctgtcatctg tgggtgtggg
```

FIGURE 4 (cont.'d)

```
13201 gttggcctgg cactagcagg tgctaatgct cctcagagga ttctaggtgt aaaaggaaat
13261 gaaaatcttt ggacccccaat tcactctgcc aaaagggaaa aattaagctg aaagctgagt
13321 gatgcaagaa acgaagatag ctacagataa aaggtgaaaa cctccacagg tagctcttgg
13381 tgttcacctt atcaagtgct gatgtactaa gcgcaagagg aatacataac tgactattcc
13441 cctacctgct ccttttcttt tgcaacatgt ggattcagta acgtgaccat gccctccctt
13501 tcttccttcc agcctgttct cctttaaata ttgatgccct taaagacatc ttcggaaaaa
13561 ggcacagtcc accaactgtt cctgtggatt tgtgttcctt ttttccgtgt atgtcttttt
13621 ttttattatt atactttaaa ttctaggata catgtgcaca acgtgcagga ttgttacata
13681 tgtatacatg tgccatgttg gtgtgctgca cccattaact cctaattagg tatatctcct
13741 aatgctatcc ctccccctc tccccacccc atgacaggcc ctggtgtgtg atgttcccct
13801 tcctgtgtcc aagtgttctc attgttcaat tcccacctat gagtgagaac atgcggtgtt
13861 tggtttttg tccttgcgat agtttgctga gaataatggt ttccagcttc atccatgtcc
13921 ctgcaaagga cattaactca tccttttta tggctgcata gtattccata gtgcatatgt
13981 gccacatttt cttaatccag tctatcggtg atggacattt gggttggttc caagtctttg
14041 ctattgtgaa tagtgccaca ataaacatac gtgtgcatgt gtctttatag cagcatgatt
14101 tataatcctt tgggtatata cccgataatg ggatggctgg gtcaaatggt atttctagtt
14161 ctagatcctt gaggaatcgt cacactgtct tccacaatgg ttgaactagt ttacagtccc
14221 accaacagtg taaaagtgtt cctacttctc cacatcctct ccagcacctg ttgtttcctg
14281 actttttaat gattgccatt ctaactggtg taagatggta tctcattgtg gttttgattt
14341 gcatttctct gatggccagt gatgatgagc atttcttcat gtgtctattg gctgcatgaa
14401 tgtcttcttt tgagaagtgt ctgctcatat cctttgccca ctttttgatg ggttgtttt
14461 tttcttgtaa gtttgtttga gttgtttgta gattctggat atcagccttt tgtcagctga
14521 gtagattgca aaattttttt cccattctgt aggttgcctg ttcactctga tggtagtttc
14581 ttttgctgtg cagaagctct ttagtttaat tagatcccat ttgtccattt tggcttttgt
14641 tgccattgct tttggtgttt tagacatgaa gtccttgccc atgcctatgt cctgaatggt
14701 attgcctagg ttttcttcta gggtttttat ggttttaggt ctaacattta agtatttaat
14761 ccatcttgaa ttaattttg tataaggtgt aaggaaggga tccagcttca gctttctaca
14821 tatggctagc cagtcttcac ccggggctga aggtaccgct tnnnnnnnnn nnnnnnnnnn
14881 nnnnnnnnnn nnnnnnnnnn nnnnnnnnnn nnnnnnnnnn nnnnnnnnnn nnnnnnnnnn
14941 nnnnnnnnnn nnnnnnnnnn nacaatgaga acacatggac acgggttggg ggggtatcac
15001 acactggggc ctgttgggct atgggggct ggggagggat agcattaggg gaaataccta
15061 atgtagatga caggttgatg ggtgcaacaa accaccatgg cacatgtata tctatgtaac
15121 aaacctgcac attctgcaca tgtaccccag aatttaaagt ataataagaa aaataaaaat
15181 aaataagtta aaagagatta aaaaaataaa agagaacatt tgccacattc agtctttcta
15241 gatggaaaga ggttgctgac atatgataga attagaaaat cacacatctt gtaaattctc
15301 atttgtttaa aaagaaatca tacaaattag atgtttttg gagatgactt tttaaaatag
15361 agtcgttaga tcacctctgt aagggatatg tctatatctg ttcagtgggt taggggacat
15421 ggatctggaa agcctgagaa gaaaaagaag gttctatacc agacttgtga tatttagaca
15481 ttttcatatt ctatccattg ttttgtgtgc attttattcc tcactattgt atatatagtt
15541 gacaatgcta aactttttg tgtattcttt ctatgtgttc cgaatgccta atatatgtca
15601 aaattagcgg tagtaaaata atattttgta aatatctttt tgctaaaatt catatgaaat
15661 gttgtttttg gaggggaatg gccaaactac ctgttgagta atactcatcg tgtttgtgtc
15721 ctggttcagg ggaggaggaa ggaggggaaa gtgcagagag ctctatgccg ctgtgtttac
15781 agtgaggcaa gattaaccat tatctcttat gtctgtgcat tttgttttac ttatctgttt
15841 atgtagtgta tataaaggac aaacgagtcc taatttacaa catctagtct ttttagatgt
15901 taaagaggtt gccagtgtat aacaaaagta gagttagtaa actaatatat tttgtatatt
15961 ttgttttaaa attcctagga aagattgtct tcctatcttt gagcattctt gcgcactgag
16021 ttgatggaga tgggagggat tctaagctag gatgttctta tttggaagac tctttcaaat
16081 tataactatg gttacatgta tgcagtttat tcgagactgc tgtgtatata gtggacaaat
16141 taactcctta cttgaaacac ctagtttatc tagatgttta gaagtgcctg atgtacgtta
16201 aatgtagagg taataaaata ccactttgta aatatctttt tgctaaaatt cataggaaat
16261 actgtctttt agaaatttaa ttgttaagcc acctttgtga gcagtatagt actgtctata
16321 cttgttcaat ggtttagagg aggtgggagg gaagaaaaat atgtgactga cttatttcac
16381 taagcctaat gtctttaagt ttcattcatg ttgtggcatg tgtcagaatt tccttccttt
16441 ttaaagctga ataatattgc attgtataga tatattacct tttatttatc catttatcca
```

FIGURE 4 (cont.'d)

```
16501 tcaatagaaa cttgggttgc ttccatattt tagctatcat gaatattgct gccatcaaca
16561 tgttgagttc ctgtattcaa ctctttgggt aatacccaga agtgaaattg ctgaataagt
16621 atggtaattc tctgttaaat ttttgaggag ctgctgattc atacttttac gtataaaata
16681 ttagacctta aatgtattat gtaaaaacac taagtatttt taacattcta gagtaaagaa
16741 ggtgtttctt agcaagacag aaaagctgaa accctcaata gaaaagcctt gttaatgtta
16801 tcacataaaa tattcaaaat ttctgaacac acagacacac acgcactaac gaaaagctat
16861 ttacaacttg tggtagatga agaaataatt tcttaacata gcaagaaccc aggcaaatga
16921 ttaagaaaaa gaataatcat acaaatttaa tacatgtgag aagctgttca gcctttccca
16981 ttaattaaag aagtaaaata taaaacaaaa catataattt ttcacttagc agagatgaaa
17041 taccaaaaca gatgggtata ggtgtggaac atacttcctt ggttgacagt tagccaatat
17101 ctattaaaat cccttgccac agtaatttca gttctagaca tttgtcttat attactgtat
17161 ttattctgtc ctgtaaccat aaattccaca gctgcctagt gatggttcta tatttaaatg
17221 gaatgcttac tctcagtatt gtttttttctt ttgagatgga gtcttgttct gttgccaggc
17281 tggagtgcag tgccatgatc tcagctcact gcaacctcca cctcccaggt tcaagtgatt
17341 ctcctgcctc agcctcccga gtagctagga ctacaggtgt gcaccaccac gcccagctaa
17401 tttttgtatt tttagtagag atggagtttc accttgttgg ccagtatggt ctcgatctct
17461 tgacctcatg atctgcccac cttggcctcc caaagtgctg tgattacagg tgtgagccac
17521 gacacccagc cagtattttt tttttaaac cacagcttct tcattttgag tcatctctaa
17581 atagctgcaa tttactataa cttagggttt acaattttta aaattgtgta tgttaaggta
17641 tccacatgat gtttgatata cttcttttga cataaatata cacaatgaag tgattactac
17701 agccaaataa tgattaccat acccatcatt gctagcgttt agaaagacaa ctgattttta
17761 tgtgctgata ttgtaccctg caaccttact gaatttacta aatctagtag tttttggtg
17821 catcctttgg gattttctat taacagaatc atgccttctg caaatgtaag taatttagct
17881 gcttcttttt aaatatgtat gcctcttatg tctttttctt ggctatgttc ttttctctgg
17941 ctagaacttc tagtacaatg tccagtgtca gtgttgaaaa tgggcatcct tgtgttgttc
18001 ctgattttag gagtaaagct tacagttttt ctaccccctga gtatgatttt agttgtgaga
18061 ttttcctata tgccctttat catgctaaga aagttccctt ttattttagt ttgctgattt
18121 tttaaaatta tgaaagggca tttaatttta tcaaatactt ttttctgtgt ctgttgagag
18181 tttggccatt ttttttctat tgaaatggtg tattatggta gctgattttt ggatgtgaaa
18241 ccaaccttgt gtccttggga taaatcccat gtaatcatgg tgtataattc tttctatgta
18301 ttgctggatt tggtttgcta gtattttgtt gggaactttt gtgcccataa gataagaggt
18361 attgatctat ggttttcttt tcctgtgatg tctttatttg gtttttgtgt cagggaaata
18421 gtggcttcat aaaatgttca agaagtgtac cctcctcatc tttttgttgg aagagtgtga
18481 aaaattggta ttatcaaatg tttagtagaa ttcaccagtg aagccatttg cttttctttt
18541 tgggtagttt ttgattactg attcattctc ttaatttgtt ttaggtctat tcagattgtc
18601 tgtttcttct tgagtcagtc ttggtagttg tgtctttctt gaaatttttt catttcactt
18661 aaattatctt atttgtcagt gtacaattat ttttggtatt cctttataat ccttttttatt
18721 tctttaatgt cagtagtaat gtctcttctt ttatttctga ttctatagtt tgagttttct
18781 ctcctctttc cctgatgaaa ctgaagtttt ttccatttta ttgatttttt tcaaacgatc
18841 aaattatttc attaatttgt gctgttatca ttatttcctt ccttctgctt acttaaattt
18901 agtttcatat tttttgtaag tgtcttaagg tagaatttta agttattgat ttaagaactt
18961 tcttaataca agtgtttaca gctgttgata ttactctaat tacttcttta gctgcatcac
19021 aattgttttg gtatgttgtc ttcattatta ttcgtctaaa aatattatct aatttctgtc
19081 ttgatttctt ctttgactca tgaattgttt tagagtggaa atttcatttt aaatttccaa
19141 atatttgtga atttcccaaa tttcccctgt tgttgatttc taattttatt ccattgtggt
19201 taataacata ctttgcatta tttctatcct tcaaatttat tgaggtgtgt tttatggcct
19261 aatatgtggt ctatcttcta gaatgttcca tgctcacttg acatgaatgt atactttgtt
19321 gttgttgtta agtagaatgt tccatagtcc ttgaggtcta tttggtttgt agtattgctc
19381 aagtcctctt tttccttgtt gatccgtcca gttgttctat ccatttttga acgtgtagta
19441 ttgaagtcct tgactatttc tgttgactcg gttgacttgt ctatttcttt cttttctcag
19501 gtctgttttt gtttcattta ttttggtgct tcatatatat aggtgcatat atgttgataa
19561 cagttatatc ttcctaatgg atggattcct ttgtaattac aaaaggccac tctatctcta
19621 gtaacaattt ttgttttaaa gtctatttgt ctgatatcag tgtactgact ccagtgtttt
19681 tgtggttgct gtttgcataa tatatttttc ctgttctttt actttcattc tgtgtcttcg
19741 aatcaaaatt gtgttttctc cagacaatat atacttcatg ttttcttatc caatataaca
```

FIGURE 4 (cont.'d)

19801 cctttgcctt ttgattgcat tgtttattcc attcacactg catattatta tttagtggga
19861 tttatgtctg tcattttagt tctttttgt ttttgttttg agacagaatc ttgctctgtc
19921 acccaggccg gagtgcagtg gcgtgatctc ggctcactgc aagctccaac tcccgggttc
19981 aggccattct cttgcctcag cctcccaagt agctgggact acaggtgccc accaccactc
20041 gtggctaatt ttttgtattt ttagtggaga ctgggtttca ccgtgttagc caagatggtc
20101 tcgatctcct gacctcgtga tctgcccacc tcggcctccc aaagtgttgg gattacaggc
20161 atgagccacc gcacgcccgg atttttttgtt ttttatatgt atcatgtctt tgttgttcct
20221 gtttgtctt tacttctttc tatttcattg aattaatatt ttctaatata gtatttaagt
20281 tttattaata attttatcac tgtattttta tttttagtgg tttctctagg attttctgta
20341 tatatcttat cagtatgagt ttcagattca cactagctta attccagtaa tatgtagaaa
20401 tgttactcat gtagaactta attctcttgc tcttttgtgg ttattttatt tatattatat
20461 caattaatgt tacaaagata tacattgttt aaattattat tggtgctatt attagcatac
20521 ataacaccca catattaaaa ttgtatatat tgcatatatg tattatagaa ttgtatatat
20581 tatagggcca atagtatatt gtatacatgt tattttatat aattgttttt aaaatgagtt
20641 aagaaaaaag aaaaatgcat ttctactgtc tattatagaa aaataattac atcatactga
20701 acgtcttcac cnnnnnnnnn nnnnnnnnnn nnnnnnnnnn nnnnnnnnnn nnnnnnnnnn
20761 nnnnnnnnnn nnnnnnnnnn nnnnnnnnnn nnnnnnnnnn nnnnnnnnnn ncgcggaatt
20821 cctaaaagaa ttgctgagac aaagtatatg tgcctttgtc atcctgaggg cagttgtcat
20881 cctgtggagg tttaccattt gctctcccac cagcaatgta taagcatacc tgcttcccaa
20941 cacttccgcc aacacatatt atttgattaa ttttcttggc tgataatggt atctcattgt
21001 agttttaatt tgtatttctc attgtgagag aaatgaagca tcttttcatg ttttgagagc
21061 catctgtgca tcttttccca ttgtttctgt taagtcattg atttgcagta ctgtaatttg
21121 tgatgagttg taaacatgag ctcttctggc ctcttaacca tccttatcca gcctgtcttc
21181 acgttcctcc ttgcctaaaa acaagctcac tcaaacagat cattcctgtg gccctctccc
21241 ttttgaaata aatcagatgg gcaaatttgc ttttgttagg ggcctgagac ccaaatgttt
21301 aaaagtagct tagctgatga gtgaaaagga ggcccagttg ggggttgcac agaaaatgag
21361 gggcgtgggt aatagaggag gctgggcagt aacctggcag aaggcgccag aggccaagga
21421 aggtgcgctg gtgtcctgca gtgagaagga tgtgtgcact atcaactggg taaacacact
21481 gctatagctg ctccagcgac agcaggcact ctcagaaggg aactgagaaa aggggaatgc
21541 cagtttctgc caaggatata tggaaaagtt tttttcccc gtatgttctt tggcaacctt
21601 gttaaaatca tttaaaatgg tgaatttgat aacaaagcca gccactaaaa gacttggatg
21661 tagcaaaaca aattgtcaaa aagtatttat catttctaag aaataaaata aactgggatt
21721 taggcttgga tagaaatcca gaggtttgtt ttggcataat taattacaac atctgaagaa
21781 gggaggattt ttacaagaat tttttttttt gtagtgagat tgctttatat tccttttcat
21841 gactggagag tctgtcattt ggcaacccgc aaagaacttc aggaacagag ggcctaagtt
21901 ttcttgacac atttggattt ttgcatgatg aacatttgca cttttattag taattgtcga
21961 gtcgtgtgtg gtctgatcct atggagagga gagtgtaggt gtnntctctg gagctagtac
22021 ntgccccccgn gctcacacgt gccacactgc ctgctgcttt cangaaagag caggacggct
22081 ggtcctgtcc catctagtga ggtcctgtcc catctagtaa ggttctgtcc tcagagctcc
22141 taagagggga ttgctggcct ttgattacac tggcttccag aatctgacca tggaaccatt
22201 atttgaagct gtcagcttca ttttgttgtt gatcaggcca gtcttttagg tctttgttgg
22261 ttgatagatt tctctcaggt ctatagcagc aacaaataaa gctctttaaa attattttct
22321 tgaccattct gcctatggat tggttctgac ctttgaaatg tttgctgtcc tttagatcgt
22381 gacagaagga gcctcttctg ggagctgtga agaccccaca gatctcactg gttttcttgc
22441 ttttattgga agagttagca tttgttgaag tttatattta tgtaaaataa caataagtag
22501 attttaaaat ttttctttaa attctgtgat ctaataagaa gagagactct ttctctgtca
22561 ttgggaggct tgatgaggat cggacatacc tgctgagagt atcctgtaat gttttcataa
22621 gattggaaat ggtgaaatga gagcagaaat gtaggcagag gatgccaacg ctgtttccta
22681 tttcctaagt aaaactgagc agggcagaat ctccccagcc ctgccagaac tcccttcctc
22741 cttgggtccg ctgtcactgt catgctggcc ttgacatctg ctacaagtgc acacacatgg
22801 ggaaccacac agggaagtga acacatgtcc tgacgtgtgt gtgtgcctgg tgtggctgct
22861 tccttgatcc aggctttgtt ttgttacgag gctctgccct cctaccttca ggccttgctc
22921 ctcatcatgg gcatgcaagg atggaatcgt taccccagag tacacttttt gacttggatt
22981 acttgtagtt tagtactgga gttcagaact ttaatttccc atcagaaacc tgcctcccgg
23041 acccaggaca ctgaccttga ttgggcacga ttttccagat aagaccttac ctcctcccaa

FIGURE 4 (cont.'d)

```
23101 cagggtttgc cttcccttca gaatacagga aagtacacgt ggttccaaga ggaccatgct
23161 cttactaaga taaaagggag gagggtgact aggtactttc ctctgctgcc atcccttgaa
23221 ggaagggggc ttccttcaat gcctcatcag ttccagggag tatgcttgac ccagcaacac
23281 agaggaagaa gtgacctcat agcaatgagg ggcaagcatg tggatattgc tgggtatttc
23341 ttcctcaaag tctacctggg gacaggtgat gaagacgctt acttctctgc aatacaccgt
23401 gatcaggctt tggtcttcat gacacatttt agccttgcct atgtgtgttg aacagagctg
23461 gtcatcctca gaaataaaag aagagagcaa taagtacagg aaggctttca gtcccagaat
23521 agtgttagga ctaaatgtca gagaacaggg ggactgtagg agtttgggga ccttagcatg
23581 gataccctct caatctgctc ccctgtggta taaacagtaa agcccattgt actaaaaggc
23641 cttgagtgct tgtctctggg gcaggtggag ccagtgatgg gtgccccgag aggaggatgc
23701 tggagagggg acagtgtcta aggcagttgg agaaaaagga caatggctta tgcagtcagg
23761 cctagaagat gcaagggatg tcacagcata gtgtccacag gcatccctag atgtctttca
23821 ttttgtttca ggaagaatat tgacaaaggt agtgatggga gggttatttc aaggatgcta
23881 ttttcatgtg tccaagtaaa cttaagattc ctaagaactt tgacctctaa tgcttttaaa
23941 gaccgtgtac ctcatgccca tatgcacatt cagttagaaa ataaatgtag attctttggt
24001 gaattcgaag atgtgctcat ggagtggcac agcgtgatct cagtgtacac atgaagcatg
24061 ctgatgagag cttcttggat cttgtttctt caggtggact tgcattaaag tgctgttgaa
24121 tctctgcact gggagtggga gcagccatgc gatgggtgcc ttaatccgag tgccatcctg
24181 gctctctcca ggctgcttca tttgctgtga ggggtagggg gaggaggagt ttccaggcaa
24241 tggccttatc tgttctggtg gttgaccaag ggtcgggggt cccaaaggtg gagttccagg
24301 atgagagtgc accccttgggg atggtactta gaaagagtgg ggactaggcc tcagccaggg
24361 aatggtgggc cagggtggag ctcctttgta tcaaggagtt agggccaagg gccatgcagg
24421 tgggcctgca gaaggtgggt ggtgatatgg cctttctggt gataacagac tcgtggcact
24481 gtttcctgg ggctgttggg gttgcatgga gcagattctt actcaggctt actgtcttaa
24541 ggagggaaga atgctttttt atgaatacgc ataggtctgt ggggctgtgg agcctgggga
24601 atccgaggct ggcgtgggag tctgggcccc tctagcggtg gtggtgcatc ctcagctcag
24661 tgccactcac tgtccctatt tctctctgtc catttctctc ctcactgcag tgcttcctct
24721 ccttcctaga tttttttctc taagtttgac tattcaccac cccagagact ctgttctatc
24781 ccatgacctc ttgctgtact ttctttcaaa tctaaatttt cttgattatt tttcttaatt
24841 tacagtttca agattagatc tgttgggagc attctgtgct ctacctcagc ccctggttga
24901 gctatggatt ggtgtccccc atggtgacgt ggtctggact ccccttttgtg tgaagagctg
24961 tggcagggca gtgaggtttt gtggaactca gggagcatct ggcactatgt atgaggttgt
25021 gaggtgggag agagctctta aatctaccag ccttgttgat cttgggaact aggagagagt
25081 gctagggaag ccagtgccag caggcctgga gcctcatatt tctttggcat ttgtatgata
25141 ccttctagta cttcgttttt tgacttatat atgaactaac tcaatttaga tgcttagaaa
25201 ataaacggcc actggacctg caagagatta gtagtggtgt tccatagcct tagacatttc
25261 ttacactttt atccacagat aagaaaaaaa tagtgatatt tgatttgttt tgccaaggct
25321 tagaaggatc taatatgtgt tactcgttga gcagcgggaa gcagcagaca tttctagggt
25381 ttctccctgt caccattcag gagacagtgc acacaatccc cttggctctt acctgaacac
25441 tgaccacagg tctgtcattg caggctggga gtcctccgtc agcatcagct ccggctccgg
25501 tgtcctcctt ctctcgcact tctatcacgc catccagcca ggacatctgc aggtaacact
25561 ctgcttcaga tgctgccatg atcagtgtgc agccagaaat aagcattagt gtctgtaggt
25621 tcttgaattt ccatttgctt aatcaatctg cctttggtct aaacagttgg cgagttttat
25681 gtgtggtttg ctcaccaagt tacccatgct agtctcattt cttcactatg atgtctattc
25741 tcttttaaaa ttgtttttac tttctgtgct tttatcccac tgttctgcat gcagttccag
25801 tgcagtgttt tctgagtgtt gtcaccacag ttccgtgcag tctgctgttg tctcgaaagc
25861 tcctcactgc cagagttctc tgacacaagg gctcactgtg acagttatct gtaaggacac
25921 attacaggcg tcaaagagaa attcctttgg ttcagaatgg gcccaggcct tgaagcctgc
25981 taagaatacc aaagccagaa gaacactaaa gttctcaagg tccctcaatg atgtgggtga
26041 gaaggcgcag gatacttcag aaagttttgc ctatgtggaa agaacttgtt ctgaagggaa
26101 attaatactc cctcaagata cgtgtctcag aactaacagg tttcatcata aagaaaaaag
26161 aaccctgaac cacaaacctc ttggcaattc caaacattct tgtgtttcat gcctttctgc
26221 cggtcgctca actgcctcag aggtggaagc tggcaagggg ggcaggcccg gcctgctgct
26281 ggaagagaag gcggatggtg aggccacgtc ccgaagccgg caactgctcc agtacctgtt
26341 ctcactctcg cacggcttga gcgccagcag cctgcacagg ttccatgagc tggagagctg
```

FIGURE 4 (cont.'d)

26401 cgctgctcgc ctgcacactg ccaagtcctc cagcgggctg gcagggagta tgggcttctg
26461 ctctgacgag atgggagacg acgatgtctt tgaggacagc acatctgcaa aactgaagag
26521 tagggttctg cgggcgcccc tctgctccac ggaaaaggac agcgacctgg attgtccttc
26581 tcccttctct gaaaaattac cccccatatc tcccgtgtcc acgtcagggg atgtctgcag
26641 gttggtttgc caggaagtgc cattctagcc atctctgctc gcatcaggaa cctcctcttg
26701 ctttagtatg tgaagtttca ggaaaatgaa gtaataggaa gttgtaacca gttgtgggtt
26761 gatggttttc tccagaagaa tggagtatca atatcgtttg aaaaacttaa tttttatgat
26821 gtgagtccca agatagtttt acaaatgata aaagaggaag aagctggctg ggcgcagtgg
26881 ctcacgcctg taatcccagc actttgggag gctgaggcgg gtggatcacc tgaggtcagg
26941 agtttgagac cagcttggcc aacgtggcga aaccccgtct ctactaaaaa tacaaaaatt
27001 agccgggcgt ggtggcgggc gcctgtaatc ccagctactc aggaggctga ggcaggagaa
27061 ttgcttgaac ccgggaggcg gaggttgcag tgagccaaga ttgcgccatt gcactccagc
27121 ctgggcaaca agagtgaaac tctgtctaaa aaaaaacaaa acaaaacaaa aaaaaaaaga
27181 ggaagaagct acacatatta aaggccaagc tgactcttct aaactaaaaa taagtagact
27241 ttgcataaag aaactggaag aaagaaacta gtatcttcag ttttccagcc tgatggtcca
27301 gattttaagc attgttgcat ctcccagcct cttttttaac ccttgctccc tacctacccc
27361 caaaaggtgt gtggggactg gctgttctcc agtagctcct tccttccttc tttttaactg
27421 aggtgtagcc acctatgtcc catcctaact ctgtttcccc cctttatctt cccttgtgca
27481 gcatccttgt ctggcctcca taattcactt tttgtcatga ctcttgtgcc ctcctcattc
27541 tgacctttct ccagtctccg ctccttagtg ccagctgtca tcatttctaa catttggatc
27601 agagatcccc tcactaaaac agcctgagag cctggctcct tccaggacga gtgccccaac
27661 ctgttctcta gctgctggaa aagacccctc tgtttcttaa aagcctgtta agttccttca
27721 ggctagtagc tacaccttgt tgcatacttc cttggaaata gagagtgctt tcaaattaat
27781 ttctcactta ttgctattag tggtcccaag aaaaagagat gaaattgcag catcttgtaa
27841 tggtgagttt tttaggtcta ggagagaggt actgtcatct ttgtttactt gctgagagac
27901 gacagaaatg tgtagttgtg gggtatgaag gtaaagtcag tgattatagc taaaaagcaa
27961 acgtcattta aggtcactgg tatttttgga tgttggaatg cagcgcttac catccataca
28021 agaacccgct gggagggcca agaccatccc gtgcgcggcg ggaaccgcga catccgccac
28081 tcggatgccc gctggagcgg gcggagaccc acgcgcgcgc caatgtcccg gcgcgcgggc
28141 tgctcaccca gggcagcggc gtagtcgccg ggggcacaag cccgagccgc ccggggcggc
28201 gcgcggagaa ggagcgcaga ccccgtgaac acgccggagg accgtccgcg cggcccgtcg
28261 cgccactgcc tactgccagg ggcggcgggt gacgacaaaa ccctcggtgc gccgcgcctg
28321 gcagtccgcg gcccccgccc ccccagcggc gcgcacccgg gggcgcgggc cgaacccggc
28381 aaggtgagag ggccgtggcg cccgggcgct gaccactatc attctccgcc acacggacga
28441 aggcaggagc accacgggcg gccggcgggc cgcccgctcg ggccaaagag cccgcccgcc
28501 agcggannnn nnnnnnnnnn nnnnnnnnnn nnnnnnnnnn nnnnnnnnnn nnnnnnnnnn
28561 nnnnnnnnnn nnnnnnnnnn nnnnnnnnnn nnnnnnnnnn nnnnnngagg ccgggcgagc
28621 gcaggcgggc ggagagcaga ccacgcggaa gaggccgaga gagaaagcgg ggcacccggc
28681 cgggggggtc atttacaagg gacgctgggc acgaaggagg ctggggcgaa gatgagtcca
28741 ggggttgggt tgagagcgct gcgcagccgg gctgagaaga gaagctgacg agtgactccc
28801 gacaagggac gggggagagg gaacctgggg gcaggcagag gcctaggggg tgggctctga
28861 gggcagccac tcccaccggc cctcccccag ccccgcaggc cagccacatg ccccgtgctc
28921 cagacgaccc agctacatgg atggcagcgt cctgaagggg gatgatcggt agggagtggg
28981 tgcggaggct cacgcctgta atcccagtgt tcggggattc ccgagcggga ggatcgcttg
29041 agccggggag gtggaagctg cagtgatctg cgccactgaa ctcccgcctg ggcggcagag
29101 tgagaccctg tttcaaaagg caccaggggt gtagggaagg agcgatatcc cccaggcaag
29161 gaaggctgcg gaggggccag gccaggagag aagggccctg agctcagtgg acgggcaggg
29221 tgcctgtgga ggaagggagg gacgtagcag caggaggaag ggtgaggacc caggctgggg
29281 atcgggagaa gtgatggcgg aggaaagaga ggccggaaga ggagggggcc tgctggcctg
29341 gcactggaaa gcaaagcgtg ggtttgtata tgggaagaag accacatccc ctcttatcgt
29401 catcccaact cagaaaccat ttggccccaa gtcaccaaag cactcatagg aaccactttt
29461 cctgtgacac aagtaggatt ctcccacttt taacttccca aatgctaccc gaaagcctct
29521 gaaatccttg gaaatttaaa aaataatccc cttctattaa ctgatgccta taaaacatat
29581 tgactttcat taaattttgt tatgaaatca gggatgtgtc ccattgtaaa ataaatttgt
29641 ttggaaaatg tagggtggta tcccatctaa aaatcagacg aggctagaaa atttcaattt FIGURE 4 (cont.'d)

29701 tatttgctaa ggtagcatca tgttgttaaa aatgcatcat aaaataagac caagagttaa
29761 tacaaagcat gaagtcatgt ttccctcaaa aaaatgattt gttctgtagt caaattaatt
29821 tggaaaacat tgcaaactct tcagcagtgg ttctcaaagt atagcttgcg tcagaatccc
29881 ctggggccct tgctaaaatc tggatggcta cactccccgc ctagagtggg ttaaactcag
29941 tgcccactgg caggaaactg aaacttggct gaagtcaccg aggaggcctt ccccgttaaa
30001 cctctggctg gcgacagctt ggtttcctcg ccgctgcttc tgagtaattc tggcacgcag
30061 ttcctcctag ccacctgctg tacctggaag gggccagcc ctcctcagca ggctttgctc
30121 ctgccctgca cagcacaact gtggcgtaaa aaatggaaaa gctggtagca gaaggaaaga
30181 gcagggagac agaggttagg tgaacctcaa tggcctcatt aaagcaaatt gagaaagaga
30241 gtttccttcc cagtgaggcg ggacagtgca gaaatgcggc ccgtcctggg agaagtaggg
30301 gcgaggggtg gggggctcac cgggcacatg gccaacagct ggtgcccagc ctgggccaca
30361 gtttggcaca ggagaaagct gaagatgcag gagaaagcta ggtcactgcc cctaggccag
30421 gtgatcaagg tggctgttac ctgcctgtgt ggccttgaaa aagcctggtg ccctctctgg
30481 cttgcagggt ccttcttttt acaaaagcgg gtcttcgaag ccctgaatat tccagttatc
30541 tgtaaggata tagaaatatt ttgcctctag atgacatgta aatatgttcc tcctaactcc
30601 acttcttcct acatctgtgg cttcttctga gaactaccag acccaccctg ttttcagagt
30661 aaacctcctg ttttgaggtc aaacagaccc agctgggtaa ttggtgactc actcctggtt
30721 cctccaaaga acaggggcaa gggaccaccc gggacctcag gtgccccagc acaggacctc
30781 tttctggggc accctctggc actgggccat cttcaggccc tacagggctc tcggggcctg
30841 cgtaggcctc tcatctccca gaaataagtt cttttcccca cccagactga caccagatgc
30901 tacagtgagg tttacccctc cagcttgaca agcattccta gcccagaaca ctcagctgac
30961 gaggggtgct gggggaggaa ggaggcagca aggctgaaag aagcttctct gggtattcca
31021 gtgcctggct gctggtcgta gccatggtga gaccacagca gcctccctgg aagcaagcac
31081 ctgtgtaaaa gcccctcctt ccccacaagg ggctggatcc aagtgaagaa ggtaccagaa
31141 ggactggaag atgatgctgg tattattcga cagctccagg gtgctgtagc actgagcacc
31201 tactgtatgc agcccatcac aaagccagcc acactgccca ggctgtgcca tggcaacttc
31261 cagcagtaca ccctctcggt cacctgcagg ctccttgttc atcctgacac atgaggagaa
31321 aaagacagta ctcacaaagg cctctagcct tgtggcccca ggaccctctc ctgagcatca
31381 tggcctccta ggagacccag ggtagccagg acaaaggaga gaagcatttg ctaagctaag
31441 aaaggatgga aggggattgc tgttctgcct ggatgcaccc ctagacctgg cagggcaggc
31501 aggagagacc cccagtgtct cttgcttatc ctaggagttc ccccctgtgg ttgctccagt
31561 ttgctgcctt catgcatgtt cacagggtga ttcccctgag acaacagagc tgggatgtca
31621 ccaagccctg tgtcccatca gccaggctct ccccagcctc catcctctca ttctgctgga
31681 tcaggaggat gtggggaggt ccctgactcc ccagctttcc ccatgacaag gtgtgtgtct
31741 acagctcaga cccagccatg ctccacctga gaagtgggtc caggcagagc actgggtcct
31801 ggccacctag ggctgcctcc tcaggggtgg gcaggaaggg gagccactgg aggagtgccc
31861 cgggcacagt cccctgcacc aggtgaggtc acctcttagt ccatgaggcg atgctgcatg
31921 agcccctctg gacactagaa ggcctgggct caatgctgag taaagtgcag gcatgactgt
31981 gccctcagca tgcatagggc agcaggcata gattcataca cgtgagtttg cacttaagct
32041 gcagtaagag ctacagagga aatgaacaga gacagcatca ctccagtgag ccctccagat
32101 acaccccatg tgcgcagtaa gagaatggca tagtctattg ggacagccac atcaaaatac
32161 cacagaccag atggcttaaa cggcagatat ttgtctctca caggtccgga ggctagaagt
32221 ccaagattag ggtgccagcc aatccacttg ctggtgaggg ccctcttccc agcttgcaga
32281 tgtctctgtg ttcccacagc atggtcacgt ggcagagaga gggggacagg gcatgaataa
32341 gccctcggtg ccttcctctt cttacgagga tgctaatccc atcacgggta ccccaccctc
32401 gtgacctcgt ctaaccctaa tcacctccca aaggccccat ctcctaatgc catcacactg
32461 ggggtcaggg cttcaacaca tgaatttggg gagcacaatt tagtccacag cagaaaagaa
32521 aggggcacag agcattccag cctgaaggaa acagatgtgc aaaggcccaa ggcaaaggcc
32581 tgagctctga ggggcaacca gagtcaaggc tgaagagtgg gcagtgattg agcactgacg
32641 gtggagaggc aacaggctat cttgttaatc tcagtctttt gtgtgccaga gagagaaact
32701 gaggcacagt gtgtcatggt gaacactggg cagcactccc acgctcctgt cctgcactct
32761 gcagggttat ggaggaagcc tgggaagtct ctcccctctt ttccaccttt cctggaccca
32821 tcccacaccc tgcctcctcc aggaagccct ggggattgct catacactca catctcactc
32881 cttagtacct gcagcctgca ttctgaattt agcaagctct ggccttgggt ttctattttc
32941 ttgtcctgtg cagtgagcat ttggaaactt ctcctcagca ccaaacacgg agccatttag

FIGURE 4 (cont.'d)

```
33001 cagaaaatac atgagttttc aagtcaattg aactgttcat cgcccccaaaa gccaggcaac
33061 acggtagagc agctggatct ctgttcgtag aagctttctc agggactggc ccaccgagtg
33121 ggggactgca agtgccccgat gagtgaatga atgaacacat gtgtgaatgg aattcaaggc
33181 actgcaggct attctggagg gtactggcct gtctcttcga caggtgaggt gcagtagaac
33241 agcatcccgt atagatgcca gtttctgacc tggttctgaa aagccagtca cctacctctg
33301 cagagctgcc tggagggggc gggggttgtg aggacccctg agagcttggt gtgaaggggc
33361 tctgcagagg gaggcatggc tagtgtgcgc aaggtgacct ctctcctggt ctgcaggatg
33421 gagaacctgt tcatcaaccg cttcatgcac atgttccagt cttcttggaa tgacttcgcc
33481 gactttgaga aaatctttgt caagatcagc aacactattt ctggtgagtg tgcctctggg
33541 ggcccaagtg gtgctgggga caggggatgc tgctctcctg tctgatactt gccgggaaat
33601 tgacaagggc cttcctgcct gctgcagcat gggggcctcg ctgccaccat gccaccctgg
33661 acagcacccc ctacactcca cacctttac catcactgtg gtcacccttg tgcccagagg
33721 tttctcctcc tcagatattc aagctcgagc accctcaacc tcatttcact atcaaaagtc
33781 tcaaaagtat cagaactttt tcttggcaca aatcaatcat ttgtgcttct gaacagagca
33841 aaggcagaac ttggcttgtg ttttaggtat ttacacaaaa gcaactttgg gttcctttgg
33901 actaggatgt gtttgatgag agcactagct tcatagtggc cagtcatggc atgggaagga
33961 cgttaggaag gcaggaatgg ctggacaaga agaggtgctg aaatcaggac atggggaacc
34021 aaacttggca aactgccccc agggactctc ctccacgccc tccttcttcc atcctggaca
34081 ctccatgctg ggctgaagga cctgagtgct ccaggaggct tctgagccac gaagggccag
34141 ctcaggtatg atgagttggt gccacagcct gacccagtga tgggcagggg gcagcagttg
34201 gagctgtgcc catccaggga gcactcggga gaggagacca agcagggact ctgctcttag
34261 gtgaggtcag gagggccatg gccctggctg ccctctactc agagctcagg gtgggcctcg
34321 cttttctcct ggtagagcgg gtcatgaatc actggcagga agacctgatg tttggctacc
34381 agttcctgaa tggctgcaac cctgtgttga tccggcgctg cacagagctg cccgagaagc
34441 tcccggtgac cacggagatg gtagagtgca gcctggagcg gcagctcagc ttggagcagg
34501 aggtccaggt aggggttgat gggctgggga agtggccaag gtcacagtct gtcaggtgga
34561 agccagttcc tcctggccag tgctcatagg ccaccaagac gctaactgca ggcccatctg
34621 gcctacagca gccgcttcct tttcctggca gcagtgtcag ccagggtcct gggcattatg
34681 cagactgtct tgtgcaacat cagaggagga attgcgggga atgtttctcc atgatgctcg
34741 agtctgggaa cataatgtca atattttcac tatcagtatc aataattaca ggagctaccc
34801 ttgattaggg gcctgtggtg ggacaggcat tgtgacaggt gctttacaca caaggtcatc
34861 agttgtcacc caccttgcaa aggggagaac actggagaaa gaagcagacc ttgtgtgaca
34921 atacacaagg ggcacgagga gaacccaaca gaatggttga ttttctcgtt agaaatgctg
34981 ctgcccatgc tcctgtcgca ccctcctccc caccctcacc tgcagactca gctgcctccg
35041 gctgcaaggc tgacctagtc ttgagacaga agaagttcaa accaactcca cctggatctg
35101 gtggggctca gcaacaggcg ctggcccatc agcctgcctc ttccccatgg atccagcgtg
35161 atggggcctc ctgccaccca ggccctgctg cctatcccca ggtgtccagg tggcctctgc
35221 tgcttccagt cttttgagct cagcttaccc tgaggcccta gttggagagg gatggttggt
35281 gccctttaga gataaaccta cagccccagt acctggccca cctgaatcta gagggccacc
35341 cacccagctg aagtccctgg gcaagtctcc tgccccagtg caggcagtgt ttcctaacct
35401 cctcctcctc ctgcacccaa ccaggcccag aacacttcct ggtcatgtga acagctgaca
35461 gttacaatcc cccacacact gagagagcat ctgtgttcct gagtggactg aattgctaga
35521 tgtagtaaca ttgatttggt ggctataggt ttcaaacttc aagtcagaga tcatagaact
35581 ttaagccata tagaatccta gaattggaag actctgagca gccatctctg cacccagcag
35641 ccaaggagtg gccatcctca gcacctggca gggcatcagc ctcccactgg gagtcccggc
35701 cacctccagg gcacgtgggt tatgagtcac ctttcctttg agctgaccca cccctcactg
35761 actagactct taaacacaca ctgccccgtc taatacacac cagcatgatt cttaatcccc
35821 acagtcattc acgctgccca tctggcagca ccttaatgat ctacagcaag cttgtggcct
35881 actaaaaacg cctccattgt tttttaaaat gtgcagttat tttccggatc atgaatagag
35941 aaattgtatc cctgttgttg gtattgattc agtgttccag ctcaagtttg agttcttaga
36001 ctttatattt ggattctttg gtttcaaatc acaaaaatca actccatctg gtttaatcca
36061 agaactctat tggctcaggc aacagtaaaa agcaatgcta actcatttgg gaccagggct
36121 cagatcatcc cctgcactgt ctctctctcg ctccatgtct caatcctctg cctctggtga
36181 ttttttcctt aggagggttt ccttatgtgg aggtaaaaaa tgatcaccgg cagcttcaga
36241 tttaccttcc accagcttag caaacaccac ccactcccag caagaaagac cctgtttccc
```

FIGURE 4 (cont.'d)

```
36301 aatgctccca gcagatgtct taggccatcc tcgggcctca ctgattctgt gagccagtgc
36361 ccacggccag gagaatggaa tacactgacc tagaggggac agggactcta gacaggcaaa
36421 aactccactg tcagaagcag aatcctaaaa tgtcagaact gaaaggtagg cccgcccctc
36481 gttttccaga aatatgaaag ggaggcttgg gataacagag aaatgctgca ggcattggcc
36541 ccaaatctca ggcctcctat tcccagtatc accttcacca gcctgggtgg tctcaagatt
36601 ggattagcag ccattccttc tgggtagagt ctgatggtca cttcagctct caaagtccag
36661 ctatccagcc atagtcctag aaggcaagac atcactgtgc ccgaccaacc caagggtctc
36721 cacctgcccc cctcaacaca aggtgccctg agtgcctccg cggggatagt ccccgtcccc
36781 acccctgctt cccccgccca tcgcgacaga tgctcagagc tcatccctgg tgtcacacca
36841 cataaaggag gagggcggtg gccaggctcc gagctcctgc cgtcctgggt gggtggcttc
36901 tgtcctgcgt gccgccgggc agcccggggg tcctgcgcgc gggcgcggtc ggtggagctg
36961 caggggggcg ctctgggatg tctccaggca gagtagatac tgacccctcc gcagccggga
37021 ccctcacccct ttccttcatc actcaggaaa cagaaaaggc ttcagaagga gcggccatgc
37081 ccccggccta agcgctgcgt tcccggccca gcaggcctac cctgcacctg gcgttcctag
37141 gggcccctct gcgggaccca ctgcgcggct cgcagcggcc gcccgcctcc cacttcaccg
37201 gcacgctcgt tgcgtgtcga ggtgtgttga ctcctacagc aaagggcacg gatccgcggg
37261 tcagcaagcc cgacgaattt acaccaatga cccgccgtgt cgccagtctc agaccagggc
37321 acaacacgcc aaccctgcag accaccccca cctccccagc cactgcagac ccttccccct
37381 ctgcttctgc agcacctgtc ccgaaacacg ctcattcccg cccccgcaga ccttccctac
37441 ctcctggaga ccccccctcaa cccctgtaga gtcccctgcc cgtgcagaat cccctccccc
37501 ttcccccgca gccccccctac cccacccggc ggacagcccc gctcgcttcc tgttcttctc
37561 ccaagggaga cccctgtcct ggctctgact ggggttgagt tcgccagttt tgacttatgt
37621 gtagagtctt caccacgggc tggaagtacg gtnnnnnnnn nnnnnnnnnn nnnnnnnnnn
37681 nnnnnnnnnn nnnnnnnnnn nnnnnnnnnn nnnnnnnnnn nnnnnnnnnn nnnnnnnnnn
37741 nnnnnnnnnn nngagcgtac ttcagcccgg gtgaagattc cttacacctt atacaaaaat
37801 taattcaagt tggattaaag acttacatgt cagacctaaa accataaaat ccttagaaga
37861 aaacctaggc aataccattc aggacatagg catgggcaag gacttcatgt ctgaaacacc
37921 aaaagcaatg ggaacaaaag ccaaaataga caaatgggat ctaattaaac taaagagctt
37981 ctgcacagca aaagaaacta ccatcagagt gaacaggcaa cccacagaat gggagaaaat
38041 ttttgcacct actcatctga caaagggcta atatccagaa tctacaatga actcaaacaa
38101 atttacaagc aaaaaacaaa caaccccatc aaaaagtagg caaaggatat gaacagacac
38161 ttctcaaaag aagacattta tgcagccaaa aaacacatga aaaaatgctc atcatcactg
38221 gccatcagag aaatgcaaat caaaaccaca gtgagatgcc atctcacacc agttagaatg
38281 gcgatcatta aaaagtcagg aaacaacagg tgctggagag gatgtggaga aataggaaca
38341 cttttacact gttggtggga ctgtaaacta gttcaaccat tgtggaagtc agtgtggcaa
38401 ttcctcaagg atctagaact agaaatacca tttgacccag caatcccatt actgggtata
38461 tacccaaagg actataaatc atgctgctat aaagacacat gcacacgtag gtttattgtg
38521 gcactattcc caagagcaaa gacttggaac caacccaaat ttccaacaat gatagactgg
38581 attaagaaaa tgtggcacat atacaccatg gaatactatg cagccataaa aaatgatgag
38641 ttcatgtcct ttgtagggac atggatgaag ctggaaacta tcattctcag caaactattg
38701 caaggacaaa aaaccaaaca cctcatgttc tcactcatag gtgggaattg aacaatgaga
38761 acacatggac acaggaaggg gaacatcaca cactgggcac tgttgtgggg tggggggctg
38821 ggggagggat agcattagga gatataccta atgctaaatg acgagttaat gggtgcagca
38881 caccaacatg gcacatgtat acatatgtaa ctgacctgca cgttgtgcac atgtacccta
38941 aaacttaaag tataataata aaaaaaaata aataaaaata aaaaataaaa gaaaatgaag
39001 aaaatcatgt catttgcagc aacatggatt tggctagagg actttatcct aggcaaacaa
39061 atacagaaac agaaaatcaa ataccacata ttctcactca taaggggggag gtaaacactg
39121 ggtactgatg gacataaaga tagcaacaat agacactggg gactattggg gtggtgaagg
39181 agggaaggga gaaagtgttg aaaaactgtt gagtactatt ctcagtatct gggtaatggg
39241 accattcata ccccaaacct caacatcaca caatataccc aggttacaaa cttgcacaag
39301 tgccctctga atctaaaata aaagttgaaa aagcaaaaat aaaacagtaa acaacaacaa
39361 caacaaaaca gcaaaaccct caataaatac ataaataaaa atataaataa atgtctttgc
39421 cagagctttt tgttttttgt gtggctttga gttagtatct ggggtcacgt tgcttttaag
39481 ctgtttgcta tcaactgcat cctatctaat atttcttttt cttaatagta aaccactcaa
39541 tttttgtgag gagatattac attgtggttt tgatttacat ttctctaatg atttcctttc
```

FIGURE 4 (cont.'d)

```
39601 cagtttggat gctgagcatt ttttcttatg ttttttgccc attcatatat aattttaaaa
39661 gaaatgtcta ttcaaatcct tttgccattt taaaatcata ttatttttaa atattgtgtt
39721 gtagaaatta tttatatatt ctggatatta actctttatc agatatataa tttactaata
39781 ttttcttcca tccacaagtt ttttttaaca ttgttatgtc ctttaatgca taaaagtttt
39841 aaaaagtttg atgtagtccc aattgtctat tttttctttt gttgtctgta cttttggtgt
39901 catattaaaa aataattgcc atatcccctt attctaagag ttttatagtt ttagatcttc
39961 catttaagtt ttaaatccat tttgagttaa ttcttgtata tggcataaga caaagtttca
40021 acttcactct ttcatgtgtg gatatccaag tttcccaaca ctgtttgttg aagagaatgt
40081 tcttccctca ttgagcggat ctggaatgct gtaaatatta tttgaccata tatgtggagt
40141 tttcttttaa tgggttcttt attctattcc attggtctat atgtctctct ttaagccagt
40201 gtcatgctgt tttaattact gtagtcttgt aacatgtttt gagatcacgg agcatgagac
40261 cttcaactca gttagttttc aagattgtct agtcagagta tatatgaata tttagataaa
40321 tttttctctt ttttcaaaaa atgcagctta gatttgata gggattacat ataatttgta
40381 gactgctttg ggttctattg acttttcaaa ttaatacata atgttgtaca gatttgggga
40441 atacatctga tattttggag atcttaacat taaatcttcc aatccatgaa taccaatgtc
40501 tttacattta tttgtgactt ctttcagtac tgttttgtag ttttcagtgt acaagccttt
40561 tatttccctg gctaagttta ttcctaagta ttttactatt tttgatggta ttgtaattaa
40621 attatttctt taattacctt tggattgttt atagttaatt tatagaaagg caactgattt
40681 ttgtgtgtcg atttggatc ctgcaacttt ccagaatttg tttaatagtt ccaacagttt
40741 tctggatttt atgcatatat gcatctaaca gttttctaga ttttatgcag gagtctagga
40801 ttttatgcat ataggatcaa gtcatctgtg agcagagata attttacttt tttcttttat
40861 tctttggatg tctttttcttg cttaattttt ttttcctaat tggtctgctt ggaaattcaa
40921 atactatatt gaatagaagc gaagagacag agtatacttg tcttgttcct aatccagaag
40981 aaaagtttga atcttttacc attgagtgta agtttacctg tggatttttc atatatggcc
41041 tttattatgt tattttcctt ctattcctag tttgctgagt gttttcgtga taaaaggtgt
41101 taaattttgt taaacatttt ttctacatca atataaatga tcatgctgtt ttgtccttta
41161 ttctattact atagtgtatt acattgattt ttgcatgttg tattattctt tttttttgag
41221 atgaaatctc attctgtcat tctggctgga gtgcagtggc atgacctcag ctcactgcaa
41281 catttgcctc ctgggttcaa gggattctcc tgtctcagcc tcccaaagtg ctgggattac
41341 aggcatgagc cagcacaccc tgccacatgt tctatcattc ttgcattcca ggaataaagc
41401 caacctgatc atcacaaata ttggtctgta gttttctttt catgtaatgt ctttgtttga
41461 ctttgaaatc agggtaatac tggcctcata taatgagctt tgaagtgttt tttatattca
41521 tttttgtaaa tgactttgag aaacattggt tctaattctt ccttaaatgt ttggtagtca
41581 tccggttctg ggctgttgtt tgtttggagg tttttgaacc agtttaatct ccttcgtagt
41641 tataagtctg ttcgtttttt ctacttcttc atgattcact cttattaggt tgtatatttc
41701 tagaaattta tgcacttcta aattatccaa tttgttgaca tataattaac tgttgatggt
41761 attttcttat aatccttttg atttctatgg catgggttct aatgttctct tttttatttc
41821 tgatttatta gttgaatctt ttttccttag ttaatctagc taagcatttg ttaattttgt
41881 tggtgttttc aaaaaccacc tcttagtttt gttgattttt ttctattgtt tttatattct
41941 atatttcatt tatctctgat ttaatctaat ctttaggatt ttcctccttc tgctagcttt
42001 gggtgtagtt ttttttctct cctagtttcc tgaggtataa agttaggttg ttgatttgca
42061 aactttcttc tacttctttt tttttttttc ttaagttgtg gagatggggt cttgctttgt
42121 tgcccaggct ggtctcaaat tcctggcctc cagaagttct cctccctcag cctgtcaaag
42181 tgctgggatt gcaggcatga cccaccatgc ctagccactt tcttcctttt ataatgcaca
42241 tatttatagc tataaaattc tctgttagca ctgcttctgc tgcatcttac acattttggt
42301 acattgtatt tttattttcc tttatctcaa gatatttctt aacttccctt gtgatttctt
42361 ttttgaccca ttgcttgttg aaaactgtgt tgtttaattt tcacatattt gtgaattttt
42421 tgttttcctt ctgctactga tgtctagttt tatgtcattt tcatcaaaat agatatttttg
42481 tataatttca atcttttaaa atttgttaca agttttttttg tggtataaca tgtgatttat
42541 ctttgggaat attccatgta aacttgagaa aaatactatt ctgattttat tgggtggaat
42601 gttctgcaca tgtttgttag cactatttat agtgttgttc aagtactgta tttccttatc
42661 gattttctgt cttgttgttc tagccattat tgtaagtgag gaattgaagt cgcctaccat
42721 tattatgctg tttatgtttc ctctctgatc tgtcaatgtt tgcttcagat atttaggagc
42781 tctggtatta gaggtatata tatttgtaat tgttatatct ttctgctgaa ttgacttttt
42841 gttatataat atccattttt ttgtcttgtg actatttttg actttaagtc tattttgttg
```

FIGURE 4 (cont.'d)

```
42901 gatagtagta tagtcacttc tgcttgcttt tatttaccat ttgcatggca tttacttttc
42961 cttttttcca ttttaagcat atttgtttct tagacctaaa tgacaggata aagttggatc
43021 ctttttacaa atccattttc cagtctatat cttttgattc aggagtttaa tccatttaca
43081 tttaaagtaa ttactgatag ggaaggacct acacttgcca ttttgttgtt tcctgtatgt
43141 tttgtaaatt ttgtttttta ttccttctct tactgacctc ttttgggttt tgtcgatttt
43201 tttttgtggt gacattttga ttcccttcct gtttcctttt gtgtgtattc tatagatttt
43261 tttatggtta ccataagaat tataaaaaac atcttaaagt gttaacaagc tattttaaac
43321 tgttaagaga ataacttcga ctgtgtacaa aaactatttc ttcaaagctc ctaccctcac
43381 cttaggttac ttatgtcaca agttacatct tcatatgtaa tgtattcatt aacacagttt
43441 tatagttatt tttaagcttt tgtcttgtaa attctataca agaattaaaa gtgcatttat
43501 gtaccaaaac tgcatagtac agtctctata tatgtccata tatttatctt tactggagag
43561 ctttatattt tcataagact tcatgttact atttagcatc cttttgtttc aacttgcaag
43621 atactacagc aggtccagtg gtaatgaact ccccagtttt tgttcatcct ggaaaggctg
43681 atttttcctt tatgtttgaa ggatggtttt gctggatata atatttttgg ttgaaatttt
43741 cttttctttc agctctttga atatattatc cccctgcctt ctggcctgca aggtttctgt
43801 tgataaatcc actgataatt ttataaaggc ttccttttac atgacaagtt actttctttt
43861 gctgctttca agattgtctc tttgtctttg acttttgaga gtttgattat agtgtgtctc
43921 actgtgagtc tctgggtttt ctttaacatt tttttttgt tcatatcttc tgatgatgaa
43981 ttcctttaac ttttatattt gtgaaatgtt ttttcttcat tttcagaagg tatttttagt
44041 gagtgtaaaa ttctacattg acagtttttt tctttcagta ctgtttagtg tttctctact
44101 gtcttcttgc ttgtactgat tgtatagaaa ctctgctgta attcttatct ttgtgtcttt
44161 gtacttaatg tgccttttta ctctgcctgt ttttaagatt ttatttttat tattgatttt
44221 gatcatgtgg cttggtgtga gtttcttcat atttattgtg cttggggttc attgagctta
44281 ttaagtctgt aggtttatat ttttcattac atttagaaaa attgtagcca ttattcattc
44341 aaattttttt ctgttcttct cccatttctc atgcccttat ggggtctaat tatatgtata
44401 ttaggctatt tgaggttgtc ttacagctca cttacagttc ttatgtttat ttttccactt
44461 ctatttcatt tgggcaggtt tattatactt ttccctaatt tgctaatttt tttgcaatgt
44521 ctaatccact gttaatctca tccaatgtat tattaatttc agacattgta gttttcatct
44581 ctagaaattg ttcatctttt tatatcttct ttgtctctat ttgatatgct aagtcttttc
44641 tctagcttct tgagcatatg aaatatagtt atgacaacta ttttatttta ttacaacttt
44701 taccttaggt tcagaggtac atgtgcaggt ttgttatgta ggtaaactcg tgtcacagga
44761 gtttgtttat tatttcatca ctcaggtact aagcctagta cccaatagtt gtttttctgt
44821 tcctctccct tctcctaccc tccaacttca agtaggcccc agtgtttatt gttcctctct
44881 ttgtatcact actattttaa tgtctctact agttctctta tttttgtcat ttctgagttg
44941 atttatttt tctcactatg gccatattct cctacttctt tgaatatctg gtatgcaaat
45001 tatacctagt atggatatta tatcaagacc ctgtcgcaat atggatacct aaaagaaaat
45061 aacaatgttt accagtttgc tctaagcctt tcttagctct tttgcttgtt tctcaagaac
45121 aagcacagag ggtggagctc aaccaagact gaagttaaag atgtagaaag attgagatgg
45181 gaagtaatta agttgaggag ctctgataca atggtatttc tctttttaat catgtaagat
45241 gcaagcccaa gataatatgt tgggaaagtt gaaggcgaat gtcttgagaa atatgaaatg
45301 cacccaaggc tatggctggg tgatagaaat aactaaaaag ttttaaaagg attgttttat
45361 agctggtcct tgctgaggtt aggggatagg cctggaaaaa ttgagcagtg gtattgccca
45421 ggcaggactc ctcatgacat tctccagatc cctaagtttt tccaagtttc caagcatttc
45481 cttggccagc aagtcatctc gcagcacaga tcctactctc tttcagtcag tcattccaca
45541 actctacaaa gcatttttct ccatcaaatg ggaacttttg gggttctgca taatttttca
45601 gggttccacc acttttgact ctttctggat accttgtaag gatattataa ctctttaatt
45661 catgtccttg attttctctt ttaactttta atactgttca ttgcctgttt acctctttca
45721 ccctcttctt ttcacttccg ccctctttct tgtgtaagta tataatcatc cttttttttct
45781 tcctcgaatc tcagttctcg ggagtaacat atacaattca ttcttacttc cagtctttta
45841 ttcctaagtt ccttatctct agttctcttg catatttgtg gcaattatta gtttttttcc
45901 aaaaatccat tctccctttt tcctgtacat gtatctttcc agcttgacca catttcccag
45961 cttccctggc agctaggtga agcaatgtaa ctaaactttt gcctgtaaaa tatgagcaga
46021 agttatgtgc acaatatctg cctcacttgc ttaaaataaa ttgtattatt tgagctttct
46081 atattgtccc tttttacaac taaaatgtag aggttatggc aacttttatg gtaaagagaa
46141 tcatcacgta ggagatcaag aatcattgat ttgagaggaa cctaaatcct ttaatgactt
```

FIGURE 4 (cont.'d)

46201 agtggagcaa gactgcccca tcagtctgga agctacccca caacttatgt atatcttcag
46261 attgttgagc aaaagagaaa aaatgaagcc actatatatt taggtctctt catgttaaca
46321 gtttagcttt taacctaaca cacatttatt cctgaatggt agcatattat taacatcaca
46381 ggaagggaat tccttgttca tggatctttt attttgttga aataaaggta atctgcttgg
46441 gcttaatact gccaaggcag aattttttgg aataattatt tctatagatg acccattcat
46501 aatgacaact aacatggttt ctaaaatgga ttcatgtacg tcatcttatt tagtccccgc
46561 aaaaattctg aaggtaggta taattattcc cattctatat attgaaaaat tgggattcag
46621 agagactacg gacttataca agtttctgca gctatttaag aaacagagta aagtctcaaa
46681 gccattaatg aactgtttag tttagtgctg cttagtaaaa ttagaactgt ttgaagtgcg
46741 ttttaatagt aaacccatcg atatttagtc agctctctgc ttgctaacta atatggaaga
46801 aaaaacatac atctacgtac atcctgaatt gggagaaggg aaataaaata ttgccaatcc
46861 cctttcctgt attaggtact gtgataaggc gataaggctt ttcattatta taaatgagtc
46921 ctggagaggt taagcgcagt cacccaaagt cacatgacca gtaactttca gagattttac
46981 cccaggtctg gaaagactct gaagcccatg ttattgcctc cagagcctgg tggagaaccc
47041 ctgaatggga cagagactca gcagacagag tggtcctttc cttccaggga gtcagggaag
47101 gtttggtagg ggagatagag ttagatctgg gtgggatttg gatgaaatga gatcaagcag
47161 ggataaataa gatccaagct gtttatgagg gacagggaga ggccagctct gttagaaaga
47221 gtggtttata cagagaagca tggaaacatt tgctccatgc ctcgccttcc atggatagca
47281 gtccagaaat gctacttgcc tgcctgacag tctttctcca gtccccaggt gtggacacgt
47341 tctgagcacc tgagcctggg tctgccctga cccagattct gtgagctggg acagagaatg
47401 tgtcctgctg tccctcctcc cccacttggg cccacaccct tttctacaca tttggattag
47461 aaatctgaat tggcctttct gtgaacccca atgacaggca agtccccagt aaagaagcac
47521 ttaatttaat tgctccttca gggtccactt agagtaatag ttgtgaacag ctctccctag
47581 tgtctcccac aggcagtgac aaatgttgct aaagataagt cacaaattct tggcaaggcc
47641 atcttaaata tgggaaggaa accttgttca gtcctgaaca gtcctgttca gactgatctt
47701 atcacaggtt gcacactgcc tcaatgtcac catgtttcta ccctcagttg tgcttggcag
47761 agagaggaca gctatacata aagtctgttc actctacaaa ggtgaaatca ttttttttaa
47821 ggtaattatg attgttctga ggatggtgat tgagtgacat ttaaaaaatg ggaaaagttc
47881 tactcataac tctgtctgct taatttgctt atataaaaga cttaatggtt tttgttgagt
47941 tgatccagag tcagtaacat ttgaatatgt gttattacca tttgatcagt aacaaaacaa
48001 cagggtaagt gggatgccaa atgtggctga gagtttaggg tttacattcc acaccccagc
48061 cttaaatacg tttgtataaa ttattggttg atttttcttt ttcatggctt ttctttgaca
48121 tttgatgggg ctggatttat ggaggcaacc aacaaattac acagcaatga attctggact
48181 gtagtcccac agccttgagc ctagatacta gctgtgtcac taatactctg tgtgaccagg
48241 gtaagttatt tagatacatt tatgactttc caaatcaata ggttggacaa agttatcttc
48301 aaaatgtctt tcagatttga ccctgaacat atgcgattct ggcatgttct gatttttagt
48361 tttctgttct tgaagcatgt ctacaataga aatgcctacc ttcatataca ataaaaggac
48421 attagattaa tatggtgtct gtgaaaatca ttgaacagct ttagagataa aaataatgaa
48481 atgagtcaag ttctccatta ttaattaaat cttttaaatt ttctgtttat gaaactatga
48541 acaataaatt ggaacaaaga tataatctca ctacaagtaa attgtatttt atgtaaaata
48601 taatttgtct ttagaaaata ctcaatgaaa ttaccttttt aatttcagag attttgagga
48661 ctattattgt tatttcttta aagtgataaa tgtaatccaa gatgcctttt ttcccccttc
48721 agaagcttga gtgcccaagg gtttgataaa tgtggaaaat aaccgctgtt cgaatatcct
48781 gttggcctgc tggtgagatg tcatcgtgtt gtctgaatgc agtatgtgtt taaacttgcc
48841 atttattacc tgaaattgtg ttattttgcc tcataccctt agtaatactc ttgtaatgct
48901 ggctgagaat tgaagcaaat gccctatgaa actcaaggga gcaaggtctt tgttattttt
48961 cagaagaaat gactggctga ggctgtaaag aaatcttgtg gtcattctca tggaaagagg
49021 attggagccc cgattctttg atctcattat tgaccagttg attgagaaga ctgtcctcct
49081 gtccccaccc aatcacaata agtgggtaat tacctgaggg ctaatttgct ccttgaatgt
49141 gaatacattt gtggaaattt ccttgtgctc agcacctgtt caaaacatcc atttgtattg
49201 cagagctatt gtttttctaa tctcattgtg gagctaagag agagattgtg tttaaggttt
49261 ccttcgtaat aggttttctt gctccaggaa ggatgcgtga cagactctgc acactgctgc
49321 ttggtaggtg ttcagtgatg gatgcgtttt ccatctccca ggtacagctg cagctgtgct
49381 gactctggtg cgtttgtaat atgcactgtg gagtgcacca tgatttcatg atggctggag
49441 aaatctggtg gctagaattc tagggaggag gacatgagtc ggaagtgcag aaacctcaca

FIGURE 4 (cont.'d)

49501 ctgggacatt gatggagaaa atccaattct gtccctggag ttaaagagga gtcactcact
49561 gggccatcat aagagcaaat aaagttacag ttatttcttc agatccacaa ctcaaactca
49621 gcgaaagtaa ttattcactc tttttgtccc aaacaataat gaaatcagct aaagcatatt
49681 gtatttatta cttccactca agttattgag ctgttctgac accttgttgc tgggaagata
49741 cacagatgga acaccatcat ttccattgat tctgatcata ccccacgcta atatagcctt
49801 attgctctga gtcataggga ttttatgctt gcctattcaa aaaacagttt ttaccttatt
49861 aaaaggtgat atgacctgag ctggagatga tgtttggtca ttttgtgtaa accttttaat
49921 attttagtgg taaatacatt tcttgaatct tgacaaaaac ataattaaaa tgaacatatt
49981 taaaatggac atcttccaaa tgttcatttt taaaacaaac atcttccaaa tgttcatttt
50041 taaaatgaat atcttcgtta actttttttt ttttttttga gacggagtct cgctctgtca
50101 cccaggctgg agtgcagtgg cgcgatctcg gctcactgca agctccgcct cccgggttca
50161 cgccattctc ctgcctcagc ctccagagta gctaggacta caggcgcccg ccaccacgcc
50221 cggctaattt ttgtattttt agtagagacg gggtttcacc gtgttagcca ggaaggtctc
50281 gatctcctga ccttctgatc caccctccac ggcctcccaa agtgctggga ttacaggcgt
50341 gagtcaccac gcccagcctc ttccttaact tttaatgaat aaagagttga aagggaaaaa
50401 ccaaatgtgc actatgctga ttttatcttg agctgtacag aatgtgcagt aacttaagaa
50461 tataagtcat tctgctgtta ttcatactag cctattcttt agcattattt aaacacacat
50521 atttgagtgt ctacacactg cctgctaggc aggggctgg gtgccaagaa gggatgtcca
50581 gagataaacg ggcatatgtg ttaatctttt agggcacagt ccagtaacct gatcaaggag
50641 tgacgtgtat tgtgtactag gatagaagtc agtatcagag gaaacacaaa ggaaagagtg
50701 gtactttctc cccagggaag ggatgctcag aaagaggggg ctgattatgt ccctggttca
50761 tgagaaaaag ggcattcctg gctcagggag tgggaagaac aaaaccaaga aatcctggaa
50821 tggcttggtg catcagccag tctgtgagtg cagggcatgg ctggagttct ggctttaaga
50881 tgagtgggaa gaaaggctgg agaggaggtg gatccaggaa aagttgctgg gagcatttat
50941 tcttttggca atgggaagcc atggaagaac tgttgtaagg aggattctgt gtgatacatc
51001 tgccttttag agaggtcatt ttatagaaaa agtagaaaat acagaccagc aaaaatttaa
51061 aaagtgaaaa caatcactgt tcaagctctg gtctagcact caccagtgtt tttcctacag
51121 gtgcatatac aaacatgctt ttacatttta tttttatttt aaatttttca ctatcctcaa
51181 tatcagtgga aacaaatctg ctttttttaat tttttttttta aaaatgagat cctattgtac
51241 acattatttt aaattttttt tcattctttc ctttttttaa aattaaaaca attttttttg
51301 agacagtctc actctgtcgc ccaggctaga gtgcagcatc gtggtctcag ctcaccgaaa
51361 ccttgcctcc caggttcaag cgattctcct gcctcagcct tccaagtagc tgggattaca
51421 gacatccacc accaccgtgt caggttaatt tttgtatttt tagtagagaa tggggtttca
51481 ccattttgga caggctggtc ttnnnnnnnn nnnnnnnnnn nnnnnnnnnn nnnnnnnnnn
51541 nnnnnnnnnn nnnnnnnnnn nnnnnnnnnn nnnnnnnnnn nnnnnnnnnn nnnnnnnnnn
51601 nnagcgtatt cgcccgtggt gaagatcgta gtagagtcta ccacctcggc cgtgaacctg
51661 gctcaggggg cgcagccggg gtgggcgacc cagccaggtc tgcggagcgg tgcccggcgg
51721 caaccccctc acggacgctg ggactccccc accccgtccc cattcagcgc tagcggtgga
51781 ggggccaggc ccgccccagg tagtcaggca ggggtcccgg ctcctccccc aggaccaccg
51841 ccccgcgggc gctcacgtcc tgatggcttc ccacaccagg agcccgtcgt cccggtagaa
51901 gtagtagggg atgtcttctt tgctctccat gccccgggcc ttgatggcct cgggaaagca
51961 cagggaggca taggtcaggt ccttcatggc cctctgcacc atctgcacgt gcccaccgcc
52021 ccctgtggcg ttggcctgga gtgggaggta gagtgccctg agcgggtggc tcctcccaca
52081 gctgtccaga cccatccctg aggaaatgtg ccaggggagg cgaggaggcc aggcaggcag
52141 aggtgcaagc ccttgtcctg tgagatgggg gagggatgtt taacgcagag aatgacaagg
52201 gcagccgggt ggagaggtgc tagggaggag cctcccgccc aatccaatgc aagggactga
52261 accgtggggc tgcagagtac aagagggaag ggtgcgctcc cagccacagg agggcagcag
52321 gcgtgggcag gtgtgtgggg gaccccagca ccagcgggcc tgggctgtga agtctgctct
52381 agtgctgagc acacgaccct cagtcattgc tctcagtgac cctcagtttc caggacccat
52441 gcaactctgt tgagggcctg ttgtgtgctc aggtgagggc tggagagacc cacaaggagg
52501 gatcctggtc ctgatcccga tcccggcttc tgagtgatgc agacacactc acaagctcac
52561 tggcacatat gtgtgtccac gtgcacacac acacatgcaa atacacccag gggctgggc
52621 tgtcggtgcc acagaggttt tgaagaagga cttgggtgct ggggtgccag agattggtcc
52681 acggtgggca ttcagcccaa gcaggaccaa ccagagctgc cccccagcac tttctgttta
52741 gatgcggctg ggagataatg gccacatgag aacctgaggt ggagctacta tgatgagctc FIGURE 4 (cont.'d)

```
52801 ctgtgccctc tcccatgggg gcctgtctgc agcaggagag tgtgatgcca acacaggtga
52861 aagagacaga aagagggagc cagtgtgcat gcaccctggg gcattgcttg agtccctgga
52921 tccatttctg gctgaggccc ccgaccctct attgtgtcca ggtatttgag ataaggcatg
52981 tcttgtccag ctgcagctgg tttgagttgg gttttgtcat ttgcagccca aacagtgtct
53041 caacttcagt ggtcatctgg cctggtcact aatgggctgg ggaaaggagg aaggttgggg
53101 caagggccca tgtgagagtc caagcttggt aaggctacag agggctcaaa acgaggtggg
53161 gtgctacctg agggatgcga gggctgggca gggcctggag tccccgatgc aggagacagt
53221 gggttgggag ggttgggacc cgggaagcag agtgctgggg aggtccaggt cagggtggca
53281 ggggtgtggc agattaagag gcagacacag gttcctggtg cgtaggaggt caggggggcca
53341 taaggagtgt gttccagagg ggggtctaca cccaggtccc agaggctggg agaggggagg
53401 ggtgggagga ggggaccagg agccatcagt gagaaggaag acctggtggt gcgcctggag
53461 gagtgctcct ggctgaatgg cacgggctgg agacatcagg aggatgctgg agccagtgct
53521 ctgagcagac tccagccttc accccttccag gcctcctgaa agggtgtcta gatctcagat
53581 agggagtgaa ggcggccagg ctgggctctt ccaggcaaca agtagggtag gagggcaccc
53641 accttgtcaa agaggccaca ctcgcagatg agctgctcac gggccttggt gttgattgca
53701 atggtgaatc tcacgtgtgc caccagcagc tggggagggg agaggaggag gcctcagagg
53761 gggcccagtc aggtgacctg gtgcctcagg gacccgcagc tcccccaccc aggcctgccc
53821 tataggatga tgctgggcgc agggaggaag tgaaggctgg gtgctgatct ttctgctgaa
53881 taagtgctgg aggcctgcac ccctctgatg cttactaagc atgataatga ttcagagggt
53941 cctggccagc acttgtacaa tgcttacctc tttgctccct gagttcactg tcttaatctg
54001 accatcattc tgtaaggcag ctgtactatt tgacctgttt tactggtgag gaaactgagg
54061 cacatgggta cttttagcat gcagtcaccc cagcagccaa tgcttgtagg attcgagaac
54121 agggacggag agtgatggca ggggcggcca tcagcatcag ccgaggatca ccatgaactc
54181 atttgccttt tccaactcta ctggctggcc agcgaggccc gtgtgtcagg cccatgcccc
54241 agccgcgtgt cctggggaac agcaggctcc tagctgtttt cttcctttag ggcattact
54301 gactctgaga acatctctcc agggctccct ttctgccacc cactcccagc cacaggtccc
54361 cctgtgggat gtcagtgatc cctcccactc cacatctcag atgccctccc atagcaggtg
54421 gggcggtagc tggctgtacc ttgaaaatgg ggtgcacagc aggcagctgg cggtacattg
54481 caatgccaaa aacctcagac accagatgtg ttcgcagaag gtgggtgatg gtctggtgga
54541 cgtggaagtc actggaacgc acccagattt tggccaaaag ccagtcgtat tttgcatccg
54601 aagggaggaa aatagggttc tcatctcccg ggatttggtt gagctgatac attgggggaa
54661 aggaaacaca ctgctatatt tcacttcaga gtatagttgt tggagaactt cgcctcttgg
54721 gaagttccag aagtatctga atttctttaa cagtgacttt ggaatcagaa gagcctggag
54781 ggggtaaagg gccctgcggt ggtatttcct gtcccagcca tattacttac aacctgcatg
54841 actctggatg acacactggg ctttctaagc tccggcttca gcatctgtca tgtggggaca
54901 gtgatcgctc ggctcacagt tactcaggag ctggcagcat ggaaggagcg ggcaggccga
54961 aggcccagca gcggaggggg aggatcgctg tccccctctt ccctccttgc cctgctccct
55021 cttctactgc ctctccttgg tctctcatac tttcctccct ctcctcttcc ctgaaatgct
55081 ggagctcccc agggtctgcc atggtgctcc tgtcttcttt tcttgcccta agtcagctcc
55141 tcctgtttaa aggcttgggg ccctcctggt actgagcctc ccagatcagg gtctgcagct
55201 tgagctctgc ctggagccca cacctgtggc caggcacctc ctgtagcaga ggctggacct
55261 gtcttccctt tccagtttcc actccacact gggacaaggt gagttttttt cttttccaaa
55321 atgcaaatca tgtcatgtta actgcctcct caatcacctc ttaatgccag aaaataaaat
55381 ccccaagctc tgtggtgacc tggttgctga tgcctctgta cacacagcct cactttcgtg
55441 cccccacacc agcacccagc cccaggtccc tccatgccag cagccctgca cgttgccccc
55501 ttattgagag cccagcacag cctcagcacc cgacagtgag ttctcacggg agccggcagc
55561 aggtgctggc attgcccatt tttacatgaa gacatggggt attggagggg ttgacagaaa
55621 gaatgaggtg ggtggcaggg ctgcagccaa gagcggccag gaaggggcat ggccagactt
55681 taggtgctgg gaaagaccag tgtcactgca gcacagtggt catggctggg gagggagaac
55741 tgtcccagag cacacagctg tgtcacttgc tataagtatt gtggaaggtg gggtccttgg
55801 gcgtctctcc ctcgaaaaca gtgctgtcca atagacatat aatgctaccc cacacatgga
55861 attgtatata ttcaggaagc catattaata aaaataaaag gaaacaggtg aaatgccggt
55921 gaataatata attttatttt acccaatata tccagaatat tatcacttca acatgaaacc
55981 aatctaaaac tattaaatga gatatttcac attccccacc tccttattct aagtcttaaa
56041 aatcaggtgt gaactttgca cttgcagcag gttttggttt ggacgagcca aatcccaagt
```

FIGURE 4 (cont.'d)

```
56101 gctccagagc cctggtggcc agtggctcca ccctggtcag agagacccca gaagcctcag
56161 cactccctga ggaccaagga gggggg agg aggagggaga gcagagtgtg acttgcacat
56221 taggcgtgcc tgtctgttta tacttgagat tagttggctg cttttaaata ccagacagtt
56281 tcacataaaa atttgaatga cctggttttc ttgaaaaatt agaaggtctc agaactctgc
56341 acccaggttc tcacagaact acgctcttgt ccctttttaca gagtcccagc tctcagggtc
56401 cccactgcca cacccgtttg catgagatgc ctgggccact gatacctgat ctgtgcccta
56461 gaatgctggg ctgcctggca tgctctgaga cactttctga catgtcccca catgctctga
56521 catgttcctg atggctctgg gacactgaca tgttcctgat ggctctggga cactgacatg
56581 ttcctgacat cctctggggc cgaggagccc ccctgttgtg tgctaggggc tttacccatg
56641 ctatctcact taatcctcac tttgaccctg caaggcagat attccttgct gtacccattt
56701 tacatggggg gaaactgagg ctccagctgg tttagcagct ctcccaagtc acacagtagg
56761 taaagagctc agccggcaac atgatattga acaggcaaaa attggaagca atccccctaa
56821 aaactggaac aagacaagga tgtccactct cacccctcct attcaataga gtactggaag
56881 tcctagtcag agcaattagg caagagaaag aaataaaagg gatccaaatg aaaaaaaaaa
56941 aaagaggaag tcaaattatc tttgttcatc catgatatga ttctatacct agaaaaccct
57001 gaagattcct ccaaaagact cctagacttg ataaacaact tcagtaaagt ctcaatgtta
57061 taagtaaaat gcttgtttag aaacagaatg cttgttcctc ggtactgcaa ggaaaaatca
57121 gcatttagac aaaaagtttt tttagcaagc caattttact ttctgcagaa agggtgctcc
57181 tcgcagatgg aacaatggcg agagcacacc tgaataatgg agagaagcaa tttttattcc
57241 ttacgcagct tgtccctgct accgtgtcct gtctccattg gctggagcca aacctcacag
57301 tctaaactaa aacccgactg gctaataact taaaactttt ctaaataggt aaaagcagtg
57361 gaaagacaaa ggaaaagagg aagttgctta tgaaaggact tagaaaagta ataacatttc
57421 caaataagga aggggcatgg gctgcaagct gggacatgcc tgtgagcacg tccagcacaa
57481 atatcttggt taaagtacaa ggacatagaa tgtactcatt cccttatatc taacagctac
57541 atatgatagg gcttaacaaa aagttattag cacaaagcga aaaggcttaa aaaaagttag
57601 tctttagaaa aaactattat ttctaacaca taatttactc cttaacaaaa aaaaaacttt
57661 tgactttcta cactcaagat acaaaatcag tgtacaaaaa tcagtagcat ttctttttat
57721 ttgagacgga gtctcactat cacccaggct ggagtgcagt ggtgtgatcg cagctcactg
57781 caacctccgc ctcccaggtt caagcaattc tcctgcctca gcctcccaag tagctgggat
57841 tacaggcagg tgttaccaca cctggctaat ttttgtattt ttaattgaga cggggtttca
57901 ccatgttggt caggctggtc tcaaactcct gacctcaggt gatctgccca cctcggcctc
57961 ccaaagtgct gggattacag gcgtgagcca ctgtgcctgg cctaaaaatc agtagcattt
58021 ctatgcacca acaatgttca ggttcaggct gagaaccata tcaggaacgt ggtgatctca
58081 gttacaatag tcccccatac acaaaataaa ataccaaaga atgtatccag ccaaggaggt
58141 gaaagagctc tacagagaga actataaaac actgatgaaa gaaatcatag atgacacaaa
58201 aaaatggaaa aacatcccag ctaatgggtt ggaagaaagc aatctacaga tacaacacaa
58261 ttcctatcaa attatcaaca tcatttttca cagaattaga aaaaaaaatc ctaaaattca
58321 tatggaacca aaaaatagcc gaatagccaa agcaatccta ggcaaaaata caaagctgga
58381 ggcatcacat tacctgactt caaactatac tacaagacta cagtaacaaa aacagcatgg
58441 tatactggta caaaaatagg cacagagatc aatggaacag aacagagaac ccagaaataa
58501 agccatatac ctgcaaccaa ctgatttttg acaaaatcaa caaaaataaa caataaggaa
58561 aggacatcct attcaataaa tagtgttgga aaaactggct acctatatgc agaagaatga
58621 cgctgggccc ctacctctca ccatatacaa aaattacctc tagatggatt acagacttaa
58681 atgtaagact tcaaacttta aacattctag aagaaaacct aggaaaaaat cttatggaca
58741 tttcctaggc aaagaattta tgactagacc tcaaaggcat atgcaacaaa aacaaaaatt
58801 gacaaatgag acttaatcaa attaaagagc ttctgcacag caaaacaaac tatcaacaaa
58861 gtaaacagac aacctacaga atgagagaaa atatttgcaa ctatgcatcc acaaacgact
58921 aatacccaga atctatgagg aacttaagaa aaaacaccac cattaaaaag tgggcaaagg
58981 acaggaacag acacttctca aaagaagaca tacaagtggc caacaaacat atgaaaaaat
59041 gcccaacatc actaatcatc agagaaatgc aaattaaaac cacaaaggga taccagtcag
59101 aatggctatt attaaaaagt aaaaaaatga cagatgttgg caggatgcag acaaaaggga
59161 atgcttacac actgttggtg gcagtgtaaa ttacttccat ccctgtggaa agcagtttgg
59221 agattttgca aagaactgca aatagaatta ccagttgacc caacaacccc attactgtgt
59281 acctacccaa aggaaaagaa attgttttac caaaaggaca taggcacaca tatgtttatt
59341 gcagcactgt tcacaatatc aaaatcatgt aatcaaccta ggtgcccatc aatagtggca
```

FIGURE 4 (cont.'d)

```
59401 ccagataaag aaaatgtgat acatgtactc caaggaatac tacatagcca taaaaaagaa
59461 tgaaatcgtg ttctttgcag caacatggat gcagcttagg attggcactt aagccataat
59521 cttaagtgaa ttaacccaga aacagaaaat cgaatactgc atgttcttat ttataagtgg
59581 gagctaagca ttgtgtacac atgggcataa aagtgggaac aaaagacact ggggactcca
59641 ggaaggggag ggagggagga aagggttgaa aaactgggta ttgggtacta tgctcagtat
59701 ttgagtgatg ggttcaatag aagcctaacc ccagcattat gcaatataac catgtaacaa
59761 acctgcacat gtacctgaat ctaaaatttt atatattaaa aaaaaaaaaa ctgttctgac
59821 cagtaaaaaa agagctgaat gaggatgggc ccagtgctct gcctatttca gcccatcact
59881 ctcccttctg cttctcttca cctccccggcc tgaccgggcc tcacctgccc atctccttga
59941 gctcttgtac cactgagctg ggccttcccc aacccatcct tcacatcctc ccactcctgt
60001 ccaggatttt ggcctgccat gggatgccag aacttgccct gagcaatttg tgtttcttaa
60061 atttgttttt tgggtaagga agtagctttg cgtttctgat tagaaaagaa tatgtgctta
60121 tcgtaaaaag aaatctgagt catgacagga gagcctgaga aagaaaacat catctcatct
60181 tccagcgccc agggataacc accaaattct ggggagcctc ctttcatagg tctttgcatg
60241 tgtgcacatt tatctgtcca attttccatc aactgaatat gattataatc aacatctgtc
60301 tctttgtttt gctcacctgt cccccactgg gccatcactg tgttcctacc tggtgacact
60361 gcgtccttgt gtccccatgc tggcacagta ggcctgctgc atccttgcat tcattttaca
60421 taagtgagac catgcccatt gccttagcag tttgaaggag ctatttgtat acgacagata
60481 tgtatccttt atcggtccct tgtgtcttgt ttttccactg ttaactcatt gtggagaccc
60541 ctccaggtca gctggaaggg aaccaaagca ttcctttcaa agacgcctca acattttatg
60601 gtgaggacat ggaagggctc actcactcaa tcctcttctg ccttcagact gttttcaatt
60661 tttttcccca tcacaaacta tgctcctgtt gctacccaca cacatttgtg ctttcatttc
60721 tgctgagtgg ctgctagcga aggctgagcc ttgggggttt gggtatgttt tcgagtagac
60781 agtgcctgcc ctactgttcc tcagacagtt tcactctcct ggtgcacacc tgttcagtgc
60841 tactggctgt cagaacactt aaacaataaa gtcccctcca gtgctcctcc aattgagacg
60901 gggcaggggc ctcctcttag ggcactgtag ccccccagcc ccgcaacagg gcatggaaat
60961 gaaggaaaat cccgagttcc ttgaagggaa gttccaggca cctagctagc cctgagaaat
61021 aaatgagcaa cttgacaaac aagagggtaa cagcagccta aaacaacagc caaggaagcc
61081 agagtcctgg gctgtttggt tcccctctgga aactaaagag aacccctgaa catgtgtctc
61141 tgagttgttt ttcagaaacc cagaccccca ccaaaccgat ccactggcac agagacctca
61201 gataagacgg aactgaggac tgaactctga gcaggctctt tgttctaaat ttcttcctgg
61261 ggggcctggg ggaagtcccg cccacaagcc acagctaaca ttcctttctg gtaacccaaa
61321 tttttaaatg aaacttctct tccttaacca atttcaaaac aacaaatttt tgaatctacc
61381 tatgacctgg aagcccaccc ccacttcaag atatcccgcc cttttaggcc aaaaccaatg
61441 tgtaccctcc atgtattgat taatgatttt gcctgttaac ttctgcaatt cctgaaattc
61501 actctgcctt taaaaaccct tacctgcaag ccatcaggga gttccggtct taagagtgag
61561 ctgcccaatt ctcctttttt ggtccccgca ataaatgcct tgtgttctcg tagattatat
61621 cccaatctca gtgtttggtt ttgctgcact gggcaagcag atcccagtcc agctcggtaa
61681 cacaactgtc ctcgccacga cagcctcaac cccaggaccc tctgaccgcc cactgcaaca
61741 tgcacctggt acagcaggcg ctgtgggatc tgctccggtg ctggccgaag ctctgacctt
61801 gctccggtgc tggccgaagc tctgaccttg ggctgcccag gcccaccagt tatcccgtga
61861 acactgccag gctgcaacaa ctcatgagca gagcatgggg ctccgtcctt gctggtgtct
61921 gggagttacc cctttgtttt tccaaccagg catgtcagaa atgatatctc attgttaact
61981 ttcatttgca tttctctaac tacaggtgaa gttaggagtt tttccatatg ctggttgccc
62041 atttacattt cttcttttgt gaattgccta ttcatattct ctgctcattt ttccactgga
62101 gtattggtat tttcccgtca atgtaaagga gctacctgtg tatcatagat aggcatctct
62161 tagctgtcac ttctgttatg gttactcacc ctaatctctg ttttgctttt tggctttgtt
62221 tatggtttat cactcaagtt ttaaaacatt acataatcaa atatgcttag ctttcccctt
62281 ataacttctt ggtttccttt tccttctaaa agtcttctga gtgtctgcgt aattagtttt
62341 tctaaattcg tttacttttt tcattttaat ttttacttca tctgaatttt ttctttttct
62401 tctaagcaac tcctctacat gatgagattt atttttgtaa atggcatgac agagcagtcc
62461 aatttaattt tcttctcatg caaaggcagt gtgatagcat cattaaaata atatcccttt
62521 ttcactgagt tgaaaaacct ccattgtgat acactgaatt cctctgtggg ggagtccatt
62581 tctggatctt actctatact gtcccccaat tctctctgtt ttcaagcaca gtgtctgctt
62641 aacagtaacc ttacaaatcc agcaaggaaa gtgttccttc tgtgttttct tttacttttt
```

FIGURE 4 (cont.'d)

```
62701 tttttttttt taaagatagg gtcttactct gttgcccagt gtggagtgca gtggagcgac
62761 catggctcac tgcagcctca aactcctgga ctcaagccat cctcccacct cagcctcctg
62821 agcagttggg attacaggca tgcgccacca tacctaattt tttctattaa tttttttttt
62881 ttttaagaca tgaggtctca cttggttgcc ctgcctctct atgtggtttt aatttttttc
62941 aaaaaatttt tgactatgct agatttcttt ttccatatga atctttcaat tttttaattg
63001 ttttctctcc tttttagttc ctcttcacca ccaccacacc cccaccaaga aagataaaaa
63061 attctggctg aaattttact tggaagtgca ttaagttttt ataatagaat ttggtagaac
63121 tgacattttt acagtttcct ccccaatatc aaatcactgt taagagttca ttgtatatcc
63181 tttaaaataa ctttatagtt ggccgggtgc ggtagctcac gcctgtaatg ccaacacttt
63241 gggaggctga ggcaggcaaa tcacaaggtc aggagttcga gaccagcctg gccaacatgg
63301 tgaaatgccg tctctactaa aaatacaaaa aattagctgg gcgtggtggc aggtgcctgt
63361 aatcccagct actcgggagg ctgaggcagg agaattgctt gaacctggga ggtggaggtt
63421 gcagtgagcc gagatcacgc cactgcactc tagcctgggt gacagtgcga aactccatct
63481 caaataaata aataaataaa taaataaata aataaataaa taactttata gtttttcctt
63541 atatgggcat tatattttat tgttagtatg gagaaaggct attgattttt ttgagaaata
63601 tatttatcta aacactttgc caaatgaatt tattaatcta gtagctttta aaaaaattag
63661 aatctcttgt gttttctagg tctaccatag cattaccaga aaagatcatc ttccctgttc
63721 tttgacaata tgtttattga ttgttttcct gttttatcat gtggtatgac ctctaaaata
63781 atgttgaata aaaacagtga tatcagcatt cttattattt taatggaaat ggcattagag
63841 ttgcaccttt ttgatgttag ctatctttat catataaagt aaggttcctc ctattaattt
63901 ttattagttg tggctattaa atgttattaa attccctttt agtgtgaatt gatataatca
63961 taaactttat ccttatgggt ataataaatt atggtggtag ctctcttgat attgaaatat
64021 ctggaataaa ccctgcttgg ttattacata tagtcattta atacactgct gcactcactt
64081 cgctaatatc acctttagtt ttcttttaaa tctttattta atacttggat tggtcttcag
64141 ccttcttttg aagcctgcct gtatccagtt tcagaactaa gcttacacca gctttatatg
64201 atcaatttgg ggctgataaa gagccctgga aatgtcagct gtctagtggc tgggtgagac
64261 tcagctgctc gctgtgtagg tctgtttcca atcactatat ggaaattggc ctattttcta
64321 caatttcttc taatttatct tttcctaggt ttttatccat ttctctaatt tttcaaattt
64381 ttgccatatt actctcattt aaaaaatatg taatcataat tactgttctt tttttttttt
64441 aagagacggg gtcttgatat gttgctcagg ctagactgct gtggctattc acaggtgtga
64501 tcatagcaca ctacagcctc aagtgagcct cctgcctcag cctctcaagt agctgggact
64561 acagttgtgt accaccatgg tgcctggcta taattactct ttttatgatt cctttttttat
64621 tccgaatctt gcattttttt tttctatctc tttttttcca tcagcctcat gaggaggtta
64681 ttattattat tttttggacc tttcaaagaa ccagatcttg gatttactat cctctggctt
64741 tcatttgctt gagtctttat agtttgcaaa gtttccattt tcagaagaag aaagagaccc
64801 aggaacattc tgtggcttgc tcaaggtccc acagcctgct agcaagtggc tgaactggaa
64861 tttaagctag gcccctgact ccaggctgct ccaagagatc tctgagccaa gcttttgaag
64921 gcaccatcag tggtgcctgg gatctccggg gatctcccag caattttgtc ttcttttagg
64981 tcacctgtcc ctttacctgc tgcttcagtt tcttaggcac agggcttctc tctggtaaca
65041 gacaggaagc tcctctgagg ctacgtgccc ctgggagact gtggggaggc tggaatctag
65101 agtcagatga cctggcttga atcctagctc tgtggctggc tgtgggcacc tgtgtctcag
65161 ttttcttatc tgggtaaaat gatcaacatc aatagagccc actacctagg atggttgtgg
65221 tgatgattac acaaataaag ataggttatc taaaacccca gtggtcaaat gtgcttcaga
65281 atccagaatt tttaggattt tagcagtggg tatacttcat tatgtgccat acccccctccc
65341 acccccagtc tagggcaaca tactatttta caatcgaaca gagcagtatt tctgcagtga
65401 tccacataca tatcacattg aatggaaaaa gcctctaaat aacctcacct attgcttcaa
65461 agaaggtttg tttacaaaca atgaatttgc tgcacagttt tgaaatatgc agcagttttc
65521 agatttttta gatttagaat cgagggtaag ggattgcgga ctgtgcaggt taacccatag
65581 gatagccttg gcatgtggct ggtgcctgac ctatccagct gctattgtgt ccacagctcc
65641 caaggtccag ttcatggaca ttatttgctg aatgctcatc tgccagtctc ccacggtgtc
65701 ctctgcgcag ttcctcccta ctcccaggga cctatgccca gtccagtcct ggccttggcc
65761 cctgctgtct gcacaccagc tcccagcctg gcagcaggct ggtgccagga acagggggag
65821 acaaagccct gtgcccgcct gcctttcctc cagggtctcc ctcttcctcc tgcctcatct
65881 ccggtggaca taagaactca catcatcatc aaaggtggca taccaggact ggcctggttc
65941 ctgaccccag aacccatggt gcccctcagt ggtcttggtc tccagcttag tccacagctt
```

FIGURE 4 (cont.'d)

```
66001 cacctgcctg gcccctggca gcaccttgac tgggggccct tggtcagggt gctggggtgg
66061 agagtgcaga atatgatccc agggcaggtc ctccacagtg tgcctcgact ggccaggggc
66121 ttctcaagtg tgccttgggg agtagaaccc tctccgcccc tatggacagc ccacctcagg
66181 gcctgcagga agccctagtg tctttcaaga catagcttcc tcagctggag tgtgaatgga
66241 gccacccagg agccctggat cgcagaggac tgagctgctc agaaaggtgt gcccccccagc
66301 agcctacctg gatggcaatg gggacaatct tgttggccag gttcttatac agcaagcaga
66361 tgggagcggc caggaactgg agtgtgcagg ggtctgtttt gttggcatcg atgccatcca
66421 gcagctcaaa gtccacgatg aaaatgttcc cttgctgcag gaggcagaga gatgtgtcca
66481 aatcaggctc agcagacgga ccaaaaatca ggcctgggga aagagtgatg acctctgggc
66541 acccctctcc ctttcctgcg actcagcgga gctcagaatg tgtacttctc tcctctgact
66601 ccaaggctga ttgattcaca tggaaggtgt tcacaggttg tggcagttcg gggtaagatg
66661 aaggaatggc agcagctcat tcggcatttg tggtgtctga aacctgcttg actggcacga
66721 aagatgagag accgacccga gtgtcagttt actaagaaga aagaggttag gtgaaataga
66781 tgtgacgagt taaatgccaa tcttcaccac ggggctgaag gtccgnnnnn nnnnnnnnnn
66841 nnnnnnnnnn nnnnnnnnnn nnnnnnnnnn nnnnnnnnnn nnnnnnnnnn nnnnnnnnnn
66901 nnnnnnnnnn nnnnnnnnnn nnnnngggt cctcagggac tgggcctcag cccgccggtg
66961 gttccaccct aggcttcccc aagtcggtca agagccggga gcagctgtcg gagtacctga
67021 ccgtggtgat cttcaccgcc tccgcccagc acgccgcggt caacttcggc caggtaggca
67081 gggccgggcc cgctgggcag ggctcccttc tcaaggccgc tgcctcctcc cccgccccgg
67141 ttctgcacgc gtactgcacc ctcggacagc ctcggggcct ggcacgggac ttgcaggatg
67201 gattctgccc gctcagccaa gggcgctggc cgcggggaaa gaggatggac ggactgcagg
67261 gcccgctgga gttgggggc acggggagga cggggcccag ggggcagctg ggcagcaggg
67321 cttcgggggt gcccacgctt gctggcggtc gtctccgcag tacgactggt gctcctggat
67381 ccccaatgcg cccccaacca tgcgagcccc gccaccgact gccaagggcg tggtgaccat
67441 tgagcagatc gtggacacgc tgcccgaccg cggccgctcc tgctggcatc tgggtgcagt
67501 gtgggcgctg agccagttcc aggaaaacga ggtgaagctg ggcagggcgg ggcacagccc
67561 caggtcaccc caggttaagc ggttcctcag cctcagggct ttgtgactcg ggccccaagg
67621 ctcacttgga gcaaaggaat cctgacttcc aaggctggaa gggcccagaa ggctgcagcc
67681 gccaccaggt cccccggcct cagcctggac agagctcagg gtgtgcaggg caggagagca
67741 cacagcccag gctttgctca ctgtcaccag agggtcgtgt gtgacgcccc ctcccccag
67801 ctattgacaa agttcttgca catgtgtttt accctggtac tccagaggga atgaccaaga
67861 gtttcctggg ttccttccgg acacgtgcat ctcatttaac ctaacaactg aatccggtgt
67921 gtcttcgtgg atgcacccgc tttggggtag ctcagtactg catagaatgg ccggaccagt
67981 ccaacctgct ccagactgct gggtgtctga gttgttcccg gccaatgtgt tggtccctca
68041 ctggacatcc ttgtttttgt ggctttgcac atgtgttcag tatgaccgca cacattccta
68101 gcagacaaat tccttggtca aagaatattg atactgaatt gccctccaca aactaaattc
68161 aaaatcccat tatcaatagc ctatgtttct tggacctttc cagctcagaa gctttgtgat
68221 cttaatccaa tacagtattt ttttaaaatg atatctagct ctgccccgca gacatctgtg
68281 tgagaatgca aataagcaca ggaccccaac agggcagcca ccccttcagg ctccctggcc
68341 cgctttctgc cttcctgggc tggagaggcc agtgctggcc ccagcgcccc tgatgggagg
68401 tgagagtgct gcgcaggggt ggcccaagac agcaggatac catggctgca aacaccagca
68461 gcccccagct tcatctgcat catctcgtaa ccacttggca gcaggcagtt attttcccac
68521 ttatccatga agccccagcc ctggagcctt ccttagagaa gcaggttgga ggcgacgaca
68581 cttgccttcc cgaggccctc ttgtcaggca gcagagggtg aatatgggga ggtgaataga
68641 tgctccctcc ttcatctccc aaacggtggc tggccccttg ggatgagaca ggcctgtcag
68701 tttacacggg tagtggattg acctatgtgt gtgtccatgt ctgggccctc agctgttcct
68761 gggcatgtac ccagaagagc attttatcga gaagcctgtg aaggaagcca tggcccgatt
68821 ccgcaagaac ctcgaggcca ttgtcagcgt gattgctgag cgcaacaaga agaagcagct
68881 gccatattac tacttgtccc cagaccggat tccgaacagt gtggccatct gagcacactg
68941 ccagtctcac tgtgggaagg ccagctgccc cagccagatg gactccagcc tgcctggcag
69001 gctgtctggc caggcctctt ggcagtcaca tctcttcctc cgaggccagt acctttccat
69061 ttattctttg atcttcaggg aactgcatag attgatcaaa gtgtaaacac catagggacc
69121 cattctacac agagcaggac tgcacagcgt cctgtccaca cccagctcag catttccaca
69181 ccaagcagca acagcaaatc acgaccactg atagatgtct attcttgttg gagacatggg
69241 atgattattt tctgttctat ttgtgcttag tccaattcct tgcacatagt aggtacccaa
```

FIGURE 4 (cont.'d)

```
69301 ttcaattact attgaatgaa ttaagaattg gttgccataa aaataaatca gttcatttaa
69361 aatgggtctt gttccatgtg ttatattcca atcaccccaa acagctcact gccatctccc
69421 acaccaagag aaaaaaaaag ccatagtcac cgtgatttta tcaaggcaaa agcctcccca
69481 cccaagtctg gatagaaggt gctttttccc tcaagcagtg tctactctct ttggaacaca
69541 tcccaaatgt caccacctct gggaaggcat ccttggttcc tgtctctacc ctggatttgt
69601 cagaacctct gttcttgccc cctctgtggt ctctcccttg ggacaggagc ccctggaagg
69661 acagaaaacc cactttattt atgtctgtgc cccagggctg gcataaggca ccagcactca
69721 gctgttctct ccttttcctc ctggaagggc acctagctaa tggatattag gcattgtctt
69781 gggagctggg ggcttatttt ttcctgaggc agggttctta acatgacata aaaaataaaa
69841 atgggcaggg cgcggtggct cacgcctgta atcccagcat tttgggaggc caaggtggga
69901 ggatcatttg aggtcagaat tcaagaccag cctggccaac acggtgaaac cccatctcta
69961 ctgaaaatac aaaaattagc caggcatggt agcaggtacc tgtaatccca gctactcagg
70021 aggctgaggc aggaaaattg catgaacctg ggagacagag gttgcagaga gtggatatcg
70081 caccactgca ctccagcctg ggcaatagag cgagactctg tctcaaatag ttaataaata
70141 aataaattaa attaaataaa aacgcattct ctttccccag ccccaagtag cagagcccgc
70201 tctgagcctg ggcatggtga cccattctcc tcgtgctcac atgcccaact cccagccctc
70261 cagcccctgg cttcggaatc atgtcatcag ggtctcccat gtctctggaa ggtgcttcca
70321 gtgtggcagg ccatcagctc agtgtctggg taaaggcttc tacagggcca gcatggcata
70381 gggggaggt gtgcatgcgt tcctgaagcc acaaggtctt ctgaggagac ctgactattg
70441 gggtggggac tagagactga ggtccagccc cttaatgccc cagactccct gccatccctc
70501 ggagaatttc ccaccacact tatgaatgat cttcgggaca ggtgacataa acatacagct
70561 atggtagagg cattcagctc catgccactg tgagaatgaa cataccaact tttaggcaac
70621 aaggccatgt ggtcaaggag agaggagaaa cgaataggag taggcagggg tggtgaagca
70681 ggtctgacat tggcaaaagt gacagagaag gattgggttg gaagggcttc agatggcaga
70741 gaacctctga aaaagtctca tgccagctaa tgaagagtcc tcaaagtcac catcacagaa
70801 atcttacatc tggcagaaat gacagcaata gtttggcatg aaccccacag tggatccaaa
70861 cgtgtggcag ctgagatcgt cagttaatta tgttctctgc agctggtcct tctggttccc
70921 tggagctggg tatctgagta gcacagctcc actgctacca caggagaggg agaatcccaa
70981 attctgtgca tagactgtct aaacctctgg atgaccccta agacacatgt acataaggca
71041 aactgcaaac agcccaattt aggataaaac agcctgtctt actctgtttg tgctgctata
71101 ataaaatacc tcagactggg tcatttatat agaacagaaa ttgattcctc acagttctgg
71161 aggctggaag tctaagagga ggcactggca gtttcagtgt ctggtaaggg agggatcagt
71221 gtctgctccc aagaggatgc cctctgtgct gtgtcctcac ccagcagaag agcaaaaaag
71281 ggcgaacatt ctcaaaagcc tcttttataa ggacatcaat ccattcatga gggcagaacc
71341 ctcaagaatt aatcatttct caaaaggccc ctcctcctaa tgccatcacc ttggggttta
71401 agttccaaca catgattttt ggaaggacac atacattcaa atcattgcac aaccaaagtg
71461 atatttgaac tttcaaatag tttgcagttt gagatcaact aagttaattg cttgcttgaa
71521 taaaaacatc acagccgggc acgatggctc acgcctgtaa ttccagcact ttgggaagcc
71581 aaggtgggca gatcacttga ggtcaggagt tcgaaaccag cctgaccaac atggtgaaac
71641 cccatttcta ctaaaaatac aaaaattagc caggcggccg ggcgtggtgg ctcatgcctg
71701 taatcccagc tctttgggag gccgaggcgg gtggatcaca aggtcaggag attgagacca
71761 tcctggccaa cacagtgaaa ccctgtctct actaaaaatg caaaaattag ctgttgagac
71821 tactcgggaa gctgaggcag gagaattgct tgagccgaga tcgtgccatc gcactccagc
71881 ctgggggaca agagcaagac ttcgtctcaa aaaaaaaaaa agaaaagaaa ttttctggat
71941 taggataatg ttctatattt ggataagggt ttaggttacc tagatagata catttatcaa
72001 aagtcatcaa atggtacact tcagatgtac gcatgtcact gtatgtaaat attaccccaa
72061 aatcaacaag aaccatgagc aaatactgac ttctagtgaa cgacatgcat actgaaactt
72121 tcgtagtgaa gtataattat ggctgcagtt gactctgaaa tacataaaaa cctaagttga
72181 tgggtgaata cagtgattaa tagatagaaa tctgtggtaa agcatacgga gaaaaatgtt
72241 aattgtagat tctagggttt atatatattc tcactatata attaaacgtt tttatgttta
72301 aaaattttta taatgttgaa aaaccatgaa atcctaccta acgcagtaag acaagaaaaa
72361 gagataaaag gtatatgtac tgggaagtaa gaaataaaac cgtctttgtt agcagatgac
72421 atgctcatct atgtagaaaa tccaaaagaa tggataaaga aactcctgga actaataagt
72481 ggttacagta aggttgtagg atacaaggtt aatatacaaa agtcaatcac tctcttattc
72541 accagtaatg aacaagtgga aattgaaatt caaaacaaaa tactatttac attaatactc
```

FIGURE 4 (cont.'d)

```
72601 caaaaataca tacttaggtt taaatctaat aaaatacata caagatcttt atgaggaaaa
72661 ctgcaaccct gatgacagaa atcaaagaga aactaaagaa atagacataa gtaaatattc
72721 cccagaaaga ctcaatattg tcaagatgtc agttcttcaa aacttgacct atagattcaa
72781 tgcaatccta atcaaaatct cagcaagtta tgttgtggat actgacaaac ttattctttt
72841 tttttttttt tttttttttg agacggagtt tcgctctgtt gcccaggctg gagtgcagtg
72901 gcgcgatctc gactcactgc aagctccgcc tcccgggttc acgccattct cctgcctcag
72961 cctcccatgt agctgggact acaggcacgc gccaccatgc ccggctaatt tttgtatttt
73021 tagtagagac ggggtttcac cgtgttagcc aggatggtct cgatctcctg acctcgtgat
73081 ccacccgtct cggcctccca aagtgctggg attacaggcg tgagccaccg cgcccggcca
73141 acttattcta aaatttagat agggaagcaa aagacccaga acagctaaca caacaatata
73201 gtaggaaaac aacaaatttg gaaaatggat actacccaac tccaagactt actataaagc
73261 tacagtaatc aagatagtgc cgtattggtg aaagaataga caaatagatc aatggaacag
73321 aatagagagc ctaagaaata gaccttcata aatacagtca actcatcctt gacaaagtag
73381 catagacact acaatggagc aaagattgtc ttttcaacaa gtggtgcagg aacaactgga
73441 tatccacatg caaaaacaaa caaacaagca tgaatctaga tacagacctt atgctcttca
73501 caaaaattaa ctcaaaatgg attatagatc taaatgtaaa attcaaaact ataaaattcc
73561 cataacatag gataaaatct agatgaccta ggtatggcta tgacttttta gacataacac
73621 caaagccatg gtccatgaaa gaaataattg gtaagttgga cttaattaaa attaaaacct
73681 tccgctctgc aaaagaccac actaggagag ggaggaaata tttacaaaga cacatctgat
73741 aaagaattgt tacttaaatt atacaaagcc ttcttaaact taacagtaag gaaacaatct
73801 gattgaaaaa tgggccaaag actttaacaa acaaaagaag atatacaaat ggcaagtaag
73861 tatgtgaaaa gaagctgcac agctgggggg cgtggtggct cacgccttta atcccagcac
73921 tttgggaggt caaggcgggc agatcacctg aggtcaagag accagcctgt ccaacatgga
73981 aaaacctgtc tctactaaaa atataaaatt agctaggcat ggtgatgcat gcctgtcatc
74041 ccagctactt gggaagctga ggcaggagaa tcgcttgaac ccggaaggtg gaggttgcag
74101 tgagccaaga tcgcgccatt gcactccagc ctgggcaaca agagtaaaac tctgtctcaa
74161 gaaaaaaaaa aaaaagctgc acattctatg ttatcaggga aatgcaaatt tagaataacg
74221 caataacaag ataccactac atacatatta gaatggccaa aattgagaac actgacagca
74281 ccaaatgtgg aggaggatgt ggagcaacag gaactagaga gaatgcaaaa tggtatagcc
74341 acttaggaag acagcttggc agtttcttac aaaactaaat atactcttac cacacaatcc
74401 agcaatcaca ctccttggta tttacttaca tcccaacaaa aaccctcata tggatgtcta
74461 gagcagcttt gttcataatt gtcaaaactt ggaagcaacc aaagatgccc ttcggtaggt
74521 gagtaaataa ataatatcca gacaatggaa ataccattca gtactaaaga gaaatgagct
74581 atcaagccat gaaaaggcgt ggaagaaact gaagtgtgta tcactaaaag tcaatctgaa
74641 aagggtgcat aagtttccaa agatatgata ttgcagaaaa ggcaaaactg tggagacagt
74701 aaaaagattg ccaggggcta gggcagtggg agggatgaat aggcagggca cagaggattt
74761 tcagggcaat aacactactc tgtatgacac tataatgttg gatacatggc cagatccaca
74821 gaatgtagaa caccaagagt gaaccttgaa ctatggactt tgagtgatga ggatgagtca
74881 gtgtaggctc atggattgta ataaatgcac cactgtgggg ggggggggat attgataact
74941 ggggggctgt acatgtgtag ggacaggagt aaatgggaaa tctctacttt tgttaccggt
75001 ggagggtgta ccgcattttg aacaaaaaat tggacaaaac gcacaaagca aggaaagaat
75061 gaagcaacaa aagcagagat ttattgaaaa cgaaagtaca ctccacaggg tgggagcagg
75121 cctaagcagg tggctcaagg gcctgaatac agattttttct ggggtttaaa taccctctag
75181 aggtttccat tggttacttg gtgtataccc tacgcaaatg aagaggatga agggaggtta
75241 caaagttatt tacttggtgt agaaaattag ggtttttccc ttttatttag ttgtaggaag
75301 cccttaggtt acctgcctcc agaccctatt ctcctgcctc attttattcc taattttgtt
75361 gtgaacctaa aattgctcta aaaaatgaaa tcttttaaac aagaaaataa acttataaat
75421 tgcaaatatg tgtcacttac ataaaaacaa agaattagtg tccctacatc aggaaaaaaa
75481 cacctataat tcaatgtaaa aatgcaaaaa agccaagaga aatggccaag ccatggaaat
75541 tcacagaagt agaaataggc agtaaataaa caatgctcaa tttcatttat ctgagaaatg
75601 gagagtaaaa cttcagtgac atacaaagga gtaacaatca ttttaggaac aattttaaaa
75661 ataacacttg tgatgtggct caggaaagat tcatattctc actgtaggaa ggtaagtgaa
75721 tcattttaga ggtcagtttt gcaacttaga agatcaaatg catctaccct ttttctactt
75781 ctagaaatgt atcttcagaa gtgcccctcc ctccctcaca cacccccaag tgtacaaaaa
75841 taaatgacat ggatgtggac tgcagccttg tttctaatac caaaaatcag taaacaacct
```

FIGURE 4 (cont.'d)

75901 aaaaatctgt atccatgagg atttaaagaa atcctgcatg agttagaaag aataaggtag
75961 atgcctgggt tctaacatag aaaatatcaa actggttgtt agatgaaaaa agcaagttgc
76021 aaagtgaggt aatgtgtaaa tgcagtaagc aaaatacatc atatatatag tactttctat
76081 gtatttacct atatgagcgt gatgcctcca actgcatagc tgtggctccg ggagcaggac
76141 cttgtaacag agcctctgcc cctgactgtc ctgaggggcc tttccctggg aaaggaacca
76201 ggtttgattt tcagtctctt ttgttatcac catgctgaca gctttgcttg tcatatgcct
76261 ttccctccgc tgtactgatt ttaccttaca gaagctctcc ttagtgcttc atcagacact
76321 ccctcttttc caaagaaaag acagccgcat tccatggtca tctggttgag ctcgaggtga
76381 gccccaggga tcatgtgcct cccaccaggc tgacaccccca gtggtgagga gttgcccctt
76441 ggctttttcg aggccaagca actcagaggt gtggcaggat tgcatgtcac agtggcactt
76501 ccaaggccct ggagagtgac tcaacgcctc tgttattaag atgtcacaca ggctgtgcag
76561 caacaactct agggacaccc ttcacactga cagagttggc aagcttttcc tataaagggg
76621 cacacagtga atactgtagg ctttgtaggc catactatct gtcccaacaa ttcaactttg
76681 cccactgtag ctgtgaatca accgtagata atattaagtg aatgtgcact gctgtttgct
76741 aatagtttat tgacaaaaac agctgctttt gagcagtttg ctacccgac agagactgtg
76801 gggagtccct ggtggcagcg agctacaggc agccagtacc ccatcagtgt ggctggttcc
76861 atcctctcaa gcctgcctgc acccagacac tgtcgagtgt gtcttcagaa aaactcctaa
76921 aattccccaa aagcacagtg gctccccgag agccacctcc ctcaccttct tacaggggca
76981 ggttcctctt ccggttccac cctcctcagc acggagctca ggggccatcc ccacctcctc
77041 ttggccgcaa gcacagacct tcccacacag gctcagcagc tctgcgggcc tgtccccccac
77101 ctggagctgc aggcctccac tcctggggac agctgtgacc atggctctgc aaagcagcct
77161 tgtgcctagc tcccaagtca gctggcagcc cagagtggaa caattctgtg gatcacctct
77221 gagacagcag cacatctggg caagcctggc ttcccacccc tcacctcctg caacctctga
77281 cccttgccat gcatgtggta gggaagctgc aaccaggcct cagcactccc agacctgtgg
77341 gcggtttgct gtctgaggat cgtggcactg ccttccctca gaggccttgc cagagccagg
77401 ggatgcagcg tggcagagct gtcactggca accctgctgg tctccctggt gctttctcag
77461 ctgggctgtg ggtcaggaca aatttctatg gataaggctg gatcataatc tagtgctcca
77521 tggtcatgca gcgacagact cgagtctgcc ttctctcagg gtggtgagct caggtaggaa
77581 cgggatgttt gaagcaagca cacctgtgag aaatgcctgt tttcactccc atcccacaca
77641 ctcgtccaga cactgccagc ccacccccga cacacgtgtc tgagggaggc tgaggaaaac
77701 agacacctcc aggagccgca tactatttcc tgatgtgtaa gccagacaac cctggaaagg
77761 aggtcaggga accggagtgc ctgccaacgt ccccagcctc cctgcagcaa aacactctca
77821 tggcaaaact cctttttaaa gaaaggcttt attgctgcaa ttagacatcc cagtgtatag
77881 cacaaacccc cctgtacaga gaattattca agtggtaata ctgagaaaca gtgaacacac
77941 acaaaagaat acaaaactag acatttagat cactagaaac tttctaaggt aagaaaaatt
78001 tcaaatgtga agtgcctttt agaaactaca ccacacatgc cagtgtaaat ttggtttaac
78061 aatcaatttc tataaacatt gcatctaact gtgcactgat caactgcaca acttcaacaa
78121 ttacttccaa gacaaagata aatgctttta tttccctatg ttttggtctt tccttgggct
78181 agagacagaa gctgcatgtt tcaaaccaga ttcaaaaggg aaagcacttc aaaacagaaa
78241 gtacttcaat tgtgtatttg ccttcagcca catccagaga cttgtggatc tcacccggtt
78301 ggtcccagcc cttctccaac cctgaagccc acagcagggg tgcagaggca gccccagatc
78361 gtgcagacat caccccgaggc tcccaaactg gcccagctgc ctgaggcctg catgcctgtg
78421 gccaggtagg acacatgtgc aggtttgaaa actaggccta caagactgaa gagtggactg
78481 aagcaaaaag gggagaaaca ttagaggcct acagtaggaa gagacctttt atagagtttt
78541 caggaaattc tcacaataaa cttgggcaca aagaccaaat tgctgaggcc agaagcctgc
78601 ttatggtact gtgacttatg gggagtagag gccaaatcag agagggctgg ctggtgatac
78661 cccagaccac ttgcctcttc cccttccctg gcctacaaat accaggcctc ctggccctga
78721 gacctcattc tgggtttcta tatgggtcaa ccaaatgcca tcctttcact aaacccaggt
78781 gcaaaatggg gggggaaggg gggaagctgg ggagtacaca gcacccaaaa gaaccgagag
78841 agcaagtttt ccaaggctac aggaacattg gcagagctgg tggccacacc agatgggagt
78901 accacatccc caccaggctt catgcttcac tgctagatgc agggggctag aagggtctga
78961 tgaatcagga gctgaactag aacccttcaag aaaagaaaag gcaagggggt ggctctgtgc
79021 cccgccagga gaggaaagaa gaatgtgtgt ggattgtcca cagtgaggcc agaaacgatg
79081 agatggtgtt aggcagaaaa gaagggagag ggcttcccat gagaatctgg ctgggcatgg
79141 gagggataca gggctcagtt atcaaggcac ctttgccata gtggggtgcc agctacattg FIGURE 4 (cont.'d)

79201 ggtgggatgc ccaggggctg tccctaccta agcactttct tgtctacagg aagtcttggt
79261 gcttttcaag ttcagcataa ggggttccat atgtgaagtg ggattcaca cttagaaaat
79321 ctatcctggt cttcacctga aacactcatc tactgctggg tggcaggaac aagtatacaa
79381 aaccaggggc cttgcctggg cagttcctaa gggacattgg cagggctgac ctgggattca
79441 gctcccctga gtggacagtc tgtggttgcc tggggtcccc aggctgagaa ggggtatggg
79501 taattgcact tcggggcaca gtgaacacag gcacgggctg gatgtgccct gggagacaga
79561 aaggagaggc tgacctattc tcaggagctg gctatggctg gacagtgcct gcccggccag
79621 aggaaggcca cagcagagcc actccacaga ctaagacctg tgttgccaag gaatcagaca
79681 ctggcttgga ggagacagga ggacaaagcc tgctgctatt aagcccacac cgtagcttag
79741 agatccttca gcctcctggc cttcaaaaca aactccaggg cttccactct gaaaggcaaa
79801 ggaatcacct cgtgtttgct tcatcccctt agcaggatga acgaaacgcc taaggcccaa
79861 aaagactgag ggcaggaccc ccagcatctc ccatctcctc cgtgcaggct gggtgagaga
79921 atggcctgga aaggaagcat ctgcgctaca ttgtgcttca ggccccccca gcaactttcc
79981 cggaggtaac tatttgcctg gaaaactagg aaactgggtt ttaaaaacag aattttaagc
80041 agacttttta gagggacaag gccatttgat ggtagtgatt ttggttttgt tttatgaaaa
80101 tggtacaggt ggtaatccct gatgacagaa tgcactgaga gtggggccaa gggccctgaa
80161 ggatcctgtc tgttcagtct ggttaaggcg acagctgggc gggcatgtgg ccggggagca
80221 gtggcacagc ggaccctggc agtttgctca cacctggccc tcgtcccaga gccagcccac
80281 ctgcctcttg gccctggtag tgactccaca gaacttcccc gagcagaagc ctcacagtgg
80341 gccagcaccc atcttgcatg caagggagaa cctgcatgca gtgcacacac cccggccagg
80401 gtggcacatg gctgctcttt caatgtgaag ccaacaccaa ctggagagat ttaactataa
80461 aggaatattt tttaaatatt cagttttgtt gtcattactc acttcctttc cttccatttc
80521 gatctcagaa actgttcttt ttcagtgttg acaaaaaaga aatgtatggg ccaggtctac
80581 aaagtaacac cttgtcataa aacaggctca aaagcatagg aatcatgctt taattgccat
80641 ttagcatcca ctaattccca tgagatctgt gattaaaaaa aaagcctctg gcctgcttgt
80701 cctgtcttaa aagtcatgag tctgttttat gaacagaaag aatgccacgc ttcttagcat
80761 atgtaaggca aaatggattt ttgatctctc atgatgtaaa ggagatacaa aggtaaggaa
80821 gggaagattt ctaagtgaga ctttttttga gtgtcaatcc cgctggacac acatattaca
80881 aaataaagat tttcttctgt aaagtgctgt ttgctcagtg aatcatgcgc caccacagag
80941 caccatggct ccacctgctc aagagcatgg aggaggcagc atcggcagag ggcaggcagg
81001 agtctgtgtt tgggggtctg tttcaatacc atctcctggg gttcgccgtg atgcagaggg
81061 aatcttctcg tcatggctag acactcccca atgctctgct ccaggctggg gaccactgca
81121 agctggaggc ggctgggtat cagggcctgg gcacccctgc tcctcctctt cccttgggat
81181 tggcatttta ttctctcatt cagctcaaga ccatgggcag gaactctgct ggctccccat
81241 gatgtcatca tggggtcttc cactttccca cagagctgcc aggcagaggc aggacccagg
81301 catgcctggc ccacaggaag gttttctagg agactaagga gggtttagaa aaagagaagc
81361 cactataaat agtcacctgt ccagtctatg ctattaaagg acataagaaa ggtatacaat
81421 tggcagtaaa caatttcctt cagctcttca tggatgtcca ggaaaatgac aacccgcaca
81481 caatcagacg tgaatgattt ctgctccagt gtcttcaggc tctgtgcaac aagaagagtt
81541 tgtgtcggaa tgacagattc catatccatg tttattttca aagttgggct ctgttagtgg
81601 agattttca aaaatattct ttttgcttgt ttctggacag ttttgaacat agatcactct
81661 attataggcc ttgagtctct tccacaattg cacatacact ttacactgaa catacataaa
81721 aagaagtcct ccggtgaagc cgatggccac aaccaccaat ttagtccaaa agggccattc
81781 taggattcct ggaaggaaa aactcagcct attagatttt atttaagata tgtcttcacc
81841 acggggctga agnnnnnnnn nnnnnnnnnn nnnnnnnnnn nnnnnnnnnn nnnnnnnnnn
81901 nnnnnnnnnn nnnnnnnnnn nnnnnnnnnn nnnnnnnnnn nnnnnnnnnn nnggcggtga
81961 ctgtgacatt gaggttcggc gtcgggggag agggaaaagg agagggagag ggagagggag
82021 agggagaggg agagggagag ggagagccat atgtagttta aagtagtttt tttccaattc
82081 tgagaagaag gtcattggta gcttgatggg gatggcaatg actctataaa ttaccttggg
82141 cagtatggct attttcacga tattgattct tcctacccat gagcatggaa tgttcttcca
82201 tttgtttgta tcctctttta tttccttgag cagtggttta tatttctcct tgaagaggtc
82261 cttcacatcc cttgtaagtt ggattcctag gtattttatt ctctttgaag caattgtgaa
82321 tgggagttca ctcatgattt ggctctctgt ttgtctgtta ttggtgtata agaatgcttg
82381 tgatttttac acattgattt tgtatactga gactctgctg aagttgccta tcagcttaag
82441 gagattttgg gctgagacga tggggttttc taggtataca atcatgtcat ctgcagacag FIGURE 4 (cont.'d)

```
82501 ggacaatttg acttcctctt ttcctaatcg aatgcccttt atttccttct cttgcctgat
82561 tgccctggct agaacttcca acactatgtt gaataggagt ggtgagagag ggcatccctg
82621 tcttgtgcca gttttcaaag ggaatgcttc cagtttttgc ccatgatgta tgatattggc
82681 tgtgggtttg tcatagatag ctcttattat tttgagatac atctcatcaa tacctaattt
82741 attgagagtt tttagcatga agcgttgctg aatttgtca aaggcctttt ctgcatctat
82801 tgaaataatc atgtggtttt tgtcattggt tctgtttgta tactgggtta catttattga
82861 tttgtgtacg ttgaaccagc ccttgcatcc cagggatgaa gcccacttga tcatggtgga
82921 taagcttttt gatgtgctgc tggattcgtt tgccagtatt tattgaggat ttttgcatcg
82981 atgttcatca aggatattgg tctaaaatgg gtttttgtt gggtctctgc ccagctttgg
83041 tctcaggatg atgcctcccc tattaaaaga gggagggagg attccctctt tttctattga
83101 ttggaatagt ttcagaagga atggtaccag ctcctccttg tacctctggt agaattcggc
83161 tgtgaatcct tcaggtcctg gactgttttt ggttggtaag gtattaattg ttgcctcaat
83221 ttcagagcct gttattggtc tattcagaga ttcatcttct tcctggttta gtcttgggag
83281 ggtgtatgta tggaggaatt tttccatttc ttctagattt tctagtttat ttgcatagag
83341 gtgtttataa tattctctga tggtagttta tatttctgtg ggatcagtgg cgatatcccc
83401 tttatcattt tttattgcat ctatttgatt cttctgtctt ttcttcttta ttagtcttgc
83461 tagcggtcta tcaattttgt tgatcttttc aaaaaaccag ctcctggatt cattgatttt
83521 ctgaagggtt ttttgtgtct ctatttcctt cagttctgct ctgatcttag ttatttcttg
83581 ccttctgcta gcttttgaat gtgtttgctc ttgcttctct atttcttttc attgtgatgt
83641 tagggtgtca attttagatc tttcctgctt tctcatgcgg gcatttagtg ctataaattt
83701 ccttctacat attgctttga atatgtccca gagattctgg tatgttgtgt gtttgttctc
83761 attggtttca aagaatatct ttgtttctgc cttcatttca ttatgtaccc agtagtcatt
83821 caggagcagg ttgttcagtt tccatgtagt tgagtggttt tgagtgagtt tcttagtcct
83881 gagttctagt ttgattgcac tgtggtctga gagatagttt gttacaattt ctgttctttt
83941 acatttgctg aggagagctt tacttccaac tatgtggtca attttggaat aggtgtggtg
84001 tggtgctaaa aaaaatgtat attctgttga tttggggtgg agagttctgt agatgtctat
84061 taggtccgct tggtgcagag ctgagttcaa ttcctgggta tccttgttaa ctttctgtct
84121 cgttgatctg tctaatgttg acagtggggt gttaaagtct cccattatta ttgtgtgggt
84181 gtctaattct ctttgtagat ctctaaggac ttgctttatg aatctgggtg cccctgtact
84241 gggtgcatgt atgtttagta tagttagctc ttcttgttga attgatccct ttaccattgt
84301 gtaatggcct tctttgtctc ttttgatctt tgttggttta aagtctgttt tatcagagac
84361 taggattgca acccctgcct ttgttttcca tttgcttggt agatcttcct ccatcccttt
84421 attttgaacc tatgtgtgtc tctgcatgtg agatgggttt cctgaataca gcacactgat
84481 gggtcttgac tctttatcca gttttccagt ctgtgtcttt taactggaac atttagccca
84541 tttactttta aggttaatat tgttatgtgt gaatttgatc ctgtcattat gatgttagct
84601 ggttattttg ctagttagtt gatgcagttt cttcctagca tcgatggtct ttacaatgtg
84661 gcatgttttt gtggtggctg gtatgggttg ccccttttcca tgtttagtgc ttccttcagg
84721 agctctttta gggcaggcct ggtggtgaca aaatctctca gcatttgctt gtctgtaaag
84781 gattttatgt ctccttcatt tatgaagctt agtttggttg gatatgaaat tctgggttga
84841 aaattctttt ctttaagaat gttgaatatt ggccctcact ctcttctggc ttgtagagtt
84901 tctgccaaga catgagctgt tagtctgatg ggcttcccctt tgtgggtaac ctgacctttc
84961 tctctggctg ctctcaacat tttttccttg atttcaactt tggtgaatct gacaattatg
85021 tgtcttggag ttgctcctct cgaggagtat ctttgtggca ttctctgtag ttcctgaatt
85081 tgaatgttgg gctgccttgc tagattgggg aagttctcct ggataatatc ctgcagagtg
85141 ttttccaact tggttccatt ctccccgtct ctttcaggta caccaattag atgtagattt
85201 ggtcttttca catagtccca tgtttcttgg aggctttgtt catttttttt ttctttttc
85261 tctaaacttc tcttcatgct tcatttcatt gatttgattt tccatcccca ataccctttc
85321 ttccagttga ttgaatcagc tactgaggct tgtgcattca tcatgtagtt ctcatgccat
85381 ggttttctgc tccatcaggt catttaagga cttctctgca ttggttattc tagttagcca
85441 ttcatctaat tttttttcaa ggtttttaac tgctttgcca tgggttcgga cttcctcctt
85501 tagctcagag tagtttgatc atctgaagcc ttcttctctc aactcgtcaa agtcattctc
85561 catccaggtt tgttctgttg ctggtgagga gccgtgttcc tttggaggag gagaggcact
85621 ctgattttta gagcttccag tttttctgct ctgtttgttc ctcatctttg tggttttatc
85681 tacctttggt ctttgatgat ggtgacgtac agatggggtt ttggtgtgga tgtcctttct
85741 gtttgttagt tttccttcta gaattcagga ccctcagctg caggtctgtt ggagtttact
```

FIGURE 4 (cont.'d)

85801 ggaggtccac tccagaccct gtttgcctgg gtatcagcag cagaggctgc agaacagtgg
85861 atattggtga acagcaaatg ttgctgcctg atcattcctc tggaagtttt gtctgagagg
85921 agtacccagc cgtgtgaggt gtcagtctgc ccctactagg gggtgcctcc cagttaggct
85981 attcggggt cagggaccca cttgaggagg cagtctgccc attctcagat gtcaagctgt
86041 gtgctgggag aaccacttct ttcttcaaag ctgtcagaca gggacattta agtctgcagt
86101 ggttattgct gtcttttgtt tgtctgtgcc ctgcccctgg aggtggagtg tacagaggca
86161 tgcaggcctc cttgagctgt ggtgggctcc agccagttca agcttcccgg ctgctttgtt
86221 tacctactca agcctgggca atggcgggca cccctccccc agcctcgctg ccgccttaca
86281 gtttggtctc agactgctgt gctagcaaag agtgaggctc tgtgggtgta gaaccctcca
86341 agctatgtgt gggatataat ctcctggtgt gctgtttatt aagcccattg gaaaagcaca
86401 atattagggc aggagtgacc caattttcca ggtgccatct gtgaatgctt tctttgacta
86461 ggaaagggaa ttccctgacc tcttgccctt cccaggtgag gtgatccctc accctgcttt
86521 gggtcacgca tggtgtgcta cacccactgt cctgcaacca ctgtctggca ctccccagtt
86581 agatgaaccc ggtacctcag ttggaaatgt ggaaatcacc tgtcttttgc atcgctcatg
86641 ctgggagctg tagactggaa ctgttcctat tcagccatct tggctccacg tatatccact
86701 gccacacttc tttagtcata aagtgagtgc cttggtcaga ggcaatgctg tgtggaatac
86761 catgatggtg gataaggcat tctgtgagtc catgaatggt agtcttggca gagcattgtg
86821 ttcagtttag gcaaacccat atccagagta agtgtctgtt tcagtgagga caaacctctg
86881 ccccttttcag gatggaagag gtccagtata accaaccttc caccaggtaa cagactgatc
86941 accccgagga atggtgccat attgagggct cagtgttagt ctctgctgct gtcaaattgg
87001 gcactcagct gtagccatag ccaggccagt tttggtgagt ggaagtccat gttgctgagc
87061 ccatgtataa cctccatccc tgccaccatg gccactttgt ttatgggccc attgggtgat
87121 aacaggggtg gctggggaaa gaggctgagt gatgtccaca gaacaggtca tcttatccac
87181 ttgattatta aaatcctcct ctgctgagat cacccattgg tgagcactca catgggatcc
87241 aaatatcttc acaggtttg gccactcaga gaggtccatc cacatacctc ttccccaaat
87301 ttctttgtca ccaatttcc aatcatgctt cttccaagtc cctgaccatc cagccaaacc
87361 attggctaca gcccatgaat caatatataa tcgcacatct ggccatttat ccttccatga
87421 aaagtgcaca accaggtgca ctgcttgaag ttctgcccac tgggaagatt tcccttcacc
87481 actgcccttc agtgatgtcc tagaaagggg ctgtagtgct gcagctgtcc acttttgggt
87541 ggtgcctgca tatcgtgcag aaccatctgt gaaccaggcc ctagtcttct cttcctctgt
87601 caactgatca tagagaactc cccatgaggc catcggtgca ggctggggaa gagaaggtgg
87661 ggtggcagtt gtggagacca tgggcatttg agctacttcc ttgtgtaact tacttgtgcc
87721 tttaggacct gctcgagccc aatcacatat atatcacttc catttgatga tggaatgctg
87781 ctgtgcatga cccattttat ggctacatgg gtcagaaagc acccagttca tgatagacag
87841 ttcagttcac atggtgactt gatgacccat aatcaaatgt tcagtttcca ccaaagctca
87901 gtaacaggcc aagagctgtc tttcaaaagc acagtagtta tatgcagaaa atggcagggc
87961 cttgtttcaa aattttagag gcatctgctg tgattcacct gtgggggcct gccaaaggct
88021 ccaaacagca tccctatctg ccactgatgc ctcaagcacc attggatctg ctgagtcata
88081 tggcccaaac agcagagcag gttggacagc agcctggacc tgaggcagag ccttatcctg
88141 ttctggaccc cactcaaaac tggcagcctt ttgagtcact cgataaatgg gcctgagtaa
88201 cacacccaaa tgaggaaagt gttacctcca aaatccaagt aggcccacta catattgtgc
88261 ctttttctta gttgtaggag gggccaaatg cagcaactta tccttcatct tacaaggagt
88321 atcttgacag gccccacacc agtggacccc tagaaatgtt actgaggtag aaggtccctg
88381 aattttagtc aaatttattt ctcatcctct ggcacacaaa catctcacaa ataagtccag
88441 tgtgtttgct acttcttgct cactggatcc gatcagcata atgtcatcaa tgtaatggac
88501 cagtgtgata tcttgcagaa gcaaaaagtg gtcaagatct ctccaaataa gattatgatg
88561 caaagccaga gtttatatac tcttgaggta ggagagtaaa gatatattgc tagtcttgcc
88621 agctgaaggc aaattgcttc tagtgggcct tatgaatagg aatggagaaa aaggcatttg
88681 ccaagtcaat ggctgcatac caggtaccag gaaatgtgtt aatttgctca agcaatgaaa
88741 ccgtatctgg tacagcagct gcaattggag tcaccactta gttaagctta tgataatcca
88801 ctgtcattct ccaagatcca tctgtcttat gcacatgcca aatgggagag ttgaatgggg
88861 gtgtgatgaa aatcaccacc cttgcgcctt tcaagtcctt gatcatggca ctaatctctg
88921 caatccctcc agggatgtga tattgttttt gatttaccat ttttctaggt agaggcagct
88981 ctaatgcctt ccatttggcc tttcccacca taataggcct caccctacca gtcagggagc
89041 caatgtgggt gttcttccag ctgctaagta tgtctatgcc aattatgcat tctggcactg

FIGURE 4 (cont.'d)

```
89101 gggaaatgaa cacaggatga gcctggggac ccattggacc cactgtaagt cagacctgag
89161 ctaaaactcc attaattacc tcacctccat aagctcctgc tttaactgga ggaccacaat
89221 gacgttttga gtcccttaga attaacgtca gctcagagct agtgtcctgt aatcccccaa
89281 atgactgata atttcccttt ccccaatgca cagttacctt gataaaaggc tggaggtctc
89341 cttgggaaaa aatgggagaa agattaacag cataaattgt tggtagtgta gtgggctcct
89401 tccttaatgg gacccaactt ccccttttatt caaggggttc tgtgtctgta aactggctca
89461 agtcaaaaat tgattgaggg gccatgattc tctattttta taattcaaag tagtgttttg
89521 tccatttgac ctggaagttt tctgcttata taaattaagt aggaaagaag taggcatcct
89581 aacaatttca cttctgggaa cactgtgatt aattagcgaa tgccagaact ctacatgagt
89641 cagactattc tgattgctgc tttgccacta ctgtctgtta tggtagttat gcccaccttg
89701 cctttgatgg ttgagtgcca ccacttggcc tctgccacct tgggatccaa ttattcccat
89761 tgtatttacc tttattagtt gagtgactgt ggttctcacc attggatctg atatgcagag
89821 aattacgggg ctcttcaaag atgcaggtgc taccctcaca gatctatttt gcaaggtatt
89881 ggtcaagggt atatcttctg ggcccttcca tctgggatga gtaggtctaa agtgactaat
89941 ccactccacc atctcaatct ctctaagcct ttggatccct tcctctacat taaaccaaga
90001 gtgatcagac atttccagct ccctcacagt ggccatcttt caatccatat ttcagctaac
90061 taagcaaata aattattaga acctttttttt aactccctga gctgcaatat taaatgcaga
90121 gtctctactt agtgggccca aatcaacaaa ttcagcctga tccaactcta tgttccttcc
90181 accattatcc cacaccctta atatccattc tcatgcctgt tctccagatt tctgtttata
90241 taaattagaa aactcaagta gttcttttca agtatagtga acctcctcat gggtttcact
90301 ctcaacctca cctcttgggg cccataagga ctttagtctg gttataggtc tagaagcaga
90361 caggggtgtt gggggtggct cctgaggaga atcaacatta ttttgcctgg caactgctca
90421 ggggggggcca tcactgttgc cttaggcagc acagtgttta tctccccaga caaatatgga
90481 aaggctgatg gcagcatggg tcagggagag gatgtcacca ctactgggga tggggaagct
90541 gtttttttttc tggcaaaaaa ggtttcctga gactttacaa actcagtgtc cccagcttca
90601 tcagggtcct cccacatgtc ccctttccaa gttgcagggt cccattcttt tccaaacgat
90661 gccctcactt taatagtaca tacctggtga ggctgtgcat gcacccttca ttggaagtca
90721 gccacttgca caataagagc tcatatccat tttcccacaa tttcagctct ttctctgcag
90781 gagataatac tttcactcag ggcaatctta gcagatttga ggctcagtat ctgcttctga
90841 agccaggagt tagaatccct aagttcattt tctttcatca ctttgtccat tgaacttagg
90901 agaaaccaac caacttcatt atgtttccac atatggtcaa aggtattatt tatagagtca
90961 ctaaactcct tgcctctcat gagcgctgaa tcaggaatgt caaatgcatt tattttgctt
91021 aactctctaa acagttcata gaaaggaaca ctgaatcagt gttctccata ctatcagaag
91081 tagagtcctt agcatttttg agtctaatca tattaaacag ccactccaga aaccctaaaa
91141 ccaatgaaag aactgcatcc ttaatgttct gttcctctag aaccactcct ggtacaaaaa
91201 tctgtgttag ggttctctag aggggcagaa ctaataggat agagatatat aagaaggaaa
91261 gtttattaag tattaactca catgatcaca aggtcccaca ataggatatc tgcaagctga
91321 ggaacaagga gagccagtcc aagtcctaaa ctgaagaact tcgagtctga tgttcaaggg
91381 cagggagcat ccagtaccag agaaagatgt aggctgggaa gctaggccag tttagtcttt
91441 tcatgttttt ctgccaactt ttcatattct agctgcactg gcagctgatt agatggtgcc
91501 cacccaggtt aagcgtgggt ctgcctttcc cagcccactg actcaaatgt taatctcctt
91561 tggcaacacc ttcacagaca cacctaggat caatactttg catccttcaa tccaatcaag
91621 ttgacactca gtattaacca tcacagaagc attatctact aataccacca tataaaagat
91681 gcggatgtta gcatagttat cacactgttt cctcacacaa tccactaccc atggcttggt
91741 ttctatggac atattattgg atctgagcca gcttattata atgttttaaa taatattcaa
91801 gaattgttac aattgcattt tgaattgtta ttatttaaat ataggtcaat ttctaaatag
91861 attcttgtcc atagtcagat tttacatcat gatttcctca ctcatgacat ttaaaagttt
91921 atttgttaaa tttagccaat atatacaagt ctgcatttgg ggatgggtaa ttgaatgcca
91981 tttttaattt ttgggtaatg gagacttttt ttatgttgcc tttatatttg atccataact
92041 aggctatgta gtacatttct gggtcaaatc tctattgctt taaaactttg tggttttgct
92101 tcattatctc ctagtatcta cagttactga agtgatacgt acaaccagct ttggacatga
92161 tgaatgtttt aggctaaaga cttgggtgtt ctttggtctt tggaagtttt ctttaatact
92221 ctctttaaat ttgtctgatt ccacttcttg gttccctttt caggaacacc aagtattcac
92281 acagtggata gtcatctgtc ctctacttct aaaatttgt tatttaacaa aatgttataa
92341 aagtagaatc acatttatgt aaccttttttg gattgatgtt ttttgctcag cataatttcc
```

FIGURE 4 (cont.'d)

```
92401 tggcaatcca tccaagttgt tgcatgcatc aatcatccat tcctttacat tgctaagtag
92461 tattccatgc tatgtattta caacagtttg tttacccatt cacctgttga aaaacatctt
92521 ggctgaatct agttcttagc tattaatatt ataaacaaag atgctataaa catttgtttg
92581 acagtttttt gtgtgaagtt tttatttttc tgggataaat gcctgggagt gcaattgctg
92641 ggtcatatga tagttgtgtg tttttctttg agaaactccc aaaatttccc agagtggatg
92701 aagtatttta tgtttctatc agtaatgtat cagtgatccg gtttctacac atccttacca
92761 gcatttggtg gtgtcatgat ttttaatttt agccattctg atagatgagt agtgatagct
92821 tattgttgtt tcaatttgca tttccctaaa acctaataat tttgaacatc ttttcatgtg
92881 attatttgct gtccatgaaa tatctgtgga aacagtgagt agaaggatgc tttccacagt
92941 ctgagaagga cagctgggag aggtggatga agagaggttg gtatatgggt acaaaaatac
93001 aattaagacc tctggtccat gctgggcaca gtggctcatg cctgcaatcc cagcactttg
93061 ggaggccaaa gcgggtggat cacctgaggt caggagctta agaccagctt ggccaacatg
93121 gtgaaaccct gtctctactg aacatacaaa aattagccgg gcatggtggt gcgtgcctgt
93181 aatcccagct actcaggagg ctgaggtggg agaatcactt aaacccggga ggcgaagttt
93241 gcagtaagcc gaggtcacac cactgcactc cagcctgggc aacagagcac tccagccggg
93301 gcaacagagc aagactctgt ctcaaaaaaa taaaataaaa taaagtaaaa caaaataaag
93361 agttccaatc cagcagagag tgtggtgaga tggtgcggga ccagctccct gggacttctg
93421 agcctttgcc ctggccagtg gggagctga gccaggatag gctgtagcct ctgccccgtg
93481 acaccaggac ccttgtggtg gctgccacca ggacccttgg ggtgggtgcc tgggccttga
93541 agatgcagca agcctccctt cccccctacac ctcagtgact gagggtggtg gtggcctttc
93601 ccaggccgca ccctgccggg tatagacgaa gtccccactg agcctggatg cagtgccttt
93661 gggtggtggt gggagtggca ggggcagctt ggtgactatc cgggtgtgag gattgggaag
93721 gtgctcttgg gatgcaggac acgggctcag ccacctcttt aggccatggc gctgccagat
93781 ccgggtcctg gtgaccactc tgtcccagct gggtgagact tacctagtcc tgaggacaac
93841 agacaatggc cttaataggc ctggaaggtg agtggaggca cagaggagga cagtgtggaa
93901 cagttagcag gcattgggct gttggtcttc cttctaccag acctggaagg acctcacatt
93961 tggcctatgg gaaatgcccg ccacactttg ggaagattta ctatctgctt ctagaaggct
94021 gtgtgtatat tatgaaaaag ctattctcaa ctcaccccca accttttaat agataacatc
94081 tgtggggagg ctgacaagat ggctgaatag aaacagctca ggtgtgcagc tcacagtgag
94141 atcaatgcag aaggtgggtg atttctgcat ttccaactga ggtacccggc tcatctcatt
94201 tggactggtt agacagtggg tgcagcccat ggagggtgaa ctgaggcagg gtggggtgtt
94261 gcctcacctg ggaagtgcaa ggggtcagaa aactcccctg ttagccaagg gaagctgtaa
94321 ggagctgtgc catgaggagt ggtgcattcc agcccagata ctatgctttt cccatggtct
94381 ttgcaaccca cagaccagga gattccctcc agtgcttatg ccaccagggt cttgggtttc
94441 aagcacaaaa ctgggtggcc atttgggtag acaccaaggt agctgcagga gtcttttttc
94501 ataccccagg gatgcctgga atgtcagcga gacagaacca ttcactcccc tggaaagggg
94561 gccgaagcca gggaaccagg tggtctagct cagtggatcc cacccccatg gagcccagca
94621 agctaagatc cactggcttg aaattcttgc tgccagcaca gtagtctgaa gttgacctgg
94681 gatgctggag cttggtatgg ggagggggcgt ctgccattac tgaggcttga gtaggcagtg
94741 ttcctctcac agtgtaaaca aaactgcaag gaagttccaa ctgggtggaa cacaccacag
94801 cgctgccagg ctgctgtagc aagactgcct ctctagattc ctcctgtctg ggcagggcat
94861 ctctgaaaaa aaggcagaag ccccagtcag ggacttatag ataaaactcc catctctctg
94921 ggacagagca cctgggggaa ggggcagctg tgggtgcagc ttcagcagat tttaacatcc
94981 ctgcctgcca gctctgaaga gagcagtgga tctcccagca cagtgtttga gcagactgcc
95041 acctcaagtg ggtccctgac cccctggcct cctgaccggg agataccttc cagaagaagc
95101 caacagacac ctcacacaag agagctccag ctggcatctg gcaggtgccc ctctgggaca
95161 aagctttcag aggaaggaac aggcagcaat ctttgctgtt ctgcagcctc cactggtgat
95221 acccaggcaa acaaggtctg aagtagatgt ccagcacact ccagcagacc tgcagcagag
95281 aggcctgact gttagaagaa aaactaacaa acagaaagga atagcatcaa catcaacaaa
95341 aaggacatcc actcagaaac cccatccaaa ggtcaccaac atcaaacaca aaaggtaggt
95401 aaatccatga agatggggag aaaccagcac aaaaaggctg aaaattccaa aaaccagaat
95461 gcctcttctt ctccaaaaaa tcacaacttc tcaccatcaa gggaacaaaa ctggatggag
95521 aatgaatttg atgaattggc agaagtaggc ttcaaaggtg gataataaca aactcctctg
95581 agctaaagga gaatgttcta acccaacgca aggaagcaaa gaaacttgaa aaaagattag
95641 atgaattgct aactagaata acgagtttag agaagaacat aaatgacctg atggagctga
```

FIGURE 4 (cont.'d)

95701 aaaacacagc acaagaactt agtgaagcat acacacatat caatagctga atcgatcaag
95761 tggaagaaag gatatcagag attgaagatc aacttgcaga aaccctataa gccagaagag
95821 actaggggcc aatattcaac attcttaaag aaaagaattt tcaatgctga atttcatatc
95881 cagccaaact aagcttcata agtgaaggag aaataaaatt ctttacagac aagcaaatgt
95941 gagacatttt gtcgtcacca cgcctgcatt acaagagctc ctgaagggag caataagcat
96001 ggaaaggaaa aaatggtgcc agccactgca aaaacatgcc aaatggtaaa gaccatcaac
96061 gctatgaaga aactgcatca agtaatgggc aaaataacca gctagcatca taatgatagg
96121 atcaaattta cacataacat attaacctta aatgtaaatg ggctaaatgc cccaattaaa
96181 agacacagac tggcaacatg gataaagagt caagacccat cagtgtgcag tattcaggag
96241 acccatctca catgcaaaaa cacacatagg cccaaaataa agggatggag gaatatttac
96301 caagcaaatg gaaagcaaaa aacaaacaaa caaacaaaca aacaaacaaa caggggttgc
96361 aatcatagtc tctgataaaa cagactttaa accaacaaag atcaaaagag aaaaagaaag
96421 ccattacata gtggctaaga agagctaact atcctaaata tacatgcacc caatacagga
96481 gcacccagat tcataaggca agttcttaaa cacctacaag gagacttaga ctcccacaca
96541 ataatagtgg gagattttaa taccccactg tcaatatcag acaggtcaat gagacagaaa
96601 attaacaagg atatctagga attgaactca gctccagact aagcagacct aatagacatc
96661 tatagaactc tccaccccaa atcaacagaa tatacattct tctcagcacc acatcgcact
96721 tattctaaaa ttgaccacat aattggaagt aaaacactcc tcagcaaatg cagaagaatg
96781 gaaatcataa caaacagtct ctcacaccac agcgcaatta aattagaatt cagaattaag
96841 aaactcactc aaaacctcac acttacatgg aaactgaaca acctgctcct gaatgactgc
96901 tggataaata atgaaatgaa gaaggataaa gatgttgttt gaaaacaata agaataatgt
96961 accagaaact ctgggacata tttaaagcag tgtgtagagg aaaatttata gcagtaattg
97021 cctacaaaag aacacaggaa agatctaaaa tcgacaccct aacatcacaa ttaaaagaac
97081 tagagaagca agagcaaaca aattcaaaag ctagcagaaa acaagagata actaagatca
97141 gggcagaact gaaagagata gagacatgaa aaacccttaa aaatcaatta atcgctctcc
97201 ctctccctct ccctctccct ctccgtctcc ctctccgtct ccctctcccc acggtctccc
97261 tctccctctc tttccacggt ctccctctga tgccgagccg aagctggact gtactgctgc
97321 catctcggct cactgcaacc tccctgcctg attctcctgc ctcagcctgc cgagtgcctg
97381 cgattgcagg tgcgcgccgc cacgcctgac tggttttctc tgcccggcca gccgccccgt
97441 ccgggaggga ggtaggaggt cagccccccg cccggccagc cgccccatcc gggaggtgag
97501 gggtgcctct gcccggccgc ccctactggg aagtgaggag cccctctgcc cagccaccac
97561 cccgtctggg aggtgtaccc aacagctcat tgagaagggg ccatgatgac aatggcggtt
97621 ttgtggaata gaaagggggg aaaggtgggg aaaagattga gaaatcggat ggttgccgtg
97681 tctgtgtaga aagaagtaga catgggagac ttttcatttt gttctgtact aagaaaaatt
97741 cttctgccgt gggatcctgt ggatctgtga ccttaccccc aaccctgtgc tctctgaaac
97801 atgtgctgtg tccactcatg gttaaatgga ttaagggtgg tgcaagatgt gctttgttaa
97861 acagatgctt gaaggcagca tgctccttaa gagtcatcac cactccctaa tctcaagtac
97921 ccagggacac aaacactgcg gaaggcagca gggtcctctg cttgggaaaa ccagagacct
97981 ttgttcactt gtttatctgc tgaccctccc tccattattg tcctatgacc ctgccaaatc
98041 cccctctgcg agaaacaccc aagaatgatc aataaaaaaa taaataaata aaaataaaaa
98101 taaaataaaa taaaataaaa aaagaaataa acacaaataa aatgttaaaa ttcccattct
98161 acataaaatc atctatagat gtttttaaat atacaacatg attatcaagg acttaatctg
98221 taccacattc ttgtagatgt aaagttaaaa ttcttgtaac catcactctc aaccctaccc
98281 tatcttccag cataaatgag actttcacat gttttctctt gcccagatgg agacactaac
98341 tgtaggcttt ggaaatgtct taaaaaaaaa aaaaaaaaaa agagagccag gcatcttcaa
98401 acagagaaaa gctgtttgaa cacatttatc taagtctatc aaaagctatg attgttagca
98461 agaggtaacc ttgtaatgcc aaggcagaaa actgccacca aaccacaaaa agcttgttca
98521 actgctgaac ctaaaattaa acaatttatc tctcattaaa aaaaaaaaat caattaatcc
98581 aggagctggt tttttttaa agatcaacaa aatagataga ccactagcca gactaataaa
98641 gaggaaaaga gagaagagtc aaatagacat aataaaaaat gataaaggag atatcaccac
98701 tgatccccaca gaaatacaac ctaccatcag agaatattat aaacacctct atgcaaataa
98761 accagaaaat ctagaagaaa tggataaatt cctggacaca tacaccctcc caagactaaa
98821 ccaggaagaa gtcaaatccc tgaataagcc aataacaaac tctgaaattg aggtggtaat
98881 taatagccta ccaaccaaaa aaagtccagg accagacgga ttcacagctg aattctacca
98941 gaggtacaaa aggagctggt accattcctt ctgaaactat tccaaacaat agaaaaagag

FIGURE 4 (cont.'d)

```
99001 agaatctccc taactcattt tacgaggcca gcatcatcct gataccaaag cctggcagag
99061 acacaacaaa aaaagaaaat ttcaggccga aatccctaat gaatattgat gcaaaaatcc
99121 tcagtaaaat tctggcaaac cgaatccagc agcacatcaa aaagcttatc caccatgatc
99181 aagttggctt catccctggg atgcaaggct ggttcaacat atgcaaatta atgaacgtaa
99241 tgcatcacat aaacagaacc aatgacaaaa accatgtgat tatctcaata gatgcagaaa
99301 agaccttcga caaaattcaa cagcccttca cgctaaaaac tctcaataaa ctagatattc
99361 atggaacatg tctcaaaaca atcagagcta tttatgagaa acccacagca gccaatatca
99421 tactgaatgg gcaaaaactg gaagcattcc ctttgaaaac tggcataaga caaggatgcc
99481 ctctctcacc actcctattc aacatagtat tgggagttct ggccagggca atcaggcaac
99541 agaaagaaat gaaggatatt caattaggaa aagaggaagt caaattgtct ctgtttgcag
99601 atgacatgac tgtatattta gaaaacccca tcatctcagc ccaaaatctc cttaagctga
99661 taagcaactt cagcaaagtc ttgggataca aaatcaatgt gcaaaaatca caagcattcc
99721 tatacaccaa taacagacaa accgagagcc aaatcacgag tgaactccca ttcacagttg
99781 ctgcaaagag aataaaatac ttaggaatcc aacttacaag ggatgtgaag gacctcttca
99841 aggagaacta caaatcactg ctcaatgaca tcagagagga cacaaacaaa tggaaaaaca
99901 ttccatgctc atggatagga agaatcaata tcgtgaaaat ggccataata tccaaagtaa
99961 tttatagatt gaatgctatc cccatcaagc taccactgac tttcttcaca gaattggaaa
100021 aaactacttt aaatttcata tagaaccaaa aaagagcctg catagccaag ccaatcttaa
100081 gcaaaaataa caaagctgga ggcatcacac tacctgactt taaactatac tacatggctg
100141 cagtaaccaa aacagcatgg tactagtacc aaaacagata tatagaccaa tggaacagaa
100201 cagaggcctc agaaataaca ccacacatct acaactatct gatctttgac aaacctgaca
100261 aaaacaagca atggggaaag gattctctac ttaataaatg gcattgggaa aactggttag
100321 ccatatgcag aaagctgaaa ctagatccct tccttccact gtatacaaaa attaactcaa
100381 gatgggctaa agacttaaat gtaagaccta aaaccataaa aaccctaaaa gaaaacatag
100441 gtaataccat tcaggacata ggcatgggca aagacttcat gactaaaaca caaaaagcaa
100501 tggcaacaaa agccaaaatt gacaaatggg atctaattaa actaaggagc ttctgcacag
100561 cgaaagtaac taccatcaga gtgaacaggc aaccaacaga atgggagaac atttttgcaa
100621 tctatccatc taacaaaggg ctaatatcca gaatctacaa agaacttaaa caaatttaca
100681 agaaaaaaca aacaattcca tcaaaaagtg ggtgaaggat aagaaaagac tcttctcaaa
100741 agaagacatt tatgcagtca acaagcatag gaaaaaaagc tcatcatcac tggtcattag
100801 agaagtgcaa atcaaaaaca caatgagata ccatttcatg ccagttagaa tggccatcat
100861 taaaaagtca agaaacaaca gatactagag agcatgtgga gaaataggac cacttttaca
100921 ctgttggtgg gagtggaaat tagttcaacc attgtggaag acagtgtggt attcctcatc
100981 ttcaccacgg ggtggaggta cgnnnnnnnn nnnnnnnnnn nnnnnnnnnn nnnnnnnnnn
101041 nnnnnnnnnn nnnnnnnnnn nnnnnnnnnn nnnnnnnnnn nnnnnnnnnn nnnnnnnnnn
101101 nnagaaacat agaccctgcc caacgcatat tcctgaaagg gatggcaagg tttttttaaa
101161 ggttttatgg gtttaggtgt actctaaagg attttaaccc ttctaaaatt atttttgtat
101221 aaaggtgtaa gaaagggatc caacttcact cttttacaaa tgggaagcca gtttttcccg
101281 gccccttttt ttaaaaagga ttccctttcc cattggttgt ttttttcaag gttgtcaaag
101341 atcagaaggt tgtagatgtg ggttggtaat ttttaggggt ttgttttggt cccattggtc
101401 cataggtcgg ttgtggtacc agggccatgt tgttttggtt actgtaagcc tcgtagtatg
101461 gtttgaagtc aggtagcatg atgcctccag ctctgttctt ttggcttagg attgtcttgg
101521 caatgcgggc tctttttttgg gttccatatg aactttaaag tagtttttcc caattctgtg
101581 cagaaagtca ttggtagttt gatggggatg gcattgatct ataaattacc ttgggagtat
101641 ggccattttc atgatattga ttcttcctat ccatgagcat ggaatgttct tccatttgtt
101701 tgtgtcctct tttattttgt tgagcagtgg tttgtagttc tccttgaaga ggtccttcac
101761 atcccttgta agttggattc ctaggtattt tattctcttt gaagcaattg tgaatgggag
101821 ttcactcatg atttggctgt ctgtctgtta ttggtatata agaatgcttg tgatttttgc
101881 acattgattt tgtatcctga gactttgctg aagttcctta tcagcttaag gagattttgg
101941 gctgagacga tggggttttc tagatataaa atcatgtcat ctacaaacag ggacaatttg
102001 acttcctctt ttcctaattg aataccccttt atttccttct cctgcctgat tgccctggcc
102061 agaacttcca acactatgtt gaataggagt ggtgagagag ggcatccctg tcttgtgcca
102121 gttttcaaag ggaatgcttc cagtttttgc tccttcagta tgatattggc tgtgggtctg
102181 tcataaatag ctcttattat tttgagatac atcccatcaa tacctaattt attgagagtt
102241 ttcagcatga atggttgttg aattttgtca aaggcctttt ctgcatctat tgagataatc
```

FIGURE 4 (cont.'d)

102301 atgtgttttt tgtcattggt tctgtttata tgctagatta catttattga tttgcgtatg
102361 ttgaaccagc cttccatccc agggatgaag cccacttgat catggtggat aagctttctg
102421 atgtactgct ggattcggtt tgccagtatt ttattgagga ttttcgcatt gatgttcatc
102481 agggatattg gtctaaaatt ctctttgttt gttgtgtgtc tgccaggctt tggtatcggg
102541 atgatgctgg cctcatataa tgagttaggg aggattccct ctttttctat tgattggaat
102601 agtttcgcca aactgacatg atttttaaaa ttccctatag ggtcaatgtg cagatttaaa
102661 gatccctaca ctcagtagtc ctgggatagg gtcgggggat ccatatgttt aacaagcagc
102721 ctagagtctc ccgatagcct gggcaagctt taaaaagccc tgcggacatt cggatgaaac
102781 aaaggtgcac agaacctata tctctgccat ttattagctg ggggccttag gcaaggaagg
102841 tagtcaacct ccgtattcct cagttcctca actgtaaaat ggggatgatg actgtggctc
102901 cctcgtgggg ttgtgacgga ggaacagggg acatatgtcc tgggatcagc actggcaatt
102961 tggccattct taccatagca cctgccatct tggtgacagc ctggacacaa agccttcaca
103021 cctttgaagt ggccatagag agcatgagat atggatgggg aggaggcatt ccaactaaag
103081 acccctgctt tgggccaaaa acacatgtat gtctggtgtc tggagtcctc tggttatgcc
103141 ttttttaaga taccggttgt cctgcaattg tgcgttgaga atccactcta tggccaacat
103201 atcatcaaag cgtttggctc agctaggctg ttccccccaac ccaaggaccc catgaggaaa
103261 ggagtgaggg ttccaccccc agcaccagcc actggagggg ctgcccagag tccctcagtt
103321 ctcgtaaact tacgctttgg agtaattcag aacaaagtcc actccttttt cactatcaaa
103381 ctggatatca cggggtaaat ccttgtggca tttggcatcg atgctcaagg ggaagccagg
103441 gttccactcc atccatctga gcatgagaaa ggagaagaaa ttgagttaaa tgccagcctt
103501 tggtctgccc cctcagctga gggccgccca cactgtcaga cgatgttaca cagggagatt
103561 gatgtactca aaataaagtc aacacatcat aggctgaccc tgtgtccagt aaggttctgg
103621 gacctcttcc aaagtccagt cgcaccaact ttgctgtgcc ctgagcatca gagtgggaac
103681 cctgagactg ggcttatagt ggtacaggtg tgcaccactg cataaaaagt tctgtaggta
103741 gtctagggag acctcactta ctagaggtga cattgaacag tagaggcctg ccttgccagt
103801 cactggaggt agaaggtatt aaggctgccc agccacgccc aacctggaca tccaccattc
103861 tgccaacttg atcagtgtgt gccctggact gcgtgcatgt cctgcatgtg gcatttgggg
103921 aaatgggaca gttcttctgc cttcacaata ggacgacacg gcagcaggtg gcctgggaga
103981 gggacccagg cacagatggc taaaaggctt ccctctctca cctgctggcc aatagcagct
104041 ttagagatta ttacaatcaa aacagcttcc ccaaagacaa gccacggact gcatccagta
104101 aacatgctca gatcctgaca tccttgaaac gtatcccgtg gcattgggca tttgtgtttt
104161 tgaaaaatgt ttattttgct tttttgttta cttattgagt aaacttaaat tgtgaaaatg
104221 tcagaggtgt ttgaaccaca gcaactccat cttgaatagg ggctgggtaa aataaggctg
104281 agacctactg ggcagcattc ccaggaggtt aggcattcta agtcacagga tgagacagga
104341 cattgatgca agatacaggg cagaaagacc ttgctgataa aatgggttgt ggtaaagaag
104401 ccggccaaaa cccaacaaaa ctaagatggt gatgaaagtg acctctgttc atcctcacca
104461 ctcattatat gctaattata atgcattagc atgctaaaag aaactcccac cagtgccatg
104521 acagtttaca aatgccatag taatgtcagg aagttaccct atatggtcta aaaaagggag
104581 gaaccttcag ttcctggaat tgcccacccc tctcctggaa aactcatgaa taatccactc
104641 attgtttagc acatgatcac gaagtgactg taagtatgct cagtcgagta gcccatgcta
104701 ctgccttgcc tatggagtag cctttcttta ttgctttact ttcctaataa acttgctttc
104761 actttatgga ttcaccctga attctttcct gtggaggtcc aagaactctc tcttggggtc
104821 tggatcagga cccctttctg gtaacaaaaa caaaatgaaa tcctgttagt ttctttgggg
104881 agggagaatg attttgtgtt tgtttaaaaa ccagatttta cattttaggg ttttagcttt
104941 ttcatttata ttcctaattc tccttccttt taaaatttc ttttgagagg aaagtaaaat
105001 atcgagattt tgggtcttaa aaaagtcctg agttatttta atatgatctt gtgctttgac
105061 tttccccaaa tcccaactgt cacagtgtcc tcttggccca gtagcctctc cttaggatca
105121 caagaagtga acagggaccg ggtatgatcc ttctgacagc aaaggcattt tgtcaagtgt
105181 tttctgttat gtggcacctt acatttctca ctgttggttt atttagaata ttctacgtcc
105241 tcagatttta agaaaacctt ccatttttgc tgtttgtatt aatgccaatg atagtatatt
105301 aacaaggata aaaatgtgga caagtctaca catttttgt ttgtttgttt tggaaaatga
105361 ctcaaggcat ctccaatata tatctaaaat tgagccattc agtagcctca ctggtagtaa
105421 tgatcaatta attagctatc attagtcata tcaatttaaa tattactgat gattttctct
105481 ttgcctggac agttcaaggg ctctagttaa ttttaaaagc tcagtggagc tagatgtttt
105541 tcagtatgta aacaatgagc catgcaaggg catctgtgcc agcaaatggc attaatgttt FIGURE 4 (cont.'d)

105601 tcttaagtga atagtccact tggacggatg tggaatactt cttcagcacc aaaaagacct
105661 tcttgcccca tgccctgccc tggtctatgg agggtggcag caccaatggg cagaaatgcc
105721 ccacttgtgt ggttagaaga tgatggcctc acagcacatg gagacaggac agcttgcttg
105781 ctagttcact actgcccccc tgaaaccaaa tgtttatgtc ccttccactg caggtcactg
105841 ctgcttaaga gaccctgaca ggctgacctg cacaggagcc gaaggcctgc atggccacag
105901 acattaactg gtggagatgg aatcccactc cattgaggaa gaccaagtgg aacacccagg
105961 cagaaggaac aaagaagtag aaaggcattt aatttattgg aaaaaaaatg agagagagag
106021 agaaagagag agagagaaag caagagagac agagagacag agagagagag agagagaaag
106081 agagagagag aaagcaagag agacagagag acagagagag agagagagag agagagacag
106141 acagacagag agatcctaag gggatgcagt tagtataatt ggagtgtaaa aagactttct
106201 gtaaccacaa acatgatttc tgaatgaaga cttcaataga gaaacagaca aagagaataa
106261 tcactgtgag atgtttggtc tcttgtatta aaagaaaagc tttagacaaa ttaaatttag
106321 cagtttaatt gagcaaagaa caattcaaga atagggcagc ccctaaacca gagcaggctc
106381 cgagtgactt tgatgctgtc tcatagttgg ataggattta tgggcagaaa aaggaacgtg
106441 atgtacagaa aatggaagtg aggtacagaa acagccagat tggtgatggc tcagcatttg
106501 ccttacttga gcccagtttg aacagctggc cactgtgagt ggctgaagtc tggccgctgt
106561 gattggctga gacttggtta cttgctatga gagtaggtga cagtctgttt acacatccag
106621 ttaggttaca gttcactatg tacagagaaa cttttaggct gaatttaaaa tatgtaagga
106681 gaaaagttta agctaaactc attaacacct agaagagaga aggtgttcat tcgacaacta
106741 attatggagc acctactatg tgccaggaag tgctttgtgc aaaatagaag aacatgtaac
106801 ccaaatacag ggtgaaacta caaagaaatg gaagccataa atgaaactat gagagacata
106861 aaccaaaaat aaaattctaa gcccctgaac tgactgatgg accctcccct tggccaaggg
106921 cattccaaag ttaacctgaa aaattagttc aggccatgat aggaatgggt ggctaaacgt
106981 gcctcattgt actctcctcc tcttggaatt caggcacaac tgatcagcat tcacatcaac
107041 acagagatgt taagcccatt agaacagact ctttaagatt gataagaaac atttacaatt
107101 gattctacct gaagcctgct acctggaggc ttcatctgca tgataaaaaa ctttgtttcc
107161 acaacccctt atcttaacct agacattcca agtttttaga taataattct tttaagcagt
107221 tgccaatcag aaactctttg aatctgccta tgacctggaa gctcccctcc cccaagttgt
107281 cccacctttc caaaaccaaa ccactgtcca tcttacatgt attgactgat gtcttatgtc
107341 tccctaaaat gcacaaaagc aagctgtacc ccaaccacct tgggtgcatg ttctcaggat
107401 ctcctggggc tgcatcatgg gccactggtc actcatattt ggctcagaat aagtcttttc
107461 aaatatttca cagagtgtga ctcttttcat taacagacat gaaagccaga tacagatgta
107521 atatgcaagg agtaaaagct ccaaaaggag agagagtaat atatggagaa gtgaaaaaaa
107581 tcaaagaaat aaaagaagaa ctcctttaag ctgaaaaata cttcaatatc ttaagtctgt
107641 gaaaggaaat taaattttag gaccccaaac tcatttagcc aaagggaaat gtcaagctgg
107701 gaactgtgtc atgcaaacct gcctcccccct tttggttcct aaataagatg gctatgatga
107761 aaagctacat gtctccacca tatttgctc acaaggaaat tcctagtgaa ccgttaaaat
107821 ttcaccatgg caatgcaaat tgatagctta tctttacaag tgcagtcacc caccagatac
107881 aaatgcatat ctgattgttc ccctgcctta ctttatctat gttctcttat gtaaaatgca
107941 gactccctgc atttttcctc tgcctcattt gtttatgtca tcttatgtta aaaaaaatgc
108001 agattcactg agccagagaa aggcatgaat aactattttt ccctgccctg ctcttacatg
108061 aaaattgtgt acttctcaat atcccgccct tttcccttta aatttggagc cctcaaaatc
108121 accttcagag aaaggcatag tgctgtctcc cgggcatgcg tccttaactt tcgcaaataa
108181 atttcctaaa atgattgaga cttgtctcgt catttttctc aatgacaagt cctaggtggg
108241 ggggaaaaaa aaaaaggaaa aagatacacc taggtatata ctgaatacat tttaaaatgt
108301 ccaagagaca ggagaaacag agacagagag aaggaaagag atgcagagag tgaacgagag
108361 aggaagaaag tgggggaggg agggagatag aaactctagg aaaagaaaca aactatcatt
108421 agatttctcc tctgtcattc tgaaaatggg aagactgaag tgtatacaca ctttttttag
108481 atcgtcatct aagcctctca tattgtcatc aatgagggca ggggaatttg tttgagggga
108541 tgggtagggg gacaggacga caagcacaga ctcagatctt acactacaca tggaccttct
108601 gaggaaatta attgaacaag ttcagctgaa caaaaattaa attagaatga atcaataaac
108661 tcctaaatac agcaaagaat atgcattata aaactacagc aaatataata gtaaacaaag
108721 aaacaaaaat atgagaggga tgttcatcac tactaccact acttgttttg ggaattccag
108781 acatggaata agaaaagaat atcagtggtg tagataatgg aaagtaagag acaaaattat
108841 taacatttag ataatatgag cacattaact aaccagactc actaacaaca aacaaacaaa FIGURE 4 (cont.'d)

108901 aacaagtgat tagaaccaat gaaagaattc agtaagggac caacacacag taaatgtaag
108961 aaacaagtaa tttacattta tcccagcaat atttttgcaa acagaaaaat atcctactca
109021 gaacagcaaa tgctaaatgt agagtagcta gaaaggtgaa ggacctgcat gaagaaaact
109081 agaaattcta tggaagtacg ttgacacagg atctagagag gtggaaagac acgctgtgtt
109141 cctggatgga aagactgaat ctcagtaaaa tgccaacaca taacacagtt atgtgaagtt
109201 caaagtaatt ctcattatga aaaacttaag aaagaacagt gagatatgta acagacatta
109261 acatttatta gaaagttatg ataaccaaaa gctggtgctg ggtctcgag tagaaaaata
109321 ggctaacaca taaagtgcgg aaacagaccc agagactatg tatacataat acaaaactcg
109381 ccaacactta tccagtgctt tctatgtgcc tactactatt ctctgtgttt tcatggttta
109441 acctattatc tcaaacccct aaaaggaagg cactgttatt tccctcattt tacagatgag
109501 ggaagtgagg cacagacaga ttaaacaact ttcacaggac tggagaaagt gccagtaagt
109561 gtgagttgag cccagacact cgaatccaga gctcatgact gccatcctat gccagcttgt
109621 accgtgggta tcatcatccc tgtcatccaa gtcaggagga aagacatcat ccctgtcatc
109681 caagtcagga acgaatgcta ccgggagagt tccacccagg tatgtatgaa aacacgtggc
109741 aggagtgggg catggtggcg cacgcctgta gccccagcta cttgggaggc tgacgtggga
109801 agatggattg agcctgggtt agtttgaggc agcagtgaac catgatcatg ccactgcact
109861 ccagcctagg aaacagagca agactctgtc tcaaaaaaaa aaaaaaaggt agatgaatga
109921 aagctctaaa ctcaaagggg aaattataaa agtattagac aaaattacgg gggaagtatt
109981 tgtgtaacac tgggatggaa agggttttct taagcaaagg aggaaaccca aaagttatag
110041 atgtaaacaa tacatagtta ataaaataaa gaactaaaat ctcctgtggc aaaagcaaca
110101 gaagacaaat aataaatgct atacatatgt aacaaacgga tactatcctg atatagaaag
110161 agctccttta gattaataat tgaaagaaca atagggaaaa aaagcttata aataggcaat
110221 gcagtgatgc ttattagtgg tcaggggagt gcagactaaa acaaccacaa ggtcttaggg
110281 atttttagac tgtcaaacaa ggtcatcggg tactgacaaa tgtatggatg ggcaaaagta
110341 tcttttcata cacagctggt aggaccgcaa attacgatac aattttgtga aaggattttt
110401 gtcggtattt cttaagatga aaaaatgctg atttgttcca gcaatctgag ttctggaaat
110461 ggatctgcca ttaattaaag caccagtaca tcaagatgtt tgtacaaggt tggttctggc
110521 agcattgttt gtactgcaat acccaaaaca aacaaacaca tctacaaatg ggaaatgaac
110581 tgaacgtcag tgaatagggg aatggctaag taaattatgg tgcattccca gaaggcaaga
110641 aatagtagca gtttaagaag gggaaaatat atgagatact atttcacacg caagaatgaa
110701 aacatctgaa gatgcgaagt gttgatgatg cagggaaaca gtgaatctca gaaacagtta
110761 ctggggtgtc tactggcaga atgcctttgg aaaacaatca gcaatatcta gaaagcttaa
110821 aaacacgtgg tctgcaaccc tgcaactcta cttcttggaa tattccctac agtaactctt
110881 ccatgagagc acagagagat gtgtgagaaa gctcactgtc gcttggtttg caacagctag
110941 aaattaaaga cagcccgcct gcccatcagc aggagagcgg acgagcgcat gggttattca
111001 gatactgata tgccatgaag aagttaactg catgaaccac atctatctgt gtcaaccaga
111061 tcctcttcaa tacttagtga tgagtgaaaa gtgcaggtca cataatgatt agattaaatt
111121 atatcgatta acaaacacct acactttgcc atttactgct gtgtgtgagt gtgcatgtaa
111181 cacagacaga tgtggtcaca gtgggagagc acaagctgtg ggctatgacc tgggtctgct
111241 tctccttctc cctgcgtggc tgagtgagta aggagggcct gcaagaagcg ccagctttct
111301 gacatagtgt ggactattct tagtcattgc tttacttcca aactctgatc tggaagcctg
111361 agaaatcttc tgagaaagag gaactccaag attgtgcaga cagtgcaaag ttcagtgttt
111421 cctgaacgga agcaaaggag ggtttctgaa aaggacagat gagtggaagg aggaagaaaa
111481 aaatgattaa atctaagaaa gggggaaacg atctcaccag aagccccctg ctgcaagatt
111541 atgataatgt taagtagctc ccagataatt gggctagttt gtgttatctt agatgagtag
111601 atagcaaagt ctaattagag ccccactaat tcatactaaa gtgttagtgg cttataacaa
111661 attaaatgaa ttttatgggc attttatctt aacccagatt cacaggccag aagtgctctg
111721 agaactggct gcaggggctt tgccataggt gtctgaaaca gggagggaag ccaaggaaga
111781 agcatagaaa caacagccct ttgggatggg aggcagagct caagcacaac gtgtgcactg
111841 caccaggtat ggaagtctgg aaacacatca tatggtgcct gagctgagag gcttgtgcac
111901 aaatactcta aaacaaatca cacatttata aacccttaac atgacccaca gcacagcagg
111961 ttactctccc acacttgatg ctaatggcat gtaagtttta tttttgattt ttcaattggg
112021 aaatagaata tataaaatat gtatggatat gtatatatgc acacacacac tcacacatgc
112081 agaaaaatgt acaaaacacc tgtacgaaca ccatccaggt aaaaaatcag aacattgtcc
112141 gtaccctcac ccccaccttt cccaatcaac cctccttcca tccccggtaa tgaccatcct

FIGURE 4 (cont.'d)

```
112201 cggctttatg ataatcattt tcttgttatt gtttaaggtt ccgctatgac acacctccct
112261 aaacaatttc attccaaagt tatgaattgg ccagacacgc tcctggcttc tttccttcaa
112321 cactgcgtca gtgaggtttg tccatgttag cagcagtttg ttgattttcc ttgcagtgta
112381 gaattttcct tgacaatttg tctgttctac tgtttgttgg acattgagtt gttgccattt
112441 tttggccatc atgagtaatg ctgttgtgag tatccaggcg cacatgcaca caaatttgga
112501 tcccactata ggatttctgg gtcatagatt ataatgtagc ttcagtttta tgacatattg
112561 ctaaattgtt ttccacggag gtcttaccaa cttgtcctcc tgccggtggt atatgagtgt
112621 tcccagccct ctggatcttc tttaatactc aggtgttgtc agttgttgaa gtgttgccca
112681 tctgggggca tatgtgtggt agtagcagca gttcactgtg atcttctgat ttccccgagt
112741 cctaatgaag ttgaacacct tttgtatact tgctgcttat attttgtaca gtaagtactc
112801 aaacttcttg cccattttct agtgaatgac actccccttc ttaaagattt gtaggtcctt
112861 cacatactag gaataattct cgtcaatcac tccatgactt gccttcactc tctcctggtg
112921 tctttcaatg aacagagtgt ccttatcttg agggaggcaa acttaccaat cttttccttt
112981 gtgtttaata tgttctgagt cttgtttgaa aaatcctttt agcttgagac ctggaagaat
113041 aatcacctgt agtctaaatg tcttacagtt ttgcctttaa cttttaagtc taatcaaccc
113101 caagctgagt ctcctgaatg gcaagaggtg gagtctgatt tcttctcctt ctccttcagc
113161 cctccgtgct ggctggcccc tgtcctcgag atgcatgtcc agtggcccag tgccacccat
113221 cagccgagcc ctccgtagca gacccagtac ccacatacgt gtggctgttt gttgtttctt
113281 tattctgttt caaggaatgt ttttgatgaa aagggggatg aagctaagac agttttgagg
113341 tggggcaatt gtgttcttgg tgtgggattt ctcacccctt gacagcagtg ggtggctggg
113401 catagggggaa gaaggagcta cagggttgag ggatgctgtt gcaacttaga aaaattaaga
113461 aaaatgaaga tattgctcag ttatggcaag tgtttgatga aacagggacc catacatggc
113521 tcgtgaaaac tggttaaaga tttttttttt tttttttttt gagacggagt ctcgctctgt
113581 cgcccaggct ggagtgcagt ggtgcaatct cggctcactg caagctccgc ctcccaggtt
113641 cacgccattc tcttgcctca gcctcccgag cagctgggac tacaggcgcc cgccaccacg
113701 cccggctaat tttttgtatt ttttagtaga gacggggttt caccgtgtta gccaggatgg
113761 tctcgatctc ctgacctggt gatccaccca cctcagcctc ccaaatggtt aaagattttt
113821 gaggagaaat ttgtcaatgt atactaataa cttttactat ttggtaattt catatctggg
113881 catctgtcct aggaaaatac ttaataatgt atacaaattt cacatacaag ggttttcact
113941 ttgcttataa gaatacaaaa attagaaacc tcctaaatgt ccagggaagc tgggtgttta
114001 agtgaatgat gaggcatcca tccaatggaa tagtacatag aaactagaat aatgtttatg
114061 atgagatttt gaaaatatgg gaaaatgatt tttgctacac tgctaaaggg cagcaaggag
114121 gatgcaaagt ggtatatata gcacaatccc aaattttaaa aagtgaataa gacaaagtga
114181 aaacaattaa acatgaattt ttatgaaaaa gttcataaaa ttcataattc atacagaaaa
114241 taggtatttt tctggctcta tattattttc cttcttttac tttttttgagt taaaaaaaca
114301 acccagatat actacatatt ccttgtaaga agttcaacta ttgagggata tgtagaaaag
114361 tatcacaata ttggctccca aaggcccctc cacagcccag gtaacttcac tgtccatgta
114421 gaatgattcc ttccactttc ttcccttgga aggaggcaca gactcaaatg tttccagggg
114481 ccaaagcagg aaatgaaatg aaagaaaacc ttgatataga caacagacaa gtgtggactg
114541 gggaagcctg aagaatatct ctgtttactc ataagtcaat aatgatccat caaacacttg
114601 tagaggctgg atacagccca tcagccaccc atttccagag gagcactctg taatgtgtta
114661 ttatcttcca aaaagcttta ctgagataca tttacatacc attaaattca cccccttaaaa
114721 atatgctatc aaaagatttt aatatatttg cagagttgta tgtgtaacca tcattataac
114781 ccaattctga aataatctca tccccagagg acacctcgaa cccattaaca ttcactcctt
114841 gtttcccctc cccaactcct agtgctaggc aactactcac ctactaacct gactctgtgg
114901 gtttgcctat tctggacatt tcatacagat agaatcacac aatatggggt cttccgtaag
114961 tgagttttcc atttagcata tttttgaagt tcattcagtg tttggcatct atctgtagtt
115021 catttctttt cttttctttt cttttttgga aatggagtct tgctctgtca cccaggctgg
115081 agtgcagtgg cgggatctag gctcactgca acctccgcct cccgggttca agtgattctc
115141 ctgccttagc ctcccaagca gctgggatta caggcgtgca ccaacatgcc cggctaattt
115201 ttgtattttt gtagacatgg ggtttcacca tgttggccag gttggtctca aactcctgac
115261 ctcaagtgat ctgcccgtct caacctccca aagtgctagg attacaggtg tgagcctccg
115321 cgcttggcat tcattccttt ttgatgccaa aaaatatccc attgtatgga taaactatat
115381 tttgtttatt cattcctcag ttaatggaat ttaggttgtt tctacttttt gactattgtg
115441 aacaatggtg ctataaatat gtgtgtacaa gttttgtata gacatgtggt ttcaatattc
```

FIGURE 4 (cont.'d)

115501 ttgggtagag gcctaggagt agaattgctg ggtcatattg tagctgggtt tcagattttg
115561 aggaaccact aaactgtttt ctgaagtggc tgcatcatct tacattccgg tagcagcatc
115621 agggttccag tttctccaca tccttggcag cacttgttac tatctgtctt ttttattcta
115681 accattttag tggttagaat tgtatcttgt ggttttgatt tgaaatttcc tgatgattaa
115741 taatgttgag catatttca cgtgcttatt ggagattcac aaatttctc tggagaacta
115801 tttaattaaa tcctttgcta atttttaaac ggggtttttt gtacagaata ttttaaaatt
115861 gagttgtcag agttctttat atattctgga tacaagtccc ttatcagaca tatgatttag
115921 atattttctc cattctgtgg attgtctttt cactttattg atgatgtcct ttgaagcata
115981 gatcttttac attttaatga catctaactt gtctactttc ttttgctgcc tgtgctcttg
116041 gtgccatatc taagagactt tgccgaaccc aagattatga agacttactt gtatgttttc
116101 ttccaagagt gttatgttgt tagcccttac ttttagatct atcatccatt ttgaattaat
116161 ttttaaattt atctagcagc gttattgaaa tataatgcac atactgtaaa atttatccat
116221 ttaaagtgtt caattcaagg atgtttagta ttaattttta cacaatggac aaccatcagt
116281 tttagaacat tttcatcccc ggcaaaagga acactgtatc ctttagctgt cactcccatg
116341 accacttcct cattccctgc ccctaggcaa ccagtaatct actttatatc tgtacagatt
116401 tttctttcc agaaatttca tataaaagga atcatacaat atatgatctt ttgtgactgg
116461 tttctttcac ttagcataat gtttttgaga ttcatccatg ttgtaacaag tgtcagtatt
116521 tcattcttct ttcatggtca aattatatag atatactata ttttatccat tcatccatta
116581 atggacgttt gggttgtgta cactttttga tagttacagg tcatgctgct ataatcatgc
116641 atgtacaagt ttttgtgtgg gcatatgttt ccatttctgt tgggaatatg cttaagagtg
116701 gaaatgctgt catattgtaa ctctctgttg aacagtcagg agctagcaga ctgtttccca
116761 agcagctgtg ccattttaca ttcccaccag cagtgtatga gggttctgat ttctccacat
116821 ccttgtcaac acttgttctt gtcggatttt tttattctag ccatcctagt atcaagtggt
116881 atctcattgt ggtgttgatt tgcatttcct agatgactaa tgggtccttg gagaaatatc
116941 tattcagatc ctcactcatt tttttcattt tttaattgga ctatttgtct ttattgagtt
117001 gtaagagttc tttataaatt atggatggaa ggcccttatc agatatacaa tttgtaaata
117061 tttcttccat tctgtggttc atcttttcac tttcttgatg gtgtcctttg aaacataaag
117121 gtttgtaaat ttgatgacat cactttatca ctttatctat ttttctttttg ttgctgatgc
117181 ttttggtgtc atatcaagag tcctttgtca aatccaaagt catgaaggtt tactcctgtg
117241 ttttcttaaa agagttttat agttttagct cttacattta ggtaggtatt tgactcattt
117301 tgtgttaatt tatgtatatg gtgtgagcta aggatccaac ttcattcttt tgcatgtggc
117361 tatccagttt tgctaggacc atttgttgaa aagactattc tttctctgtt aaactgtctt
117421 gctgcttctg tcaaaaatta attggccata agtgtaaggg cttatttctg gactctcaag
117481 tctatttcat tgatctatat atctatcctt atgccgatat cacattgtct tgaatactat
117541 agctgtgtag taattttgat attgagaagt gcaagtcctc catctttgtt ttcttttat
117601 caagattgtt ttggctattc tgggtccctt ccatttccat atgaatttgc agaattgaca
117661 gcttgtcaat ttctgcaaag aaatcagcta gaattttgat aagggttgtg ttgaacgtgt
117721 acattaattt gtggggtatt gccattttaa caaaattaag tcctctgatt catgaacatg
117781 aaatgtcttt caacctattt agatcttctt taataatgtt aaacaatgtt ttgtagtttc
117841 attgtacaag tctcagacta ctttgttaaa tttattcata aatgtttact gtttttgatg
117901 ctattgtaaa ttgaactttt tcttactttt atttcacata gttggttgtt aatgtataga
117961 aaaacaattg attatcttgt atcttgcaat cttggtggtt tattagttct aataatttct
118021 tttggtgaat gccttcagat tttctatata taagatcatg ttatttgtaa attgtggtag
118081 ttttacttac tgtactccat tgtgggtgcc tttacttatc tttttattcc ctaactgagc
118141 tggctagacc ctccagtaca atgttgaata gaagtagcaa aagtgaacat ctttatcctg
118201 tttctggatt cagcctttca tcattaagta taatgttaac tgtgaatttt cttttttgt
118261 gtatgtgggg ggacggagtc ttgcttgtca ccatgctgga gtgcagtggc atgatctcag
118321 ctcactgcaa cctccgcctt ctgggttcaa gtgattctcc tgcctcagcc tcctgagtag
118381 ctgggactac aggcgcatgc caccacacac agctactttt tgtattttag tatagacggg
118441 gtttcaccat gttggccagg atggtctcaa tctcttgaca tcgtgatcca cccgccttgg
118501 cctcccaaag tgctgggatt acaggtgtga accaccacgc ccagcctaat tgtgaatttt
118561 caaaccttta tcaggttgag gacattttct tcaattccta tttttgagt gttttatcat
118621 gaatgggtgt tggattttgt caaatgcctt ttttgtatgt ctattgaaat gattatgtac
118681 tttgttttgt tttgttattt actctattga tatggtgaat tcaattaatt gatttttgga
118741 tgttaaacca actttgcatt cctgggctaa atcccacatg ttcatattgt ttaatgcctt FIGURE 4 (cont.'d)

```
118801 ttatatactt ctgggttagg tttgctagta tttcgttgaa aatgtttata tctatattgc
118861 taagggatat tggtttatag ttttcttgtg atgcctttag ttttggtata atatgggtat
118921 gagacaatga attgggaagt gttccttcta tttcttaaaa gagtttatgc aagatcagta
118981 ttaattcttt aaatgtttga tagaattagc cagtgaagct atctgggtct gggcttctat
119041 ttgtgggaaa ttttagaatt agtaattcaa tctctttggt tgtgattgtt ttattcagat
119101 taactatttc ttcatgagtc agttttggca gtttgcgtct ttctaggaat ttgcgcattt
119161 catttaacta gtttgttggc atgcaattgt tcatagtatt ctttttttatt aattttaatt
119221 tctgtattga ttttccctca ttttatgagt ctcatttttc cttttttatt cattttaatt
119281 tctgtattga ttttctctta ttgctcattt taatggtttg aatcctctgg tcagttggct
119341 gaagagttgt caattttatt gctgatcatg tatcactttt ataattgaat tgttataaga
119401 agacataaga agtaagaggc aacccctaca atggagaaca ttaaggtaca ctcaagcttt
119461 tctgcccatt cttcctacat gccaatatgg ttgatccaaa gttattttca ttactctcct
119521 ctccatctct tgtctggagt tgtaggtaag gtgaagtttg ggattgtgc acccacactg
119581 ggagctggtg ccttggtgac tttccagcag tgacaggcca tacactgtgg aaagggttta
119641 tttcatacca tgctcttgag atagaagaaa ccatggcccc gtggccactc gatctgatgt
119701 cataactcac cgatattgtt tttgccgtgt ttccagttct ttacgtcggt gttgcttgag
119761 aatgtgaatt tggtcatctc gggccaactt tgctgtaaag aaagaacaac atgagaggag
119821 cctgaggaag aacaataaca atgcccaatg ccaagtgttc aggcttccct cagatgccct
119881 gcccatgccg agtgctttat gtgcatgacc tcatttgagc ctcagagcac ttccccaatt
119941 aatgatgaag aaactgaggc ttagggaagt tgtgtagctt tgctcttgaa ctttacccaa
120001 ggtcacacac ctaattagtg aatttttcttt tttttttttt aattctactt taagttctag
120061 gatacatgtg cacaacgtgc aggtttgtta catatgtata catgtgtcat gttggtgtgc
120121 tgcacccatt aactcgtcat ttacattagt tatatctcct aatgctatcc ctccccccta
120181 cccccacccc atgacagacc ttggtgtgtg atgttcccct tcctgtgtcc aagtgttctc
120241 attgttcaat tcccacctat gagtgagaac atgtagtgtt tgttttttttg tccttgcgat
120301 agtttgctga gaagggtgat ttccagcttc atccatgtcc ctacaaagga catgaattca
120361 tccttttttta tggctgcata gtattccatg gtgtatatgt gccacatttt cttaattcag
120421 tctatcattg atggacattt gggttggttc caagtctttg ctattgtgaa tagtgctgca
120481 ataaacatac gtgtgcatgt gtctttatag cagcatgatt tataatcctt tgggtatata
120541 cccagtaatg ggatggctgg gtcaaatggt atttctagtt ctagatccct gaggaattgc
120601 cacagtgtct tccacaaagg ttgaactagt ttacagtccc accaacagta taaaagtgtt
120661 cccatttctc cacaccctct ccagcacctg ttgtttcctg acttttttaat gattgccatt
120721 gtaactggtg tgagatggta tatcattatg gttttgattt gcatttctct gatggccagt
120781 gatgatgagc attttttcat gtgtctgttg gctgcataaa cgtcttcttt tgagaagtgt
120841 ctgttcatat ccttcgccca ctttttgatg gggttgtttg ttttttttctt gtaaatttgt
120901 ttgagttgtt tgtagattct ggatattagc cctttgtcag atgagtagat tgcaaaattt
120961 ttttcccatt ctgtaggttg cctgttcact ctgatggtag tttcttttgc tgtgcagaag
121021 ctctttagtt taattagatc ccatttgtcc attttggctt ttgttgccat tgcttttggt
121081 gttttagaca tgaagtcctt gcccatgctt atgtcctgaa tggtattgcc taggttttcc
121141 tctagggttt tgatggtttt aggtctaaca tttaagtctt taatccacct tgaattaatt
121201 tttgtataag gtgtaaggaa gggatccagc ttcagctgtc tacctatggc tagccagttt
121261 tcccagcacc atttattaaa tagggaatcc tttccccatt gcttgttttt gtcaggtttg
121321 tcaaagatca gatggttgta gatgtgtggt gtcatttctg agggctctgt tctgttccat
121381 tggtctatat ctctgttttg gtaccagtac catgctgttt tggttactgt agccttgtag
121441 tatagtttga agtcaggtag catgatgcct ccagctttgt tcttttggct taggattgtc
121501 ttggcaatgc gggctctttt ttggttccat atgaacttta acgtagattt ttccaattct
121561 gagaagaaag tcattggtag tttgatgggg atgacattga atctataaat taccttggga
121621 gtatggccat ttttatgata ttcattcttc ctatccatga gcatgggatg ttcttccatt
121681 tgtttgtgtc ttcctttatt tcgttgagca gtgatttgta gttctccttg aagaggtcct
121741 tcacatccct tgtaagttgg attcttaggt attttattct ctttgtagca attgtgaatg
121801 ggagttcact cctgatttgg ctctctgttt gtctgttatt ggtgtataag aatgcttgtg
121861 attcttgcac attgattttg tatcctgaga ctttgctgaa gttgcctatc agctttaagg
121921 agattttggg ctgagacaat ggggttttct aaatatacaa tcatgtcatc tggaaacagg
121981 gacaatttga cttcctcttt tcctaattaa ataccctttta tttctttctc ctgcctgatt
122041 gccctggcca gaacttccaa cactatgttg aataggagtg gtgagagagg gcatccctgt
```

FIGURE 4 (cont.'d)

122101 cttgtgccag ttttcaaagg gaatgcttcc agtttttgcc cattcagtat gatattggtt
122161 gtgggtttgt cataaatagc tcttattatt ttgagatacg tcccatcaat acctaattta
122221 ttgagagttt ttagcatgaa tggttgttga attttgtcaa aggccttttc tgcatctatt
122281 gagataatca tgtggttttt gtctttggtt ctgtttatat gctggattac atttattgat
122341 ttgtgtatgt tgaaccagct ttgcatccca gggatgatgc ccacttgatc ctggtggata
122401 agctttttga tgtgctgctg gattcggttt gccagtattt tattgaggat ttttgcatcg
122461 atgttcatca gggatattgg tctaaaattg tttttttgt gtgtgtatct gccaggcttt
122521 ggtatcagga tgatgctggc ctcataaaat gagttaggga ggattccctc tttttctatt
122581 gattggaata gtttcagaag gaatggtacc agctcctcct tgtacctctg gtagaattcg
122641 gctgtgaatc catctggtcc tgaacttttc tgggttggta ggctgttaat tattgcctca
122701 atttcagagc ctgttattgg tctattcagg gattcaactt cttcctggtt tagtcttggg
122761 agggtgtatg tgtcgaggaa tttatccatt ttttctagat tttctagtta atttgcttag
122821 agttgtttat agtattctct gatggtagtt tgtatttctg tggaatccgt ggtgatgtcc
122881 cctttatcac ttttattgc gtctaattga ttcttctctt ctttttttt tctttttttt
122941 taattgatca ttcttgggtg tttctcgcag agggggattt ggcagggtca taggacaata
123001 gtggagggaa ggtcagcaga taaacaagtc aacaaaggtc tctggttttc ctaggcagag
123061 gaccctgcgg ccatccgcag tgtttgtgtc cctgggtact tgagattagg gagtggtgat
123121 gactcttaag gagcctgctg ccttcaagca tctgtttaac aaagcacatc ttgcactgcc
123181 cttaatccat ttaaccctga gtggacacag cacatgtttc agagagcaca gggttggggg
123241 taaggtcata gatcaacagg atcccaaggc agaagaattt ttcttagtac agaacaaaat
123301 gaaaagtctc ccatgtctac ctctttctac acagacacag caaccatccg atttctcaat
123361 cttttcccca cctttccccc ttttctattc cacaaaacca ccattgtcat catggcccgt
123421 tctcaatgag ctgttggcta cacctcccag atggggtggt ggccaggcag aggggctcct
123481 cacttcccag taggggtggc caggcagagg cacccctcac ctcccggacg gggcagctgg
123541 ccgggcgggg ggctgacccc cccacctccc tctcggacgg ggcggctggc cgggcggggg
123601 gctgaacccc tcccctcccg gacggggcgg ctggccgggc gggggctga ccgccccccca
123661 cctcccctccc ggacagggtg gctgccgggc ggagacgctc ctcacttccc agacggggcg
123721 gctgccgggc ggaggggctc ctcacttctc agaaggggcg gctgccgggc ggaggggctc
123781 ctcacttctc agatggaggg gctcctcact tctcagatgg ggcggctgcc gggcggaggg
123841 tctcctcact tctcagacag ggcggccggg cagaggcgct cctcacctcc cagacagggt
123901 ggtggggcag tggtgctccc cacatctcag atgatgggcg gctgggcaga gacgctcctc
123961 acttcatccc agacgatggg cggccaggca gagacgctcc tcacttccta gacaggatgg
124021 cggccgggca gagacgctcc tcactttcca gactgggcag ccaggcagag gggctcctta
124081 catcccagac gatgggtggc caggcagaga cgctcctcac ttcccagacg ggtggcggc
124141 cgggcagagg ctgcaatctc ggcactttgg gaggccaagg caggcggctg ggaggcggag
124201 gttgtagccg agccgagatc acgccactgc accccagcct gggcaccatt gagcactgag
124261 tgaatgagac tccgtctgct atcccggcac ctctgggagg ccgaggctgg cggatcactc
124321 gcggttagga tctggatatt agcctgttct acacagtgaa tctccgtctt taccatttta
124381 ttatgttata ttagttctgc gtggtggtgc gcacctgtct ctctcatgca ctcggctatg
124441 ctgtagcatg acaatccgtc agtgttgttg tttcgactct tgagtcgcct cgacactcag
124501 tcttggtgct ccttatcata tggagatcgt tggtcgtcgt ttcttgtttg ggttttgctt
124561 gtgccttttc tgtttattgt atcgcttatg atcgtgatgt tgtcttagtt gcttgttggt
124621 ctctagtgtg ttttttgtgt tgtatcttgt tcttgcgttg agtgggttgg gcgttggccc
124681 gaggctttct tttggttctg tggtgtctct gacgttttgt tgctctnnnn nnnnnnnnnn
124741 nnnnnnnnnn nnnnnnnnnn nnnnnnnnnn nnnnnnnnnn nnnnnnnnnn nnnnnnnnnn
124801 nnnnnnnnnn nnnnnnnnnn nnnnnntaga tttggacgtt atgttttgag tattttattt
124861 gattgggtat ggttagtagt attgaggggc atgtgggtta attaggtttt gtatagatta
124921 tatttatttt atttattgta ttttaatgat tagatgttgg ttttaacgtg atagatggtg
124981 ggtatagatt atagatgtga gtcggtgagc tatatgggat aggtaggttg ggtgtgtcgt
125041 gcttctcgcg gcctctctca gcagtgtgct tcggcctcga gaccaccaac tcaacatcac
125101 gtccatctca tttcgcgcta cgacacactc atgtctgtac gcacgagtgt atcttctcgc
125161 gagcgcttct gtctggcgtg ctgggggggc gtgggggggg ggggcggggc gggggagat
125221 aggacgtgga agaggagaga tggcagaggg gagatggcag agggagagct gaatcttctc
125281 ttttcttctt tattagtctt gctagcagtc tatcaatttt gttgatcctt tcaaaaaatc
125341 agctcctgga ctcattgatt ttttgaaggg atttttgtgt ctctacctcc ttcagttctg

FIGURE 4 (cont.'d)

```
125401 ctctgatctt aattatttct tgccttctgc tagcttttga atgtgtttgc tcttgcttct
125461 ctagttcttt taactgtgat gttagggtgt caattttaga tcttccctgc tttctcttgt
125521 gggcatgtag tgctataaat ttccctctac acactgcttt aaatgtgtcc cagagattct
125581 ggtatgttgt gtctttgttc tcattggttt caaagaaaat ctttatttct gccttcattt
125641 cgttatgtac ccagtagtca ttcaggtgca ggttgttcag tgtccatgta gttgagaggt
125701 tttgagtgag tttcttaatc ttgagttcta gcttgattgc actgtggtct gagagacagt
125761 ttgttatggt ttctgttctt ttacatttgc taaggagtgc tttacttcca actatgtggt
125821 caatttcaga ataggtgtga tgcagtgctg agaagaatgt acattctgtt gatttggggt
125881 ggagagttct gtagatgtct attagctccg cttgctggag agctgagttc aattcctgga
125941 tatccttgtt aactttctgt ctcattgatc tgtctaatgt tgacagtggg gtgttaaagt
126001 ctctcattat tattgtgtgg gagtctaggt ctctttgtag gtttttaaga acttgcttaa
126061 taaatttggg tgctcctgta ttgggtgcat atacgtttcg gatagttagc tcttcttgtt
126121 gaattgatcc ctttaccatt atgtaatggc cttctttgtc tcttttgatc tttgttggtt
126181 taaagtctgt tttatcagag actaggattg caacccctgc ctttgttttc catttgcttg
126241 gtagatcttc ctccaatccc tttatttga gcttatgtgt gtctccgcac atgagatggg
126301 tttcctgaat acagcacact gatgggtctt gactctttat ccaatttgcc agtctgtgtc
126361 ttttaattgg agcatttagc ccatttacat ttatggttaa tattgttatg tgtgaatttg
126421 atcttgtctt tacgatgtta gatggttatt ttgctcatta gttgatgcag tttcttccta
126481 gcattgatgg tctttacaat gtggcatgtt tttgcagtgg ctggtaccag ttgttcattt
126541 ccatgtttag tgcttccttc aggagttctt ttagggcagg cctggtggtg acaaaatctc
126601 tcagcatttg cttgtctgta aaggatttta tttctccttc acttatgaag cttagtttgg
126661 ctggatatga aattctgggt tgaaaattct tttctttaag aatgttgaat attggccccc
126721 agtctcttct ggcttgtagg gtttctgccg agagatcagc tgttagtctg atgggcttcc
126781 ctttgtgggt aacctgacct ttctctctgg ctgcccttaa catcttttcc ttcatttcaa
126841 ctttggtgaa tctgacaatt atgtgtctcg gagttgctct tctcaaggag tatctttgtg
126901 gtgttctctg tatttcctga atttgaatgt tggcctgcct tgctagggtg agcaagttct
126961 cctgcataat atcctgcaga gtgttttcca acctggttcc attctcccca tcactttcag
127021 gtacaccaat cagatgtaga tttggtcttt tcacatagtc ccatatttct tggaggcttc
127081 gttcatttct ttttattctt ttttctctaa acttatcttc tcgcttcatt tcattcattt
127141 gatcttcagt cactgatacc ctttcttaca gttgatcgaa tcggctactg aagcttgtgc
127201 attcgtcaca tagttctcgt gccatgtttt tcagctccat caggtcattt aaggacttct
127261 ctacattggt tattctagtt agccattcgt ctaatctttt ttcaaggttt ttagcttttt
127321 ttgcgatggg ttccaacttc cttctttagc tgggagaagt ttgatcatct gaagccttct
127381 tctctcaact cgtcaaagtc attctccatc cagctttgtt ccaccactcg cgaggagctg
127441 ccttcctttg gaaggggaga ggcactctga tttgtagaat gttcagcttt tctgctctgt
127501 ttttccccat ctttgtggtt ttatttacct ttggtctttg atgatggtga cgtacagatg
127561 gggtttggt ggtgtggatg tcctttctgt ttgttagttt tccttctaac agtcaggacc
127621 ctcagctgca ggtttgttga tgtttgctag aggtccactc cagaccctgt ttgcccgagt
127681 atcagcagca gaggctgcag aacagcgaat attgctgaac agcaaatgtt gctgcctgat
127741 tgctcctctg gaagctttgt ctcagaggtg tacctggcca tgtggggtgt cagtctgccc
127801 ctactggagg gtgcctccca gttaggctac tctggggtca gggagccact tgagggggca
127861 gtctgtccct tctcagatct caaattccat gttgggtgaa ccactagtca cttcaaagct
127921 gtcagacagg gacatttaag tctgcagagg tttctgctgc cttttgttcg gctatgacct
127981 gcccccagag gtggagtcta cagaggctgg caggccttct gagctgcgat gggctccacc
128041 cagttcgagc ttgctggcaa tgagcaaggc tctgtgggca tgggaccctc cgagccagac
128101 atgggatata atctcctggt atgctgtttg ctaagactgt tggaaaagta cagtattagg
128161 gtgggagtga cccaatttc caggtgctgt ccgtcaccac ttccccttggc taggaaaggg
128221 aattccctga ctccttgcac ttcccaggtg aggtgatgct cacactcaat gggctgcccc
128281 cactgttctg cccccactgt ccaacaatcc ccagtgagat gaacccagtg cctcagttgg
128341 aaatgcagaa atcacccatc ttctgcattg ctcatgttgg gagctgtaga ctggagctgt
128401 tcctattcgg ccatcttgga accagtctga attagtgaat tttcaacata aaactcaact
128461 cctgtgctct tagccactca ctttacaaaa gccaaatcca gttcctcatc ctcttgccca
128521 ctcactcagc aagccttggg gcccctgcct ttcagtgctt agagaatcat gttcagatgc
128581 aagagccagg cttggttctc actgggcttg gcaggcacag tacatgccta actctggcct
128641 gcgtgtgcat ttccacttga ggtcctaacc ttccactcag cccctcaaga ctcttcaggg
```

FIGURE 4 (cont.'d)

```
128701 acctaagggc ccctggtgca gagctgcctt tttgctccag gagaaaggca tttcgtggcc
128761 cttggtgggt atctttaaat cactgcagaa tagtttactc ctcttctctg aaattcttat
128821 actgagcaaa aacgggagtt cactctgggt tttagtgttg cctgtgagag cagcagttct
128881 cacagctctt atgtttctaa gtccatttca ttgtttcatg gagaaatgtg tgacgatgac
128941 acaacccggt ttcctgtcgt gcctacacag aggattgaga atgagctcca ttctaaaaga
129001 gtgcagtgtc ctagatggct ttagaagaga cacatgtgct tggacttggg ctctgtcact
129061 gaagctgtgt gaccaagagt tgccctgacc ccctcacatg taaaatggag atgataatgc
129121 ctacttctcc gggtcatggt gtgcatttgg ggagagaatg caggaaagcc ctccacacgg
129181 cgcctggcac gcagtaaatg ccaatggatg ggaacaatga tcattatcat tatgcctata
129241 gtcatcactg gcctgagggt tctgctcctc cctctaagcc tagctctgag agcatcttat
129301 ctctcagcct gtcctgctgc cgtctctcac tgcaggagtt ggagcaggta gcaggtagct
129361 aagggcgggg ctgcttctca gagcctttag agcagatgag gtcatatcat gaccactctt
129421 taaactattg cttaaggcca agcctgtgaa cgcagcccat agagctgtga ataggggggag
129481 cccagatctc ctgaaaacag gtcctggaat agtttctcta gctctcgtgg taaagcattg
129541 tgttttaaaa cttacttttc aacacagatt attatatttt tgtaaaatat aataaaaatt
129601 aattactaga aaaatgaaat tttaaaaacc caaagatatt caaaatccaa gtcttttttt
129661 ttcttattag gtgcaaaagt cacaaaattg ttctgttaag ttgctataaa agtttctaaa
129721 acccctcctc tgagtctttg tattttattt tgtatttatt ttatttttat ttttttaag
129781 agacagggtc tccctctgtc tcccaggcta gagtgcagtg gcatgatcat agctccctgc
129841 agccttgaac ttcaggactc aagtgattcc ccaacctcag cctcctaagt agttgggact
129901 ataggcacac accaccacac ctggctaatt tttttttttt ttttgagaca gagtcttgct
129961 ctgttgccca ggctggggta cagtggcatg atctcagctc actgcaagct ccacttccca
130021 ggttcacgcc attctcctgc ctcagcctcc caagtagctg ggactacagt tgcccaccac
130081 cacatccagc taattttttg tatttttagt agagacgggg ttttactgtg ttagccagga
130141 tggtctcgat ctcctgacct tgtgatccac ccgcctcggc ccctagctaa ttttcaattt
130201 tttttgtaga gatggggtct ctctacattg cccaggcttg tgacaaaatc ctagactcaa
130261 acaatcctcc cgccttagcc acccaaagtg ctggaactat aggcttcaac ctctgtactg
130321 atctaattgc agacctggac gcagttagtt ctcagatgac actcaggcca cattctgagc
130381 tgtccacccg acagcacttc caggctgaga catcttcatc cttgagcttg gaactggggt
130441 ccaaaaagga atattaacgg gatacctctg catcctcccc tggggatgta aagccagcca
130501 ggaggggagg cttgaggcca cagaaggcaa gctgagtatt aatggtgaca ataactgtta
130561 tcattggcta tgggggtaat tctggaggca ctcaacattc atcatctctt atctacctta
130621 aggaaccagc taatctcttg ggcaccttga ctctgaggag ctggatctct tcagtttcac
130681 tggtatgaat aagtcagtac atgcggaatt gcaacatgcc aagtttcaaa aagagaatag
130741 ttctgtctcc cctggtcccg aaggtgtttg aagaatttat ccaatggctg atgaagttct
130801 gggagcacag caggatgaga aagcctggac tgacggcaga agagctcagc agggcaggtt
130861 ccaaggactg acacagtgcc ttaatgaagc tgtcccttca cacagatgct ctggatctgt
130921 ggggccacag taatggccct ctgacattca tgttcaccca aggtgtagtg gtgaaatatt
130981 agatttaagg ggtgatcata tggtgagtaa ttgaatcact tgtaggctgg ccccccctcat
131041 ttccaggttg ttcaagggat tggttgtttt gccatgtggt ggattaataa ttggccacag
131101 ctggacatgg tagctcatga ctgtaatccc agcactttgg gaggccgagc cgggtggatc
131161 acctgaggtc aggagttcca gactagcctg gccaacatgg caaaaccctt tctctagtaa
131221 aaatacaaaa attagccagg cttggtggct acctggagcc tgtaaaccaa gctccctagg
131281 aggctgaggc aggagaatcg cttgaacctg ggaggcagag gttgcagtgg gctgagatcg
131341 tgccactgcc ctccagcttg ggcaatagag tgagactctg tcccaaaata ataataataa
131401 taataataat aggccacaaa ttctttgaca ttccttccat tgagagatgg gggggtctgc
131461 atccccaccc ccaccccccgg agtctgggtg ggctctgtga ctgcttggac cagtagaata
131521 tgatggaagt tacagtgtgc cagtttccag gcccaagcct gaagagattg gcagcttcca
131581 ctttctgtct cttagaaaac ttgctcttgg aagccagcca tcatgtaaga aatgcaggca
131641 cccagaggac accattctgt gagaagcctt aaagaatgag actccatatg gacagagagg
131701 ccaaggagcc tagaggtgcc agacacatga cagaagaagg cccagccccc ttcagctgat
131761 gctacatggc cacagatgaa ctgcccagtg aagcctttcc taaattcctg acctgcaaga
131821 gcatgaacaa aattaaatgg ctgtttaaag ttaccaagga ggttggtttt acagcagtag
131881 agagaatgga acttgctgga cagcttctct atgctcaccc tccaacctgt gctgtccctg
131941 aaagtgattg gaatgagatg cctcaatggg ttttccactg ggaactctga ccagaaagga
```

FIGURE 4 (cont.'d)

```
132001 gggaatgtgt agaggaagga gaggccaatc actccccaga acctttctac tgagggccgc
132061 agctcctcca agggtgctgt ctccaggata cttctgcatt actcccacaa ccttcccccct
132121 cccccctgcat caggactagt ggtgctgatg gccccgcact ctgcatggtc cctctgcaca
132181 tgggcccaca cctttgtgat gcccctttgt taaaccctca tcctagtgta ccatctgttt
132241 tttgccaaga tgagctgaag ggtctgcagg aagaagggct tcataaccga gaccttgggt
132301 agatgtgcag gagggagttt cagagccagc attttctaac taccagaaaa agagaagtgc
132361 cctgtccaca accttccaca ttctgttgac cacaggaata aatgaacttt gtgatttttt
132421 ttcctgtcat taggtagggg gacaaaaatc ctcttaactc catgttcaga aatattctgg
132481 aaatttggtt tcttaagtca aattccacat cagaaacgat gggatgtggc ctggtagctt
132541 aagaacagca ggtacagaat aacttttttc tcctttgtct cagttttctt agctataaaa
132601 tgggggtaac agtcatctct tcctacctac cccaccaaac ttcgtgaaga acacactagc
132661 tacaggaaac ttggcaaaga gaaagagttt gacgctgtca tggcagaagc agtggctttc
132721 tcttattacg gtggctgcct ggcctttgaa ggcttatctt tccaggttta aactgagagc
132781 aagctgaagg gttatgactc gaagtgaggt aggattttgc caggcacact aggaggctgg
132841 gtatgcaagg tggttcattc agggagcctt ggctgacctt gacgcctgcg tccgtctctg
132901 atgctctgta ccaggtcagc tgtgtgtccc taacaaagaa tggcctccta actggggtct
132961 gcacatctgg gcatcttagt aaggggaaca gatttgaggt tcttctttct ttcagcgaaa
133021 ggtgagactt cgggttgaag aactggtaac tgtgatttgc aggcttgtcc atggctcctc
133081 agagctggca cttggggtgc tccttgtcca ccccttccct ccctaggccc acatggggca
133141 ccctgagctt gcctgagccc tactgtgatc tcacggaggg caggctatga actagaaagt
133201 gatgccacac cctggcaact agagaagtgc ccatccaggg gcatgtccca taggtatctg
133261 cctgtatgga ccctagttac ccactgacaa aaagaggggc acaaccctcc cctgtagaac
133321 tgtagcgcag agtgaggaca tgacgacagt gaggcctggg gccacccgct ccaccctcag
133381 gggcttgtaa gaatcccaag gaaagtcatg cctcctgcag gtgtgtcgag gcacagggca
133441 gagccctccc acttcccgcc cctgcacagc agtgtcattc ctcctatgac tacagtgctt
133501 tgaggacagg aagaactttc ggttcttggg aagcccgggg cagaaggggc ctgagctgct
133561 caccgcgtcc atccctcagg acaacctcga catcgccggt gatccagcgg tagcagggga
133621 actcgatgta gtcccccgtgg ggcgtcttca gcgtgatgta cttcaggtac cagtcgtcat
133681 tcagccagta cttgcgcttc tcgattctga ccagctggat ctcgcccagt tcctcgtcca
133741 cagtcacgtc gtatgaatcc acctgggaag gagaacaggc aatcaggcca tgcgtggtct
133801 cctgagcctt tgttctggag gtgttaagaa tttgtcaccc caaggtatgc tgctgtggca
133861 cagggactac gttgaatgaa aagcacttaa aaaaacagca ggtgcaagat actctgacat
133921 tcgtgctgtt tcttagaagc aggagatgaa agtcccctat gaaagatgtc ctcactatac
133981 caaaaggaaa gtaacactct tttcatcaag gttgggaagt tgaagccaaa ggaaatccat
134041 acaaacagat cttgtacaat gaacgcttac ctcccgagtc acttccctgc ccagttacct
134101 gccctagccc aagccccttg gccttatcac atctcacgat gattcattca atgcagtatc
134161 taagggggat tgactctaac tgcttcttgg ggtcttcatc tttttaagag ggctcccatg
134221 ccacgtacaa cttgtattaa agaaatctgt aggctttcgc ccatgaatct gtcttatgcc
134281 gattctcaga cctagctgaa atgggaagag gtggagtttt gcctccacta cagttcatgg
134341 agccaagatt cttcatgaac accttaaatg aactcctgaa ttcatttacc caagacattc
134401 actgaaggcc tgcccctgac aaggctcagt gctacgaccc aggcaggtga aagaaatgga
134461 caaatcctgg gccctgccct tgaggagaga gaatccagtg agccaggatg gtgctgtgct
134521 gctcagaggg caacgcctgc tgactgcact tagctcaggc tggaggatgg ggagatgccc
134581 aggctcatgc ctgcacctgc gaggctgtgc ccagtgaggg tccgcagctg cccccacatg
134641 ggatagcctt gtgggagacc tttacaactg gagatgggct tgctgacagt ggatccccac
134701 aatgactctg ggagtgcagg ggagttacca ccccttccac agatgaagac agcgaggctc
134761 agtgactccc acctctgcca cttgccagca gagctggagt cacaccccag gtctttccat
134821 catagccact tcctctcttt ccagttttca gtggggataa taagtgagtg aaaatggtga
134881 ggcttagata cagggagctt gcatggattc gagtcgtcct gggacatttg cagttcacag
134941 ctgcatggtg atgcccagag aacagtgaga ccaagcagct ctgctgcacc tgtggcatta
135001 ctggtggcag ggtgaggcta gccttgcagc tagaaggcac caccccaggc tgtgtacagc
135061 gcagctgccc aggcctctgg gacaaggctg cttggccccc tccctgccag gctcctgctt
135121 ccaggacaca ggcggctctg aggcaacagc catagcttct ggagggcttt tgtctctgca
135181 gcaatggatg gcagacagga agttgggatg agaggctcag gcattgcatc acgcattctg
135241 atgaccagca ggtttggaaa gccccggact cgatgccctc caaggcatgt tctttttat
```

FIGURE 4 (cont.'d)

```
135301 tttgaggtgg agtctcactg tgttgctcag gctggagtgc agtggctcga tctcggctca
135361 ctgcaacctc cacttccagg gttcaagtga ttctcctgcc tcagtctccc aagtagctgg
135421 gactacaggc acctgccacc acatctggtt aagttttgta ttttcagtag agacagggtt
135481 tcaccatgtt ggccaggctg gtctcaaact cctgacctca agtgatccac ctgcctcggt
135541 ctcccaaagt gctgggatta caggcatgag ccactgtgcc tggcccctgc aaggcacttt
135601 ctaagccaga ttcatcaacc cttgaacttt atccctggcg gcagaaccta gagttctcag
135661 catgatggca aagtggaagg ggcgaggggt atcatccttt gtgcgagcgc aggcatcccc
135721 attccatgcc ctgcctccaa gctgccagga ggacccctgg agggcttcct aagaggaatg
135781 ggaacttgag tgttttccac aaacctcctg gctctgaata ccgtgagcag tttggggtgg
135841 ctgacgctga ggccagacgc ttgtggtcag aaagcggaag cttcctccct gtgctctgta
135901 gtctaggcca gaggccctag gaacagtttc tgatgacaga ggagccaggc ccatgtggtg
135961 ggatgacatg tcttgggtcc agccacatgt ggaccagcct cggccccacg acaatgcccc
136021 tcctgcaggg agagtatcag cctcatctgc cacctctgag aaagccttcc tgccacagct
136081 tgtcctcagg agagcagggc cacacacaag gcctcgccca tcatggacag ggtgggcagg
136141 ttctgatggg acaggagtct cagcatctca ggggctcggg cccatctgga ggagcagagt
136201 gggggctgag tggcccagga ctggatacgc gtcgggcctg ccccacgcca ggccctgcat
136261 gccacaggga tttacagagg ccttagctgc aggttgtgag ccaagacaga gattcctgat
136321 cccaccgagg agtggggaga gggcagtgag gggtagaagg ctcggtgggc cctggggtct
136381 ggagctctga attcacatcc cagcttcagg caagtagctg gatggcctgg gcacattgct
136441 tcattctctg aagctgtttc ttcatctacc caaaggagat acccctcact tgcaggacca
136501 ttgagaaaat gaaatgacac catcctgggt ggcctccttt ctccagaggc acaggccacc
136561 ggttgtgtgc atcagaacca ccagtgcccc ttcctgaatc caggggggttg cagggcacca
136621 ggccccacac cgcctgtgag ctagcatggg cccctgcgtc acggccactt cgtgactaca
136681 tgtgccaatc cgagtaactg gagcacacat gggaggagga aactgaacct gtgacctcaa
136741 actccttcac tcaaagccca gaaggaactc ctgaaaggct ggagacaggg ctgtgaggac
136801 agagggagag tgggaggcat tctgaatgct ggtggggcag gcagagcaag tctgtgtgcg
136861 gtgaggactg aggggcggcc accagaggcc cgggcctggt ctgagtgtgg ctgctgcagg
136921 ggaagtagct ttcctatggc tctgaggggc tggagaggga ggaaggtgtc cccaggggat
136981 agatgacagg aaagctgggg tggggtggga ggagctaaca gggacactct catgggaggg
137041 aggctcccag taccttggac taagagggga gggagatggg ctgaggaggc attccaggac
137101 tgggcaggtc ccacagggag ggcccgatgt ctacctgggg gtgacgaccc acacgaagag
137161 actgagcagc ttctctgagg gagtggacag tggggtgacc ctccagcaca cctgtggtgc
137221 agtcacaggg gactgggaca ctcctggccc cctgccctac ctacacctgc aggcacctgg
137281 tggagagccc ctgagtttca cttggggtga aatcactagg cagatttaca aggactccat
137341 ctgccatctg acagggactt ccacagcagg agggggccag gcctgcagtc tggctggtct
137401 atggccagcc cagccacttt cctggtgctg gcttcaagcc tgaatatgat aagaggtgaa
137461 caaggggcag agggctccag ccttgaccca actcagggag taaaagacaa agcttgatgg
137521 ctgtggttct aacatcccag gggccactaa tggaagaatg acagataaag gcctccttcc
137581 aggaaaatac cagggtcaca tgtgtcaaac tgcaaaatat cttcggaagg tttgtggaac
137641 tacaatggcc accttcctcc ctcctctctg ggccaagtac actgggctga tgctatattt
137701 gtctatttgc tgtgacacat taaattctca ggtgacacac tgaattatgg tgggcactat
137761 caacagtgga caccccccaa caggccctca ggaagcactg ggcctgggaa tggccgagcg
137821 agtgattatc ctgctttaca gatagaaact gaggctcaga gagcaatggt ggcctcaaga
137881 tcagaaccta cacctgtgtg atggccaagc ccaggttcct cccacagttc cccaaggcca
137941 catcttgaga aaagccctga accggaagct agaaggccca gctttgagcc ctggtttgta
138001 ccctggatgg agtgtaaagg ggcaatgtgg agtggcatgg aaggacaggg aaaagcttca
138061 taagagggta tttcaggcag cttttagggg ctgatcagat ttcagagggc agatgagtag
138121 gaggatgggc atgggtagca catttcagat gtggggaact gggagggcag ggtccccggg
138181 ggattcacac gtgggaggag gaaggctgga cacagtttct ggggacagaa gtgggtggcg
138241 tggtggtgca gatgctggag agaaacaagg gaaacctgca actcaccggc ctcatttcac
138301 aaggggccac tttgctgatt ttgcttgttg cttttaactt tttattggat atgtagtttt
138361 aaagcttttg aatatttcgg caaagagtca gttggtcagt tttcatgtga gctttctatc
138421 agcatttttag gaaagttttc atctgtcttt catcagatct ctgctgttgc tgggacaggg
138481 agacggatct ctctgcggaa gcaaggatgt gtgcccccacc cccagactac ccatcttgga
138541 gggggactaa tgaggggctg tgggaggagg aagctgtaga gcagagagga agattggggg
```

FIGURE 4 (cont.'d)

```
138601 ccagacaaaa cagagactcg ggatgagaga gggggaggct atggggaaga gctgaggaaa
138661 acaagggacg gagagaggga ttggggtagt ggatagggag accaaggggc agagaagggg
138721 gaaaatgtgg gacagagagc cggagattga gggagcagag aaggggcctc tgagaggtgg
138781 ctggaagaca gagtgtagag gaaaattcag agcaaaaaag aagggagagt tgtagggtag
138841 agagcagaaa cggggggcat ttagggaact gggagcaggg gaaggaagag gaggcagaag
138901 agggggcaga atgtagggaa aagatggctc agagggggag actgggagat gagagacgga
138961 ttgagggtca taccaaagaa atatttatgc tccactaata tattcccatt cacaagaagg
139021 aggtattcta gaattaattt ttcatgaatg taagaatact cactgactta agaagcatga
139081 atcattataa cacttttcta cacttgttga acatattcaa gtatcatata ttaaacacca
139141 cgctattgcc cttagctttc ttaaaagtac cagcacagaa tgaaatgggc caactaagat
139201 ttctcagaaa tcttcagatc tgttacagtt atcgtatccg atctgaatta ctttaaattt
139261 acagagttaa agaaataaat caacttgtta aatttgccta gacttgggtt agcctctgga
139321 aacagggcca ttctgtgtag gatcccggct ttctccagca gacagtgagg agccaaggaa
139381 gacacaaccg tttataggat aatcccacct gcgaaggact tgattcccag tcctgactga
139441 atcactatgc ggaactctga tgagaataac aagggacctg tgactcactt tatcaaggaa
139501 aaaatcagtc ctgtccatta tttgactgaa ctatgccctg gaggaggggg gtgttgacct
139561 gccaataact tggaaatgat taaattgtgt ggaaatacct ttattgttat tgttatcgtt
139621 actactgtta acaatacaga ttttaacact tttccctgta aaatgggata accttgtctt
139681 ctcagcaagt acttcctcta gggtttctct tttaccttta cccaaaaagg atgattgtct
139741 ttacagatac caagctggga gaatgaggaa gtagttctgg gctgggcaag agaaagtgtt
139801 gagtaacttt gcatcaacag gaactttctc aaaagctgat tttttcaagg aaactttcag
139861 ccttagctgg ttccccaccc tgcggtagcc cccaccccca accacccccc gccccacccc
139921 tgacttatag ccctctcaac ccaatggaaa tgtgacatgc aaatctctcc tgaaatttgc
139981 ccctgggatt ccggctgagg tgtttaatta taatgtcatt tgaatgactt ctcagggtag
140041 gggaagacag accgagagag ggagatagtg gacaaaacag tgccttcact ctttgtccga
140101 agagcccgct atggccacgt tatcatgtcc cctgcaggag gaaagcacac acggggtgcc
140161 cgtgctgtgc agtgtgagca caccaatggc ctgtgcttct agaaccttat gatgtgtgga
140221 ggagaatggg gaggaggaag cacttacaaa ggggaagtag cctgtaccct gtccttctcc
140281 cccaggtgtg gggaatccat gaaataatgg aagtaaatga aggtgcgtca gaaatggcag
140341 agggtgccat caccctaaat ggacgacaca ttaactccag ggcaccgcag tcctcagggt
140401 cagttccccg actggggcaa ctaagcaact gaaggttgct cttgtactca acacctaact
140461 cttcttgaag ggagctcaag ccaggatgct agtgaacttg gctgagggcc atgtcgtgct
140521 acagcgaggg tatgggctcc tggataggaa tcgagcccat ggagagcttg gaatccagaa
140581 aaagagtagt ttttacttac tttaggctct gcacacctaa aacacaaatt ttatccaaga
140641 gtaatcagtt gaaacatgaa cttgccggtt gtatttgtcc attatgagca atttcacaag
140701 gtttgatcaa ataataaact aaatggtgag aaggcagctt ggtaaagtct aaatcttttt
140761 ggtccagtta ggagctgggg tggggtggaa gggaactgat attccctgcg cacctgcagt
140821 atgtctggga ctattaccag tcatttacgg agcgcttcct ctgtgccagg tactggatta
140881 ggcacttcat taaaggctca gtgagaactg cgacctgccc atgctcatgg aaaagagtcg
140941 tggggctgga attcaggtcc agatcagcat taggaactag cttccaaatg ctgagggctc
141001 cctcgcgtcc tcacacctag cgtggaagtg ttccctggtg tacattctgc tgggagggag
141061 tgcagcccct ccatttagga aaagcctctc ctggcctggg ttctgttcct tccctttaat
141121 ttcctctggg gactgtcctg agaatgtaag ctgcccaggt gccgtctgag ccaccagatg
141181 ggcctgggct cacccatgac tcatggacca gactgaagcc aaccctccat tttcagctgg
141241 ggaaactgag gcccagacag acggtagagt gagctggtgg tcatgtctgg acagaactca
141301 ggcctctgga cccgctgacg tgcacccttc cccacggctc acagctggct gctccgaggt
141361 gccctcagag ttctgtgagc atgactcatc tgcctctccc tccctgtgcg acctgcagaa
141421 ggagcctaag gaagaggtgg cacaagaaac gcggcccagt gaagggggct ccggagcctc
141481 ggagcccaga tcttgaagtg gaggggaaac cttgggcctt ctcctcccag ggaagacgcc
141541 ttgcaggcgg cacgcgggaa gtctccgttt ccgacagggg tcgcggccgc cgcgaggggt
141601 cctggacgct tgcccaccag ggtacccacc ggccactggg agcccagggc acgccccacc
141661 gcagttctgc cctccctgac agggtcctgg acacccccag tcctgtccgg gccgccccga
141721 cgggccctcg gcgcccccgc ccaggcctct gccgtccaaa ccgggtcccg gacgcacctc
141781 agcccgcgct ccacccgtgc cccgcccgcg ctcaccgcgc cacgctcgaa gtcgttgtag
141841 aagggcttgt ccagcaggtg cttctcgctg cagcccgccg agcccacgag gctgaggtag
```

FIGURE 4 (cont.'d)

141901 atgtagtcgt cagtgtcttc accacggggt gaagtacggt ccnnnnnnnn nnnnnnnnnn
141961 nnnnnnnnnn nnnnnnnnnn nnnnnnnnnn nnnnnnnnnn nnnnnnnnnn nnnnnnnnnn
142021 nnnnnnnnnn nnnnnnnnnn nntttttggg ttgttgttgt ctctttgttt ttgcgagcgg
142081 tccttccgcc ccgtggtgaa gacaagtggg cgcctctgcc tggccatccc atctgggagg
142141 tgaggagtgc ctctgccccgg ccaccccgtc tgggaagtga ggagcgtgtc tacccagcca
142201 ccacgtctgg gaggtgagga gcgcttctgc ctggccgccc catctgggaa gtgaggagcg
142261 cctctatctg gccacccctt ctgggaagtg aggagtgcct ctgcccggcc gccaccccgc
142321 ctcggaggcg aggagcacct ctgcccggcc accaccccat ctgagaggca aggaccacct
142381 ctgcctggcc gccatcctgt ctgggaggcg aggagcacct ctgcccagcc gccgccccac
142441 ctaggaggtg aggagcgcct ctggccagcc gccccacctg ggaggcgagg agcgcctctg
142501 cctggccgcc ccatctggga ggtgaggagc gcctctgccc agccaccacc ccatctggga
142561 agtgaggagc gtctctgcca ggccgccccg tctgggaagt gtacccaaca gctccgaaga
142621 gacagcgacc attgagaacg ggccatgatg acgatggcgg ttttgtcaaa aagaaaaggg
142681 ggaaatgtgg ggaaaagaaa gagagatcag attgttactg tgtctgtgta gaaagaaggt
142741 gacataggag acaccatttt gttctgtact aagaaaaatt cttctgcctt gggatgctgt
142801 taatgtacaa ccttaccccc aaccccgtgc tcgctgaaac atgtgctgtg tcaactcagg
142861 gttaaatgga ttaagggtgg tgcaagatgt gctttgttaa acagatgctt gaaggcagca
142921 cgctcattaa gagtcatcac cactccctaa tctcaagtac ccagggacac aaacactgct
142981 gaaggctgca gggacctctg cctaggaaaa ccagagacct ttgttcacct gtttatctgc
143041 tgaccttctc tccactatta tactatgact ctgccacatc cccctctctg agaaacaccc
143101 aagaatgatc aataaatact aaaaaaacaa attaattaat taaataaatt tcatatggaa
143161 ccaaaaaaga gcctgcattg ccaagtcaat cttaagccaa aggaacaaag ctggaggcat
143221 cacactacct gacttcaaac tatactacaa ggctacagta accaaaacag cacggtactg
143281 gtaccaaaac agaggtatag accaatggaa cagaacagag ccttcagtaa taatgccaca
143341 tatgtacaac tatctgatct ttgacaaacc tgacaaaaac aagaaatggg gaaaggattc
143401 cctatttcat aaatggtgtt gggaaaactg gctagccaat aaatggtgta gggaaaactg
143461 gctagccata tgtagaaagc tgaaactgga tcccttcctt acatcttata caaaaattaa
143521 ttcaagatgg attaaagact tacatgttag acctaaaacc ataaaaaccc tagaagaaaa
143581 cctaggcaat accattcagg acataggcat gggcaaggac ttcatgccta aaacaccaaa
143641 agcaatggca atgaaagcca aaattgacaa atgggatcta attaaactaa agagcttctg
143701 cacagcaaaa gaaactacca tcagagtgaa caggcaaccc acagaatggg agaaaatttt
143761 tgcaatctac tcatctgaca aagggctaat atccagactc tacaatgaac tcaaacaaat
143821 ttacaagaaa aaaacaaaca accccatcaa aatgtgggcc aaggaaaaga acagacactt
143881 ctcaaaagaa ggcatttatg cagccaaaag acacatgaaa aaatgctcat catcactggc
143941 catcagagaa atgcaaatca aaaccacaat gagataccat ctcacaccag ttagaatggt
144001 gatcgttaaa aagtcaggaa acaacaggtg ctggagagga tatggagaaa taggaatact
144061 tttacactgt tggtgggact gtaaactagt tcaaccattg tggaagtcag tgtggcgatt
144121 cctcagggat ctagaactag aaataccatt tgacccagca atcccattac tgggtatata
144181 cccaaagtat tataaatcat gctgctataa agacacatgc acacatatgt ttattgtggc
144241 actattcaca agagcaaaga cttggaacca acccaaatgt ccaacaatga tagactggat
144301 taagaaaatg tggcacttat acaccatgga ataccaagca gccataaaaa atgatgagtt
144361 catgtccttt gtagggacat ggatgaagct agaaaccatc attctcagca aactattgca
144421 aggacaaaaa accaaacact gcatgttctc actcataggt gggaattgaa caatgagaac
144481 acatggacac aggaagggga acatcacaca ctggagcctg ctgtggggtg gggggttggg
144541 ggagggatag cattaggaga tatacctaat gctaaatgac gagttaatgg gtgcagcaca
144601 ccaacatggc acatgtatac atatgtaact aacctgcatg ttgtgcacat gtaccctaaa
144661 acctaaagta taataataaa aaaataagct tataaaatgc ttttaatgct atataacttt
144721 ataactctga aagaataata gatttgtatt atgctgtcag tgagtaggtc tattaagtga
144781 taacattaaa cacaaatacc accatttata aagtatgatt ttgatatcat cggttgtgta
144841 ttttcacccc aaactctgta gatagtaact ttgttttctc atttgaccat gctcaatctt
144901 tagagaccat gctcttctct caaaatgact gtaggttcat ccaagtatgt ttgctaccca
144961 aaatcaatga aacacagtca caactatgtc tgtctaggaa taaagccagc taattagatt
145021 cttattctaa ggaacaagaa gagggcaggt aagaatttga ttatggcaga attctgacca
145081 taatcaataa ctgttttcta ttttttctcc atgttgtcgg gtggttcata cctgactttc
145141 atcatttcca atgattcctg tttgttttgt ttataaattt caaaatcatc atgaaaagtt

FIGURE 4 (cont.'d)

```
145201 tcactgaatg aaaacctgaa aattgggaaa taaacatttt tctgcaaaaa aaaaaaaaca
145261 atgaacactg acttctccta tttctcaaag tcatctcaaa gccatatgag gattaccaca
145321 aacttgcagg tgagaaaatt ctttgcaatg taagaagtgc catgcaaatt agttgatgct
145381 attataatta gtctcaggga tcaaaaatgc ttgaacccta aatctaacac ttcaaaggaa
145441 agcattattt ttcattcatt ttacaagtta cacctccctt cttccccaca tctttgttta
145501 gaatctggac cctgaagtta gaggaccaag attcaaatcc cagcctcatc agtactagct
145561 atgtgatatt gggaatgtta cttgatccct gcttatctta ctttctgcat ttattaaatg
145621 gggatgagaa taatatctac ccaaataagg tgcccaatgc agtgcccaac agcatgaagc
145681 ccaataaagg ttagttaaca tcacatccat aattgacacc tttaggtatt agattttcat
145741 catcccagaa cattttcctt ctttaagcct ttttctttct aagtggcact ttcttggata
145801 ctgattgcac tcctcacaaa cttgaaacgt tcaaacacac aagatgccat ttaggagaca
145861 ttggaacttg ggtttccttc tctgtaaaac tgagtaatga cagtcacctc ccagggctgt
145921 tgtaagaatg aatgagctag agtatgtaaa atatcttagc acagagtgct taagaaatta
145981 ttagttccag ccaagcgtgg tggctcacgc ctgtaatccc agcacttagg gaggccaagg
146041 caggcggctc atctggggtc aggagttcaa gaccacctgg tcaacatggt gaaaccccgt
146101 ctctactaaa aatacaaaaa ttagccaggc gtggtggcat gtgcatgtaa tcccagctac
146161 tcaggaggct gagacaggag aatcacttga acccaggagg tggaggttgc agtgagccga
146221 gatcgtgcca ttgcactcca gcctgggcaa caagagtgaa actctgtctc aaaaaaaaaa
146281 aaaaaaaaaa gaagaagaag aagaaagaag gaaagaaaga gagagagaga aagaaagaaa
146341 gaaagaaaga aagaaagaaa gaaagaaaga aaaagaaaga aagaaaagaa agaaagaagg
146401 aaagagacag aaagaaagaa gggaagaaag aaagaaagaa agaaagaaag aaagaaagaa
146461 agaaagaaag aaagaaagaa gggaagaaag aaagaaagaa agaaaaaaag aaagaaagaa
146521 agaaaaagaa agaaagagag aaagagaaag aaagaaagaa agaaaggaga gacagaacga
146581 aggaaagaag gaaggaatta tttccctttt tcccacccac gcctcaccac aaaccttgtt
146641 gtggggataa catgtaaaag tgaacaaaac tgagaagatc acatcgcata tgcactcagc
146701 ctctagtggg agacacaggc aataaacagg aaaagttaaa aacagtacta ggtagtggtg
146761 agtgcaatta gcctcccgca gcataaaggg aggagaataa ccagtggctc tttcatgcag
146821 agaatcaggg tagacctctg gggagagacc cgcactcaga ctgggatgga attatttatt
146881 ttatgcgtgt tcagttagga gtagaggtgc tctgtcgtga ttatctaatc ttgggaggaa
146941 caatgtcaga cgggtttcaa gatgagtatg agaattggtc ttccttctga aaaaacaaga
147001 attgagttca cactaatcac aaatacatca agcctatttg agtcttgtgt gtgtcatgga
147061 ttgaagtgta tctttccact tagtcaagaa gttccaatga gaagaatgct ccttaacttc
147121 ctaagtgcaa cagagtagtt gaactgagcc atggatggta aatctactta agaaagcaca
147181 tgccatggaa agatagcatt ggctgccctg cctacttctg atggcacagc cttgcaggaa
147241 gggaaagaag ccaagaggca aaagcctggt cttgttctga aaggcacaag gaggtggaag
147301 attaggggaa actcacccaa aaatgactca gctctgaact cagactcaag aagccacaat
147361 aagcaacatg aatggaactg gagggaaata aaccaggcgt agaaacacaa atgttgcata
147421 ttcttactca tgtgggaact aaaaacatgc atttcaagga gaatagaatg atggttatca
147481 gagactggga acagttgtgg gtgggggtgt taagagaggt tgcttaatgg gtacaaacat
147541 atagttagat agaaggtata agttctaatg tttgacagca gagtaggaga actatagtta
147601 acagtaatat attgtatact ccaaaatagc tagacaggaa gatttgaaat gttcccaaca
147661 catagaaatg acaaaagctt gaggtaatgg ataccctaaa tatcctgact tgatcattac
147721 acagtctatg cgtgtaacga aataccatat gtaccccata aatatgtaca aatattatgt
147781 atcaataaaa atttttaaaa agaagctgca atcaacattt catcattatc ttttcagcag
147841 catccttaca aagttacaga gacatcttaa gatgtatccc tcttcctctg aatcttcctg
147901 ggatagaaca aatgaaaact aaacaaggag tgggctggga ggagctgtca acatccatcc
147961 taaggaaaag tctgttaggg ctatgagctt cctctgtcct agagtagagc tgggaaaata
148021 gagtcttgac aattgatttc ttattctttc tttctctaaa tccccaatga atatgttttt
148081 ctttttagtg ctcagtggta gacagggctt aattctgttt agttatgcaa acaggccaga
148141 agaaactgaa ataggctata aatgtttgaa gctggccaaa agaagatgta gtcacacaag
148201 ataccctctg gaggaaagtg actgtcagga aagtcacttt cctgaccagc aaaaggacca
148261 gcactatttt gtcctgctga agaagtacat ttgtcctgct gctgtcatgg ggacagtggc
148321 tccagggctt cctgtggaca tgccacaagt tccactccat gagtcaggag atcatgcggt
148381 cagctggggg gaacttaggg ttgctctctt gagcttagcc ttatgctgcg tgtctgcttt
148441 gccaaccaca aaaacgatag tttcatagca agttgcaggc tccctggaaa cttaacctac
```

FIGURE 4 (cont.'d)

```
148501 ctactaggat acatttacag ctgcttttct cctggcatca ggctggagat caagaaatac
148561 ataaaacata gtccctgccc tcagttagct cagaatatgg tgggggaatg gagacagaag
148621 caaatactgg tgggacaagt gacgatgggc caaaatatgg gcttaaacaa aggttgtggg
148681 agctcagaaa aggagcaact cactctgcct gaaagagtca tggagggctc cacggaaaaa
148741 gcaacatttg tgcaggagga gattagaaca cagaggagaa ggatagcagc actccagatg
148801 aagggaagga aatgtgccaa gatttcatgg gaatgagaag atgtaaactg ctcaggaaaa
148861 accatggttg aagctcttca cagtggctga agcatggtgt gattgtcagt tttgcttgtc
148921 aacttggtca ggctgtagta ctcaactatt caaccaagca ctgatctagg tattgctgtg
148981 aaggtatttt gtagtcgcaa ttaacctcta caatcagttg actctattta aaggacatta
149041 ttctgtacta tctgagtgga cctgatccac ttcatcccaa aggtaaatga ttctccaaca
149101 gtgttctcat ctacatctag ggcttggaag atgaaggtga aggagaatat ggaaaaacaa
149161 caagaaaaaa gtcaatcaat cagaacttcc agccctgtgt ttgttagttc actttatgtt
149221 caaccagtat gtctccactt ttatctgctt ccttgtaaga tttcatctga aaaagggaat
149281 tcactcttca ggtgttggaa atcaattatg agagaagcac ttacagaatg actatctgaa
149341 gagctctgca gacattctcc agagtaaaac aaccataacc ggtgaaaatt aaaaacaaac
149401 aaaataaaaa aatgttagag tattggaaat tgttctaagg gccgacagca aatgaagaaa
149461 tccaagaaag cctaccaatt tcagtgagag gagtgagagt ctatggtgtt gagtctatgg
149521 tgtttaagtt ctgttcattt cctccctctc ctgcaatcag ttcagtgaaa cagaaaccct
149581 gctccagaga tgtgcagcca aaaagacagg gtgccctttc ccctcagctc ccaatctagg
149641 gcagactacc agcatttccc aagcccatct ctggctctat gttgcagaag ttctattcca
149701 agaaagtttg actgagaatc tgaagcttcc ttcttccact cagcctctac tattaaggcg
149761 taagttctat ccccagtgcc acgggccaag aatactgatg ctgaatgtcc ttgctccgct
149821 acactcatag ggcagagatt ccatgggagg agtgaagttt ccattccaga aaaggcagaa
149881 aaacagaaat tactgcccaa tccagtaccc cacccataaa gaaggaaaga catctgagaa
149941 aagcatgaca ctgtccccaa aaccacctgc agagtagtgg cagtagaggc agtagggaga
150001 ctagaggacc tgcctagagg gagaagtagg ccataagaag aaaagtctct agttctccct
150061 aaagggacaa actttatttg caacagaaca tgcggaagtt caagcctaag ggcactgtca
150121 aaaacaatga atattttggt ggtaagcaat taataggtta atggcagctt agtgagagca
150181 acaaactaaa ccataaacca gctagacata tacaataaaa atccaagaaa gagagagcca
150241 agaagggcct tcctgaggtt aaaacaaaca tcaaagtctt gtctgaaaaa ctgctcctgc
150301 aaaggaagca aaatatattt ggatcagact gtggagcaat ttatgcccct aaaaagctgt
150361 caaaaccaaa agagcaatta tctagcaatt gctggaggtt aacagttggg tatgatacca
150421 aaagaggcaa acaactgaac agatcagaga aagaggcagt caaagagagc actgctaaat
150481 gcactgtaat tccaatttga gagaaaatgt gcccagtgct gtgactccct caggaacaac
150541 atcagaggcc acaaattatg gtggaaatag gcttcactat atagtctagc caggcaatta
150601 aacaaataaa caattaaaca acagtaacat agtgaggggg gcagaaatga gtattgcaac
150661 tagctagaac atatttttga acaaaaaaat tatgagtcaa gcagagatat ggaaaagaca
150721 gagccataca ccagaaaaaa ggtaagcaag agaaactgcc tttgtgagtg ccaagatgtc
150781 agacatagca gaaaaaaaac ctcaaagtaa ttattataaa tatgttcaaa aactaaaaga
150841 aaatgtgctt aaaaaataaa agatggtatg ataatttctt gtcaattcaa aaataccaat
150901 aatagattaa aaatattttt tcaaaagtta attaaccaaa tggaaattct ggggtttaaa
150961 agtaaaataa caacaataag aacattttgc tagaggaaat gaacaataga tttgtaccag
151021 aaggaaaaat aatcaaataa acagggattt catcaacacc aaacctgtct tacaagaaat
151081 actaaaggga gttcaatctg aaagaaagaa cattaacaag caacaggaaa tcatctgaag
151141 gtacaaaact cactgtacct tcagatgata ataagtcctc aaaaaacaca gaatattata
151201 acactgtaat tatggtgtgt aagctactta tatcataagt agaaagagga aaagatgaac
151261 tgattaaaaa acaattacaa cagcttttca agacagtata ataagatata taaataacag
151321 aaagcttaaa agcatataaa taaagttaaa atgtagaggt tttttagtt ttctttttgc
151381 ttgattgtgt atttatttat gcaatcagtg ttgttttcat cagcataaaa taatgggtta
151441 taagatagta tttgcaagcc tcatagtaac ctcaaattta aaaacataca atgtatacac
151501 aaaaagtgaa gagcaagaaa ttaaaacata ccaccaaaaa aaatactttc actaaaaagg
151561 agacaggaag taagaaaaga tgggagagaa gatcacaaaa caaccagaaa ataaataaca
151621 aaatggcaag caagtcctta tttgtcaata ataatattga atgtaaatgg actatactct
151681 ccagtaaaaa gatacagagt ggttgaatgg attaaaaaaa aggacccaat gatctgttac
151741 ctacaagaaa taaacttcac ttataacaat acacagacta aaaataaagt catgggaaat
```

FIGURE 4 (cont.'d)

```
151801 gatacttcac gacaatggaa accaaaaaag aacaggagta gctatacctt tatcagacta
151861 aatagatttc aagacaaaaa ttgttaagaa aaaccaaata aggtcattat ataatgataa
151921 agagatcagt taagcaagag gatgtaacaa ttgtaaatat atatgcactc aacattggag
151981 cacctagata aataaaacaa atattattag agctaaagaa agatagaccc cctcccccaa
152041 aacaataata gctgtagatt tcaatgctcc actttcagca ttggacagat cttccagaca
152101 gaaaatcagc aaggaaacat cagatgtaat ctgaactata gaccaaatgg gcctaataag
152161 tatttacaga atatttcatc caaaggttac agaagacaca tttttctcct tagcacatac
152221 atcattctca agaacaggcc atatattagg tcatgaatca agtctcaaaa cattcaaaaa
152281 aactgaaata atctcaagca tcttctttga ccacaatgga ataaaactag aaaccaataa
152341 caaggggaat tttggaaact atacaaaaac atggaaatta aacaatatgt tcctaaatga
152401 taagtgggtc aatgaagaaa ttatgaattg aattgaaaat tttctaaaaa caaatgacaa
152461 tggaaacata atgcaccaga acctatggga tacaacaaaa gcagtaccaa gagtgatatt
152521 tccagataag ggcctacatc aaaaaggaag aaaaacttca agtgaataac ctgatgatgc
152581 atcttaaaga attaaaaagg caagagtaaa ccaaacccaa aattagtaga agaaaagaac
152641 taataaagat cacagtagaa ataaataaaa ttggacttct gctccaagat ggcctaatag
152701 aaacagctcc agtctgcagc tcccagcatg attggcacag aagatgggtg atttctgcat
152761 ttccaactga ggtaccaggt tcatctcatt gggactggtt ggacaatgga tgcagcccat
152821 ggagggtgag gtgaagcagg gtgaggagtc acctcacccc ggaagcacaa gtgattgggg
152881 gatttccctt tcctagccaa gggaagccgt gacagactgt acctggaaaa tcggttcact
152941 cccacccaaa tactgtgctt ttcccatagt cttagcaacc ggcagaccag gagattctct
153001 cccaagccta gctcatcagg tcccatgccc acggagcctg gctcactgct agcacagcaa
153061 tctgagatca acctgcgagg ctgcagctgg gtgggggggag gggtgtcagc cattgctgag
153121 gactgagtag gtaaacaaag tggccaggaa gctcaaactg ggcagagccc accgcagctc
153181 agcaaggcct actgcctcta tagattccac ctctgtgggc agggcataac tgaacaaaag
153241 gcagcagaca acttctgcag atttaaacgt ccctgcctga cagctctgaa gagagcagtg
153301 gttgccccag catggcatct gagctctgag aacagacaga ctgcctcctc aagtgggtcc
153361 ctaaactcca tgtagcctaa ctgggagaca tctccccata ggggccgaca gacacctcat
153421 acaggtgggt gccactctgg gacaaagctc tcagaggaag gatcaggaag caatatttgc
153481 tcttctgcaa tatttgctgt tctgcagcct ctgctggtga tacccaggca aacagagtct
153541 ggaatggacc tccagcaaac tccagcagac ctgcagctga gggacctgac tgctagaagg
153601 aaaactaaca aacaaaaagg aatagcatca acatcaacaa aaaggacatt cacaccaaaa
153661 cctcatctgt agtcaccaat atcaaagacc aaaggtagat aaaaccacaa agatggggag
153721 aaaccagagc agaaaagctg aaaattctaa aaactgagca ccgcttctcc tccagaggat
153781 tgcaactcct caccggcaac ggaatgaagc tgggtggaga atgactttga caagttggca
153841 gaagtaggct tcagaaggtc ggtaataaca aactactcca aactaaagga gcatgttcta
153901 acccattgca aggaagctaa aaaaccttca aaaaaggtta gacaaatggc taactagaat
153961 aaacagtgta gagaggaact taaatgacct gatggagctg aaaaccgtgg catgaggaca
154021 tcatgatgca tgcacaagct taaatagctg attaaatcaa gtggaagaaa gaatatcagt
154081 gactgaagat caaattaaca aaataaagca agaagataag attagagaaa aaagagtaaa
154141 aagaaatgaa aagcacctcc aagaaatatg ggactatgtg aaaaaaccaa atctacactt
154201 gattggtgta cctgaaagtg atggggagaa ggaaaccaag ttggaaaaca ctcttcagaa
154261 tactatccag gagaacttcc ccaaactagc aaggcaggcc aacattcaaa ttcaagaaat
154321 acagagaaca ccacaaagat attcctcaag aagagcaacc ccaagacaca taattgtcag
154381 cttcaccaag gttgaaatga aggaaaaaaa tgttaagggc agccagagag aaacgttggg
154441 ttaccaacaa agggaagccc atcagactaa aagtagctct ctcagcagac accctgtaag
154501 ccagaagaga gtaggggtca atattcaaca ttcttaaaga aaataatttt caacccagaa
154561 tttcatatcc agccaaacta agcttcataa gtgaaggaga aataaaatcc tttacagaca
154621 agcaaatgct gagagatttt gtcaccatca ggcctgcctt acaagagctc ctgaaggaaa
154681 cactgaacat ggaaaggaac aactgttacc agccactgca aaaacacgcc acattgtaaa
154741 gaccatcgat gacatgaaga aactgcaaca attaactggc aaaataagca gctcacagca
154801 taatgacagg atcaagttca cacataacaa tattaacctt aaatgtaaat gggctaaatg
154861 cctcaattaa agacacagac tggcaaattg catagagtca agacccatca gtgtgcggta
154921 ttcaggagac ccatctcaca tgcaaagaca cacataggga tggaggaaga tccaccaagc
154981 aaatggaaag ccaaaaaaaa aaaaaaaaaa aaaaaaagca ggggttgcaa tcctagtctc
155041 tgataaaaca gagtttaaac caacaaagat ccaaagagac aaagaaagcc attacataat
```

FIGURE 4 (cont.'d)

155101 ggtaaaggga tcaatacaac aagaagaaca aactatccta aatatatatg caaccaatat
155161 gggagcaccc agattcataa agcaagtctg tagagacgta caaagagatg tagacttcca
155221 cacaataata atgggagact ttaacactcc actgtcaata ttagacagat caatgacaca
155281 gaagggtcac aaagatatcc aggacttgaa ttcagctatt caccaagtgg acctaataga
155341 catctacaga actctacacc ccaaatcaac agaatgtaca tacttctcag caccacatca
155401 tacttattct aaaattgacc acataattgg aagtaaaaca ctcctcagca aatgtaaaag
155461 aacagaaatc acaacaaact gtgtctcaga ctacagtgca aacaaattag aactctggat
155521 taataaactc actcaaaatc acacaactac atggaaactg aataacctgc tcctgaatga
155581 ctactgggta cataatgaaa tgaaggcaga aataaagatg ttctttgcaa ccaataagaa
155641 caaagacaca acataccaga ttctccggga cacatttaaa gcagtgtgta cagggaaaat
155701 tatagcacta aatgcccaca agagaaagca ggaaagaact aaaatcaaca acctaacatc
155761 gcaattaaaa gaactagaga agcaagagca aacacattca aaagctagca gaaggcaaga
155821 aataactaag atcagaacag aactgaagga gatagagaca caaaaagcac ttcaaaaaaa
155881 tcaatgaatc caggagctgg tttttaaaaa gatcaacaaa attaatagac cgctagcaag
155941 aataataaag aaaagagaga agaatcaaat tagactcaat aaaaaaagat aaaggggata
156001 tcaccactga tcccatagaa atacaaacta ccatcagaga atactataaa cacctctaca
156061 taaataaact agaaaatcta gaagaagggg gaggagccaa gatggccaaa taggaacagc
156121 tccagtctac agctcccagc gtgagtgaca cagaagacgg gtgatttctg catttccatc
156181 tgaggtaccg ggttcatctc actagggagt gccagacagt gggcacaggt cagtgggtgc
156241 gcgcactgtg tgcgagccaa tgcagggtga ggcgttgcct cactcgggat gtgcaagggg
156301 tcagagagtt ccctttccta gtcaaagaaa ggggtgacag atggcacctg gaaattcggg
156361 tcactcccac ctgaatactg cacttttcca acgggcttaa aaaacggcgc acctggagag
156421 tatatcccgc acctggcttg gagggtccta tgcccacgga gtcttgctga ttgctagcac
156481 agcagtctga gatcaaactg caaggcagcg gcgaggctgg gggaggggcg cctgccattg
156541 cccaggcttg cttaggtaaa caaagcagct gggaacctca aactgggtgg atcccaccac
156601 agctcaagga ggcctgcctg cctctgtagg ctccacctct gggggcaggg cacaggcaaa
156661 caaaaagaca gcagtaacca ctgcagactt aaatgtccct gtctgacagc tttgaagaga
156721 gcagtggttc tcccagcacg cagctggaga tctgagaacg ggcagactgc ctcctcaagt
156781 gggtccctga cccctgaccc ccgagcagcc taactgggag gcatccccga gcagaggcag
156841 actgacacct cacacagccg ggtactccaa cagacctgca gctgagggtc ctgtctgtta
156901 gaaggaaaac taacaaacag aaggacatcc acaccaaaaa cccatctgta catcaccatc
156961 atcaaagacc aaaagtagat aaaaccacaa agatggggaa aaaacagagc agaaaaacta
157021 gaaactctaa aaggcaaagc gcctctcctc ctccaaagga atgcagttcc tcaccaggaa
157081 tggaacaaag ctggacggag aatgactttg acgagctgag agaagaaggc ttcagatgat
157141 caaattactc cgaactacgg gaggacattc aaaccaaagg caaagaagtt gaaaacgttc
157201 aaaaaattta gaagaatgta taactagaat aaccaataca gagaagtgct taaaggagct
157261 gatggagctg aaaaccaagg ctcgagaact acgtgaagac tcaggagccg atgcgatcaa
157321 ctggaagaaa gggtatcagc gatggaagat gaaatgaatg aaatgaagtg agaaggaaag
157381 tttagagaaa aaagaataaa aagaaatgaa caaagcctcc aagaaatatg ggactatgtg
157441 aaaagaccaa atctacatct gattggcgta cctgaaagtg acggggagaa tggaaccaag
157501 ttggaaaaca ctctgcagga tattatccag gagaacttcc ccaatctagc aaggcaggcc
157561 aacattcaga ttcaggaaat acagagaacg ccacaaagat actcctcgag aagagcaaca
157621 ccaagacaca taattgtcag attcaccaaa gttgaaatga agggaacaat gttaagggca
157681 gccagagaga aaggtcgggt taccctcaaa gggaagccca tcagactaac agcggatctc
157741 tcggcagaaa ctctacaagc cagaagagag tggtggccaa tattcaacat tcttaaggaa
157801 aagaattttc aaaccagaat ttcatataca gccaaactaa gcttcataag tgaaggagaa
157861 ataaaatcct ttacagacaa gcaaatgctg agaaattttg tcaccaccag gcctgcccta
157921 aaagagctcc tgaaggaagt gctaaacatg gaaaggaaca accggtacca gccgctgcaa
157981 aatcatgcca aaatgtaaag accatcgagg ctaggaagaa actgcatcaa ctaacgagca
158041 aaacaacctg ctaacatcat aatgacagga tcaaattcac acataacaat attaacttta
158101 catgtaaatg gactaaatgc tgcaattaaa agacacagac tggcaaattg cataaagatt
158161 caagacccat cagtgtgctg tattcaggaa acccatctca cgggcagaga cacacatagg
158221 ctcaaaataa agggatggag gaagacctac caagcaaatg gaaaacaaaa aaaaggcagg
158281 ggttgcaatc ctagtctctg ataaaacaga ctttaaacca acacagatca aaagagacaa
158341 agaaggccat tacttaatgg taaagggatc aattcaacaa gaagagctaa caatcctaaa FIGURE 4 (cont.'d)

```
158401 tatatatgca cccaatacag gagcacccag attcataaag caagtcctga gtgacctaca
158461 aagagactta gactaccaca cattaataat gggaaacttt aacaccccac tgtcaacatt
158521 agacagatca acaagacaga aagtcaacaa ggatacccag gaattgaact cagctctgca
158581 ccaagcagac ctaatagaca tctacagaac tctccacccc aaatcaacag aatatacatt
158641 tttttcagca ccacaccata cctatttcaa aattgaccac atacttggaa gtaaagctct
158701 cctcagcaaa tgtaaaagaa cagaaattat aacaaactgt ctctctaacc acagtgcaat
158761 caaactacaa ctcaggatga agaaactcac tcaaaactgc tcaactacat ggaaactgaa
158821 caacctgctc ctgaatgact actgggtaca caacgaaatg aaggcagaaa taaagatgtt
158881 ctttgaaacc aatgagaaca aagacacaac ataccagaaa ttctgggatg cattcaaagc
158941 agtgtgtaga gggaaatttg tagcactaaa tgcccacaag agaaagcagg aaagatccaa
159001 aattgacacc ctaacatcac aattaaaaga actagaaaag caagagcaaa cacattcaaa
159061 agctagcaga aggcaagaaa taactaaaat cagagcagaa ctgaaggaaa cagagacaaa
159121 aaaaaccctt caaaaattaa tgaatccagg agctggtttt ttgaaaggat caacaaaatt
159181 gatagaccgc tagcaagaat aataaagaaa aaaagagaga agaatcaaat agatgcaata
159241 aaaaatgata aaggggatat caccaccgat cccacagaaa taaaaactat catcagagaa
159301 tactacaaac acctctatgc aaataaacta gaaaatctag aagaaatgga taaattcctc
159361 gacacataca ctctcccaag actaaaccag gaagaagttg aatctctgaa tagaccaata
159421 acaggagctg aaattgtggc aataatcaat agcttaccaa ccaaaaagag tccaggacca
159481 gatggattca cagccgaatt ttaccagagg tacaaggagg aactggtacc attccttctg
159541 aaactattcc aatcaataga aaaagaggga atcctcccta actcatttta tgaggccagc
159601 atcatcctga taccaaagcc gggcagagac aaaaccaaaa aagaggattt tagaccaata
159661 tccttgagga acattgatgc caaaatcctc aataaaatac tggcaaacca aatccagcag
159721 cacatcaaaa agcttatcca ccatgatcaa gtaggcttca tccctaggat gcaaggcttg
159781 ttcaacatat gcaaatcaat aaatgtaatc cagcatataa acagaaccaa agacaaaaac
159841 cacatgatta tctcaataga tgcagaaaag gcctttgaca aaattcaaca acacttcatg
159901 ttaaaaactc tcaataaatt aggtattgct gggacgtatc tcaaaataat aagagctatc
159961 tatgtcaaac ccacagccaa tatcatactg aatgggcaaa aactggaagc attccctttg
160021 aaaattggca caagacaggg atgccctctc tcaccactcc tattcaacat agtgctggaa
160081 gatctgtcca gggcaatcag gcaggagaag gaaataaagg gtattcaatt aggaaaagag
160141 gaagtcaaat tgtccctgtt tgcagatgac atgattttat atctagaaaa ccccattgtc
160201 tcagcccaaa acctccttaa gctgataagc aacttcagca aagtctcagg atacaaaatc
160261 aatgtacaaa aatcacaagc attcttatac accaacaaca gacaaacaga gagccaaatc
160321 atgagtgaac tcccattcac aattgcttca aagagaataa aatacctagg aatccacctt
160381 acaagggatg tgaagcacct cttcaaggag aactacaaac cactgctcaa cgaaataaaa
160441 gaggatacaa acaaatggaa gaacattcca tgctcatggg taggaagaat caatattgtg
160501 aaaatggcca tactgcccaa ggtaatttac agattcaatg ccatccccat caagctacca
160561 attactttct tcacataatt ggaaaaaact actttaaagt tcatatggaa ccaaaaaaga
160621 gcccgcatca ccaagtcaat cctgagccaa aagaacaagg ctggaggcat cacactacct
160681 gacttcaagc tatactacaa ggctacagta accaaaacag cttggtactg ttaccaaaac
160741 agagatatag atcaatggaa cagaacagag ccctcagaaa taatgctgca tatcgacaac
160801 tgtctgatct ttgacaaacc tgagaaaaac aagaaatggg gaaaggattc cctatttaat
160861 aaatggtgct gggaaaactg gctagccata tgtagaaaga tgaaactgga tcccttcctt
160921 acaccttata caaaaattaa ttcaagatgg attaaagact taaatgtcag acctaaaacc
160981 ataaaaaccc tagaagaaaa cctaggcatt accattcagg acataggcat gggcaaggac
161041 ttcatgtcta aaacaccaaa agcaatggca acaaaagcca aaattgacaa atgggatcta
161101 attaaactaa agagcttctg cacagcaaaa gaaactacca tcagagtgaa taggcaacct
161161 acagaatggg agaaaatttt tgcaatctac tcatctgaca aagggctaat attcagaatc
161221 tacaaagaac ttaaacaaat gttcaagaaa aaaacaaccc catcaaaaag tgggcaaaat
161281 acatgaaaag acacttctca aaagaagaca tttatgcagc caacagacac atgaaaaaat
161341 gctcatcatc actggccatc agagaaatgc aaatcaaaac cacaatgaga taccatctca
161401 caccagttag aatgacgatc attaaagtca ggaaacaaca gatgctggag aggacatgga
161461 gaaataggaa tgcttttaca ctgttggtgg gggtgtaaat tagttcaatc attgttgaag
161521 acagtgtggc aattcctcaa ggatctagaa ctagaaatac catttgaccc agcaatccca
161581 ttactgggta tataccgaaa agattacaaa tggtgcaact ataaagacac atgcacacga
161641 atgtttattg tggcactatt cacaatagca aagacttcta acaaacccag atgtccatca
```

FIGURE 4 (cont.'d)

161701 atgatagact ggattaagaa aatgtggcac atatacacca tggaatacta tgcagccata
161761 aaaaaggatg agttcatgtc cttttcaggg acatggatga agctggaaac catcattctc
161821 agcaaactat gacaaggaca gaaaaccaaa caccgcatgt tctcactcat agatgggaac
161881 tgaacaatga gaacacttgg acacagggca gggaacatca cacaccaggg cctgttgggg
161941 ggtggtggac tgggggagag atagcattag gagaaatacc taatgtaaat gatgagttga
162001 tggatgcagc aaaccaacag ggcacatcta tacctatgta agaaacctgc actttgtgca
162061 caggtaccct agaacttgaa gtataataaa aatgaaaaaa agaaaatgtt actagcaaat
162121 tgtagatggg tatacctaat ataactctgc atgtgcacta tgtgtctgga tacacatgga
162181 aagtattcag gcatacacac caaattgtta aaataaatcc ccttccaaca ttaggagtgg
162241 ctggggagca gatggctttc acttccgcac attccatggt gccagggtaa taccacatca
162301 caatagtaaa tagcaaaaat aacaacctta agtttagatt ttcttatcta aattttaatt
162361 ctgtgaagaa gtttccattt cccttttttca cacaggatag tagaatgcag tttagaaaga
162421 gtgagatcac ttgttagact gtacaatttt taagcatcag cgaagtatac cattaaactt
162481 ctctatcaat ccattctcta aacttcccaa cccaaaaaaa aagaaacaca taaaattgaa
162541 atgaagaaaa caatacaaaa gatcaacaaa aatgaaaggt tggcttttta aagagataaa
162601 caaaattgac aaatgtttag ccagactaag aaaaagagaa ggcccaaata aataaaatca
162661 gagatgaaaa agcagacatt ataactgata ctgcggaaat tcaaaggatc attaatggct
162721 actatgagca actgtatgcc aaacattgga aaatattgaa gaaatagata aattcgtaga
162781 cacacgcaac ctaacaagat tcaaccatga agaaattcaa aatctgaaca gaccaaaaac
162841 aagtaacaag atcaaagcca taattaaaat tttcccagca aagaaaagcc tgagacccaa
162901 tggcttcact gctgaattct atcaaacatt taaagaacta ataccaatcc tactcaaact
162961 attccaaaaa gtagaagagg agggaatatt tccaaactta ttctatgagg ccattactgc
163021 tcctatatca aaaccaagga cacatcaaaa aaagaaaact ataggccaat atctcacatg
163081 aatattgatg aatcctcaaa aaatgctagc aaactgaatt caacatcaca ttaaaaatca
163141 ttcattatga ccaaatggga tttatcccag ggatgcaaat atggttcaac atatacacat
163201 cagtcagtgt aacatatcat atcaacagaa tgaagaagaa aaaccatatg gtcatgttaa
163261 ttgatgctga aaaagtattt gagagaatta aacatctctt catgacaaaa accctcaaaa
163321 acactggaga cagaaggaac atacctcaac acaataaaca gacatatatg acagactcac
163381 agctagaatc atactaaatg gggagaaact gaaagtcatt cctctaagat ctggaacaag
163441 acaaggatgc tcattttcac cagtgttagt ggaacatagt actgaaagtc ctagctagaa
163501 cagactagag acagaaataa ggggcatcca aactgggaag agagaagtca aattaccttt
163561 gttcgcagat ggtatgatct tctgtttgga aaaacctaga ctccataaaa aaatgattag
163621 aactgataaa ttcagtaaag tttcaggata caaaattaac atacaaaaat cagtagcatt
163681 tctatatgtc aatagcaaac aatctgaaaa tgaaatcaag gaagtaatcc catttcccat
163741 ttgcaatagc tataaataaa attaatataa tctcatctct tcaataagtg gtgttgggaa
163801 aactgcatat ccacatacaa aagaataaaa ttagaccctt ttaatataca aaactggacc
163861 caagttaata tacaaaaatt aacttgaaat gaattaaaga cttaaatgta agatctgaaa
163921 ccaaaaactc ctagagagaa acatagggga aaagctcctt gacgttggcc ttggcaataa
163981 ttttttggga tattacacca aaagcacaga cttttgaaaa aataaacaag taggactaca
164041 tcaaactaaa aagcttctgc atggcaaaag aaagtcaaca acatgaaaag gcaacctaca
164101 gaatggaggg aaatatttgc aaaccatata cctgatgaga agttaatatc aaaatataga
164161 aaatatataa ggaactcaca tatctcaata ccaaaaaaat aataacctgt tttataatgg
164221 gcaaaggacc tgaatagaca ttttttcaaa gaagacacac agatggccaa cgagtgcagg
164281 aaaaagcgtt caacatcact aatcatcagg gaaatgcaaa tcaaaaccac aatgagatat
164341 cactccacac ctgttaggaa agctattatg aaaaacacaa gagacaatga atattggcaa
164401 gggcatggag aaaaaagaac ccttgtacac tgttggtaga aatgtaaatt gcaacagcct
164461 ttatggaaaa tagaatggag gttcctcaaa aaataaaaat agaactacca tacaatctag
164521 caattccact tatgagtgta catccaaagg aatcaaatca ctatgtcaaa gagatatctg
164581 tacttccttg tttattgcag ctttactcac agtagccaag ataaggaaaa aatctaaatg
164641 tccatcaacg gataaagaaa atggggggag gggtgtgcat gtatacatac acaatggact
164701 atttttcagc cataacaaag aaggaaaccc tgccatttgt gacgatatga atgaacccag
164761 aggacattat gttaagtgaa ataagccaga cacagaaata caaatattgt atgatctcat
164821 ttatatgcga atctaaaaat ttcaaacttg aagacgaata agtagaacag tatttatcag
164881 gagctagggg atgtggggaa gaagcaaaat attgggcaaa gagtataaac tttcagttat
164941 gagatgaagg ccaggtgcga tggctcatgt tggtaatccc aatactttgg aaggctgagg

FIGURE 4 (cont.'d)

```
165001 cagagggatt gcttgagacc agcctaggca agaaagtgag acctcatctc tacaaaaaat
165061 aaaaataaaa gaatcagctg ggagtggtgg catacacctg tagtcccagc tagtcaggag
165121 gctgaggggg gaggatcatt tgaaattgga aagtcaaggc tgcagtcagc caagatagtg
165181 ccactgcatt gcagcctggg tgacagagcg aaaccctgtc tcaaaaaaaa aaaaaaaaaa
165241 aagatgaata agttctgggg atcaaatgta cagcatggtg actatagttt ataactgcgt
165301 tattacttga aattggataa gagcagattt taagcatccc cagcaccccc ccaacataca
165361 cacacacaaa tggtaactat aggtggtgat agatatgtta atttgactgt gacaatcagc
165421 attcaatata tacatatatc aaatcatcac attttacccc ttgaaataga aactttgatt
165481 tgtcaatcaa atattttaaa acgaaaataa tcataatatt aatatagcat acaggaaaaa
165541 atttcgtatc tcgactgata cagaaaattt catgataaaa acactttaaa acaaaagaaa
165601 taaaagggaa ctccctcaac ctgataaatg gcatctgtgg aaacccccag ctagcatcaa
165661 acttaataca gaaaggctgg gtgttcacct cttgaaccag gaacaagaca aagatgcctg
165721 cttttgccac ttccatttga ccttgtactg aggttctggc tagggcaatt atccctgaaa
165781 aagaaataaa aggcttccaa ataaaagaag aagtaaaact atctctactc gctcatgaca
165841 tgatcttgca tatagaaaat gtgcacatgt acacacacac aaaccattag aactaataaa
165901 caagttcagc aagtttgcag aatataaaat gaatgtacaa aaatcaagtg tttttctata
165961 tactagcaat taacaatctc aaaatgaatt aaaattccat ttacaatagt atcaaacata
166021 aattatttag aaataaaaag tgcactgaaa actacaaaat attttgaaat aaatcagaaa
166081 agatttaagt aaatggatca cttgaacctg ggaagcagag gttgcagtgt gccgagattg
166141 taccactgca ctttagcctg ggcaacagag ggagactcca aagagtcgaa aagaaaagaa
166201 aagatttaaa taagctgaaa catattctat ggatcagaag acttaatatt gttaaagtga
166261 caatattccc caaattgatc tacagcttca actcaacccc tatcaaaatc ctagcttgct
166321 ttttggctga aattgacaag ctgattctat aatttatatg gaatctcaaa ggatccagaa
166381 taaccaaaac aatattgaaa aataaagaac agcgttggtg gattaacatt ttccaatttc
166441 aaaacttact atagcactgc ggtaatcaag cagtgtggca ctgtatagca tgtacattac
166501 agatcagtgg actagaatca atgtccagaa ataaaccgtt atgtttataa tgaattactt
166561 tttaataagg tgtcaagaca acgcaatggg aaaagaataa tgaattcaac aaatgatgca
166621 tggacaaccg gacatgcaca tgcaacacaa tgaatttgaa ttcttctatc gctccatgca
166681 taaaaactaa ctcaaaatgg gtcacggatg taaatgaaaa gctaaaacta taataatcct
166741 agaggaaaac ctaggagtaa atctttaaga tgttattgta ggcagtggtt tctcagatag
166801 gaccccaaaa tcacaagcga caaaagaaat tggacttaaa gttaaatact tttgtgcttc
166861 aaacatcatc aagaaagtga aaacacaacc cgcagaagca ataaaaatgt ctgtaagtca
166921 tgtatccgat tagagacttc tatccaggat atataaataa tgcaattcaa tgataaaaaa
166981 gataaatagc ccagttttcc aaagagtcaa gcatctgaat atacatctct ccaaaaatat
167041 acagatatcc aacaagcatg tgaaaagatg ttcaaagcca tttgccaggt gcacaaaccc
167101 aagacagtat gaggagatgc tacagggact ctgctgcttc acagacatga agcgttggtg
167161 agaatgtagg cagccgcctt tggggacttc acatccccgc cgcccccacgc acggtgagct
167221 agtgtttaaa cttagccgag atcaatacac gcgactgtgt gcccgtcaga ccctgcgctg
167281 ccggcggggc tgggagaggc gggcgccagg agtgggcggg aacctggggg tcaggcccca
167341 gccgcgggaa gccgcccagg agcgcgcgaa accttctcca caccccttcca ggcatttgcc
167401 cgccgcgatt cagagagccg acccgtgacc cctggcctcc cctagacagc cccgcatgtc
167461 cagatgtgcc gtcccgcctg cctcccgcga ccactggcca tctctgggcc tgggcgcggt
167521 ctcggcgccc gcctgccccc gccaggagcc gcaggtccag ccagtgaaga agcccgcgct
167581 gaaggagcct ctgtgctcca gaatccatcc tcagtatcag cgctggggtg gcctcctcca
167641 ggaagccctt ctgattctct catgggtcgc tcttcctctg cagactcccg gagcacccct
167701 gctccaagta ccgcaagtgg cactgagaac ttggggagag cagaggctgt gcctagattt
167761 gtagggagtc cccgcagctc caccccaggg cctacaggag cctggccttg ggcgaagccg
167821 aggcaggcag gcagggcaaa gggtggaagc aattcaggag agaacgagtg aacgaatgga
167881 tgaggggtgg cagccgaggt tgccccagtc ccctggctgc aggaacagac acctcgctga
167941 ggagagaccc aggagcgagg cccctgcccc gcccgaggcg aggtcccgcc cagtcggcgc
168001 cgcgtgaaga gtgggagaga atactgcggg ggcgggggcg ggggcggggg cgggggcggg
168061 ggccgccggg agcctggagc cagaccgggc ggggccggca ccgggccagg gacagtgggg
168121 gaggaggctg cgggctgagc gaccctgacc ccccccagtc cgcgctggtt ccgg
```

DETECTION OF POLYMORPHISMS IN THE HUMAN 5-LIPOXYGENASE GENE

RELATED APPLICATIONS

This application claims priority to U.S. Provisional Application No. 60/267,515 filed on Feb. 8, 2001 and Application No.60/314,248 filed Aug. 21, 2001, the contents of which are incorporated herein by reference.

BACKGROUND OF THE INVENTION 5-lipoxygenase (5-LO) is the first committed enzyme in the pathway leading to leukotriene synthesis and is responsible for the conversion of arachidonic acid to LTA4 via the unstable intermediate 5-hydroperoxy eicosotetraenoic acid (Samuelsson et al., (1987) *Science* 237:1171; Samuelsson (1983) *Science*220:568). Leukotriene A4 can, in turn, be converted to leukotriene B4, C4, D4, or E4. Leukotrienes are potent local mediators which influence inflammatory and allergic response, including asthma, rheumatoid arthritis, psoriasis, thrombotic disease, ulcerative colitis, bronchitis, sinusitis, allergic and non-allergic rhinitis, and lupus. Leukotrienes (LTs) B4, C4, D4, and E4 have been shown experimentally to mimic the pathologic changes seen in asthma and to play a role in several inflammatory mechanisms that lead to airflow obstruction in asthma. Such mechanisms include bronchoconstriction, mucosal edema, increased secretion of mucus, and an inflammatory-cell infiltrate that is rich in eosinophils. (O'Bryne (1997) *Chest* 111:27S–34S). The slow-reacting substance of anaphylaxis is now known to be a mixture of leukotrienes C4, D4, and E4, all of which are potent bronchoconstrictors that exert their biological actions through specific ligand-receptor interactions thereby increasing vascular permeability and constricting smooth muscle (U.S. Pat. No. 5,750,565; Silverman, et al. (1998) *Clin Exp Allergy* 28 Suppl 5:164–70).

There have been research efforts to develop specific receptor antagonists or inhibitors of leukotriene biosynthesis, to prevent or minimize pathogenic inflammatory responses mediated by these compounds, including the inhibition of 5-LO. For example, European Patent Application Nos. 90117171.0 and 901170171.0 disclose indole, benzofuran, and benzothiophene lipoxygenase inhibiting compounds (U.S. Pat. No. 5,750,565). It has been established that treating patients with agents that have the capacity to inhibit 5-LO results in improvement in lung function, reduction in asthma symptoms, and decreased need for alternative asthma treatments (Persson et al., (1995) *Anesthesiology* 82:969; Israel et al., (1993) *Ann. Int. Med.* 119:1059). However, in patients with asthma, there is a heterogeneous response to treatment with 5-LO inhibitors. Mutations in the 5-LO gene sequence may be associated with responsiveness to therapy and/or susceptibility to diseases or disorders, e.g., 5 asthma.

The 5-LO gene has been cloned, both as a cDNA (Matsumoto et al., (1988) *Proc. Natl. Acad. Sci. USA* 85:3406; Dixon et al., (1988) *Proc. Natl. Acad. Sci. USA* 85:416; Balcarek et al., (1988) *J. Biol. Chem.* 263:13937) and as a genomic clone (Hoshiko et al., (1990) *Proc. Natl. Acad. Sci. USA* 87:9073; Funk et al., (1989) *Proc. Natl. Acad. Sci. USA* 86:2587). The 5-LO gene is approximately 85 kilobases in size and contains 14 exons and 15 introns. The region 88 to 212 base pairs upstream of the 5-LO translation start site contains a number of sequences known to be recognition sites for transcriptional regulators (Hoshiko et al., (1990) *Proc. Natl. Acad. Sci. USA* 87:9073, incorporated herein by reference). For example, binding sites for AP1 and Sp1, each of which can act as either a transcriptional activator or a transcriptional repressor, depending on context, are found in this region. With respect to the Sp1 binding site, it comprises 5 tandem Sp1 motifs (GGGCGG) found –147 to –176 base pairs upstream of the ATG translation start site. Deletions of the Sp1 motifs reduce transcription from this 5' upstream regulatory element (Hoshiko et al. (1990) *Proc. Natl. Acad. Sci. USA* 87:9073). Sp1 binding sites comprising such motifs are similarly found in the promoter region of a variety of other genes (Li et al., (1995) *Gene* 164:229; Wariishi et al., (1995) *Biochem. Biophys. Res. Commun.* 216:729; Tang et al., (1995) *Biochem. Biophys. Res. Commun.* 213:673; Khachigian et al., (1995) *J. Bio. Chem.* 270:27679).

Certain polymorphisms in the 5-LO gene have been shown to be correlated with patient responsiveness to 5-LO inhibitor therapy (U.S. Pat. No. 6,090,547 by Drazen, et al. (2000)). Drazen et al. disclosed that asthma patients having polymorphisms associated with reduced 5-LO gene expression are less responsive to 5-LO inhibitor therapy than patients having normal 5-LO gene expression. Specifically, Drazen et al. showed that 5-LO promoters comprising a variant Sp1 binding site having 3, 4 or 6 Sp1 motifs were less active than the wild-type 5-LO promoter comprising a Sp1 bind site having 5 Sp1 motifs, and that asthma patients homozygous or heterozygous for 5-LO alleles comprising S-LO promoters having such variant Sp1 binding sites were less responsive to S-LO inhibitor therapy than patient homozygous for the wild-type 5-LO allele. Drazen et al. also showed that the 3 Sp1 motif binding site is in linkage disequilibrium with a G to A polymorphism in exon 2 of the 5-LO gene, and that the 4 Sp1motif binding site is in linkage disequilibrium with a C to T polymorphism in exon 1 of the 5-LO gene.

It would also be desirable to identify additional polymorphisms within the 5-LO gene which are in linkage disequilibrium with a variant Sp1 binding site in the 5-LO promoter. It would further be desirable, to provide prognostic, diagnostic, pharmacogenomic and therapeutic methods utilizing the identified polymorphisms.

SUMMARY OF THE INVENTION

The present invention relates to polymorphisms in the 5-LO gene. The invention is based, in part, on the discovery of a novel 5-LO haplotype which comprises five sequence polymorphisms within the 5-LO gene that are in linkage disequilibrium with each other. The five 5-LO polymorphisms are set forth in Table 1. Three of these, 5loprr1, 5lo01a and 5lo04a, are newly identified polymorphisms. The other two, 5lonrra and 5lonrrb, have been described by In et al. in *J. Clinical invest.* 99:1130–1137 (1997). The present invention is based, also in part, on the discovery that the haplotype of the invention is in linkage disequilibrium with any one of three variant Sp1 binding sites in the 5-LO promoter region that were previously reported by Drazen et al. U.S. Pat. No. 6,090,547). Accordingly, any one of the five polymorphisms of the invention is a marker for the other four polymorphisms and a variant Sp1 binding site having 3, 4 or 6 Sp1 motifs in the 5-LO promoter region. Moreover, since Drazen et al. (id.) demonstrated that asthma patients homozygous or heterozygous for a 5-LO allele comprising any one of such variant Sp1 binding sites are less susceptible to effective treatment with 5-LO inhibitor therapy, the haplotype of the invention is also a marker of reduced responsiveness amongst inflammatory or allergy disease patients to 5-LO inhibitor therapy.

The present invention is based further, in part, on the discovery that the 5lo01a polymorphism of the invention is associated with an abnormally low eosinophil count. That is, individuals heterozygous or homozygous for the 5lo01a polymorphism have been found to have significantly lower eosinophil levels compared to individuals not having the polymorphism. Thus, the haplotype of the invention and each of its component polymorphisms are all markers of low eosinophil levels.

The invention provides a method for identifying an inflammatory or allergy disease patient who is less susceptible to effective treatment with a 5-LO inhibitor, comprising determining the presence or absence of a 5-LO allelic variant comprising a sequence selected from the group consisting of those set forth in SEQ ID NO: 4, SEQ ID NO:5, and SEQ ID NO:6, or the complement of the sequence in a nucleic acid sample from an inflammatory or allergy disease patient, wherein the presence of the 5-LO allelic variant in the sample indicates that the patient is less susceptible to effective treatment with a 5-LO inhibitor. In one embodiment, the 5-LO allelic variant comprises the sequences of those set forth in SEQ ID NO:4, SEQ ID NO:5, and SEQ ID NO:6, or the complement of each of those sequences. In another embodiment, the 5-LO allelic variant comprises the sequences of those set forth in SEQ ID NO:4, SEQ ID NO:5, and SEQ ID NO:6, SEQ ID NO:7, and SEQ ID NO:8, or the complement of each of those sequences. In yet another embodiment, the 5-LO allelic variant comprises: (a) a sequence selected from the group consisting of those set forth in SEQ ID NO: 4, SEQ ID NO:5, and SEQ ID NO:6, or the complement of each of those sequences; and (b) a variant Sp1 binding site having a 3, 4 or 6 Sp1 motif. In yet another embodiment, the 5-LO allelic variant comprises: (a) a sequence selected from the group consisting of those set forth in SEQ ID NO: 4, SEQ ID NO:5, and SEQ ID NO:6, SEQ ID NO:7, and SEQ ID NO:8, or the complement of each of those sequences; and (b) a variant Sp1 binding site having a 3, 4 or 6 Sp1 motif.

The invention also provides a method for identifying a patient with an abnormally low eosinophil level, comprising determining the presence or absence of a 5-LO allelic variant comprising a sequence selected from the group consisting of those set forth in SEQ ID NO: 4, SEQ ID NO:5, and SEQ ID NO:6, or the complement of the sequence in a nucleic acid sample from a patient, wherein the presence of the 5-LO allelic variant in the sample indicates that the patient has an abnormally low eosinophil level. In one embodiment, the 5-LO allelic variant comprises the sequences of those set forth in SEQ ID NO:4, SEQ ID NO:5, and SEQ ID NO:6, or the complement of each of those sequences. In another embodiment, the 5-LO allelic variant comprises the sequences of those set forth in SEQ ID NO:4, SEQ ID NO:5, and SEQ ID NO:6, SEQ ID NO:7, and SEQ ID NO:8, or the complement of each of those sequences. In yet another embodiment, the 5-LO allelic variant comprises: (a) a sequence selected from the group consisting of those set forth in SEQ ID NO: 4, SEQ ID NO:5, and SEQ ID NO:6, or the complement of each of those sequences; and (b) a variant Sp1 binding site having a 3, 4 or 6 Sp1 motif In yet another embodiment, the 5-LO allelic variant comprises: (a) a sequence selected from the group consisting of those set forth in SEQ ID NO: 4, SEQ ID NO:5, and SEQ ID NO:6, SEQ ID NO:7, and SEQ ID NO:8, or the complement of each of those sequences; and (b) a variant Sp1 binding site having a 3, 4 or 6 Sp1 motif. In a preferred embodiment, the patient is an inflammatory or allergy disease patient. In a more preferred embodiment, the patient is an asthma patient.

It is believed that inflammatory or allergy disease patients having abnormally low eosinophil levels have milder disease symptoms than patients having normal eosinophil levels. Accordingly, the instant invention further provides a method for determining the severity of disease symptoms in an inflammatory or allergy disease patient comprising determining the presence or absence of a 5-LO allelic variant comprising a sequence selected from the group consisting of those set forth in SEQ ID NO: 4, SEQ ID NO:5, and SEQ ID NO:6, or the complement of the sequence in a nucleic acid sample from the patient, wherein the presence of the 5-LO allelic variant in the sample indicates that the patient has or will less severe disease symptoms than patients having wild-type 5-LO alleles. In one embodiment, the 5-LO allelic variant comprises the sequences of those set forth in SEQ ID NO:4, SEQ ID NO:5, and SEQ ID NO:6, or the complement of each of those sequences. In another embodiment, the 5-LO allelic variant comprises the sequences of those set forth in SEQ ID NO:4, SEQ ID NO:5, and SEQ ID NO:6, SEQ ID NO:7, and SEQ ID NO:8, or the complement of each of those sequences. In yet another embodiment, the 5-LO allelic variant comprises: (a) a sequence selected from the group consisting of those set forth in SEQ ID NO: 4, SEQ ID NO:5, and SEQ ID NO:6, or the complement of each of those sequences; and (b) a variant Sp1 binding site having a 3, 4 or 6 Sp1 motif. In yet another embodiment, the 5-LO allelic variant comprises: (a) a sequence selected from the group consisting of those set forth in SEQ ID NO: 4, SEQ ID NO:5, and SEQ ID NO:6, SEQ ID NO:7, and SEQ ID NO:8, or the complement of each of those sequences; and (b) a variant Sp1 binding site having a 3, 4 or 6 Sp1 motif. In a preferred embodiment, the patient is an asthma patient.

The invention also provides isolated nucleic acids comprising the novel 5-LO polymorphisms and the haplotype of the invention. The nucleic acid molecules of the invention include specific 5-LO allelic variants which differ from the reference 5-LO sequences set forth in SEQ ID NO:1 (GI 187166), SEQ ID NO: 2 (GI 8247778), SEQ ID NO:3 (GI 4502056). The preferred nucleic acid molecules of the invention comprise newly identified 5-LO allelic variants or portions thereof having the any of the novel polymorphisms shown in Table 1 (i.e., those comprising the sequence of any of those set forth in SEQ ID NOs:4–6 or the complement thereof), polymorphisms in linkage disequilibrium with the polymorphisms shown in Table 1, and combinations thereof. The haplotype also includes known polymorphisms. These known polymorphisms include a guanine to adenine change in the 5' upstream regulatory element at residue 84 of SEQ ID NO:1 (GI 187166) and a guanine to adenine change in the 5' upstream regulatory element at residue 137 of SEQ ID NO:1 (GI 187166) (In, et al. (1997) *J. Clinical Invest.* 99:1130–1137). These known polymorphisms are also listed in Table 1 under "Known SNPs" and correspond to SEQ ID NOs.:7 and 8. These known polymorphisms may be used in combination with the newly identified polymorphisms of the present invention in the diagnostic, prognostic, pharmacogenomic and therapeutic methods described herein.

The haplotype of the invention is in linkage disequilibrium with known polymorphisms in the promoter region of the 5-LO gene. These polymorphisms are variations at the Sp1 binding site as described in U.S. Pat. No. 6,090,547 and In, et al. ((1997) *J. Clin. Invest.* 99(5):1130–1137). The wild-type 5-LO gene has a Sp1 binding site comprising five Sp1 motifs in tandem. Each of the Sp1 motifs consists of the nucleotide sequence "GGCGGG" (SEQ ID NO:61). The wild-type Sp1 site is located at nucleotide residues 1670–1699 in the reference sequence GI 187166 (SEQ ID NO:1). Polymorphisms contained within the Sp1 binding site repeat which are referred to herein as "variant Sp1 binding sites" have the deletion of one, the deletion of two, or the addition of one, Sp1 binding motif in the promoter region of the 5-LO gene resulting in three, four, or six Sp1 motifs.

The nucleic acid molecules of the invention can be double- or single-stranded. Accordingly, in one embodiment of the invention, a complement of the nucleotide sequence is provided wherein the polymorphism has been identified. For example, where there has been a single nucleotide change from a guanine to an adenine in a single strand, the complement of that strand will contain a change from cytidine to thymine at the corresponding nucleotide residue.

Nucleic acids of the invention can function as probes or primers, e.g., in methods for determining the allelic identity of a 5-LO polymorphic region in a nucleic acid of interest. The invention further provides vectors comprising the nucleic acid molecules of the present invention; host cells transfected with said vectors whether prokaryotic or eukaryotic; and transgenic non-human animals which contain a heterologous form of a functional or non-functional 5-LO allele described herein. Such a transgenic animal can serve as an animal model for studying the effect of specific 5-LO allelic variations, including mutations, as well as for use in drug screening and/or recombinant protein production.

The invention further provides methods for determining the molecular structure of at least a portion of a 5-LO gene. In a preferred embodiment, the method comprises contacting a sample nucleic acid comprising a 5-LO gene sequence with a probe or primer having a sequence which is complementary to a 5-LO gene sequence, carrying out a reaction that would amplify and/or detect differences in a region of interest within the 5-LO gene sequence, and comparing the result of each reaction with that of a reaction with a control (known) 5-LO gene (e.g., a 5-LO gene from a human not afflicted with an inflammatory condition e.g., asthma, or another disease associated with an aberrant 5-LO activity) so as to determine the molecular structure of the 5-LO gene sequence in the sample nucleic acid. The method of the invention can be used for example in determining the molecular structure of at least a portion of an exon, an intron, a 5' upstream regulatory element, or the 3' untranslated region. In a preferred embodiment, the method comprises determining the identity of at least one nucleotide. In another preferred embodiment, the method comprises determining the nucleotide at residue 1000 of the reference sequence GI 8247778, any one of residues 472–477 of the reference sequence GI 187166, and/or residue 559 of the reference sequence GI 187166, and combinations thereof. In another embodiment, the method comprises determining the nucleotide at residue 1000 of the reference sequence GI 8247778, any one of residues 472–477 of the reference sequence GI 187166, and/or residue 559 of the reference sequence GI 187166, the nucleotide at residue 84 of GI 187166, and/or the nucleotide at residue 137 of GI 187166. In a further embodiment, the method comprises determining the nucleotide at residue 1000 of the reference sequence GI 8247778, any one of residues 472–477 of the reference sequence GI 187166, and/or residue 559 of the reference sequence GI 187166, and the number of Sp1 motifs in the promoter region of the 5-LO gene.

In another preferred embodiment, the method comprises determining the nucleotide content of at least a portion of a 5-LO gene, such as by sequence analysis. In yet another embodiment, determining the molecular structure of at least a portion of a 5-LO gene is carried out by single-stranded conformation polymorphism (SSCP). In yet another embodiment, the method is an oligonucleotide ligation assay (OLA). Other methods within the scope of the invention for determining the molecular structure of at least a portion of a 5-LO gene include hybridization of allele-specific oligonucleotides, sequence specific amplification, primer specific extension, and denaturing high performance liquid chromatography (DHPLC). In at least some of the methods of the invention, the probe or primer is allele specific. Preferred probes or primers are single stranded nucleic acids, which optionally are labeled.

The invention further provides forensic methods based on detection of polymorphisms in the 5-LO gene.

The invention also provides probes and primers comprising oligonucleotides which hybridizes to at least 6 consecutive nucleotides of any of the sequences set forth in SEQ ID NOs: 4–6, or to the complement of any of such sequences, or naturally occurring mutants or variants thereof. In preferred embodiments, the probe/primer further includes a label attached thereto, which is capable of being detected.

In another embodiment, the invention provides a kit for amplifying and/or for determining the molecular structure of at least a portion of a 5-LO gene, comprising a probe or primer capable of hybridizing to a 5-LO gene and instructions for use. In one embodiment, the probe or primer is capable of hybridizing to a 5-LO intron. In another embodiment, the probe or primer is capable of hybridizing to a 5-LO allelic variant, preferrably a variant corresponding to 5 loprr1, 5lo01a or 5lo04a. In another preferred embodiment, the polymorphic region is located in the 5' upstream regulatory element. In a preferred embodiment, determining the molecular structure of a region of a 5-LO gene comprises determining the identity of the allelic variant of the polymorphic region. Determining the molecular structure of at least a portion of a 5-LO gene can comprise determining the identity of at least one nucleotide or determining the nucleotide composition, e.g., the nucleotide sequence.

A kit of the invention can be used, e.g., for determining whether a patient will or will not be responsive to effective treatment of a disease associated with a specific 5-LO allelic variant, e.g., asthma, with a 5-LO inhibitor. In a preferred embodiment, the invention provides a kit for determining whether a patient will or will not be responsive to treatment of a inflammatory or allergic disease or condition associated with abnormal leukotriene synthesis, for example, asthma. The kit of the invention can also be used in selecting the appropriate drug to administer to a patient to treat such a disease or condition.

In another aspect, the invention provides a kit for determining whether a inflammatory or allergic disease patient has a more moderate or more severe disease phenotype associated with a specific 5-LO allelic variant of a polymorphic region. In one embodiment, the disease or disorder is characterized by an abnormal 5-LO activity, e.g., aberrant 5-LO expression. In another embodiment, the disease or disorder is characterized by an abnormal eosinophil levels.

Other features and advantages of the invention will be apparent from the following detailed description and claims.

BRIEF DESCRIPTION OF THE FIGURES

FIG. 1 depicts the nucleotide sequence corresponding to reference sequence GI 87166 (SEQ ID NO:1).

FIG. 2 depicts the nucleotide sequence corresponding to reference sequence GI 8247778 (SEQ ID NO:2).

FIG. 3 depicts the nucleotide sequence corresponding to reference sequence GI 4502056 (SEQ ID NO:3).

FIG. 4 depicts the nucleotide sequence corresponding to reference sequence GI 9887688 (SEQ ID NO:63).

DETAILED DESCRIPTION OF THE INVENTION

The present invention is based, in part, on the identification of polymorphisms in the 5-LO gene which are associated with inflammatory or allergic disease phenotypes, including the asthma phenotype. The present invention is based, also in part, on the discovery of a haplotype comprising five polymorphisms within the promoter region of the 5-LO gene. As used herein, the term "haplotype" refers to a set of polymorphisms which are in linkage disequilibrium with each other. That is, the polymorphisms comprising the haplotype segregate together. The haplotype identified herein comprises novel polymorphisms and previously known polymorphisms as described herein and as set forth in Table 1.

The haplotype of the invention also has been found to be in linkage disequilibrium with any one of the three variant Sp1 binding sites disclosed in U.S. Pat. No. 6,090,047. Ethnic populations differ in the linked variant Sp1 binding site. In Caucasian and Chinese populations, the haplotype is in linkage disequilibrium with the variant Sp1 binding site containing four Sp1 motifs. Whereas in the African American population, the haplotype is in linkage disequilibrium with any one of the three variant Sp1 binding sites (i.e., variant Sp1 binding sites having 3, 4 or 6 Sp1 motifs).

It has been determined that the presence of a variant Sp1 binding site in the 5-LO promoter region reduced 5-LO gene expression (U.S. Pat. No. 6,090,547). Therefore, given that the haplotype of invention is linked to a variant Sp1 binding site, the haplotype and its constituent polymorphisms are all markers of reduced 5-LO gene expression. That is, detection of the haplotype or any of its constituent polymorphims can be used to predict whether or not a patient has decreased 5-LO gene expression as compared to patients homozygous for the wild-type 5-LO gene.

The present invention also relates to the discovery that asthmatic individual heterozygous or homozygous for a 5-LO allele comprising the 5lo01a polymorphism have significantly decreased eosinophil levels as compared to related family members having no such allele. While not intending to be bound by any specific theory, the association between the 5lo01a polymorphism and reduced eosinophil levels may be explained by recent studies that showed that some metabolites of 5-LO can induce production of eosinophils (Urasaki, et al. (2001) *J. Leukocyle Biol.* 69(1):105–112 and Powell et al., (2001) *J. Allergy. Clin. Immunol.* 107(2):272–278). Specifically, where an allele comprises the 5lo01a polymorphism, the allele also necessarily comprises the haplotype of the invention and a variant Sp1 binding site. 5-LO alleles comprising a variant Sp1 binding site have reduced levels of 5-LO expression which, in turn, result in reduced levels of 5-LO metabolites, thereby ultimately resulting in a reduction in the number of activated eosinophils. Thus, the presence of the haplotype or one or more polymorphisms comprising the haplotype can be used to predict whether a patient has a greater chance of having abnormally low eosinophil count. Eosinophil counts are used as an index of asthmatic disease, and reflect an asthma-related phenotype (see, for example, Jatakanon, A., et al. (2000) *Am. J. Respir. Crit. Care Med* 161(1):64; Kamfar, et al. (1999) *J. Asthma* 36(2):153; and Lonnkivist, K. et al. (2001) *J. Allergy Clin. Immunol.* 107(5):812). High eosinophil counts in asthma patients are associated with a more severe asthma phenotype as compared to the asthma phenotype in asthma patients having low eosinophil counts. Accordingly, determination of any polymorphism comprising the haplotype of the invention can be used to predict whether an asthma patient has or will have a moderate disease phenotype. Moreover, determination of any polymorphism comprising the haplotype can be used to differentiate among asthmatic populations to those having a moderate disease phenotype and those having a relatively more severe disease phenotype. A disease phenotype, e.g., the asthma phenotype, may be defined by established clinical parameters (see, for example, Moffitt et al. (1994) *Am. Fam. Phys.* 50:1039).

Pharmacogenetic studies have shown that the genetic background of individuals play a role in determining the response of an individual to a specific drug. Thus, determining the allelic variants of 5-LO polymorphic regions of an individual can be useful in predicting how an individual will respond to a specific drug, e.g., a drug for treating a disease or disorder associated with aberrant 5-LO activity and/or an inflammatory or allergic disease such as asthma As described above, specific 5-LO polymorphisms comprising the haplotype of the present invention result in increased or decreased production or expression of the 5-LO polypeptide. Accordingly, the action of a drug necessitating interaction with a 5-LO protein will be different in individuals carrying such a 5-LO allele. Furthermore, identification of polymorphisms in the 5-LO gene which indicate responsiveness to 5-LO inhibitor therapy are beneficial in the treatment of inflammatory diseases such as asthma because they can serve as markers by which the most appropriate treatment for inflammatory diseases or disorders can be identified.

Accordingly, preferred embodiments of the present invention include methods of identifying inflammatory or allergy disease patients who are likely to be more or less responsive to treatment with 5-LO inhibitors (e.g., a 5-LO inhibitor as described in U.S. Pat. Nos. 5,703,093, 5,750,565 or 6,025,384, the contents of which are incorporated herein by reference). For example, the presence of a variant Sp1 binding site indicates decreased expression of the 5-LO gene and decreased responsiveness to treatment with 5-LO inhibitors (see U.S. Pat. No. 6,090,547 and In, et al. (1997), supra). Accordingly, the presence of any one of the polymorphisms comprising the haplotype of the present invention indicates the presence of a variant Sp1 binding site and thus the associated decreased expression of the 5 -LO gene and decreased responsiveness to treatment with 5-LO inhibitors.

Therefore, the methods of the invention can be used to predict or determine whether a patient will be more or less responsive to treatment with a 5-LO inhibitor or other compounds or agents which interfere with the leukotriene metabolic pathway. These methods are applicable to all inflammatory and allergic diseases in which treatment with 5-LO inhibitors or related agents is appropriate, and in particular, to asthma.

There are multiple alleles of the 5-LO gene. The reference 5-LO gene sequence designated herein is presumed to be the wild-type 5-LO gene sequence and comprises nucleotide sequences that have been deposited in GENBANK™ and assigned the Accession Number GI 187166, GI 8247778, and GI 4502056 (corresponding to SEQ ID NO:1, SEQ ID NO:2, and SEQ ID NO:3, respectively). The present invention relates to variant alleles of the 5-LO gene that differ from the reference 5-LO gene sequence by at least one of the polymorphisms identified in Table 1, and those in linkage equilibrium therewith. The present invention thus relates to nucleic acids comprising such variant 5-LO alleles.

The invention further relates to nucleic acids comprising portions of such variant 5-LO alleles that contain the haplotype of the invention or any of the novel 5-LO polymorphisms identified in Table 1 and are at least 5 nucleotides or basepairs in length. Portions can be, for example, 5–10, 5–15, 10–20, 2–25, 10–30, 10–50 or 10–100 nucleotides or basepairs long. For example, a portion of a variant allele which is 21 nucleotides or basepairs in length includes a 5-LO polymorphism (i.e., a nucleotide which differs from the corresponding nucleotide in the reference 5-LO sequence) and twenty additional nucleotides or basepairs which flank the polymorphism in the variant allele. These additional nucleotides and basepairs can be on one or both sides of the polymorphism. Polymorphisms of the invention are defined in Table 1 with respect to specific reference 5-LO sequences identified in Table 1 (GI 187166, GI 8247778, or GI 4502056). For example, the 5loprr1 polymorphism consists of an adenine substitution for the guanine at residue 1000 of the GI 187166 reference sequence (SEQ ID NO:1).

The 5-LO polymorphisms of the present invention have been identified in the human 5-LO gene by analyzing the DNA of human populations. In particular, DNA samples from 144 individuals were obtained and used for polymorphism discovery. These 144 DNA samples included samples from a population of forty-eight North American Caucasian individuals, forty-eight African American individuals, and forty-eight individuals from throughout the Anhui province in East Central China. The same frequency of 5-LO allelic variants was identified in all three of these groups. Furthermore, the forty-eight DNA samples from the Chinese individuals are from unrelated control patients, enrolled at random. Those patients were assessed for a number of traits related to asthma and allergies. Among the primary variables of interest were lung function, a response to "skin-prick" tests, physician's diagnosis of asthma, total serum IgE, and peripheral blood eosinophils. The peripheral blood eosinophil count was measured using the Coulter counter technique as described in Barnard D. F., et al. (1989) *Clin Lab Haematol* 11 (3):255–66, and is expressed in terms of eosinophils per microliter. The allelic variants of the present invention were identified by performing denaturing high performance liquid chromatography (DHPLC) analysis, the polymerase chain reaction (PCR), and/or single stranded conformation polymorphism (SSCP) analysis of genomic DNA from independent individuals as described in Example 1, using PCR primers complementary to intronic sequences surrounding each of the exons, 3' UTR, and 5' upstream regulatory element sequences of the 5-LO gene. The nucleotide sequence of these PCR primers (having SEQ ID NOs.:9–60) is shown in Table 3 (see the Examples).

The presence of three novel polymorphisms in the human 5-LO gene were identified in the populations studied. Two of the polymorphisms were characterized as single nucleotide polymorphisms (SNPs). The remaining polymorphism comprises deletions of two or more nucleotides from the reference 5-LO sequence. This variant is referred to herein as a "deletion variant."

One polymorphism found in the population screened is a change from a guanine to an adenine in the 5' upstream regulatory element of the 5-LO gene at residue 1000 of the reference sequence GI 187166 polymorphism ID No. 5loprr1). A second polymorphism is a deletion in the 5' upstream regulatory element at residues 472–477 of the reference sequence GI 187166 (polymorphism ID No. 5lo01a). A third polymorphism is a change from a guanine to an adenine in the 5' upstream regulatory element at residue 559 of the reference sequence GI 187166 (polymorphism ID No. 5lo04a). These polymorphisms are listed in Table 1 and correspond to SEQ ID NOs: 4–6.

Additional polymorphisms which are included in the haplotype of the present invention have also been identified in the 5-LO gene. These polymorphisms include a guanine to adenine change in the 5' upstream regulatory element at residue 84 of the reference sequence GI 187166 (polymorphism ID No. 5lonrra) and a guanine to adenine change in the 5' upstream regulatory element at residue 137 of the reference sequence GI 187166 (polymorphism ID No. 5lonrrb (In, et al. (1997) *J. Clinical Invest* 99:1130–1137). These known polymorphisms are also listed in Table 1 under "Known SNPs" and correspond to SEQ ID NOs.:7 and 8. These known polymorphisms may be used in combination with the polymorphisms of the present invention in the diagnostic, prognostic, pharmacogenomic and therapeutic methods described herein.

The haplotype of the present invention were found to be in linkage disequilibrium with polymorphisms that have been identified in the promoter region of the 5-LO gene. These polymorphisms are variations in the Sp1 binding site as described in U.S. Pat. No. 6,090,547 and In, et al. ((1997) *J. Clin. Invest.* 99(5): 1130–1137), the contents of which are incorporated herein by reference. The wild-type 5-LO gene has a Sp1 binding site that comprises five Sp1 motifs in tandem at nucleotide residues 1670–1699 in the reference sequence GI 187166 (SEQ ID NO;1). Each of the motifs has the nucleotide sequence "GGCGGG" (SEQ ID NO:61). Polymorphisms at the Sp1 binding site are referred to herein as "variant Sp1 binding sites" and have the deletion of one or two Sp1 motifs from, or the addition of one Sp1 motif to the wild-type Sp1 binding site, resulting variant Sp1 binding sites containing three, four, or six Sp1 motifs. These known Sp1 binding site polymorphisms may be used in combination with the polymorphisms and haplotype of the present invention in the diagnostic, prognostic, pharmacogenomic and therapeutic methods described herein.

Table 1 contains a "polymorphism ID No." in column 2, which is used herein to identify each individual 5-LO polymorphism. In Table 1, the nucleotide sequence flanking each polymorphism is provided in column 3, wherein the polymorphic residue(s), having the wild-type or reference nucleotide, is indicated in lower-case letters. There are 10 nucleotides flanking the polymorphic nucleotide residue (i.e., 10 nucleotides 5' of the polymorphism and 10 nucleotides 3' of the polymorphism). Column 1 indicates the sequence listing identifier number (SEQ ID NO.) of the sequence shown in column 3 but with a variant nucleotide at the residue(s) shown in lower-case letter(s) or with a deletion of the sequences contained within the parenthesis. For example, SEQ ID NO:4 contains an adenine ("a") at the location indicated by the lower-case letter "g" in the corresponding sequence in column 3. Therefore, SEQ ID NO:4 is identical to the corresponding sequence in column 3, except that the "g" (guanine) residue is replaced by an "a" (adenine residue). The deletion variant, polymorphism ID Nos. 5lo1a, lacks the deleted residues, which are identified by parenthesis in column 3. In Table 1, the location of some primers that may be used to detect each polymorphism is indicated in column 4. For example, primer location "2" indicates that the primers were designed to flank exon 2 and a portion of the surrounding intronic sequence. In column 5, the location of the polymorphism within the 5-LO gene is also provided, identifying the polymorphism as located in the 5' upstream regulatory element, the 3' untranslated region, or in an intron or an exon. Column 5 also identifies, for each SNP or deletion, the specific nucleotide change (i.e., "5' upstream regulatory element G/A" refers to a single nucleotide polymorphism within the 5' upstream regulatory element resulting in a change from a guanine in the reference sequence to an adenine in the variant allele).

Each polymorphism is identified based on a change in the nucleotide sequence from a "reference sequence." As used herein, the reference sequence is the nucleotide sequence of SEQ ID NO:1 which corresponds to GI 187166 (see FIG. 1), the nucleotide sequence of SEQ ID NO:2 which corresponds to GI 247778 (see FIG. 2), or the nucleotide sequence of SEQ ID NO:3, which corresponds to GI 4502056 (see FIG. 3).

To identify the location of each polymorphism in Table 1, a specific nucleotide residue in a reference sequence is listed for each polymorphism, where nucleotide residue number 1 is the first (i.e., 5') nucleotide in GI 187166 (corresponding to SEQ ID NO:1), the first nucleotide in GI 8247778 (corresponding to SEQ ID NO:2) or the first nucleotide in GI 450205 (corresponding to SEQ ID NO:3). Column 6 lists the reference sequence and polymorphic residue(s) for each polymorphism. For example, polymorphism ID No. 5loprr1 is a single nucleotide polymorphism (SNP) in the 5' upstream regulatory element of the 5-LO gene which results in a change from a guanine to an adenine in the reference sequence GI 187166 (corresponding to SEQ ID NO:1). The SNP is located at residue number 1000 in the reference sequence (SEQ ID NO:1) starting from residue 1 at the 5' end of the nucleotide sequence.

As can be seen in Table 1, one polymorphism found in the population is a change from a guanine to an adenine in the 5' upstream regulatory element region of the 5-LO gene at residue 1000 of GI 18766 (polymorphism ID No. 5loprr1) (SEQ ID NO:4). A second polymorphism is a deletion in the 5' upstream regulatory element at residues 472477 of GI 18766 (polymorphism ID No. 5lo01a) (SEQ ID NO:5). A third polymorphism is a change from a guanine to an adenine in the 5' upstream regulatory element at residue 559 of GI 18766 (polymorphism ID No. 5lo04a) (SEQ ID NO:6). The nucleic acid molecules of the invention can be double- or single-stranded. Accordingly, the invention further provides for the nucleic acid strands comprising sequences complementary to the sequences listed in column 3 of Table 1.

The invention further provides allele-specific oligonucleotides that hybridize to a gene comprising a polymorphism of the invention. Such oligonucleotides will hybridize to one polymorphic form of the nucleic acid molecules described herein but not to the other polymorphic form(s) of the sequence. Thus such oligonucleotides can be used to determine the presence or absence of particular alleles of the polymorphic sequences described herein. These oligonucleotides can be probes or primers.

Not only does the present invention provide for polymorphisms in linkage disequilibrium with the polymorphisms of Table 1, it also provides methods for revealing the existence of yet other polymorphisms in the human 5-LO gene. For example, the polymorphism studies described herein can also be applied to populations in which other inflammatory diseases or allergic disease or disorders are prevalent.

Other aspects of the invention are described below or will be apparent to one of skill in the art in light of he present disclosure.

Definitions

For convenience, the meaning of certain terms and phrases employed in the specification, examples, and appended claims are provided below.

The term "inflammatory disease or allergic disease or disorder" as used herein refers to any disease or disorder characterized by an aberrant inflammatory response. An aberrant inflammatory response includes, for example, abnormal (e.g., an increased or decreased) production of leukotriene molecules. Examples of inflammatory or allergic diseases or disorders include, but are not limited to, asthma, bronchitis, sinusitis, ulcerative colitis, nephritis, amyloidosis, rheumatoid arthritis, sarcoidosis, scleroderma, lupus, non-allergic rhinitis, polymyositis, Reiter's syndrome, psoriasis, pelvic inflammatory disease, orbital inflammatory disease, thrombotic disease, and inappropriate allergic responses to environmental stimuli such as poison ivy, pollen, insect stings and certain foods, including atopic dermatitis and contact dermatitis.

The term "allele," which is used interchangeably herein with "allelic variant" and "variant allele", refers to alternative forms of a gene or portions thereof. Alleles occupy the same locus or position on homologous chromosomes. When a patient has two identical alleles of a gene, the patient is said to be homozygous for the gene or allele. When a patient has two different alleles of a gene, the patient is said to be heterozygous for the gene. Alleles of a specific gene, including 5-LO, can differ from each other in a single nucleotide, or several nucleotides, and can include substitutions, deletions, and insertions of nucleotides. An allele of a gene can also be a form of a gene containing one or more mutations.

The term "allelic variant of a 5-LO gene" or "5-LO allelic variant" refers to an alternative form of the 5-LO gene having one of several possible nucleotide sequences found in same position within the gene in the population. The predominate alleles in the population are referred to as "wild-type" alleles.

"Biological activity" or "bioactivity" or "activity" or "biological function", which are used interchangeably, for the purposes herein when applied to 5-LO, means an effector or antigenic function that is directly or indirectly performed by a 5-LO polypeptide (whether in its native or denatured conformation), or by a fragment thereof Biological activities include modulation of the stereo-specific addition of molecular oxygen to arachidonic acid to form leukotriene A4, thereby modulating synthesis of leukotrienes and modulating inflammatory response, and other biological activities, whether presently known or inherent. A 5-LO bioactivity can be modulated by directly affecting a 5-LO protein effected by, for example, changing the level of effector or substrate level. Alternatively, a 5-LO bioactivity can be modulated by modulating the level of a 5-LO protein, such as by modulating expression of a 5-LO gene. Antigenic functions include possession of an epitope or antigenic site that is capable of cross-reacting with antibodies that bind a native or denatured 5-LO polypeptide or fragment thereof.

Biologically active 5-LO polypeptides include polypeptides having both an effector and antigenic function, or only one of such functions. 5-LO polypeptides include antagonist polypeptides and native 5-LO polypeptides, provided that such antagonists include an epitope of a native 5-LO polypeptide. An effector function of 5-LO polypeptide can be the ability to bind to a ligand, e.g., an arachidonic acid or modified form thereof As used herein the term "bioactive fragment of a 5-LO protein" refers to a fragment of a fill-length 5-LO protein, wherein the fragment specifically mimics or antagonizes the activity of a wild-type 5-LO protein. The bioactive fragment preferably is a fragment capable of binding to a second molecule, such as a ligand.

The term "an aberrant activity" or "abnormal activity", as applied to an activity of a protein such as 5-LO, refers to an activity which differs from the activity of the wild-type (i.e., normal) protein or which differs from the activity of the protein in a healthy subject, e.g., a subject not afflicted with a disease associated with a 5-LO allelic variant. An activity of a protein can be aberrant because it is stronger than the activity of its wild-type counterpart. Alternatively, an activity of a protein can be aberrant because it is weaker or absent relative to the activity of its wild-type counterpart. An aberrant activity can also be a change in reactivity. For example an aberrant protein can interact with a different protein or ligand relative to its wild-type counterpart. A cell can also have aberrant 5-LO activity due to overexpression or underexpression of the 5-LO gene. Aberrant 5-LO activity can result from a mutation in the gene, which results, e.g., in lower or higher binding affinity of a lipid to the 5-LO protein encoded by the mutated gene. Aberrant 5-LO activity can also result from a lower or higher level of 5-LO receptor on cells, which can result, e.g., from a mutation in the 5' flanking region of the 5-LO gene or any other regulatory element of the 5-LO gene, such as a regulatory element located in an intron. Accordingly, aberrant 5-LO activity can result from an abnormal 5-LO 5' upstream regulatory element activity.

The terms "abnormal 5-LO 5' upstream regulatory element activity", "aberrant 5-LO 5' upstream regulatory element activity", "abnormal 5-LO promoter activity", "aberrant 5-LO promoter activity", "abnormal 5-LO transcriptional activity" and "aberrant 5-LO transcriptional activity", which are used interchangeably herein, refer to the transcriptional activity of a 5-LO 5' upstream regulatory element which differs from the transcriptional activity of the corresponding 5' upstream regulatory element in the wild-type 5-LO allele. Abnormal 5-LO activity can result from a higher or lower transcriptional activity as compared to transcriptional activity of a wild-type 5-LO allele. Aberrant 5-LO 5' upstream regulatory element activity can result, for example, from the presence of a genetic lesion in a regulatory element, such as in a 5' upstream regulatory element. An "aberrant 5-LO 5' upstream regulatory element activity" is also intended to refer to the transcriptional activity of a 5-LO 5' upstream regulatory element which is functional (capable of inducing transcription of a gene to which it is operably linked) in tissues or cells in which the normal or wild-type 5-LO 5' upstream regulatory element is not functional or which is non functional in tissues or cells in which the normal or wild-type 5-LO 5' upstream regulatory element is functional. Thus, a tissue distribution of 5-LO in a patient which differs from the tissue distribution of 5-LO in a normal (e.g., healthy) individual, can be the result of abnormal transcriptional activity from the 5-LO 5' upstream regulatory element. Such abnormal transcriptional activity can result from e.g., one or more mutations in a regulatory element, such as in a 5' upstream regulatory element thereof Abnormal transcriptional activity can also result from a mutation in a transcription factor involved in the control of 5-LO gene expression.

"Cells," "host cells" or "recombinant host cells" are terms used interchangeably herein. It is understood that such terms refer not only to the particular patient cell but to the progeny or derivatives of such a cell. Because certain modifications may occur in succeeding generations due to either mutation or environmental influences, such progeny may not, in fact, be identical to the parent cell, but are still included within the scope of the term as used herein.

As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389–3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, (1988) *CABIOS* 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444–2448. When using the FASTA algorithm for comparing nucleotide or amino acid sequences, a PAM120 weight residue table can, for example, be used with a k-tuple value of 2.

The term "a homolog of a nucleic acid" refers to a nucleic acid having a nucleotide sequence having a certain degree of homology with the nucleotide sequence of the nucleic acid or complement thereof. For example, a homolog of a double stranded nucleic acid having SEQ ID NO:N is intended to include nucleic acids having a nucleotide sequence which has a certain degree of homology with SEQ ID NO:N or with the complement thereof. Preferred homologs of nucleic acids are capable of hybridizing to the nucleic acid or complement thereof.

The term "hybridization probe" or "primer" as used herein is intended to include oligonucleotides which hybridize bind in a base-specific manner to a complementary strand of a target nucleic acid. Such probes include peptide nucleic acids, and described in Nielsen et al., (1991) *Science* 254:1497–1500. Probes and primers can be any length suitable for specific hybridization to the target nucleic acid sequence. The most appropriate length of the probe and primer may vary depending on the hybridization method in which it is being used; for example, particular lengths may be more appropriate for use in microfabricated arrays, while other lengths may be more suitable for use in classical hybridization methods. Such optimizations are known to the skilled artisan. Suitable probes and primers can range form about 5 nucleotides to about 30 nucleotides in length. For example, probes and primers can be 5, 6, 8, 10, 12, 14, 16, 18, 20, 22, 24, 25, 26, 28 or 30 nucleotides in length. The probe or primer of the invention comprises a sequence that flanks and/or preferably overlaps, at least one polymorphic site occupied by any of the possible variant nucleotides. The nucleotide sequence of an overlapping probe or primer can correspond to the coding sequence of the allele or to the complement of the coding sequence of the allele.

The term "interact" as used herein is meant to include detectable interactions between molecules, such as can be detected using, for example, a binding or hybridization assay. The term interact is also meant to include "binding" interactions between molecules. Interactions may be, for example, protein-protein, protein-nucleic acid, protein-small molecule or small molecule-nucleic acid in nature.

The term "intronic sequence" or "intronic nucleotide sequence" refers to the nucleotide sequence of an intron or portion thereof.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "linkage" describes the tendency of genes, alleles, loci or genetic markers to be inherited together as a result of their location on the same chromosome. It can be measured by percent recombination between the two genes, alleles, loci, or genetic markers. The term "linkage disequilibrium" refers to a greater than random association between specific alleles at two marker loci within a particular population. In general, linkage disequilibrium decreases with an increase in physical distance. If linkage disequilibrium exists between two markers within one gene, then the genotypic information at one marker can be used to make probabilistic predictions about the genotype of the second marker.

The term "locus" refers to a specific position in a chromosome. For example, a locus of a 5-LO gene refers to the chromosomal position of the 5-LO gene.

The term "modulation" as used herein refers to both upregulation, (i.e., activation or stimulation), for example by agonizing; and downregulation (i.e. inhibition or suppression), for example by antagonizing of a bioactivity (e.g. expression of a gene).

The term "molecular structure" of a gene or a portion thereof refers to the structure as defined by the nucleotide content (including deletions, substitutions, additions of one or more nucleotides), the nucleotide sequence, the state of methylation, and/or any other modification of the gene or portion thereof.

The term "mutated gene" refers to an allelic form of a gene that differs from the predominant form in a population. A mutated gene is capable of altering the phenotype of a patient having the mutated gene relative to a patient having the predominant form of the gene. If a patient must be homozygous for this mutation to have an altered phenotype, the mutation is said to be recessive. If one copy of the mutated gene is sufficient to alter the phenotype of the patient, the mutation is said to be dominant. If a patient has one copy of the mutated gene and has a phenotype that is intermediate between that of a homozygous and that of a heterozygous (for that gene) patient, the mutation is said to be co-dominant.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine", "cytidine", "guanosine", and thymidine" are used. It is understood that if the nucleic acid is RNA, a nucleotide having a uracil base is uridine.

The term "nucleotide sequence complementary to the nucleotide sequence set forth in SEQ ID NO:N" refers to the nucleotide sequence of the complementary strand of a nucleic acid strand having SEQ ID NO:N. The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID NO:N refers to the complementary strand of the strand having SEQ ID NO:N or to any nucleic acid having the nucleotide sequence of the complementary strand of SEQ ID NO:N. When referring to a single stranded nucleic acid having the nucleotide sequence SEQ ID NO:N, the complement of this nucleic acid is a nucleic acid having a nucleotide sequence which is complementary to that of SEQ ID NO:N. The nucleotide sequences and complementary sequences thereof are always given in the 5' to 3' direction. The term "complement" and "reverse complement" are used interchangeably herein.

A "non-human animal" of the invention can include mammals such as rodents, non-human primates, sheep, goats, horses, dogs, cows, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which an exogenous sequence is found, or in which an exogenous sequence is expressed in some but not all cells of the animal. The term "tissue-specific chimeric animal" indicates that an exogenous sequence is present and/or expressed or disrupted in some tissues, but not others.

The term "oligonucleotide" is intended to include and single- or double stranded DNA or RNA. Oligonucleotides can be naturally occurring or synthetic, but are typically prepared by synthetic means. Preferred oligonucleotides of the invention include segments of 5-LO gene sequence or their complements, which include and/or flank any one of the polymorphic sites shown in Table 1. The segments can be between 5 and 250 bases, and, in specific embodiments, are between 5–10, 5–20, 10–20, 10–50, 20–50 or 10–100 bases. For example, the segments can be 21 bases. The polymorphic site can occur within any position of the segment or a region next to the segment. The segments can be from any of the allelic forms of 5-LO gene sequence shown in Table 1.

The term "operably-linked" is intended to mean that the 5' upstream regulatory element is associated with a nucleic acid in such a manner as to facilitate transcription of the nucleic acid from the 5' upstream regulatory element.

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic locus can be a single nucleotide, the identity of which differs in the other alleles. A polymorphic locus can also be more than one nucleotide long. The allelic form occurring most frequently in a selected population is often referred to as the reference and/or wild-type form. Other allelic forms are typically designated or alternative or variant alleles. Diploid organisms may be homozygous or heterozygous for allelic forms. A diallelic or biallelic polymorphism has two forms. A trialleleic polymorphism has three forms.

A "polymorphic gene" refers to a gene having at least one polymorphic region.

The term "primer" as used herein, refers to a single-stranded oligonucleotide which acts as a point of initiation of template-directed DNA synthesis under appropriate conditions (e.g., in the presence of four different nucleoside triphosphates and as agent for polymerization, such as DNA or RNA polymerase or reverse transcriptase) in an appropriate buffer and at a suitable temperature. The length of a primer may vary but typically ranges from 15 to 30 nucleotides. A primer need not match the exact sequence of a template, but must be sufficiently complementary to hybridize with the template.

The term "primer pair" refers to a set of primers including an upstream primer that hybridizes with the 3' end of the complement of the DNA sequence to be amplified and a downstream primer that hybridizes with the 3' end of the sequence to be amplified.

The terms "protein", "polypeptide" and "peptide" are used interchangeably herein when referring to a gene product.

The term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

A "regulatory element", also termed herein "regulatory sequence" is intended to include elements which are capable of modulating transcription from a 5' upstream regulatory sequence, including, but not limited to a basic promoter, and include elements such as enhancers and silencers. The term "enhancer", also referred to herein as "enhancer element", is intended to include regulatory elements capable of increasing, stimulating, or enhancing transcription from a 5' upstream regulatory element, including a basic promoter. The term "silencer", also referred to herein as "silencer element" is intended to include regulatory elements capable of decreasing, inhibiting, or repressing transcription from a 5' upstream regulatory element, including a basic promoter. Regulatory elements are typically present in 5' flanking regions of genes. Regulatory elements also may be present in other regions of a gene, such as introns. Thus, it is possible that 5-LO genes have regulatory elements located in introns, exons, coding regions, and 3' flanking sequences. Such regulatory elements are also intended to be encompassed by the present invention and can be identified by any of the assays that can be used to identify regulatory elements in 5' flanking regions of genes.

The term "regulatory element" further encompasses "tissue specific" regulatory elements, i.e., regulatory elements which effect expression of an operably linked DNA sequence preferentially in specific cells (e.g., cells of a specific tissue). Gene expression occurs preferentially in a specific cell if expression in this cell type is significantly higher than expression in other cell types. The term "regulatory element" also encompasses non-tissue specific regulatory elements, i.e., regulatory elements which are active in most cell types. Furthermore, a regulatory element can be a constitutive regulatory element, i.e., a regulatory element which constitutively regulates transcription, as opposed to a regulatory element which is inducible, i.e., a regulatory element which is active primarily in response to a stimulus. A stimulus can be, e.g., a molecule, such as a protein, hormone, cytokine, heavy metal, phorbol ester, cyclic AMP (cAMP), or retinoic acid.

Regulatory elements are typically bound by proteins, e.g. transcription factors. The term "transcription factor" is intended to include proteins or modified forms thereof, which interact preferentially with specific nucleic acid sequences, i.e., regulatory elements, and which in appropriate conditions stimulate or repress transcription. Some transcription factors are active when they are in the form of a monomer. Alternatively, other transcription factors are active in the form of a dimer consisting of two identical proteins or different proteins (heterodimer). Modified forms of transcription factors are intended to refer to transcription factors having a postranslational modification, such as the attachment of a phosphate group. The activity of a transcription factor is frequently modulated by a postranslational modification. For example, certain transcription factors are active only if they are phosphorylated on specific residues. Alternatively, transcription factors can be active in the absence of phosphorylated residues and become inactivated by phosphorylation. A list of known transcription factors and their DNA binding site can be found, e.g., in public databases, e.g., TFMATRIX Transcription Factor Binding Site Profile database.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than 11100 or 1/1000 members of a population). SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site.

SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect.

As used herein, the term "specifically hybridizes" or "specifically detects" refers to the ability of a nucleic acid molecule of the invention to hybridize to at least approximately 6, 12, 20, 30, 40, 50, 60, 70, 80, 90, 100, 110, 120, 130 or 140 consecutive nucleotides of either strand of a 5-LO gene.

"5-LO" refers to a 5-lipoxygenase molecule that catalyzes the stereo-specific addition of molecular oxygen to arachidonic acid to form leukotriene A4 (LTA4) (Silverman, et al. 1998) *Clin Exp Allergy* 5:164; In, et al. (1997) *J. Clin. Invest.* 99:1130–1137), and therefore functions as a modulator of leukotriene synthesis. It has been found that 5-LO expression is dependent on the presence of a 5' GC-rich transcription factor binding region; this region contains sequences characteristic of binding motifs, e.g., Sp1 binding motifs (In, et al., supra).

The term "5-LO therapeutic" refers to various forms of 5-LO protein or polypeptides, as well as peptidomimetics, nucleic acids, or small molecules, which can modulate at least one activity of a 5-LO protein by mimicking or potentiating (agonizing) or inhibiting (antagonizing) the effects of a naturally-occurring 5-LO protein. A 5-LO therapeutic which mimics or potentiates the activity of a wild-type 5-LO protein is a "5-LO agonist". Conversely, a 5-LO therapeutic which inhibits the activity of a wild-type 5-LO protein is a "5-LO antagonist". 5-LO therapeutics can be used to treat diseases which are associated with a specific 5-LO allele which encodes a protein having an amino acid sequence that differs from that of the wild-type 5-LO protein.

As used herein, the term "transfection" means the introduction of a nucleic acid, e.g., an expression vector, into a recipient cell by nucleic acid-mediated gene transfer. The term "transduction" is generally used herein when the transfection with a nucleic acid is by viral delivery of the nucleic acid. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of a naturally-occurring form of the recombinant protein is disrupted.

As used herein, the term "transgene" refers to a nucleic acid sequence which has been genetic-engineered into a cell. Daughter cells deriving from a cell in which a transgene has been introduced are also said to contain the transgene (unless it has been deleted). A transgene can encode, e.g., a polypeptide, or an antisense transcript, partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). Alternatively, a transgene can also be present in an episome. A transgene can include one or more transcriptional regulatory sequence and any other nucleic acid, (e.g. intron), that may be necessary for optimal expression of a selected nucleic acid.

A "transgenic animal" refers to any animal, preferably a non-human animal, e.g. a mammal, bird or an amphibian, in which one or more of the cells of the animal contain heterologous nucleic acid introduced by genetic engineering, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of a protein, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques.

The term "treatment," or "treating" as used herein, is defined as the application or administration of a therapeutic agent to a subject, implementation of lifestyle changes (e.g., changes in diet or environment), administration of medication, or application or administration of a therapeutic agent to a patient who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

As used herein, the term "vector" refers to a nucleic acid molecule capable of transporting or replicating another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively-linked are referred to herein as "expression vectors". In general, expression vectors of utility in recombinant DNA techniques are often in the form of "plasmids" which refer generally to circular double stranded DNA circles which, in their vector form are not physically linked to the host chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a patient results in a wild-type phenotype. There can be several different wild-type alleles of a specific gene, since certain nucleotide changes in a gene may not affect the phenotype of a patient having two copies of the gene with the nucleotide changes. The terms "wild-type" and "reference sequence" are used interchangeably herein.

Polymorphisms of the Invention

The nucleic acid molecules of the invention include specific 5-LO allelic variants, which differ from the reference sequences set forth in SEQ ID NO:1, SEQ ID NO:2, or SEQ ID NO:3, or at least a portion thereof, having a polymorphic region. The preferred nucleic acid molecules of the present invention comprise 5-LO sequences having one or more of the polymorphisms shown in Table 1, those in linkage disequilibrium therewith, and those included in the haplotype, as described herein. Nucleic acid molecules of the invention can function as probes or primers, e.g., in methods for determining the allelic identity of a 5-LO polymorphic region. The nucleic acids of the invention can also be used to determine whether a patient is or is not at risk of developing a disease associated with a specific allelic variant of a 5-LO polymorphic region, e.g., a disease or disorder associated with an aberrant 5-LO activity. The nucleic acids of the invention can further be used to prepare or express 5-LO polypeptides encoded by specific alleles, such as mutant alleles. Such nucleic acids can be used in gene therapy. Polypeptides encoded by specific 5-LO alleles, such as mutant 5-LO polypeptides, can also be used in therapy or for preparing reagents, e.g., antibodies, for detecting 5-LO proteins encoded by these alleles. Accordingly, such reagents can be used to detect mutant 5-LO proteins.

As described herein, several allelic variants of human 5-LO genes have been identified. The invention is intended to encompass all of these allelic variants as well as, those in linkage disequilibrium which can be identified, e.g., according to the methods described herein. "Linkage disequilibrium" refers to an association between specific alleles at two marker loci within a particular population. In general, linkage disequilbrium decreases with an increase in physical distance. If linkage disequilbrium exists between two markers within one gene, then the genotypic information at one marker can be used to make predictions about the genotype of the second marker.

The invention also provides isolated nucleic acids comprising at least one polymorphic region of a 5-LO gene having a nucleotide sequence which differs from the reference nucleotide sequence set forth in SEQ ID NO:1, SEQ ID NO:2, or SEQ ID NO:3. Preferred nucleic acids have a variant allele located in the 5' upstream regulatory element of the 5-LO gene. Accordingly, preferred nucleic acids of the invention comprise an adenine at residue 1000 of the 5' upstream regulatory element of GI 187166 (as set forth in SEQ ID NO:4) or a thymine at the corresponding position in an otherwise complementary sequence; a deletion of the nucleotides GTTAAA (SEQ ID NO:62) at residues 472–477 of GI 187166 (as set forth in SEQ ID NO:5) or deletion of the nucleotides TTTAAC at the corresponding positions in an otherwise complementary sequence; and/or an adenine at residue 559 of the 5' upstream regulatory element of GI 187166 (as set forth in SEQ ID NO:6) or a thymine at the corresponding position in an otherwise complementary sequence.

The nucleic acid molecules of the invention can be single stranded DNA (e.g., an oligonucleotide), double stranded DNA (e.g., double stranded oligonucleotide) or RNA. Preferred nucleic acid molecules of the invention can be used as probes or primers. Primers of the invention refer to nucleic acids which hybridize to a nucleic acid sequence which is adjacent to the region of interest or which covers the region of interest and is extended. As used herein, the term "hybridizes" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions vary according to the length of the involved nucleotide sequence but are known to those skilled in the art and can be found or determined based on teachings in *Current Protocols in Molecular Biology,* Ausubel et al., eds., John Wiley & Sons, Inc. (1995), sections 2, 4 and 6. Additional stringent conditions and formulas for determining such conditions can be found in *Molecular Cloning: A Laboratory Manual,* Sambrook et al., Cold Spring Harbor Press, Cold Spring Harbor, N.Y. (1989), chapters 7, 9 and 11. A preferred, non-limiting example of stringent hybridization conditions for hybrids that are at least basepairs in length includes hybridization in 4×sodium chloride/sodium citrate (SSC), at about 65–70° C. (or hybridization in 4×SSC plus 50% formamide at about 42–50° C.) followed by one or more washes in 1×SSC, at about 65–70° C. A preferred, non-limiting example of highly stringent hybridization conditions for such hybrids includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions for such hybrids includes hybridization in 4×SSC, at about 50–60° C. (or alternatively hybridization in 6×SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete.

The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$(° C.)=2(# of A+T bases)+4(# of G+C bases). For hybrids between 18 and 49 base pairs in length, $T_m$(° C.)=81.5+16.6($\log_{10}[Na^+]$)+0.41(%G+C)−(600/N), where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M $NaH_2PO_4$, 7% SDS at about 65° C., followed by one or more washes at 0.02M NaH2PO$_4$, 1% SDS at 65° C., see e.g., Church and Gilbert (1984) *Proc. Natl. Acad. Sci. USA* 81:1991–1995, (or alternatively 0.2×SSC, 1% SDS).

A primer or probe can be used alone in a detection method, or a primer can be used together with at least one other primer or probe in a detection method. Primers can also be used to amplify at least a portion of a nucleic acid. Probes of the invention refer to nucleic acids which hybridize to the region of interest and which are not further extended. For example, a probe is a nucleic acid which specifically hybridizes to a polymorphic region of a 5-LO gene, and which by hybridization or absence of hybridization to the DNA of a patient or the type of hybrid formed will be indicative of the identity of the allelic variant of the polymorphic region of the 5-LO gene.

Numerous procedures for determining the nucleotide sequence of a nucleic acid molecule, or for determining the presence of mutations in nucleic acid molecules include a nucleic acid amplification step, which can be carried out by, e.g. polymerase chain reaction (PCR). Accordingly, in one embodiment, the invention provides primers for amplifying portions of a 5-LO gene, such as portions of exons and/or portions of introns. In a preferred embodiment, the exons and/or sequences adjacent to the exons of the human 5-LO gene will be amplified to, e.g., detect which allelic variant, if any, of a polymorphic region is present in the 5-LO gene of a patient. Preferred primers comprise a nucleotide sequence complementary a specific allelic variant of a 5-LO polymorphic region and of sufficient length to selectively hybridize with a 5-LO gene. In a preferred embodiment, the primer, e.g., a substantially purified oligonucleotide, comprises a region having a nucleotide sequence which hybridizes under stringent conditions to about 6, 8, 10, or 12, preferably 25, 30, 40, 50, or 75 consecutive nucleotides of a 5-LO gene. In an even more preferred embodiment, the primer is capable of hybridizing to a 5-LO nucleotide sequence and comprises a nucleotide sequence of any sequence set forth in any of SEQ ID NOs:4–6, or complements thereof For example, primers comprising a nucleotide sequence of at least about 15 consecutive nucleotides, at least about 25 nucleotides or having from about 15 to about 20 nucleotides set forth in any of SEQ ID NOs:4–6 or complement thereof are provided by the invention. Primers having a sequence of more than about 25 nucleotides are also within the scope of the invention. Preferred primers of the invention are primers that can be used in PCR for amplifying each of the exons of a 5-LO gene.

Primers can be complementary to nucleotide sequences located close to each other or further apart, depending on the use of the amplified DNA. For example, primers can be chosen such that they amplify DNA fragments of at least about 10 nucleotides or as much as several kilobases. Preferably, the primers of the invention will hybridize selectively to 5-LO nucleotide sequences located about 150 to about 350 nucleotides apart.

For amplifying at least a portion of a nucleic acid, a forward primer (i.e., 5' primer) and a reverse primer (i.e., 3' primer) will preferably be used. Forward and reverse primers hybridize to complementary strands of a double stranded nucleic acid, such that upon extension from each primer, a double stranded nucleic acid is amplified. A forward primer can be a primer having a nucleotide sequence or a portion of the nucleotide sequence shown in Table 1 (SEQ ID NOs:4–6) or in SEQ ID NOs.: 9, 11, 13, 15, 17, 19, 21, 23, 25, 27, 29, 31, 33, 35, 37, 39, 41, 43, 45, 47, 49, 51, 53, 55, 57, or 59. A reverse primer can be a primer having a nucleotide sequence or a portion of the nucleotide sequence that is complementary to a nucleotide sequence shown in Table 1 (SEQ ID NOs:4–6) or in SEQ ID NOs.: 10, 12, 14, 16, 18, 20, 22, 24, 26, 28, 30, 32, 34, 36, 38, 40, 42, 44, 46, 48, 50, 52, 54, 56, 58, or 60. Preferred pairs of primers for amplifying each of the exons of human 5-LO are set forth in Table 3 (see Example 2).

Yet other preferred primers of the invention are nucleic acids which are capable of selectively hybridizing to an allelic variant of a polymorphic region of a 5-LO gene. Thus, such primers can be specific for a 5-LO gene sequence, so long as they have a nucleotide sequence which is capable of hybridizing to a 5-LO gene. Preferred primers are capable of specifically hybridizing to any of the allelic variants listed in Table 1 (i e., sequences comprising any of SEQ ID NOs:4–6 or a complement thereof). Such primers can be used, e.g., in sequence specific oligonucleotide priming as described further herein.

The 5-LO nucleic acids of the invention can also be used as probes, e.g., in therapeutic and diagnostic assays. For instance, the present invention provides a probe comprising a substantially purified oligonucleotide, which oligonucleotide comprises a region having a nucleotide sequence that is capable of hybridizing specifically to a region of a 5-LO gene which is polymorphic (i.e., sequences comprising any of SEQ ID NOs:4–6 or a complement thereof). In an even more preferred embodiment of the invention, the probes are capable of hybridizing specifically to one allelic variant of a 5-LO gene having a nucleotide sequence which differs from the nucleotide sequence set forth in SEQ ID NO:1, 2, or 3. Such probes can then be used to specifically detect which allelic variant of a polymorphic region of a 5-LO gene is present in a patient. The polymorphic region can be located in the 5' upstream regulatory element, exon, or intron sequences of a 5-LO gene.

For example, preferred probes of the invention comprise a sequence listed in Table 2 or a complement thereof, wherein the bold nucleotides represent the location of the nucleotide polymorphism.

Particularly, preferred probes of the invention have a number of nucleotides sufficient to allow specific hybridization to the target nucleotide sequence. Where the target nucleotide sequence is present in a large fragment of DNA, such as a genomic DNA fragment of several tens or hundreds of kilobases, the size of the probe may have to be longer to provide sufficiently specific hybridization, as compared to a probe which is used to detect a target sequence which is present in a shorter fragment of DNA. For example, in some diagnostic methods, a portion of a 5-LO gene may first be amplified and thus isolated from the rest of the chromosomal DNA and then hybridized to a probe. In such a situation, a shorter probe will likely provide sufficient specificity of hybridization. For example, a probe having a nucleotide sequence of about 10 nucleotides may be sufficient.

In preferred embodiments, the probe or primer further comprises a label attached thereto, which, e.g., is capable of being detected, e.g. the label group is selected from amongst radioisotopes, fluorescent compounds, enzymes, and enzyme co-factors.

In a preferred embodiment of the invention, the isolated nucleic acid, which is used, e.g., as a probe or a primer, is modified, so as to be more stable than naturally occurring nucleotides. Exemplary nucleic acid molecules which are modified include phosphoramidate, phosphothioate and methylphosphonate analogs of DNA (see also U.S. Pat. Nos. 5,176,996; 5,264,564; and 5,256,775).

The nucleic acids of the invention can also be modified at the base moiety, sugar moiety, or phosphate backbone, for example, to improve stability of the molecule. The nucleic acids, e.g., probes or primers, may include other appended groups such as peptides (e.g., for targeting host cell receptors in vivo), or agents facilitating transport across the cell membrane (see, e.g., Letsinger et al., 1989, *Proc. Natl. Acad. Sci. U.S.A.* 86;6553–6556; Lemaitre et al., 1987, *Proc. Natl. Acad. Sci.* 84:648–652; PCT Publication No. WO88/09810, published Dec. 15, 1988), hybridization-triggered cleavage agents. (See, e.g., Krol et al., 1988, *BioTechniques* 6:958–976) or intercalating agents. (Sec, e.g., Zon, 1988, *Pharm. Res.* 5:539–549). To this end, the nucleic acid of the invention may be conjugated to another molecule, e.g., a peptide, hybridization triggered cross-inking agent, transport agent, hybridization-triggered cleavage agent, etc.

The isolated nucleic acid comprising a 5-LO intronic sequence may comprise at least one modified base moiety which is selected from the group including but not limited to 5-fluorouracil, 5-bromouracil, 5-chlorouracil, 5-iodouracil, hypoxanthine, xantine, 4-acetylcytidine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytidine, 5-methylcytidine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytidine, 5-methyl-2-thiouracil, 2-thiouracil, 4thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The isolated nucleic acid may also comprise at least one modified sugar moiety selected from the group including but not limited to arabinose, 2-fluoroarabinose, xylulose, and hexose.

In yet another embodiment, the nucleic acid comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the nucleic acid is an α-anomeric oligonucleotide. An α-anomeric oligonucleotide forms specific double-stranded hybrids with complementary RNA in which, contrary to the usual β-units, the strands run parallel to each other (Gautier et al., 1987, *Nucl. Acids Res.* 15:6625–6641). The oligonucleotide is a 2'-0-methylribonucleotide (Inoue et al., 1987, *Nucl. Acids Res.* 15:6131–6148), or a chimeric RNA-DNA analogue (Inoue et al., 1987, *FEBS Lett.* 215:327–330).

Any nucleic acid fragment of the invention can be prepared according to methods well known in the art and described, e.g., in Sambrook, J. Fritsch, E. F., and Maniatis, T. (1989) *Molecular Cloning: A Laboratory Manual,* Cold Spring Harbor Laboratory Press, Cold Spring Harbor, N.Y. For example, discrete fragments of the DNA can be prepared and cloned using restriction enzymes. Alternatively, discrete fragments can be prepared using the Polymerase Chain Reaction (PCR) using primers having an appropriate sequence.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, *Nucl. Acids Res.* 16:3209), methylphosphonate oligonucleotides can be prepared by use of controlled pore glass polymer supports (Sarin et al., 1988, *Proc. Natl. Acad Sci. U.S.A.* 85:7448–7451), etc.

The invention also provides vectors and plasmids comprising the nucleic acids of the invention. For example, in one embodiment, the invention provides a vector comprising at least a portion of a 5-LO gene comprising a polymorphic region. Thus, the invention provides vectors for expressing at least a portion of the newly identified allelic variants of the human 5-LO gene reference, as well as other allelic variants, comprising a nucleotide sequence which is different from the nucleotide sequence disclosed in GI 187166, GI 8247778, or GI 450256. The allelic variants can be expressed in eukaryotic cells, e.g., cells of a patient, or in prokaryotic cells.

In one embodiment, the vector comprising at least a portion of a 5-LO allele is introduced into a host cell, such that a protein encoded by the allele is synthesized. The 5-LO protein produced can be used, e.g., for the production of antibodies, which can be used, e.g., in methods for detecting mutant forms of 5-LO. Alternatively, the vector can be used for gene therapy, and be, e.g., introduced into a patient to produce 5-LO protein. Host cells comprising a vector having at least a portion of a 5-LO gene are also within the scope of the invention.

Methods

The invention further provides predictive medicine methods, which are based, at least in part, on the discovery of 5-LO polymorphisms which are associated with specific physiological states and/or diseases or disorders.

For example, information obtained using the diagnostic assays described herein is useful for determining that a patient suffering from an inflammatory or allergy disease or disorder, e.g., asthma, has a more or less severe disease phenotype, e.g., a more or less severe asthma phenotype. Alternatively, the information can be used prognostically for predicting whether a patient will be responsive to treatment of an inflammatory or allergy disease or disorder, including, but not limited to, asthma, with a 5-LO inhibitor or other related agent. Based on the prognostic information, a health care provider can recommend a regimen (e.g., diet or exercise) or therapeutic protocol, (e.g., administration of a 5-LO inhibitor) useful for preventing the particular disease or disorder, or symptoms of the disease or disorder in the patient e.g., asthma.

In addition, knowledge of the identity of a particular 5-LO allele in an individual (the 5-LO genetic profile, including the presence or absence of the polymorphisms of the haplotype as described herein), alone or in conjunction with information on other genetic defects contributing to the same disease (the genetic profile of the particular disease, e.g., asthma) allows customization of therapy for a particular disease to the individual's genetic profile. For example, an individual's 5-LO genetic profile or the genetic profile of a disease or condition associated with a specific allele of a 5-LO polymorphic region, can enable a health care provider: 1) to more effectively prescribe a drug that will address the molecular basis of the disease or condition (e.g., a 5-LO inhibitor as described in U.S. Pat. Nos. 5,703,093, 5,750,565, or 6,025,384); and 2) to better determine the appropriate dosage of a particular drug. For example, the expression level of 5-LO proteins, alone or in conjunction with the expression level of other genes, known to contribute to the same disease, can be measured in many patients at various stages of the disease to generate a transcriptional or expression profile of the disease. Expression patterns of individual patients can then be compared to the expression profile of the disease to determine the appropriate drug and dose to administer to the patient.

The ability to target populations expected to show the highest clinical benefit, e.g., subgroups of asthmatic populations which respond or do not respond to specific therapies, e.g., treatment with 5-LO inhibitors, or subgroups of asthmatic populations with more or less severe asthma phenotypes, based on the 5-LO or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g., since the use of 5-LO as a marker is useful for optimizing effective dose).

These and other methods are described in further detail in the following sections.

A. Prognostic and Diagnostic Assays

The present methods provide means for determining if a patient has a disease, condition or disorder that is associated a specific 5-LO allele, e.g., aberrant, e.g., decreased, eosinophil levels, or the severity of an inflammatory disease or disorder phenotype, e.g. the severity of an asthma phenotype among an asthmatic population. The present methods also provide means for predicting or determining if a patient will be more or less responsive to treatment with a 5-LO inhibitor, based on determination of a specific 5-LO allele.

The present invention provides methods for determining the molecular structure of a 5-LO gene, such as a human 5-LO gene, or a portion thereof. For example, the present invention provides methods for determining the presence or absence of the haplotype described herein. In one embodiment, determining the molecular structure of at least a portion of a 5-LO gene comprises determining the identity of the allelic variant of at least one polymorphic region of a 5-LO gene (determining the presence or absence of one or more of the allelic variants, or their complements, of SEQ ID NOs.:4–6, thereby determining the presence of the haplotype as described herein). A polymorphic region of a 5-LO gene can be located in an exon, an intron, at an intron/exon border, or, preferably, in the 5' upstream regulatory element of the 5-LO gene.

The invention provides methods for determining whether a patient has a specific disease or disorder phenotype, e.g., asthma phenotype, associated with a specific allelic variant of a polymorphic region of a 5-LO gene. Such disease phenotypes are associated with aberrant 5-LO activity, e.g., aberrant 5-LO expression, or increased or decreased eosinophil counts in the patient. Aberrant 5-LO protein level can result from aberrant transcription or post transcriptional regulation. Thus, allelic differences in specific regions of a 5-LO gene result in differences of 5-LO protein due to differences in regulation of expression. In particular, some of the identified polymorphisms in the human 5-LO gene are associated with differences in the level of transcription, RNA maturation, splicing, or translation of the 5-LO gene or transcription product. For example, the presence of a variant Sp1 binding site, which is associated with the haplotype of the invention, result in reduced levels of 5-LO expression. Therefore, presence of any of the polymorphisms of the haplotype predicts a reduced levels of 5-LO expression.

Analysis of one or more 5-LO polymorphic regions in a patient, including the identities of the polymorphisms included in the haplotype of the present invention can be useful for predicting or determining whether a patient has more or less severe inflammatory disease phenotype, e.g., a more or less severe asthma phenotype, associated with increased or decreased eosinophil levels resulting in more or less severe symptoms of the inflammatory disease or disorder.

In preferred embodiments, the methods of the invention can be characterized as comprising detecting, in a sample of cells or nucleic acid from the patient, the presence or absence of a specific allelic variant of one or more polymorphic regions of a 5-LO gene. The allelic differences can be: (i) a difference in the identity of at least one nucleotide or (ii) a difference in the number of nucleotides, which difference can be a single nucleotide or several nucleotides. The invention also provides methods for detecting differences in 5-LO genes such as chromosomal rearrangements, e.g., chromosomal dislocation. The invention can also be used in prenatal diagnostics.

A preferred detection method is allele specific hybridization using probes overlapping the polymorphic site and having about 5, 10, 20, 25, or 30 nucleotides around the polymorphic region. Examples of probes for detecting specific allelic variants of the polymorphic region located in the 5' upstream regulatory element of the 5-LO gene are probes comprising a nucleotide sequence set forth in any of SEQ ID NOs.:64, 65, and 66 or the complement thereof. In a preferred embodiment of the invention, several probes capable of hybridizing specifically to allelic variants are attached to a solid phase support, e.g., a "chip". Oligonucleotides can be bound to a solid support by a variety of processes, including lithography. For example a chip can hold up to 250,000 oligonucleotides (GeneChip, Affymetrix). Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment. For example, the identity of the allelic variant of the nucleotide polymorphism in the 5' upstream regulatory element can be determined in a single hybridization experiment.

In other detection methods, it is necessary to first amplify at least a portion of a 5-LO gene prior to identifying the allelic variant. Amplification can be performed, e.g., by PCR and/or LCR (see Wu and Wallace, (1989) *Genomics* 4:560), according to methods known in the art. In one embodiment, genomic DNA of a cell is exposed to two PCR primers and amplification for a number of cycles sufficient to produce the required amount of amplified DNA. In preferred embodiments, the primers are located between 150 and 350 base pairs apart. Preferred primers, such as primers for amplifying each of the exons of the human 5-LO gene, are listed in Table 3.

Alternative amplification methods include: self sustained sequence replication (Guatelli, J. C. et al., 1990, *Proc. Natl. Acad. Sci. USA* 87:1874–1878), transcriptional amplification system (Kwoh, D. Y. et al., 1989, Proc. Natl. Acad. Sci. USA 86:1173–1177), Q-Beta Replicase (Lizardi, P. M. et al., 1988, Bio/Technology 6:1197), and self-sustained sequence replication (Guatelli et al, (1989) *Proc. Nat. Acad. Sci.* 87:1874), and nucleic acid based sequence amplification (NABSA), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment, any of a variety of sequencing reactions known in the art can be used to directly sequence at least a portion of a 5-LO gene and detect allelic variants, e.g., mutations, by comparing the sequence of the sample sequence with the corresponding wild-type (control) sequence. Exemplary sequencing reactions include those based on techniques developed by Maxam and Gilbert (*Proc. Natl Acad Sci USA (*1977) 74:560) or Sanger (Sanger et al (1977) *Proc. Nat. Acad. Sci* 74:5463). It is also contemplated that any of a variety of automated sequencing procedures may be utilized when performing the subject assays (*Biotechniques* (1995) 19:448), including sequencing by mass spectrometry (see, for example, U.S. Pat. No. 5,547,835 and international patent application Publication Number WO 94/16101, entitled *DNA Sequencing by Mass Spectrometry* by H. Köster, U.S. Pat. No. 5,547,835 and international patent application Publication Number WO 94/21822 entitled "DNA Sequencing by Mass Spectrometry Via Exonuclease Degradation" by H. Köster), and U.S. Pat. No. 5,605,798 and International Patent Application No. PCT/US96/03651 entitled *DNA Diagnostics Based on Mass Spectrometry* by H. Köster;. Cohen et al. (1996) *Adv Chromatogr* 36:127–162; and Griffin et al. (1993) *Appl Biochem Biotechnol* 38:147–159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732 entitled "Method of DNA sequencing employing a mixed DNA-polymer chain probe" and U.S. Pat. No. 5,571,676 entitled "Method for mismatch-directed in vitro DNA sequencing".

In some cases, the presence of a specific allele of a 5-LO gene in DNA from a patient can be shown by restriction enzyme analysis. For example, a specific nucleotide polymorphism can result in a nucleotide sequence comprising a restriction site which is absent from the nucleotide sequence of another allelic variant.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (Myers, et al. (1985) *Science* 230:1242). In general, the technique of "mismatch cleavage" starts by providing heteroduplexes formed by hybridizing a control nucleic acid, which is optionally labeled, e.g., RNA or DNA, comprising a nucleotide sequence of a 5-LO allelic variant with a sample nucleic acid, e.g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, Cotton et al (1988) *Proc. Natl Acad Sci USA* 85:4397; Saleeba et al (1992) *Methods Enzymol.* 217:286–295. In a preferred embodiment, the control or sample nucleic acid is labeled for detection.

In another embodiment, an allelic variant can be identified by denaturing high-performance liquid chromatography (DHPLC) (Oefner and Underhill, (1995) *Am. J. Human Gen.* 57: Suppl. A266). DHPLC uses reverse-phase ion-pairing chromatography to detect the heteroduplexes that are generated during amplification of PCR fragments from individuals who are heterozygous at a particular nucleotide locus within that fragment (Oefner and Underhill (1995) *Am. J. Human Gen.* 57: Suppl. A266). In general, PCR products are produced using PCR primers flanking the DNA of interest. DHPLC analysis is carried out and the resulting chromatograms are analyzed to identify base pair alterations or deletions based on specific chromatographic profiles (see O'Donovan et al. (1998) *Genomics* 52:44–49).

In other embodiments, alterations in electrophoretic mobility is used to identify the type of 5-LO allelic variant. For example, single strand conformation polymorphism (SSCP) may be used to detect differences in electrophoretic mobility between mutant and wild type nucleic acids (Orita et al. (1989) *Proc Natl. Acad. Sci USA* 86:2766, see also Cotton (1993) *Mutat Res* 285:125–144; and Hayashi (1992) *Genet Anal Tech Appl* 9:73–79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the identity of an allelic variant of a polymorphic region is obtained by analyzing the movement of a nucleic acid comprising the polymorphic region in polyacrylamide gels containing a gradient of denaturant is assayed using denaturing gradient gel electrophoresis (DGGE) (Myers et al (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) *Biophys Chem* 265:1275).

Examples of techniques for detecting differences of at least one nucleotide between 2 nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) Nature 324:163); Saiki et al (1989) *Proc. Natl Acad. Sci USA* 86:6230; and Wallace et al. (1979) *Nucl. Acids Res.* 6:3543). Such allele specific oligonucleotide hybridization techniques may be used for the simultaneous detection of several nucleotide changes in different polylmorphic regions of 5-LO. For example, oligonucleotides having nucleotide sequences of specific allelic variants are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238; Newton et al. (1989) *Nucl. Acids Res.* 17:2503). This technique is also termed "PROBE" for Probe Oligo Base Extension. In addition it may be desirable to introduce a novel restriction site in the region of the mutation to create cleavage-based detection (Gasparini et at (1992) *Mol. Cell Probes* 6:1).

In another embodiment, identification of the allelic variant is carried out using an oligonucleotide ligation assay (OLA), as described, e.g. in U.S. Pat. No. 4,998,617 and in Landegren, U. et al., (1988) *Science* 241:1077–1080. The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., (1990) *Proc. Natl. Acad. Sci. (U.S.A)* 87:8923–8927. In this method, PCR is used to achieve the exponential amplification of target DNA, which is then detected using OLA.

Several techniques based on this OLA method have been developed and can be used to detect specific allelic variants of a polymorphic region of a 5-LO gene. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) *Nucleic Acids Res* 24: 3728), OLA combined with PCR permits typing of two alleles in a single microtiter well. By marking each of the allele-specific primers with a unique hapten, i.e., digoxigenin and fluorescein, each OLA reaction can be detected by using hapten specific antibodies that are labeled with different enzyme reporters, alkaline phosphatase or horseradish peroxidase.

This system permits the detection of the two alleles using a high throughput format that leads to the production of two different colors.

The invention further provides methods for detecting single nucleotide polymorphisms in a 5-LO gene. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms.

In one embodiment, the single base polymorphism can be detected by using a specialized exonuclease-resistant nucleotide, as disclosed, e.g., in Mundy, C. R. (U.S. Pat. No. 4,656,127). According to the method, aprimer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. W091/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., *Nucl. Acids. Res.* 17:7779–7784 (1989); Sokolov, B. P., Nucl. Acids Res. 18:3671 (1990); Syvanen, A.-C., et al., *Genomics* 8:684–692 (1990); Kuppuswamy, M. N. et al., *Proc. Natl. Acad. Sci. (U.S.A.)* 88:1143–1147 (1991); Prezant, T. R. et al., *Hum. Mutat.* 1:159–164 (1992); Ugozzoli, L. et al., GATA 9:107–112 (1992); Nyren, P. et al., *Anal. Biochem.* 208:171–175 (1993)). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., *Amer. J. Hum. Genet.* 52:46–59 (1993)).

If a polymorphic region is located in an exon, either in a coding or non-coding portion of the gene, the identity of the allelic variant can be determined by determining the molecular structure of the mRNA, pre-mRNA, or cDNA. The molecular structure can be determined using any of the above described methods for determining the molecular structure of the genomic DNA, e.g., see Example 1.

The methods described herein may be performed, for example, by utilizing pre-packaged diagnostic kits, such as those described above, comprising at least one probe or primer nucleic acid described herein, which may be conveniently used, e.g., to determine whether a patient has a specific disease phenotype associated with a specific 5-LO allelic variant.

Sample nucleic acid to be analyzed by any of the above-described diagnostic and prognostic methods can be obtained from any cell type or tissue of a patient. For example, a patient's bodily fluid (e.g., blood) can be obtained by known techniques (e.g. venipuncture). Alternatively, nucleic acid tests can be performed on dry samples (e.g. hair or skin). Fetal nucleic acid samples can be obtained from maternal blood as described in International Patent Application No. WO91/07660 to Bianchi. Alternatively, amniocytes or chorionic villi may be obtained for performing prenatal testing.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

B. Pharmacogenomics

Knowledge of the identity of the allele of one or more 5-LO gene polymorphic regions in a patient (the 5-LO genetic profile), alone or in conjunction with information on other genetic defects contributing to the same disease (the genetic profile of the particular disease, including, for example, the determination of the presence of the haplotype described herein) also allows a customization of the therapy for a particular disease to the patient's genetic profile.

It has been determined that the presence of a variant Sp1 binding site in the promoter region of the 5-LO gene results in reduced responsiveness to treatment with particular therapies, including treatment with 5-LO inhibitors, or other agents which antagonize 5-LO in asthmatic patients (U.S. Pat. No. 6,090,547). Therefore, based on the existence of the haplotype as described herein which is in linkage disequilibrium with any one of three variant Sp1 binding site, the detection in an asthmatic patient of an allele present in at least one of the polymorphic sites included in the haplotype of the present invention can be used to predict whether or not that the patient has reduced responsiveness to treatment with a specific treatment, e.g., treatment with a 5-LO inhibitor. The methods of the invention further provide methods for identifying a candidate for treatment with a 5-LO inhibitor by the detection in a patient of an allele present in at least one of the polymorphic sites included in the haplotype of the present invention, or a complement thereof.

For example, patients having a specific allele of a 5-LO gene may or may not exhibit symptoms of a particular disease or be predisposed to developing symptoms of a particular disease. Further, if those patients are symptomatic, they may or may not respond well to a certain drug, e.g., a specific 5-LO therapeutic, such as a 5-LO inhibitor, but may respond to another. Thus, generation of a 5-LO genetic profile (e.g., categorization of alterations in 5-LO genes which are associated with the development of a particular disease, including determination of the presence of the haplotype described herein), from a population of patients, who are symptomatic for a disease or condition that is caused by or contributed to by a defective and/or aberrantly expressed 5-LO gene and/or protein (a 5-LO genetic population profile) and comparison of an individual's 5-LO profile to the population profile, permits the selection or design of drugs that are expected to be safe and efficacious for a particular patient or patient population (i.e., a group of patients having the same genetic alteration).

For example, a 5-LO population profile can be performed by determining the 5-LO profile, e.g., the identity of 5-LO alleles, in particular the identity of 5-LO alleles included in the haplotype as described herein, in a patient population having a disease, which is associated with one or more specific alleles of 5-LO polymorphic regions. Optionally, the 5-LO population profile can further include information relating to the response of the population to a 5-LO therapeutic, using any of a variety of methods, including, monitoring: 1) the severity of symptoms associated with the 5-LO related disease, 2) 5-LO gene expression level, 3) 5-LO mRNA level, 4) 5-LO protein level, 5) eosinophil level, and/or 6) leukotriene level, and dividing or categorizing the population based on particular 5-LO alleles. The 5-LO genetic population profile can also, optionally, indicate those particular 5-LO alleles which are present in patients that are either responsive or non-responsive to a particular therapeutic, e.g., a 5-LO inhibitor. This information or population profile, is then useful for predicting which individuals should respond to particular drugs, based on their individual 5-LO profile.

In a preferred embodiment, the 5-LO profile is a transcriptional or expression level profile and is comprised of determining the expression level of 5-LO proteins, alone or in conjunction with the expression level of other genes known to contribute to the same disease at various stages of the disease.

Pharmacogenomic studies can also be performed using transgenic animals. For example, one can produce transgenic mice, e.g., as described herein, which contain a specific allelic variant of a 5-LO gene. These mice can be created, e.g., by replacing their wild-type 5-LO gene with an allele of the human 5-LO gene. The response of these mice to specific 5-LO therapeutics can then be determined.

C. Monitoring Effects of 5-LO Therapeutics During Clinical Trials

The present invention provides a method for monitoring the effectiveness of treatment of a patient with an agent (e.g., an agonist, antagonist peptidomimetic, protein, peptide, nucleic acid, small molecule, or other drug candidate identified, e.g., by the screening assays described herein) comprising the steps of (i) obtaining a preadministration sample from a patient prior to administration of the agent; (ii) detecting the level of expression or activity of a 5-LO protein, mRNA or gene in the preadministration sample; (iii) obtaining one or more post-administration samples from the patient; (iv) detecting the level of expression or activity of the 5-LO protein, mRNA or gene in the post-administration samples; (v) comparing the level of expression or activity of the 5-LO protein, mRNA, or gene in the preadministration sample with those of the 5-LO protein, mRNA, or gene in the post administration sample or samples; and (vi) altering the administration of the agent to the patient accordingly. For example, increased administration of the agent may be desirable to increase the expression or activity of 5-LO to higher levels than detected, i.e., to increase the effectiveness of the agent. Alternatively, decreased administration of the agent may be desirable to decrease expression or activity of 5-LO to lower levels than detected, i.e., to decrease the effectiveness of the agent.

Cells of a patient may also be obtained before and after administration of a 5-LO therapeutic to detect the level of expression of genes other than 5-LO, to verify that the 5-LO therapeutic does not increase or decrease the expression of genes which could be deleterious. This can be done, e.g., by using the method of transcriptional profiling. Thus, mRNA from cells exposed in vivo to a 5-LO therapeutic and mRNA from the same type of cells that were not exposed to the 5-LO therapeutic could be reverse transcribed and hybridized to a chip containing DNA from numerous genes, to thereby compare the expression of genes in cells treated and not treated with a 5-LO therapeutic. If, for example a 5-LO therapeutic turns on the expression of a proto-oncogene in an individual, use of this particular 5-LO therapeutic may be undesirable.

D. Methods of Treatment

The present invention provides for both prophylactic and therapeutic methods of treating a patient having a disorder associated with specific 5-LO alleles and/or aberrant 5-LO expression or activity, e.g., inflammatory or allergy diseases or disorders, such as asthma.

i) Prophylactic Methods

In one aspect, the invention provides a method for preventing in a patient, a disease or condition associated with a specific 5-LO allele such as an inflammatory or allergy disease or disorder, e.g., asthma, and medical conditions resulting therefrom, by administering to the patient an agent which counteracts the unfavorable biological effect of the specific 5-LO allele. Subjects at risk for such a disease can be identified by a diagnostic or prognostic assay, e.g., as described herein. Administration of a prophylactic agent can occur prior to the manifestation of symptoms associated with specific 5-LO alleles, such that a disease or disorder is prevented or, alternatively, delayed in its progression. Depending on the identity of the 5-LO allele in a patient, a compound that counteracts the effect of this allele is administered. The compound can be a compound modulating the activity of 5-LO, e.g., a 5-LO inhibitor. The treatment can also be a specific diet, or environmental alteration. In particular, the treatment can be undertaken prophylactically, before any other symptoms are present. Such a prophylactic treatment could thus prevent the development of an aberrant inflammatory response, e.g., asthma. The prophylactic methods are similar to therapeutic methods of the present invention and are further discussed in the following subsections.

(ii) Therapeutic Methods

The invention further provides methods of treating patients having a specific disease or disorder phenotype associated with a specific allelic variant of a polymorphic region of a 5-LO gene, e.g., a more moderate or more severe phenotype. Preferred diseases or disorders include those associated with aberrant leukotriene synthesis, eosinophil levels, and 5-LO expression, and disorders resulting therefrom.

In one embodiment, the method comprises (a) determining the identity of one or more allelic variants of the invention; and (b) administering to the patient a compound that compensates for the effect of the specific allelic variant. The polymorphic region can be localized at any location of the gene, e.g., in a regulatory element (e.g. in a 5' upstream regulatory element), in an exon, (e.g., coding region of an exon), in an intron, or at an exon/intron border. Thus, depending on the site of the polymorphism in the 5-LO gene, a patient having a specific variant of the polymorphic region which is associated with a specific disease or condition, can be treated with compounds which specifically compensate for the effect of the allelic variant.

In a preferred embodiment, the identity of any one of the polymorphisms included in the haplotype is determined. In another preferred embodiment, the identity of one or more of the following nucleotides of a 5-LO gene of a patient is determined: adenine at residue 1000 of the reference sequence GI 187166, a deletion at residues 472–477 (GTTAAA) (SEQ ID NO:62) of the reference sequence GI 187166, and/or adenine at residue 559 of the reference sequence GI 187166 may be determined.

In another preferred embodiment, the identity of at least one of the nucleotides listed above is determined, in combination with one or more of the known nucleotide polymorphisms from Table 1, i.e., adenine at residue 94 of the reference sequence GI 187166, adenine at residue 137 of the reference sequence GI 187166, and/or variant Sp1 binding site e.g., sites containing three, four, or six Sp1 motifs, may be determined. In a particularly preferred embodiment, it is determined that a patient has one or more of the following: an adenine at residue 1000 of the reference sequence GI 187166, a deletion of residues 472–477 (GTTAAA) (SEQ ID NO:62) of the reference sequence GI 187166, an adenine at residue 559 of the reference sequence GI 187166, in combination with one or more of the following previously known polymorphisms, preferably an adenine at residue 84 of GI 187166, and/or an adenine at residue 137 of GI 187166, or a variant Sp1 binding site If a patient having an inflammatory or allergy disease or disorder, e.g., asthma, has one or more of the polymorphisms of the invention (as set forth in Table 1), or one or more of the polymorphisms of the invention in combination with one or more of the previously known polymorphisms listed in Table 1 or a variant Sp1 binding site allele, that patient has a decreased risk of having high eosinophil levels, has a more moderate inflammatory disease phenotype, has a decreased risk of having increased 5-LO expression, and can be identified as having decreased responsiveness to a 5-LO inhibitor, as compared to a patient without one of the aforementioned polymorphisms.

Similarly, if a patient having an inflammatory disease or disorder, e.g., asthma does not have one or more of the polymorphisms of the invention (as set forth in Table 1), or one or more of the polymorphisms of the invention in combination with one or more of the previously known polymorphisms listed in Table 1 or a variant Sp1 binding site, that patient has an increased risk of having increased eosinophil levels, an increased risk of having a more severe inflammatory disease phenotype, an increased risk of having increased 5-LO expression, and can be identified as having increased responsiveness to a 5-LO inhibitor as compared to a patient with one of the aforementioned polymorphisms.

Generally, the allelic variant can be a mutant allele, i.e., an allele which when present in one, or preferably two copies, in a patient results in a change in the phenotype of the patient. A mutation can be a substitution, deletion, and/or addition of at least one nucleotide relative to the wild-type allele (i.e., the reference sequence). Depending on where the mutation is located in the 5-LO gene, the patient can be treated to specifically compensate for the mutation. For example, if the mutation is present in the coding region of the gene and results in a more active 5-LO protein, the patient can be treated, e.g., by administration to the patient of a 5-LO inhibitor, such that the administration of the inhibitor prevents aberrant leukotriene synthesis by the 5-LO protein. Normal 5-LO protein can also be used to counteract or compensate for the endogenous mutated form of the 5-LO protein. Normal 5-LO protein can be directly delivered to the patient or indirectly by gene therapy wherein some cells in the patient are transformed or transfected with an expression construct encoding wild-type 5-LO protein. Nucleic acids encoding wild-type human 5-LO protein are set forth in SEQ ID NOs.:1, 2, and 3 (GI Accession Nos. 187166, 8247778 and 4502056).

Furthermore, depending on the site of the mutation in the 5-LO protein and the specific effect on its activity, specific treatments can be designed to compensate for that effect. The 5-LO protein is a lipoxygenase which interacts with arachidonic acid to synthesize leukotrienes (LTs), e.g., LTA4, B4, C4, D4, and E4. The structure of the 5-LO protein is further described, e.g., in Silverman, et al. (1999) *Proc. Assoc. Am. Physicians* 111 (6):525–36 and Matsunoto, et al. (1988) supra). Thus, if the mutation results in a 5-LO protein which causes as increased ability of 5-LO to synthesize leukotrienes, resulting in an accumulation of leukotrienes in the patient, a treatment can be designed which removes excess leukotrienes from the patient or inhibits 5-LO from synthesis of leukotrienes. In one embodiment, a compound which inhibits 5-LO synthesis of leukotrienes is administered to the patient. For example, a compound described in U.S. Pat. No. 5,703,093, 5,750,565, or 6,025,384 can be administered to the patient.

Yet in another embodiment, the invention provides methods for treating a patient having a mutated 5-LO gene, in which the mutation is located in a regulatory region of the gene. Such a regulatory region can be localized in the 5' upstream regulatory element of the gene, in the 5' or 3' untranslated region of an exon, or in an intron. A mutation in a regulatory region can result in increased production of 5-LO protein, decreased production of 5-LO protein, or production of 5-LO having an aberrant tissue distribution. The effect of a mutation in a regulatory region upon the 5-LO protein can be determined, e.g., by measuring the 5 -LO protein level or mRNA level in cells having a 5-LO gene having this mutation and which, normally (i.e., in the absence of the mutation) produce 5-LO protein. The effect of a mutation can also be determined in vitro. For example, if the mutation is in the 5' upstream regulatory element, a reporter construct can be constructed which comprises the mutated 5' upstream regulatory element linked to a reporter gene, the construct transfected into cells, and comparison of the level of expression of the reporter gene under the control of the mutated 5' upstream regulatory element and under the control of a wild-type 5' upstream regulatory element. Such experiments can also be carried out in mice transgenic for the mutated 5' upstream regulatory element. If the mutation is located in an intron, the effect of the mutation can be determined, e.g., by producing transgenic animals in which the mutated 5-LO gene has been introduced and in which the wild-type gene may have been knocked out. Comparison of the level of expression of 5-LO in the mice transgenic for the mutant human 5-LO gene with mice transgenic for a wild-type human 5-LO gene will reveal whether the mutation results in increased, or decreased synthesis of the 5-LO protein and/or aberrant tissue distribution of 5-LO protein. Such analysis could also be performed in cultured cells, in which the human mutant 5-LO gene is introduced and, e.g., replaces the endogenous wild-type 5-LO gene in the cell. Thus, depending on the effect of the mutation in a regulatory region of a 5-LO gene, a specific treatment can be administered to a patient having such a mutation. Accordingly, if the mutation results in decreased 5-LO protein levels, the patient can be identified as being less responsive to treatment with a 5-LO inhibitor. For example, the presence of a non-wild-type Sp1 binding site allele or a polymorphism included in a haplotype as described herein, may indicate reduced levels of 5-LO expression, reduced eosinophil levels, a less severe asthma phenotype, and reduced responsiveness to 5-LO inhibition by a 5-LO inhibitor, e.g., a 5-LO inhibitor described in U.S. Pat. No. 5,703,093, 5,750,565 or 6,025,384.

A correlation between drug responses and specific alleles of 5-LO can be shown, for example, by clinical studies wherein the response to specific drugs of patients having different allelic variants of a polymorphic region of a 5-LO gene is compared. Such studies can also be performed using animal models, such as mice having various alleles of human 5-LO genes and in which, e.g., the endogenous 5-LO has been inactivated such as by a knock-out mutation. Test drugs are then administered to the mice having different human 5-LO alleles and the response of the different mice to a specific compound is compared. Accordingly, the invention provides assays for identifying the drug which will be best suited for treating a specific disease or condition in a patient. For example, it will be possible to select drugs which will be devoid of toxicity, or have the lowest level of toxicity possible for treating a patient having a disease or condition.

Other Uses for the Nucleic Acid Molecules of the Invention

The identification of different alleles of 5-LO can also be useful for identifying an individual among other individuals from the same species. For example, DNA sequences can be used as a fingerprint for detection of different individuals within the same species (Thompson, J. S. and Thompson, eds., Genetics in Medicine, WB Saunders Co., Philadelphia, Pa. (1991)). This is useful, for example, in forensic studies and paternity testing, as described below.

A. Forensics

Determination of which specific allele occupies a set of one or more polymorphic sites in an individual identifies a set of polymorphic forms that distinguish the individual from others in the population. See generally National Research Council, *The Evaluation of Forensic DNA Evidence* (Eds. Pollard et al., National Academy Press, DC, 1996). The more polymorphic sites that are analyzed, the lower the probability that the set of polymorphic forms in one individual is the same as that in an unrelated individual. Preferably, if multiple sites are analyzed, the sites are unlinked. Thus, the polymorphisms of the invention can be used in conjunction with known polymorphisms in distal genes. Preferred polymorphisms for use in forensics are biallelic because the population frequencies of two polymorphic forms can usually be determined with greater accuracy than those of multiple polymorphic forms at multiallelic loci.

The capacity to identify a distinguishing or unique set of polymorphic markers in an individual is useful for forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers is the same in the sample as in the suspect, one can conclude that the DNA from the suspect is consistent with that found at the crime scene. If frequencies of the polymorphic forms at the loci tested have been determined (e.g., by analysis of a suitable population of individuals), one can perform a statistical analysis to determine the probability that a match of suspect and crime scene sample would occur by chance.

p(ID) is the probability that two random individuals have the same polymorphic or allelic form at a given polymorphic site. For example, in biallelic loci, four genotypes are possible: AA, AB, BA, and BB. If alleles A and B occur in a haploid genome of the organism with frequencies x and y, the probability of each genotype in a diploid organism is (see WO 95/12607):

Homozygote: $p(AA)=x^2$

Homozygote: $p(BB)=y^2=(1-x)^2$

Single Heterozygote: $p(AB)=p(BA)=xy=x(1-x)$

Both Heterozygotes: $p(AB+BA)=2xy=2x(1-x)$

The probability of identity at one locus (i.e., the probability that two individuals, picked at random from a population will have identical polymorphic forms at a given locus) is given by the equation: $p(ID)=(x^2)$.

These calculations can be extended for any number of polymorphic forms at a given locus. For example, the probability of identity p(ID) for a 3-allele system where the alleles have the frequencies in the population of x, y, and z, respectively, is equal to the sum of the squares of the genotype frequencies: $P(ID)=x^4+(2xy)^2+(2yz)^2+(2xz)^2+z^4+y^4$.

In a locus of n alleles, the appropriate binomial expansion is used to calculate p(ID) and p(exc).

The cumulative probability of identity (cum p(ID)) for each of multiple unlinked loci is determined by multiplying the probabilities provided by each locus:

$$cum\ p(ID)=p(DI1)p(ID2)p(ID) \ldots p(IDn).$$

The cumulative probability of non-identity for n loci (i.e., the probability that two random individuals will be difference at 1 or more loci) is given by the equation:

$$cum\ p(nonID)=1-cum\ p(ID).$$

If several polymorphic loci are tested, the cumulative probability of non-identity for random individuals becomes very high (e.g., one billion to one). Such probabilities can be taken into account together with other evidence in determining the guilt or innocence of the suspect.

B. Paternity Testing

The object of paternity testing is usually to determine whether a male is the father of a child. In most cases, the mother of the child is known, and thus, it is possible to trace the mother's contribution to the child's genotype. Paternity testing investigates whether the part of the child's genotype not attributable to the mother is consistent to that of the puntative father. Paternity testing can be performed by analyzing sets of polymorphisms in the putative father and in the child.

If the set of polymorphisms in the child attributable to the father does not match the set of polymorphisms of the putative father, it can be concluded, barring experimental error, that that putative father is not the real father. If the set of polymorphisms in the child attributable to the father does match the set of polymorphisms of the putative father, a statistical calculation can be performed to determine the probability of a coincidental match.

The probability of parentage exclusion (representing the probability that a random male will have a polymorphic form at a given polymorphic site that makes him incompatible as the father) is given by the equation (see WO 95/12607): $p(exc)=xy(1-xy)$, where x and y are the population frequencies of alleles A and B of a biallelic polymorphic site.

(At a triallelic site $p(exc)=xy(1-xy)+yz(1-yz)+xz(1-xz)+3xyz(1-xyz))$, where x, y, and z and the respective populations frequencies of alleles A, B, and C).

The probability of non-exclusion is: $p(non\text{-}exc)=1-p(exc)$.

The cumulative probability of non-exclusion (representing the values obtained when n loci are is used) is thus:

$$Cum\ p(non\text{-}exc)=p(non\text{-}exc1)p(non\text{-}exc2)p(non\text{-}exc3) \ldots p(non\text{-}excn).$$

The cumulative probability of the exclusion for n loci (representing the probability that a random male will be excluded: cum p(exc)=1−cum p(non-exc).

If several polymorphic loci are included in the analysis, the cumulative probability of exclusion of a random male is very high. This probability can be taken into account in assessing the liability of a putative father whose polymorphic marker set matches the child's polymorphic marker set attributable to his or her father.

Kits

As set forth herein, the invention provides methods, e.g., diagnostic and therapeutic methods, e.g., for determining the type of allelic variant of a polymorphic region present in a 5-LO gene, such as a human 5-LO gene. In preferred embodiments, the methods use probes or primers comprising nucleotide sequences which are complementary polymorphic region of a 5-LO gene (SEQ ID NOs:4–6). In a more preferred embodiment, the methods are used to determine the identity of one or more allelic variants in polymorphic region which is included in the haplotype described herein. Accordingly, the invention provides kits for performing these methods.

In a preferred embodiment, the invention provides a kit for determining whether a patient has a more moderate or more severe inflammatory or allergy disease phenotype associated with a specific allelic variant of a 5-LO polymorphic region. In an even more preferred embodiment, the disease or disorder is characterized by an abnormal 5-LO activity, e.g., aberrant 5-LO expression. In an even more preferred embodiment, the inflammatory or allergy disease is, e.g., asthma, lung inflammation, nephritis, amyloidosis, rheumatoid arthritis, chronic bronchitis, sarcoidosis, scleroderma, lupus, polymyositis, Reiter's syndrome, psoriasis, pelvic inflammatory disease, orbital inflammatory disease, thrombotic disease, and inappropriate allergic responses to environmental stimuli such as poison ivy, pollen, insect stings and certain foods, including atopic dermatitis and contact dermatitis.

A preferred kit provides reagents for determining whether a patient will or will not be responsive to treatment of a disease or disorder associated with a specific allelic variant of a polymorphic region of a 5-LO gene, e.g., asthma, with, for example, a 5-LO inhibitor. In a preferred embodiment, the inflammatory disease is, e.g., asthma, lung inflammation, nephritis, amyloidosis, rheumatoid arthritis, chronic bronchitis, sarcoidosis, scleroderma, lupus, polymyositis, Reiter's syndrome, psoriasis, pelvic inflammatory disease, orbital inflammatory disease, thrombotic disease, and inappropriate allergic responses to environmental stimuli such as poison ivy, pollen, insect stings and certain foods, including atopic dermatitis and contact dermatitis. In a preferred embodiment, the kit of the invention can be used in selecting the appropriate drug to administer to a patient suffering from an inflammatory disease or disorder.

Preferred kits comprise at least one probe or primer which is capable of specifically hybridizing under stringent conditions to a 5-LO sequence or polymorphic region and instructions for use. The kits preferably comprise at least one of the above described nucleic acids. Preferred kits for amplifying at least a portion of a 5-LO gene, e.g., the 5' upstream regulatory element, comprise two primers, at least one of which is capable of hybridizing to an allelic variant sequence. Even more preferred kits comprise a pair of primers selected from the group consisting of SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16 SEQ ID NO: 17and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, SEQ ID NO: 33 and SEQ ID NO: 34, SEQ ID NO: 35 and SEQ ID NO: 36, SEQ ID NO: 37 and SEQ ID NO: 38, SEQ ID NO: 39 and SEQ ID NO: 40, SEQ ID NO: 41 and SEQ ID NO: 42, SEQ ID NO: 43 and SEQ ID NO: 44, SEQ ID NO: 45 and SEQ ID NO: 46, SEQ ID NO: 47 and SEQ ID NO: 48, SEQ ID NO: 49 and SEQ ID NO: 50, SEQ ID NO: 51 and SEQ ID NO: 52, SEQ ID NO: 53 and SEQ ID NO: 54, SEQ ID NO: 55 and SEQ ID NO: 56, SEQ ID NO: 57 and SEQ ID NO: 58, and SEQ ID NO: 59 and SEQ ID NO: 60 (see Table 3).

The kits of the invention can also comprise one or more control nucleic acids or reference nucleic acids, such as nucleic acids comprising a 5-LO intronic sequence. For example, a kit can comprise primers for amplifying a polymorphic region of a 5-LO gene and a control DNA corresponding to such an amplified DNA and having the nucleotide sequence of a specific allelic variant. Thus, direct comparison can be performed between the DNA amplified from a patient and the DNA having the nucleotide sequence of a specific allelic variant. In one embodiment, the control nucleic acid comprises at least a portion of a 5-LO gene of an individual who does not have an inflammatory disease, aberrant synthesis of leukotrienes, decreased eosinophil levels, or a disease or disorder associated with an aberrant 5-LO activity.

Yet other kits of the invention comprise at least one reagent necessary to perform the assay. For example, the kit can comprise an enzyme. Alternatively the kit can comprise a buffer or any other necessary reagent.

The present invention is further illustrated by the following examples which should not be construed as limiting in any way. The contents of all cited references (including, without limitation, literature references, issued patents, published patent applications as well as the Figures, Tables, and database references) as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

EXAMPLES

Example 1

Determination of the Genomic Structure of the 5-LO Gene

This example describes the determination of the genomic structure of the 5-LO gene. Identification of the various functional regions of the gene, including, but not limited to, 5' and 3' untranslated regions (UTR) and intron/exon boundaries was necessary for subsequent variant detection experiments. Two sequence comparison software applications were used to elucidate genomic structure of the 5-LO gene. Both applications involve the comparison of the cDNA sequence of the 5-LO gene to the sequence of large genomic DNA clones (bacterial artificial chromosomes or BACs) that encode the 5-LO gene in it's untranscribed form. One application is the Basic Local Alignment Search Tool™ or BLAST™ (Altschul et al. (1990) *J. Mol. Biol.* 215(3):403–410; Altschul et al. (1993) *Nature Genetics* 3:266–272; Altschul et al. (1997) *Nuc. Acids Res.* 25:3389–3402; Karlin and Altschul (1990) *Proc. Natl. Acad. Sci. USA* 87:2267–2268). The other application is Sequencher 3.1.1 (Gene Codes Corporation). Although based on different algorithms, these applications aid in the determination of genomic structure by the same principle.

These applications allow the comparison of two or more different nucleotide sequences (in the case of BLAST™, amino acid sequences can also be aligned) and identification or alignment of regions of high similarity or identity. Aligning cDNA sequence of the 5-LO gene with the corresponding BAC sequences with either tool allows visualization of regions of identity between the transcribed sequence and the sequence of the genomic region from which it was derived. Regions of sequence identity between the two sources are exonic regions and can be confirmed by the presence of known conserved splice elements flanking them. Regions of sequence contained in the BAC sequences but not in the cDNA sequence are considered to be either intronic sequence or lay outside of the 5' and 3' boundaries of the gene.

Once the genomic structure of the 5-LO gene, e.g., intron/exon boundaries, was determined, PCR primers were designed for use with variant nucleotide detection experiments. Exonic sequences (including intron/exon junctions), 5'UTR, 3'UTR and approximately of 1 kbp upstream of the transcription start site were scanned for variant nucleotide detection as described in Examples 2, 3, 4, and 5.

Example 2

Identification of Primer Pairs to Isolate Intronic, Exonic, and 5' Upstream Regulatory Element Sequences for Detection of Polymorphisms and Mutations Multiple pairs of primers were synthesized in order to amplify each of the exons or portions thereof and adjacent intronic regions. Genomic DNA from a human subject was subjected to PCR in 25 μl reactions (1×PCR Amplitaq polymerase buffer, 0.1 mM dNTPs, 0.8 μM 5' primer, 0.8 μM 3' primer, 0.75 units of Amplitaq polymerase, 50 ng genomic DNA) using each of the above described pairs of primers under the following cycle conditions: 94° C. for 2 min, 35×[94° C. for 40 sec, 57° C. for 30 sec, 72° C. for 1 min], 72° C. for 5 min, 4° C. hold. The resulting PCR products were analyzed on a 2% agarose gel. The identity of the PCR product was confirmed by digestion with a restriction enzyme and subsequent agarose electrophoresis. Twenty-three pairs of oligomers were chosen to serve as PCR primers to amplify regions containing each of the 14 coding exons of the human 5-LO gene and eleven pairs of primers were chosen to serve as PCR primers to amplify the 5' upstream regulatory element. The nucleotide sequences of the forward and reverse primers are indicated in Table 3, as well as the SEQ ID NOs for each primer and the location of the primers (e.g., exon, 3'UTR, or 5'UTR/5' upstream regulatory element) within the 5-LO gene. The expected sizes of the PCR products are also set forth in Table 3. In addition, polymorphism ID numbers corresponding to those listed in Table 1 are included where there was a polymorphism identified with a particular primer pair.

Example 3

Detection of Polymorphic Regions in the Human 5-LO Gene by DHPLC

This example describes the use of denaturing high performance liquid chromatography (DHPLC) for the identification of DNA sequence variations.

DNA samples for these experiments were obtained from a population of 144 individuals to be used for polymorphism discovery. These 144 DNA samples included DNA samples from a population of forty-eight North American Caucasian individuals, forty-eight African American individuals, and forty-eight individuals from throughout the Anhui province in East Central China. Furthermore, the forty-eight DNA samples from the Chinese individuals are from unrelated control subjects, obtained at random, and have been assessed for a number of traits related to asthma and allergies. Among the primary variables of interest are lung function, a response to "skin-prick" tests, physician's diagnosis of asthma, total serum IgE, and peripheral blood eosinophils. The peripheral blood eosinophil count was measured using the Coulter counter technique as described in Barnard D F, et al. (1989) *Clin Lab Haematol* 11(3):255–66, and is expressed in terms of eosinophils per microliter.

DHPLC uses reverse-phase ion-pairing chromatography to detect the heteroduplexes that are generated during amplification of PCR fragments from individuals who are heterozygous at a particular nucleotide locus within that fragment (Oefner and Underhill (1995) *Am. J. Human Gen.* 57:Suppl. A266).

Generally, the analysis was carried out as described in O'Donovan et al. ((1998) Genomics 52:44–49). PCR products having product sizes ranging from about 150–400 bp were generated using the primers and PCR conditions described in Example 2. Two PCR reactions were pooled together for DHPLC analysis (4 ul of each reaction for a total of 8 ul per sample). DHPLC was performed on a DHPLC system purchased from Transgenomic, Inc. The gradient was created by mixing buffers A (0.1M TEAA) and B (0.1M TEAA, 25% Acetontitrile). WAVEmaker™ software was utilized to predict a melting temperature and calculate a buffer gradient for mutation analysis of a given DNA sequence. The resulting chromatograms were analyzed to identify base pair alterations or deletions based on specific chromatographic profiles.

Example 4

Detection of Polymorphic Regions in the Human 5-LO Gene by SSCP

Genomic DNA from each of the 144 individuals described in Example 3 was subjected to PCR in 25 μl reactions (1×PCR Amplitaq polymerase buffer, 0.1 mM dNTPs, 0.8 μM 5' primer, 0.8 μM 3' primer, 0.75 units of Amplitaq polymerase, 50 ng genomic DNA) using each of the above described pairs of primers under the following cycle conditions: 94° C. for 2 min, 35×[94° C. for 40 sec, 57° C. for 30 sec, 72° C. for 1 min], 72° C. 5 min, 4° C. hold. The expected sizes of the PCR products, are also indicated in Table 3.

The amplified genomic DNA fragments were then analyzed by SSCP (Orita et al. (1989) *PNAS USA* 86:2766, see also Cotton (1993) *Mutat Res* 285:125–144; and Hayashi (1992) *Genet Anal Tech Appl* 9:73–79). From each 25 μl PCR reaction, 3 μl was taken and added to 7 μl of loading buffer. The mixture was heated to 94° C. for 5 min and then immediately cooled in a slurry of ice-water. 3–4 μl were then loaded on a 10% polyacrylamide gel either with 10% glycerol or without 10% glycerol, and then subjected to electrophoresis either overnight at 4 Watts at room temperature, overnight at 4 Watts at 4° C. (for amplifying a 5' upstream regulatory element), or for 5 hours at 20 Watts at 4° C. The secondary structure of single-stranded nucleic acids varies according to sequence, thus allowing the detection of small differences in nucleic acid sequence between similar nucleic acids. At the end of the electrophoretic period, the DNA was analyzed by gently overlaying a mixture of dyes onto the gel (1× the manufacturer's recommended concentration of SYBR GREEN I™ and SYBR GREEN II™ in 0.5×TBE buffer (MOLECULAR PROBES™)) for 5 min, followed by rinsing in distilled water and detection in a FLUOROIMAGER 575™ (MOLECULAR DYNAMICS™).

Example 5

Identification of Polymorphic Regions in the Human 5-LO Gene by Direct Sequencing of PCR Products To determine the sequences of the polymorphisms identified, the regions containing the polymorphisms were reamplified using the aforementioned primers. The genomic DNA from the subjects was subjected to PCR in 50 μl reactions (1×PCR Amplitaq polymerase buffer, 0.1 mM dNTPs, 0.8 μM 5' primer, 0.8 μM 3' primer, 0.75 units of Amplitaq polymerase, 50 ng genomic DNA) using each of the above described pairs of primers under the following cycle conditions: 94° C. for 2 min, 35×[94° C. for 40 sec, 57° C. for 30 sec, 72° C. for 1 min], 72° C. 5 min, 4° C. hold. The newly amplified products were then purified using the Qiagen Qiaquick™ PCR purification kit according to the manufacturer's protocol, and subjected to sequencing using the aforementioned primers which were utilized for amplification.

The results indicate that there is a change from a guanine to an adenine in the 5' upstream regulatory element of the 5-LO gene at residue 1000 of the reference sequence GI 187166 (polymorphism ID No. 5loprr1). A second polymorphism is a deletion in the 5' upstream regulatory element at residues 472477 of the reference sequence GI 187166 (polymorphism ID No. 5lo01a). A third polymorphism is a change from a guanine to an adenine in the 5' upstream regulatory element at residue 559 of the reference sequence GI 187166 (polymorphism ID No. 5lo04a). These polymorphisms are listed in Table 1 and correspond to SEQ ID NOs: 4–6.

Example 6

Identification of a Variant Haplotype in the Promoter Region of 5-LO

Three populations comprised of individuals of different racial backgrounds, i.e., North American Caucasian, Asian Chinese, and African American, were screened for variants in the promoter region of 5-LO using the methods described herein. It was found that polymorphism Id Nos. 5loprr1, 5lo01a, 5lo04a, 5lonrra, and 5lonrrb all segregate together such that when an individual has one of these polymorphisms, all five polymorphisms are present. This five polymorphism haplotype is conserved at an identical frequency between these three different racial backgrounds (North American Caucasian, Asian Chinese, and African American). The five polymorphisms (polymorphism Id Nos. 5loprr1, 5lo01a, 5lo04a, 5lonrra, and 5lonrrb) are in complete linkage disequilibrium and are present at a frequency of approximately 18% in all three populations screened. Moreover the haplotype was in linkage disequilibrium with any one of the three variant 5-LO Sp-1 binding sites. In Caucasian and Chinese populations, the haplotype was associated with the variant Sp1 binding site having four Sp1 motifs. In the African American population, the haplotype was found to be associates with any one of the three variant Sp1 binding sites (i.e., binding sites having 3, 4 or 6 Sp1 motifs).

Example 7

Association of 5-LO Variants with Eosinophil Levels in Chinese Asthmatic Families This example describes the determination of the association between the presence of one or more polymorphisms, low eosinophil levels in a sample of Chinese asthmatic families.

Method

A study of 275 families was conducted to determine whether the variant identified as "Polymorphism ID No. 5lo01a" (see Table 1) is associated with asthma-related phenotypes. Selected individuals from these families were genotyped at the 5lo01a polymorphism. Two statistical tests were then conducted to determine whether evidence exists of an association between this locus and asthma-related phenotypes.

For this study, genomic DNA was isolated from peripheral blood lymphocytes using the Puregene™ kit (Gentra Systems Inc.™), according to manufacturer's suggested protocol. SSCP analysis (see Example 4) was used to determine each subjects' genotype at the promoter deletion/insertion polymorphism 5lo01a (e.g., the deletion/insertion of (GTTAAA) (SEQ ID NO:62).

To determine whether genotype is associated with peripheral blood eosinophil count (an index of asthmatic disease), counts (per ml) were compared between individuals carrying at least one copy of the deletion polymorphism (e.g., those with at least one allele that is missing the residues "GTTAAA" (SEQ ID NO:62)), and those carrying no copies of the polymorphism. One individual was selected from each family; the selections were based solely on genotype, and were designed to make the sizes of these two comparison groups as similar as possible. A Student T-TEST was used to determine whether the difference in mean eosinophil count between these two groups was significant.

Results

For the first test, 138 unrelated individuals with at least one copy of the deletion were analyzed, as were 137 unrelated individuals with no copies of the deletion. The mean eosinophil level among individuals with the deletion was 222.17 (standard deviation=246.38); the mean among individuals without the deletion was 324.09 (standard deviation=482.75). The Student T-TEST comparing the mean eosinophil level between these two groups revealed that there is a significant difference (p=0.029) between these means.

Discussion

An association test was performed to determine whether a 5-LO promoter variant is associated with asthma-related phenotypes. Specifically, it was examined whether genotype at the 5-LO polymorphism associates with peripheral blood eosinophil counts. The test gave evidence that such an association exists. The test demonstrated that eosinophil counts are significantly lower among individuals carrying at least one copy of the rare deletion allele at this locus. Thus, the promoter genotype can be used predict whether an individual has a greater chance of having a abnormally low eosinophil count.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for determining the identity of an allelic variant of a 5-LO gene in a nucleic acid obtained from a patient, wherein the sample comprises a 5-lipoxygenase (5-LO) gene sequence, comprising contacting a sample nucleic acid from the patient with a probe or primer having a sequence which is complementary to a 5-LO gene sequence, wherein the allelic variant comprises one or more nucleotide sequences selected from the group consisting of those set forth in SEQ ID NO: 4, SEQ ID NO:5, and SEQ ID NO:6, or the complements thereof, thereby determining the identity of the allelic variant.

2. The method of claim 1, wherein determining the identity of the allelic variant comprises determining the identity of at least one nucleotide at any one of the nucleotide residues selected from the group consisting of: residue 1000 of SEQ ID NO:1, any one of residues 472–477 of SEQ ID NO:1, and residue 559 of SEQ ID NO:1.

3. The method of claim 1, wherein determining the nucleotide content comprises sequencing the nucleotide sequence.

4. The method of claim 1, wherein determining the identity of the allelic variant comprises performing a restriction enzyme site analysis.

5. The method of claim 1, wherein determining the identity of the allelic variant is carried out by single-stranded conformation polymorphism.

6. The method of claim 1, wherein determining the identity of the allelic variant is carried out by allele specific hybridization.

7. The method of claim 1, wherein determining the identity of the allelic variant is carried out by primer specific extension.

8. The method of claim 1, wherein determining the identity of the allelic variant is carried out by an oligonucleotide ligation assay.

9. The method of claim 1, wherein the probe or primer comprises a nucleotide sequence from 15 to about 30 nucleotides.

10. The method of claim 1, wherein the probe or primer is labeled.

* * * * *

UNITED STATES PATENT AND TRADEMARK OFFICE

CERTIFICATE OF CORRECTION

PATENT NO. : 6,797,475 B2
APPLICATION NO. : 10/071411
DATED : September 28, 2004
INVENTOR(S) : Glenn Barnes et al.

It is certified that error appears in the above-identified patent and that said Letters Patent is hereby corrected as shown below:

<u>In the Specification</u>:

Col. 45, line 46, before the Sequence Listing, please insert attached Tables 1 – 3.

Signed and Sealed this

Second Day of September, 2008

JON W. DUDAS
*Director of the United States Patent and Trademark Office*

Table 1

| | | SNPs and Deletion Variants | | | |
|---|---|---|---|---|---|
| 1 | 2 | 3 | 4 | 5 | 6 |
| SEQ ID NO. | Polymorphism ID No. | Sequence | Primers | Location and Change | Position and Reference Sequence |
| | | | | | |
| 4 | Sloprr1 | AGGAGCGCGCgAAACCTTCTC | 5' upstream reg. elem. | 5' upstream reg. elem. G/A | GI:187166 residue 1000 |
| 5 | Slo81a | TGGACTTAAA(GTTAAA del)TACTTTTGTG | 5' upstream reg. elem. | 5' upstream reg. elem. Deletion | GI:187166 residue 472-477 |
| 6 | Slo04a | TCATGTATCCgATTAGAGACT | 5' upstream reg. elem. | 5' upstream reg. elem. G/A | GI:187166 residue 559 |
| | | | | | |
| | | [redacted] | [redacted] | | |
| | KNOWN SNPs | | | | |
| SEQ ID NO. | Polymorphism ID No. | Sequence | Primers | Location and Change | Position and Reference Sequence |
| 7 | Slonrra | ACTTACTATAgCACTGCGGTA | 5' upstream reg. elem. | 5' upstream reg. elem. G/A | GI:187166 residue 84 |
| 8 | Slonrrb | TTACAGATCAgTGGACTAGAA | 5' upstream reg. elem. | 5' upstream reg. elem. G/A | GI:187166 residue 137 |

TABLE 2.

| SEQ ID NO: | Residue/ Reference Sequence | Probe Sequence |
|---|---|---|
| 64 | 1000/GI 187166 | AGGAGCGCGCRAAACCTTCTC |
| 65 | 472-477/GI 187166 | TGGACTTAAA(GTTAAA del)TACTTTTG |
| 66 | 559/GI 187166 | TCATGTATCCRATTAGAGACT |

Table 3.

| Exon | SEQ ID NO: | Sequence (5' -> 3') | Product Length | Polymorphism ID No. |
|---|---|---|---|---|
| 1 | 9 | GGGCCAGGGACCAGTGGT | 296 | |
| | 10 | AACCGGGTCCCGGACGCA | | |
| 2 | 11 | AGGCTCAGGAGACCACGCA | 356 | |
| | 12 | TCCCGCCCCTGCACAG | | |
| 3 | 13 | CATTGGGCATTGTTATTGTTCTTC | 313 | |
| | 14 | AGTTGTAGGTAAGGTGAAGTTTGGG | | |
| 4 | 15 | TCGTCTGACAGTGTGGGCG | 294 | |
| | 16 | CCATGAGGAAAGGAGTGAGGGT | | |
| 5 | 17 | TGGTGTGAAGGGGCTCTGC | 244 | |
| | 18 | AAGTATCAGACAGGAGAGCAGCATC | | |
| 6 | 19 | GCCTCGCTTTTCTCCTGGTAG | 213 | |
| | 20 | CCACTTCCCCAGCCCATCA | | |
| 7 | 21 | GATTTTTGGTCCGTCTGCTGAG | 228 | |
| | 22 | GAAAGGTGTGCCCCCCAG | | |
| 8 | 23 | TTTCCTTTCCCCCAATGTATCA | 246 | |
| | 24 | GGGCGGTAGCTGGCTGTA | | |
| 9 | 25 | GAGCTGCGGGTCCCTGAG | 226 | |
| | 26 | AGATAGGGAGTGAAGGCGGC | | |
| 10 | 27 | AGCCACCCGCTCAGGGCA | 266 | |
| | 28 | AGGCAGGGGTCCCGGCT | | |
| 11 | 29 | TCCGCAGACCTGGCTGG | 242 | |
| | 30 | GAGGGGTGGCGGAGGG | | |
| 12 | 31 | CCGGTGGTTCCACCCTAG | 177 | |
| | 32 | GGGAGGAGGCAGCGGCCTT | | |
| 13 | 33 | TGCTGGCGGTCGTCTCC | 210 | |
| | 34 | CGCCCTGCCCAGCTTC | | |
| 14/3'UTR | 35 | TGGGATGATTATTTTCTGTTCTATTTG T | 292 | |
| | 36 | GAGTAGACACTGCTTGAGGGAAAAA | | |
| 14/3'UTR | 37 | GCGTCCTGTCCACACCCA | 209 | |
| | 38 | TGAACTGATTTATTTTTATGGCAACC | | |
| 14/3'UTR | 39 | GCCCGATTCCGCAAGAAC | 228 | 5lo7a |
| | 40 | GAGGAAGAGATGTGACTGCCAAGA | | |
| 14/3'UTR | 41 | CAGTTTACACGGGTAGTGGATTGAC | 340 | |
| | 42 | GAAGAGATGTGACTGCCAAGAGG | | |
| 14/3'UTR | 43 | CCTCTTGGCAGTCACATCTCTTC | 252 | |
| | 44 | ACAAATAGAACAGAAAATAATCATCCC A | | |
| 5'UTR/prom | 45 | CTAACTCAAAATGGGTCACGGAT | 217 | 5lo1a |
| | 46 | ATTGCTTCTGCGGGTTGTGT | | |
| 5'UTR/prom | 47 | GAGAGCCGACCCGTGACC | 212 | |
| | 48 | GCTGATACTGAGGATGGATTCTGG | | |
| 5'UTR/prom | 49 | TGAAAACACAACCCGCAGAAG | 216 | 5lo4a |
| | 50 | TGCACCTGGCAAATGGCTT | | |
| 5'UTR/prom | 51 | AAAGAACAGCGTTGGTGGAT | 255 | 5lonrra, 5lonrrb |
| | 52 | CAAATTCATTGTGTTGCATGTG | | |
| 5'UTR/prom | 53 | AACTTAGCCGAGATCAATACACGC | 172 | |
| | 54 | GCAAATGCCTGGAAGGGTG | | |
| 5'UTR/prom | 55 | GCACAAACCCAAGACAGTATGAGG | 112 | |
| | 56 | CGGCGGGGATGTGAAGTC | | |
| 5'UTR/prom | 57 | TGGCACTGAGAACTTGGGGA | 192 | |
| | 58 | ACTGGGGCAACCTCGGCT | | |
| 5'UTR/prom | 59 | GCTCCAGAATCCATCCTCAGTATC | 154 | |
| | 60 | GCCTCTGCTCTCCCCAAGTTC | | |

SEQUENCE LISTING

```
<160> NUMBER OF SEQ ID NOS: 66

<210> SEQ ID NO 1
<211> LENGTH: 2189
<212> TYPE: DNA
<213> ORGANISM: Homo sapiens

<400> SEQUENCE: 1

ggatccagaa taaccaaaac aatattgaaa aataaagaac agcgttggtg gattaacatt      60

ttccaatttc aaaacttact atagcactgc ggtaatcaag cagtgtggca ctgtatagca     120

tgtacattac agatcagtgg actagaatca atgtccagaa ataaaccgtt atgtttataa     180

tgaattactt tttaataagg tgtcaagaca acgcaatggg aaaagaataa tgaattcaac     240

aaatgatgca tggacaaccg gacatgcaca tgcaacacaa tgaatttgaa ttcttctatc     300
```

-continued

```
gctccatgca taaaaactaa ctcaaaatgg gtcacggatg taaatgaaaa gctaaaacta    360

taataatcct agaggaaaac ctaggagtaa atctttaaga tgttattgta ggcagtggtt    420

tctcagatag gaccccaaaa tcacaagcga caaaaagaaa ttggacttaa agttaaatac    480

ttttgtgctt caaacatcat caagaaagtg aaaacacaac ccgcagaagc aataaaaatg    540

tctgtaagtc atgtatccga ttagagactt ctatccagga tatataaata atgcaattca    600

atgataaaaa agataaatag cccagttttc caaagagtca agcatctgaa tatacatctc    660

tccaaaaata tacagatatc caacaagcat gtgaaaagat gttcaaagcc atttgccagg    720

tgcacaaacc caagacagta tgaggagatg ctacagggac tctgctgctt cacagacatg    780

aagcgttggt gagaatgtag gcagccgcct ttggggactt cacatccccg ccgccccacg    840

cacggtgagc tagtgtttaa acttagccga gatcaataca cgcgactgtg tgcccgtcag    900

accctgcgct gccggcgggg ctgggagagg cgggcgccag gagtgggcgg gaacctgggg    960

gtcaggcccc agccgcggga agcgcgccca ggagcgcgcg aaaccttctc cacacccttc   1020

caggcatttg cccgccgcga ttcagagagc cgacccgtga cccctggcct cccctagaca   1080

gccccgcatg tccagatgtg ccgtcccgcc tgcctcccgc gaccactggc catctctggg   1140

cctgggcgcg gttctcggcg cccggcctgc ccccgccagg agccgcaggt ccagccagtg   1200

aagaagcccg cgcctgaagg agcctctgtg ctccagaatc catcctcagt atcagcgctg   1260

gggtggcctc ctccaggaag cccttctgat tctctcatgg gtcgctcttc ctctgcagac   1320

tcccggagca ccccctgctc caagtaccgc aagtggcact gagaacttgg ggagagcaga   1380

ggctgtgcct agatttgtag ggagtccccg cagctccacc ccagggccta caggagcctg   1440

gccttgggcg aagccgaggc aggcaggcag ggcaaagggt ggaagcaatt caggagagaa   1500

cgagtgaacg aatggatgag gggtggcagc cgaggttgcc ccagtcccct ggctgcagga   1560

acagacacct cgctgaggag agacccagga gcgaggcccc tgccccgccc gaggcgaggt   1620

cccgcccagt cggcgccgcg cgtgaagagt gggagagaag tactgcgggg gcgggggcgg   1680

gggcgggggc gggggcgggg gcagccggga gcctggagcc agaccggggc ggggccggga   1740

ccggggccag ggaccagtgg tgggaggagg ctgcggcgct agatgcggac acctggaccg   1800

ccgcgccgag gctcccggcg ctcgctgctc ccgcggcccg cgccatgccc tcctacacgg   1860

tcaccgtggc cactggcagc cagtggttcg ccggcactga cgactacatc tacctcagcc   1920

tcgtgggctc ggcgggctgc agcgagaagc acctgctgga caagcccttc tacaacgact   1980

tcgagcgtgg cgcggtgagc gcgggcgggg cacgggtgga gcgcgggctg aggtgcgtcc   2040

gggacccggt ttggacggca gaggcctggg cgggggcgcc gagggcccgt cggggcggcc   2100

cggacaggac tgggggtgtc caggaccctg tcagggaggg cagaactgcg gtggggcgtg   2160

ccctgggctc ccagtggccg gtgggtacc                                     2189
```

<210> SEQ ID NO 2
<211> LENGTH: 168273
<212> TYPE: DNA
<213> ORGANISM: Homo sapiens
<220> FEATURE:
<221> NAME/KEY: misc_feature
<222> LOCATION: (1)...(168273)
<223> OTHER INFORMATION: n = A,T,C or G

<400> SEQUENCE: 2

```
ttgcacgctn ctcagccccg gctgtactat tggtctacac gtgccatcgt ggtttgctgc     60

acccatcaac ccatcatcta cattaggtat ttctcctaat gctctctttc cccttgcccc    120
```

-continued

```
ccaccctcta acacgccctg ttgtgtgatg ttgacctccc tgtgtacatg tgttgtcatt    180
gtacaactcc tgcttatgag tgacaacatc tgtctgattt tctgtcttgt gttagtttgc    240
tgagaatgat ggttcccatc ttcatccttg tacctgcaaa ggacatgaac tcatccttta    300
atatggctgc ttagaatccc acagtataga tgtgcctcat tttctttatc cagactatca    360
ttgatgggca tttgggttgg atccaagact ttgctattgt gaacagtgat tcaataaaca    420
tacgagtgca tgtgtcttta tggatgaatg attgataatc ctttgggcat atacccacta    480
atgggattgc tggacctaat ggtttgcctg gatcctgatc cttgaggaat caccacactc    540
tcttacagtg taaaagtgtc tctatatata ctcatcccct ccagcatctg ttatttactg    600
actctttaat catcaacctt cttactggag agagaaggtt taattaccac taatgacgag    660
cctttaatca aattgttgtt ggacccttcc caacttactt gcgaaggggt catttgtaaa    720
cttacgccac cttttgatgg ggcagttttt ctcgtttatc cgcaaagatc ctgggggacc    780
ccttttttta actcttttga agaccgttat atctgaacaa tttctcccat accgagaggt    840
ggcgggttac aacccttgaa agtttctttt tttttttggg gccccttagt ttcacaaaaa    900
tcccttcgga ccaatttgcc ttttgttgcc aaggaatttt tccccctaag tcactaggaa    960
tttttcccag ggcacacagg tgtagtggcc ttccccagaa tttttctcct gggtatccaa   1020
tgttataaga aaaaaaattg gggaattttt ttaaacctcc aataaaattt tttatagaga   1080
taaggccggt ttcatttnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnncgc   1200
ggtcttcagc ccgtggtgaa gactgattaa cagtcataag aaggtaaagc tctaagtgac   1260
ctgtaagaaa catacagtct cacacaatta ggcaaggagt ccaacttgga agaaagagtg   1320
gcatagattc aaaccctgat gccacaactt atgttaaccc tcctgaggct caacttctca   1380
cacatgacag gagaatctca tcatgtacct caattaattg atatacagat tatggtaaac   1440
attcaatgaa aaagtatgta aagtttctat cattctacta cagttggtat tcaacaaatg   1500
ccactttatt cactttctgt taagcctgaa agaagtactg aatgacatca acgagtgcaa   1560
ttcaacaaat ataatttgag cactgattac tcaataagca ttatgaggaa ctaaaatatt   1620
atcagcaaat gatggctgac atagaggaaa tgtgacagag taggaagatc cctgtactcc   1680
ctgtatcaaa ggactgagat tcttccactc aggaccatgt gtgaccccaa cagaaagtag   1740
aaatttacag aaagatacct ggcaaaacac ccaaatagtt tgaagttaaa aaatatacct   1800
ctgaataaca ccccatggaa atttttaaag attataatgt gaattaaaat gaaaacatat   1860
aaccataaca aaaattgtag gatacaggaa aactggtgct catatagcat taactgttta   1920
cattacattt tagagaatca acttaattca attatctaag tttctatttt agaaaactat   1980
gtaaaaaaag gagagcatat ttaaaaagta agcagaagaa caaaagataa gcatgacaga   2040
caatgaaatt gaaaatggaa aaatcataga gaagaatcaa atgaatcaaa agtagtttct   2100
tggaaaagat caataaataa aattggttga tataatttac tgatattagg agtgggaaag   2160
ataatcactg atcatagatc catgatgaac aagcttattt caataaatta ataaactcag   2220
caacttcaac aaaatggaca gattacttgg aagacaccaa ttaccaaagc tcaaaaaaag   2280
agaatctaaa tagtcctata tttatgaaaa aaaaaaacaa aactgaattt gtatttaaaa   2340
actttgccac aaagaaaatt ttaggttcag atgggtttcc taataaattt ttcccattta   2400
gtaagaataa tatcaattct acacaaactc attcaaaaaa aaaggagaga gaatacttta   2460
```

-continued

```
caacacgttc tgcaaggtca gtattaccct gataccaaaa caaaggatat tacataaaaa   2520
cgacaccaat atccttcatg aacatagatt cttcaccacg gggctggaag gatccgnnnn   2580
nnnnnnnnnn nnnnnnnnnn nnnnnnnnnn nnnnnnnnnn nnnnnnnnnn nnnnnnnnnn   2640
nnnnnnnnnn nnnnnnnnnn nnnnnnnnnn nnnnnnatag cacgcccttg agcccctggt   2700
gaatataaga gattaggcta cagcgtgttc tactccaact ttatttgctt tctgagcatc   2760
taattccact ttgcaaaatg gacatttttt ttccctcttg agagtcagga aattaccagg   2820
tgtgccagga taatccttag tatcaactgt aaaatatcag tataaaataa tgagtaagca   2880
tatttcagtg ggtgtttata tgcttttggt tgcatagcat gagccaaagg cagataaaaa   2940
atgtgggctc cagatagtga ctcaatctcc agaaatcata atgtcagtta cacaatgata   3000
tttctatatt ggcatcacaa aataatccac ttgtcatagg ataattgctc tagatgaggg   3060
catggagctg tgctgaggaa tctgccattt ttctttatcc agactctgtc tcataccgac   3120
cacaggcccc aatcattgtc tatcaaaaaa catgcttgtg tctcttttgg cttactatga   3180
aaggaagcaa gatcttttcc tcaagcattt aagtgttgac tgtgggctac ccagtgtgct   3240
agacactgng gatcaaattc tgtgaggtta aaaataccc ataactcact ggatagaaat   3300
tcaaaatgct cgctatgttg attctatgat caacttccaa ggggaccttt ntacctccta   3360
tcttcatcag caagcaacta cattgatttt gtagcccagg atctattccc acgtcaaccg   3420
tgggtttcaa atgtttgctc tagctcaatg gcctcttaag ccactaaccc aatatgttgc   3480
tttttaccag taaaaaagtg catctgggga ataagttggt gtatatttgt ggttcagcca   3540
gcccatagat cgtccagagg accccaggct taggaggaat cctcagattt gagagccact   3600
gtcctgtatg atgcagatag cacagctctt cctgaaaata ggaattcaaa tgaggaaaaa   3660
tgaaaactct cctaattatt ttcttctgcc tctttcattc caagctcatc taattatcat   3720
gctctattgt gaagaatcaa agaaagaact cataaatata ccttttgtgc ctgtattttg   3780
aatgtacgtt gtgcatgtaa gcctttgtgg ttaagcaaat gtcaagaaaa tccctagtcc   3840
cattgcttac agtcaatatg gggcaattca agcaaagtat atgcctctaa tatggtttga   3900
aaattctgaa agttcagaaa aaatgttgct acttcagcca tctgatgtta ctggatattg   3960
agaatgagac ctcctctccc tctgctttcc tcatttccat ctcctccttc ctctttctcc   4020
tctctccctc tcctttattc tccttctccc tcctctctct ccatgcttac tcccttcctc   4080
ttctccctct ttcttcttta ttctccttct ccctcctctc tctctctccc ctttttcctc   4140
ccttcctctc ctccctccct ctcctttatt ctccttctcc ctcctctctc tctctccccc   4200
ttttcctata ttcccagatt aggccatttt caaaactggt taaacattcc ccaaaagcat   4260
ttatgacaga gaattgacta ggatctcacc tgaatcacag agcttgccca ttgaacacag   4320
gcaaagatca agccattttc tcttgatgtg atgcttcagc attttatgca tttgaaacaa   4380
attttatgta aaaaaaagct tagccctttg gtgacgggga ttccttttct ggatgatctg   4440
ccaaagaatc aagacccaac gtccagctta tcaaattttc tctggacctt tannnnnnnn   4500
nnnnnnnnnn nnnnnnnnnn nnnnnnnnnn nnnnnnnnnn nnnnnnnnnn nnnnnnnnnn   4560
nnnnnnnnnn nnnnnnnnnn nnnnnnnnnn nnccgtggtg aagacttcca cgtgaacttt   4620
aaagtagttt tttccaattc tgtgaagaat gtcattggta gcttgatggg gatggcactg   4680
aagattttct tcatttttat gactgcatag cattccatgg agtatatgta ccacattttc   4740
tttatccaat tcactgttgg tgggcaccta ggtcaattcc atgactttgc tgttgtgaat   4800
agtactgcaa tgaacatgtg agtgcatgtg tctttttgga ggaataattt gttctctttt   4860
```

-continued

```
ggatatatac ccagtaatgg ggttgctggg ccaaatggta gttctgtttt aagttctttg   4920
agaaatctcc aaactgcttt ccacagaggc tgaactaatt gacattccca ctgccatgca   4980
tgagcattcc cttttctcct cagctccacc aacatctgtt gctttctgac tttttgataa   5040
tagccattct gatgtgtgag atggtagccc attggggttt cttttttttt ttttaagaca   5100
gagtctcact ctgtcaccta ggctgtggca caatgttggc tcgctgcaac ctctgcctcc   5160
tgggttcaag tgattctcct acctcagcct actgagaagc tagggttaca ggcacctgcc   5220
accacaccca gctaattttg gtatttttgg tagagacagg gtttagccat attggcaagg   5280
ctggtctcta actcctgacc tcaggtgacc cacctgcctc ggcttcccaa agtgctggga   5340
ttgcatgcgt tagctaccat gggtggtttt tgacttgcat ttctctgatg attagtaatg   5400
atgatccttt tttcatacat ttgttggcca cttgtatgtc ttcttttgag aagtgtctgt   5460
tcatatcttt tgcccatttt tcaatggggt tgtttttttcc ttgtccagtt gtttaagtta   5520
tttatagatt ctggatatta gtcctttgtt gggtgcataa tttgcaaata ttttatctca   5580
ttctgtaggt tatctattta atctgttgat agtgtctttt cttgtacaga agttgttcag   5640
tttaattagg tctcacttgt caatttctgt ttttgttgta attgcttttg aggacttaat   5700
cataaattct ttcccaaggc ccatgtccag aatggtgttt ctgagatttt cttctaggat   5760
tcttttactt caaggtctta tatttaaatc tttaatccat ctggagttaa tttttgtatg   5820
tggcaaaagt taggtgtctt gttttatttt tctgcatatg gctagtcagc tatcccagga   5880
ccattcattc actagggagt cctttcccca ttgtttactt ttggcaactt tgtcaaagat   5940
tagatggctg taagtgtgca gatttatttc tcagctctct attctgttca actggtgtag   6000
gtatctgttt tcgtactagc accatgctgt tttggttact gtagtcttat tagtatagtt   6060
tgaagccagg taatgtgatg cctctggctt tgttcttttt gcttaggatt gctttttggg   6120
ctctctgttg ttgttgttcc atatgaattt taggacactt ttttccaatt ctataaaaaa   6180
atgacattgg tagtttggta ataatagcat tgaatctgta gatagattgc tttgggcagt   6240
atggccattt taatgatatt gattcttcca atccctgagc atggaatgtt tttccattta   6300
tttgtgtcct ctctgatttc ttttagcagc gttttatagt tctccttgta gagatctttc   6360
acctccttgg ttagctgttt tcctaggtat tttaattttt tgggcctttg taagtgggat   6420
tgcaagcttg aattggttct tagcctgaat gttattggtt tatagaaata ctactaattt   6480
ttgccatcca ttttgtatcc tgaaacgtcc ctgagtcatt tgttaattcc cagaggcttt   6540
gtggagtctt taggttttct atttttagaa tctattcttc ccaaagagaa atactttccc   6600
ctctctttc ctaatcggac ccctttattt attcctttgc ccaaggcttg gaaagccctt   6660
ccatactttt ttaaaaagaa cgtggaaaaa ggcccctttc ttattctcgt ttaaaggaac   6720
cttccatttt cgctgtcaaa tggnnnnnnn nnnnnnnnnn nnnnnnnnnn nnnnnnnnnn   6780
nnnnnnnnnn nnnnnnnnnn nnnnnnnnnn nnnnnnnnnn nnnnnnnnnn nnnnnnnnnn   6840
nnntttgttg ggaatatccg gtgcttattc ctcttcagga gttttattct tccaaaaatg   6900
cagcttttca ttcctcctcg tttttctttc tgtgccaaat gcctccagcc tttccatgtt   6960
ggtgcggtaa gctagacatt tttagtttgt agtgattgtt ttcgtttgtg tttgtatgtt   7020
tttgtgccca tagtcacttc tgtaatgttc gtttctgagt ttcctttggg gggattaacc   7080
tgccactgaa gtgtcagctt ccctgtcatg ggactgtcct tggaatgaca ggttttcctt   7140
ccaccatagg atctgccact gtgaaggaga tgatgagagc cccctgatca ccccctgcca   7200
```

-continued

```
ctgcacagga agcctccact tcgtgcacca ggcctgcctg cagcagtgga tcaagagctc   7260
cgacacgcgc tgctgcgagc tctgcaagta tgagttcatc atggagacca agctgaagcc   7320
actgagaaaa gtacgtggga ggaagggatg cttcaccctt cctgaaacca gtgaccccca   7380
gaaagctggt gtctcagatc atgaggtcat ggcttgcctg cgttcatttc cttaaaaagc   7440
tggggctggt gcttacattt gcattgtaga gattgttgtt tctggtgctg attttcaagt   7500
ccctcttctc aggaagaagc tctttctgac cattcataat ccttcttttc ccttcaaagt   7560
aagactgctt gcttgtcggt gtcagtcctc tggcctttga ctacagactg tttgtgacat   7620
atcttagcac ctaattttat acatattaac tgttgacgtc ctgcttctct gattaggact   7680
gtctgttgga gattagtatc tccccagcac ccagcacagt gtagcataca gtaaatttat   7740
ttgtatacac ccatgataac tatttgctgg atgggagtgt gagtaggtgg atagggaaaa   7800
gaaaggaagc acaaacgttg cgtgatgtgc aactgtcttc agaaaggacc cacaggcatt   7860
gcatgacacg cagctgtctg gaggcccatg tcactgctcc ctctgagagg agctttgtcc   7920
gccacactgg cttcctgttt aaattttgac tgtttcatat atctctctag atgcccagca   7980
caaaaggttt tgtctggaag aataaaaaac tgttcctatc tcagaacatt aatatataaa   8040
ttgcaagata agtcacataa tcaaatacta gccaattaaa tgctaaatgg tgtgctggta   8100
gagcataaca gtcattcaga aaaggaaatg ctcattatga gctagagtgc tggggaagtg   8160
gagcgatggt agcctcatag ggtgtttggg ttttagagca gttcttgaag gatcactagg   8220
atttggaggc agagtgcaag gagtttagag aggtcaggct gtctgtggag taaagcatac   8280
cctagaaagg tgaaggtgaa cattgacagg gtgtcaagct acgtgcgttg taggaagtag   8340
cagggagcat ggggcactga ggcactgact ctgtattata ggtaggaaga ccagggaact   8400
tgctagtgta taaaatccca gcagaaaaca accagattta gagaaggctt gtgcaaactg   8460
cttaaaaaaa tgttttgccc agtagaaacc ttgtaattta ttgggtgcct actctatgct   8520
aatctctcaa catgggaagt ccttgaggct ctattttcaa ctaccctgca tagactcatc   8580
tggaaagagg ctgtgactag ggttggcaaa ggatatgtgc agagtgttta cacattgttc   8640
tttctctcta cctttatgtg ttttctcctg attcggaaac cagtaaatga aaaagaaagt   8700
ctggctattt ggagtaaatt aatgagctcc tagaggagat gggactagca gagtctgctt   8760
gtaccaggaa ctcttagcgt cgatttcgag ctgttgctgc caaagtagca aggaccaaag   8820
agtgagcgtc ttctgccatt caccttcaca atgtagtgtg acccatctgc tagtgtgttg   8880
tggcatcatc aaccctcttc ttccgctcgt ccatgccagt cagcacatca gggagactta   8940
aaacgtagta cctgggtcct gggccaacat actgttttca ttaggactga aatcatagaa   9000
ttctttatca ggccatctta tgtctgcttg caagaataag cagacaaggg gatttttgat   9060
ggtagttctg cattcatctt gatcctggct tcttttcatt gcatagaaag ttggctgcac   9120
ctggtacctg gttgaagcca agtggtttta ggagaacaat acttgggga atgcatctag    9180
tttgggaagg gagaagtggg gtggaaagcc aatcttacct acctacaatg ctctcacccc   9240
accggagccc ttccccagaa gcctgagcct cacactctgt gttgtctttc tagtgggaga   9300
agttgcagat gacgtccagc gagcgcagga agatcatgtg ctcagtgaca ttccacgtca   9360
ttgccatcac atgtgtggtc tggtccttgt atgtgctcat tgaccgtact gctgaggaga   9420
tcaagcaggg gcaggcaaca ggtgagttct caggctggag caagctcagc atgggggccg   9480
ggatagctca caggagtcct ggggtcagag gattttccag ttagccaaaa acgtctgggt   9540
ttccggagga gggacatcag ttaggaggca ctagcctcct ttttggcatt tcttttgctg   9600
```

-continued

```
tggtggtagt ttttgaaacc cagtcaggag agttcatatt ctggagcatg agaatctccg   9660
caaactacat cctataaaag caggaagtag ctggacactg tcttccactc ttctttgact   9720
gagcaacatt ggatgagttg tgaatccatt ggtcagtggt gcaggcttgt ggtccccaga   9780
tacttgaggc tgagggatgg aggattgctg aggctcagga gttcaaggct gtagtgtgcc   9840
atgatcacac ctgtgaatag ccactgcact ccagcgtggg caacatagca agactccatc   9900
tcttaaaaaa caacaacaac aacaaaggtc ttcaccaggg atctgcctag gtcagcgagg   9960
tggttcatca agannnnnnn nnnnnnnnnn nnnnnnnnnn nnnnnnnnnn nnnnnnnnnn  10020
nnnnnnnnnn nnnnnnnnnn nnnnnnnnnn nnnnnnnnnn nnnnnnnnnn nnnggagtgt  10080
acttcacccc gtggtgaaga tgcggcacag actggcgttt cctacggcgc cttcactgga  10140
aagcgcccct gtggtcctgg ggagagggcg gctccatccg ccacccttcc cggagctgcc  10200
cccgcccatt ctcatgggag gaaatcgcag ggcgtgtgag cccccgaccc ctcgccccca  10260
cctctgccag gaccggccgc atttctgcac tgtcccgccc cactgggaag gaaactctct  10320
ttctcaattt cctttaatga ggacattgtc ttttcagccc tgccaccccc tgcaatcgtc  10380
ttccaggctg caaacagcga gtggggaggt gaacacatca gcttttcctc cctccacacc  10440
accaggaaat ttcgcaaacc acttggctct cggcggcctg gcctcgccac acctgtgccc  10500
acagtctctc tccgctgcag ccccctgtgc cattctccag gccccacgta cctctgcctg  10560
ggcccagtaa gacctggtca gatggccccc ggctgcaaag ccttcctggg ccccatcaga  10620
gaggacgccc aggtgaagcg agggtcccct gcccaccctg caagcgcagg ggcccttcca  10680
agagtgcagc cctaggccgg tgtgtgatgg tggagacgcg gtcccagagg gcctgaacca  10740
agaatggaga agacaaaggc tgtctttagg gagaaacttc cctgaggggc tgatgtgtgc  10800
gatcccattt taatctcaca accctgggga ggagctgggg ccgggtctca ttgttcattt  10860
gaggacaccg aggctcaggg aacttagacg actttcctag ggtcccccca acccccaccg  10920
gcccagggcc ctctcccagg caccccctcat ccccacacag gctcctctaa gctgcttcct  10980
tgtggtccag ccccccttggc tcagctcctc aaatacaggg acacctcttc tctcccccgc  11040
agaactcaag ggtctccatc cactgtgcca gcacagaggc ggtgctcaga gtggggctaa  11100
gcttactgtc cagcctgctg ggccaggagg ggcagaaggg cccctctcag gattccttcg  11160
ctctgctcct gccaataggc catcactcaa ggggctaatg acaggacgat gtggagaaac  11220
gtgggctgca gcacttctgg ggccaaggc agggtgggcg gcactgggga gtacagggga  11280
ggggacctca ctggggccag aggcttctag aagcttctgc aagaaggggc ccctcaccca  11340
tgtcttggcc aagaagtggg gagggtgggt gtggcaaagg aaacagctag gtcagagaca  11400
agagatgctc tgcaaagccc tgctggctcc ccacggtgga gcatcctatg catgtaggac  11460
ctgagagatg gcaggggcgg gtgcgtccct atggatgtat ctccatttct gggcagagac  11520
atctgggctc tcacctgcaa ttgagccaac caagaaatta tatttacttt ttagagcgag  11580
cctccaacaa attatacaag cacttgagaa taagccctcc cactgtcttg agagatggag  11640
cccagggagg cagctggaaa gatgctcctg ccctcactca ggagagatgg tggagctggg  11700
agaggaggag gcactccctg ggacccagca gatggacttg actcagcaaa tagatgcaac  11760
catatgtggg gggtggggag gcccagaaag gcattacagg ccagtgttct taatcctggc  11820
tatacactgg aatccaccag tagccctaaa atataactgt gctggacttc ccctggttcc  11880
acagtttgtg cagagtgggc agcatggagt ctgtaacact aaacacacag gattgagaac  11940
```

-continued

```
catatgtcta ggctgttgtt agccatgatg gggatacatg aaaaggaggt gcacagttac  12000
cttctatacc acaggatagg tgctcattaa accctgttaa aatggactgt gacccagctg  12060
gcactcaggg gcactcaggg gccaggtggg tcacactttc attttaatag gatttaatga  12120
gcacctattc tgtgacagct gctaagatac agaggctcct gagatacaga gatgacaatg  12180
accttcagaa acactgaaca gagataagaa aggcacagtc tggccttcac tccaccatta  12240
attcctccat ccatccatcc atccatctat ccatccatct ctctgtctat acttccatcc  12300
atccaccatc cattcaccat ccacccatca atccatccac ccatctatcc atccatccat  12360
ctcactatct gtcatccatc catccatcca ccatccatga atccatccat ccgtatatca  12420
atttctcatc tatctctcca tccatccccc atccacctct tcttccatcc ttcctccttc  12480
ccttcatcca tccattcatc atccatccct caacccatcc atctgcctgt ccatcggttt  12540
gattgtccat ctgtccagta ttcctccatt ccctccaaac tgggtggcag tactctccac  12600
ctcactacct caccatcctt attattccct ccaaactgtc tctttcacaa gggccttctg  12660
tcctgcctgt cccatcctgg tctgggacct atcccactaa agctacatgg ctttgatcaa  12720
caatcccaat cccagagtag gggaagggaa gtgagcccct aactgccgtg atgtttccag  12780
ggagatggtg gatactgctg cattactaat ccagatgtta ggttttaatt tttctctcca  12840
gtagacccca attgtggtag gagaaaaatg ccccagcttt ggacacaaac agacctggat  12900
tcaaatcctg gttttgccaa tttctgccta aatgacttta ggcaaactcc ttgaccttga  12960
ccccttggag actcagtttc ctcacctaga aatggtcaat aatattattt acctcccagg  13020
atggccatga agcttaaaat agattattgt accccccaaa acaccgacac aatgtttaga  13080
aataaataat attattttaa gctttgaagt ctggctgggt tctcagcctc gtctacctgc  13140
tgggtgtgca gactcaaagc cagggtccca ccctcataga ctgtcatctg tgggtgtggg  13200
gttggcctgg cactagcagg tgctaatgct cctcagagga ttctaggtgt aaaaggaaat  13260
gaaaatcttt ggaccccaat tcactctgcc aaaagggaaa aattaagctg aaagctgagt  13320
gatgcaagaa acgaagatag ctacagataa aaggtgaaaa cctccacagg tagctcttgg  13380
tgttcacctt atcaagtgct gatgtactaa gcgcaagagg aatacataac tgactattcc  13440
cctacctgct ccttttcttt tgcaacatgt ggattcagta acgtgaccat gccctccctt  13500
tcttccttcc agcctgttct cctttaaata ttgatgccct taaagacatc ttcggaaaaa  13560
ggcacagtcc accaactgtt cctgtggatt tgtgttcctt ttttccgtgt atgtcttttt  13620
ttttattatt atactttaaa ttctaggata catgtgcaca acgtgcagga ttgttacata  13680
tgtatacatg tgccatgttg gtgtgctgca cccattaact cctaattagg tatatctcct  13740
aatgctatcc ctccccccctc tccccacccc atgacaggcc ctggtgtgtg atgttcccct  13800
tcctgtgtcc aagtgttctc attgttcaat tcccacctat gagtgagaac atgcggtgtt  13860
tggtttttttg tccttgcgat agtttgctga gaataatggt ttccagcttc atccatgtcc  13920
ctgcaaagga cattaactca tcctttttta tggctgcata gtattccata gtgcatatgt  13980
gccacatttt cttaatccag tctatcggtg atggacattt gggttggttc caagtctttg  14040
ctattgtgaa tagtgccaca ataaacatac gtgtgcatgt gtctttatag cagcatgatt  14100
tataatcctt tgggtatata cccgataatg ggatggctgg gtcaaatggt atttctagtt  14160
ctagatcctt gaggaatcgt cacactgtct tccacaatgg ttgaactagt ttacagtccc  14220
accaacagtg taaaagtgtt cctacttctc cacatcctct ccagcacctg ttgtttcctg  14280
actttttaat gattgccatt ctaactggtg taagatggta tctcattgtg gttttgattt  14340
```

-continued gcatttctct gatggccagt gatgatgagc atttcttcat gtgtctattg gctgcatgaa 14400
tgtcttcttt tgagaagtgt ctgctcatat cctttgccca ctttttgatg ggttgtttt 14460
tttcttgtaa gtttgtttga gttgtttgta gattctggat atcagccttt tgtcagctga 14520
gtagattgca aaattttttt cccattctgt aggttgcctg ttcactctga tggtagtttc 14580
ttttgctgtg cagaagctct ttagtttaat tagatcccat ttgtccattt tggcttttgt 14640
tgccattgct tttggtgttt tagacatgaa gtccttgccc atgcctatgt cctgaatggt 14700
attgcctagg ttttcttcta gggtttttat ggttttaggt ctaacattta agtatttaat 14760
ccatcttgaa ttaatttttg tataaggtgt aaggaaggga tccagcttca gctttctaca 14820
tatggctagc cagtcttcac ccggggctga aggtaccgct tnnnnnnnnn nnnnnnnnnn 14880
nnnnnnnnnn nnnnnnnnnn nnnnnnnnnn nnnnnnnnnn nnnnnnnnnn nnnnnnnnnn 14940
nnnnnnnnnn nnnnnnnnnn nacaatgaga acacatggac acgggttggg ggggtatcac 15000
acactggggc ctgttgggct atgggggct ggggagggat agcattaggg gaaataccta 15060
atgtagatga caggttgatg ggtgcaacaa accaccatgg cacatgtata tctatgtaac 15120
aaacctgcac attctgcaca tgtaccccag aatttaaagt ataataagaa aaataaaaat 15180
aaataagtta aaagagatta aaaaaataaa agagaacatt tgccacattc agtctttcta 15240
gatggaaaga ggttgctgac atatgataga attagaaaat cacacatctt gtaaattctc 15300
atttgtttaa aaagaaatca tacaaattag atgtttttg gagatgactt tttaaaatag 15360
agtcgttaga tcacctctgt aagggatatg tctatatctg ttcagtgggt taggggacat 15420
ggatctggaa agcctgagaa gaaaaagaag gttctatacc agacttgtga tatttagaca 15480
ttttcatatt ctatccattg ttttgtgtgc attttattcc tcactattgt atatatagtt 15540
gacaatgcta aactttttg tgtattcttt ctatgtgttc cgaatgccta atatatgtca 15600
aaattagcgg tagtaaaata atattttgta aatatctttt tgctaaaatt catatgaaat 15660
gttgtttttg gaggggaatg gccaaactac ctgttgagta atactcatcg tgtttgtgtc 15720
ctggttcagg ggaggaggaa ggaggggaaa gtgcagagag ctctatgccg ctgtgtttac 15780
agtgaggcaa gattaaccat tatctcttat gtctgtgcat tttgttttac ttatctgttt 15840
atgtagtgta tataaaggac aaacgagtcc taatttacaa catctagtct ttttagatgt 15900
taaagaggtt gccagtgtat aacaaaagta gagttagtaa actaatatat tttgtatatt 15960
ttgttttaaa attcctagga aagattgtct tcctatcttt gagcattctt gcgcactgag 16020
ttgatggaga tgggagggat tctaagctag gatgttctta tttggaagac tctttcaaat 16080
tataactatg gttacatgta tgcagtttat tcgagactgc tgtgtatata gtggacaaat 16140
taactcctta cttgaaacac ctagtttatc tagatgttta gaagtgcctg atgtacgtta 16200
aatgtagagg taataaaata ccactttgta aatatctttt tgctaaaatt cataggaaat 16260
actgtctttt agaaatttaa ttgttaagcc acctttgtga gcagtatagt actgtctata 16320
cttgttcaat ggtttagagg aggtgggagg gaagaaaaat atgtgactga cttatttcac 16380
taagcctaat gtctttaagt ttcattcatg ttgtggcatg tgtcagaatt tccttccttt 16440
ttaaagctga ataatattgc attgtataga tatattacct tttatttatc catttatcca 16500
tcaatagaaa cttgggttgc ttccatattt tagctatcat gaatattgct gccatcaaca 16560
tgttgagttc ctgtattcaa ctctttgggt aatacccaga agtgaaattg ctgaataagt 16620
atggtaattc tctgttaaat ttttgaggag ctgctgattc atacttttac gtataaaata 16680

-continued

```
ttagacctta aatgtattat gtaaaaacac taagtatttt taacattcta gagtaaagaa  16740
ggtgtttctt agcaagacag aaaagctgaa accctcaata gaaaagcctt gttaatgtta  16800
tcacataaaa tattcaaaat ttctgaacac acagacacac acgcactaac gaaaagctat  16860
ttacaacttg tggtagatga agaaataatt tcttaacata gcaagaaccc aggcaaatga  16920
ttaagaaaaa gaataatcat acaaatttaa tacatgtgag aagctgttca gcctttccca  16980
ttaattaaag aagtaaaata taaaacaaaa catataattt ttcacttagc agagatgaaa  17040
taccaaaaca gatgggtata ggtgtggaac atacttcctt ggttgacagt tagccaatat  17100
ctattaaaat cccttgccac agtaatttca gttctagaca tttgtcttat attactgtat  17160
ttattctgtc ctgtaaccat aaattccaca gctgcctagt gatggttcta tatttaaatg  17220
gaatgcttac tctcagtatt gttttttctt ttgagatgga gtcttgttct gttgccaggc  17280
tggagtgcag tgccatgatc tcagctcact gcaacctcca cctcccaggt tcaagtgatt  17340
ctcctgcctc agcctcccga gtagctagga ctacaggtgt gcaccaccac gcccagctaa  17400
tttttgtatt tttagtagag atggagtttc accttgttgg ccagtatggt ctcgatctct  17460
tgacctcatg atctgcccac cttggcctcc caaagtgctg tgattacagg tgtgagccac  17520
gacacccagc cagtattttt ttttttaaac cacagcttct tcattttgag tcatctctaa  17580
atagctgcaa tttactataa cttagggttt acaattttta aaattgtgta tgttaaggta  17640
tccacatgat gtttgatata cttcttttga cataaatata cacaatgaag tgattactac  17700
agccaaataa tgattaccat acccatcatt gctagcgttt agaaagacaa ctgattttta  17760
tgtgctgata ttgtaccctg caaccttact gaatttacta aatctagtag ttttttggtg  17820
catcctttgg gattttctat taacagaatc atgccttctg caaatgtaag taatttagct  17880
gcttcttttt aaatatgtat gcctcttatg tctttttctt ggctatgttc ttttctctgg  17940
ctagaacttc tagtacaatg tccagtgtca gtgttgaaaa tgggcatcct tgtgttgttc  18000
ctgattttag gagtaaagct tacagttttt ctacccctga gtatgatttt agttgtgaga  18060
ttttcctata tgccctttat catgctaaga aagttccctt ttattttagt ttgctgattt  18120
tttaaaatta tgaaagggca tttaatttta tcaaatactt ttttctgtgt ctgttgagag  18180
tttggccatt ttttttctat tgaaatggtg tattatggta gctgattttt ggatgtgaaa  18240
ccaaccttgt gtccttggga taaatcccat gtaatcatgg tgtataattc tttctatgta  18300
ttgctggatt tggtttgcta gtattttgtt gggaactttt gtgcccataa gataagaggt  18360
attgatctat ggttttcttt tcctgtgatg tctttatttg gtttttgtgt cagggaaata  18420
gtggcttcat aaaatgttca agaagtgtac cctcctcatc tttttgttgg aagagtgtga  18480
aaaattggta ttatcaaatg tttagtagaa ttcaccagtg aagccatttg cttttctttt  18540
tgggtagttt ttgattactg attcattctc ttaatttgtt ttaggtctat tcagattgtc  18600
tgtttcttct tgagtcagtc ttggtagttg tgtctttctt gaaatttttt catttcactt  18660
aaattatctt atttgtcagt gtacaattat ttttggtatt cctttataat ccttttttatt  18720
tctttaatgt cagtagtaat gtctcttctt ttatttctga ttctatagtt tgagttttct  18780
ctcctctttc cctgatgaaa ctgaagtttt ttccatttta ttgatttttt tcaaacgatc  18840
aaattatttc attaatttgt gctgttatca ttatttcctt ccttctgctt acttaaattt  18900
agtttcatat tttttgtaag tgtcttaagg tagaatttta agttattgat ttaagaactt  18960
tcttaataca agtgtttaca gctgttgata ttactctaat tacttcttta gctgcatcac  19020
aattgttttg gtatgttgtc ttcattatta ttcgtctaaa aatattatct aatttctgtc  19080
```

-continued

```
ttgatttctt ctttgactca tgaattgttt tagagtggaa atttcatttt aaatttccaa  19140
atatttgtga atttcccaaa tttcccctgt tgttgatttc taattttatt ccattgtggt  19200
taataacata ctttgcatta tttctatcct tcaaatttat tgaggtgtgt tttatggcct  19260
aatatgtggt ctatcttcta gaatgttcca tgctcacttg acatgaatgt atactttgtt  19320
gttgttgtta agtagaatgt tccatagtcc ttgaggtcta tttggtttgt agtattgctc  19380
aagtcctctt tttccttgtt gatccgtcca gttgttctat ccatttttga acgtgtagta  19440
ttgaagtcct tgactatttc tgttgactcg gttgacttgt ctatttcttt cttttctcag  19500
gtctgttttt gtttcattta ttttggtgct tcatatatat aggtgcatat atgttgataa  19560
cagttatatc ttcctaatgg atggattcct ttgtaattac aaaaggccac tctatctcta  19620
gtaacaattt ttgttttaaa gtctatttgt ctgatatcag tgtactgact ccagtgtttt  19680
tgtggttgct gtttgcataa tatatttttc ctgttctttt actttcattc tgtgtcttcg  19740
aatcaaaatt gtgttttctc cagacaatat atacttcatg ttttcttatc caatataaca  19800
cctttgcctt ttgattgcat tgtttattcc attcacactg catattatta tttagtggga  19860
tttatgtctg tcattttagt tctttttttgt ttttgttttg agacagaatc ttgctctgtc  19920
acccaggccg gagtgcagtg gcgtgatctc ggctcactgc aagctccaac tcccgggttc  19980
aggccattct cttgcctcag cctcccaagt agctgggact acaggtgccc accaccactc  20040
gtggctaatt ttttgtattt ttagtggaga ctgggtttca ccgtgttagc caagatggtc  20100
tcgatctcct gacctcgtga tctgcccacc tcggcctccc aaagtgttgg gattacaggc  20160
atgagccacc gcacgcccgg attttttgtt ttttatatgt atcatgtctt tgttgttcct  20220
gttttgtctt tacttctttc tatttcattg aattaatatt ttctaatata gtatttaagt  20280
tttattaata attttatcac tgtattttta tttttagtgg tttctctagg attttctgta  20340
tatatcttat cagtatgagt ttcagattca cactagctta attccagtaa tatgtagaaa  20400
tgttactcat gtagaactta attctcttgc tcttttgtgg ttattttatt tatattatat  20460
caattaatgt tacaaagata tacattgttt aaattattat tggtgctatt attagcatac  20520
ataacaccca catattaaaa ttgtatatat tgcatatatg tattatagaa ttgtatatat  20580
tatagggcca atagtatatt gtatacatgt tattttatat aattgttttt aaaatgagtt  20640
aagaaaaaag aaaaatgcat ttctactgtc tattatagaa aaataattac atcatactga  20700
acgtcttcac cnnnnnnnnn nnnnnnnnnn nnnnnnnnnn nnnnnnnnnn nnnnnnnnnn  20760
nnnnnnnnnn nnnnnnnnnn nnnnnnnnnn nnnnnnnnnn nnnnnnnnnn ngctctaata  20820
aatttgcggc cgctaatacg actcactata gggagaggat ccgcggaatt cctaaaagaa  20880
ttgctgagac aaagtatatg tgcctttgtc atcctgaggg cagttgtcat cctgtggagg  20940
tttaccattt gctctcccac cagcaatgta taagcatacc tgcttcccaa cacttccgcc  21000
aacacatatt atttgattaa ttttcttggc tgataatggt atctcattgt agttttaatt  21060
tgtatttctc attgtgagag aaatgaagca tcttttcatg ttttgagagc catctgtgca  21120
tcttttccca ttgtttctgt taagtcattg atttgcagta ctgtaatttg tgatgagttg  21180
taaacatgag ctcttctggc ctcttaacca tccttatcca gcctgtcttc acgttcctcc  21240
ttgcctaaaa acaagctcac tcaaacagat cattcctgtg gccctctccc ttttgaaata  21300
aatcagatgg gcaaatttgc ttttgttagg ggcctgagac ccaaatgttt aaaagtagct  21360
tagctgatga gtgaaaagga ggcccagttg gggggttgcac agaaaatgag gggcgtgggt  21420
```

-continued

```
aatagaggag gctgggcagt aacctggcag aaggcgccag aggccaagga aggtgcgctg  21480
gtgtcctgca gtgagaagga tgtgtgcact atcaactggg taaacacact gctatagctg  21540
ctccagcgac agcaggcact ctcagaaggg aactgagaaa aggggaatgc cagtttctgc  21600
caaggatata tggaaaagtt ttttttcccc gtatgttctt tggcaacctt gttaaaatca  21660
tttaaaatgg tgaatttgat aacaaagcca gccactaaaa gacttggatg tagcaaaaca  21720
aattgtcaaa aagtatttat catttctaag aaataaaata aactgggatt taggcttgga  21780
tagaaatcca gaggtttgtt ttggcataat taattacaac atctgaagaa gggaggattt  21840
ttacaagaat tttttttttt gtagtgagat tgctttatat tccttttcat gactggagag  21900
tctgtcattt ggcaacccgc aaagaacttc aggaacagag ggcctaagtt ttcttgacac  21960
atttggattt ttgcatgatg aacatttgca cttttattag taattgtcga gtcgtgtgtg  22020
gtctgatcct atggagagga gagtgtaggt gtnntctctg gagctagtac ntgcccccgn  22080
gctcacacgt gccacactgc ctgctgcttt cangaaagag caggacggct ggtcctgtcc  22140
catctagtga ggtcctgtcc catctagtaa ggttctgtcc tcagagctcc taagagggga  22200
ttgctggcct ttgattacac tggcttccag aatctgacca tggaaccatt atttgaagct  22260
gtcagcttca ttttgttgtt gatcaggcca gtcttttagg tctttgttgg ttgatagatt  22320
tctctcaggt ctatagcagc aacaaataaa gctctttaaa attattttct tgaccattct  22380
gcctatggat tggttctgac ctttgaaatg tttgctgtcc tttagatcgt gacagaagga  22440
gcctcttctg ggagctgtga agaccccaca gatctcactg gttttcttgc ttttattgga  22500
agagttagca tttgttgaag tttatattta tgtaaaataa caataagtag attttaaaat  22560
ttttctttaa attctgtgat ctaataagaa gagagactct ttctctgtca ttgggaggct  22620
tgatgaggat cggacatacc tgctgagagt atcctgtaat gttttcataa gattggaaat  22680
ggtgaaatga gagcagaaat gtaggcagag gatgccaacg ctgtttccta tttcctaagt  22740
aaaactgagc agggcagaat ctccccagcc ctgccagaac tcccttcctc cttgggtccg  22800
ctgtcactgt catgctggcc ttgacatctg ctacaagtgc acacacatgg ggaaccacac  22860
agggaagtga acacatgtcc tgacgtgtgt gtgtgcctgg tgtggctgct tccttgatcc  22920
aggctttgtt ttgttacgag gctctgccct cctaccttca ggccttgctc ctcatcatgg  22980
gcatgcaagg atggaatcgt taccccagag tacacttttt gacttggatt acttgtagtt  23040
tagtactgga gttcagaact ttaatttccc atcagaaacc tgcctcccgg acccaggaca  23100
ctgaccttga ttgggcacga ttttccagat aagaccttac ctcctcccaa cagggtttgc  23160
cttcccttca gaatacagga aagtacacgt ggttccaaga ggaccatgct cttactaaga  23220
taaaagggag gagggtgact aggtactttc ctctgctgcc atcccttgaa ggaaggggc   23280
ttccttcaat gcctcatcag ttccagggag tatgcttgac ccagcaacac agaggaagaa  23340
gtgacctcat agcaatgagg ggcaagcatg tggatattgc tgggtatttc ttcctcaaag  23400
tctacctggg gacaggtgat gaagacgctt acttctctgc aatacaccgt gatcaggctt  23460
tggtcttcat gacacatttt agccttgcct atgtgtgttg aacagagctg gtcatcctca  23520
gaaataaaag aagagagcaa taagtacagg aaggctttca gtcccagaat agtgttagga  23580
ctaaatgtca gagaacaggg ggactgtagg agtttgggga ccttagcatg gataccctct  23640
caatctgctc ccctgtggta taaacagtaa agcccattgt actaaaaggc cttgagtgct  23700
tgtctctggg gcaggtggag ccagtgatgg gtgccccgag aggaggatgc tggagagggg  23760
acagtgtcta aggcagttgg agaaaaagga caatggctta tgcagtcagg cctagaagat  23820
```

-continued

```
gcaagggatg tcacagcata gtgtccacag gcatccctag atgtctttca ttttgtttca  23880
ggaagaatat tgacaaaggt agtgatggga gggttatttc aaggatgcta ttttcatgtg  23940
tccaagtaaa cttaagattc ctaagaactt tgacctctaa tgcttttaaa gaccgtgtac  24000
ctcatgccca tatgcacatt cagttagaaa ataaatgtag attctttggt gaattcgaag  24060
atgtgctcat ggagtggcac agcgtgatct cagtgtacac atgaagcatg ctgatgagag  24120
cttcttggat cttgtttctt caggtggact tgcattaaag tgctgttgaa tctctgcact  24180
gggagtggga gcagccatgc gatgggtgcc ttaatccgag tgccatcctg gctctctcca  24240
ggctgcttca tttgctgtga ggggtagggg gaggaggagt ttccaggcaa tggccttatc  24300
tgttctggtg gttgaccaag ggtcgggggt cccaaaggtg gagttccagg atgagagtgc  24360
acccttgggg atggtactta gaaagagtgg ggactaggcc tcagccaggg aatggtgggc  24420
cagggtggag ctcctttgta tcaaggagtt agggccaagg gccatgcagg tgggcctgca  24480
gaaggtgggt ggtgatatgg cctttctggt gataacagac tcgtggcact gttttcctgg  24540
ggctgttggg gttgcatgga gcagattctt actcaggctt actgtcttaa ggagggaaga  24600
atgctttttt atgaatacgc ataggtctgt ggggctgtgg agcctgggga atccgaggct  24660
ggcgtgggag tctggggccc tctagcggtg gtggtgcatc ctcagctcag tgccactcac  24720
tgtccctatt tctctctgtc catttctctc ctcactgcag tgcttcctct ccttcctaga  24780
tttttttctc taagtttgac tattcaccac cccagagact ctgttctatc ccatgacctc  24840
ttgctgtact ttctttcaaa tctaaatttt cttgattatt tttcttaatt tacagtttca  24900
agattagatc tgttgggagc attctgtgct ctacctcagc ccctggttga gctatggatt  24960
ggtgtccccc atggtgacgt ggtctggact cccttttgtg tgaagagctg tggcagggca  25020
gtgaggtttt gtggaactca gggagcatct ggcactatgt atgaggttgt gaggtgggag  25080
agagctctta aatctaccag ccttgttgat cttgggaact aggagagagt gctagggaag  25140
ccagtgccag caggcctgga gcctcatatt tctttggcat ttgtatgata ccttctagta  25200
cttcgttttt tgacttatat atgaactaac tcaatttaga tgcttagaaa ataaacggcc  25260
actggacctg caagagatta gtagtggtgt tccatagcct tagacatttc ttacactttt  25320
atccacagat aagaaaaaaa tagtgatatt tgatttgttt tgccaaggct tagaaggatc  25380
taatatgtgt tactcgttga gcagcgggaa gcagcagaca tttctagggt ttctccctgt  25440
caccattcag gagacagtgc acacaatccc cttggctctt acctgaacac tgaccacagg  25500
tctgtcattg caggctggga gtcctccgtc agcatcagct ccggctccgg tgtcctcctt  25560
ctctcgcact tctatcacgc catccagcca ggacatctgc aggtaacact ctgcttcaga  25620
tgctgccatg atcagtgtgc agccagaaat aagcattagt gtctgtaggt tcttgaattt  25680
ccatttgctt aatcaatctg cctttggtct aaacagttgg cgagttttat gtgtggtttg  25740
ctcaccaagt tacccatgct agtctcattt cttcactatg atgtctattc tcttttaaaa  25800
ttgtttttac tttctgtgct tttatcccac tgttctgcat gcagttccag tgcagtgttt  25860
tctgagtgtt gtcaccacag ttccgtgcag tctgctgttg tctcgaaagc tcctcactgc  25920
cagagttctc tgacacaagg gctcactgtg acagttatct gtaaggacac attacaggcg  25980
tcaaagagaa attcctttgg ttcagaatgg gcccaggcct tgaagcctgc taagaatacc  26040
aaagccagaa gaacactaaa gttctcaagg tccctcaatg atgtgggtga gaaggcgcag  26100
gatacttcag aaagttttgc ctatgtggaa agaacttgtt ctgaagggaa attaatactc  26160
```

-continued

```
cctcaagata cgtgtctcag aactaacagg tttcatcata aagaaaaaag aaccctgaac  26220
cacaaacctc ttggcaattc caaacattct tgtgtttcat gcctttctgc cggtcgctca  26280
actgcctcag aggtggaagc tggcaagggg ggcaggcccg gcctgctgct ggaagagaag  26340
gcggatggtg aggccacgtc ccgaagccgg caactgctcc agtacctgtt ctcactctcg  26400
cacggcttga gcgccagcag cctgcacagg ttccatgagc tggagagctg cgctgctcgc  26460
ctgcacactg ccaagtcctc cagcgggctg gcagggagta tgggcttctg ctctgacgag  26520
atgggagacg acgatgtctt tgaggacagc acatctgcaa aactgaagag tagggttctg  26580
cgggcgcccc tctgctccac ggaaaaggac agcgacctgg attgtccttc tcccttctct  26640
gaaaaattac cccccatatc tcccgtgtcc acgtcagggg atgtctgcag gttggtttgc  26700
caggaagtgc cattctagcc atctctgctc gcatcaggaa cctcctcttg ctttagtatg  26760
tgaagtttca ggaaaatgaa gtaataggaa gttgtaacca gttgtgggtt gatggttttc  26820
tccagaagaa tggagtatca atatcgtttg aaaaacttaa tttttatgat gtgagtccca  26880
agatagtttt acaaatgata aaagaggaag aagctggctg ggcgcagtgg ctcacgcctg  26940
taatcccagc actttgggag gctgaggcgg gtggatcacc tgaggtcagg agtttgagac  27000
cagcttggcc aacgtggcga aaccccgtct ctactaaaaa tacaaaaatt agccgggcgt  27060
ggtggcgggc gcctgtaatc ccagctactc aggaggctga ggcaggagaa ttgcttgaac  27120
ccgggaggcg gaggttgcag tgagccaaga ttgcgccatt gcactccagc ctgggcaaca  27180
agagtgaaac tctgtctaaa aaaaaacaaa acaaaacaaa aaaaaaaaga ggaagaagct  27240
acacatatta aaggccaagc tgactcttct aaactaaaaa taagtagact ttgcataaag  27300
aaactggaag aaagaaacta gtatcttcag ttttccagcc tgatggtcca gattttaagc  27360
attgttgcat ctcccagcct ctttttaac ccttgctccc tacctacccc caaaaggtgt  27420
gtggggactg gctgttctcc agtagctcct tccttccttc tttttaactg aggtgtagcc  27480
acctatgtcc catcctaact ctgtttcccc cctttatctt cccttgtgca gcatccttgt  27540
ctggcctcca taattcactt tttgtcatga ctcttgtgcc ctcctcattc tgacctttct  27600
ccagtctccg ctccttagtg ccagctgtca tcatttctaa catttggatc agagatcccc  27660
tcactaaaac agcctgagag cctggctcct tccaggacga gtgccccaac ctgttctcta  27720
gctgctggaa aagacccctc tgtttcttaa aagcctgtta agttccttca ggctagtagc  27780
tacaccttgt tgcatacttc cttggaaata gagagtgctt tcaaattaat ttctcactta  27840
ttgctattag tggtcccaag aaaaagagat gaaattgcag catcttgtaa tggtgagttt  27900
tttaggtcta ggagagaggt actgtcatct ttgtttactt gctgagagac gacagaaatg  27960
tgtagttgtg gggtatgaag gtaaagtcag tgattatagc taaaaagcaa acgtcattta  28020
aggtcactgg tatttttgga tgttggaatg cagcgcttac catccataca agaacccgct  28080
gggagggcca agaccatccc gtgcgcggcg ggaaccgcga catccgccac tcggatgccc  28140
gctggagcgg gcggagaccc acgcgcgcgc caatgtcccg gcgcgcgggc tgctcaccca  28200
gggcagcggc gtagtcgccg ggggcacaag cccgagccgc ccggggcggc gcgcggagaa  28260
ggagcgcaga ccccgtgaac acgccggagg accgtccgcg cggcccgtcg cgccactgcc  28320
tactgccagg ggcggcgggt gacgacaaaa ccctcggtgc gccgcgcctg gcagtccgcg  28380
gcccccgccc ccccagcggc gcgcacccgg gggcgcgggc cgaacccggc aaggtgagag  28440
ggccgtggcg cccgggcgct gaccactatc attctccgcc acacggacga aggcaggagc  28500
accacgggcg gccggcgggc cgcccgctcg ggccaaagag cccgcccgcc agcggannnn  28560
```

-continued nnnnnnnnnn nnnnnnnnnn nnnnnnnnnn nnnnnnnnnn nnnnnnnnnn nnnnnnnnnn 28620
nnnnnnnnnn nnnnnnnnnn nnnnnnnnnn nnnnnngagg ccgggcgagc gcaggcgggc 28680
ggagagcaga ccacgcggaa gaggccgaga gagaaagcgg ggcacccggc cggggggtc 28740
atttacaagg gacgctgggc acgaaggagg ctggggcgaa gatgagtcca ggggttgggt 28800
tgagagcgct gcgcagccgg gctgagaaga gaagctgacg agtgactccc gacaagggac 28860
gggggagagg gaacctgggg gcaggcagag gcctaggggg tgggctctga gggcagccac 28920
tcccaccggc cctcccccag ccccgcaggc cagccacatg ccccgtgctc cagacgaccc 28980
agctacatgg atggcagcgt cctgaagggg gatgatcggt agggagtggg tgcggaggct 29040
cacgcctgta atcccagtgt tcggggattc ccgagcggga ggatcgcttg agccggggag 29100
gtggaagctg cagtgatctg cgccactgaa ctcccgcctg ggcggcagag tgagaccctg 29160
tttcaaaagg caccaggggt gtagggaagg agcgatatcc cccaggcaag gaaggctgcg 29220
gaggggccag gccaggagag aagggccctg agctcagtgg acgggcaggg tgcctgtgga 29280
ggaagggagg gacgtagcag caggaggaag ggtgaggacc caggctgggg atcgggagaa 29340
gtgatggcgg aggaaagaga ggccggaaga ggaggggggcc tgctggcctg gcactggaaa 29400
gcaaagcgtg ggtttgtata tgggaagaag accacatccc ctcttatcgt catcccaact 29460
cagaaaccat ttggccccaa gtcaccaaag cactcatagg aaccactttt cctgtgacac 29520
aagtaggatt ctcccacttt taacttccca aatgctaccc gaaagcctct gaaatccttg 29580
gaaatttaaa aaataatccc cttctattaa ctgatgccta taaaacatat tgactttcat 29640
taaattttgt tatgaaatca gggatgtgtc ccattgtaaa ataaatttgt ttggaaaatg 29700
tagggtggta tcccatctaa aaatcagacg aggctagaaa atttcaattt tatttgctaa 29760
ggtagcatca tgttgttaaa aatgcatcat aaaataagac caagagttaa tacaaagcat 29820
gaagtcatgt ttccctcaaa aaaatgattt gttctgtagt caaattaatt tggaaaacat 29880
tgcaaactct tcagcagtgg ttctcaaagt atagcttgcg tcagaatccc ctggggccct 29940
tgctaaaatc tggatggcta cactccccgc ctagagtggg ttaaactcag tgcccactgg 30000
caggaaactg aaacttggct gaagtcaccg aggaggcctt ccccgttaaa cctctggctg 30060
gcgacagctt ggtttcctcg ccgctgcttc tgagtaattc tggcacgcag ttcctcctag 30120
ccacctgctg tacctggaag gggccagcc ctcctcagca ggctttgctc ctgccctgca 30180
cagcacaact gtggcgtaaa aaatggaaaa gctggtagca gaaggaaaga gcagggagac 30240
agaggttagg tgaacctcaa tggcctcatt aaagcaaatt gagaaagaga gtttccttcc 30300
cagtgaggcg ggacagtgca gaaatgcggc ccgtcctggg agaagtaggg gcgaggggtg 30360
gggggctcac cgggcacatg gccaacagct ggtgcccagc ctgggccaca gtttggcaca 30420
ggagaaagct gaagatgcag gagaaagcta ggtcactgcc cctaggccag gtgatcaagg 30480
tggctgttac ctgcctgtgt ggccttgaaa aagcctggtg ccctctctgg cttgcagggt 30540
ccttcttttt acaaaagcgg gtcttcgaag ccctgaatat tccagttatc tgtaaggata 30600
tagaaatatt ttgcctctag atgacatgta aatatgttcc tcctaactcc acttcttcct 30660
acatctgtgg cttcttctga gaactaccag acccaccctg ttttcagagt aaacctcctg 30720
ttttgaggtc aaacagaccc agctgggtaa ttggtgactc actcctggtt cctccaaaga 30780
acaggggcaa gggaccaccc gggacctcag gtgccccagc acaggacctc tttctggggc 30840
accctctggc actgggccat cttcaggccc tacagggctc tcggggcctg cgtaggcctc 30900

-continued

```
tcatctccca gaaataagtt cttttcccca cccagactga caccagatgc tacagtgagg  30960
tttacccctc cagcttgaca agcattccta gcccagaaca ctcagctgac gaggggtgct  31020
gggggaggaa ggaggcagca aggctgaaag aagcttctct gggtattcca gtgcctggct  31080
gctggtcgta gccatggtga gaccacagca gcctccctgg aagcaagcac ctgtgtaaaa  31140
gcccctcctt ccccacaagg ggctggatcc aagtgaagaa ggtaccagaa ggactggaag  31200
atgatgctgg tattattcga cagctccagg gtgctgtagc actgagcacc tactgtatgc  31260
agcccatcac aaagccagcc acactgccca ggctgtgcca tggcaacttc cagcagtaca  31320
ccctctcggt cacctgcagg ctccttgttc atcctgacac atgaggagaa aaagacagta  31380
ctcacaaagg cctctagcct tgtggcccca ggaccctctc ctgagcatca tggcctccta  31440
ggagacccag ggtagccagg acaaaggaga gaagcatttg ctaagctaag aaaggatgga  31500
aggggattgc tgttctgcct ggatgcaccc ctagacctgg cagggcaggc aggagagacc  31560
cccagtgtct cttgcttatc ctaggagttc ccccctgtgg ttgctccagt ttgctgcctt  31620
catgcatgtt cacagggtga ttcccctgag acaacagagc tgggatgtca ccaagccctg  31680
tgtcccatca gccaggctct ccccagcctc catcctctca ttctgctgga tcaggaggat  31740
gtggggaggt ccctgactcc ccagctttcc ccatgacaag gtgtgtgtct acagctcaga  31800
cccagccatg ctccacctga gaagtgggtc caggcagagc actgggtcct ggccacctag  31860
ggctgcctcc tcaggggtgg gcaggaaggg gagccactgg aggagtgccc cgggcacagt  31920
cccctgcacc aggtgaggtc acctcttagt ccatgaggcg atgctgcatg agcccctctg  31980
gacactagaa ggcctgggct caatgctgag taaagtgcag gcatgactgt gccctcagca  32040
tgcatagggc agcaggcata gattcataca cgtgagtttg cacttaagct gcagtaagag  32100
ctacagagga aatgaacaga gacagcatca ctccagtgag ccctccagat acaccccatg  32160
tgcgcagtaa gagaatggca tagtctattg ggacagccac atcaaaatac cacagaccag  32220
atggcttaaa cggcagatat ttgtctctca caggtccgga ggctagaagt ccaagattag  32280
ggtgccagcc aatccacttg ctggtgaggg ccctcttccc agcttgcaga tgtctctgtg  32340
ttcccacagc atggtcacgt ggcagagaga gggggacagg gcatgaataa gccctcggtg  32400
ccttcctctt cttacgagga tgctaatccc atcacgggta ccccaccctc gtgacctcgt  32460
ctaaccctaa tcacctccca aaggccccat ctcctaatgc catcacactg ggggtcaggg  32520
cttcaacaca tgaatttggg gagcacaatt tagtccacag cagaaaagaa aggggcacag  32580
agcattccag cctgaaggaa acagatgtgc aaaggcccaa ggcaaaggcc tgagctctga  32640
ggggcaacca gagtcaaggc tgaagagtgg gcagtgattg agcactgacg gtggagaggc  32700
aacaggctat cttgttaatc tcagtctttt gtgtgccaga gagagaaact gaggcacagt  32760
gtgtcatggt gaacactggg cagcactccc acgctcctgt cctgcactct gcagggttat  32820
ggaggaagcc tgggaagtct ctcccctctt ttccaccttt cctggaccca tcccacaccc  32880
tgcctcctcc aggaagccct ggggattgct catacactca catctcactc cttagtacct  32940
gcagcctgca ttctgaattt agcaagctct ggccttgggt ttctattttc ttgtcctgtg  33000
cagtgagcat ttggaaactt ctcctcagca ccaaacacgg agccatttag cagaaaatac  33060
atgagttttc aagtcaattg aactgttcat cgccccaaaa gccaggcaac acggtagagc  33120
agctggatct ctgttcgtag aagctttctc agggactggc ccaccgagtg ggggactgca  33180
agtgcccgat gagtgaatga atgaacacat gtgtgaatgg aattcaaggc actgcaggct  33240
attctggagg gtactggcct gtctcttcga caggtgaggt gcagtagaac agcatcccgt  33300
```

-continued

```
atagatgcca gtttctgacc tggttctgaa aagccagtca cctacctctg cagagctgcc  33360
tggagggggc gggggttgtg aggaccccctg agagcttggt gtgaaggggc tctgcagagg  33420
gaggcatggc tagtgtgcgc aaggtgacct ctctcctggt ctgcaggatg gagaacctgt  33480
tcatcaaccg cttcatgcac atgttccagt cttcttggaa tgacttcgcc gactttgaga  33540
aaatctttgt caagatcagc aacactattt ctggtgagtg tgcctctggg ggcccaagtg  33600
gtgctgggga caggggatgc tgctctcctg tctgatactt gccgggaaat tgacaagggc  33660
cttcctgcct gctgcagcat gggggcctcg ctgccaccat gccaccctgg acagcacccc  33720
ctacactcca cacctttac catcactgtg gtcacccttg tgcccagagg tttctcctcc  33780
tcagatattc aagctcgagc accctcaacc tcatttcact atcaaaagtc tcaaaagtat  33840
cagaactttt tcttggcaca aatcaatcat ttgtgcttct gaacagagca aaggcagaac  33900
ttggcttgtg ttttaggtat ttacacaaaa gcaactttgg gttcctttgg actaggatgt  33960
gtttgatgag agcactagct tcatagtggc cagtcatggc atgggaagga cgttaggaag  34020
gcaggaatgg ctggacaaga agaggtgctg aaatcaggac atggggaacc aaacttggca  34080
aactgccccc agggactctc ctccacgccc tccttcttcc atcctggaca ctccatgctg  34140
ggctgaagga cctgagtgct ccaggaggct tctgagccac gaagggccag ctcaggtatg  34200
atgagttggt gccacagcct gacccagtga tgggcagggg gcagcagttg gagctgtgcc  34260
catccaggga gcactcggga gaggagacca agcagggact ctgctcttag gtgaggtcag  34320
gagggccatg gccctggctg ccctctactc agagctcagg gtgggcctcg cttttctcct  34380
ggtagagcgg gtcatgaatc actggcagga agacctgatg tttggctacc agttcctgaa  34440
tggctgcaac cctgtgttga tccggcgctg cacagagctg cccgagaagc tcccggtgac  34500
cacggagatg gtagagtgca gcctggagcg gcagctcagc ttggagcagg aggtccaggt  34560
aggggttgat gggctgggga agtggccaag gtcacagtct gtcaggtgga agccagttcc  34620
tcctggccag tgctcatagg ccaccaagac gctaactgca ggcccatctg gcctacagca  34680
gccgcttcct tttcctggca gcagtgtcag ccagggtcct gggcattatg cagactgtct  34740
tgtgcaacat cagaggagga attgcgggga atgtttctcc atgatgctcg agtctgggaa  34800
cataatgtca atattttcac tatcagtatc aataattaca ggagctaccc ttgattaggg  34860
gcctgtggtg ggacaggcat tgtgacaggt gctttacaca caaggtcatc agttgtcacc  34920
caccttgcaa aggggagaac actggagaaa gaagcagacc ttgtgtgaca atacacaagg  34980
ggcacgagga gaacccaaca gaatggttga ttttctcgtt agaaatgctg ctgcccatgc  35040
tcctgtcgca ccctcctccc caccctcacc tgcagactca gctgcctccg gctgcaaggc  35100
tgacctagtc ttgagacaga agaagttcaa accaactcca cctggatctg gtggggctca  35160
gcaacaggcg ctggcccatc agcctgcctc ttccccatgg atccagcgtg atggggcctc  35220
ctgccaccca ggccctgctg cctatcccca ggtgtccagg tggcctctgc tgcttccagt  35280
cttttgagct cagcttaccc tgaggcccta gttggagagg gatggttggt gcccttttaga  35340
gataaaccta cagccccagt acctggccca cctgaatcta gagggccacc cacccagctg  35400
aagtccctgg gcaagtctcc tgccccagtg caggcagtgt ttcctaacct cctcctcctc  35460
ctgcacccaa ccaggcccag aacacttcct ggtcatgtga acagctgaca gttacaatcc  35520
cccacacact gagagagcat ctgtgttcct gagtggactg aattgctaga tgtagtaaca  35580
ttgatttggt ggctataggt ttcaaacttc aagtcagaga tcatagaact ttaagccata  35640
```

-continued

```
tagaatccta gaattggaag actctgagca gccatctctg cacccagcag ccaaggagtg  35700
gccatcctca gcacctggca gggcatcagc ctcccactgg gagtcccggc cacctccagg  35760
gcacgtgggt tatgagtcac ctttcctttg agctgaccca cccctcactg actagactct  35820
taaacacaca ctgccccgtc taatacacac cagcatgatt cttaatcccc acagtcattc  35880
acgctgccca tctggcagca ccttaatgat ctacagcaag cttgtggcct actaaaaacg  35940
cctccattgt tttttaaaat gtgcagttat tttccggatc atgaatagag aaattgtatc  36000
cctgttgttg gtattgattc agtgttccag ctcaagtttg agttcttaga ctttatattt  36060
ggattctttg gtttcaaatc acaaaaatca actccatctg gtttaatcca agaactctat  36120
tggctcaggc aacagtaaaa agcaatgcta actcatttgg gaccagggct cagatcatcc  36180
cctgcactgt ctctctctcg ctccatgtct caatcctctg cctctggtga ttttttcctt  36240
aggagggttt ccttatgtgg aggtaaaaaa tgatcaccgg cagcttcaga tttaccttcc  36300
accagcttag caaacaccac ccactcccag caagaaagac cctgtttccc aatgctccca  36360
gcagatgtct taggccatcc tcgggcctca ctgattctgt gagccagtgc ccacggccag  36420
gagaatggaa tacactgacc tagaggggac agggactcta gacaggcaaa aactccactg  36480
tcagaagcag aatcctaaaa tgtcagaact gaaaggtagg cccgcccctc gttttccaga  36540
aatatgaaag ggaggcttgg gataacagag aaatgctgca ggcattggcc ccaaatctca  36600
ggcctcctat tcccagtatc accttcacca gcctgggtgg tctcaagatt ggattagcag  36660
ccattccttc tgggtagagt ctgatggtca cttcagctct caaagtccag ctatccagcc  36720
atagtcctag aaggcaagac atcactgtgc ccgaccaacc caagggtctc cacctgcccc  36780
cctcaacaca aggtgccctg agtgcctccg cggggatagt ccccgtcccc accccctgctt  36840
cccccgccca tcgcgacaga tgctcagagc tcatccctgg tgtcacacca cataaaggag  36900
gagggcggtg gccaggctcc gagctcctgc cgtcctgggt gggtggcttc tgtcctgcgt  36960
gccgccgggc agcccggggg tcctgcgcgc gggcgcggtc ggtggagctg caggggggcg  37020
ctctgggatg tctccaggca gagtagatac tgacccctcc gcagccggga ccctcaccct  37080
ttccttcatc actcaggaaa cagaaaaggc ttcagaagga gcggccatgc ccccggccta  37140
agcgctgcgt tcccggccca gcaggcctac cctgcacctg gcgttcctag gggcccctct  37200
gcgggaccca ctgcgcggct cgcagcggcc gcccgcctcc cacttcaccg gcacgctcgt  37260
tgcgtgtcga ggtgtgttga ctcctacagc aaagggcacg gatccgcggg tcagcaagcc  37320
cgacgaattt acaccaatga cccgccgtgt cgccagtctc agaccagggc acaacacgcc  37380
aaccctgcag accaccccca cctccccagc cactgcagac ccttccccct ctgcttctgc  37440
agcacctgtc ccgaaacacg ctcattcccg cccccgcaga ccttccctac ctcctggaga  37500
ccccccctcaa cccctgtaga gtcccctgcc cgtgcagaat cccctccccc ttcccccgca  37560
gccccccctac cccacccggc ggacagcccc gctcgcttcc tgttcttctc ccaagggaga  37620
cccctgtcct ggctctgact ggggttgagt tcgccagttt tgacttatgt gtagagtctt  37680
caccacgggc tggaagtacg gtnnnnnnnn nnnnnnnnnn nnnnnnnnnn nnnnnnnnnn  37740
nnnnnnnnnn nnnnnnnnnn nnnnnnnnnn nnnnnnnnnn nnnnnnnnnn nnnnnnnnnn  37800
nngagcgtac ttcagcccgg gtgaagattc cttacacctt atacaaaaat taattcaagt  37860
tggattaaag acttacatgt cagacctaaa accataaaat ccttagaaga aaacctaggc  37920
aataccattc aggacatagg catgggcaag gacttcatgt ctgaaacacc aaaagcaatg  37980
ggaacaaaag ccaaaataga caaatgggat ctaattaaac taaagagctt ctgcacagca  38040
```

-continued

```
aaagaaacta ccatcagagt gaacaggcaa cccacagaat gggagaaaat ttttgcacct  38100
actcatctga caaagggcta atatccagaa tctacaatga actcaaacaa atttacaagc  38160
aaaaaacaaa caaccccatc aaaaagtagg caaaggatat gaacagacac ttctcaaaag  38220
aagacattta tgcagccaaa aacacatga aaaaatgctc atcatcactg gccatcagag  38280
aaatgcaaat caaaaccaca gtgagatgcc atctcacacc agttagaatg gcgatcatta  38340
aaaagtcagg aaacaacagg tgctggagag gatgtggaga aataggaaca cttttacact  38400
gttggtggga ctgtaaacta gttcaaccat tgtggaagtc agtgtggcaa ttcctcaagg  38460
atctagaact agaaatacca tttgacccag caatcccatt actgggtata tacccaaagg  38520
actataaatc atgctgctat aaagacacat gcacacgtag gtttattgtg gcactattcc  38580
caagagcaaa gacttggaac caacccaaat ttccaacaat gatagactgg attaagaaaa  38640
tgtggcacat atacaccatg gaatactatg cagccataaa aaatgatgag ttcatgtcct  38700
ttgtagggac atggatgaag ctggaaacta tcattctcag caaactattg caaggacaaa  38760
aaaccaaaca cctcatgttc tcactcatag gtgggaattg aacaatgaga acacatggac  38820
acaggaaggg gaacatcaca cactgggcac tgttgtgggg tggggggctg ggggagggat  38880
agcattagga gatataccta atgctaaatg acgagttaat gggtgcagca caccaacatg  38940
gcacatgtat acatatgtaa ctgacctgca cgttgtgcac atgtacccta aaacttaaag  39000
tataataata aaaaaaaata aataaaaata aaaaataaaa gaaaatgaag aaaatcatgt  39060
catttgcagc aacatggatt tggctagagg actttatcct aggcaaacaa atacagaaac  39120
agaaaatcaa ataccacata ttctcactca taagggggag gtaaacactg ggtactgatg  39180
gacataaaga tagcaacaat agacactggg gactattggg gtggtgaagg agggaaggga  39240
gaaagtgttg aaaaactgtt gagtactatt ctcagtatct gggtaatggg accattcata  39300
ccccaaacct caacatcaca caatataccc aggttacaaa cttgcacaag tgccctctga  39360
atctaaaata aaagttgaaa aagcaaaaat aaaacagtaa acaacaacaa caacaaaaca  39420
gcaaaaccct caataaatac ataaataaaa atataaataa atgtctttgc cagagctttt  39480
tgttttttgt gtggctttga gttagtatct ggggtcacgt tgcttttaag ctgtttgcta  39540
tcaactgcat cctatctaat atttcttttt cttaatagta aaccactcaa tttttgtgag  39600
gagatattac attgtggttt tgatttacat ttctctaatg atttcctttc cagtttggat  39660
gctgagcatt ttttcttatg ttttttgccc attcatatat aattttaaaa gaaatgtcta  39720
ttcaaatcct tttgccattt taaaatcata ttatttttaa atattgtgtt gtagaaatta  39780
tttatatatt ctggatatta actctttatc agatatataa tttactaata ttttcttcca  39840
tccacaagtt ttttttaaca ttgttatgtc ctttaatgca taaaagtttt aaaaagtttg  39900
atgtagtccc aattgtctat tttttctttt gttgtctgta cttttggtgt catattaaaa  39960
aataattgcc atatcccctt attctaagag ttttatagtt ttagatcttc catttaagtt  40020
ttaaatccat tttgagttaa ttcttgtata tggcataaga caaagtttca acttcactct  40080
ttcatgtgtg gatatccaag tttcccaaca ctgtttgttg aagagaatgt tcttccctca  40140
ttgagcggat ctggaatgct gtaaatatta tttgaccata tatgtggagt tttcttttaa  40200
tgggttcttt attctattcc attggtctat atgtctctct ttaagccagt gtcatgctgt  40260
tttaattact gtagtcttgt aacatgtttt gagatcacgg agcatgagac cttcaactca  40320
gttagttttc aagattgtct agtcagagta tatatgaata tttagataaa tttttctctt  40380
```

-continued

```
ttttcaaaaa atgcagctta gattttgata gggattacat ataatttgta gactgctttg  40440
ggttctattg acttttcaaa ttaatacata atgttgtaca gatttgggga atacatctga  40500
tattttggag atcttaacat taaatcttcc aatccatgaa taccaatgtc tttacattta  40560
tttgtgactt ctttcagtac tgttttgtag ttttcagtgt acaagccttt tatttccctg  40620
gctaagttta ttcctaagta ttttactatt tttgatggta ttgtaattaa attattttct  40680
taattacctt tggattgttt atagttaatt tatagaaagg caactgattt ttgtgtgtcg  40740
attttggatc ctgcaacttt ccagaatttg tttaatagtt ccaacagttt tctggatttt  40800
atgcatatat gcatctaaca gttttctaga ttttatgcag gagtctagga ttttatgcat  40860
ataggatcaa gtcatctgtg agcagagata attttacttt tttcttttat tctttggatg  40920
tcttttcttg cttaattttt ttttcctaat tggtctgctt ggaaattcaa atactatatt  40980
gaatagaagc gaagagacag agtatacttg tcttgttcct aatccagaag aaaagtttga  41040
atcttttacc attgagtgta agtttacctg tggatttttc atatatggcc tttattatgt  41100
tattttcctt ctattcctag tttgctgagt gttttcgtga taaaaggtgt taaattttgt  41160
taaacatttt ttctacatca atataaatga tcatgctgtt ttgtccttta ttctattact  41220
atagtgtatt acattgattt ttgcatgttg tattattctt ttttttgag atgaaatctc  41280
attctgtcat tctggctgga gtgcagtggc atgacctcag ctcactgcaa catttgcctc  41340
ctgggttcaa gggattctcc tgtctcagcc tcccaaagtg ctgggattac aggcatgagc  41400
cagcacaccc tgccacatgt tctatcattc ttgcattcca ggaataaagc caacctgatc  41460
atcacaaata ttggtctgta gttttctttt catgtaatgt ctttgtttga ctttgaaatc  41520
agggtaatac tggcctcata taatgagctt tgaagtgttt tttatattca tttttgtaaa  41580
tgactttgag aaacattggt tctaattctt ccttaaatgt ttggtagtca tccggttctg  41640
ggctgttgtt tgtttggagg tttttgaacc agtttaatct ccttcgtagt tataagtctg  41700
ttcgtttttt ctacttcttc atgattcact cttattaggt tgtatatttc tagaaattta  41760
tgcacttcta aattatccaa tttgttgaca tataattaac tgttgatggt attttcttat  41820
aatccttttg atttctatgg catgggttct aatgttctct tttttatttc tgatttatta  41880
gttgaatctt ttttccttag ttaatctagc taagcatttg ttaattttgt tggtgttttc  41940
aaaaaccacc tcttagtttt gttgattttt ttctattgtt tttatattct atatttcatt  42000
tatctctgat ttaatctaat ctttaggatt ttcctccttc tgctagcttt gggtgtagtt  42060
ttttttctct cctagtttcc tgaggtataa agttaggttg ttgatttgca aactttcttc  42120
tacttctttt tttttttttc ttaagttgtg gagatggggt cttgctttgt tgcccaggct  42180
ggtctcaaat tcctggcctc cagaagttct cctccctcag cctgtcaaag tgctgggatt  42240
gcaggcatga cccaccatgc ctagccactt tcttcctttt ataatgcaca tatttatagc  42300
tataaaattc tctgttagca ctgcttctgc tgcatcttac acattttggt acattgtatt  42360
tttattttcc tttatctcaa gatattttct aacttccctt gtgatttctt ttttgaccca  42420
ttgcttgttg aaaactgtgt tgtttaattt tcacatattt gtgaattttt tgttttcctt  42480
ctgctactga tgtctagttt tatgtcattt tcatcaaaat agatattttg tataatttca  42540
atcttttaaa atttgttaca agttttttttg tggtataaca tgtgatttat ctttgggaat  42600
attccatgta aacttgagaa aaatactatt ctgattttat tgggtggaat gttctgcaca  42660
tgtttgttag cactatttat agtgttgttc aagtactgta tttccttatc gattttctgt  42720
cttgttgttc tagccattat tgtaagtgag gaattgaagt cgcctaccat tattatgctg  42780
```

-continued

```
tttatgtttc ctctctgatc tgtcaatgtt tgcttcagat atttaggagc tctggtatta  42840
gaggtatata tatttgtaat tgttatatct ttctgctgaa ttgacttttt gttatataat  42900
atccattttt ttgtcttgtg actatttttg actttaagtc tattttgttg gatagtagta  42960
tagtcacttc tgcttgcttt tatttaccat ttgcatggca tttacttttc cttttttca  43020
ttttaagcat atttgtttct tagacctaaa tgacaggata aagttggatc ctttttacaa  43080
atccattttc cagtctatat cttttgattc aggagtttaa tccatttaca tttaaagtaa  43140
ttactgatag ggaaggacct acacttgcca ttttgttgtt tcctgtatgt tttgtaaatt  43200
ttgtttttta ttccttctct tactgacctc ttttgggttt tgtcgatttt tttttgtggt  43260
gacattttga ttcccttcct gtttcctttt gtgtgtattc tatagatttt tttatggtta  43320
ccataagaat tataaaaaac atcttaaagt gttaacaagc tattttaaac tgttaagaga  43380
ataacttcga ctgtgtacaa aaactatttc ttcaaagctc ctaccctcac cttaggttac  43440
ttatgtcaca agttacatct tcatatgtaa tgtattcatt aacacagttt tatagttatt  43500
tttaagcttt tgtcttgtaa attctataca agaattaaaa gtgcatttat gtaccaaaac  43560
tgcatagtac agtctctata tatgtccata tatttatctt tactggagag ctttatattt  43620
tcataagact tcatgttact atttagcatc cttttgtttc aacttgcaag atactacagc  43680
aggtccagtg gtaatgaact ccccagtttt tgttcatcct ggaaaggctg atttttcctt  43740
tatgtttgaa ggatggtttt gctggatata atatttttgg ttgaaatttt cttttctttc  43800
agctctttga atatattatc cccctgcctt ctggcctgca aggtttctgt tgataaatcc  43860
actgataatt ttataaaggc ttccttttac atgacaagtt actttctttt gctgctttca  43920
agattgtctc tttgtctttg acttttgaga gtttgattat agtgtgtctc actgtgagtc  43980
tctgggtttt ctttaacatt tttttttgt tcatatcttc tgatgatgaa ttcctttaac  44040
ttttatattt gtgaaatgtt ttttcttcat tttcagaagg tatttttagt gagtgtaaaa  44100
ttctacattg acagtttttt tctttcagta ctgtttagtg tttctctact gtcttcttgc  44160
ttgtactgat tgtatagaaa ctctgctgta attcttatct ttgtgtcttt gtacttaatg  44220
tgccttttta ctctgcctgt ttttaagatt ttatttttat tattgatttt gatcatgtgg  44280
cttggtgtga gtttcttcat atttattgtg cttggggttc attgagctta ttaagtctgt  44340
aggtttatat ttttcattac atttagaaaa attgtagcca ttattcattc aaattttttt  44400
ctgttcttct cccatttctc atgcccttat ggggtctaat tatatgtata ttaggctatt  44460
tgaggttgtc ttacagctca cttacagttc ttatgtttat ttttccactt ctatttcatt  44520
tgggcaggtt tattatactt ttccctaatt tgctaatttt tttgcaatgt ctaatccact  44580
gttaatctca tccaatgtat tattaatttc agacattgta gttttcatct ctagaaattg  44640
ttcatctttt tatatcttct ttgtctctat ttgatatgct aagtcttttc tctagcttct  44700
tgagcatatg aaatatagtt atgacaacta ttttatttta ttacaacttt taccttaggt  44760
tcagaggtac atgtgcaggt ttgttatgta ggtaaactcg tgtcacagga gtttgtttat  44820
tatttcatca ctcaggtact aagcctagta cccaatagtt gtttttctgt tcctctccct  44880
tctcctaccc tccaacttca agtaggcccc agtgtttatt gttcctctct ttgtatcact  44940
actattttaa tgtctctact agttctctta tttttgtcat ttctgagttg attttatttt  45000
tctcactatg gccatattct cctacttctt tgaatatctg gtatgcaaat tatacctagt  45060
atggatatta tatcaagacc ctgtcgcaat atggatacct aaaagaaaat aacaatgttt  45120
```

-continued

```
accagtttgc tctaagcctt tcttagctct tttgcttgtt tctcaagaac aagcacagag  45180
ggtggagctc aaccaagact gaagttaaag atgtagaaag attgagatgg gaagtaatta  45240
agttgaggag ctctgataca atggtatttc tctttttaat catgtaagat gcaagcccaa  45300
gataatatgt tgggaaagtt gaaggcgaat gtcttgagaa atatgaaatg cacccaaggc  45360
tatggctggg tgatagaaat aactaaaaag ttttaaaagg attgttttat agctggtcct  45420
tgctgaggtt aggggatagg cctggaaaaa ttgagcagtg gtattgccca ggcaggactc  45480
ctcatgacat tctccagatc cctaagtttt tccaagtttc caagcatttc cttggccagc  45540
aagtcatctc gcagcacaga tcctactctc tttcagtcag tcattccaca actctacaaa  45600
gcatttttct ccatcaaatg ggaacttttg gggttctgca taatttttca gggttccacc  45660
acttttgact ctttctggat accttgtaag gatattataa ctctttaatt catgtccttg  45720
attttctctt ttaactttta atactgttca ttgcctgttt acctctttca ccctcttctt  45780
ttcacttccg ccctctttct tgtgtaagta tataatcatc cttttttttct tcctcgaatc  45840
tcagttctcg ggagtaacat atacaattca ttcttacttc cagtctttta ttcctaagtt  45900
ccttatctct agttctcttg catatttgtg gcaattatta gttttttttcc aaaaatccat  45960
tctccctttt tcctgtacat gtatctttcc agcttgacca catttcccag cttccctggc  46020
agctaggtga agcaatgtaa ctaaactttt gcctgtaaaa tatgagcaga agttatgtgc  46080
acaatatctg cctcacttgc ttaaaataaa ttgtattatt tgagctttct atattgtccc  46140
tttttacaac taaaatgtag aggttatggc aacttttatg gtaaagagaa tcatcacgta  46200
ggagatcaag aatcattgat ttgagaggaa cctaaatcct ttaatgactt agtggagcaa  46260
gactgcccca tcagtctgga agctacccca caacttatgt atatcttcag attgttgagc  46320
aaaagagaaa aaatgaagcc actatatatt taggtctctt catgttaaca gtttagcttt  46380
taacctaaca cacatttatt cctgaatggt agcatattat taacatcaca ggaagggaat  46440
tccttgttca tggatctttt attttgttga aataaaggta atctgcttgg gcttaatact  46500
gccaaggcag aattttttgg aataattatt tctatagatg acccattcat aatgacaact  46560
aacatggttt ctaaaatgga ttcatgtacg tcatcttatt tagtccccgc aaaaattctg  46620
aaggtaggta taattattcc cattctatat attgaaaaat tgggattcag agagactacg  46680
gacttataca agtttctgca gctatttaag aaacagagta aagtctcaaa gccattaatg  46740
aactgtttag tttagtgctg cttagtaaaa ttagaactgt ttgaagtgcg ttttaatagt  46800
aaacccatcg atatttagtc agctctctgc ttgctaacta atatggaaga aaaaacatac  46860
atctacgtac atcctgaatt gggagaaggg aaataaaata ttgccaatcc cctttcctgt  46920
attaggtact gtgataaggc gataaggctt ttcattatta taaatgagtc ctggagaggt  46980
taagcgcagt cacccaaagt cacatgacca gtaactttca gagattttac cccaggtctg  47040
gaaagactct gaagcccatg ttattgcctc cagagcctgg tggagaaccc ctgaatggga  47100
cagagactca gcagacagag tggtcctttc cttccaggga gtcagggaag gtttggtagg  47160
ggagatagag ttagatctgg gtgggatttg gatgaaatga gatcaagcag ggataaataa  47220
gatccaagct gtttatgagg gacagggaga ggccagctct gttagaaaga gtggtttata  47280
cagagaagca tggaaacatt tgctccatgc ctcgccttcc atggatagca gtccagaaat  47340
gctacttgcc tgcctgacag tctttctcca gtccccaggt gtggacacgt tctgagcacc  47400
tgagcctggg tctgccctga cccagattct gtgagctggg acagagaatg tgtcctgctg  47460
tccctcctcc cccacttggg cccacaccct tttctacaca tttggattag aaatctgaat  47520
```

-continued tggcctttct gtgaacccca atgacaggca agtccccagt aaagaagcac ttaatttaat 47580
tgctccttca gggtccactt agagtaatag ttgtgaacag ctctccctag tgtctcccac 47640
aggcagtgac aaatgttgct aaagataagt cacaaattct tggcaaggcc atcttaaata 47700
tgggaaggaa accttgttca gtcctgaaca gtcctgttca gactgatctt atcacaggtt 47760
gcacactgcc tcaatgtcac catgtttcta ccctcagttg tgcttggcag agagaggaca 47820
gctatacata aagtctgttc actctacaaa ggtgaaatca ttttttttaa ggtaattatg 47880
attgttctga ggatggtgat tgagtgacat ttaaaaaatg ggaaaagttc tactcataac 47940
tctgtctgct taatttgctt atataaaaga cttaatggtt tttgttgagt tgatccagag 48000
tcagtaacat ttgaatatgt gttattacca tttgatcagt aacaaaacaa cagggtaagt 48060
gggatgccaa atgtggctga gagtttaggg tttacattcc acaccccagc cttaaatacg 48120
tttgtataaa ttattggttg atttttcttt ttcatggctt ttctttgaca tttgatgggg 48180
ctggatttat ggaggcaacc aacaaattac acagcaatga attctggact gtagtcccac 48240
agccttgagc ctagatacta gctgtgtcac taatactctg tgtgaccagg gtaagttatt 48300
tagatacatt tatgactttc caaatcaata ggttggacaa agttatcttc aaaatgtctt 48360
tcagatttga ccctgaacat atgcgattct ggcatgttct gatttttagt tttctgttct 48420
tgaagcatgt ctacaataga aatgcctacc ttcatataca ataaaaggac attagattaa 48480
tatggtgtct gtgaaaatca ttgaacagct ttagagataa aaataatgaa atgagtcaag 48540
ttctccatta ttaattaaat cttttaaatt ttctgtttat gaaactatga acaataaatt 48600
ggaacaaaga tataatctca ctacaagtaa attgtatttt atgtaaaata taatttgtct 48660
ttagaaaata ctcaatgaaa ttaccttttt aatttcagag attttgagga ctattattgt 48720
tatttcttta aagtgataaa tgtaatccaa gatgcctttt ttcccccttc agaagcttga 48780
gtgcccaagg gtttgataaa tgtggaaaat aaccgctgtt cgaatatcct gttggcctgc 48840
tggtgagatg tcatcgtgtt gtctgaatgc agtatgtgtt taaacttgcc atttattacc 48900
tgaaattgtg ttattttgcc tcataccctt agtaatactc ttgtaatgct ggctgagaat 48960
tgaagcaaat gccctatgaa actcaaggga gcaaggtctt tgttattttt cagaagaaat 49020
gactggctga ggctgtaaag aaatcttgtg gtcattctca tggaaagagg attggagccc 49080
cgattctttg atctcattat tgaccagttg attgagaaga ctgtcctcct gtccccaccc 49140
aatcacaata agtgggtaat tacctgaggg ctaatttgct ccttgaatgt gaatacattt 49200
gtggaaattt ccttgtgctc agcacctgtt caaaacatcc atttgtattg cagagctatt 49260
gtttttctaa tctcattgtg gagctaagag agagattgtg tttaaggttt ccttcgtaat 49320
aggttttctt gctccaggaa ggatgcgtga cagactctgc acactgctgc ttggtaggtg 49380
ttcagtgatg gatgcgtttt ccatctccca ggtacagctg cagctgtgct gactctggtg 49440
cgtttgtaat atgcactgtg gagtgcacca tgatttcatg atggctggag aaatctggtg 49500
gctagaattc tagggaggag gacatgagtc ggaagtgcag aaacctcaca ctgggacatt 49560
gatggagaaa atccaattct gtccctggag ttaaagagga gtcactcact gggccatcat 49620
aagagcaaat aaagttacag ttatttcttc agatccacaa ctcaaactca gcgaaagtaa 49680
ttattcactc tttttgtccc aaacaataat gaaatcagct aaagcatatt gtatttatta 49740
cttccactca agttattgag ctgttctgac accttgttgc tgggaagata cacagatgga 49800
acaccatcat ttccattgat tctgatcata ccccacgcta atatagcctt attgctctga 49860

-continued

```
gtcataggga ttttatgctt gcctattcaa aaaacagttt ttaccttatt aaaaggtgat  49920
atgacctgag ctggagatga tgtttggtca ttttgtgtaa accttttaat attttagtgg  49980
taaatacatt tcttgaatct tgacaaaaac ataattaaaa tgaacatatt taaaatggac  50040
atcttccaaa tgttcatttt taaaacaaac atcttccaaa tgttcatttt taaaatgaat  50100
atcttcgtta actttttttt ttttttttga gacggagtct cgctctgtca cccaggctgg  50160
agtgcagtgg cgcgatctcg gctcactgca agctccgcct cccgggttca cgccattctc  50220
ctgcctcagc ctccagagta gctaggacta caggcgcccg ccaccacgcc cggctaattt  50280
ttgtattttt agtagagacg gggtttcacc gtgttagcca ggaaggtctc gatctcctga  50340
ccttctgatc caccctccac ggcctcccaa agtgctggga ttacaggcgt gagtcaccac  50400
gcccagcctc ttccttaact tttaatgaat aaagagttga aagggaaaaa ccaaatgtgc  50460
actatgctga ttttatcttg agctgtacag aatgtgcagt aacttaagaa tataagtcat  50520
tctgctgtta ttcatactag cctattcttt agcattattt aaacacacat atttgagtgt  50580
ctacacactg cctgctaggc agggggctgg gtgccaagaa gggatgtcca gagataaacg  50640
ggcatatgtg ttaatctttt agggcacagt ccagtaacct gatcaaggag tgacgtgtat  50700
tgtgtactag gatagaagtc agtatcagag gaaacacaaa ggaaagagtg gtactttctc  50760
cccagggaag ggatgctcag aaagaggggg ctgattatgt ccctggttca tgagaaaaag  50820
ggcattcctg gctcagggag tgggaagaac aaaaccaaga aatcctggaa tggcttggtg  50880
catcagccag tctgtgagtg cagggcatgg ctggagttct ggctttaaga tgagtgggaa  50940
gaaaggctgg agaggaggtg gatccaggaa aagttgctgg gagcatttat tcttttggca  51000
atgggaagcc atggaagaac tgttgtaagg aggattctgt gtgatacatc tgccttttag  51060
agaggtcatt ttatagaaaa agtagaaaat acagaccagc aaaaatttaa aaagtgaaaa  51120
caatcactgt tcaagctctg gtctagcact caccagtgtt tttcctacag gtgcatatac  51180
aaacatgctt ttacatttta tttttatttt aaatttttca ctatcctcaa tatcagtgga  51240
aacaaatctg ctttttttaat tttttttttta aaaatgagat cctattgtac acattatttt  51300
aaattttttt tcattctttc cttttttttaa aattaaaaca attttttttg agacagtctc  51360
actctgtcgc ccaggctaga gtgcagcatc gtggtctcag ctcaccgaaa ccttgcctcc  51420
caggttcaag cgattctcct gcctcagcct tccaagtagc tgggattaca gacatccacc  51480
accaccgtgt caggttaatt tttgtatttt tagtagagaa tggggtttca ccattttgga  51540
caggctggtc ttgaattccg cggatccttc tatagtgtca cctaaatgtc gacggccagg  51600
cnnnnnnnnn nnnnnnnnnn nnnnnnnnnn nnnnnnnnnn nnnnnnnnnn nnnnnnnnnn  51660
nnnnnnnnnn nnnnnnnnnn nnnnnnnnnn nnnnnnnnnn nagcgtattc gcccgtggtg  51720
aagatcgtag tagagtctac cacctcggcc gtgaacctgg ctcagggggc gcagccgggg  51780
tgggcgaccc agccaggtct gcggagcggt gcccggcggc aaccccctca cggacgctgg  51840
gactccccca ccccgtcccc attcagcgct agcggtggag gggccaggcc cgccccaggt  51900
agtcaggcag gggtcccggc tcctccccca ggaccaccgc cccgcgggcg ctcacgtcct  51960
gatggcttcc cacaccagga gcccgtcgtc ccggtagaag tagtagggga tgtcttcttt  52020
gctctccatg ccccgggcct tgatggcctc gggaaagcac agggaggcat aggtcaggtc  52080
cttcatggcc ctctgcacca tctgcacgtg cccaccgccc cctgtggcgt tggcctggag  52140
tgggaggtag agtgccctga gcgggtggct cctcccacag ctgtccagac ccatccctga  52200
ggaaatgtgc caggggaggc gaggaggcca ggcaggcaga ggtgcaagcc cttgtcctgt  52260
```

-continued

```
gagatggggg agggatgttt aacgcagaga atgacaaggg cagccgggtg gagaggtgct  52320
agggaggagc ctcccgccca atccaatgca agggactgaa ccgtggggct gcagagtaca  52380
agagggaagg gtgcgctccc agccacagga gggcagcagg cgtgggcagg tgtgtggggg  52440
accccagcac cagcgggcct gggctgtgaa gtctgctcta gtgctgagca cacgaccctc  52500
agtcattgct ctcagtgacc ctcagtttcc aggacccatg caactctgtt gagggcctgt  52560
tgtgtgctca ggtgagggct ggagagaccc acaaggaggg atcctggtcc tgatcccgat  52620
cccggcttct gagtgatgca gacacactca caagctcact ggcacatatg tgtgtccacg  52680
tgcacacaca cacatgcaaa tacacccagg gggctgggct gtcggtgcca cagaggtttt  52740
gaagaaggac ttgggtgctg gggtgccaga gattggtcca cggtgggcat tcagcccaag  52800
caggaccaac cagagctgcc ccccagcact ttctgtttag atgcggctgg gagataatgg  52860
ccacatgaga acctgaggtg gagctactat gatgagctcc tgtgccctct cccatggggg  52920
cctgtctgca gcaggagagt gtgatgccaa cacaggtgaa agagacagaa agagggagcc  52980
agtgtgcatg caccctgggg cattgcttga gtccctggat ccatttctgg ctgaggcccc  53040
cgaccctcta ttgtgtccag gtatttgaga taaggcatgt cttgtccagc tgcagctggt  53100
ttgagttggg ttttgtcatt tgcagcccaa acagtgtctc aacttcagtg gtcatctggc  53160
ctggtcacta atgggctggg gaaaggagga aggttggggc aagggcccat gtgagagtcc  53220
aagcttggta aggctacaga gggctcaaaa cgaggtgggg tgctacctga gggatgcgag  53280
ggctgggcag ggcctggagt ccccgatgca ggagacagtg ggttgggagg gttgggaccc  53340
gggaagcaga gtgctgggga ggtccaggtc agggtggcag gggtgtggca gattaagagg  53400
cagacacagg ttcctggtgc gtaggaggtc agggggccat aaggagtgtg ttccagaggg  53460
gggtctacac ccaggtccca gaggctggga gaggggaggg gtgggaggag gggaccagga  53520
gccatcagtg agaaggaaga cctggtggtg cgcctggagg agtgctcctg gctgaatggc  53580
acgggctgga gacatcagga ggatgctgga gccagtgctc tgagcagact ccagccttca  53640
cccttccagg cctcctgaaa gggtgtctag atctcagata gggagtgaag gcggccaggc  53700
tgggctcttc caggcaacaa gtagggtagg agggcaccca ccttgtcaaa gaggccacac  53760
tcgcagatga gctgctcacg ggccttggtg ttgattgcaa tggtgaatct cacgtgtgcc  53820
accagcagct ggggagggga gaggaggagg cctcagaggg ggcccagtca ggtgacctgg  53880
tgcctcaggg acccgcagct cccccaccca ggcctgccct ataggatgat gctgggcgca  53940
gggaggaagt gaaggctggg tgctgatctt tctgctgaat aagtgctgga ggcctgcacc  54000
cctctgatgc ttactaagca tgataatgat tcagagggtc ctggccagca cttgtacaat  54060
gcttacctct ttgctccctg agttcactgt cttaatctga ccatcattct gtaaggcagc  54120
tgtactattt gacctgtttt actggtgagg aaactgaggc acatgggtac ttttagcatg  54180
cagtcacccc agcagccaat gcttgtagga ttcgagaaca gggacggaga gtgatggcag  54240
gggcggccat cagcatcagc cgaggatcac catgaactca tttgcctttt ccaactctac  54300
tggctggcca gcgaggcccg tgtgtcaggc ccatgcccca gccgcgtgtc ctggggaaca  54360
gcaggctcct agctgttttc ttcctttagg ggcattactg actctgagaa catctctcca  54420
gggctccctt tctgccaccc actcccagcc acaggtcccc ctgtgggatg tcagtgatcc  54480
ctcccactcc acatctcaga tgccctccca tagcaggtgg ggcggtagct ggctgtacct  54540
tgaaaatggg gtgcacagca ggcagctggc ggtacattgc aatgccaaaa acctcagaca  54600
```

-continued

```
ccagatgtgt tcgcagaagg tgggtgatgg tctggtggac gtggaagtca ctggaacgca  54660
cccagatttt ggccaaaagc cagtcgtatt ttgcatccga agggaggaaa atagggttct  54720
catctcccgg gatttggttg agctgataca ttgggggaaa ggaaacacac tgctatattt  54780
cacttcagag tatagttgtt ggagaacttc gcctcttggg aagttccaga agtatctgaa  54840
tttctttaac agtgactttg gaatcagaag agcctggagg gggtaaaggg ccctgcggtg  54900
gtatttcctg tcccagccat attacttaca acctgcatga ctctggatga cacactgggc  54960
tttctaagct ccggcttcag catctgtcat gtggggacag tgatcgctcg gctcacagtt  55020
actcaggagc tggcagcatg gaaggagcgg gcaggccgaa ggcccagcag cggaggggga  55080
ggatcgctgt ccccctcttc cctccttgcc ctgctccctc ttctactgcc tctccttggt  55140
ctctcatact ttcctccctc tcctcttccc tgaaatgctg gagctcccca gggtctgcca  55200
tggtgctcct gtcttctttt cttgccctaa gtcagctcct cctgtttaaa ggcttggggc  55260
cctcctggta ctgagcctcc cagatcaggg tctgcagctt gagctctgcc tggagcccac  55320
acctgtggcc aggcacctcc tgtagcagag gctggacctg tcttcccttt ccagtttcca  55380
ctccacactg ggacaaggtg agttttttc ttttccaaaa tgcaaatcat gtcatgttaa  55440
ctgcctcctc aatcacctct taatgccaga aaataaaatc cccaagctct gtggtgacct  55500
ggttgctgat gcctctgtac acacagcctc actttcgtgc ccccacacca gcacccagcc  55560
ccaggtccct ccatgccagc agccctgcac gttgcccccct tattgagagc ccagcacagc  55620
ctcagcaccc gacagtgagt tctcacggga gccggcagca ggtgctggca ttgcccattt  55680
ttacatgaag acatggggta ttggaggggt tgacagaaag aatgaggtgg gtggcagggc  55740
tgcagccaag agcggccagg aaggggcatg gccagacttt aggtgctggg aaagaccagt  55800
gtcactgcag cacagtggtc atggctgggg agggagaact gtcccagagc acacagctgt  55860
gtcacttgct ataagtattg tggaaggtgg ggtccttggg cgtctctccc tcgaaaacag  55920
tgctgtccaa tagacatata atgctacccc acacatggaa ttgtatatat tcaggaagcc  55980
atattaataa aaataaaagg aaacaggtga aatgccggtg aataatataa ttttatttta  56040
cccaatatat ccagaatatt atcacttcaa catgaaacca atctaaaact attaaatgag  56100
atatttcaca ttccccacct ccttattcta agtcttaaaa atcaggtgtg aactttgcac  56160
ttgcagcagg ttttggtttg gacgagccaa atcccaagtg ctccagagcc ctggtggcca  56220
gtggctccac cctggtcaga gagaccccag aagcctcagc actccctgag gaccaaggag  56280
gggggaggga ggagggagag cagagtgtga cttgcacatt aggcgtgcct gtctgtttat  56340
acttgagatt agttggctgc ttttaaatac cagacagttt cacataaaaa tttgaatgac  56400
ctggttttct tgaaaaatta gaaggtctca gaactctgca cccaggttct cacagaacta  56460
cgctcttgtc ccttttacag agtcccagct ctcagggtcc ccactgccac acccgtttgc  56520
atgagatgcc tgggccactg atacctgatc tgtgccctag aatgctgggc tgcctggcat  56580
gctctgagac actttctgac atgtccccac atgctctgac atgttcctga tggctctggg  56640
acactgacat gttcctgatg gctctgggac actgacatgt tcctgacatc ctctggggcc  56700
gaggagcccc cctgttgtgt gctaggggct ttacccatgc tatctcactt aatcctcact  56760
ttgaccctgc aaggcagata ttccttgctg tacccatttt acatgggggg aaactgaggc  56820
tccagctggt ttagcagctc tcccaagtca cacagtaggt aaagagctca gccggcaaca  56880
tgatattgaa caggcaaaaa ttggaagcaa tccccctaaa aactggaaca agacaaggat  56940
gtccactctc acccctccta ttcaatagag tactggaagt cctagtcaga gcaattaggc  57000
```

-continued

```
aagagaaaga aataaaaggg atccaaatga aaaaaaaaaa aagaggaagt caaattatct  57060
ttgttcatcc atgatatgat tctataccta gaaaaccctg aagattcctc caaaagactc  57120
ctagacttga taaacaactt cagtaaagtc tcaatgttat aagtaaaatg cttgtttaga  57180
aacagaatgc ttgttcctcg gtactgcaag gaaaaatcag catttagaca aaaagttttt  57240
ttagcaagcc aattttactt tctgcagaaa gggtgctcct cgcagatgga acaatggcga  57300
gagcacacct gaataatgga gagaagcaat ttttattcct tacgcagctt gtccctgcta  57360
ccgtgtcctg tctccattgg ctggagccaa acctcacagt ctaaactaaa acccgactgg  57420
ctaataactt aaaacttttc taaataggta aaagcagtgg aaagacaaag gaaaagagga  57480
agttgcttat gaaaggactt agaaaagtaa taacatttcc aaataaggaa ggggcatggg  57540
ctgcaagctg ggacatgcct gtgagcacgt ccagcacaaa tatcttggtt aaagtacaag  57600
gacatagaat gtactcattc ccttatatct aacagctaca tatgataggg cttaacaaaa  57660
agttattagc acaaagcgaa aaggcttaaa aaaagttagt ctttagaaaa aactattatt  57720
tctaacacat aatttactcc ttaacaaaaa aaaaactttt gactttctac actcaagata  57780
caaaatcagt gtacaaaaat cagtagcatt tctttttatt tgagacggag tctcactatc  57840
acccaggctg gagtgcagtg gtgtgatcgc agctcactgc aacctccgcc tcccaggttc  57900
aagcaattct cctgcctcag cctcccaagt agctgggatt acaggcaggt gttaccacac  57960
ctggctaatt tttgtatttt taattgagac ggggtttcac catgttggtc aggctggtct  58020
caaactcctg acctcaggtg atctgcccac ctcggcctcc caaagtgctg ggattacagg  58080
cgtgagccac tgtgcctggc ctaaaaatca gtagcatttc tatgcaccaa caatgttcag  58140
gttcaggctg agaaccatat caggaacgtg gtgatctcag ttacaatagt cccccataca  58200
caaaataaaa taccaaagaa tgtatccagc caaggaggtg aaagagctct acagagagaa  58260
ctataaaaca ctgatgaaag aaatcataga tgacacaaaa aaatggaaaa acatcccagc  58320
taatgggttg gaagaaagca atctacagat acaacacaat tcctatcaaa ttatcaacat  58380
catttttcac agaattagaa aaaaaaatcc taaaattcat atggaaccaa aaaatagccg  58440
aatagccaaa gcaatcctag gcaaaaatac aaagctggag gcatcacatt acctgacttc  58500
aaactatact acaagactac agtaacaaaa acagcatggt atactggtac aaaaataggc  58560
acagagatca atggaacaga acagagaacc cagaaataaa gccatatacc tgcaaccaac  58620
tgatttttga caaaatcaac aaaaataaac aataaggaaa ggacatccta ttcaataaat  58680
agtgttggaa aaactggcta cctatatgca gaagaatgac gctgggcccc tacctctcac  58740
catatacaaa aattacctct agatggatta cagacttaaa tgtaagactt caaactttaa  58800
acattctaga agaaaaccta ggaaaaaatc ttatggacat ttcctaggca aagaatttat  58860
gactagacct caaaggcata tgcaacaaaa acaaaaattg acaaatgaga cttaatcaaa  58920
ttaaagagct tctgcacagc aaaacaaact atcaacaaag taaacagaca acctacagaa  58980
tgagagaaaa tatttgcaac tatgcatcca caaacgacta atacccagaa tctatgagga  59040
acttaagaaa aaacaccacc attaaaaagt gggcaaagga caggaacaga cacttctcaa  59100
aagaagacat acaagtggcc aacaaacata tgaaaaaatg cccaacatca ctaatcatca  59160
gagaaatgca aattaaaacc acaaagggat accagtcaga atggctatta ttaaaaagta  59220
aaaaaatgac agatgttggc aggatgcaga caaaagggaa tgcttacaca ctgttggtgg  59280
cagtgtaaat tacttccatc cctgtggaaa gcagtttgga gattttgcaa agaactgcaa  59340
```

-continued atagaattac cagttgaccc aacaacccca ttactgtgta cctacccaaa ggaaaagaaa 59400
ttgttttacc aaaaggacat aggcacacat atgtttattg cagcactgtt cacaatatca 59460
aaatcatgta atcaacctag gtgcccatca atagtggcac cagataaaga aaatgtgata 59520
catgtactcc aaggaatact acatagccat aaaaaagaat gaaatcgtgt tctttgcagc 59580
aacatggatg cagcttagga ttggcactta agccataatc ttaagtgaat taacccagaa 59640
acagaaaatc gaatactgca tgttcttatt tataagtggg agctaagcat tgtgtacaca 59700
tgggcataaa agtgggaaca aaagacactg gggactccag gaaggggagg gagggaggaa 59760
agggttgaaa aactgggtat tgggtactat gctcagtatt tgagtgatgg gttcaataga 59820
agcctaaccc cagcattatg caatataacc atgtaacaaa cctgcacatg tacctgaatc 59880
taaaatttta tatattaaaa aaaaaaaaac tgttctgacc agtaaaaaaa gagctgaatg 59940
aggatgggcc cagtgctctg cctatttcag cccatcactc tcccttctgc ttctcttcac 60000
ctcccggcct gaccgggcct cacctgccca tctccttgag ctcttgtacc actgagctgg 60060
gccttcccca acccatcctt cacatcctcc cactcctgtc caggattttg gcctgccatg 60120
ggatgccaga acttgccctg agcaatttgt gtttcttaaa tttgtttttt gggtaaggaa 60180
gtagctttgc gtttctgatt agaaaagaat atgtgcttat cgtaaaaaga aatctgagtc 60240
atgacaggag agcctgagaa agaaaacatc atctcatctt ccagcgccca gggataacca 60300
ccaaattctg gggagcctcc tttcataggt ctttgcatgt gtgcacattt atctgtccaa 60360
ttttccatca actgaatatg attataatca acatctgtct ctttgttttg ctcacctgtc 60420
ccccactggg ccatcactgt gttcctacct ggtgacactg cgtccttgtg tccccatgct 60480
ggcacagtag gcctgctgca tccttgcatt cattttacat aagtgagacc atgcccattg 60540
ccttagcagt ttgaaggagc tatttgtata cgacagatat gtatccttta tcggtccctt 60600
gtgtcttgtt tttccactgt taactcattg tggagacccc tccaggtcag ctggaaggga 60660
accaaagcat tcctttcaaa gacgcctcaa cattttatgg tgaggacatg gaagggctca 60720
ctcactcaat cctcttctgc cttcagactg ttttcaattt ttttccccat cacaaactat 60780
gctcctgttg ctacccacac acatttgtgc tttcatttct gctgagtggc tgctagcgaa 60840
ggctgagcct tgggggtttg ggtatgtttt cgagtagaca gtgcctgccc tactgttcct 60900
cagacagttt cactctcctg gtgcacacct gttcagtgct actggctgtc agaacactta 60960
aacaataaag tcccctccag tgctcctcca attgagacgg ggcaggggcc tcctcttagg 61020
gcactgtagc cccccagccc cgcaacaggg catggaaatg aaggaaaatc ccgagttcct 61080
tgaagggaag ttccaggcac ctagctagcc ctgagaaata aatgagcaac ttgacaaaca 61140
agagggtaac agcagcctaa aacaacagcc aaggaagcca gagtcctggg ctgtttggtt 61200
ccctctggaa actaaagaga acccctgaac atgtgtctct gagttgtttt tcagaaaccc 61260
agacccccac caaaccgatc cactggcaca gagacctcag ataagacgga actgaggact 61320
gaactctgag caggctcttt gttctaaatt tcttcctggg gggcctgggg gaagtcccgc 61380
ccacaagcca cagctaacat tcctttctgg taacccaaat ttttaaatga aacttctctt 61440
ccttaaccaa tttcaaaaca acaaattttt gaatctacct atgacctgga agcccacccc 61500
cacttcaaga tatcccgccc ttttaggcca aaaccaatgt gtaccctcca tgtattgatt 61560
aatgattttg cctgttaact tctgcaattc ctgaaattca ctctgccttt aaaaaccctt 61620
acctgcaagc catcagggag ttccggtctt aagagtgagc tgcccaattc tcctttttttg 61680
gtccccgcaa taaatgcctt gtgttctcgt agattatatc ccaatctcag tgtttggttt 61740

-continued

```
tgctgcactg ggcaagcaga tcccagtcca gctcggtaac acaactgtcc tcgccacgac  61800
agcctcaacc ccaggaccct ctgaccgccc actgcaacat gcacctggta cagcaggcgc  61860
tgtgggatct gctccggtgc tggccgaagc tctgaccttg ctccggtgct ggccgaagct  61920
ctgaccttgg gctgcccagg cccaccagtt atcccgtgaa cactgccagg ctgcaacaac  61980
tcatgagcag agcatggggc tccgtccttg ctggtgtctg ggagttaccc ctttgttttt  62040
ccaaccaggc atgtcagaaa tgatatctca ttgttaactt tcatttgcat ttctctaact  62100
acaggtgaag ttaggagttt ttccatatgc tggttgccca tttacatttc ttcttttgtg  62160
aattgcctat tcatattctc tgctcatttt tccactggag tattggtatt ttcccgtcaa  62220
tgtaaaggag ctacctgtgt atcatagata ggcatctctt agctgtcact tctgttatgg  62280
ttactcaccc taatctctgt tttgcttttt ggctttgttt atggtttatc actcaagttt  62340
taaaacatta cataatcaaa tatgcttagc tttcccctta taacttcttg gtttcctttt  62400
ccttctaaaa gtcttctgag tgtctgcgta attagttttt ctaaattcgt ttactttttt  62460
cattttaatt tttacttcat ctgaattttt tctttttctt ctaagcaact cctctacatg  62520
atgagattta tttttgtaaa tggcatgaca gagcagtcca atttaatttt cttctcatgc  62580
aaaggcagtg tgatagcatc attaaaataa tatccctttt tcactgagtt gaaaaacctc  62640
cattgtgata cactgaattc ctctgtgggg gagtccattt ctggatctta ctctatactg  62700
tcccccaatt ctctctgttt tcaagcacag tgtctgctta acagtaacct tacaaatcca  62760
gcaaggaaag tgttccttct gtgttttctt ttactttttt tttttttttt aaagataggg  62820
tcttactctg ttgcccagtg tggagtgcag tggagcgacc atggctcact gcagcctcaa  62880
actcctggac tcaagccatc ctcccacctc agcctcctga gcagttggga ttacaggcat  62940
gcgccaccat acctaatttt ttctattaat tttttttttt tttaagacat gaggtctcac  63000
ttggttgccc tgcctctcta tgtggtttta attttttttca aaaaattttt gactatgcta  63060
gatttctttt tccatatgaa tctttcaatt ttttaattgt tttctctcct ttttagttcc  63120
tcttcaccac caccacaccc ccaccaagaa agataaaaaa ttctggctga aattttactt  63180
ggaagtgcat taagttttta taatagaatt tggtagaact gacattttta cagtttcctc  63240
cccaatatca aatcactgtt aagagttcat tgtatatcct ttaaaataac tttatagttg  63300
gccgggtgcg gtagctcacg cctgtaatgc caacactttg ggaggctgag gcaggcaaat  63360
cacaaggtca ggagttcgag accagcctgg ccaacatggt gaaatgccgt ctctactaaa  63420
aatacaaaaa attagctggg cgtggtggca ggtgcctgta atcccagcta ctcgggaggc  63480
tgaggcagga gaattgcttg aacctgggag gtggaggttg cagtgagccg agatcacgcc  63540
actgcactct agcctgggtg acagtgcgaa actccatctc aaataaataa ataaataaat  63600
aaataaataa ataaataaat aactttatag tttttcctta tatgggcatt atattttatt  63660
gttagtatgg agaaaggcta ttgatttttt tgagaaatat atttatctaa acactttgcc  63720
aaatgaattt attaatctag tagcttttaa aaaaattaga atctcttgtg ttttctaggt  63780
ctaccatagc attaccagaa aagatcatct tccctgttct ttgacaatat gtttattgat  63840
tgttttcctg ttttatcatg tggtatgacc tctaaaataa tgttgaataa aaacagtgat  63900
atcagcattc ttattatttt aatggaaatg gcattagagt tgcacctttt tgatgttagc  63960
tatctttatc atataaagta aggttcctcc tattaatttt tattagttgt ggctattaaa  64020
tgttattaaa ttccctttta gtgtgaattg atataatcat aaactttatc cttatgggta  64080
```

-continued

```
taataaatta tggtggtagc tctcttgata ttgaaatatc tggaataaac cctgcttggt  64140
tattacatat agtcatttaa tacactgctg cactcacttc gctaatatca cctttagttt  64200
tcttttaaat ctttatttaa tacttggatt ggtcttcagc cttcttttga agcctgcctg  64260
tatccagttt cagaactaag cttacaccag ctttatatga tcaatttggg gctgataaag  64320
agccctggaa atgtcagctg tctagtggct gggtgagact cagctgctcg ctgtgtaggt  64380
ctgtttccaa tcactatatg gaaattggcc tattttctac aatttcttct aatttatctt  64440
ttcctaggtt tttatccatt tctctaattt ttcaaatttt tgccatatta ctctcattta  64500
aaaaatatgt aatcataatt actgttcttt ttttttttta agagacgggg tcttgatatg  64560
ttgctcaggc tagactgctg tggctattca caggtgtgat catagcacac tacagcctca  64620
agtgagcctc ctgcctcagc ctctcaagta gctgggacta cagttgtgta ccaccatggt  64680
gcctggctat aattactctt tttatgattc ctttttttatt ccgaatcttg catttttttt  64740
ttctatctct ttttttccat cagcctcatg aggaggttat tattattatt ttttggacct  64800
ttcaaagaac cagatcttgg atttactatc ctctggcttt catttgcttg agtctttata  64860
gtttgcaaag tttccatttt cagaagaaga aagagaccca ggaacattct gtggcttgct  64920
caaggtccca cagcctgcta gcaagtggct gaactggaat ttaagctagg cccctgactc  64980
caggctgctc caagagatct ctgagccaag cttttgaagg caccatcagt ggtgcctggg  65040
atctccgggg atctcccagc aattttgtct tcttttaggt cacctgtccc tttacctgct  65100
gcttcagttt cttaggcaca gggcttctct ctggtaacag acaggaagct cctctgaggc  65160
tacgtgcccc tgggagactg tggggaggct ggaatctaga gtcagatgac ctggcttgaa  65220
tcctagctct gtggctggct gtgggcacct gtgtctcagt tttcttatct gggtaaaatg  65280
atcaacatca atagagccca ctacctagga tggttgtggt gatgattaca caaataaaga  65340
taggttatct aaaaccccag tggtcaaatg tgcttcagaa tccagaattt ttaggatttt  65400
agcagtgggt atacttcatt atgtgccata ccccctccca cccccagtct agggcaacat  65460
actattttac aatcgaacag agcagtattt ctgcagtgat ccacatacat atcacattga  65520
atggaaaaag cctctaaata acctcaccta ttgcttcaaa gaaggtttgt ttacaaacaa  65580
tgaatttgct gcacagtttt gaaatatgca gcagttttca gattttttag atttagaatc  65640
gagggtaagg gattgcggac tgtgcaggtt aacccatagg atagccttgg catgtggctg  65700
gtgcctgacc tatccagctg ctattgtgtc cacagctccc aaggtccagt tcatggacat  65760
tatttgctga atgctcatct gccagtctcc cacggtgtcc tctgcgcagt tcctccctac  65820
tcccagggac ctatgcccag tccagtcctg gccttggccc ctgctgtctg cacaccagct  65880
cccagcctgg cagcaggctg gtgccaggaa caggggggaga caaagccctg tgcccgcctg  65940
cctttcctcc agggtctccc tcttcctcct gcctcatctc cggtggacat aagaactcac  66000
atcatcatca aaggtggcat accaggactg gcctggttcc tgaccccaga acccatggtg  66060
cccctcagtg gtcttggtct ccagcttagt ccacagcttc acctgcctgg cccctggcag  66120
caccttgact gggggccctt ggtcagggtg ctggggtgga gagtgcagaa tatgatccca  66180
gggcaggtcc tccacagtgt gcctcgactg gccaggggct tctcaagtgt gccttgggga  66240
gtagaaccct ctccgcccct atggacagcc cacctcaggg cctgcaggaa gccctagtgt  66300
ctttcaagac atagcttcct cagctggagt gtgaatggag ccacccagga gccctggatc  66360
gcagaggact gagctgctca gaaaggtgtg ccccccagca gcctacctgg atggcaatgg  66420
ggacaatctt gttggccagg ttcttataca gcaagcagat gggagcggcc aggaactgga  66480
```

-continued gtgtgcaggg gtctgttttg ttggcatcga tgccatccag cagctcaaag tccacgatga 66540
aaatgttccc ttgctgcagg aggcagagag atgtgtccaa atcaggctca gcagacggac 66600
caaaaatcag gcctggggaa agagtgatga cctctgggca cccctctccc tttcctgcga 66660
ctcagcggag ctcagaatgt gtacttctct cctctgactc caaggctgat tgattcacat 66720
ggaaggtgtt cacaggttgt ggcagttcgg ggtaagatga aggaatggca gcagctcatt 66780
cggcatttgt ggtgtctgaa acctgcttga ctggcacgaa agatgagaga ccgacccgag 66840
tgtcagttta ctaagaagaa agaggttagg tgaaatagat gtgacgagtt aaatgccaat 66900
cttcaccacg gggctgaagg tccgnnnnnn nnnnnnnnnn nnnnnnnnnn nnnnnnnnnn 66960
nnnnnnnnnn nnnnnnnnnn nnnnnnnnnn nnnnnnnnnn nnnnnnnnnn nnnnnnnnnn 67020
nnnnggggtc ctcagggact gggcctcagc ccgccggtgg ttccacccta ggcttcccca 67080
agtcggtcaa gagccgggag cagctgtcgg agtacctgac cgtggtgatc ttcaccgcct 67140
ccgcccagca cgccgcggtc aacttcggcc aggtaggcag ggccgggccc gctgggcagg 67200
gctcccttct caaggccgct gcctcctccc ccgccccggt tctgcacgcg tactgcaccc 67260
tcggacagcc tcggggcctg gcacgggact tgcaggatgg attctgcccg ctcagccaag 67320
ggcgctggcc gcggggaaag aggatggacg gactgcaggg cccgctggag ttggggggca 67380
cggggaggac ggggcccagg gggcagctgg gcagcagggc ttcgggggtg cccacgcttg 67440
ctggcggtcg tctccgcagt acgactggtg ctcctggatc cccaatgcgc ccccaaccat 67500
gcgagccccg ccaccgactg ccaagggcgt ggtgaccatt gagcagatcg tggacacgct 67560
gcccgaccgc ggccgctcct gctggcatct gggtgcagtg tgggcgctga gccagttcca 67620
ggaaaacgag gtgaagctgg gcagggcggg gcacagcccc aggtcacccc aggttaagcg 67680
gttcctcagc ctcagggctt tgtgactcgg gccccaaggc tcacttggag caaaggaatc 67740
ctgacttcca aggctggaag ggcccagaag gctgcagccg ccaccaggtc ccccggcctc 67800
agcctggaca gagctcaggg tgtgcagggc aggagagcac acagcccagg ctttgctcac 67860
tgtcaccaga gggtcgtgtg tgacgccccc tccccccagc tattgacaaa gttcttgcac 67920
atgtgtttta ccctggtact ccagagggaa tgaccaagag tttcctgggt tccttccgga 67980
cacgtgcatc tcatttaacc taacaactga atccggtgtg tcttcgtgga tgcacccgct 68040
ttggggtagc tcagtactgc atagaatggc cggaccagtc caacctgctc cagactgctg 68100
ggtgtctgag ttgttcccgg ccaatgtgtt ggtccctcac tggacatcct tgtttttgtg 68160
gctttgcaca tgtgttcagt atgaccgcac acattcctag cagacaaatt ccttggtcaa 68220
agaatattga tactgaattg ccctccacaa actaaattca aaatcccatt atcaatagcc 68280
tatgtttctt ggacctttcc agctcagaag ctttgtgatc ttaatccaat acagtatttt 68340
tttaaaatga tatctagctc tgccccgcag acatctgtgt gagaatgcaa ataagcacag 68400
gaccccaaca gggcagccac cccttcaggc tccctggccc gctttctgcc ttcctgggct 68460
ggagaggcca gtgctggccc cagcgcccct gatgggaggt gagagtgctg cgcaggggtg 68520
gcccaagaca gcaggatacc atggctgcaa acaccagcag cccccagctt catctgcatc 68580
atctcgtaac cacttggcag caggcagtta ttttcccact tatccatgaa gccccagccc 68640
tggagccttc cttagagaag caggttggag gcgacgacac ttgccttccc gaggccctct 68700
tgtcaggcag cagagggtga atatggggag gtgaatagat gctccctcct tcatctccca 68760
aacggtggct ggccccttgg gatgagacag gcctgtcagt ttacacgggt agtggattga 68820

-continued

```
cctatgtgtg tgtccatgtc tgggccctca gctgttcctg ggcatgtacc cagaagagca  68880
ttttatcgag aagcctgtga aggaagccat ggcccgattc cgcaagaacc tcgaggccat  68940
tgtcagcgtg attgctgagc gcaacaagaa gaagcagctg ccatattact acttgtcccc  69000
agaccggatt ccgaacagtg tggccatctg agcacactgc cagtctcact gtgggaaggc  69060
cagctgcccc agccagatgg actccagcct gcctggcagg ctgtctggcc aggcctcttg  69120
gcagtcacat ctcttcctcc gaggccagta cctttccatt tattctttga tcttcaggga  69180
actgcataga ttgatcaaag tgtaaacacc atagggaccc attctacaca gagcaggact  69240
gcacagcgtc ctgtccacac ccagctcagc atttccacac caagcagcaa cagcaaatca  69300
cgaccactga tagatgtcta ttcttgttgg agacatggga tgattatttt ctgttctatt  69360
tgtgcttagt ccaattcctt gcacatagta ggtacccaat tcaattacta ttgaatgaat  69420
taagaattgg ttgccataaa aataaatcag ttcatttaaa atgggtcttg ttccatgtgt  69480
tatattccaa tcaccccaaa cagctcactg ccatctccca caccaagaga aaaaaaaagc  69540
catagtcacc gtgattttat caaggcaaaa gcctccccac ccaagtctgg atagaaggtg  69600
ctttttccct caagcagtgt ctactctctt tggaacacat cccaaatgtc accacctctg  69660
ggaaggcatc cttggttcct gtctctaccc tggatttgtc agaacctctg ttcttgcccc  69720
ctctgtggtc tctcccttgg gacaggagcc cctggaagga cagaaaaccc actttattta  69780
tgtctgtgcc ccagggctgg cataaggcac cagcactcag ctgttctctc cttttcctcc  69840
tggaagggca cctagctaat ggatattagg cattgtcttg ggagctgggg gcttattttt  69900
tcctgaggca gggttcttaa catgacataa aaaataaaaa tgggcagggc gcggtggctc  69960
acgcctgtaa tcccagcatt ttgggaggcc aaggtgggag gatcatttga ggtcagaatt  70020
caagaccagc ctggccaaca cggtgaaacc ccatctctac tgaaaataca aaaattagcc  70080
aggcatggta gcaggtacct gtaatcccag ctactcagga ggctgaggca ggaaaattgc  70140
atgaacctgg gagacagagg ttgcagagag tggatatcgc accactgcac tccagcctgg  70200
gcaatagagc gagactctgt ctcaaatagt taataaataa ataaattaaa ttaaataaaa  70260
acgcattctc tttccccagc cccaagtagc agagcccgct ctgagcctgg gcatggtgac  70320
ccattctcct cgtgctcaca tgcccaactc ccagccctcc agcccctggc ttcggaatca  70380
tgtcatcagg gtctcccatg tctctggaag gtgcttccag tgtggcaggc catcagctca  70440
gtgtctgggt aaaggcttct acagggccag catggcatag gggggaggtg tgcatgcgtt  70500
cctgaagcca caaggtcttc tgaggagacc tgactattgg ggtggggact agagactgag  70560
gtccagcccc ttaatgcccc agactccctg ccatccctcg gagaatttcc caccacactt  70620
atgaatgatc ttcgggacag gtgacataaa catacagcta tggtagaggc attcagctcc  70680
atgccactgt gagaatgaac ataccaactt ttaggcaaca aggccatgtg gtcaaggaga  70740
gaggagaaac gaataggagt aggcaggggt ggtgaagcag gtctgacatt ggcaaaagtg  70800
acagagaagg attgggttgg aagggcttca gatggcagag aacctctgaa aaagtctcat  70860
gccagctaat gaagagtcct caaagtcacc atcacagaaa tcttacatct ggcagaaatg  70920
acagcaatag tttggcatga accccacagt ggatccaaac gtgtggcagc tgagatcgtc  70980
agttaattat gttctctgca gctggtcctt ctggttccct ggagctgggt atctgagtag  71040
cacagctcca ctgctaccac aggagaggga gaatcccaaa ttctgtgcat agactgtcta  71100
aacctctgga tgacccctaa gacacatgta cataaggcaa actgcaaaca gcccaattta  71160
ggataaaaca gcctgtctta ctctgtttgt gctgctataa taaaatacct cagactgggt  71220
```

-continued

```
catttatata gaacagaaat tgattcctca cagttctgga ggctggaagt ctaagaggag  71280
gcactggcag tttcagtgtc tggtaaggga gggatcagtg tctgctccca agaggatgcc  71340
ctctgtgctg tgtcctcacc cagcagaaga gcaaaaaagg gcgaacattc tcaaaagcct  71400
cttttataag gacatcaatc cattcatgag ggcagaaccc tcaagaatta atcatttctc  71460
aaaaggcccc tcctcctaat gccatcacct tggggtttaa gttccaacac atgatttttg  71520
gaaggacaca tacattcaaa tcattgcaca accaaagtga tatttgaact ttcaaatagt  71580
ttgcagtttg agatcaacta agttaattgc ttgcttgaat aaaaacatca cagccgggca  71640
cgatggctca cgcctgtaat tccagcactt tgggaagcca aggtgggcag atcacttgag  71700
gtcaggagtt cgaaaccagc ctgaccaaca tggtgaaacc ccatttctac taaaaataca  71760
aaaattagcc aggcggccgg gcgtggtggc tcatgcctgt aatcccagct ctttgggagg  71820
ccgaggcggg tggatcacaa ggtcaggaga ttgagaccat cctggccaac acagtgaaac  71880
cctgtctcta ctaaaaatgc aaaaattagc tgttgagact actcgggaag ctgaggcagg  71940
agaattgctt gagccgagat cgtgccatcg cactccagcc tgggggacaa gagcaagact  72000
tcgtctcaaa aaaaaaaaaa gaaaagaaat tttctggatt aggataatgt tctatatttg  72060
gataagggtt taggttacct agatagatac atttatcaaa agtcatcaaa tggtacactt  72120
cagatgtacg catgtcactg tatgtaaata ttaccccaaa atcaacaaga accatgagca  72180
aatactgact tctagtgaac gacatgcata ctgaaacttt cgtagtgaag tataattatg  72240
gctgcagttg actctgaaat acataaaaac ctaagttgat gggtgaatac agtgattaat  72300
agatagaaat ctgtggtaaa gcatacggag aaaaatgtta attgtagatt ctagggttta  72360
tatatattct cactatataa ttaaacgttt ttatgtttaa aaatttttat aatgttgaaa  72420
aaccatgaaa tcctacctaa cgcagtaaga caagaaaaag agataaaagg tatatgtact  72480
gggaagtaag aaataaaacc gtctttgtta gcagatgaca tgctcatcta tgtagaaaat  72540
ccaaaagaat ggataaagaa actcctggaa ctaataagtg gttacagtaa ggttgtagga  72600
tacaaggtta atatacaaaa gtcaatcact ctcttattca ccagtaatga acaagtggaa  72660
attgaaattc aaaacaaaat actatttaca ttaatactcc aaaaatacat acttaggttt  72720
aaatctaata aaatacatac aagatcttta tgaggaaaac tgcaaccctg atgacagaaa  72780
tcaaagagaa actaaagaaa tagacataag taaatattcc ccagaaagac tcaatattgt  72840
caagatgtca gttcttcaaa acttgaccta tagattcaat gcaatcctaa tcaaaatctc  72900
agcaagttat gttgtggata ctgacaaact tattcttttt tttttttttt ttttttttga  72960
gacggagttt cgctctgttg cccaggctgg agtgcagtgg cgcgatctcg actcactgca  73020
agctccgcct cccgggttca cgccattctc ctgcctcagc ctcccatgta gctgggacta  73080
caggcacgcg ccaccatgcc cggctaattt ttgtattttt agtagagacg ggtttcacc   73140
gtgttagcca ggatggtctc gatctcctga cctcgtgatc cacccgtctc ggcctcccaa  73200
agtgctggga ttacaggcgt gagccaccgc gcccggccaa cttattctaa aatttagata  73260
gggaagcaaa agacccagaa cagctaacac aacaatatag taggaaaaca acaaatttgg  73320
aaaatggata ctacccaact ccaagactta ctataaagct acagtaatca agatagtgcc  73380
gtattggtga aagaatagac aaatagatca atggaacaga atagagagcc taagaaatag  73440
accttcataa atacagtcaa ctcatccttg acaaagtagc atagacacta caatggagca  73500
aagattgtct tttcaacaag tggtgcagga acaactggat atccacatgc aaaaacaaac  73560
```

-continued aaacaagcat gaatctagat acagacctta tgctcttcac aaaaattaac tcaaaatgga 73620
ttatagatct aaatgtaaaa ttcaaaacta taaaattccc ataacatagg ataaaatcta 73680
gatgacctag gtatggctat gacttttttag acataacacc aaagccatgg tccatgaaag 73740
aaataattgg taagttggac ttaattaaaa ttaaaacctt ccgctctgca aaagaccaca 73800
ctaggagagg gaggaaatat ttacaaagac acatctgata aagaattgtt acttaaatta 73860
tacaaagcct tcttaaactt aacagtaagg aaacaatctg attgaaaaat gggccaaaga 73920
ctttaacaaa caaaagaaga tatacaaatg gcaagtaagt atgtgaaaag aagctgcaca 73980
gctggggggc gtggtggctc acgcctttaa tcccagcact ttgggaggtc aaggcgggca 74040
gatcacctga ggtcaagaga ccagcctgtc caacatggaa aaacctgtct ctactaaaaa 74100
tataaaatta gctaggcatg gtgatgcatg cctgtcatcc cagctacttg ggaagctgag 74160
gcaggagaat cgcttgaacc cggaaggtgg aggttgcagt gagccaagat cgcgccattg 74220
cactccagcc tgggcaacaa gagtaaaact ctgtctcaag aaaaaaaaaa aaaagctgca 74280
cattctatgt tatcagggaa atgcaaattt agaataacgc aataacaaga taccactaca 74340
tacatattag aatggccaaa attgagaaca ctgacagcac caaatgtgga ggaggatgtg 74400
gagcaacagg aactagagag aatgcaaaat ggtatagcca cttaggaaga cagcttggca 74460
gtttcttaca aaactaaata tactcttacc acacaatcca gcaatcacac tccttggtat 74520
ttacttacat cccaacaaaa accctcatat ggatgtctag agcagctttg ttcataattg 74580
tcaaaacttg gaagcaacca aagatgccct tcggtaggtg agtaaataaa taatatccag 74640
acaatggaaa taccattcag tactaaagag aaatgagcta tcaagccatg aaaaggcgtg 74700
gaagaaactg aagtgtgtat cactaaaagt caatctgaaa agggtgcata agtttccaaa 74760
gatatgatat tgcagaaaag gcaaaactgt ggagacagta aaaagattgc caggggctag 74820
ggcagtggga gggatgaata ggcagggcac agaggatttt cagggcaata acactactct 74880
gtatgacact ataatgttgg atacatggcc agatccacag aatgtagaac accaagagtg 74940
aaccttgaac tatggacttt gagtgatgag gatgagtcag tgtaggctca tggattgtaa 75000
taaatgcacc actgtggggg gggggggata ttgataactg gggggctgta catgtgtagg 75060
gacaggagta aatgggaaat ctctactttt gttaccggtg gagggtgtac cgcattttga 75120
acaaaaaatt ggacaaaacg cacaaagcaa ggaaagaatg aagcaacaaa agcagagatt 75180
tattgaaaac gaaagtacac tccacagggt gggagcaggc ctaagcaggt ggctcaaggg 75240
cctgaataca gatttttctg ggtttaaat accctctaga ggtttccatt ggttacttgg 75300
tgtataccct acgcaaatga agaggatgaa gggaggttac aaagttattt acttggtgta 75360
gaaaattagg gtttttccct tttatttagt tgtaggaagc ccttaggtta cctgcctcca 75420
gaccctattc tcctgcctca ttttattcct aattttgttg tgaacctaaa attgctctaa 75480
aaaatgaaat cttttaaaca agaaaataaa cttataaatt gcaaatatgt gtcacttaca 75540
taaaaacaaa gaattagtgt ccctacatca ggaaaaaaac acctataatt caatgtaaaa 75600
atgcaaaaaa gccaagagaa atggccaagc catggaaatt cacagaagta gaaataggca 75660
gtaaataaac aatgctcaat ttcatttatc tgagaaatgg agagtaaaac ttcagtgaca 75720
tacaaaggag taacaatcat tttaggaaca attttaaaaa taacacttgt gatgtggctc 75780
aggaaagatt catattctca ctgtaggaag gtaagtgaat cattttagag gtcagttttg 75840
caacttagaa gatcaaatgc atctaccctt tttctacttc tagaaatgta tcttcagaag 75900
tgcccctccc tccctcacac acccccaagt gtacaaaaat aaatgacatg gatgtggact 75960

-continued

```
gcagccttgt ttctaatacc aaaaatcagt aaacaaccta aaaatctgta tccatgagga  76020
tttaaagaaa tcctgcatga gttagaaaga ataaggtaga tgcctgggtt ctaacataga  76080
aaatatcaaa ctggttgtta gatgaaaaaa gcaagttgca aagtgaggta atgtgtaaat  76140
gcagtaagca aaatacatca tatatatagt actttctatg tatttaccta tatgagcgtg  76200
atgcctccaa ctgcatagct gtggctccgg gagcaggacc ttgtaacaga gcctctgccc  76260
ctgactgtcc tgaggggcct ttccctggga aaggaaccag gtttgatttt cagtctcttt  76320
tgttatcacc atgctgacag ctttgcttgt catatgcctt tccctccgct gtactgattt  76380
taccttacag aagctctcct tagtgcttca tcagacactc cctcttttcc aaagaaaaga  76440
cagccgcatt ccatggtcat ctggttgagc tcgaggtgag ccccagggat catgtgcctc  76500
ccaccaggct gacaccccag tggtgaggag ttgccccttg gctttttcga ggccaagcaa  76560
ctcagaggtg tggcaggatt gcatgtcaca gtggcacttc caaggccctg gagagtgact  76620
caacgcctct gttattaaga tgtcacacag gctgtgcagc aacaactcta gggacaccct  76680
tcacactgac agagttggca agcttttcct ataaaggggc acacagtgaa tactgtaggc  76740
tttgtaggcc atactatctg tcccaacaat tcaactttgc ccactgtagc tgtgaatcaa  76800
ccgtagataa tattaagtga atgtgcactg ctgtttgcta atagtttatt gacaaaaaca  76860
gctgcttttg agcagtttgc taccccgaca gagactgtgg ggagtccctg gtggcagcga  76920
gctacaggca gccagtaccc catcagtgtg gctggttcca tcctctcaag cctgcctgca  76980
cccagacact gtcgagtgtg tcttcagaaa aactcctaaa attccccaaa agcacagtgg  77040
ctccccgaga gccacctccc tcaccttctt acaggggcag gttcctcttc cggttccacc  77100
ctcctcagca cggagctcag gggccatccc cacctcctct tggccgcaag cacagacctt  77160
cccacacagg ctcagcagct ctgcgggcct gtccccccacc tggagctgca ggcctccact  77220
cctggggaca gctgtgacca tggctctgca aagcagcctt gtgcctagct cccaagtcag  77280
ctggcagccc agagtggaac aattctgtgg atcacctctg agacagcagc acatctgggc  77340
aagcctggct tcccacccct cacctcctgc aacctctgac ccttgccatg catgtggtag  77400
ggaagctgca accaggcctc agcactccca gacctgtggg cggtttgctg tctgaggatc  77460
gtggcactgc cttccctcag aggccttgcc agagccaggg gatgcagcgt ggcagagctg  77520
tcactggcaa ccctgctggt ctccctggtg ctttctcagc tgggctgtgg gtcaggacaa  77580
atttctatgg ataaggctgg atcataatct agtgctccat ggtcatgcag cgacagactc  77640
gagtctgcct tctctcaggg tggtgagctc aggtaggaac gggatgtttg aagcaagcac  77700
acctgtgaga aatgcctgtt ttcactccca tcccacacac tcgtccagac actgccagcc  77760
cacccccgac acacgtgtct gagggaggct gaggaaaaca gacacctcca ggagccgcat  77820
actatttcct gatgtgtaag ccagacaacc ctggaaagga ggtcagggaa ccggagtgcc  77880
tgccaacgtc cccagcctcc ctgcagcaaa acactctcat ggcaaaactc ctttttaaag  77940
aaaggcttta ttgctgcaat tagacatccc agtgtatagc acaaaccccc ctgtacagag  78000
aattattcaa gtggtaatac tgagaaacag tgaacacaca caaaagaata caaaactaga  78060
catttagatc actagaaact ttctaaggta agaaaaattt caaatgtgaa gtgcctttta  78120
gaaactacac cacacatgcc agtgtaaatt tggtttaaca atcaatttct ataaacattg  78180
catctaactg tgcactgatc aactgcacaa cttcaacaat tacttccaag acaaagataa  78240
atgcttttat ttccctatgt tttggtcttt ccttgggcta gagacagaag ctgcatgttt  78300
```

-continued

```
caaaccagat tcaaaaggga aagcacttca aaacagaaag tacttcaatt gtgtatttgc  78360
cttcagccac atccagagac ttgtggatct cacccggttg gtcccagccc ttctccaacc  78420
ctgaagccca cagcaggggt gcagaggcag ccccagatcg tgcagacatc acccgaggct  78480
cccaaactgg cccagctgcc tgaggcctgc atgcctgtgg ccaggtagga cacatgtgca  78540
ggtttgaaaa ctaggcctac aagactgaag agtggactga agcaaaaagg ggagaaacat  78600
tagaggccta cagtaggaag agacctttta tagagttttc aggaaattct cacaataaac  78660
ttgggcacaa agaccaaatt gctgaggcca gaagcctgct tatggtactg tgacttatgg  78720
ggagtagagg ccaaatcaga gagggctggc tggtgatacc ccagaccact tgcctcttcc  78780
ccttccctgg cctacaaata ccaggcctcc tggccctgag acctcattct gggtttctat  78840
atgggtcaac caaatgccat cctttcacta aacccaggtg caaaatgggg ggggaagggg  78900
ggaagctggg gagtacacag cacccaaaag aaccgagaga gcaagttttc caaggctaca  78960
ggaacattgg cagagctggt ggccacacca gatgggagta ccacatcccc accaggcttc  79020
atgcttcact gctagatgca gggggctaga agggtctgat gaatcaggag ctgaactaga  79080
accttcaaga aaagaaaagg caagggggtg gctctgtgcc ccgccaggag aggaaagaag  79140
aatgtgtgtg gattgtccac agtgaggcca gaaacgatga gatggtgtta ggcagaaaag  79200
aagggagagg gcttcccatg agaatctggc tgggcatggg agggatacag ggctcagtta  79260
tcaaggcacc tttgccatag tggggtgcca gctacattgg gtgggatgcc caggggctgt  79320
ccctacctaa gcactttctt gtctacagga agtcttggtg cttttcaagt tcagcataag  79380
gggttccata tgtgaagtgg ggattcacac ttagaaaatc tatcctggtc ttcacctgaa  79440
acactcatct actgctgggt ggcaggaaca agtatacaaa accaggggcc ttgcctgggc  79500
agttcctaag ggacattggc agggctgacc tgggattcag ctcccctgag tggacagtct  79560
gtggttgcct ggggtcccca ggctgagaag gggtatgggt aattgcactt cggggcacag  79620
tgaacacagg cacgggctgg atgtgccctg ggagacagaa aggagaggct gacctattct  79680
caggagctgg ctatggctgg acagtgcctg cccggccaga ggaaggccac agcagagcca  79740
ctccacagac taagacctgt gttgccaagg aatcagacac tggcttggag gagacaggag  79800
gacaaagcct gctgctatta agcccacacc gtagcttaga gatccttcag cctcctggcc  79860
ttcaaaacaa actccagggc ttccactctg aaaggcaaag gaatcacctc gtgtttgctt  79920
catcccctta gcaggatgaa cgaaacgcct aaggcccaaa aagactgagg gcaggacccc  79980
cagcatctcc catctcctcc gtgcaggctg ggtgagagaa tggcctggaa aggaagcatc  80040
tgcgctacat tgtgcttcag gcccccccag caactttccc ggaggtaact atttgcctgg  80100
aaaactagga aactgggttt taaaaacaga attttaagca gactttttag agggacaagg  80160
ccatttgatg gtagtgattt tggttttgtt ttatgaaaat ggtacaggtg gtaatccctg  80220
atgacagaat gcactgagag tggggccaag ggccctgaag gatcctgtct gttcagtctg  80280
gttaaggcga cagctgggcg ggcatgtggc cggggagcag tggcacagcg gaccctggca  80340
gtttgctcac acctggccct cgtcccagag ccagcccacc tgcctcttgg ccctggtagt  80400
gactccacag aacttccccg agcagaagcc tcacagtggg ccagcaccca tcttgcatgc  80460
aagggagaac ctgcatgcag tgcacacacc ccggccaggg tggcacatgg ctgctctttc  80520
aatgtgaagc caacaccaac tggagagatt taactataaa ggaatatttt ttaaatattc  80580
agttttgttg tcattactca cttcctttcc ttccatttcg atctcagaaa ctgttctttt  80640
tcagtgttga caaaaaagaa atgtatgggc caggtctaca aagtaacacc ttgtcataaa  80700
```

-continued

```
acaggctcaa aagcatagga atcatgcttt aattgccatt tagcatccac taattcccat  80760
gagatctgtg attaaaaaaa aagcctctgg cctgcttgtc ctgtcttaaa agtcatgagt  80820
ctgttttatg aacagaaaga atgccacgct tcttagcata tgtaaggcaa aatggatttt  80880
tgatctctca tgatgtaaag gagatacaaa ggtaaggaag ggaagatttc taagtgagac  80940
tttttttgag tgtcaatccc gctggacaca catattacaa aataaagatt ttcttctgta  81000
aagtgctgtt tgctcagtga atcatgcgcc accacagagc accatggctc cacctgctca  81060
agagcatgga ggaggcagca tcggcagagg gcaggcagga gtctgtgttt gggggtctgt  81120
ttcaatacca tctcctgggg ttcgccgtga tgcagaggga atcttctcgt catggctaga  81180
cactccccaa tgctctgctc caggctgggg accactgcaa gctggaggcg gctgggtatc  81240
agggcctggg cacccctgct cctcctcttc ccttgggatt ggcattttat tctctcattc  81300
agctcaagac catgggcagg aactctgctg gctccccatg atgtcatcat ggggtcttcc  81360
actttcccac agagctgcca ggcagaggca ggacccaggc atgcctggcc cacaggaagg  81420
ttttctagga gactaaggag ggtttagaaa aagagaagcc actataaata gtcacctgtc  81480
cagtctatgc tattaaagga cataagaaag gtatacaatt ggcagtaaac aatttccttc  81540
agctcttcat ggatgtccag gaaaatgaca acccgcacac aatcagacgt gaatgatttc  81600
tgctccagtg tcttcaggct ctgtgcaaca agaagagttt gtgtcggaat gacagattcc  81660
atatccatgt ttattttcaa agttgggctc tgttagtgga gatttttcaa aaatattctt  81720
tttgcttgtt tctggacagt tttgaacata gatcactcta ttataggcct tgagtctctt  81780
ccacaattgc acatacactt tacactgaac atacataaaa agaagtcctc cggtgaagcc  81840
gatggccaca accaccaatt tagtccaaaa gggccattct aggattcctg gaagggaaaa  81900
actcagccta ttagatttta tttaagatat gtcttcacca cggggctgaa gnnnnnnnnn  81960
nnnnnnnnnn nnnnnnnnnn nnnnnnnnnn nnnnnnnnnn nnnnnnnnnn nnnnnnnnnn  82020
nnnnnnnnnn nnnnnnnnnn nnnnnnnnnn nggcggtgac tgtgacattg aggttcggcg  82080
tcgggggaga gggaaaagga gagggagagg gagagggaga gggagaggga gagggagagg  82140
gagagccata tgtagtttaa agtagttttt ttccaattct gagaagaagg tcattggtag  82200
cttgatgggg atggcaatga ctctataaat taccttgggc agtatggcta ttttcacgat  82260
attgattctt cctacccatg agcatggaat gttcttccat ttgtttgtat cctcttttat  82320
ttccttgagc agtggtttat atttctcctt gaagaggtcc ttcacatccc ttgtaagttg  82380
gattcctagg tattttattc tctttgaagc aattgtgaat gggagttcac tcatgatttg  82440
gctctctgtt tgtctgttat tggtgtataa gaatgcttgt gatttttaca cattgatttt  82500
gtatactgag actctgctga agttgcctat cagcttaagg agattttggg ctgagacgat  82560
ggggttttct aggtatacaa tcatgtcatc tgcagacagg gacaatttga cttcctcttt  82620
tcctaatcga atgcccttta tttccttctc ttgcctgatt gccctggcta gaacttccaa  82680
cactatgttg aataggagtg gtgagagagg gcatccctgt cttgtgccag ttttcaaagg  82740
gaatgcttcc agtttttgcc catgatgtat gatattggct gtgggtttgt catagatagc  82800
tcttattatt ttgagataca tctcatcaat acctaattta ttgagagttt ttagcatgaa  82860
gcgttgctga attttgtcaa aggccttttc tgcatctatt gaaataatca tgtggttttt  82920
gtcattggtt ctgtttgtat actgggttac atttattgat ttgtgtacgt tgaaccagcc  82980
cttgcatccc agggatgaag cccacttgat catggtggat aagctttttg atgtgctgct  83040
```

-continued

```
ggattcgttt gccagtattt attgaggatt tttgcatcga tgttcatcaa ggatattggt  83100
ctaaaatggg ttttttgttg ggtctctgcc cagctttggt ctcaggatga tgcctcccct  83160
attaaaagag ggagggagga ttccctcttt ttctattgat tggaatagtt tcagaaggaa  83220
tggtaccagc tcctccttgt acctctggta gaattcggct gtgaatcctt caggtcctgg  83280
actgtttttg gttggtaagg tattaattgt tgcctcaatt tcagagcctg ttattggtct  83340
attcagagat tcatcttctt cctggtttag tcttgggagg gtgtatgtat ggaggaattt  83400
ttccatttct tctagatttt ctagtttatt tgcatagagg tgtttataat attctctgat  83460
ggtagtttat atttctgtgg gatcagtggc gatatcccct ttatcatttt ttattgcatc  83520
tatttgattc ttctgtcttt tcttctttat tagtcttgct agcggtctat caattttgtt  83580
gatcttttca aaaaaccagc tcctggattc attgattttc tgaagggttt tttgtgtctc  83640
tatttccttc agttctgctc tgatcttagt tatttcttgc cttctgctag cttttgaatg  83700
tgtttgctct tgcttctcta tttcttttca ttgtgatgtt agggtgtcaa ttttagatct  83760
ttcctgcttt ctcatgcggg catttagtgc tataaatttc cttctacata ttgctttgaa  83820
tatgtcccag agattctggt atgttgtgtg tttgttctca ttggtttcaa agaatatctt  83880
tgtttctgcc ttcatttcat tatgtaccca gtagtcattc aggagcaggt tgttcagttt  83940
ccatgtagtt gagtggtttt gagtgagttt cttagtcctg agttctagtt tgattgcact  84000
gtggtctgag agatagtttg ttacaatttc tgttctttta catttgctga ggagagcttt  84060
acttccaact atgtggtcaa ttttggaata ggtgtggtgt ggtgctaaaa aaaatgtata  84120
ttctgttgat ttggggtgga gagttctgta gatgtctatt aggtccgctt ggtgcagagc  84180
tgagttcaat tcctgggtat ccttgttaac tttctgtctc gttgatctgt ctaatgttga  84240
cagtggggtg ttaaagtctc ccattattat tgtgtgggtg tctaattctc tttgtagatc  84300
tctaaggact tgctttatga atctgggtgc ccctgtactg ggtgcatgta tgtttagtat  84360
agttagctct tcttgttgaa ttgatccctt taccattgtg taatggcctt ctttgtctct  84420
tttgatcttt gttggtttaa agtctgtttt atcagagact aggattgcaa cccctgcctt  84480
tgttttccat ttgcttggta gatcttcctc catcccttta ttttgaacct atgtgtgtct  84540
ctgcatgtga gatgggtttc ctgaatacag cacactgatg ggtcttgact ctttatccag  84600
ttttccagtc tgtgtctttt aactggaaca tttagcccat ttacttttaa ggttaatatt  84660
gttatgtgtg aatttgatcc tgtcattatg atgttagctg gttattttgc tagttagttg  84720
atgcagtttc ttcctagcat cgatggtctt tacaatgtgg catgtttttg tggtggctgg  84780
tatgggttgc ccctttccat gtttagtgct tccttcagga gctcttttag ggcaggcctg  84840
gtggtgacaa aatctctcag catttgcttg tctgtaaagg attttatgtc tccttcattt  84900
atgaagctta gtttggttgg atatgaaatt ctgggttgaa aattcttttc tttaagaatg  84960
ttgaatattg gccctcactc tcttctggct tgtagagttt ctgccaagac atgagctgtt  85020
agtctgatgg gcttcccttt gtgggtaacc tgacctttct ctctggctgc tctcaacatt  85080
ttttccttga tttcaacttt ggtgaatctg acaattatgt gtcttggagt tgctcctctc  85140
gaggagtatc tttgtggcat tctctgtagt tcctgaattt gaatgttggg ctgccttgct  85200
agattgggga agttctcctg gataatatcc tgcagagtgt tttccaactt ggttccattc  85260
tccccgtctc tttcaggtac accaattaga tgtagatttg gtcttttcac atagtcccat  85320
gtttcttgga ggctttgttc attttttttt tctttttct ctaaacttct cttcatgctt  85380
catttcattg atttgatttt ccatccccaa taccctttct tccagttgat tgaatcagct  85440
```

-continued

```
actgaggctt gtgcattcat catgtagttc tcatgccatg gttttctgct ccatcaggtc  85500
atttaaggac ttctctgcat tggttattct agttagccat tcatctaatt ttttttcaag  85560
gtttttaact gctttgccat gggttcggac ttcctccttt agctcagagt agtttgatca  85620
tctgaagcct tcttctctca actcgtcaaa gtcattctcc atccaggttt gttctgttgc  85680
tggtgaggag ccgtgttcct ttggaggagg agaggcactc tgatttttag agcttccagt  85740
ttttctgctc tgtttgttcc tcatctttgt ggttttatct acctttggtc tttgatgatg  85800
gtgacgtaca gatggggttt tggtgtggat gtcctttctg tttgttagtt ttccttctag  85860
aattcaggac cctcagctgc aggtctgttg gagtttactg gaggtccact ccagaccctg  85920
tttgcctggg tatcagcagc agaggctgca gaacagtgga tattggtgaa cagcaaatgt  85980
tgctgcctga tcattcctct ggaagttttg tctgagagga gtacccagcc gtgtgaggtg  86040
tcagtctgcc cctactaggg ggtgcctccc agttaggcta ttcgggggtc agggacccac  86100
ttgaggaggc agtctgccca ttctcagatg tcaagctgtg tgctgggaga accacttctt  86160
tcttcaaagc tgtcagacag ggacatttaa gtctgcagtg gttattgctg tcttttgttt  86220
gtctgtgccc tgcccctgga ggtggagtgt acagaggcat gcaggcctcc ttgagctgtg  86280
gtgggctcca gccagttcaa gcttcccggc tgctttgttt acctactcaa gcctgggcaa  86340
tggcgggcac ccctccccca gcctcgctgc cgccttacag tttggtctca gactgctgtg  86400
ctagcaaaga gtgaggctct gtgggtgtag aaccctccaa gctatgtgtg ggatataatc  86460
tcctggtgtg ctgtttatta agcccattgg aaaagcacaa tattaggca ggagtgaccc  86520
aattttccag gtgccatctg tgaatgcttt ctttgactag gaaagggaat tccctgacct  86580
cttgcccttc ccaggtgagg tgatccctca ccctgctttg ggtcacgcat ggtgtgctac  86640
acccactgtc ctgcaaccac tgtctggcac tccccagtta gatgaacccg gtacctcagt  86700
tggaaatgtg gaaatcacct gtcttttgca tcgctcatgc tgggagctgt agactggaac  86760
tgttcctatt cagccatctt ggctccacgt atatccactg ccacacttct ttagtcataa  86820
agtgagtgcc ttggtcagag gcaatgctgt gtggaatacc atgatggtgg ataaggcatt  86880
ctgtgagtcc atgaatggta gtcttggcag agcattgtgt tcagtttagg caaacccata  86940
tccagagtaa gtgtctgttt cagtgaggac aaacctctgc ccttttcagg atggaagagg  87000
tccagtataa ccaaccttcc accaggtaac agactgatca ccccgaggaa tggtgccata  87060
ttgagggctc agtgttagtc tctgctgctg tcaaattggg cactcagctg tagccatagc  87120
caggccagtt ttggtgagtg gaagtccatg ttgctgagcc catgtataac ctccatccct  87180
gccaccatgg ccactttgtt tatgggccca ttgggtgata acaggggtgg ctggggaaag  87240
aggctgagtg atgtccacag aacaggtcat cttatccact tgattattaa aatcctcctc  87300
tgctgagatc acccattggt gagcactcac atgggatcca aatatcttca caggttttgg  87360
ccactcagag aggtccatcc acatacctct tccccaaatt tctttgtcac caattttcca  87420
atcatgcttc ttccaagtcc ctgaccatcc agccaaacca ttggctacag cccatgaatc  87480
aatatataat cgcacatctg gccatttatc cttccatgaa aagtgcacaa ccaggtgcac  87540
tgcttgaagt tctgcccact gggaagattt cccttcacca ctgcccttca gtgatgtcct  87600
agaaaggggc tgtagtgctg cagctgtcca cttttgggtg gtgcctgcat atcgtgcaga  87660
accatctgtg aaccaggccc tagtcttctc ttcctctgtc aactgatcat agagaactcc  87720
ccatgaggcc atcggtgcag gctggggaag agaaggtggg gtggcagttg tggagaccat  87780
```

-continued

```
gggcatttga gctacttcct tgtgtaactt acttgtgcct ttaggacctg ctcgagccca  87840
atcacatata tatcacttcc atttgatgat ggaatgctgc tgtgcatgac ccattttatg  87900
gctacatggg tcagaaagca cccagttcat gatagacagt tcagttcaca tggtgacttg  87960
atgacccata atcaaatgtt cagtttccac caaagctcag taacaggcca agagctgtct  88020
ttcaaaagca cagtagttat atgcagaaaa tggcagggcc ttgtttcaaa attttagagg  88080
catctgctgt gattcacctg tgggggcctg ccaaaggctc caaacagcat ccctatctgc  88140
cactgatgcc tcaagcacca ttggatctgc tgagtcatat ggcccaaaca gcagagcagg  88200
ttggacagca gcctggacct gaggcagagc cttatcctgt tctggacccc actcaaaact  88260
ggcagccttt tgagtcactc gataaatggg cctgagtaac acacccaaat gaggaaagtg  88320
ttacctccaa aatccaagta ggcccactac atattgtgcc tttttcttag ttgtaggagg  88380
ggccaaatgc agcaacttat ccttcatctt acaaggagta tcttgacagg ccccacacca  88440
gtggacccct agaaatgtta ctgaggtaga aggtccctga attttagtca aatttatttc  88500
tcatcctctg gcacacaaac atctcacaaa taagtccagt gtgtttgcta cttcttgctc  88560
actggatccg atcagcataa tgtcatcaat gtaatggacc agtgtgatat cttgcagaag  88620
caaaaagtgg tcaagatctc tccaaataag attatgatgc aaagccagag tttatatact  88680
cttgaggtag gagagtaaag atatattgct agtcttgcca gctgaaggca aattgcttct  88740
agtgggcctt atgaatagga atggagaaaa aggcatttgc caagtcaatg gctgcatacc  88800
aggtaccagg aaatgtgtta atttgctcaa gcaatgaaac cgtatctggt acagcagctg  88860
caattggagt caccacttag ttaagcttat gataatccac tgtcattctc caagatccat  88920
ctgtcttatg cacatgccaa atgggagagt tgaatggggg tgtgatgaaa atcaccaccc  88980
ttgcgccttt caagtccttg atcatggcac taatctctgc aatccctcca gggatgtgat  89040
attgtttttg atttaccatt tttctaggta gaggcagctc taatgccttc catttggcct  89100
ttcccaccat aataggcctc accctaccag tcagggagcc aatgtgggtg ttcttccagc  89160
tgctaagtat gtctatgcca attatgcatt ctggcactgg ggaaatgaac acaggatgag  89220
cctggggacc cattggaccc actgtaagtc agacctgagc taaaactcca ttaattacct  89280
cacctccata agctcctgct ttaactggag gaccacaatg acgttttgag tcccttagaa  89340
ttaacgtcag ctcagagcta gtgtcctgta atcccccaaa tgactgataa tttccctttc  89400
cccaatgcac agttaccttg ataaaaggct ggaggtctcc ttgggaaaaa atgggagaaa  89460
gattaacagc ataaattgtt ggtagtgtag tgggctcctt ccttaatggg acccaacttc  89520
ccctttattc aaggggttct gtgtctgtaa actggctcaa gtcaaaaatt gattgagggg  89580
ccatgattct ctatttttat aattcaaagt agtgttttgt ccatttgacc tggaagtttt  89640
ctgcttatat aaattaagta ggaaagaagt aggcatccta acaatttcac ttctgggaac  89700
actgtgatta attagcgaat gccagaactc tacatgagtc agactattct gattgctgct  89760
ttgccactac tgtctgttat ggtagttatg cccaccttgc ctttgatggt tgagtgccac  89820
cacttggcct ctgccacctt gggatccaat tattcccatt gtatttacct ttattagttg  89880
agtgactgtg gttctcacca ttggatctga tatgcagaga attacggggc tcttcaaaga  89940
tgcaggtgct accctcacag atctattttg caaggtattg gtcaagggta tatcttctgg  90000
gcccttccat ctgggatgag taggtctaaa gtgactaatc cactccacca tctcaatctc  90060
tctaagcctt tggatccctt cctctacatt aaaccaagag tgatcagaca tttccagctc  90120
cctcacagtg gccatctttc aatccatatt tcagctaact aagcaaataa attattagaa  90180
```

-continued

```
cctttttta actccctgag ctgcaatatt aaatgcagag tctctactta gtgggcccaa  90240
atcaacaaat tcagcctgat ccaactctat gttccttcca ccattatccc acacccttaa  90300
tatccattct catgcctgtt ctccagattt ctgtttatat aaattagaaa actcaagtag  90360
ttcttttcaa gtatagtgaa cctcctcatg ggtttcactc tcaacctcac ctcttggggc  90420
ccataaggac tttagtctgg ttataggtct agaagcagac aggggtgttg ggggtggctc  90480
ctgaggagaa tcaacattat tttgcctggc aactgctcag ggggggccat cactgttgcc  90540
ttaggcagca cagtgtttat ctccccagac aaatatggaa aggctgatgg cagcatgggt  90600
cagggagagg atgtcaccac tactggggat ggggaagctg tttttttttct ggcaaaaaag  90660
gtttcctgag actttacaaa ctcagtgtcc ccagcttcat cagggtcctc ccacatgtcc  90720
cctttccaag ttgcagggtc ccattctttt ccaaacgatg ccctcacttt aatagtacat  90780
acctggtgag gctgtgcatg caccccttcat tggaagtcag ccacttgcac aataagagct  90840
catatccatt ttcccacaat ttcagctctt tctctgcagg agataatact ttcactcagg  90900
gcaatcttag cagatttgag gctcagtatc tgcttctgaa gccaggagtt agaatcccta  90960
agttcatttt ctttcatcac tttgtccatt gaacttagga gaaaccaacc aacttcatta  91020
tgtttccaca tatggtcaaa ggtattattt atagagtcac taaactcctt gcctctcatg  91080
agcgctgaat caggaatgtc aaatgcattt attttgctta actctctaaa cagttcatag  91140
aaaggaacac tgaatcagtg ttctccatac tatcagaagt agagtcctta gcatttttga  91200
gtctaatcat attaaacagc cactccagaa accctaaaac caatgaaaga actgcatcct  91260
taatgttctg ttcctctaga accactcctg gtacaaaaat ctgtgttagg gttctctaga  91320
ggggcagaac taataggata gagatatata agaaggaaag tttattaagt attaactcac  91380
atgatcacaa ggtcccacaa taggatatct gcaagctgag gaacaaggag agccagtcca  91440
agtcctaaac tgaagaactt cgagtctgat gttcaagggc agggagcatc cagtaccaga  91500
gaaagatgta ggctgggaag ctaggccagt ttagtctttt catgtttttc tgccaacttt  91560
tcatattcta gctgcactgg cagctgatta gatggtgccc acccaggtta agcgtgggtc  91620
tgcctttccc agcccactga ctcaaatgtt aatctccttt ggcaacacct tcacagacac  91680
acctaggatc aatactttgc atccttcaat ccaatcaagt tgacactcag tattaaccat  91740
cacagaagca ttatctacta ataccaccat ataaaagatg cggatgttag catagttatc  91800
acactgtttc ctcacacaat ccactaccca tggcttggtt tctatggaca tattattgga  91860
tctgagccag cttattataa tgttttaaat aatattcaag aattgttaca attgcatttt  91920
gaattgttat tatttaaata taggtcaatt tctaaataga ttcttgtcca tagtcagatt  91980
ttacatcatg atttcctcac tcatgacatt taaaagttta tttgttaaat ttagccaata  92040
tatacaagtc tgcatttggg gatgggtaat tgaatgccat ttttaatttt tgggtaatgg  92100
agactttttt tatgttgcct ttatatttga tccataacta ggctatgtag tacatttctg  92160
ggtcaaatct ctattgcttt aaaactttgt ggttttgctt cattatctcc tagtatctac  92220
agttactgaa gtgatacgta caaccagctt tggacatgat gaatgtttta ggctaaagac  92280
ttgggtgttc tttggtcttt ggaagttttc tttaatactc tctttaaatt tgtctgattc  92340
cacttcttgg ttccctttc aggaacacca agtattcaca cagtggatag tcatctgtcc  92400
tctacttcta aaattttgtt atttaacaaa atgttataaa agtagaatca catttatgta  92460
acctttttgg attgatgttt tttgctcagc ataatttcct ggcaatccat ccaagttgtt  92520
```

-continued gcatgcatca atcatccatt cctttacatt gctaagtagt attccatgct atgtatttac 92580
aacagtttgt ttacccattc acctgttgaa aaacatcttg gctgaatcta gttcttagct 92640
attaatatta taaacaaaga tgctataaac atttgtttga cagttttttg tgtgaagttt 92700
ttatttttct gggataaatg cctgggagtg caattgctgg gtcatatgat agttgtgtgt 92760
ttttctttga gaaactccca aaatttccca gagtggatga agtattttat gtttctatca 92820
gtaatgtatc agtgatccgg tttctacaca tccttaccag catttggtgg tgtcatgatt 92880
tttaatttta gccattctga tagatgagta gtgatagctt attgttgttt caatttgcat 92940
ttccctaaaa cctaataatt ttgaacatct tttcatgtga ttatttgctg tccatgaaat 93000
atctgtggaa acagtgagta gaaggatgct ttccacagtc tgagaaggac agctgggaga 93060
ggtggatgaa gagaggttgg tatatgggta caaaaaataca attaagacct ctggtccatg 93120
ctgggcacag tggctcatgc ctgcaatccc agcactttgg gaggccaaag cgggtggatc 93180
acctgaggtc aggagcttaa gaccagcttg gccaacatgg tgaaaccctg tctctactga 93240
acatacaaaa attagccggg catggtggtg cgtgcctgta atcccagcta ctcaggaggc 93300
tgaggtggga gaatcactta aacccgggag gcgaagtttg cagtaagccg aggtcacacc 93360
actgcactcc agcctgggca acagagcact ccagccgggg caacagagca agactctgtc 93420
tcaaaaaaat aaaataaaat aaagtaaaac aaaataaaga gttccaatcc agcagagagt 93480
gtggtgagat ggtgcgggac cagctccctg ggacttctga gcctttgccc tggccagtgg 93540
gggagctgag ccaggatagg ctgtagcctc tgccccgtga caccaggacc cttgtggtgg 93600
ctgccaccag gacccttggg gtgggtgcct gggccttgaa gatgcagcaa gcctcccttc 93660
cccctacacc tcagtgactg agggtggtgg tggcctttcc caggccgcac cctgccgggt 93720
atagacgaag tccccactga gcctggatgc agtgcctttg ggtggtggtg ggagtggcag 93780
gggcagcttg gtgactatcc gggtgtgagg attgggaagg tgctcttggg atgcaggaca 93840
cgggctcagc cacctcttta ggccatggcg ctgccagatc cgggtcctgg tgaccactct 93900
gtcccagctg ggtgagactt acctagtcct gaggacaaca gacaatggcc ttaataggcc 93960
tggaaggtga gtggaggcac agaggaggac agtgtggaac agttagcagg cattgggctg 94020
ttggtcttcc ttctaccaga cctggaagga cctcacattt ggcctatggg aaatgcccgc 94080
cacactttgg gaagatttac tatctgcttc tagaaggctg tgtgtatatt atgaaaaagc 94140
tattctcaac tcacccccaa ccttttaata gataacatct gtggggaggc tgacaagatg 94200
gctgaataga aacagctcag gtgtgcagct cacagtgaga tcaatgcaga aggtgggtga 94260
tttctgcatt tccaactgag gtacccggct catctcattt ggactggtta gacagtgggt 94320
gcagcccatg gagggtgaac tgaggcaggg tggggtgttg cctcacctgg gaagtgcaag 94380
gggtcagaaa actcccctgt tagccaaggg aagctgtaag gagctgtgcc atgaggagtg 94440
gtgcattcca gcccagatac tatgcttttc ccatggtctt tgcaacccac agaccaggag 94500
attccctcca gtgcttatgc caccagggtc ttgggtttca agcacaaaac tgggtggcca 94560
tttgggtaga caccaaggta gctgcaggag tcttttttca taccccaggg atgcctggaa 94620
tgtcagcgag acagaaccat tcactcccct ggaaaggggg ccgaagccag ggaaccaggt 94680
ggtctagctc agtggatccc acccccatgg agcccagcaa gctaagatcc actggcttga 94740
aattcttgct gccagcacag tagtctgaag ttgacctggg atgctggagc ttggtatggg 94800
gaggggcgtc tgccattact gaggcttgag taggcagtgt tcctctcaca gtgtaaacaa 94860
aactgcaagg aagttccaac tgggtggaac acaccacagc gctgccaggc tgctgtagca 94920

-continued

```
agactgcctc tctagattcc tcctgtctgg gcagggcatc tctgaaaaaa aggcagaagc  94980
cccagtcagg gacttataga taaaactccc atctctctgg gacagagcac ctgggggaag  95040
gggcagctgt gggtgcagct tcagcagatt ttaacatccc tgcctgccag ctctgaagag  95100
agcagtggat ctcccagcac agtgtttgag cagactgcca cctcaagtgg gtccctgacc  95160
ccctggcctc ctgaccggga gataccttcc agaagaagcc aacagacacc tcacacaaga  95220
gagctccagc tggcatctgg caggtgcccc tctgggacaa agctttcaga ggaaggaaca  95280
ggcagcaatc tttgctgttc tgcagcctcc actggtgata cccaggcaaa caaggtctga  95340
agtagatgtc cagcacactc cagcagacct gcagcagaga ggcctgactg ttagaagaaa  95400
aactaacaaa cagaaaggaa tagcatcaac atcaacaaaa aggacatcca ctcagaaacc  95460
ccatccaaag gtcaccaaca tcaaacacaa aaggtaggta aatccatgaa gatggggaga  95520
aaccagcaca aaaaggctga aaattccaaa aaccagaatg cctcttcttc tccaaaaaat  95580
cacaacttct caccatcaag ggaacaaaac tggatggaga atgaatttga tgaattggca  95640
gaagtaggct tcaaaggtgg ataataacaa actcctctga gctaaaggag aatgttctaa  95700
cccaacgcaa ggaagcaaag aaacttgaaa aaagattaga tgaattgcta actagaataa  95760
cgagtttaga gaagaacata aatgacctga tggagctgaa aaacacagca caagaactta  95820
gtgaagcata cacacatatc aatagctgaa tcgatcaagt ggaagaaagg atatcagaga  95880
ttgaagatca acttgcagaa accctataag ccagaagaga ctaggggcca atattcaaca  95940
ttcttaaaga aaagaatttt caatgctgaa tttcatatcc agccaaacta agcttcataa  96000
gtgaaggaga aataaaattc tttacagaca agcaaatgtg agacattttg tcgtcaccac  96060
gcctgcatta caagagctcc tgaagggagc aataagcatg gaaaggaaaa aatggtgcca  96120
gccactgcaa aaacatgcca aatggtaaag accatcaacg ctatgaagaa actgcatcaa  96180
gtaatgggca aaataaccag ctagcatcat aatgatagga tcaaatttac acataacata  96240
ttaaccttaa atgtaaatgg gctaaatgcc ccaattaaaa gacacagact ggcaacatgg  96300
ataaagagtc aagacccatc agtgtgcagt attcaggaga cccatctcac atgcaaaaac  96360
acacataggc ccaaaataaa gggatggagg aatatttacc aagcaaatgg aaagcaaaaa  96420
acaaacaaac aaacaaacaa acaaacaaac aggggttgca atcatagtct ctgataaaac  96480
agactttaaa ccaacaaaga tcaaaagaga aaaagaaagc cattacatag tggctaagaa  96540
gagctaacta tcctaaatat acatgcaccc aatacaggag cacccagatt cataaggcaa  96600
gttcttaaac acctacaagg agacttagac tcccacacaa taatagtggg agattttaat  96660
accccactgt caatatcaga caggtcaatg agacagaaaa ttaacaagga tatctaggaa  96720
ttgaactcag ctccagacta agcagaccta atagacatct atagaactct ccacccccaaa  96780
tcaacagaat atacattctt ctcagcacca catcgcactt attctaaaat tgaccacata  96840
attggaagta aaacactcct cagcaaatgc agaagaatgg aaatcataac aaacagtctc  96900
tcacaccaca gcgcaattaa attagaattc agaattaaga aactcactca aaacctcaca  96960
cttacatgga aactgaacaa cctgctcctg aatgactgct ggataaataa tgaaatgaag  97020
aaggataaag atgttgtttg aaaacaataa gaataatgta ccagaaactc tgggacatat  97080
ttaaagcagt gtgtagagga aaatttatag cagtaattgc ctacaaaaga acacaggaaa  97140
gatctaaaat cgacacccta acatcacaat taaaagaact agagaagcaa gagcaaacaa  97200
attcaaaagc tagcagaaaa caagagataa ctaagatcag ggcagaactg aaagagatag  97260
```

-continued

```
agacatgaaa aaccccttaaa aatcaattaa tcgctctccc tctccctctc cctctccctc  97320
tccgtctccc tctccgtctc cctctcccca cggtctccct ctccctctct ttccacggtc  97380
tccctctgat gccgagccga agctggactg tactgctgcc atctcggctc actgcaacct  97440
ccctgcctga ttctcctgcc tcagcctgcc gagtgcctgc gattgcaggt gcgcgccgcc  97500
acgcctgact ggtttctct gcccggccag ccgccccgtc cgggagggag gtaggaggtc  97560
agcccccgc ccggccagcc gccccatccg ggaggtgagg ggtgcctctg cccggccgcc  97620
cctactggga agtgaggagc ccctctgccc agccaccacc ccgtctggga ggtgtaccca  97680
acagctcatt gagaaggggc catgatgaca atggcggttt tgtggaatag aaaggggga  97740
aaggtgggga aaagattgag aaatcggatg gttgccgtgt ctgtgtagaa agaagtagac  97800
atgggagact tttcattttg ttctgtacta agaaaaattc ttctgccgtg ggatcctgtg  97860
gatctgtgac cttaccccca accctgtgct ctctgaaaca tgtgctgtgt ccactcatgg  97920
ttaaatggat taagggtggt gcaagatgtg ctttgttaaa cagatgcttg aaggcagcat  97980
gctccttaag agtcatcacc actccctaat ctcaagtacc cagggacaca aacactgcgg  98040
aaggcagcag ggtcctctgc ttgggaaaac cagagacctt tgttcacttg tttatctgct  98100
gaccctccct ccattattgt cctatgaccc tgccaaatcc ccctctgcga gaaacaccca  98160
agaatgatca ataaaaaaat aaataaataa aaataaaaat aaaataaaat aaaataaaaa  98220
aagaaataaa cacaaataaa atgttaaaat tcccattcta cataaaatca tctatagatg  98280
tttttaaata tacaacatga ttatcaagga cttaatctgt accacattct tgtagatgta  98340
aagttaaaat tcttgtaacc atcactctca accctaccct atcttccagc ataaatgaga  98400
ctttcacatg ttttctcttg cccagatgga gacactaact gtaggctttg gaaatgtctt  98460
aaaaaaaaaa aaaaaaaaaa gagagccagg catcttcaaa cagagaaaag ctgtttgaac  98520
acatttatct aagtctatca aaagctatga ttgttagcaa gaggtaacct tgtaatgcca  98580
aggcagaaaa ctgccaccaa accacaaaaa gcttgttcaa ctgctgaacc taaaattaaa  98640
caatttatct ctcattaaaa aaaaaaaatc aattaatcca ggagctggtt tttttttaaa  98700
gatcaacaaa atagatagac cactagccag actaataaag aggaaaagag agaagagtca  98760
aatagacata ataaaaaatg ataaaggaga tatcaccact gatcccacag aaatacaacc  98820
taccatcaga gaatattata aacacctcta tgcaaataaa ccagaaaatc tagaagaaat  98880
ggataaattc ctggacacat acaccctccc aagactaaac caggaagaag tcaaatccct  98940
gaataagcca ataacaaact ctgaaattga ggtggtaatt aatagcctac caaccaaaaa  99000
aagtccagga ccagacggat tcacagctga attctaccag aggtacaaaa ggagctggta  99060
ccattccttc tgaaactatt ccaaacaata gaaaaagaga gaatctccct aactcatttt  99120
acgaggccag catcatcctg ataccaaagc ctggcagaga cacaacaaaa aaagaaaatt  99180
tcaggccgaa atccctaatg aatattgatg caaaaatcct cagtaaaatt ctggcaaacc  99240
gaatccagca gcacatcaaa aagcttatcc accatgatca agttggcttc atccctggga  99300
tgcaaggctg gttcaacata tgcaaattaa tgaacgtaat gcatcacata aacagaacca  99360
atgacaaaaa ccatgtgatt atctcaatag atgcagaaaa gaccttcgac aaaattcaac  99420
agcccttcac gctaaaaact ctcaataaac tagatattca tggaacatgt ctcaaaacaa  99480
tcagagctat ttatgagaaa cccacagcag ccaatatcat actgaatggg caaaaactgg  99540
aagcattccc tttgaaaact ggcataagac aaggatgccc tctctcacca ctcctattca  99600
acatagtatt gggagttctg gccagggcaa tcaggcaaca gaaagaaatg aaggatattc  99660
```

-continued

```
aattaggaaa agaggaagtc aaattgtctc tgtttgcaga tgacatgact gtatatttag  99720
aaaaccccat catctcagcc caaaatctcc ttaagctgat aagcaacttc agcaaagtct  99780
tgggatacaa aatcaatgtg caaaaatcac aagcattcct atacaccaat aacagacaaa  99840
ccgagagcca aatcacgagt gaactcccat tcacagttgc tgcaaagaga ataaaatact  99900
taggaatcca acttacaagg gatgtgaagg acctcttcaa ggagaactac aaatcactgc  99960
tcaatgacat cagagaggac acaaacaaat ggaaaaacat tccatgctca tggataggaa 100020
gaatcaatat cgtgaaaatg gccataatat ccaaagtaat ttatagattg aatgctatcc 100080
ccatcaagct accactgact ttcttcacag aattggaaaa aactacttta aatttcatat 100140
agaaccaaaa aagagcctgc atagccaagc caatcttaag caaaaataac aaagctggag 100200
gcatcacact acctgacttt aaactatact acatggctgc agtaaccaaa acagcatggt 100260
actagtacca aaacagatat atagaccaat ggaacagaac agaggcctca gaaataacac 100320
cacacatcta caactatctg atctttgaca aacctgacaa aaacaagcaa tggggaaagg 100380
attctctact taataaatgg cattgggaaa actggttagc catatgcaga aagctgaaac 100440
tagatccctt ccttccactg tatacaaaaa ttaactcaag atgggctaaa gacttaaatg 100500
taagacctaa aaccataaaa accctaaaag aaaacatagg taataccatt caggacatag 100560
gcatgggcaa agacttcatg actaaaacac aaaaagcaat ggcaacaaaa gccaaaattg 100620
acaaatggga tctaattaaa ctaaggagct tctgcacagc gaaagtaact accatcagag 100680
tgaacaggca accaacagaa tgggagaaca tttttgcaat ctatccatct aacaaagggc 100740
taatatccag aatctacaaa gaacttaaac aaatttacaa gaaaaaacaa acaattccat 100800
caaaaagtgg gtgaaggata agaaaagact cttctcaaaa gaagacattt atgcagtcaa 100860
caagcatagg aaaaaaagct catcatcact ggtcattaga gaagtgcaaa tcaaaaacac 100920
aatgagatac catttcatgc cagttagaat ggccatcatt aaaaagtcaa gaaacaacag 100980
atactagaga gcatgtggag aaataggacc acttttacac tgttggtggg agtggaaatt 101040
agttcaacca ttgtggaaga cagtgtggta ttcctcatct tcaccacggg gtggaggtac 101100
gnnnnnnnnn nnnnnnnnnn nnnnnnnnnn nnnnnnnnnn nnnnnnnnnn nnnnnnnnnn 101160
nnnnnnnnnn nnnnnnnnnn nnnnnnnnnn nnnnnnnnnn nagaaacata gaccctgccc 101220
aacgcatatt cctgaaaggg atggcaaggt ttttttaaag gttttatggg tttaggtgta 101280
ctctaaagga ttttaaccct tctaaaatta tttttgtata aaggtgtaag aaagggatcc 101340
aacttcactc ttttacaaat gggaagccag tttttcccgg cccctttttt taaaaaggat 101400
tccctttccc attggttgtt tttttcaagg ttgtcaaaga tcagaaggtt gtagatgtgg 101460
gttggtaatt tttaggggtt tgttttggtc ccattggtcc ataggtcggt tgtggtacca 101520
gggccatgtt gttttggtta ctgtaagcct cgtagtatgg tttgaagtca ggtagcatga 101580
tgcctccagc tctgttcttt tggcttagga ttgtcttggc aatgcgggct ctttttttggg 101640
ttccatatga actttaaagt agtttttccc aattctgtgc agaaagtcat tggtagtttg 101700
atggggatgg cattgatcta taaattacct tgggagtatg gccattttca tgatattgat 101760
tcttcctatc catgagcatg gaatgttctt ccatttgttt gtgtcctctt ttattttgtt 101820
gagcagtggt ttgtagttct ccttgaagag gtccttcaca tcccttgtaa gttggattcc 101880
taggtatttt attctctttg aagcaattgt gaatgggagt tcactcatga tttggctgtc 101940
tgtctgttat tggtatataa gaatgcttgt gatttttgca cattgatttt gtatcctgag 102000
```

-continued

```
actttgctga agttccttat cagcttaagg agattttggg ctgagacgat ggggttttct 102060
agatataaaa tcatgtcatc tacaaacagg gacaatttga cttcctcttt tcctaattga 102120
ataccettta tttccttctc ctgcctgatt gccctggcca gaacttccaa cactatgttg 102180
aataggagtg gtgagagagg gcatccctgt cttgtgccag ttttcaaagg gaatgcttcc 102240
agtttttgct ccttcagtat gatattggct gtgggtctgt cataaatagc tcttattatt 102300
ttgagataca tcccatcaat acctaattta ttgagagttt tcagcatgaa tggttgttga 102360
attttgtcaa aggccttttc tgcatctatt gagataatca tgtgtttttt gtcattggtt 102420
ctgtttatat gctagattac atttattgat ttgcgtatgt tgaaccagcc ttccatccca 102480
gggatgaagc ccacttgatc atggtggata agctttctga tgtactgctg gattcggttt 102540
gccagtattt tattgaggat tttcgcattg atgttcatca gggatattgg tctaaaattc 102600
tctttgtttg ttgtgtgtct gccaggcttt ggtatcggga tgatgctggc ctcatataat 102660
gagttaggga ggattccctc tttttctatt gattggaata gtttcgccaa actgacatga 102720
tttttaaaat tccctatagg gtcaatgtgc agatttaaag atccctacac tcagtagtcc 102780
tgggataggg tcgggggatc catatgttta acaagcagcc tagagtctcc cgatagcctg 102840
ggcaagcttt aaaaagccct gcggacattc ggatgaaaca aaggtgcaca gaacctatat 102900
ctctgccatt tattagctgg gggccttagg caaggaaggt agtcaacctc cgtattcctc 102960
agttcctcaa ctgtaaaatg gggatgatga ctgtggctcc ctcgtggggt tgtgacggag 103020
gaacagggga catatgtcct gggatcagca ctggcaattt ggccattctt accatagcac 103080
ctgccatctt ggtgacagcc tggacacaaa gccttcacac ctttgaagtg gccatagaga 103140
gcatgagata tggatgggga ggaggcattc caactaaaga cccctgcttt gggccaaaaa 103200
cacatgtatg tctggtgtct ggagtcctct ggttatgcct tttttaagat accggttgtc 103260
ctgcaattgt gcgttgagaa tccactctat ggccaacata tcatcaaagc gtttggctca 103320
gctaggctgt tcccccaacc caaggacccc atgaggaaag gagtgagggt tccaccccca 103380
gcaccagcca ctggaggggc tgcccagagt ccctcagttc tcgtaaactt acgctttgga 103440
gtaattcaga acaaagtcca ctcctttttc actatcaaac tggatatcac ggggtaaatc 103500
cttgtggcat ttggcatcga tgctcaaggg gaagccaggg ttccactcca tccatctgag 103560
catgagaaag gagaagaaat tgagttaaat gccagccttt ggtctgcccc ctcagctgag 103620
ggccgcccac actgtcagac gatgttacac agggagattg atgtactcaa aataaagtca 103680
acacatcata ggctgaccct gtgtccagta aggttctggg acctcttcca aagtccagtc 103740
gcaccaactt tgctgtgccc tgagcatcag agtgggaacc ctgagactgg gcttatagtg 103800
gtacaggtgt gcaccactgc ataaaaagtt ctgtaggtag tctagggaga cctcacttac 103860
tagaggtgac attgaacagt agaggcctgc cttgccagtc actggaggta gaaggtatta 103920
aggctgccca gccacgccca acctggacat ccaccattct gccaacttga tcagtgtgtg 103980
ccctggactg cgtgcatgtc ctgcatgtgg catttgggga aatgggacag ttcttctgcc 104040
ttcacaatag gacgacacgg cagcaggtgg cctgggagag ggacccaggc acagatggct 104100
aaaaggcttc cctctctcac ctgctggcca atagcagctt tagagattat tacaatcaaa 104160
acagcttccc caaagacaag ccacggactg catccagtaa acatgctcag atcctgacat 104220
ccttgaaacg tatcccgtgg cattgggcat ttgtgttttt gaaaaatgtt tattttgctt 104280
ttttgtttac ttattgagta aacttaaatt gtgaaaatgt cagaggtgtt tgaaccacag 104340
caactccatc ttgaataggg gctgggtaaa ataaggctga gacctactgg gcagcattcc 104400
```

-continued caggaggtta ggcattctaa gtcacaggat gagacaggac attgatgcaa gatacagggc 104460
agaaagacct tgctgataaa atgggttgtg gtaaagaagc cggccaaaac ccaacaaaac 104520
taagatggtg atgaaagtga cctctgttca tcctcaccac tcattatatg ctaattataa 104580
tgcattagca tgctaaaaga aactcccacc agtgccatga cagtttacaa atgccatagt 104640
aatgtcagga agttacccta tatggtctaa aaaagggagg aaccttcagt tcctggaatt 104700
gcccacccct ctcctggaaa actcatgaat aatccactca ttgtttagca catgatcacg 104760
aagtgactgt aagtatgctc agtcgagtag cccatgctac tgccttgcct atggagtagc 104820
ctttctttat tgctttactt tcctaataaa cttgctttca ctttatggat tcaccctgaa 104880
ttctttcctg tggaggtcca agaactctct cttggggtct ggatcaggac ccctttctgg 104940
taacaaaaac aaaatgaaat cctgttagtt tctttgggga gggagaatga ttttgtgttt 105000
gtttaaaaac cagattttac attttagggt tttagctttt tcatttatat tcctaattct 105060
ccttcctttt aaaattttct tttgagagga aagtaaaata tcgagatttt gggtcttaaa 105120
aaagtcctga gttattttaa tatgatcttg tgctttgact ttccccaaat cccaactgtc 105180
acagtgtcct cttggcccag tagcctctcc ttaggatcac aagaagtgaa cagggaccgg 105240
gtatgatcct tctgacagca aaggcatttt gtcaagtgtt ttctgttatg tggcacctta 105300
catttctcac tgttggttta tttagaatat tctacgtcct cagattttaa gaaaaccttc 105360
catttttgct gtttgtatta atgccaatga tagtatatta acaaggataa aaatgtggac 105420
aagtctacac atttttgtt tgtttgtttt ggaaaatgac tcaaggcatc tccaatatat 105480
atctaaaatt gagccattca gtagcctcac tggtagtaat gatcaattaa ttagctatca 105540
ttagtcatat caatttaaat attactgatg attttctctt tgcctggaca gttcaagggc 105600
tctagttaat tttaaaagct cagtggagct agatgttttt cagtatgtaa acaatgagcc 105660
atgcaagggc atctgtgcca gcaaatggca ttaatgtttt cttaagtgaa tagtccactt 105720
ggacggatgt ggaatacttc ttcagcacca aaaagacctt cttgccccat gccctgccct 105780
ggtctatgga gggtggcagc accaatgggc agaaatgccc cacttgtgtg gttagaagat 105840
gatggcctca cagcacatgg agacaggaca gcttgcttgc tagttcacta ctgccccccct 105900
gaaaccaaat gtttatgtcc cttccactgc aggtcactgc tgcttaagag accctgacag 105960
gctgacctgc acaggagccg aaggcctgca tggccacaga cattaactgg tggagatgga 106020
atcccactcc attgaggaag accaagtgga acacccaggc agaaggaaca aagaagtaga 106080
aaggcattta atttattgga aaaaaaatga gagagagaga gaaagagaga gagagaaagc 106140
aagagagaca gagagacaga gagagagaga gagagaaaga gagagagaga aagcaagaga 106200
gacagagaga cagagagaga gagagagaga gagagacaga cagacagaga gatcctaagg 106260
ggatgcagtt agtataattg gagtgtaaaa agactttctg taaccacaaa catgatttct 106320
gaatgaagac ttcaatagag aaacagacaa agagaataat cactgtgaga tgtttggtct 106380
cttgtattaa aagaaaagct ttagacaaat taaatttagc agtttaattg agcaaagaac 106440
aattcaagaa tagggcagcc cctaaaccag agcaggctcc gagtgacttt gatgctgtct 106500
catagttgga taggatttat gggcagaaaa aggaacgtga tgtacagaaa atggaagtga 106560
ggtacagaaa cagccagatt ggtgatggct cagcatttgc cttacttgag cccagtttga 106620
acagctggcc actgtgagtg gctgaagtct ggccgctgtg attggctgag acttggttac 106680
ttgctatgag agtaggtgac agtctgttta cacatccagt taggttacag ttcactatgt 106740

-continued acagagaaac ttttaggctg aatttaaaat atgtaaggag aaaagtttaa gctaaactca 106800
ttaacaccta gaagagagaa ggtgttcatt cgacaactaa ttatggagca cctactatgt 106860
gccaggaagt gctttgtgca aaatagaaga acatgtaacc caaatacagg gtgaaactac 106920
aaagaaatgg aagccataaa tgaaactatg agagacataa accaaaaata aaattctaag 106980
cccctgaact gactgatgga ccctcccctt ggccaagggc attccaaagt taacctgaaa 107040
aattagttca ggccatgata ggaatgggtg gctaaacgtg cctcattgta ctctcctcct 107100
cttggaattc aggcacaact gatcagcatt cacatcaaca cagagatgtt aagcccatta 107160
gaacagactc tttaagattg ataagaaaca tttacaattg attctacctg aagcctgcta 107220
cctggaggct tcatctgcat gataaaaaac tttgtttcca caaccccta tcttaaccta 107280 gacattccaa gtttttagat aataattctt ttaagcagtt gccaatcaga aactctttga 107340
atctgcctat gacctggaag ctcccctccc ccaagttgtc ccacctttcc aaaaccaaac 107400
cactgtccat cttacatgta ttgactgatg tcttatgtct ccctaaaatg cacaaaagca 107460
agctgtaccc caaccacctt gggtgcatgt tctcaggatc tcctggggct gcatcatggg 107520
ccactggtca ctcatatttg gctcagaata agtcttttca aatatttcac agagtgtgac 107580
tcttttcatt aacagacatg aaagccagat acagatgtaa tatgcaagga gtaaaagctc 107640
caaaaggaga gagagtaata tatggagaag tgaaaaaaat caaagaaata aaagaagaac 107700
tcctttaagc tgaaaaatac ttcaatatct taagtctgtg aaaggaaatt aaattttagg 107760
accccaaact catttagcca aagggaaatg tcaagctggg aactgtgtca tgcaaacctg 107820
cctccccctt ttggttccta aataagatgg ctatgatgaa aagctacatg tctccaccat 107880
attttgctca caaggaaatt cctagtgaac cgttaaaatt tcaccatggc aatgcaaatt 107940
gatagcttat ctttacaagt gcagtcaccc accagataca aatgcatatc tgattgttcc 108000
cctgccttac tttatctatg ttctcttatg taaaatgcag actccctgca tttttcctct 108060
gcctcatttg tttatgtcat cttatgttaa aaaaaatgca gattcactga gccagagaaa 108120
ggcatgaata actatttttc cctgccctgc tcttacatga aaattgtgta cttctcaata 108180
tcccgccctt ttccctttaa atttggagcc ctcaaaatca ccttcagaga aaggcatagt 108240
gctgtctccc gggcatgcgt ccttaacttt cgcaaataaa tttcctaaaa tgattgagac 108300
ttgtctcgtc atttttctca atgacaagtc ctaggtgggg gggaaaaaaa aaaaggaaaa 108360
agatacacct aggtatatac tgaatacatt ttaaaatgtc caagagacag gagaaacaga 108420
gacagagaga aggaaagaga tgcagagagt gaacgagaga ggaagaaagt gggggaggga 108480
gggagataga aactctagga aaagaaacaa actatcatta gatttctcct ctgtcattct 108540
gaaaatggga agactgaagt gtatacacac ttttttaga tcgtcatcta agcctctcat 108600
attgtcatca atgagggcag gggaatttgt ttgaggggat gggtaggggg acaggacgac 108660
aagcacagac tcagatctta cactacacat ggaccttctg aggaaattaa ttgaacaagt 108720
tcagctgaac aaaaattaaa ttagaatgaa tcaataaact cctaaataca gcaaagaata 108780
tgcattataa aactacagca aatataatag taaacaaaga aacaaaaata tgagagggat 108840
gttcatcact actaccacta cttgttttgg gaattccaga catggaataa gaaaagaata 108900
tcagtggtgt agataatgga aagtaagaga caaaattatt aacatttaga taatatgagc 108960
acattaacta accagactca ctaacaacaa acaaacaaaa acaagtgatt agaaccaatg 109020
aaagaattca gtaagggacc aacacacagt aaatgtaaga aacaagtaat ttacatttat 109080
cccagcaata tttttgcaaa cagaaaaata tcctactcag aacagcaaat gctaaatgta 109140

-continued gagtagctag aaaggtgaag gacctgcatg aagaaaacta gaaattctat ggaagtacgt 109200
tgacacagga tctagagagg tggaaagaca cgctgtgttc ctggatggaa agactgaatc 109260
tcagtaaaat gccaacacat aacacagtta tgtgaagttc aaagtaattc tcattatgaa 109320
aaacttaaga aagaacagtg agatatgtaa cagacattaa catttattag aaagttatga 109380
taaccaaaag ctggtgctgg ggtctcgagt agaaaaatag gctaacacat aaagtgcgga 109440
aacagaccca gagactatgt atacataata caaaactcgc caacacttat ccagtgcttt 109500
ctatgtgcct actactattc tctgtgtttt catggtttaa cctattatct caaaccccta 109560
aaaggaaggc actgttattt ccctcatttt acagatgagg gaagtgaggc acagacagat 109620
taaacaactt tcacaggact ggagaaagtg ccagtaagtg tgagttgagc ccagacactc 109680
gaatccagag ctcatgactg ccatcctatg ccagcttgta ccgtgggtat catcatccct 109740
gtcatccaag tcaggaggaa agacatcatc cctgtcatcc aagtcaggaa cgaatgctac 109800
cgggagagtt ccacccaggt atgtatgaaa acacgtggca ggagtggggc atggtggcgc 109860
acgcctgtag ccccagctac ttgggaggct gacgtgggaa gatggattga gcctgggtta 109920
gtttgaggca gcagtgaacc atgatcatgc cactgcactc cagcctagga aacagagcaa 109980
gactctgtct caaaaaaaaa aaaaaaggta gatgaatgaa agctctaaac tcaaagggga 110040
aattataaaa gtattagaca aaattacggg ggaagtattt gtgtaacact gggatggaaa 110100
gggttttctt aagcaaagga ggaaacccaa aagttataga tgtaaacaat acatagttaa 110160
taaaataaag aactaaaatc tcctgtggca aaagcaacag aagacaaata ataaatgcta 110220
tacatatgta acaaacggat actatcctga tatagaaaga gctcctttag attaataatt 110280
gaaagaacaa tagggaaaaa aagcttataa ataggcaatg cagtgatgct tattagtggt 110340
caggggagtg cagactaaaa caaccacaag gtcttaggga tttttagact gtcaaacaag 110400
gtcatcgggt actgacaaat gtatggatgg gcaaaagtat cttttcatac acagctggta 110460
ggaccgcaaa ttacgataca attttgtgaa aggatttttg tcggtatttc ttaagatgaa 110520
aaaatgctga tttgttccag caatctgagt tctggaaatg gatctgccat taattaaagc 110580
accagtacat caagatgttt gtacaaggtt ggttctggca gcattgtttg tactgcaata 110640
cccaaaacaa acaaacacat ctacaaatgg gaaatgaact gaacgtcagt gaatagggga 110700
atggctaagt aaattatggt gcattcccag aaggcaagaa atagtagcag tttaagaagg 110760
ggaaaatata tgagatacta tttcacacgc aagaatgaaa acatctgaag atgcgaagtg 110820
ttgatgatgc agggaaacag tgaatctcag aaacagttac tggggtgtct actggcagaa 110880
tgcctttgga aaacaatcag caatatctag aaagcttaaa aacacgtggt ctgcaaccct 110940
gcaactctac ttcttggaat attccctaca gtaactcttc catgagagca cagagagatg 111000
tgtgagaaag ctcactgtcg cttggtttgc aacagctaga aattaaagac agcccgcctg 111060
cccatcagca ggagagcgga cgagcgcatg ggttattcag atactgatat gccatgaaga 111120
agttaactgc atgaaccaca tctatctgtg tcaaccagat cctcttcaat acttagtgat 111180
gagtgaaaag tgcaggtcac ataatgatta gattaaatta tatcgattaa caaacaccta 111240
cactttgcca tttactgctg tgtgtgagtg tgcatgtaac acagacagat gtggtcacag 111300
tgggagagca caagctgtgg gctatgacct gggtctgctt ctccttctcc ctgcgtggct 111360
gagtgagtaa ggagggcctg caagaagcgc cagctttctg acatagtgtg gactattctt 111420
agtcattgct ttacttccaa actctgatct ggaagcctga gaaatcttct gagaaagagg 111480

-continued aactccaaga ttgtgcagac agtgcaaagt tcagtgtttc ctgaacggaa gcaaaggagg 111540
gtttctgaaa aggacagatg agtggaagga ggaagaaaaa aatgattaaa tctaagaaag 111600
ggggaaacga tctcaccaga agccccctgc tgcaagatta tgataatgtt aagtagctcc 111660
cagataattg ggctagtttg tgttatctta gatgagtaga tagcaaagtc taattagagc 111720
cccactaatt catactaaag tgttagtggc ttataacaaa ttaaatgaat tttatgggca 111780
ttttatctta acccagattc acaggccaga agtgctctga gaactggctg caggggcttt 111840
gccataggtg tctgaaacag ggagggaagc caaggaagaa gcatagaaac aacagccctt 111900
tgggatggga ggcagagctc aagcacaacg tgtgcactgc accaggtatg gaagtctgga 111960
aacacatcat atggtgcctg agctgagagg cttgtgcaca aatactctaa aacaaatcac 112020
acatttataa accottaaca tgacccacag cacagcaggt tactctccca cacttgatgc 112080
taatggcatg taagttttat ttttgatttt tcaattggga aatagaatat ataaaatatg 112140
tatggatatg tatatatgca cacacacact cacacatgca gaaaaatgta caaaacacct 112200
gtacgaacac catccaggta aaaaatcaga acattgtccg taccctcacc cccacctttc 112260
ccaatcaacc ctccttccat ccccggtaat gaccatcctc ggctttatga taatcatttt 112320
cttgttattg tttaaggttc cgctatgaca cacctcccta aacaatttca ttccaaagtt 112380
atgaattggc cagacacgct cctggcttct ttccttcaac actgcgtcag tgaggtttgt 112440
ccatgttagc agcagtttgt tgattttcct tgcagtgtag aattttcctt gacaatttgt 112500
ctgttctact gtttgttgga cattgagttg ttgccatttt ttggccatca tgagtaatgc 112560
tgttgtgagt atccaggcgc acatgcacac aaatttggat cccactatag gatttctggg 112620
tcatagatta taatgtagct tcagttttat gacatattgc taaattgttt tccacggagg 112680
tcttaccaac ttgtcctcct gccggtggta tatgagtgtt cccagccctc tggatcttct 112740
ttaatactca ggtgttgtca gttgttgaag tgttgcccat ctgggggcat atgtgtggta 112800
gtagcagcag ttcactgtga tcttctgatt tccccgagtc ctaatgaagt tgaacacctt 112860
ttgtatactt gctgcttata ttttgtacag taagtactca aacttcttgc ccattttcta 112920
gtgaatgaca ctccccttct taaagatttg taggtccttc acatactagg aataattctc 112980
gtcaatcact ccatgacttg ccttcactct ctcctggtgt ctttcaatga acagagtgtc 113040
cttatcttga gggaggcaaa cttaccaatc ttttcctttg tgtttaatat gttctgagtc 113100
ttgtttgaaa aatcctttta gcttgagacc tggaagaata atcacctgta gtctaaatgt 113160
cttacagttt tgcctttaac ttttaagtct aatcaacccc aagctgagtc tcctgaatgg 113220
caagaggtgg agtctgattt cttctccttc tccttcagcc ctccgtgctg gctggcccct 113280
gtcctcgaga tgcatgtcca gtggcccagt gccacccatc agccgagccc tccgtagcag 113340
acccagtacc cacatacgtg tggctgtttg ttgtttcttt attctgtttc aaggaatgtt 113400
tttgatgaaa aggggggatga agctaagaca gttttgaggt ggggcaattg tgttcttggt 113460
gtgggatttc tcaccccttg acagcagtgg gtggctgggc atagggggaag aaggagctac 113520
agggttgagg gatgctgttg caacttagaa aaattaagaa aaatgaagat attgctcagt 113580
tatggcaagt gtttgatgaa acagggaccc atacatggct cgtgaaaact ggttaaagat 113640
tttttttttt tttttttttg agacggagtc tcgctctgtc gcccaggctg gagtgcagtg 113700
gtgcaatctc ggctcactgc aagctccgcc tcccaggttc acgccattct cttgcctcag 113760
cctcccgagc agctgggact acaggcgccc gccaccacgc ccggctaatt ttttgtattt 113820
tttagtagag acggggtttc accgtgttag ccaggatggt ctcgatctcc tgacctggtg 113880

-continued atccacccac ctcagcctcc caaatggtta aagatttttg aggagaaatt tgtcaatgta 113940
tactaataac ttttactatt tggtaatttc atatctgggc atctgtccta ggaaaatact 114000
taataatgta tacaaatttc acatacaagg gttttcactt tgcttataag aatacaaaaa 114060
ttagaaacct cctaaatgtc cagggaagct gggtgtttaa gtgaatgatg aggcatccat 114120
ccaatggaat agtacataga aactagaata atgtttatga tgagattttg aaaatatggg 114180
aaaatgattt ttgctacact gctaaagggc agcaaggagg atgcaaagtg gtatatatag 114240
cacaatccca aattttaaaa agtgaataag acaaagtgaa aacaattaaa catgaatttt 114300
tatgaaaaag ttcataaaat tcataattca tacagaaaat aggtattttt ctggctctat 114360
attattttcc ttcttttact tttttgagtt aaaaaaacaa cccagatata ctacatattc 114420
cttgtaagaa gttcaactat tgagggatat gtagaaaagt atcacaatat tggctcccaa 114480
aggcccctcc acagcccagg taacttcact gtccatgtag aatgattcct tccactttct 114540
tcccttggaa ggaggcacag actcaaatgt ttccaggggc caaagcagga aatgaaatga 114600
aagaaaacct tgatatagac aacagacaag tgtggactgg ggaagcctga agaatatctc 114660
tgtttactca taagtcaata atgatccatc aaacacttgt agaggctgga tacagcccat 114720
cagccaccca tttccagagg agcactctgt aatgtgttat tatcttccaa aaagctttac 114780
tgagatacat ttacatacca ttaaattcac cccttaaaaa tatgctatca aaagatttta 114840
atatatttgc agagttgtat gtgtaaccat cattataacc caattctgaa ataatctcat 114900
ccccagagga cacctcgaac ccattaacat tcactccttg tttcccctcc ccaactccta 114960
gtgctaggca actactcacc tactaacctg actctgtggg tttgcctatt ctggacattt 115020
catacagata gaatcacaca atatggggtc ttccgtaagt gagttttcca tttagcatat 115080
ttttgaagtt cattcagtgt ttggcatcta tctgtagttc atttcttttc ttttcttttc 115140
tttttttgaa atggagtctt gctctgtcac ccaggctgga gtgcagtggc gggatctagg 115200
ctcactgcaa cctccgcctc ccgggttcaa gtgattctcc tgccttagcc tcccaagcag 115260
ctgggattac aggcgtgcac caacatgccc ggctaatttt tgtatttttg tagacatggg 115320
gtttcaccat gttggccagg ttggtctcaa actcctgacc tcaagtgatc tgcccgtctc 115380
aacctcccaa agtgctagga ttacaggtgt gagcctccgc gcttggcatt cattcctttt 115440
tgatgccaaa aaatatccca ttgtatggat aaactatatt ttgtttattc attcctcagt 115500
taatggaatt taggttgttt ctactttttg actattgtga acaatggtgc tataaatatg 115560
tgtgtacaag ttttgtatag acatgtggtt tcaatattct tgggtagagg cctaggagta 115620
gaattgctgg gtcatattgt agctgggttt cagattttga ggaaccacta aactgttttc 115680
tgaagtggct gcatcatctt acattccggt agcagcatca gggttccagt ttctccacat 115740
ccttggcagc acttgttact atctgtcttt tttattctaa ccattttagt ggttagaatt 115800
gtatcttgtg gttttgattt gaaatttcct gatgattaat aatgttgagc atattttcac 115860
gtgcttattg gagattcaca aattttctct ggagaactat ttaattaaat cctttgctaa 115920
tttttaaacg gggtttttttg tacagaatat tttaaaattg agttgtcaga gttctttata 115980
tattctggat acaagtccct tatcagacat atgatttaga tattttctcc attctgtgga 116040
ttgtcttttc actttattga tgatgtcctt tgaagcatag atcttttaca ttttaatgac 116100
atctaacttg tctactttct tttgctgcct gtgctcttgg tgccatatct aagagacttt 116160
gccgaaccca agattatgaa gacttacttg tatgttttct tccaagagtg ttatgttgtt 116220

-continued agcccttact tttagatcta tcatccattt tgaattaatt tttaaattta tctagcagcg 116280
ttattgaaat ataatgcaca tactgtaaaa tttatccatt taaagtgttc aattcaagga 116340
tgtttagtat taatttttac acaatggaca accatcagtt ttagaacatt ttcatccccg 116400
gcaaaaggaa cactgtatcc tttagctgtc actcccatga ccacttcctc attccctgcc 116460
cctaggcaac cagtaatcta ctttatatct gtacagattt ttcttttcca gaaatttcat 116520
ataaaaggaa tcatacaata tatgatcttt tgtgactggt ttctttcact tagcataatg 116580
tttttgagat tcatccatgt tgtaacaagt gtcagtattt cattcttctt tcatggtcaa 116640
attatataga tatactatat tttatccatt catccattaa tggacgtttg ggttgtgtac 116700
actttttgat agttacaggt catgctgcta taatcatgca tgtacaagtt tttgtgtggg 116760
catatgtttc catttctgtt gggaatatgc ttaagagtgg aaatgctgtc atattgtaac 116820
tctctgttga acagtcagga gctagcagac tgtttcccaa gcagctgtgc cattttacat 116880
tcccaccagc agtgtatgag ggttctgatt tctccacatc cttgtcaaca cttgttcttg 116940
tcggattttt ttattctagc catcctagta tcaagtggta tctcattgtg gtgttgattt 117000
gcatttccta gatgactaat gggtccttgg agaaatatct attcagatcc tcactcattt 117060
ttttcatttt ttaattggac tatttgtctt tattgagttg taagagttct ttataaatta 117120
tggatggaag gcccttatca gatatacaat ttgtaaatat ttcttccatt ctgtggttca 117180
tcttttcact ttcttgatgg tgtcctttga aacataaagg tttgtaaatt tgatgacatc 117240
actttatcac tttatctatt tttcttttgt tgctgatgct tttggtgtca tatcaagagt 117300
cctttgtcaa atccaaagtc atgaaggttt actcctgtgt tttcttaaaa gagttttata 117360
gttttagctc ttacatttag gtaggtattt gactcatttt gtgttaattt atgtatatgg 117420
tgtgagctaa ggatccaact tcattctttt gcatgtggct atccagtttt gctaggacca 117480
tttgttgaaa agactattct ttctctgtta aactgtcttg ctgcttctgt caaaaattaa 117540
ttggccataa gtgtaagggc ttatttctgg actctcaagt ctatttcatt gatctatata 117600
tctatcctta tgccgatatc acattgtctt gaatactata gctgtgtagt aattttgata 117660
ttgagaagtg caagtcctcc atctttgttt tctttttatc aagattgttt tggctattct 117720
gggtcccttc catttccata tgaatttgca gaattgacag cttgtcaatt tctgcaaaga 117780
aatcagctag aattttgata agggttgtgt tgaacgtgta cattaatttg tggggtattg 117840
ccatttttaac aaaattaagt cctctgattc atgaacatga aatgtctttc aacctattta 117900
gatcttcttt aataatgtta aacaatgttt tgtagtttca ttgtacaagt ctcagactac 117960
tttgttaaat ttattcataa atgtttactg tttttgatgc tattgtaaat tgaacttttt 118020
cttactttta tttcacatag ttggttgtta atgtatagaa aaacaattga ttatcttgta 118080
tcttgcaatc ttggtggttt attagttcta ataatttctt ttggtgaatg ccttcagatt 118140
ttctatatat aagatcatgt tatttgtaaa ttgtggtagt tttacttact gtactccatt 118200
gtgggtgcct ttacttatct ttttattccc taactgagct ggctagaccc tccagtacaa 118260
tgttgaatag aagtagcaaa agtgaacatc tttatcctgt ttctggattc agcctttcat 118320
cattaagtat aatgttaact gtgaattttc tttttttgtg tatgtggggg gacggagtct 118380
tgcttgtcac catgctggag tgcagtggca tgatctcagc tcactgcaac ctccgccttc 118440
tgggttcaag tgattctcct gcctcagcct cctgagtagc tgggactaca ggcgcatgcc 118500
accacacaca gctacttttt gtattttagt atagacgggg tttcaccatg ttggccagga 118560
tggtctcaat ctcttgacat cgtgatccac ccgccttggc ctcccaaagt gctgggatta 118620

-continued caggtgtgaa ccaccacgcc cagcctaatt gtgaattttc aaacctttat caggttgagg 118680
acattttctt caattcctat tttttgagtg ttttatcatg aatgggtgtt ggattttgtc 118740
aaatgccttt tttgtatgtc tattgaaatg attatgtact ttgttttgtt ttgttattta 118800
ctctattgat atggtgaatt caattaattg atttttggat gttaaaccaa ctttgcattc 118860
ctgggctaaa tcccacatgt tcatattgtt taatgccttt tatatacttc tgggttaggt 118920
ttgctagtat ttcgttgaaa atgtttatat ctatattgct aagggatatt ggtttatagt 118980
tttcttgtga tgcctttagt tttggtataa tatgggtatg agacaatgaa ttgggaagtg 119040
ttccttctat ttcttaaaag agtttatgca agatcagtat taattcttta aatgtttgat 119100
agaattagcc agtgaagcta tctgggtctg ggcttctatt tgtgggaaat tttagaatta 119160
gtaattcaat ctctttggtt gtgattgttt tattcagatt aactatttct tcatgagtca 119220
gttttggcag tttgcgtctt tctaggaatt tgcgcatttc atttaactag tttgttggca 119280
tgcaattgtt catagtattc tttttttatta attttaattt ctgtattgat tttccctcat 119340
tttatgagtc tcatttttcc tttttattc attttaattt ctgtattgat tttctcttat 119400
tgctcatttt aatggtttga atcctctggt cagttggctg aagagttgtc aattttattg 119460
ctgatcatgt atcactttta taattgaatt gttataagaa gacataagaa gtaagaggca 119520
acccctacaa tggagaacat taaggtacac tcaagctttt ctgcccattc ttcctacatg 119580
ccaatatggt tgatccaaag ttattttcat tactctcctc tccatctctt gtctggagtt 119640
gtaggtaagg tgaagtttgg ggattgtgca cccacactgg gagctggtgc cttggtgact 119700
ttccagcagt gacaggccat acactgtgga aagggtttat ttcataccat gctcttgaga 119760
tagaagaaac catggccccg tggccactcg atctgatgtc ataactcacc gatattgttt 119820
ttgccgtgtt tccagttctt tacgtcggtg ttgcttgaga atgtgaattt ggtcatctcg 119880
ggccaacttt gctgtaaaga aagaacaaca tgagaggagc ctgaggaaga acaataacaa 119940
tgcccaatgc caagtgttca ggcttccctc agatgccctg cccatgccga gtgctttatg 120000
tgcatgacct catttgagcc tcagagcact tccccaatta atgatgaaga aactgaggct 120060
tagggaagtt gtgtagcttt gctcttgaac tttacccaag gtcacacacc taattagtga 120120
attttctttt ttttttttta attctacttt aagttctagg atacatgtgc acaacgtgca 120180
ggtttgttac atatgtatac atgtgtcatg ttggtgtgct gcacccatta actcgtcatt 120240
tacattagtt atatctccta atgctatccc tccccttac ccccacccca tgacagacct 120300
tggtgtgtga tgttcccctt cctgtgtcca agtgttctca ttgttcaatt cccacctatg 120360
agtgagaaca tgtagtgttt gttttttttgt ccttgcgata gtttgctgag aagggtgatt 120420
tccagcttca tccatgtccc tacaaaggac atgaattcat cctttttttat ggctgcatag 120480
tattccatgg tgtatatgtg ccacattttc ttaattcagt ctatcattga tggacatttg 120540
ggttggttcc aagtctttgc tattgtgaat agtgctgcaa taaacatacg tgtgcatgtg 120600
tctttatagc agcatgattt ataatccttt gggtatatac ccagtaatgg gatggctggg 120660
tcaaatggta tttctagttc tagatccctg aggaattgcc acagtgtctt ccacaaaggt 120720
tgaactagtt tacagtccca ccaacagtat aaaagtgttc ccatttctcc acaccctctc 120780
cagcacctgt tgtttcctga ctttttaatg attgccattg taactggtgt gagatggtat 120840
atcattatgg ttttgatttg catttctctg atggccagtg atgatgagca ttttttcatg 120900
tgtctgttgg ctgcataaac gtcttctttt gagaagtgtc tgttcatatc cttcgcccac 120960

-continued

```
tttttgatgg ggttgtttgt ttttttcttg taaatttgtt tgagttgttt gtagattctg 121020
gatattagcc ctttgtcaga tgagtagatt gcaaaatttt tttcccattc tgtaggttgc 121080
ctgttcactc tgatggtagt ttcttttgct gtgcagaagc tctttagttt aattagatcc 121140
catttgtcca ttttggcttt tgttgccatt gcttttggtg ttttagacat gaagtccttg 121200
cccatgctta tgtcctgaat ggtattgcct aggttttcct ctagggtttt gatggtttta 121260
ggtctaacat ttaagtcttt aatccacctt gaattaattt ttgtataagg tgtaaggaag 121320
ggatccagct tcagctgtct acctatggct agccagtttt cccagcacca tttattaaat 121380
agggaatcct ttccccattg cttgtttttg tcaggtttgt caaagatcag atggttgtag 121440
atgtgtggtg tcatttctga gggctctgtt ctgttccatt ggtctatatc tctgttttgg 121500
taccagtacc atgctgtttt ggttactgta gccttgtagt atagtttgaa gtcaggtagc 121560
atgatgcctc cagctttgtt cttttggctt aggattgtct tggcaatgcg ggctcttttt 121620
tggttccata tgaactttaa cgtagatttt tccaattctg agaagaaagt cattggtagt 121680
ttgatgggga tgacattgaa tctataaatt accttgggag tatggccatt tttatgatat 121740
tcattcttcc tatccatgag catgggatgt tcttccattt gtttgtgtct tcctttattt 121800
cgttgagcag tgatttgtag ttctccttga agaggtcctt cacatccctt gtaagttgga 121860
ttcttaggta ttttattctc tttgtagcaa ttgtgaatgg gagttcactc ctgatttggc 121920
tctctgtttg tctgttattg gtgtataaga atgcttgtga ttcttgcaca ttgattttgt 121980
atcctgagac tttgctgaag ttgcctatca gctttaagga gattttgggc tgagacaatg 122040
gggttttcta aatatacaat catgtcatct ggaaacaggg acaatttgac ttcctctttt 122100
cctaattaaa taccctttat ttctttctcc tgcctgattg ccctggccag aacttccaac 122160
actatgttga ataggagtgg tgagagaggg catccctgtc ttgtgccagt tttcaaaggg 122220
aatgcttcca gtttttgccc attcagtatg atattggttg tgggtttgtc ataaatagct 122280
cttattattt tgagatacgt cccatcaata cctaatttat tgagagtttt tagcatgaat 122340
ggttgttgaa ttttgtcaaa ggccttttct gcatctattg agataatcat gtggtttttg 122400
tctttggttc tgtttatatg ctggattaca tttattgatt tgtgtatgtt gaaccagctt 122460
tgcatcccag ggatgatgcc cacttgatcc tggtggataa gctttttgat gtgctgctgg 122520
attcggtttg ccagtatttt attgaggatt tttgcatcga tgttcatcag ggatattggt 122580
ctaaaattgt tttttttgtg tgtgtatctg ccaggctttg gtatcaggat gatgctggcc 122640
tcataaaatg agttagggag gattccctct ttttctattg attggaatag tttcagaagg 122700
aatggtacca gctcctcctt gtacctctgg tagaattcgg ctgtgaatcc atctggtcct 122760
gaacttttct gggttggtag gctgttaatt attgcctcaa tttcagagcc tgttattggt 122820
ctattcaggg attcaacttc ttcctggttt agtcttggga gggtgtatgt gtcgaggaat 122880
ttatccattt tttctagatt ttctagttaa tttgcttaga gttgtttata gtattctctg 122940
atggtagttt gtatttctgt ggaatccgtg gtgatgtccc ctttatcact ttttattgcg 123000
tctaattgat tcttctcttc tttttttttt cttttttttt aattgatcat tcttgggtgt 123060
ttctcgcaga gggggatttg gcagggtcat aggacaatag tggagggaag gtcagcagat 123120
aaacaagtca acaaaggtct ctggttttcc taggcagagg accctgcggc catccgcagt 123180
gtttgtgtcc ctgggtactt gagattaggg agtggtgatg actcttaagg agcctgctgc 123240
cttcaagcat ctgtttaaca aagcacatct tgcactgccc ttaatccatt taaccctgag 123300
tggacacagc acatgtttca gagagcacag ggttgggggt aaggtcatag atcaacagga 123360
```

-continued

```
tcccaaggca gaagaatttt tcttagtaca gaacaaaatg aaaagtctcc catgtctacc 123420
tctttctaca cagacacagc aaccatccga tttctcaatc ttttccccac ctttccccct 123480
tttctattcc acaaaaccac cattgtcatc atggcccgtt ctcaatgagc tgttggctac 123540
acctcccaga tggggtggtg gccaggcaga ggggctcctc acttcccagt aggggtggcc 123600
aggcagaggc accccctcacc tcccggacgg ggcagctggc cgggcggggg gctgaccccc 123660
ccacctccct ctcggacggg gcggctggcc gggcgggggg ctgaacccct cccctcccgg 123720
acggggcggc tggccgggcg gggggctgac cgcccccccac ctccctcccg gacagggtgg 123780
ctgccgggcg gagacgctcc tcacttccca gacggggcgg ctgccgggcg gaggggctcc 123840
tcacttctca gaaggggcgg ctgccgggcg gaggggctcc tcacttctca gatggagggg 123900
ctcctcactt ctcagatggg gcggctgccg ggcggagggt ctcctcactt ctcagacagg 123960
gcggccgggc agaggcgctc ctcacctccc agacagggtg gtggggcagt ggtgctcccc 124020
acatctcaga tgatgggcgg ctgggcagag acgctcctca cttcatccca gacgatgggc 124080
ggccaggcag agacgctcct cacttcctag acaggatggc ggccgggcag agacgctcct 124140
cactttccag actgggcagc caggcagagg ggctccttac atcccagacg atgggtggcc 124200
aggcagagac gctcctcact tcccagacgg ggtggcggcc gggcagaggc tgcaatctcg 124260
gcactttggg aggccaaggc aggcggctgg gaggcggagg ttgtagccga gccgagatca 124320
cgccactgca ccccagcctg ggcaccattg agcactgagt gaatgagact ccgtctgcta 124380
tcccggcacc tctgggaggc cgaggctggc ggatcactcg cggttaggat ctggatatta 124440
gcctgttcta cacagtgaat ctccgtcttt accattttat tatgttatat tagttctgcg 124500
tggtggtgcg cacctgtctc tctcatgcac tcggctatgc tgtagcatga caatccgtca 124560
gtgttgttgt ttcgactctt gagtcgcctc gacactcagt cttggtgctc cttatcatat 124620
ggagatcgtt ggtcgtcgtt tcttgtttgg gttttgcttg tgccttttct gtttattgta 124680
tcgcttatga tcgtgatgtt gtcttagttg cttgttggtc tctagtgtgt tttttgtgtt 124740
gtatcttgtt cttgcgttga gtgggttggg cgttggcccg aggctttctt ttggttctgt 124800
ggtgtctctg acgttttgtt gctctnnnnn nnnnnnnnnn nnnnnnnnnn nnnnnnnnnn 124860
nnnnnnnnnn nnnnnnnnnn nnnnnnnnnn nnnnnnnnnn nnnnnnnnnn nnnnnnnnnn 124920
nnnnntagat ttggacgtta tgttttgagt attttatttg attgggtatg gttagtagta 124980
ttgaggggca tgtgggttaa ttaggttttg tatagattat atttatttta tttattgtat 125040
tttaatgatt agatgttggt tttaacgtga tagatggtgg gtatagatta tagatgtgag 125100
tcggtgagct atatgggata ggtaggttgg gtgtgtcgtg cttctcgcgg cctctctcag 125160
cagtgtgctt cggcctcgag accaccaact caacatcacg tccatctcat ttcgcgctac 125220
gacacactca tgtctgtacg cacgagtgta tcttctcgcg agcgcttctg tctggcgtgc 125280
tgggggggcg tgggggggggg gggcggggcg gggggagata ggacgtggaa gaggagagat 125340
ggcagagggg agatggcaga gggagagctg aatcttctct tttcttcttt attagtcttg 125400
ctagcagtct atcaattttg ttgatccttt caaaaaatca gctcctggac tcattgattt 125460
tttgaaggga tttttgtgtc tctacctcct tcagttctgc tctgatctta attatttctt 125520
gccttctgct agcttttgaa tgtgtttgct cttgcttctc tagttctttt aactgtgatg 125580
ttagggtgtc aattttagat cttccctgct ttctcttgtg ggcatgtagt gctataaatt 125640
tccctctaca cactgcttta aatgtgtccc agagattctg gtatgttgtg tctttgttct 125700
```

-continued cattggtttc aaagaaaatc tttatttctg ccttcatttc gttatgtacc cagtagtcat 125760
tcaggtgcag gttgttcagt gtccatgtag ttgagaggtt ttgagtgagt ttcttaatct 125820
tgagttctag tttgattgca ctgtggtctg agagacagtt tgttatggtt tctgttcttt 125880
tacatttgct aaggagtgct ttacttccaa ctatgtggtc aatttcagaa taggtgtgat 125940
gcagtgctga gaagaatgta cattctgttg atttggggtg gagagttctg tagatgtcta 126000
ttagctccgc ttgctggaga gctgagttca attcctggat atccttgtta actttctgtc 126060
tcattgatct gtctaatgtt gacagtgggg tgttaaagtc tctcattatt attgtgtggg 126120
agtctaggtc tctttgtagg tttttaagaa cttgcttaat aaatttgggt gctcctgtat 126180
tgggtgcata tacgtttcgg atagttagct cttcttgttg aattgatccc tttaccatta 126240
tgtaatggcc ttctttgtct cttttgatct ttgttggttt aaagtctgtt ttatcagaga 126300
ctaggattgc aacccctgcc tttgttttcc atttgcttgg tagatcttcc tccaatccct 126360
ttattttgag cttatgtgtg tctccgcaca tgagatgggt ttcctgaata cagcacactg 126420
atgggtcttg actctttatc caatttgcca gtctgtgtct tttaattgga gcatttagcc 126480
catttacatt tatggttaat attgttatgt gtgaatttga tcttgtcttt acgatgttag 126540
atggttattt tgctcattag ttgatgcagt ttcttcctag cattgatggt ctttacaatg 126600
tggcatgttt ttgcagtggc tggtaccagt tgttcatttc catgtttagt gcttccttca 126660
ggagttcttt tagggcaggc ctggtggtga caaaatctct cagcatttgc ttgtctgtaa 126720
aggattttat ttctccttca cttatgaagc ttagtttggc tggatatgaa attctgggtt 126780
gaaaattctt ttctttaaga atgttgaata ttggccccca gtctcttctg gcttgtaggg 126840
tttctgccga gagatcagct gttagtctga tgggcttccc tttgtgggta acctgacctt 126900
tctctctggc tgcccttaac atcttttcct tcatttcaac tttggtgaat ctgacaatta 126960
tgtgtctcgg agttgctctt ctcaaggagt atctttgtgg tgttctctgt atttcctgaa 127020
tttgaatgtt ggcctgcctt gctagggtga gcaagttctc ctgcataata tcctgcagag 127080
tgttttccaa cctggttcca ttctccccat cactttcagg tacaccaatc agatgtagat 127140
ttggtctttt cacatagtcc catatttctt ggaggcttcg ttcatttctt tttattcttt 127200
tttctctaaa cttatcttct cgcttcattt cattcatttg atcttcagtc actgataccc 127260
tttcttacag ttgatcgaat cggctactga agcttgtgca ttcgtcacat agttctcgtg 127320
ccatgttttt cagctccatc aggtcattta aggacttctc tacattggtt attctagtta 127380
gccattcgtc taatcttttt tcaaggtttt tagctttttt tgcgatgggt tccaacttcc 127440
ttctttagct gggagaagtt tgatcatctg aagccttctt ctctcaactc gtcaaagtca 127500
ttctccatcc agctttgttc caccactcgc gaggagctgc cttcctttgg aaggggagag 127560
gcactctgat ttgtagaatg ttcagctttt ctgctctgtt tttccccatc tttgtggttt 127620
tatttacctt tggtctttga tgatggtgac gtacagatgg ggttttggtg gtgtggatgt 127680
cctttctgtt tgttagtttt ccttctaaca gtcaggaccc tcagctgcag gtttgttgat 127740
gtttgctaga ggtccactcc agaccctgtt tgcccgagta tcagcagcag aggctgcaga 127800
acagcgaata ttgctgaaca gcaaatgttg ctgcctgatt gctcctctgg aagctttgtc 127860
tcagaggtgt acctggccat gtggggtgtc agtctgcccc tactggaggg tgcctcccag 127920
ttaggctact ctggggtcag ggagccactt gagggggcag tctgtccctt ctcagatctc 127980
aaattccatg ttgggtgaac cactagtcac ttcaaagctg tcagacaggg acatttaagt 128040
ctgcagaggt ttctgctgcc ttttgttcgg ctatgacctg cccccagagg tggagtctac 128100

-continued agaggctggc aggccttctg agctgcgatg ggctccaccc agttcgagct tgctggcaat 128160
gagcaaggct ctgtgggcat gggaccctcc gagccagaca tgggatataa tctcctggta 128220
tgctgtttgc taagactgtt ggaaaagtac agtattaggg tgggagtgac ccaattttcc 128280
aggtgctgtc cgtcaccact tcccttggct aggaaaggga attccctgac tccttgcact 128340
tcccaggtga ggtgatgctc acactcaatg ggctgccccc actgttctgc ccccactgtc 128400
caacaatccc cagtgagatg aacccagtgc ctcagttgga aatgcagaaa tcacccatct 128460
tctgcattgc tcatgttggg agctgtagac tggagctgtt cctattcggc catcttggaa 128520
ccagtctgaa ttagtgaatt ttcaacataa aactcaactc ctgtgctctt agccactcac 128580
tttacaaaag ccaaatccag ttcctcatcc tcttgcccac tcactcagca agccttgggg 128640
cccctgcctt tcagtgctta gagaatcatg ttcagatgca agagccaggc ttggttctca 128700
ctgggcttgg caggcacagt acatgcctaa ctctggcctg cgtgtgcatt tccacttgag 128760
gtcctaacct tccactcagc ccctcaagac tcttcaggga cctaagggcc cctggtgcag 128820
agctgccttt ttgctccagg agaaaggcat ttcgtggccc ttggtgggta tctttaaatc 128880
actgcagaat agtttactcc tcttctctga aattcttata ctgagcaaaa acgggagttc 128940
actctgggtt ttagtgttgc ctgtgagagc agcagttctc acagctctta tgtttctaag 129000
tccatttcat tgtttcatgg agaaatgtgt gacgatgaca caacccggtt tcctgtcgtg 129060
cctacacaga ggattgagaa tgagctccat tctaaaagag tgcagtgtcc tagatggctt 129120
tagaagagac acatgtgctt ggacttgggc tctgtcactg aagctgtgtg accaagagtt 129180
gccctgaccc cctcacatgt aaaatggaga tgataatgcc tacttctccg ggtcatggtg 129240
tgcatttggg gagagaatgc aggaaagccc tccacacggc gcctggcacg cagtaaatgc 129300
caatggatgg gaacaatgat cattatcatt atgcctatag tcatcactgg cctgagggtt 129360
ctgctcctcc ctctaagcct agctctgaga gcatcttatc tctcagcctg tcctgctgcc 129420
gtctctcact gcaggagttg gagcaggtag caggtagcta agggcggggc tgcttctcag 129480
agcctttaga gcagatgagg tcatatcatg accactcttt aaactattgc ttaaggccaa 129540
gcctgtgaac gcagcccata gagctgtgaa tagggggagc ccagatctcc tgaaaacagg 129600
tcctggaata gtttctctag ctctcgtggt aaagcattgt gttttaaaac ttacttttca 129660
acacagatta ttatattttt gtaaaatata ataaaaatta attactagaa aaatgaaatt 129720
ttaaaaaccc aaagatattc aaaatccaag tctttttttt tcttattagg tgcaaaagtc 129780
acaaaattgt tctgttaagt tgctataaaa gtttctaaaa cccctcctct gagtctttgt 129840
attttatttt gtatttattt tatttttatt ttttttaaga gacagggtct ccctctgtct 129900
cccaggctag agtgcagtgg catgatcata gctccctgca gccttgaact tcaggactca 129960
agtgattccc caacctcagc ctcctaagta gttgggacta taggcacaca ccaccacacc 130020
tggctaattt tttttttttt tttgagacag agtcttgctc tgttgcccag gctggggtac 130080
agtggcatga tctcagctca ctgcaagctc cacttcccag gttcacgcca ttctcctgcc 130140
tcagcctccc aagtagctgg gactacagtt gcccaccacc acatccagct aattttttgt 130200
atttttagta gagacggggt tttactgtgt tagccaggat ggtctcgatc tcctgacctt 130260
gtgatccacc cgcctcggcc cctagctaat tttcaatttt ttttgtagag atggggtctc 130320
tctacattgc ccaggcttgt gacaaaatcc tagactcaaa caatcctccc gccttagcca 130380
cccaaagtgc tggaactata ggcttcaacc tctgtactga tctaattgca gacctggacg 130440

-continued

```
cagttagttc tcagatgaca ctcaggccac attctgagct gtccacccga cagcacttcc 130500
aggctgagac atcttcatcc ttgagcttgg aactggggtc caaaaaggaa tattaacggg 130560
atacctctgc atcctcccct ggggatgtaa agccagccag gaggggaggc ttgaggccac 130620
agaaggcaag ctgagtatta atggtgacaa taactgttat cattggctat gggggtaatt 130680
ctggaggcac tcaacattca tcatctctta tctaccttaa ggaaccagct aatctcttgg 130740
gcaccttgac tctgaggagc tggatctctt cagtttcact ggtatgaata agtcagtaca 130800
tgcggaattg caacatgcca agtttcaaaa agagaatagt tctgtctccc ctggtcccga 130860
aggtgtttga agaatttatc caatggctga tgaagttctg ggagcacagc aggatgagaa 130920
agcctggact gacggcagaa gagctcagca gggcaggttc caaggactga cacagtgcct 130980
taatgaagct gtcccttcac acagatgctc tggatctgtg gggccacagt aatggccctc 131040
tgacattcat gttcacccaa ggtgtagtgg tgaaatatta gatttaaggg gtgatcatat 131100
ggtgagtaat tgaatcactt gtaggctggc ccccctcatt tccaggttgt tcaagggatt 131160
ggttgttttg ccatgtggtg gattaataat tggccacagc tggacatggt agctcatgac 131220
tgtaatccca gcactttggg aggccgagcc gggtggatca cctgaggtca ggagttccag 131280
actagcctgg ccaacatggc aaaacccttt ctctagtaaa aatacaaaaa ttagccaggc 131340
ttggtggcta cctggagcct gtaaaccaag ctccctagga ggctgaggca ggagaatcgc 131400
ttgaacctgg gaggcagagg ttgcagtggg ctgagatcgt gccactgccc tccagcttgg 131460
gcaatagagt gagactctgt cccaaaataa taataataat aataataata ggccacaaat 131520
tctttgacat tccttccatt gagagatggg ggggtctgca tccccacccc cacccccgga 131580
gtctgggtgg gctctgtgac tgcttggacc agtagaatat gatggaagtt acagtgtgcc 131640
agtttccagg cccaagcctg aagagattgg cagcttccac tttctgtctc ttagaaaact 131700
tgctcttgga agccagccat catgtaagaa atgcaggcac ccagaggaca ccattctgtg 131760
agaagcctta aagaatgaga ctccatatgg acagagaggc caaggagcct agaggtgcca 131820
gacacatgac agaagaaggc ccagcccccct tcagctgatg ctacatggcc acagatgaac 131880
tgcccagtga agcctttcct aaattcctga cctgcaagag catgaacaaa attaaatggc 131940
tgtttaaagt taccaaggag gttggtttta cagcagtaga gagaatggaa cttgctggac 132000
agcttctcta tgctcaccct ccaacctgtg ctgtccctga aagtgattgg aatgagatgc 132060
ctcaatgggt tttccactgg gaactctgac cagaaaggag ggaatgtgta gaggaaggag 132120
aggccaatca ctccccagaa cctttctact gagggccgca gctcctccaa gggtgctgtc 132180
tccaggatac ttctgcatta ctcccacaac cttccccctc cccctgcatc aggactagtg 132240
gtgctgatgg ccccgcactc tgcatggtcc ctctgcacat gggcccacac ctttgtgatg 132300
ccccttttgtt aaaccctcat cctagtgtac catctgtttt ttgccaagat gagctgaagg 132360
gtctgcagga agaagggctt cataaccgag accttgggta gatgtgcagg agggagtttc 132420
agagccagca ttttctaact accagaaaaa gagaagtgcc ctgtccacaa ccttccacat 132480
tctgttgacc acaggaataa atgaactttg tgattttttt tcctgtcatt aggtaggggg 132540
acaaaaatcc tcttaactcc atgttcagaa atattctgga aatttggttt cttaagtcaa 132600
attccacatc agaaacgatg ggatgtggcc tggtagctta agaacagcag gtacagaata 132660
acttttttct cctttgtctc agttttctta gctataaaat gggggtaaca gtcatctctt 132720
cctacctacc ccaccaaact tcgtgaagaa cacactagct acaggaaact tggcaaagag 132780
aaagagtttg acgctgtcat ggcagaagca gtggctttct cttattacgg tggctgcctg 132840
```

-continued gcctttgaag gcttatcttt ccaggtttaa actgagagca agctgaaggg ttatgactcg 132900
aagtgaggta ggattttgcc aggcacacta ggaggctggg tatgcaaggt ggttcattca 132960
gggagccttg gctgaccttg acgcctgcgt ccgtctctga tgctctgtac caggtcagct 133020
gtgtgtccct aacaaagaat ggcctcctaa ctggggtctg cacatctggg catcttagta 133080
aggggaacag atttgaggtt cttctttctt tcagcgaaag gtgagacttc gggttgaaga 133140
actggtaact gtgatttgca ggcttgtcca tggctcctca gagctggcac ttggggtgct 133200
ccttgtccac cccttccctc cctaggccca catggggcac cctgagcttg cctgagccct 133260
actgtgatct cacggagggc aggctatgaa ctagaaagtg atgccacacc ctggcaacta 133320
gagaagtgcc catccagggg catgtcccat aggtatctgc ctgtatggac cctagttacc 133380
cactgacaaa aagaggggca caaccctccc ctgtagaact gtagcgcaga gtgaggacat 133440
gacgacagtg aggcctgggg ccacccgctc caccctcagg ggcttgtaag aatcccaagg 133500
aaagtcatgc ctcctgcagg tgtgtcgagg cacagggcag agccctccca cttcccgccc 133560
ctgcacagca gtgtcattcc tcctatgact acagtgcttt gaggacagga agaactttcg 133620
gttcttggga agcccggggc agaaggggcc tgagctgctc accgcgtcca tccctcagga 133680
caacctcgac atcgccggtg atccagcggt agcaggggaa ctcgatgtag tccccgtggg 133740
gcgtcttcag cgtgatgtac ttcaggtacc agtcgtcatt cagccagtac ttgcgcttct 133800
cgattctgac cagctggatc tcgcccagtt cctcgtccac agtcacgtcg tatgaatcca 133860
cctgggaagg agaacaggca atcaggccat gcgtggtctc ctgagccttt gttctggagg 133920
tgttaagaat ttgtcacccc aaggtatgct gctgtggcac agggactacg ttgaatgaaa 133980
agcacttaaa aaaacagcag gtgcaagata ctctgacatt cgtgctgttt cttagaagca 134040
ggagatgaaa gtcccctatg aaagatgtcc tcactatacc aaaaggaaag taacactctt 134100
ttcatcaagg ttgggaagtt gaagccaaag gaaatccata caaacagatc ttgtacaatg 134160
aacgcttacc tcccgagtca cttccctgcc cagttacctg ccctagccca agccccttgg 134220
ccttatcaca tctcacgatg attcattcaa tgcagtatct aagggggatt gactctaact 134280
gcttcttggg gtcttcatct ttttaagagg gctcccatgc cacgtacaac ttgtattaaa 134340
gaaatctgta ggctttcgcc catgaatctg tcttatgccg attctcagac ctagctgaaa 134400
tgggaagagg tggagttttg cctccactac agttcatgga gccaagattc ttcatgaaca 134460
ccttaaatga actcctgaat tcatttaccc aagacattca ctgaaggcct gcccctgaca 134520
aggctcagtg ctacgaccca ggcaggtgaa agaaatggac aaatcctggg ccctgccctt 134580
gaggagagag aatccagtga gccaggatgg tgctgtgctg ctcagagggc aacgcctgct 134640
gactgcactt agctcaggct ggaggatggg gagatgccca ggctcatgcc tgcacctgcg 134700
aggctgtgcc cagtgagggt ccgcagctgc ccccacatgg gatagccttg tgggagacct 134760
ttacaactgg agatgggctt gctgacagtg gatccccaca atgactctgg gagtgcaggg 134820
gagttaccac cccttccaca gatgaagaca gcgaggctca gtgactccca cctctgccac 134880
ttgccagcag agctggagtc acaccccagg tctttccatc atagccactt cctctctttc 134940
cagttttcag tggggataat aagtgagtga aaatggtgag gcttagatac agggagcttg 135000
catggattcg agtcgtcctg ggacatttgc agttcacagc tgcatggtga tgcccagaga 135060
acagtgagac caagcagctc tgctgcacct gtggcattac tggtggcagg gtgaggctag 135120
ccttgcagct agaaggcacc accccaggct gtgtacagcg cagctgccca ggcctctggg 135180

-continued acaaggctgc ttggccccct ccctgccagg ctcctgcttc caggacacag gcggctctga 135240
ggcaacagcc atagcttctg gagggctttt gtctctgcag caatggatgg cagacaggaa 135300
gttgggatga gaggctcagg cattgcatca cgcattctga tgaccagcag gtttggaaag 135360
ccccggactc gatgccctcc aaggcatgtt ctttttttatt ttgaggtgga gtctcactgt 135420
gttgctcagg ctggagtgca gtggctcgat ctcggctcac tgcaacctcc acttccaggg 135480
ttcaagtgat tctcctgcct cagtctccca agtagctggg actacaggca cctgccacca 135540
catctggtta agttttgtat tttcagtaga gacagggttt caccatgttg gccaggctgg 135600
tctcaaactc ctgacctcaa gtgatccacc tgcctcggtc tcccaaagtg ctgggattac 135660
aggcatgagc cactgtgcct ggcccctgca aggcactttc taagccagat tcatcaaccc 135720
ttgaacttta tccctggcgg cagaacctag agttctcagc atgatggcaa agtggaaggg 135780
gcgaggggta tcatcctttg tgcgagcgca ggcatcccca ttccatgccc tgcctccaag 135840
ctgccaggag gacccctgga gggcttccta agaggaatgg gaacttgagt gttttccaca 135900
aacctcctgg ctctgaatac cgtgagcagt ttggggtggc tgacgctgag gccagacgct 135960
tgtggtcaga aagcggaagc ttcctccctg tgctctgtag tctaggccag aggccctagg 136020
aacagtttct gatgacagag gagccaggcc catgtggtgg gatgacatgt cttgggtcca 136080
gccacatgtg gaccagcctc ggccccacga caatgcccct cctgcaggga gagtatcagc 136140
ctcatctgcc acctctgaga aagccttcct gccacagctt gtcctcagga gagcagggcc 136200
acacacaagg cctcgcccat catggacagg gtgggcaggt tctgatggga caggagtctc 136260
agcatctcag gggctcgggc ccatctggag gagcagagtg ggggctgagt ggcccaggac 136320
tggatacgcg tcgggcctgc cccacgccag gccctgcatg ccacagggat ttacagaggc 136380
cttagctgca ggttgtgagc caagacagag attcctgatc ccaccgagga gtggggagag 136440
ggcagtgagg ggtagaaggc tcggtgggcc ctggggtctg gagctctgaa ttcacatccc 136500
agcttcaggc aagtagctgg atggcctggg cacattgctt cattctctga agctgtttct 136560
tcatctaccc aaaggagata cccctcactt gcaggaccat tgagaaaatg aaatgacacc 136620
atcctgggtg gcctcctttc tccagaggca caggccaccg gttgtgtgca tcagaaccac 136680
cagtgcccct tcctgaatcc agggggttgc agggcaccag gccccacacc gcctgtgagc 136740
tagcatgggc ccctgcgtca cggccacttc gtgactacat gtgccaatcc gagtaactgg 136800
agcacacatg ggaggaggaa actgaacctg tgacctcaaa ctccttcact caaagcccag 136860
aaggaactcc tgaaaggctg gagacagggc tgtgaggaca gagggagagt gggaggcatt 136920
ctgaatgctg gtggggcagg cagagcaagt ctgtgtgcgg tgaggactga ggggcggcca 136980
ccagaggccc gggcctggtc tgagtgtggc tgctgcaggg gaagtagctt tcctatggct 137040
ctgaggggct ggagagggag gaaggtgtcc ccaggggata gatgacagga aagctggggt 137100
ggggtgggag gagctaacag ggacactctc atgggaggga ggctcccagt accttggact 137160
aagaggggag ggagatgggc tgaggaggca ttccaggact gggcaggtcc cacagggagg 137220
gcccgatgtc tacctggggg tgacgaccca cacgaagaga ctgagcagct tctctgaggg 137280
agtggacagt ggggtgaccc tccagcacac ctgtggtgca gtcacagggg actgggacac 137340
tcctggcccc ctgccctacc tacacctgca ggcacctggt ggagagcccc tgagtttcac 137400
ttggggtgaa atcactaggc agatttacaa ggactccatc tgccatctga cagggacttc 137460
cacagcagga gggggccagg cctgcagtct ggctggtcta tggccagccc agccactttc 137520
ctggtgctgg cttcaagcct gaatatgata agaggtgaac aaggggcaga gggctccagc 137580

-continued cttgacccaa ctcagggagt aaaagacaaa gcttgatggc tgtggttcta acatcccagg 137640
ggccactaat ggaagaatga cagataaagg cctccttcca ggaaaatacc agggtcacat 137700
gtgtcaaact gcaaaatatc ttcggaaggt ttgtggaact acaatggcca ccttcctccc 137760
tcctctctgg gccaagtaca ctgggctgat gctatatttg tctatttgct gtgacacatt 137820
aaattctcag gtgacacact gaattatggt gggcactatc aacagtggac accccccaac 137880
aggccctcag gaagcactgg gcctgggaat ggccgagcga gtgattatcc tgctttacag 137940
atagaaactg aggctcagag agcaatggtg gcctcaagat cagaacctac acctgtgtga 138000
tggccaagcc caggttcctc ccacagttcc ccaaggccac atcttgagaa aagccctgaa 138060
ccggaagcta gaaggcccag ctttgagccc tggtttgtac cctggatgga gtgtaaaggg 138120
gcaatgtgga gtggcatgga aggacaggga aaagcttcat aagagggtat ttcaggcagc 138180
ttttaggggc tgatcagatt tcagagggca gatgagtagg aggatgggca tgggtagcac 138240
atttcagatg tggggaactg ggagggcagg gtccccgggg gattcacacg tgggaggagg 138300
aaggctggac acagtttctg gggacagaag tgggtggcgt ggtggtgcag atgctggaga 138360
gaaacaaggg aaacctgcaa ctcaccggcc tcatttcaca aggggccact ttgctgattt 138420
tgcttgttgc ttttaacttt ttattggata tgtagtttta aagcttttga atatttcggc 138480
aaagagtcag ttggtcagtt ttcatgtgag ctttctatca gcattttagg aaagttttca 138540
tctgtctttc atcagatctc tgctgttgct gggacaggga gacggatctc tctgcggaag 138600
caaggatgtg tgccccaccc ccagactacc catcttggag gggggactaat gaggggctgt 138660
gggaggagga agctgtagag cagagaggaa gattgggggc cagacaaaac agagactcgg 138720
gatgagagag ggggaggcta tggggaagag ctgaggaaaa caagggacgg agagagggat 138780
tggggtagtg gatagggaga ccaaggggca gagaaggggg aaaatgtggg acagagagcc 138840
ggagattgag ggagcagaga aggggcctct gagaggtggc tggaagacag agtgtagagg 138900
aaaattcaga gcaaaaaaga agggagagtt gtagggtaga gagcagaaac ggggggcatt 138960
tagggaactg ggagcagggg aaggaagagg aggcagaaga gggggcagaa tgtagggaaa 139020
agatggctca gagggggaga ctgggagatg agagacggat tgagggtcat accaaagaaa 139080
tatttatgct ccactaatat attcccattc acaagaagga ggtattctag aattaatttt 139140
tcatgaatgt aagaatactc actgacttaa gaagcatgaa tcattataac acttttctac 139200
acttgttgaa catattcaag tatcatatat taaacaccac gctattgccc ttagctttct 139260
taaaagtacc agcacagaat gaaatgggcc aactaagatt tctcagaaat cttcagatct 139320
gttacagtta tcgtatccga tctgaattac tttaaattta cagagttaaa gaaataaatc 139380
aacttgttaa atttgcctag acttgggtta gcctctggaa acagggccat tctgtgtagg 139440
atcccggctt tctccagcag acagtgagga gccaaggaag acacaaccgt ttataggata 139500
atcccacctg cgaaggactt gattcccagt cctgactgaa tcactatgcg gaactctgat 139560
gagaataaca agggacctgt gactcacttt atcaaggaaa aaatcagtcc tgtccattat 139620
ttgactgaac tatgccctgg aggaggggggg tgttgacctg ccaataactt ggaaatgatt 139680
aaattgtgtg gaaatacctt tattgttatt gttatcgtta ctactgttaa caatacagat 139740
tttaacactt ttccctgtaa aatgggataa ccttgtcttc tcagcaagta cttcctctag 139800
ggtttctctt ttacctttac ccaaaaagga tgattgtctt tacagatacc aagctgggag 139860
aatgaggaag tagttctggg ctgggcaaga gaaagtgttg agtaactttg catcaacagg 139920

-continued

```
aactttctca aaagctgatt ttttcaagga aactttcagc cttagctggt tccccaccct 139980
gcggtagccc ccaccccccaa ccacccccccg ccccacccct gacttatagc cctctcaacc 140040
caatggaaat gtgacatgca aatctctcct gaaatttgcc cctgggattc cggctgaggt 140100
gtttaattat aatgtcattt gaatgacttc tcagggtagg ggaagacaga ccgagagagg 140160
gagatagtgg acaaaacagt gccttcactc tttgtccgaa gagcccgcta tggccacgtt 140220
atcatgtccc ctgcaggagg aaagcacaca cggggtgccc gtgctgtgca gtgtgagcac 140280
accaatggcc tgtgcttcta gaaccttatg atgtgtggag gagaatgggg aggaggaagc 140340
acttacaaag gggaagtagc ctgtaccctg tccttctccc ccaggtgtgg ggaatccatg 140400
aaataatgga agtaaatgaa ggtgcgtcag aaatggcaga gggtgccatc accctaaatg 140460
gacgacacat taactccagg gcaccgcagt cctcagggtc agttccccga ctggggcaac 140520
taagcaactg aaggttgctc ttgtactcaa cacctaactc ttcttgaagg gagctcaagc 140580
caggatgcta gtgaacttgg ctgagggcca tgtcgtgcta cagcgagggt atgggctcct 140640
ggataggaat cgagcccatg gagagcttgg aatccagaaa aagagtagtt tttacttact 140700
ttaggctctg cacacctaaa acacaaattt tatccaagag taatcagttg aaacatgaac 140760
ttgccggttg tatttgtcca ttatgagcaa tttcacaagg tttgatcaaa taataaacta 140820
aatggtgaga aggcagcttg gtaaagtcta aatctttttg gtccagttag gagctggggt 140880
ggggtggaag ggaactgata ttccctgcgc acctgcagta tgtctgggac tattaccagt 140940
catttacgga gcgcttcctc tgtgccaggt actggattag gcacttcatt aaaggctcag 141000
tgagaactgc gacctgccca tgctcatgga aaagagtcgt ggggctggaa ttcaggtcca 141060
gatcagcatt aggaactagc ttccaaatgc tgagggctcc ctcgcgtcct cacacctagc 141120
gtggaagtgt tccctggtgt acattctgct gggagggagt gcagcccctc catttaggaa 141180
aagcctctcc tggcctgggt tctgttcctt ccctttaatt tcctctgggg actgtcctga 141240
gaatgtaagc tgcccaggtg ccgtctgagc caccagatgg gcctgggctc acccatgact 141300
catggaccag actgaagcca accctccatt ttcagctggg gaaactgagg cccagacaga 141360
cggtagagtg agctggtggt catgtctgga cagaactcag gcctctggac ccgctgacgt 141420
gcacccttcc ccacggctca cagctggctg ctccgaggtg ccctcagagt tctgtgagca 141480
tgactcatct gcctctccct ccctgtgcga cctgcagaag gagcctaagg aagaggtggc 141540
acaagaaacg cggcccagtg aagggggctc cggagcctcg gagcccagat cttgaagtgg 141600
aggggaaacc ttgggccttc tcctcccagg gaagacgcct tgcaggcggc acgcgggaag 141660
tctccgtttc cgacaggggt cgcggccgcc gcgaggggtc ctggacgctt gcccaccagg 141720
gtacccaccg gccactggga gcccagggca cgcccccaccg cagttctgcc ctccctgaca 141780
gggtcctgga cacccccagt cctgtccggg ccgccccgac gggccctcgg cgccccccgcc 141840
caggcctctg ccgtccaaac cgggtcccgg acgcacctca gcccgcgctc cacccgtgcc 141900
ccgcccgcgc tcaccgcgcc acgctcgaag tcgttgtaga agggcttgtc cagcaggtgc 141960
ttctcgctgc agcccgccga gcccacgagg ctgaggtaga tgtagtcgtc agtgtcttca 142020
ccacggggtg aagtacggtc cnnnnnnnnn nnnnnnnnnn nnnnnnnnnn nnnnnnnnnn 142080
nnnnnnnnnn nnnnnnnnnn nnnnnnnnnn nnnnnnnnnn nnnnnnnnnn nnnnnnnnnn 142140
ntttttgggt tgttgttgtc tctttgtttt tgcgagcggt ccttccgccc cgtggtgaag 142200
acaagtgggc gcctctgcct ggccatccca tctgggaggt gaggagtgcc tctgcccggc 142260
caccccgtct gggaagtgag gagcgtgtct acccagccac cacgtctggg aggtgaggag 142320
```

-continued cgcttctgcc tggccgcccc atctgggaag tgaggagcgc ctctatctgg ccaccccttc 142380
tgggaagtga ggagtgcctc tgcccggccg ccaccccgcc tcggaggcga ggagcacctc 142440
tgcccggcca ccaccccatc tgagaggcaa ggaccacctc tgcctggccg ccatcctgtc 142500
tgggaggcga ggagcacctc tgcccagccg ccgccccacc taggaggtga ggagcgcctc 142560
tggccagccg ccccacctgg gaggcgagga gcgcctctgc ctggccgccc catctgggag 142620
gtgaggagcg cctctgccca gccaccaccc catctgggaa gtgaggagcg tctctgccag 142680
gccgccccgt ctgggaagtg tacccaacag ctccgaagag acagcgacca ttgagaacgg 142740
gccatgatga cgatggcggt tttgtcaaaa agaaaagggg gaaatgtggg gaaaagaaag 142800
agagatcaga ttgttactgt gtctgtgtag aaagaaggtg acataggaga caccattttg 142860
ttctgtacta agaaaaattc ttctgccttg ggatgctgtt aatgtacaac cttacccccca 142920
accccgtgct cgctgaaaca tgtgctgtgt caactcaggg ttaaatggat taagggtggt 142980
gcaagatgtg ctttgttaaa cagatgcttg aaggcagcac gctcattaag agtcatcacc 143040
actccctaat ctcaagtacc cagggacaca aacactgctg aaggctgcag ggacctctgc 143100
ctaggaaaac cagagacctt tgttcacctg tttatctgct gaccttctct ccactattat 143160
actatgactc tgccacatcc ccctctctga gaaacaccca agaatgatca ataaatacta 143220
aaaaaacaaa ttaattaatt aaataaattt catatggaac caaaaaagag cctgcattgc 143280
caagtcaatc ttaagccaaa ggaacaaagc tggaggcatc acactacctg acttcaaact 143340
atactacaag gctacagtaa ccaaaacagc acggtactgg taccaaaaca gaggtataga 143400
ccaatggaac agaacagagc cttcagtaat aatgccacat atgtacaact atctgatctt 143460
tgacaaacct gacaaaaaca agaaatgggg aaaggattcc ctatttcata aatggtgttg 143520
ggaaaactgg ctagccaata aatggtgtag ggaaaactgg ctagccatat gtagaaagct 143580
gaaactggat cccttcctta catcttatac aaaaattaat tcaagatgga ttaaagactt 143640
acatgttaga cctaaaacca taaaaaccct agaagaaaac ctaggcaata ccattcagga 143700
cataggcatg ggcaaggact tcatgcctaa aacaccaaaa gcaatggcaa tgaaagccaa 143760
aattgacaaa tgggatctaa ttaaactaaa gagcttctgc acagcaaaag aaactaccat 143820
cagagtgaac aggcaaccca cagaatggga gaaaattttt gcaatctact catctgacaa 143880
agggctaata tccagactct acaatgaact caaacaaatt tacaagaaaa aaacaaacaa 143940
ccccatcaaa atgtgggcca aggaaaagaa cagacacttc tcaaaagaag gcatttatgc 144000
agccaaaaga cacatgaaaa aatgctcatc atcactggcc atcagagaaa tgcaaatcaa 144060
aaccacaatg agataccatc tcacaccagt tagaatggtg atcgttaaaa agtcaggaaa 144120
caacaggtgc tggagaggat atggagaaat aggaatactt ttacactgtt ggtgggactg 144180
taaactagtt caaccattgt ggaagtcagt gtggcgattc ctcagggatc tagaactaga 144240
aataccattt gacccagcaa tcccattact gggtatatac ccaaagtatt ataaatcatg 144300
ctgctataaa gacacatgca cacatatgtt tattgtggca ctattcacaa gagcaaagac 144360
ttggaaccaa cccaaatgtc caacaatgat agactggatt aagaaaatgt ggcacttata 144420
caccatggaa taccaagcag ccataaaaaa tgatgagttc atgtcctttg tagggacatg 144480
gatgaagcta gaaaccatca ttctcagcaa actattgcaa ggacaaaaaa ccaaacactg 144540
catgttctca ctcataggtg ggaattgaac aatgagaaca catggacaca ggaaggggaa 144600
catcacacac tggagcctgc tgtggggtgg ggggttgggg gagggatagc attaggagat 144660

-continued

```
atacctaatg ctaaatgacg agttaatggg tgcagcacac caacatggca catgtataca 144720
tatgtaacta acctgcatgt tgtgcacatg taccctaaaa cctaaagtat aataataaaa 144780
aaataagctt ataaaatgct tttaatgcta tataacttta taactctgaa agaataatag 144840
atttgtatta tgctgtcagt gagtaggtct attaagtgat aacattaaac acaaatacca 144900
ccatttataa agtatgattt tgatatcatc ggttgtgtat tttcacccca aactctgtag 144960
atagtaactt tgttttctca tttgaccatg ctcaatcttt agagaccatg ctcttctctc 145020
aaaatgactg taggttcatc caagtatgtt tgctacccaa aatcaatgaa acacagtcac 145080
aactatgtct gtctaggaat aaagccagct aattagattc ttattctaag gaacaagaag 145140
agggcaggta agaatttgat tatggcagaa ttctgaccat aatcaataac tgttttctat 145200
tttttctcca tgttgtcggg tggttcatac ctgactttca tcatttccaa tgattcctgt 145260
ttgttttgtt tataaatttc aaaatcatca tgaaaagttt cactgaatga aaacctgaaa 145320
attgggaaat aaacattttt ctgcaaaaaa aaaaaaaacaa tgaacactga cttctcctat 145380
ttctcaaagt catctcaaag ccatatgagg attaccacaa acttgcaggt gagaaaattc 145440
tttgcaatgt aagaagtgcc atgcaaatta gttgatgcta ttataattag tctcagggat 145500
caaaaatgct tgaaccctaa atctaacact tcaaaggaaa gcattatttt tcattcattt 145560
tacaagttac acctcccttc ttccccacat ctttgtttag aatctggacc ctgaagttag 145620
aggaccaaga ttcaaatccc agcctcatca gtactagcta tgtgatattg ggaatgttac 145680
ttgatccctg cttatcttac tttctgcatt tattaaatgg ggatgagaat aatatctacc 145740
caaataaggt gcccaatgca gtgcccaaca gcatgaagcc caataaaggt tagttaacat 145800
cacatccata attgacacct ttaggtatta gattttcatc atcccagaac attttccttc 145860
tttaagcctt tttctttcta agtggcactt tcttggatac tgattgcact cctcacaaac 145920
ttgaaacgtt caaacacaca agatgccatt taggagacat tggaacttgg gtttccttct 145980
ctgtaaaact gagtaatgac agtcacctcc cagggctgtt gtaagaatga atgagctaga 146040
gtatgtaaaa tatcttagca cagagtgctt aagaaattat tagttccagc caagcgtggt 146100
ggctcacgcc tgtaatccca gcacttaggg aggccaaggc aggcggctca tctggggtca 146160
ggagttcaag accacctggt caacatggtg aaaccccgtc tctactaaaa atacaaaaat 146220
tagccaggcg tggtggcatg tgcatgtaat cccagctact caggaggctg agacaggaga 146280
atcacttgaa cccaggaggt ggaggttgca gtgagccgag atcgtgccat tgcactccag 146340
cctgggcaac aagagtgaaa ctctgtctca aaaaaaaaaa aaaaaaaaag aagaagaaga 146400
agaaagaagg aaagaaagag agagagagaa agaaagaaag aaagaaagaa agaaagaaag 146460
aaagaaagaa aaagaaagaa agaaaagaaa gaaagaagga aagagacaga aagaaagaag 146520
ggaagaaaga aagaaagaaa gaaagaaaga aagaaagaaa gaaagaaaga aagaaagaag 146580
ggaagaaaga aagaaagaaa gaaaaaaaga aagaaagaaa gaaaaagaaa gaaagagaga 146640
aagagaaaga aagaaagaaa gaaaggagag acagaacgaa ggaaagaagg aaggaattat 146700
ttccctttt cccacccacg cctcaccaca aaccttgttg tggggataac atgtaaaagt 146760
gaacaaaact gagaagatca catcgcatat gcactcagcc tctagtggga gacacaggca 146820
ataaacagga aaagttaaaa acagtactag gtagtggtga gtgcaattag cctcccgcag 146880
cataaaggga ggagaataac cagtggctct ttcatgcaga gaatcagggt agacctctgg 146940
ggagagaccc gcactcagac tgggatggaa ttatttattt tatgcgtgtt cagttaggag 147000
tagaggtgct ctgtcgtgat tatctaatct tgggaggaac aatgtcagac gggtttcaag 147060
```

-continued atgagtatga gaattggtct tccttctgaa aaaacaagaa ttgagttcac actaatcaca 147120
aatacatcaa gcctatttga gtcttgtgtg tgtcatggat tgaagtgtat ctttccactt 147180
agtcaagaag ttccaatgag aagaatgctc cttaacttcc taagtgcaac agagtagttg 147240
aactgagcca tggatggtaa atctacttaa gaaagcacat gccatggaaa gatagcattg 147300
gctgccctgc ctacttctga tggcacagcc ttgcaggaag ggaaagaagc caagaggcaa 147360
aagcctggtc ttgttctgaa aggcacaagg aggtggaaga ttaggggaaa ctcacccaaa 147420
aatgactcag ctctgaactc agactcaaga agccacaata agcaacatga atggaactgg 147480
agggaaataa accaggcgta gaaacacaaa tgttgcatat tcttactcat gtgggaacta 147540
aaaacatgca tttcaaggag aatagaatga tggttatcag agactgggaa cagttgtggg 147600
tgggggtgtt aagagaggtt gcttaatggg tacaaacata tagttagata gaaggtataa 147660
gttctaatgt ttgacagcag agtaggagaa ctatagttaa cagtaatata ttgtatactc 147720
caaaatagct agacaggaag atttgaaatg ttcccaacac atagaaatga caaaagcttg 147780
aggtaatgga taccctaaat atcctgactt gatcattaca cagtctatgc gtgtaacgaa 147840
ataccatatg taccccataa atatgtacaa atattatgta tcaataaaaa tttttaaaaa 147900
gaagctgcaa tcaacatttc atcattatct tttcagcagc atccttacaa agttacagag 147960
acatcttaag atgtatccct cttcctctga atcttcctgg gatagaacaa atgaaaacta 148020
aacaaggagt gggctgggag gagctgtcaa catccatcct aaggaaaagt ctgttagggc 148080
tatgagcttc ctctgtccta gagtagagct gggaaaatag agtcttgaca attgatttct 148140
tattctttct ttctctaaat ccccaatgaa tatgtttttc tttttagtgc tcagtggtag 148200
acagggctta attctgttta gttatgcaaa caggccagaa gaaactgaaa taggctataa 148260
atgtttgaag ctggccaaaa gaagatgtag tcacacaaga taccctctgg aggaaagtga 148320
ctgtcaggaa agtcactttc ctgaccagca aaaggaccag cactattttg tcctgctgaa 148380
gaagtacatt tgtcctgctg ctgtcatggg gacagtggct ccagggcttc ctgtggacat 148440
gccacaagtt ccactccatg agtcaggaga tcatgcggtc agctgggggg aacttagggt 148500
tgctctcttg agcttagcct tatgctgcgt gtctgctttg ccaaccacaa aaacgatagt 148560
ttcatagcaa gttgcaggct ccctggaaac ttaacctacc tactaggata catttacagc 148620
tgcttttctc ctggcatcag gctggagatc aagaaataca taaaacatag tccctgccct 148680
cagttagctc agaatatggt gggggaatgg agacagaagc aaatactggt gggacaagtg 148740
acgatgggcc aaaatatggg cttaaacaaa ggttgtggga gctcagaaaa ggagcaactc 148800
actctgcctg aaagagtcat ggagggctcc acggaaaaag caacatttgt gcaggaggag 148860
attagaacac agaggagaag gatagcagca ctccagatga agggaaggaa atgtgccaag 148920
atttcatggg aatgagaaga tgtaaactgc tcaggaaaaa ccatggttga agctcttcac 148980
agtggctgaa gcatggtgtg attgtcagtt ttgcttgtca acttggtcag gctgtagtac 149040
tcaactattc aaccaagcac tgatctaggt attgctgtga aggtattttg tagtcgcaat 149100
taacctctac aatcagttga ctctatttaa aggacattat tctgtactat ctgagtggac 149160
ctgatccact tcatcccaaa ggtaaatgat tctccaacag tgttctcatc tacatctagg 149220
gcttggaaga tgaaggtgaa ggagaatatg gaaaaacaac aagaaaaaag tcaatcaatc 149280
agaacttcca gccctgtgtt tgttagttca ctttatgttc aaccagtatg tctccacttt 149340
tatctgcttc cttgtaagat ttcatctgaa aaagggaatt cactcttcag gtgttggaaa 149400

-continued

```
tcaattatga gagaagcact tacagaatga ctatctgaag agctctgcag acattctcca 149460
gagtaaaaca accataaccg gtgaaaatta aaaacaaaca aaataaaaaa atgttagagt 149520
attggaaatt gttctaaggg ccgacagcaa atgaagaaat ccaagaaagc ctaccaattt 149580
cagtgagagg agtgagagtc tatggtgttg agtctatggt gtttaagttc tgttcatttc 149640
ctccctctcc tgcaatcagt tcagtgaaac agaaaccctg ctccagagat gtgcagccaa 149700
aaagacaggg tgccctttcc cctcagctcc caatctaggg cagactacca gcatttccca 149760
agcccatctc tggctctatg ttgcagaagt tctattccaa gaaagtttga ctgagaatct 149820
gaagcttcct tcttccactc agcctctact attaaggcgt aagttctatc cccagtgcca 149880
cgggccaaga atactgatgc tgaatgtcct tgctccgcta cactcatagg gcagagattc 149940
catgggagga gtgaagtttc cattccagaa aaggcagaaa aacagaaatt actgcccaat 150000
ccagtacccc acccataaag aaggaaagac atctgagaaa agcatgacac tgtccccaaa 150060
accacctgca gagtagtggc agtagaggca gtagggagac tagaggacct gcctagaggg 150120
agaagtaggc cataagaaga aaagtctcta gttctcccta aagggacaaa ctttatttgc 150180
aacagaacat gcggaagttc aagcctaagg gcactgtcaa aaacaatgaa tattttggtg 150240
gtaagcaatt aataggttaa tggcagctta gtgagagcaa caaactaaac cataaaccag 150300
ctagacatat acaataaaaa tccaagaaag agagagccaa gaagggcctt cctgaggtta 150360
aaacaaacat caaagtcttg tctgaaaaac tgctcctgca aaggaagcaa aatatatttg 150420
gatcagactg tggagcaatt tatgcccota aaaagctgtc aaaaccaaaa gagcaattat 150480
ctagcaattg ctggaggtta acagttgggt atgataccaa aagaggcaaa caactgaaca 150540
gatcagagaa agaggcagtc aaagagagca ctgctaaatg cactgtaatt ccaatttgag 150600
agaaaatgtg cccagtgctg tgactccctc aggaacaaca tcagaggcca caaattatgg 150660
tggaaatagg cttcactata tagtctagcc aggcaattaa acaaataaac aattaaacaa 150720
cagtaacata gtgagggggg cagaaatgag tattgcaact agctagaaca tatttttgaa 150780
caaaaaaatt atgagtcaag cagagatatg gaaaagacag agccatacac cagaaaaaag 150840
gtaagcaaga gaaactgcct ttgtgagtgc caagatgtca gacatagcag aaaaaaaacc 150900
tcaaagtaat tattataaat atgttcaaaa actaaaagaa aatgtgctta aaaaataaaa 150960
gatggtatga taatttcttg tcaattcaaa aataccaata atagattaaa aatatttttt 151020
caaaagttaa ttaaccaaat ggaaattctg gggtttaaaa gtaaaataac aacaataaga 151080
acattttgct agaggaaatg aacaatagat ttgtaccaga aggaaaaata atcaaataaa 151140
cagggatttc atcaacacca aacctgtctt acaagaaata ctaaagggag ttcaatctga 151200
aagaaagaac attaacaagc aacaggaaat catctgaagg tacaaaactc actgtacctt 151260
cagatgataa taagtcctca aaaaacacag aatattataa cactgtaatt atggtgtgta 151320
agctacttat atcataagta gaaagaggaa aagatgaact gattaaaaaa caattacaac 151380
agcttttcaa gacagtataa taagatatat aaataacaga aagcttaaaa gcatataaat 151440
aaagttaaaa tgtagaggtt tttttagttt tctttttgct tgattgtgta tttatttatg 151500
caatcagtgt tgttttcatc agcataaaat aatgggttat aagatagtat ttgcaagcct 151560
catagtaacc tcaaatttaa aaacatacaa tgtatacaca aaaagtgaag agcaagaaat 151620
taaaacatac caccaaaaaa aatactttca ctaaaaagga gacaggaagt aagaaaagat 151680
gggagagaag atcacaaaac aaccagaaaa taaataacaa aatggcaagc aagtccttat 151740
ttgtcaataa taatattgaa tgtaaatgga ctatactctc cagtaaaaag atacagagtg 151800
```

-continued gttgaatgga ttaaaaaaaa ggacccaatg atctgttacc tacaagaaat aaacttcact 151860
tataacaata cacagactaa aaataaagtc atgggaaatg atacttcacg acaatggaaa 151920
ccaaaaaaga acaggagtag ctataccttt atcagactaa atagatttca agacaaaaat 151980
tgttaagaaa aaccaaataa ggtcattata taatgataaa gagatcagtt aagcaagagg 152040
atgtaacaat tgtaaatata tatgcactca acattggagc acctagataa ataaaacaaa 152100
tattattaga gctaaagaaa gatagacccc ctcccccaaa acaataatag ctgtagattt 152160
caatgctcca ctttcagcat tggacagatc ttccagacag aaaatcagca aggaaacatc 152220
agatgtaatc tgaactatag accaaatggg cctaataagt atttacagaa tatttcatcc 152280
aaaggttaca gaagacacat ttttctcctt agcacataca tcattctcaa gaacaggcca 152340
tatattaggt catgaatcaa gtctcaaaac attcaaaaaa actgaaataa tctcaagcat 152400
cttctttgac cacaatggaa taaaactaga aaccaataac aaggggaatt ttggaaacta 152460
tacaaaaaca tggaaattaa acaatatgtt cctaaatgat aagtgggtca atgaagaaat 152520
tatgaattga attgaaaatt ttctaaaaac aaatgacaat ggaaacataa tgcaccagaa 152580
cctatgggat acaacaaaag cagtaccaag agtgatattt ccagataagg gcctacatca 152640
aaaaggaaga aaaacttcaa gtgaataacc tgatgatgca tcttaaagaa ttaaaaaggc 152700
aagagtaaac caaacccaaa attagtagaa gaaaagaact aataaagatc acagtagaaa 152760
taaataaaat tggacttctg ctccaagatg gcctaataga aacagctcca gtctgcagct 152820
cccagcatga ttggcacaga agatgggtga tttctgcatt tccaactgag gtaccaggtt 152880
catctcattg ggactggttg gacaatggat gcagcccatg gagggtgagg tgaagcaggg 152940
tgaggagtca cctcaccccg gaagcacaag tgattggggg atttcccttt cctagccaag 153000
ggaagccgtg acagactgta cctggaaaat cggttcactc ccacccaaat actgtgcttt 153060
tcccatagtc ttagcaaccg gcagaccagg agattctctc ccaagcctag ctcatcaggt 153120
cccatgccca cggagcctgg ctcactgcta gcacagcaat ctgagatcaa cctgcgaggc 153180
tgcagctggg tgggggagg ggtgtcagcc attgctgagg actgagtagg taaacaaagt 153240
ggccaggaag ctcaaactgg gcagagccca ccgcagctca gcaaggccta ctgcctctat 153300
agattccacc tctgtgggca gggcataact gaacaaaagg cagcagacaa cttctgcaga 153360
tttaaacgtc cctgcctgac agctctgaag agagcagtgg ttgccccagc atggcatctg 153420
agctctgaga acagacagac tgcctcctca agtgggtccc taaactccat gtagcctaac 153480
tgggagacat ctccccatag gggccgacag acacctcata caggtgggtg ccactctggg 153540
acaaagctct cagaggaagg atcaggaagc aatatttgct cttctgcaat atttgctgtt 153600
ctgcagcctc tgctggtgat acccaggcaa acagagtctg gaatggacct ccagcaaact 153660
ccagcagacc tgcagctgag ggacctgact gctagaagga aaactaacaa acaaaaagga 153720
atagcatcaa catcaacaaa aaggacattc acaccaaaac ctcatctgta gtcaccaata 153780
tcaaagacca aaggtagata aaaccacaaa gatggggaga aaccagagca gaaaagctga 153840
aaattctaaa aactgagcac cgcttctcct ccagaggatt gcaactcctc accggcaacg 153900
gaatgaagct gggtggagaa tgactttgac aagttggcag aagtaggctt cagaaggtcg 153960
gtaataacaa actactccaa actaaaggag catgttctaa cccattgcaa ggaagctaaa 154020
aaaccttcaa aaaaggttag acaaatggct aactagaata aacagtgtag agaggaactt 154080
aaatgacctg atggagctga aaaccgtggc atgaggacat catgatgcat gcacaagctt 154140

-continued

```
aaatagctga ttaaatcaag tggaagaaag aatatcagtg actgaagatc aaattaacaa 154200
aataaagcaa gaagataaga ttagagaaaa aagagtaaaa agaaatgaaa agcacctcca 154260
agaaatatgg gactatgtga aaaaaccaaa tctacacttg attggtgtac ctgaaagtga 154320
tggggagaag gaaaccaagt tggaaaacac tcttcagaat actatccagg agaacttccc 154380
caaactagca aggcaggcca acattcaaat tcaagaaata cagagaacac cacaaagata 154440
ttcctcaaga agagcaaccc caagacacat aattgtcagc ttcaccaagg ttgaaatgaa 154500
ggaaaaaaat gttaagggca gccagagaga aacgttgggt taccaacaaa gggaagccca 154560
tcagactaaa agtagctctc tcagcagaca ccctgtaagc cagaagagag taggggtcaa 154620
tattcaacat tcttaaagaa aataattttc aacccagaat ttcatatcca gccaaactaa 154680
gcttcataag tgaaggagaa ataaaatcct ttacagacaa gcaaatgctg agagattttg 154740
tcaccatcag gcctgcctta caagagctcc tgaaggaaac actgaacatg gaaaggaaca 154800
actgttacca gccactgcaa aaacacgcca cattgtaaag accatcgatg acatgaagaa 154860
actgcaacaa ttaactggca aaataagcag ctcacagcat aatgacagga tcaagttcac 154920
acataacaat attaacctta aatgtaaatg ggctaaatgc ctcaattaaa gacacagact 154980
ggcaaattgc atagagtcaa gacccatcag tgtgcggtat tcaggagacc catctcacat 155040
gcaaagacac acatagggat ggaggaagat ccaccaagca aatggaaagc caaaaaaaaa 155100
aaaaaaaaaa aaaaaagcag gggttgcaat cctagtctct gataaaacag agtttaaacc 155160
aacaaagatc caaagagaca aagaaagcca ttacataatg gtaaagggat caatacaaca 155220
agaagaacaa actatcctaa atatatatgc aaccaatatg ggagcaccca gattcataaa 155280
gcaagtctgt agagacgtac aaagagatgt agacttccac acaataataa tgggagactt 155340
taacactcca ctgtcaatat tagacagatc aatgacacag aagggtcaca aagatatcca 155400
ggacttgaat tcagctattc accaagtgga cctaatagac atctacagaa ctctacaccc 155460
caaatcaaca gaatgtacat acttctcagc accacatcat acttattcta aaattgacca 155520
cataattgga agtaaaacac tcctcagcaa atgtaaaaga acagaaatca caacaaactg 155580
tgtctcagac tacagtgcaa acaaattaga actctggatt aataaactca ctcaaaatca 155640
cacaactaca tggaaactga ataacctgct cctgaatgac tactgggtac ataatgaaat 155700
gaaggcagaa ataaagatgt tctttgcaac caataagaac aaagacacaa cataccagat 155760
tctccgggac acatttaaag cagtgtgtac agggaaaatt atagcactaa atgcccacaa 155820
gagaaagcag gaaagaacta aaatcaacaa cctaacatcg caattaaaag aactagagaa 155880
gcaagagcaa acacattcaa aagctagcag aaggcaagaa ataactaaga tcagaacaga 155940
actgaaggag atagagacac aaaaagcact tcaaaaaaat caatgaatcc aggagctggt 156000
ttttaaaaag atcaacaaaa ttaatagacc gctagcaaga ataataaaga aaagagagaa 156060
gaatcaaatt agactcaata aaaaaagata aaggggatat caccactgat cccatagaaa 156120
tacaaactac catcagagaa tactataaac acctctacat aaataaacta gaaaatctag 156180
aagaaggggg aggagccaag atggccaaat aggaacagct ccagtctaca gctcccagcg 156240
tgagtgacac agaagacggg tgatttctgc atttccatct gaggtaccgg gttcatctca 156300
ctagggagtg ccagacagtg ggcacaggtc agtgggtgcg cgcactgtgt gcgagccaat 156360
gcagggtgag gcgttgcctc actcgggatg tgcaaggggt cagagagttc cctttcctag 156420
tcaaagaaag gggtgacaga tggcacctgg aaattcgggt cactcccacc tgaatactgc 156480
acttttccaa cgggcttaaa aaacggcgca cctggagagt atatcccgca cctggcttgg 156540
```

-continued agggtcctat gcccacggag tcttgctgat tgctagcaca gcagtctgag atcaaactgc 156600
aaggcagcgg cgaggctggg ggaggggcgc ctgccattgc ccaggcttgc ttaggtaaac 156660
aaagcagctg ggaacctcaa actgggtgga tcccaccaca gctcaaggag gcctgcctgc 156720
ctctgtaggc tccacctctg gggcagggc acaggcaaac aaaaagacag cagtaaccac 156780
tgcagactta aatgtccctg tctgacagct ttgaagagag cagtggttct cccagcacgc 156840
agctggagat ctgagaacgg gcagactgcc tcctcaagtg ggtccctgac ccctgacccc 156900
cgagcagcct aactgggagg catccccgag cagaggcaga ctgacacctc acacagccgg 156960
gtactccaac agacctgcag ctgagggtcc tgtctgttag aaggaaaact aacaaacaga 157020
aggacatcca caccaaaaac ccatctgtac atcaccatca tcaaagacca aaagtagata 157080
aaaccacaaa gatggggaaa aaacagagca gaaaaactag aaactctaaa aggcaaagcg 157140
cctctcctcc tccaaaggaa tgcagttcct caccaggaat ggaacaaagc tggacggaga 157200
atgactttga cgagctgaga gaagaaggct tcagatgatc aaattactcc gaactacggg 157260
aggacattca aaccaaaggc aaagaagttg aaaacgttca aaaaatttag aagaatgtat 157320
aactagaata accaatacag agaagtgctt aaaggagctg atggagctga aaaccaaggc 157380
tcgagaacta cgtgaagact caggagccga tgcgatcaac tggaagaaag ggtatcagcg 157440
atggaagatg aaatgaatga aatgaagtga gaaggaaagt ttagagaaaa aagaataaaa 157500
agaaatgaac aaagcctcca agaaatatgg gactatgtga aaagaccaaa tctacatctg 157560
attggcgtac ctgaaagtga cggggagaat ggaaccaagt tggaaaacac tctgcaggat 157620
attatccagg agaacttccc caatctagca aggcaggcca acattcagat tcaggaaata 157680
cagagaacgc cacaaagata ctcctcgaga agagcaacac caagacacat aattgtcaga 157740
ttcaccaaag ttgaaatgaa gggaacaatg ttaagggcag ccagagagaa aggtcgggtt 157800
accctcaaag ggaagcccat cagactaaca gcggatctct cggcagaaac tctacaagcc 157860
agaagagagt ggtggccaat attcaacatt cttaaggaaa agaattttca aaccagaatt 157920
tcatatacag ccaaactaag cttcataagt gaaggagaaa taaaatcctt tacagacaag 157980
caaatgctga gaaattttgt caccaccagg cctgccctaa aagagctcct gaaggaagtg 158040
ctaaacatgg aaaggaacaa ccggtaccag ccgctgcaaa atcatgccaa aatgtaaaga 158100
ccatcgaggc taggaagaaa ctgcatcaac taacgagcaa aacaacctgc taacatcata 158160
atgacaggat caaattcaca cataacaata ttaactttac atgtaaatgg actaaatgct 158220
gcaattaaaa gacacagact ggcaaattgc ataaagattc aagacccatc agtgtgctgt 158280
attcaggaaa cccatctcac gggcagagac acacataggc tcaaaataaa gggatggagg 158340
aagacctacc aagcaaatgg aaaacaaaaa aaaggcaggg gttgcaatcc tagtctctga 158400
taaaacagac tttaaaccaa cacagatcaa aagagacaaa gaaggccatt acttaatggt 158460
aaagggatca attcaacaag aagagctaac aatcctaaat atatatgcac ccaatacagg 158520
agcacccaga ttcataaagc aagtcctgag tgacctacaa agagacttag actaccacac 158580
attaataatg ggaaacttta acaccccact gtcaacatta gacagatcaa caagacagaa 158640
agtcaacaag gatacccagg aattgaactc agctctgcac caagcagacc taatagacat 158700
ctacagaact ctccacccca aatcaacaga atatacattt ttttcagcac cacaccatac 158760
ctatttcaaa attgaccaca tacttggaag taaagctctc ctcagcaaat gtaaaagaac 158820
agaaattata acaaactgtc tctctaacca cagtgcaatc aaactacaac tcaggatgaa 158880

-continued

```
gaaactcact caaaactgct caactacatg gaaactgaac aacctgctcc tgaatgacta 158940
ctgggtacac aacgaaatga aggcagaaat aaagatgttc tttgaaacca atgagaacaa 159000
agacacaaca taccagaaat tctgggatgc attcaaagca gtgtgtagag ggaaatttgt 159060
agcactaaat gcccacaaga gaaagcagga aagatccaaa attgacaccc taacatcaca 159120
attaaaagaa ctagaaaagc aagagcaaac acattcaaaa gctagcagaa ggcaagaaat 159180
aactaaaatc agagcagaac tgaaggaaac agagacaaaa aaaacccttc aaaaattaat 159240
gaatccagga gctggttttt tgaaaggatc aacaaaattg atagaccgct agcaagaata 159300
ataaagaaaa aaagagagaa gaatcaaata gatgcaataa aaaatgataa aggggatatc 159360
accaccgatc ccacagaaat aaaaactatc atcagagaat actacaaaca cctctatgca 159420
aataaactag aaaatctaga agaaatggat aaattcctcg acacatacac tctcccaaga 159480
ctaaaccagg aagaagttga atctctgaat agaccaataa caggagctga aattgtggca 159540
ataatcaata gcttaccaac caaaaagagt ccaggaccag atggattcac agccgaattt 159600
taccagaggt acaaggagga actggtacca ttccttctga aactattcca atcaatagaa 159660
aaagagggaa tcctccctaa ctcattttat gaggccagca tcatcctgat accaaagccg 159720
ggcagagaca aaaccaaaaa agaggatttt agaccaatat ccttgaggaa cattgatgcc 159780
aaaatcctca ataaaatact ggcaaaccaa atccagcagc acatcaaaaa gcttatccac 159840
catgatcaag taggcttcat ccctaggatg caaggcttgt tcaacatatg caaatcaata 159900
aatgtaatcc agcatataaa cagaaccaaa gacaaaaacc acatgattat ctcaatagat 159960
gcagaaaagg cctttgacaa aattcaacaa cacttcatgt taaaaactct caataaatta 160020
ggtattgctg ggacgtatct caaaataata agagctatct atgtcaaacc cacagccaat 160080
atcatactga atgggcaaaa actggaagca ttccctttga aaattggcac aagacaggga 160140
tgccctctct caccactcct attcaacata gtgctggaag atctgtccag ggcaatcagg 160200
caggagaagg aaataaaggg tattcaatta ggaaaagagg aagtcaaatt gtccctgttt 160260
gcagatgaca tgattttata tctagaaaac cccattgtct cagcccaaaa cctccttaag 160320
ctgataagca acttcagcaa agtctcagga tacaaaatca atgtacaaaa atcacaagca 160380
ttcttataca ccaacaacag acaaacagag agccaaatca tgagtgaact cccattcaca 160440
attgcttcaa agagaataaa atacctagga atccacctta caagggatgt gaagcacctc 160500
ttcaaggaga actacaaacc actgctcaac gaaataaaag aggatacaaa caaatggaag 160560
aacattccat gctcatgggt aggaagaatc aatattgtga aaatggccat actgcccaag 160620
gtaatttaca gattcaatgc catccccatc aagctaccaa ttactttctt cacataattg 160680
gaaaaaacta ctttaaagtt catatggaac caaaaaagag cccgcatcac caagtcaatc 160740
ctgagccaaa agaacaaggc tggaggcatc acactacctg acttcaagct atactacaag 160800
gctacagtaa ccaaaacagc ttggtactgt taccaaaaca gagatataga tcaatggaac 160860
agaacagagc cctcagaaat aatgctgcat atcgacaact gtctgatctt tgacaaacct 160920
gagaaaaaca agaaatgggg aaaggattcc ctatttaata aatggtgctg ggaaaactgg 160980
ctagccatat gtagaaagat gaaactggat cccttcctta caccttatac aaaaattaat 161040
tcaagatgga ttaaagactt aaatgtcaga cctaaaacca taaaaaccct agaagaaaac 161100
ctaggcatta ccattcagga cataggcatg ggcaaggact tcatgtctaa aacaccaaaa 161160
gcaatggcaa caaaagccaa aattgacaaa tgggatctaa ttaaactaaa gagcttctgc 161220
acagcaaaag aaactaccat cagagtgaat aggcaaccta cagaatggga gaaaattttt 161280
```

-continued

```
gcaatctact catctgacaa agggctaata ttcagaatct acaaagaact taaacaaatg 161340
ttcaagaaaa aaacaacccc atcaaaaagt gggcaaaata catgaaaaga cacttctcaa 161400
aagaagacat ttatgcagcc aacagacaca tgaaaaaatg ctcatcatca ctggccatca 161460
gagaaatgca aatcaaaacc acaatgagat accatctcac accagttaga atgacgatca 161520
ttaaagtcag gaaacaacag atgctggaga ggacatggag aaataggaat gcttttacac 161580
tgttggtggg ggtgtaaatt agttcaatca ttgttgaaga cagtgtggca attcctcaag 161640
gatctagaac tagaaatacc atttgaccca gcaatcccat tactgggtat ataccgaaaa 161700
gattacaaat ggtgcaacta taaagacaca tgcacacgaa tgtttattgt ggcactattc 161760
acaatagcaa agacttctaa caaacccaga tgtccatcaa tgatagactg gattaagaaa 161820
atgtggcaca tatacaccat ggaatactat gcagccataa aaaaggatga gttcatgtcc 161880
ttttcaggga catggatgaa gctggaaacc atcattctca gcaaactatg acaaggacag 161940
aaaaccaaac accgcatgtt ctcactcata gatgggaact gaacaatgag aacacttgga 162000
cacagggcag ggaacatcac acaccagggc ctgttggggg gtggtggact gggggagaga 162060
tagcattagg agaaatacct aatgtaaatg atgagttgat ggatgcagca aaccaacagg 162120
gcacatctat acctatgtaa gaaacctgca ctttgtgcac aggtacccta gaacttgaag 162180
tataataaaa atgaaaaaaa gaaaatgtta ctagcaaatt gtagatgggt atacctaata 162240
taactctgca tgtgcactat gtgtctggat acacatggaa agtattcagg catacacacc 162300
aaattgttaa aataaatccc cttccaacat taggagtggc tggggagcag atggctttca 162360
cttccgcaca ttccatggtg ccagggtaat accacatcac aatagtaaat agcaaaaata 162420
acaaccttaa gtttagattt tcttatctaa attttaattc tgtgaagaag tttccatttc 162480
cctttttcac acaggatagt agaatgcagt ttagaaagag tgagatcact tgttagactg 162540
tacaattttt aagcatcagc gaagtatacc attaaacttc tctatcaatc cattctctaa 162600
acttcccaac ccaaaaaaaa agaaacacat aaaattgaaa tgaagaaaac aatacaaaag 162660
atcaacaaaa atgaaaggtt ggctttttaa agagataaac aaaattgaca aatgtttagc 162720
cagactaaga aaaagagaag gcccaaataa ataaaatcag agatgaaaaa gcagacatta 162780
taactgatac tgcggaaatt caaaggatca ttaatggcta ctatgagcaa ctgtatgcca 162840
aacattggaa aatattgaag aaatagataa attcgtagac acacgcaacc taacaagatt 162900
caaccatgaa gaaattcaaa atctgaacag accaaaaaca agtaacaaga tcaaagccat 162960
aattaaaatt ttcccagcaa agaaaagcct gagacccaat ggcttcactg ctgaattcta 163020
tcaaacattt aaagaactaa taccaatcct actcaaacta ttccaaaaag tagaagagga 163080
gggaatattt ccaaacttat tctatgaggc cattactgct cctatatcaa aaccaaggac 163140
acatcaaaaa aagaaaacta taggccaata tctcacatga atattgatga atcctcaaaa 163200
aatgctagca aactgaattc aacatcacat taaaaatcat tcattatgac caaatgggat 163260
ttatcccagg gatgcaaata tggttcaaca tatacacatc agtcagtgta acatatcata 163320
tcaacagaat gaagaagaaa aaccatatgg tcatgttaat tgatgctgaa aaagtatttg 163380
agagaattaa acatctcttc atgacaaaaa ccctcaaaaa cactggagac agaaggaaca 163440
tacctcaaca caataaacag acatatatga cagactcaca gctagaatca tactaaatgg 163500
ggagaaactg aaagtcattc ctctaagatc tggaacaaga caaggatgct cattttcacc 163560
agtgttagtg gaacatagta ctgaaagtcc tagctagaac agactagaga cagaaataag 163620
```

-continued gggcatccaa actgggaaga gagaagtcaa attacctttg ttcgcagatg gtatgatctt 163680
ctgtttggaa aaacctagac tccataaaaa aatgattaga actgataaat tcagtaaagt 163740
ttcaggatac aaaattaaca tacaaaaatc agtagcattt ctatatgtca atagcaaaca 163800
atctgaaaat gaaatcaagg aagtaatccc atttcccatt tgcaatagct ataaataaaa 163860
ttaatataat ctcatctctt caataagtgg tgttgggaaa actgcatatc cacatacaaa 163920
agaataaaat tagacccttt taatatacaa aactggaccc aagttaatat acaaaaatta 163980
acttgaaatg aattaaagac ttaaatgtaa gatctgaaac caaaaactcc tagagagaaa 164040
cataggggaa aagctccttg acgttggcct tggcaataat tttttgggat attacaccaa 164100
aagcacagac ttttgaaaaa ataaacaagt aggactacat caaactaaaa agcttctgca 164160
tggcaaaaga aagtcaacaa catgaaaagg caacctacag aatggaggga aatatttgca 164220
aaccatatac ctgatgagaa gttaatatca aaatatagaa aatatataag gaactcacat 164280
atctcaatac caaaaaaata ataacctgtt ttataatggg caaaggacct gaatagacat 164340
tttttcaaag aagacacaca gatggccaac gagtgcagga aaaagcgttc aacatcacta 164400
atcatcaggg aaatgcaaat caaaaccaca atgagatatc actccacacc tgttaggaaa 164460
gctattatga aaaacacaag agacaatgaa tattggcaag ggcatggaga aaaaagaacc 164520
cttgtacact gttggtagaa atgtaaattg caacagcctt tatggaaaat agaatggagg 164580
ttcctcaaaa aataaaaata gaactaccat acaatctagc aattccactt atgagtgtac 164640
atccaaagga atcaaatcac tatgtcaaag agatatctgt acttccttgt ttattgcagc 164700
tttactcaca gtagccaaga taaggaaaaa atctaaatgt ccatcaacgg ataaagaaaa 164760
tggggggagg ggtgtgcatg tatacataca caatggacta tttttcagcc ataacaaaga 164820
aggaaaccct gccatttgtg acgatatgaa tgaacccaga ggacattatg ttaagtgaaa 164880
taagccagac acagaaatac aaatattgta tgatctcatt tatatgcgaa tctaaaaatt 164940
tcaaacttga agacgaataa gtagaacagt atttatcagg agctagggga tgtggggaag 165000
aagcaaaata ttgggcaaag agtataaact ttcagttatg agatgaaggc caggtgcgat 165060
ggctcatgtt ggtaatccca atactttgga aggctgaggc agagggattg cttgagacca 165120
gcctaggcaa gaaagtgaga cctcatctct acaaaaaata aaaataaaag aatcagctgg 165180
gagtggtggc atacacctgt agtcccagct agtcaggagg ctgagggggg aggatcattt 165240
gaaattggaa agtcaaggct gcagtcagcc aagatagtgc cactgcattg cagcctgggt 165300
gacagagcga aaccctgtct caaaaaaaaa aaaaaaaaaa agatgaataa gttctgggga 165360
tcaaatgtac agcatggtga ctatagttta taactgcgtt attacttgaa attggataag 165420
agcagatttt aagcatcccc agcacccccc caacatacac acacacaaat ggtaactata 165480
ggtggtgata gatatgttaa tttgactgtg acaatcagca ttcaatatat acatatatca 165540
aatcatcaca ttttacccct tgaaatagaa actttgattt gtcaatcaaa tattttaaaa 165600
cgaaaataat cataatatta atatagcata caggaaaaaa tttcgtatct cgactgatac 165660
agaaaatttc atgataaaaa cactttaaaa caaaagaaat aaaagggaac tccctcaacc 165720
tgataaatgg catctgtgga aacccccagc tagcatcaaa cttaatacag aaaggctggg 165780
tgttcacctc ttgaaccagg aacaagacaa agatgcctgc ttttgccact tccatttgac 165840
cttgtactga ggttctggct agggcaatta tccctgaaaa agaaataaaa ggcttccaaa 165900
taaaagaaga agtaaaacta tctctactcg ctcatgacat gatcttgcat atagaaaatg 165960
tgcacatgta cacacacaca aaccattaga actaataaac aagttcagca agtttgcaga 166020

-continued atataaaatg aatgtacaaa aatcaagtgt ttttctatat actagcaatt aacaatctca 166080
aaatgaatta aaattccatt tacaatagta tcaaacataa attatttaga aataaaaagt 166140
gcactgaaaa ctacaaaata ttttgaaata aatcagaaaa gatttaagta aatggatcac 166200
ttgaacctgg gaagcagagg ttgcagtgtg ccgagattgt accactgcac tttagcctgg 166260
gcaacagagg gagactccaa agagtcgaaa agaaaagaaa agatttaaat aagctgaaac 166320
atattctatg gatcagaaga cttaatattg ttaaagtgac aatattcccc aaattgatct 166380
acagcttcaa ctcaacccct atcaaaatcc tagcttgctt tttggctgaa attgacaagc 166440
tgattctata atttatatgg aatctcaaag gatccagaat aaccaaaaca atattgaaaa 166500
ataaagaaca gcgttggtgg attaacattt tccaatttca aaacttacta tagcactgcg 166560
gtaatcaagc agtgtggcac tgtatagcat gtacattaca gatcagtgga ctagaatcaa 166620
tgtccagaaa taaaccgtta tgtttataat gaattacttt ttaataaggt gtcaagacaa 166680
cgcaatggga aaagaataat gaattcaaca aatgatgcat ggacaaccgg acatgcacat 166740
gcaacacaat gaatttgaat tcttctatcg ctccatgcat aaaaactaac tcaaaatggg 166800
tcacggatgt aaatgaaaag ctaaaactat aataatccta gaggaaaacc taggagtaaa 166860
tctttaagat gttattgtag gcagtggttt ctcagatagg accccaaaat cacaagcgac 166920
aaaagaaatt ggacttaaag ttaaatactt ttgtgcttca aacatcatca agaaagtgaa 166980
aacacaaccc gcagaagcaa taaaaatgtc tgtaagtcat gtatccgatt agagacttct 167040
atccaggata tataaataat gcaattcaat gataaaaaag ataaatagcc cagttttcca 167100
aagagtcaag catctgaata tacatctctc caaaaatata cagatatcca acaagcatgt 167160
gaaaagatgt tcaaagccat ttgccaggtg cacaaaccca agacagtatg aggagatgct 167220
acagggactc tgctgcttca cagacatgaa gcgttggtga gaatgtaggc agccgccttt 167280
ggggacttca catccccgcc gccccacgca cggtgagcta gtgtttaaac ttagccgaga 167340
tcaatacacg cgactgtgtg cccgtcagac cctgcgctgc cggcggggct gggagaggcg 167400
ggcgccagga gtgggcggga acctgggggt caggccccag ccgcgggaag ccgcccagga 167460
gcgcgcgaaa ccttctccac acccttccag gcatttgccc gccgcgattc agagagccga 167520
cccgtgaccc ctggcctccc ctagacagcc ccgcatgtcc agatgtgccg tcccgcctgc 167580
ctcccgcgac cactggccat ctctgggcct gggcgcggtc tcggcgcccg cctgcccccg 167640
ccaggagccg caggtccagc cagtgaagaa gcccgcgctg aaggagcctc tgtgctccag 167700
aatccatcct cagtatcagc gctggggtgg cctcctccag gaagcccttc tgattctctc 167760
atgggtcgct cttcctctgc agactcccgg agcacccctg ctccaagtac cgcaagtggc 167820
actgagaact tggggagagc agaggctgtg cctagatttg tagggagtcc ccgcagctcc 167880
accccagggc ctacaggagc ctggccttgg gcgaagccga ggcaggcagg cagggcaaag 167940
ggtggaagca attcaggaga gaacgagtga acgaatggat gaggggtggc agccgaggtt 168000
gccccagtcc cctggctgca ggaacagaca cctcgctgag gagagaccca ggagcgaggc 168060
ccctgccccg cccgaggcga ggtcccgccc agtcggcgcc gcgtgaagag tgggagagaa 168120
tactgcgggg gcgggggcgg gggcgggggc gggggcgggg gccgccggga gcctggagcc 168180
agaccgggcg gggccggcac cgggccaggg acagtggggg aggaggctgc gggctgagcg 168240
accctgaccc cccccagtcc gcgctggttc cgg 168273

<210> SEQ ID NO 3

-continued

<211> LENGTH: 2497
<212> TYPE: DNA
<213> ORGANISM: Homo sapiens

<400> SEQUENCE: 3
gggcgccgag gctccccgcc gctcgctgct ccccggcccg cgccatgccc tcctacacgg 60
tcaccgtggc cactggcagc cagtggttcg ccggcactga cgactacatc tacctcagcc 120
tcgtgggctc ggcgggctgc agcgagaagc acctgctgga caagcccttc tacaacgact 180
tcgagcgtgg cgcggtggat tcatacgacg tgactgtgga cgaggaactg ggcgagatcc 240
agctggtcag aatcgagaag cgcaagtact ggctgaatga cgactggtac ctgaagtaca 300
tcacgctgaa gacgccccac ggggactaca tcgagttccc ctgctaccgc tggatcaccg 360
gcgatgtcga ggttgtcctg agggatggac gcgcaaagtt ggcccgagat gaccaaattc 420
acattctcaa gcaacaccga cgtaaagaac tggaaacacg gcaaaaacaa tatcgatgga 480
tggagtggaa ccctggcttc cccttgagca tcgatgccaa atgccacaag gatttacccc 540
gtgatatcca gtttgatagt gaaaaaggag tggactttgt tctgaattac tccaaagcga 600
tggagaacct gttcatcaac cgcttcatgc acatgttcca gtcttcttgg aatgacttcg 660
ccgactttga gaaaatcttt gtcaagatca gcaacactat ttctgagcgg gtcatgaatc 720
actggcagga agacctgatg tttggctacc agttcctgaa tggctgcaac cctgtgttga 780
tccggcgctg cacagagctg cccgagaagc tcccggtgac cacggagatg gtagagtgca 840
gcctggagcg gcagctcagc ttggagcagg aggtccagca agggaacatt ttcatcgtgg 900
actttgagct gctggatggc atcgatgcca acaaaacaga cccctgcaca ctccagttcc 960
tggccgctcc catctgcttg ctgtataaga acctggccaa caagattgtc cccattgcca 1020
tccagctcaa ccaaatcccg ggagatgaga accctatttt cctcccttcg gatgcaaaat 1080
acgactggct tttggccaaa atctgggtgc gttccagtga cttccacgtc caccagacca 1140
tcacccacct tctgcgaaca catctggtgt ctgaggtttt tggcattgca atgtaccgcc 1200
agctgcctgc tgtgcacccc attttcaagc tgctggtggc acacgtgaga ttcaccattg 1260
caatcaacac caaggcccgt gagcagctca tctgcgagtg tggcctcttt gacaaggcca 1320
acgccacagg gggcggtggg cacgtgcaga tggtgcagag ggccatgaag gacctgacct 1380
atgcctccct gtgctttccc gaggccatca aggcccgggg catggagagc aaagaagaca 1440
tcccctacta cttctaccgg gacgacgggc tcctggtgtg ggaagccatc aggacgttca 1500
cggccgaggt ggtagacatc tactacgagg gcgaccaggt ggtggaggag gacccggagc 1560
tgcaggactt cgtgaacgat gtctacgtgt acggcatgcg gggccgcaag tcctcaggct 1620
tccccaagtc ggtcaagagc cgggagcagc tgtcggagta cctgaccgtg gtgatcttca 1680
ccgcctccgc ccagcacgcc gcggtcaact tcggccagta cgactggtgc tcctggatcc 1740
ccaatgcgcc cccaaccatg cgagccccgc caccgactgc caagggcgtg gtgaccattg 1800
agcagatcgt ggacacgctg cccgaccgcg gccgctcctg ctggcatctg ggtgcagtgt 1860
gggcgctgag ccagttccag gaaaacgagc tgttcctggg catgtaccca gaagagcatt 1920
ttatcgagaa gcctgtgaag gaagccatgg cccgattccg caagaacctc gaggccattg 1980
tcagcgtgat tgctgagcgc aacaagaaga agcagctgcc atattactac ttgtccccag 2040
accggattcc gaacagtgtg gccatctgag cacactgcca gtctcactgt gggaaggcca 2100
gctgccccag ccagatggac tccagcctgc ctggcaggct gtctggccag gcctcttggc 2160
agtcacatct cttcctccga ggccagtacc tttccattta ttctttgatc ttcagggaac 2220

-continued

```
tgcatagatt gtatcaaagt gtaaacacca tagggaccca ttctacacag agcaggactg   2280

cacaggcgtc ctgtccacac ccagctcagc atttccacac caagcagcaa cagcaaatca   2340

cgaccactga tagatgtcta ttcttgttgg agacatggga tgattatttt ctgttctatt   2400

tgtgcttagt ccaattcctt gcacatagta ggtacccaat tcaattacta ttgaatgaat   2460

taagaattgg ttgccataaa aataaatcag ttcattt                            2497


<210> SEQ ID NO 4
<211> LENGTH: 21
<212> TYPE: DNA
<213> ORGANISM: Homo sapiens

<400> SEQUENCE: 4

aggagcgcgc aaaaccttct c                                               21


<210> SEQ ID NO 5
<211> LENGTH: 20
<212> TYPE: DNA
<213> ORGANISM: Homo sapiens

<400> SEQUENCE: 5

tggacttaaa tacttttgtg                                                 20


<210> SEQ ID NO 6
<211> LENGTH: 21
<212> TYPE: DNA
<213> ORGANISM: Homo sapiens

<400> SEQUENCE: 6

tcatgtatcc aattagagac t                                               21


<210> SEQ ID NO 7
<211> LENGTH: 21
<212> TYPE: DNA
<213> ORGANISM: Homo sapiens

<400> SEQUENCE: 7

acttactata acactgcggt a                                               21


<210> SEQ ID NO 8
<211> LENGTH: 21
<212> TYPE: DNA
<213> ORGANISM: Homo sapiens

<400> SEQUENCE: 8

ttacagatca atggactaga a                                               21


<210> SEQ ID NO 9
<211> LENGTH: 18
<212> TYPE: DNA
<213> ORGANISM: Homo sapiens

<400> SEQUENCE: 9

gggccaggga ccagtggt                                                   18


<210> SEQ ID NO 10
<211> LENGTH: 18
<212> TYPE: DNA
<213> ORGANISM: Homo sapiens

<400> SEQUENCE: 10
```

|  |  |
|---|---|
| aaccgggtcc cggacgca | 18 |

<210> SEQ ID NO 11
<211> LENGTH: 19
<212> TYPE: DNA
<213> ORGANISM: Homo sapiens

<400> SEQUENCE: 11

|  |  |
|---|---|
| aggctcagga gaccacgca | 19 |

<210> SEQ ID NO 12
<211> LENGTH: 16
<212> TYPE: DNA
<213> ORGANISM: Homo sapiens

<400> SEQUENCE: 12

|  |  |
|---|---|
| tcccgcccct gcacag | 16 |

<210> SEQ ID NO 13
<211> LENGTH: 24
<212> TYPE: DNA
<213> ORGANISM: Homo sapiens

<400> SEQUENCE: 13

|  |  |
|---|---|
| cattgggcat tgttattgtt cttc | 24 |

<210> SEQ ID NO 14
<211> LENGTH: 25
<212> TYPE: DNA
<213> ORGANISM: Homo sapiens

<400> SEQUENCE: 14

|  |  |
|---|---|
| agttgtaggt aaggtgaagt ttggg | 25 |

<210> SEQ ID NO 15
<211> LENGTH: 19
<212> TYPE: DNA
<213> ORGANISM: Homo sapiens

<400> SEQUENCE: 15

|  |  |
|---|---|
| tcgtctgaca gtgtgggcg | 19 |

<210> SEQ ID NO 16
<211> LENGTH: 22
<212> TYPE: DNA
<213> ORGANISM: Homo sapiens

<400> SEQUENCE: 16

|  |  |
|---|---|
| ccatgaggaa aggagtgagg gt | 22 |

<210> SEQ ID NO 17
<211> LENGTH: 19
<212> TYPE: DNA
<213> ORGANISM: Homo sapiens

<400> SEQUENCE: 17

|  |  |
|---|---|
| tggtgtgaag gggctctgc | 19 |

<210> SEQ ID NO 18
<211> LENGTH: 25
<212> TYPE: DNA
<213> ORGANISM: Homo sapiens

<400> SEQUENCE: 18

-continued aagtatcaga caggagagca gcatc 25

<210> SEQ ID NO 19
<211> LENGTH: 21
<212> TYPE: DNA
<213> ORGANISM: Homo sapiens

<400> SEQUENCE: 19
gcctcgcttt tctcctggta g 21

<210> SEQ ID NO 20
<211> LENGTH: 19
<212> TYPE: DNA
<213> ORGANISM: Homo sapiens

<400> SEQUENCE: 20
ccacttcccc agcccatca 19

<210> SEQ ID NO 21
<211> LENGTH: 22
<212> TYPE: DNA
<213> ORGANISM: Homo sapiens

<400> SEQUENCE: 21
gatttttggt ccgtctgctg ag 22

<210> SEQ ID NO 22
<211> LENGTH: 18
<212> TYPE: DNA
<213> ORGANISM: Homo sapiens

<400> SEQUENCE: 22
gaaaggtgtg ccccccag 18

<210> SEQ ID NO 23
<211> LENGTH: 22
<212> TYPE: DNA
<213> ORGANISM: Homo sapiens

<400> SEQUENCE: 23
tttcctttcc cccaatgtat ca 22

<210> SEQ ID NO 24
<211> LENGTH: 18
<212> TYPE: DNA
<213> ORGANISM: Homo sapiens

<400> SEQUENCE: 24
gggcggtagc tggctgta 18

<210> SEQ ID NO 25
<211> LENGTH: 18
<212> TYPE: DNA
<213> ORGANISM: Homo sapiens

<400> SEQUENCE: 25
gagctgcggg tccctgag 18

<210> SEQ ID NO 26
<211> LENGTH: 20
<212> TYPE: DNA
<213> ORGANISM: Homo sapiens -continued

<400> SEQUENCE: 26
agatagggag tgaaggcggc 20

<210> SEQ ID NO 27
<211> LENGTH: 18
<212> TYPE: DNA
<213> ORGANISM: Homo sapiens

<400> SEQUENCE: 27
agccacccgc tcagggca 18

<210> SEQ ID NO 28
<211> LENGTH: 17
<212> TYPE: DNA
<213> ORGANISM: Homo sapiens

<400> SEQUENCE: 28
aggcaggggt cccggct 17

<210> SEQ ID NO 29
<211> LENGTH: 17
<212> TYPE: DNA
<213> ORGANISM: Homo sapiens

<400> SEQUENCE: 29
tccgcagacc tggctgg 17

<210> SEQ ID NO 30
<211> LENGTH: 16
<212> TYPE: DNA
<213> ORGANISM: Homo sapiens

<400> SEQUENCE: 30
gaggggtggc ggaggg 16

<210> SEQ ID NO 31
<211> LENGTH: 18
<212> TYPE: DNA
<213> ORGANISM: Homo sapiens

<400> SEQUENCE: 31
ccggtggttc caccctag 18

<210> SEQ ID NO 32
<211> LENGTH: 19
<212> TYPE: DNA
<213> ORGANISM: Homo sapiens

<400> SEQUENCE: 32
gggaggaggc agcggcctt 19

<210> SEQ ID NO 33
<211> LENGTH: 17
<212> TYPE: DNA
<213> ORGANISM: Homo sapiens

<400> SEQUENCE: 33
tgctggcggt cgtctcc 17

<210> SEQ ID NO 34
<211> LENGTH: 16
<212> TYPE: DNA
<213> ORGANISM: Homo sapiens -continued

<400> SEQUENCE: 34
cgccctgccc agcttc 16

<210> SEQ ID NO 35
<211> LENGTH: 28
<212> TYPE: DNA
<213> ORGANISM: Homo sapiens

<400> SEQUENCE: 35
tgggatgatt attttctgtt ctatttgt 28

<210> SEQ ID NO 36
<211> LENGTH: 25
<212> TYPE: DNA
<213> ORGANISM: Homo sapiens

<400> SEQUENCE: 36
gagtagacac tgcttgaggg aaaaa 25

<210> SEQ ID NO 37
<211> LENGTH: 18
<212> TYPE: DNA
<213> ORGANISM: Homo sapiens

<400> SEQUENCE: 37
gcgtcctgtc cacaccca 18

<210> SEQ ID NO 38
<211> LENGTH: 26
<212> TYPE: DNA
<213> ORGANISM: Homo sapiens

<400> SEQUENCE: 38
tgaactgatt tatttttatg gcaacc 26

<210> SEQ ID NO 39
<211> LENGTH: 18
<212> TYPE: DNA
<213> ORGANISM: Homo sapiens

<400> SEQUENCE: 39
gcccgattcc gcaagaac 18

<210> SEQ ID NO 40
<211> LENGTH: 24
<212> TYPE: DNA
<213> ORGANISM: Homo sapiens

<400> SEQUENCE: 40
gaggaagaga tgtgactgcc aaga 24

<210> SEQ ID NO 41
<211> LENGTH: 25
<212> TYPE: DNA
<213> ORGANISM: Homo sapiens

<400> SEQUENCE: 41
cagtttacac gggtagtgga ttgac 25

<210> SEQ ID NO 42
<211> LENGTH: 23
<212> TYPE: DNA

<213> ORGANISM: Homo sapiens

<400> SEQUENCE: 42
gaagagatgt gactgccaag agg 23

<210> SEQ ID NO 43
<211> LENGTH: 23
<212> TYPE: DNA
<213> ORGANISM: Homo sapiens

<400> SEQUENCE: 43
cctcttggca gtcacatctc ttc 23

<210> SEQ ID NO 44
<211> LENGTH: 28
<212> TYPE: DNA
<213> ORGANISM: Homo sapiens

<400> SEQUENCE: 44
acaaatagaa cagaaaataa tcatccca 28

<210> SEQ ID NO 45
<211> LENGTH: 23
<212> TYPE: DNA
<213> ORGANISM: Homo sapiens

<400> SEQUENCE: 45
ctaactcaaa atgggtcacg gat 23

<210> SEQ ID NO 46
<211> LENGTH: 20
<212> TYPE: DNA
<213> ORGANISM: Homo sapiens

<400> SEQUENCE: 46
attgcttctg cgggttgtgt 20

<210> SEQ ID NO 47
<211> LENGTH: 18
<212> TYPE: DNA
<213> ORGANISM: Homo sapiens

<400> SEQUENCE: 47
gagagccgac ccgtgacc 18

<210> SEQ ID NO 48
<211> LENGTH: 24
<212> TYPE: DNA
<213> ORGANISM: Homo sapiens

<400> SEQUENCE: 48
gctgatactg aggatggatt ctgg 24

<210> SEQ ID NO 49
<211> LENGTH: 21
<212> TYPE: DNA
<213> ORGANISM: Homo sapiens

<400> SEQUENCE: 49
tgaaaacaca acccgcagaa g 21

<210> SEQ ID NO 50
<211> LENGTH: 19

-continued

<212> TYPE: DNA
<213> ORGANISM: Homo sapiens

<400> SEQUENCE: 50
tgcacctggc aaatggctt 19

<210> SEQ ID NO 51
<211> LENGTH: 20
<212> TYPE: DNA
<213> ORGANISM: Homo sapiens

<400> SEQUENCE: 51
aaagaacagc gttggtggat 20

<210> SEQ ID NO 52
<211> LENGTH: 22
<212> TYPE: DNA
<213> ORGANISM: Homo sapiens

<400> SEQUENCE: 52
caaattcatt gtgttgcatg tg 22

<210> SEQ ID NO 53
<211> LENGTH: 24
<212> TYPE: DNA
<213> ORGANISM: Homo sapiens

<400> SEQUENCE: 53
aacttagccg agatcaatac acgc 24

<210> SEQ ID NO 54
<211> LENGTH: 19
<212> TYPE: DNA
<213> ORGANISM: Homo sapiens

<400> SEQUENCE: 54
gcaaatgcct ggaagggtg 19

<210> SEQ ID NO 55
<211> LENGTH: 24
<212> TYPE: DNA
<213> ORGANISM: Homo sapiens

<400> SEQUENCE: 55
gcacaaaccc aagacagtat gagg 24

<210> SEQ ID NO 56
<211> LENGTH: 18
<212> TYPE: DNA
<213> ORGANISM: Homo sapiens

<400> SEQUENCE: 56
cggcggggat gtgaagtc 18

<210> SEQ ID NO 57
<211> LENGTH: 20
<212> TYPE: DNA
<213> ORGANISM: Homo sapiens

<400> SEQUENCE: 57
tggcactgag aacttgggga 20

<210> SEQ ID NO 58

-continued

<211> LENGTH: 18
<212> TYPE: DNA
<213> ORGANISM: Homo sapiens

<400> SEQUENCE: 58
actggggcaa cctcggct 18

<210> SEQ ID NO 59
<211> LENGTH: 24
<212> TYPE: DNA
<213> ORGANISM: Homo sapiens

<400> SEQUENCE: 59
gctccagaat ccatcctcag tatc 24

<210> SEQ ID NO 60
<211> LENGTH: 21
<212> TYPE: DNA
<213> ORGANISM: Homo sapiens

<400> SEQUENCE: 60
gcctctgctc tccccaagtt c 21

<210> SEQ ID NO 61
<211> LENGTH: 6
<212> TYPE: DNA
<213> ORGANISM: Homo sapiens

<400> SEQUENCE: 61 ggcggg 6

<210> SEQ ID NO 62
<211> LENGTH: 6
<212> TYPE: DNA
<213> ORGANISM: Homo sapiens

<400> SEQUENCE: 62 gttaaa 6

<210> SEQ ID NO 63
<211> LENGTH: 168174
<212> TYPE: DNA
<213> ORGANISM: Homo sapiens
<220> FEATURE:
<221> NAME/KEY: misc_feature
<222> LOCATION: (1)...(168174)
<223> OTHER INFORMATION: n = A,T,C or G

<400> SEQUENCE: 63
ttgcacgctn ctcagccccg gctgtactat tggtctacac gtgccatcgt ggtttgctgc 60
acccatcaac ccatcatcta cattaggtat ttctcctaat gctctctttc cccttgcccc 120
ccaccctcta acacgccctg ttgtgtgatg ttgacctccc tgtgtacatg tgttgtcatt 180
gtacaactcc tgcttatgag tgacaacatc tgtctgattt tctgtcttgt gttagtttgc 240
tgagaatgat ggttcccatc ttcatccttg tacctgcaaa ggacatgaac tcatccttta 300
atatggctgc ttagaatccc acagtataga tgtgcctcat tttctttatc cagactatca 360
ttgatgggca tttgggttgg atccaagact ttgctattgt gaacagtgat tcaataaaca 420
tacgagtgca tgtgtcttta tggatgaatg attgataatc ctttgggcat atacccacta 480
atgggattgc tggacctaat ggtttgcctg gatcctgatc cttgaggaat caccacactc 540
tcttacagtg taaaagtgtc tctatatata ctcatcccct ccagcatctg ttatttactg 600

-continued

```
actctttaat catcaacctt cttactggag agagaaggtt taattaccac taatgacgag    660
cctttaatca aattgttgtt ggacccttcc caacttactt gcgaaggggt catttgtaaa    720
cttacgccac cttttgatgg ggcagttttt ctcgtttatc cgcaaagatc ctgggggacc    780
ccttttttta actcttttga agaccgttat atctgaacaa tttctcccat accgagaggt    840
ggcgggttac aacccttgaa agtttctttt tttttttggg gccccttagt ttcacaaaaa    900
tcccttcgga ccaatttgcc ttttgttgcc aaggaatttt tccccctaag tcactaggaa    960
tttttcccag ggcacacagg tgtagtggcc ttccccagaa tttttctcct gggtatccaa   1020
tgttataaga aaaaaaattg gggaattttt ttaaacctcc aataaaattt tttatagaga   1080
taaggccggt ttcatttnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnncgc   1200
ggtcttcagc ccgtggtgaa gactgattaa cagtcataag aaggtaaagc tctaagtgac   1260
ctgtaagaaa catacagtct cacacaatta ggcaaggagt ccaacttgga agaaagagtg   1320
gcatagattc aaaccctgat gccacaactt atgttaaccc tcctgaggct caacttctca   1380
cacatgacag gagaatctca tcatgtacct caattaattg atatacagat tatggtaaac   1440
attcaatgaa aaagtatgta aagtttctat cattctacta cagttggtat tcaacaaatg   1500
ccactttatt cactttctgt taagcctgaa agaagtactg aatgacatca acgagtgcaa   1560
ttcaacaaat ataatttgag cactgattac tcaataagca ttatgaggaa ctaaaatatt   1620
atcagcaaat gatggctgac atagaggaaa tgtgacagag taggaagatc cctgtactcc   1680
ctgtatcaaa ggactgagat tcttccactc aggaccatgt gtgaccccaa cagaaagtag   1740
aaatttacag aaagatacct ggcaaaacac ccaaatagtt tgaagttaaa aaatatacct   1800
ctgaataaca ccccatggaa atttttaaag attataatgt gaattaaaat gaaaacatat   1860
aaccataaca aaaattgtag gatacaggaa aactggtgct catatagcat taactgttta   1920
cattacattt tagagaatca acttaattca attatctaag tttctatttt agaaaactat   1980
gtaaaaaaag gagagcatat ttaaaaagta agcagaagaa caaaagataa gcatgacaga   2040
caatgaaatt gaaaatggaa aaatcataga gaagaatcaa atgaatcaaa agtagtttct   2100
tggaaaagat caataaataa aattggttga tataatttac tgatattagg agtgggaaag   2160
ataatcactg atcatagatc catgatgaac aagcttattt caataaatta ataaactcag   2220
caacttcaac aaaatggaca gattacttgg aagacaccaa ttaccaaagc tcaaaaaaag   2280
agaatctaaa tagtcctata tttatgaaaa aaaaaaacaa aactgaattt gtatttaaaa   2340
actttgccac aaagaaaatt ttaggttcag atgggtttcc taataaattt ttcccattta   2400
gtaagaataa tatcaattct acacaaactc attcaaaaaa aaaggagaga gaatacttta   2460
caacacgttc tgcaaggtca gtattaccct gataccaaaa caaaggatat tacataaaaa   2520
cgacaccaat atccttcatg aacatagatt cttcaccacg ggctggaag gatccgnnnn   2580
nnnnnnnnnn nnnnnnnnnn nnnnnnnnnn nnnnnnnnnn nnnnnnnnnn nnnnnnnnnn   2640
nnnnnnnnnn nnnnnnnnnn nnnnnnnnnn nnnnnnatag cacgcccttg agcccctggt   2700
gaatataaga gattaggcta cagcgtgttc tactccaact ttatttgctt tctgagcatc   2760
taattccact ttgcaaaatg gacatttttt ttccctcttg agagtcagga aattaccagg   2820
tgtgccagga taatccttag tatcaactgt aaaatatcag tataaaataa tgagtaagca   2880
tatttcagtg ggtgtttata tgcttttggt tgcatagcat gagccaaagg cagataaaaa   2940
```

-continued

```
atgtgggctc cagatagtga ctcaatctcc agaaatcata atgtcagtta cacaatgata   3000
tttctatatt ggcatcacaa aataatccac ttgtcatagg ataattgctc tagatgaggg   3060
catggagctg tgctgaggaa tctgccattt ttctttatcc agactctgtc tcataccgac   3120
cacaggcccc aatcattgtc tatcaaaaaa catgcttgtg tctcttttgg cttactatga   3180
aaggaagcaa gatcttttcc tcaagcattt aagtgttgac tgtgggctac ccagtgtgct   3240
agacactgng gatcaaattc tgtgaggtta aaaatacccc ataactcact ggatagaaat   3300
tcaaaatgct cgctatgttg attctatgat caacttccaa ggggaccttt ntacctccta   3360
tcttcatcag caagcaacta cattgatttt gtagcccagg atctattccc acgtcaaccg   3420
tgggtttcaa atgtttgctc tagctcaatg gcctcttaag ccactaaccc aatatgttgc   3480
tttttaccag taaaaaagtg catctgggga ataagttggt gtatatttgt ggttcagcca   3540
gcccatagat cgtccagagg accccaggct taggaggaat cctcagattt gagagccact   3600
gtcctgtatg atgcagatag cacagctctt cctgaaaata ggaattcaaa tgaggaaaaa   3660
tgaaaactct cctaattatt ttcttctgcc tctttcattc caagctcatc taattatcat   3720
gctctattgt gaagaatcaa agaaagaact cataaatata ccttttgtgc ctgtattttg   3780
aatgtacgtt gtgcatgtaa gcctttgtgg ttaagcaaat gtcaagaaaa tccctagtcc   3840
cattgcttac agtcaatatg gggcaattca agcaaagtat atgcctctaa tatggtttga   3900
aaattctgaa agttcagaaa aaatgttgct acttcagcca tctgatgtta ctggatattg   3960
agaatgagac ctcctctccc tctgctttcc tcatttccat ctcctccttc ctctttctcc   4020
tctctccctc tcctttattc tccttctccc tcctctctct ccatgcttac tcccttcctc   4080
ttctccctct ttcttcttta ttctccttct ccctcctctc tctctctccc ctttttcctc   4140
ccttcctctc ctccctccct ctcctttatt ctccttctcc ctcctctctc tctctccccc   4200
ttttcctata ttcccagatt aggccatttt caaaactggt taaacattcc ccaaaagcat   4260
ttatgacaga gaattgacta ggatctcacc tgaatcacag agcttgccca ttgaacacag   4320
gcaaagatca agccattttc tcttgatgtg atgcttcagc attttatgca tttgaaacaa   4380
attttatgta aaaaaaagct tagccctttg gtgacgggga ttccttttct ggatgatctg   4440
ccaaagaatc aagacccaac gtccagctta tcaaattttc tctggacctt tannnnnnnn   4500
nnnnnnnnnn nnnnnnnnnn nnnnnnnnnn nnnnnnnnnn nnnnnnnnnn nnnnnnnnnn   4560
nnnnnnnnnn nnnnnnnnnn nnnnnnnnnn nnccgtggtg aagacttcca cgtgaacttt   4620
aaagtagttt tttccaattc tgtgaagaat gtcattggta gcttgatggg gatggcactg   4680
aagattttct tcatttttat gactgcatag cattccatgg agtatatgta ccacattttc   4740
tttatccaat tcactgttgg tgggcaccta ggtcaattcc atgactttgc tgttgtgaat   4800
agtactgcaa tgaacatgtg agtgcatgtg tctttttgga ggaataattt gttctctttt   4860
ggatatatac ccagtaatgg ggttgctggg ccaaatggta gttctgtttt aagttctttg   4920
agaaatctcc aaactgcttt ccacagaggc tgaactaatt gacattccca ctgccatgca   4980
tgagcattcc cttttctcct cagctccacc aacatctgtt gctttctgac tttttgataa   5040
tagccattct gatgtgtgag atggtagccc attggggttt cttttttttt ttttaagaca   5100
gagtctcact ctgtcaccta ggctgtggca caatgttggc tcgctgcaac ctctgcctcc   5160
tgggttcaag tgattctcct acctcagcct actgagaagc tagggttaca ggcacctgcc   5220
accacaccca gctaattttg gtatttttgg tagagacagg gtttagccat attggcaagg   5280
ctggtctcta actcctgacc tcaggtgacc cacctgcctc ggcttcccaa agtgctggga   5340
```

-continued

```
ttgcatgcgt tagctaccat gggtggtttt tgacttgcat ttctctgatg attagtaatg   5400
atgatccttt tttcatacat ttgttggcca cttgtatgtc ttcttttgag aagtgtctgt   5460
tcatatcttt tgcccatttt tcaatggggt tgtttttttcc ttgtccagtt gtttaagtta   5520
tttatagatt ctggatatta gtcctttgtt gggtgcataa tttgcaaata ttttatctca   5580
ttctgtaggt tatctattta atctgttgat agtgtctttt cttgtacaga agttgttcag   5640
tttaattagg tctcacttgt caatttctgt ttttgttgta attgcttttg aggacttaat   5700
cataaattct ttcccaaggc ccatgtccag aatggtgttt ctgagatttt cttctaggat   5760
tcttttactt caaggtctta tatttaaatc tttaatccat ctggagttaa tttttgtatg   5820
tggcaaaagt taggtgtctt gttttatttt tctgcatatg gctagtcagc tatcccagga   5880
ccattcattc actagggagt cctttcccca ttgtttactt ttggcaactt tgtcaaagat   5940
tagatggctg taagtgtgca gatttatttc tcagctctct attctgttca actggtgtag   6000
gtatctgttt tcgtactagc accatgctgt tttggttact gtagtcttat tagtatagtt   6060
tgaagccagg taatgtgatg cctctggctt tgttcttttt gcttaggatt gctttttggg   6120
ctctctgttg ttgttgttcc atatgaattt taggacactt ttttccaatt ctataaaaaa   6180
atgacattgg tagtttggta ataatagcat tgaatctgta gatagattgc tttgggcagt   6240
atggccattt taatgatatt gattcttcca atccctgagc atggaatgtt tttccattta   6300
tttgtgtcct ctctgatttc ttttagcagc gttttatagt tctccttgta gagatctttc   6360
acctccttgg ttagctgttt tcctaggtat tttaattttt tgggcctttg taagtgggat   6420
tgcaagcttg aattggttct tagcctgaat gttattggtt tatagaaata ctactaattt   6480
ttgccatcca ttttgtatcc tgaaacgtcc ctgagtcatt tgttaattcc cagaggcttt   6540
gtggagtctt taggttttct atttttagaa tctattcttc ccaaagagaa atactttccc   6600
ctctcttttc ctaatcggac ccctttattt attcctttgc ccaaggcttg gaaagccctt   6660
ccatactttt ttaaaaagaa cgtggaaaaa ggcccctttc ttattctcgt ttaaaggaac   6720
cttccatttt cgctgtcaaa tggnnnnnnn nnnnnnnnnn nnnnnnnnnn nnnnnnnnnn   6780
nnnnnnnnnn nnnnnnnnnn nnnnnnnnnn nnnnnnnnnn nnnnnnnnnn nnnnnnnnnn   6840
nnntttgttg ggaatatccg gtgcttattc ctcttcagga gttttattct tccaaaaatg   6900
cagcttttca ttcctcctcg tttttctttc tgtgccaaat gcctccagcc tttccatgtt   6960
ggtgcggtaa gctagacatt tttagtttgt agtgattgtt ttcgtttgtg tttgtatgtt   7020
tttgtgccca tagtcacttc tgtaatgttc gtttctgagt ttcctttggg gggattaacc   7080
tgccactgaa gtgtcagctt ccctgtcatg ggactgtcct tggaatgaca ggttttcctt   7140
ccaccatagg atctgccact gtgaaggaga tgatgagagc cccctgatca ccccctgcca   7200
ctgcacagga agcctccact tcgtgcacca ggcctgcctg cagcagtgga tcaagagctc   7260
cgacacgcgc tgctgcgagc tctgcaagta tgagttcatc atggagacca agctgaagcc   7320
actgagaaaa gtacgtggga ggaagggatg cttcaccctt cctgaaacca gtgaccccca   7380
gaaagctggt gtctcagatc atgaggtcat ggcttgcctg cgttcatttc cttaaaaagc   7440
tggggctggt gcttacattt gcattgtaga gattgttgtt tctggtgctg attttcaagt   7500
ccctcttctc aggaagaagc tctttctgac cattcataat ccttcttttc ccttcaaagt   7560
aagactgctt gcttgtcggt gtcagtcctc tggcctttga ctacagactg tttgtgacat   7620
atcttagcac ctaattttat acatattaac tgttgacgtc ctgcttctct gattaggact   7680
```

-continued

```
gtctgttgga gattagtatc tccccagcac ccagcacagt gtagcataca gtaaatttat   7740
ttgtatacac ccatgataac tatttgctgg atgggagtgt gagtaggtgg atagggaaaa   7800
gaaaggaagc acaaacgttg cgtgatgtgc aactgtcttc agaaaggacc cacaggcatt   7860
gcatgacacg cagctgtctg gaggcccatg tcactgctcc ctctgagagg agctttgtcc   7920
gccacactgg cttcctgttt aaattttgac tgtttcatat atctctctag atgcccagca   7980
caaaaggttt tgtctggaag aataaaaaac tgttcctatc tcagaacatt aatatataaa   8040
ttgcaagata agtcacataa tcaaatacta gccaattaaa tgctaaatgg tgtgctggta   8100
gagcataaca gtcattcaga aaaggaaatg ctcattatga gctagagtgc tggggaagtg   8160
gagcgatggt agcctcatag ggtgtttggg ttttagagca gttcttgaag gatcactagg   8220
atttggaggc agagtgcaag gagtttagag aggtcaggct gtctgtggag taaagcatac   8280
cctagaaagg tgaaggtgaa cattgacagg gtgtcaagct acgtgcgttg taggaagtag   8340
cagggagcat ggggcactga ggcactgact ctgtattata ggtaggaaga ccagggaact   8400
tgctagtgta taaaatccca gcagaaaaca accagattta gagaaggctt gtgcaaactg   8460
cttaaaaaaa tgttttgccc agtagaaacc ttgtaattta ttgggtgcct actctatgct   8520
aatctctcaa catgggaagt ccttgaggct ctattttcaa ctaccctgca tagactcatc   8580
tggaaagagg ctgtgactag ggttggcaaa ggatatgtgc agagtgttta cacattgttc   8640
tttctctcta cctttatgtg ttttctcctg attcggaaac cagtaaatga aaaagaaagt   8700
ctggctattt ggagtaaatt aatgagctcc tagaggagat gggactagca gagtctgctt   8760
gtaccaggaa ctcttagcgt cgatttcgag ctgttgctgc caaagtagca aggaccaaag   8820
agtgagcgtc ttctgccatt caccttcaca atgtagtgtg acccatctgc tagtgtgttg   8880
tggcatcatc aaccctcttc ttccgctcgt ccatgccagt cagcacatca gggagactta   8940
aaacgtagta cctgggtcct gggccaacat actgttttca ttaggactga aatcatagaa   9000
ttctttatca ggccatctta tgtctgcttg caagaataag cagacaaggg gatttttgat   9060
ggtagttctg cattcatctt gatcctggct tcttttcatt gcatagaaag ttggctgcac   9120
ctggtacctg gttgaagcca agtggtttta ggagaacaat acttggggga atgcatctag   9180
tttgggaagg gagaagtggg gtggaaagcc aatcttacct acctacaatg ctctcacccc   9240
accggagccc ttccccagaa gcctgagcct cacactctgt gttgtctttc tagtgggaga   9300
agttgcagat gacgtccagc gagcgcagga agatcatgtg ctcagtgaca ttccacgtca   9360
ttgccatcac atgtgtggtc tggtccttgt atgtgctcat tgaccgtact gctgaggaga   9420
tcaagcaggg gcaggcaaca ggtgagttct caggctggag caagctcagc atgggggccg   9480
ggatagctca caggagtcct ggggtcagag gattttccag ttagccaaaa acgtctgggt   9540
ttccggagga gggacatcag ttaggaggca ctagcctcct ttttggcatt tcttttgctg   9600
tggtggtagt ttttgaaacc cagtcaggag agttcatatt ctggagcatg agaatctccg   9660
caaactacat cctataaaag caggaagtag ctggacactg tcttccactc ttctttgact   9720
gagcaacatt ggatgagttg tgaatccatt ggtcagtggt gcaggcttgt ggtccccaga   9780
tacttgaggc tgagggatgg aggattgctg aggctcagga gttcaaggct gtagtgtgcc   9840
atgatcacac ctgtgaatag ccactgcact ccagcgtggg caacatagca agactccatc   9900
tcttaaaaaa caacaacaac aacaaaggtc ttcaccaggg atctgcctag gtcagcgagg   9960
tggttcatca agannnnnnn nnnnnnnnnn nnnnnnnnnn nnnnnnnnnn nnnnnnnnnn  10020
nnnnnnnnnn nnnnnnnnnn nnnnnnnnnn nnnnnnnnnn nnnnnnnnnn nnnggagtgt  10080
```

-continued

```
acttcacccc gtggtgaaga tgcggcacag actggcgttt cctacggcgc cttcactgga  10140
aagcgcccct gtggtcctgg ggagagggcg gctccatccg ccacccttcc cggagctgcc  10200
cccgcccatt ctcatgggag gaaatcgcag ggcgtgtgag cccccgaccc ctcgccccca  10260
cctctgccag gaccggccgc atttctgcac tgtcccgccc cactgggaag gaaactctct  10320
ttctcaattt cctttaatga ggacattgtc ttttcagccc tgccaccccc tgcaatcgtc  10380
ttccaggctg caaacagcga gtggggaggt gaacacatca gcttttcctc cctccacacc  10440
accaggaaat ttcgcaaacc acttggctct cggcggcctg gcctcgccac acctgtgccc  10500
acagtctctc tccgctgcag ccccctgtgc cattctccag gccccacgta cctctgcctg  10560
ggcccagtaa gacctggtca gatggccccc ggctgcaaag ccttcctggg ccccatcaga  10620
gaggacgccc aggtgaagcg agggtcccct gcccaccctg caagcgcagg ggcccttcca  10680
agagtgcagc cctaggccgg tgtgtgatgg tggagacgcg gtcccagagg gcctgaacca  10740
agaatggaga agacaaaggc tgtctttagg gagaaacttc cctgaggggc tgatgtgtgc  10800
gatcccattt taatctcaca accctgggga ggagctgggg ccgggtctca ttgttcattt  10860
gaggacaccg aggctcaggg aacttagacg actttcctag ggtcccccca acccccaccg  10920
gcccagggcc ctctcccagg cacccctcat ccccacacag gctcctctaa gctgcttcct  10980
tgtggtccag ccccccttggc tcagctcctc aaatacaggg acacctcttc tctcccccgc  11040
agaactcaag ggtctccatc cactgtgcca gcacagaggc ggtgctcaga gtggggctaa  11100
gcttactgtc cagcctgctg ggccaggagg ggcagaaggg cccctctcag gattccttcg  11160
ctctgctcct gccaataggc catcactcaa ggggctaatg acaggacgat gtggagaaac  11220
gtgggctgca gcacttctgg ggccaagggc agggtgggcg gcactgggga gtacagggga  11280
ggggacctca ctggggccag aggcttctag aagcttctgc aagaaggggc ccctcaccca  11340
tgtcttggcc aagaagtggg gagggtgggt gtggcaaagg aaacagctag gtcagagaca  11400
agagatgctc tgcaaagccc tgctggctcc ccacggtgga gcatcctatg catgtaggac  11460
ctgagagatg gcaggggcgg gtgcgtccct atggatgtat ctccatttct gggcagagac  11520
atctgggctc tcacctgcaa ttgagccaac caagaaatta tatttacttt ttagagcgag  11580
cctccaacaa attatacaag cacttgagaa taagccctcc cactgtcttg agagatggag  11640
cccagggagg cagctggaaa gatgctcctg ccctcactca ggagagatgg tggagctggg  11700
agaggaggag gcactccctg ggacccagca gatggacttg actcagcaaa tagatgcaac  11760
catatgtggg gggtggggag gcccagaaag gcattacagg ccagtgttct taatcctggc  11820
tatacactgg aatccaccag tagccctaaa atataactgt gctggacttc ccctggttcc  11880
acagtttgtg cagagtgggc agcatggagt ctgtaacact aaacacacag gattgagaac  11940
catatgtcta ggctgttgtt agccatgatg gggatacatg aaaaggaggt gcacagttac  12000
cttctatacc acaggatagg tgctcattaa accctgttaa aatggactgt gacccagctg  12060
gcactcaggg gcactcaggg gccaggtggg tcacactttc attttaatag gatttaatga  12120
gcacctattc tgtgacagct gctaagatac agaggctcct gagatacaga gatgacaatg  12180
accttcagaa acactgaaca gagataagaa aggcacagtc tggccttcac tccaccatta  12240
attcctccat ccatccatcc atccatctat ccatccatct ctctgtctat acttccatcc  12300
atccaccatc cattcaccat ccacccatca atccatccac ccatctatcc atccatccat  12360
ctcactatct gtcatccatc catccatcca ccatccatga atccatccat ccgtatatca  12420
```

-continued

```
atttctcatc tatctctcca tccatccccc atccacctct tcttccatcc ttcctccttc  12480
ccttcatcca tccattcatc atccatccct caacccatcc atctgcctgt ccatcggttt  12540
gattgtccat ctgtccagta ttcctccatt ccctccaaac tgggtggcag tactctccac  12600
ctcactacct caccatcctt attattccct ccaaactgtc tctttcacaa gggccttctg  12660
tcctgcctgt cccatcctgg tctgggacct atcccactaa agctacatgg ctttgatcaa  12720
caatcccaat cccagagtag gggaagggaa gtgagcccct aactgccgtg atgtttccag  12780
ggagatggtg gatactgctg cattactaat ccagatgtta ggttttaatt tttctctcca  12840
gtagacccca attgtggtag gagaaaaatg ccccagcttt ggacacaaac agacctggat  12900
tcaaatcctg gttttgccaa tttctgccta aatgacttta ggcaaactcc ttgaccttga  12960
ccccttggag actcagtttc ctcacctaga aatggtcaat aatattattt acctcccagg  13020
atggccatga agcttaaaat agattattgt accccccaaa acaccgacac aatgtttaga  13080
aataaataat attattttaa gctttgaagt ctggctgggt tctcagcctc gtctacctgc  13140
tgggtgtgca gactcaaagc cagggtccca ccctcataga ctgtcatctg tgggtgtggg  13200
gttggcctgg cactagcagg tgctaatgct cctcagagga ttctaggtgt aaaaggaaat  13260
gaaaatcttt ggaccccaat tcactctgcc aaaagggaaa aattaagctg aaagctgagt  13320
gatgcaagaa acgaagatag ctacagataa aaggtgaaaa cctccacagg tagctcttgg  13380
tgttcacctt atcaagtgct gatgtactaa gcgcaagagg aatacataac tgactattcc  13440
cctacctgct ccttttcttt tgcaacatgt ggattcagta acgtgaccat gccctccctt  13500
tcttccttcc agcctgttct cctttaaata ttgatgccct taaagacatc ttcggaaaaa  13560
ggcacagtcc accaactgtt cctgtggatt tgtgttcctt ttttccgtgt atgtcttttt  13620
ttttattatt atactttaaa ttctaggata catgtgcaca acgtgcagga ttgttacata  13680
tgtatacatg tgccatgttg gtgtgctgca cccattaact cctaattagg tatatctcct  13740
aatgctatcc ctccccccctc tccccacccc atgacaggcc ctggtgtgtg atgttcccct  13800
tcctgtgtcc aagtgttctc attgttcaat tcccacctat gagtgagaac atgcggtgtt  13860
tggttttttg tccttgcgat agtttgctga gaataatggt ttccagcttc atccatgtcc  13920
ctgcaaagga cattaactca tccttttttta tggctgcata gtattccata gtgcatatgt  13980
gccacatttt cttaatccag tctatcggtg atggacattt gggttggttc caagtctttg  14040
ctattgtgaa tagtgccaca ataaacatac gtgtgcatgt gtctttatag cagcatgatt  14100
tataatcctt tgggtatata cccgataatg ggatggctgg gtcaaatggt atttctagtt  14160
ctagatcctt gaggaatcgt cacactgtct tccacaatgg ttgaactagt ttacagtccc  14220
accaacagtg taaaagtgtt cctacttctc cacatcctct ccagcacctg ttgtttcctg  14280
actttttaat gattgccatt ctaactggtg taagatggta tctcattgtg gttttgattt  14340
gcatttctct gatggccagt gatgatgagc atttcttcat gtgtctattg gctgcatgaa  14400
tgtcttcttt tgagaagtgt ctgctcatat cctttgccca ctttttgatg gggttgtttt  14460
tttcttgtaa gtttgtttga gttgtttgta gattctggat atcagccttt tgtcagctga  14520
gtagattgca aaattttttt cccattctgt aggttgcctg ttcactctga tggtagtttc  14580
ttttgctgtg cagaagctct ttagtttaat tagatcccat ttgtccattt tggcttttgt  14640
tgccattgct tttggtgttt tagacatgaa gtccttgccc atgcctatgt cctgaatggt  14700
attgcctagg ttttcttcta gggtttttat ggttttaggt ctaacattta agtatttaat  14760
ccatcttgaa ttaatttttg tataaggtgt aaggaaggga tccagcttca gctttctaca  14820
```

-continued

```
tatggctagc cagtcttcac ccggggctga aggtaccgct tnnnnnnnnn nnnnnnnnnn  14880
nnnnnnnnnn nnnnnnnnnn nnnnnnnnnn nnnnnnnnnn nnnnnnnnnn nnnnnnnnnn  14940
nnnnnnnnnn nnnnnnnnnn nacaatgaga acacatggac acgggttggg ggggtatcac  15000
acactggggc ctgttgggct atggggggct ggggagggat agcattaggg gaaataccta  15060
atgtagatga caggttgatg ggtgcaacaa accaccatgg cacatgtata tctatgtaac  15120
aaacctgcac attctgcaca tgtaccccag aatttaaagt ataataagaa aaataaaaat  15180
aaataagtta aaagagatta aaaaaataaa agagaacatt tgccacattc agtctttcta  15240
gatggaaaga ggttgctgac atatgataga attagaaaat cacacatctt gtaaattctc  15300
atttgtttaa aaagaaatca tacaaattag atgtttttttg gagatgactt tttaaaatag  15360
agtcgttaga tcacctctgt aagggatatg tctatatctg ttcagtgggt taggggacat  15420
ggatctggaa agcctgagaa gaaaaagaag gttctatacc agacttgtga tatttagaca  15480
ttttcatatt ctatccattg ttttgtgtgc attttattcc tcactattgt atatatagtt  15540
gacaatgcta aactttttttg tgtattcttt ctatgtgttc cgaatgccta atatatgtca  15600
aaattagcgg tagtaaaata atattttgta aatatctttt tgctaaaatt catatgaaat  15660
gttgtttttg gaggggaatg gccaaactac ctgttgagta atactcatcg tgtttgtgtc  15720
ctggttcagg ggaggaggaa ggaggggaaa gtgcagagag ctctatgccg ctgtgtttac  15780
agtgaggcaa gattaaccat tatctcttat gtctgtgcat tttgttttac ttatctgttt  15840
atgtagtgta tataaaggac aaacgagtcc taatttacaa catctagtct ttttagatgt  15900
taaagaggtt gccagtgtat aacaaaagta gagttagtaa actaatatat tttgtatatt  15960
ttgttttaaa attcctagga aagattgtct tcctatcttt gagcattctt gcgcactgag  16020
ttgatggaga tgggagggat tctaagctag gatgttctta tttggaagac tctttcaaat  16080
tataactatg gttacatgta tgcagtttat tcgagactgc tgtgtatata gtggacaaat  16140
taactcctta cttgaaacac ctagtttatc tagatgttta gaagtgcctg atgtacgtta  16200
aatgtagagg taataaaata ccactttgta aatatctttt tgctaaaatt cataggaaat  16260
actgtctttt agaaatttaa ttgttaagcc acctttgtga gcagtatagt actgtctata  16320
cttgttcaat ggtttagagg aggtgggagg gaagaaaaat atgtgactga cttatttcac  16380
taagcctaat gtctttaagt ttcattcatg ttgtggcatg tgtcagaatt tccttccttt  16440
ttaaagctga ataatattgc attgtataga tatattacct tttatttatc catttatcca  16500
tcaatagaaa cttgggttgc ttccatattt tagctatcat gaatattgct gccatcaaca  16560
tgttgagttc ctgtattcaa ctctttgggt aatacccaga agtgaaattg ctgaataagt  16620
atggtaattc tctgttaaat ttttgaggag ctgctgattc atacttttac gtataaaata  16680
ttagacctta aatgtattat gtaaaaacac taagtatttt taacattcta gagtaaagaa  16740
ggtgtttctt agcaagacag aaaagctgaa accctcaata gaaaagcctt gttaatgtta  16800
tcacataaaa tattcaaaat ttctgaacac acagacacac acgcactaac gaaaagctat  16860
ttacaacttg tggtagatga agaaataatt tcttaacata gcaagaaccc aggcaaatga  16920
ttaagaaaaa gaataatcat acaaatttaa tacatgtgag aagctgttca gcctttccca  16980
ttaattaaag aagtaaaata taaaacaaaa catataattt ttcacttagc agagatgaaa  17040
taccaaaaca gatgggtata ggtgtggaac atacttcctt ggttgacagt tagccaatat  17100
ctattaaaat cccttgccac agtaatttca gttctagaca tttgtcttat attactgtat  17160
```

-continued

```
ttattctgtc ctgtaaccat aaattccaca gctgcctagt gatggttcta tatttaaatg  17220
gaatgcttac tctcagtatt gttttttctt ttgagatgga gtcttgttct gttgccaggc  17280
tggagtgcag tgccatgatc tcagctcact gcaacctcca cctcccaggt tcaagtgatt  17340
ctcctgcctc agcctcccga gtagctagga ctacaggtgt gcaccaccac gcccagctaa  17400
tttttgtatt tttagtagag atggagtttc accttgttgg ccagtatggt ctcgatctct  17460
tgacctcatg atctgcccac cttggcctcc caaagtgctg tgattacagg tgtgagccac  17520
gacacccagc cagtattttt ttttttaaac cacagcttct tcattttgag tcatctctaa  17580
atagctgcaa tttactataa cttagggttt acaattttta aaattgtgta tgttaaggta  17640
tccacatgat gtttgatata cttcttttga cataaatata cacaatgaag tgattactac  17700
agccaaataa tgattaccat acccatcatt gctagcgttt agaaagacaa ctgattttta  17760
tgtgctgata ttgtaccctg caaccttact gaatttacta aatctagtag ttttttggtg  17820
catcctttgg gattttctat taacagaatc atgccttctg caaatgtaag taatttagct  17880
gcttcttttt aaatatgtat gcctcttatg tctttttctt ggctatgttc ttttctctgg  17940
ctagaacttc tagtacaatg tccagtgtca gtgttgaaaa tgggcatcct tgtgttgttc  18000
ctgattttag gagtaaagct tacagttttt ctacccctga gtatgatttt agttgtgaga  18060
ttttcctata tgccctttat catgctaaga aagttccctt ttattttagt ttgctgattt  18120
tttaaaatta tgaaagggca tttaatttta tcaaatactt ttttctgtgt ctgttgagag  18180
tttggccatt ttttttctat tgaaatggtg tattatggta gctgattttt ggatgtgaaa  18240
ccaaccttgt gtccttggga taaatcccat gtaatcatgg tgtataattc tttctatgta  18300
ttgctggatt tggtttgcta gtattttgtt gggaactttt gtgcccataa gataagaggt  18360
attgatctat ggtttttcttt tcctgtgatg tctttatttg gtttttgtgt cagggaaata  18420
gtggcttcat aaaatgttca agaagtgtac cctcctcatc tttttgttgg aagagtgtga  18480
aaaattggta ttatcaaatg tttagtagaa ttcaccagtg aagccatttg cttttctttt  18540
tgggtagttt ttgattactg attcattctc ttaatttgtt ttaggtctat tcagattgtc  18600
tgtttcttct tgagtcagtc ttggtagttg tgtctttctt gaaatttttt catttcactt  18660
aaattatctt atttgtcagt gtacaattat ttttggtatt cctttataat ccttttttatt  18720
tctttaatgt cagtagtaat gtctcttctt ttatttctga ttctatagtt tgagttttct  18780
ctcctctttc cctgatgaaa ctgaagtttt ttccatttta ttgatttttt tcaaacgatc  18840
aaattatttc attaatttgt gctgttatca ttatttcctt ccttctgctt acttaaattt  18900
agtttcatat tttttgtaag tgtcttaagg tagaatttta agttattgat ttaagaactt  18960
tcttaataca agtgtttaca gctgttgata ttactctaat tacttcttta gctgcatcac  19020
aattgttttg gtatgttgtc ttcattatta ttcgtctaaa aatattatct aatttctgtc  19080
ttgatttctt ctttgactca tgaattgttt tagagtggaa atttcatttt aaatttccaa  19140
atatttgtga atttcccaaa tttcccctgt tgttgatttc taattttatt ccattgtggt  19200
taataacata ctttgcatta tttctatcct tcaaatttat tgaggtgtgt tttatggcct  19260
aatatgtggt ctatcttcta gaatgttcca tgctcacttg acatgaatgt atactttgtt  19320
gttgttgtta agtagaatgt tccatagtcc ttgaggtcta tttggtttgt agtattgctc  19380
aagtcctctt tttccttgtt gatccgtcca gttgttctat ccatttttga acgtgtagta  19440
ttgaagtcct tgactatttc tgttgactcg gttgacttgt ctatttcttt cttttctcag  19500
gtctgttttt gtttcattta ttttggtgct tcatatatat aggtgcatat atgttgataa  19560
```

-continued

```
cagttatatc ttcctaatgg atggattcct ttgtaattac aaaaggccac tctatctcta  19620
gtaacaattt ttgttttaaa gtctatttgt ctgatatcag tgtactgact ccagtgtttt  19680
tgtggttgct gtttgcataa tatatttttc ctgttctttt actttcattc tgtgtcttcg  19740
aatcaaaatt gtgttttctc cagacaatat atacttcatg ttttcttatc caatataaca  19800
cctttgcctt ttgattgcat tgtttattcc attcacactg catattatta tttagtggga  19860
tttatgtctg tcattttagt tctttttttgt ttttgttttg agacagaatc ttgctctgtc  19920
acccaggccg gagtgcagtg gcgtgatctc ggctcactgc aagctccaac tcccgggttc  19980
aggccattct cttgcctcag cctcccaagt agctgggact acaggtgccc accaccactc  20040
gtggctaatt ttttgtattt ttagtggaga ctgggtttca ccgtgttagc caagatggtc  20100
tcgatctcct gacctcgtga tctgcccacc tcggcctccc aaagtgttgg gattacaggc  20160
atgagccacc gcacgcccgg atttttttgtt ttttatatgt atcatgtctt tgttgttcct  20220
gttttgtctt tacttctttc tatttcattg aattaatatt ttctaatata gtatttaagt  20280
tttattaata attttatcac tgtattttta tttttagtgg tttctctagg attttctgta  20340
tatatcttat cagtatgagt ttcagattca cactagctta attccagtaa tatgtagaaa  20400
tgttactcat gtagaactta attctcttgc tcttttgtgg ttatttttatt tatattatat  20460
caattaatgt tacaaagata tacattgttt aaattattat tggtgctatt attagcatac  20520
ataacaccca catattaaaa ttgtatatat tgcatatatg tattatagaa ttgtatatat  20580
tatagggcca atagtatatt gtatacatgt tattttatat aattgttttt aaaatgagtt  20640
aagaaaaaag aaaaatgcat ttctactgtc tattatagaa aaataattac atcatactga  20700
acgtcttcac cnnnnnnnnn nnnnnnnnnn nnnnnnnnnn nnnnnnnnnn nnnnnnnnnn  20760
nnnnnnnnnn nnnnnnnnnn nnnnnnnnnn nnnnnnnnnn nnnnnnnnnn ncgcggaatt  20820
cctaaaagaa ttgctgagac aaagtatatg tgcctttgtc atcctgaggg cagttgtcat  20880
cctgtggagg tttaccattt gctctcccac cagcaatgta taagcatacc tgcttcccaa  20940
cacttccgcc aacacatatt atttgattaa ttttcttggc tgataatggt atctcattgt  21000
agttttaatt tgtatttctc attgtgagag aaatgaagca tcttttcatg ttttgagagc  21060
catctgtgca tcttttccca ttgtttctgt taagtcattg atttgcagta ctgtaatttg  21120
tgatgagttg taaacatgag ctcttctggc ctcttaacca tccttatcca gcctgtcttc  21180
acgttcctcc ttgcctaaaa acaagctcac tcaaacagat cattcctgtg gccctctccc  21240
ttttgaaata aatcagatgg gcaaatttgc ttttgttagg ggcctgagac ccaaatgttt  21300
aaaagtagct tagctgatga gtgaaaagga ggcccagttg ggggttgcac agaaaatgag  21360
gggcgtgggt aatagaggag gctgggcagt aacctggcag aaggcgccag aggccaagga  21420
aggtgcgctg gtgtcctgca gtgagaagga tgtgtgcact atcaactggg taaacacact  21480
gctatagctg ctccagcgac agcaggcact ctcagaaggg aactgagaaa aggggaatgc  21540
cagtttctgc caaggatata tggaaaagtt ttttttcccc gtatgttctt tggcaacctt  21600
gttaaaatca tttaaaatgg tgaatttgat aacaaagcca gccactaaaa gacttggatg  21660
tagcaaaaca aattgtcaaa aagtatttat catttctaag aaataaaata aactgggatt  21720
taggcttgga tagaaatcca gaggtttgtt ttggcataat taattacaac atctgaagaa  21780
gggaggattt ttacaagaat ttttttttt gtagtgagat tgctttatat tccttttcat  21840
gactggagag tctgtcattt ggcaacccgc aaagaacttc aggaacagag ggcctaagtt  21900
```

-continued ttcttgacac atttggattt ttgcatgatg aacatttgca cttttattag taattgtcga 21960
gtcgtgtgtg gtctgatcct atggagagga gagtgtaggt gtnntctctg gagctagtac 22020
ntgcccccgn gctcacacgt gccacactgc ctgctgcttt cangaaagag caggacggct 22080
ggtcctgtcc catctagtga ggtcctgtcc catctagtaa ggttctgtcc tcagagctcc 22140
taagagggga ttgctggcct ttgattacac tggcttccag aatctgacca tggaaccatt 22200
atttgaagct gtcagcttca ttttgttgtt gatcaggcca gtcttttagg tctttgttgg 22260
ttgatagatt tctctcaggt ctatagcagc aacaaataaa gctctttaaa attattttct 22320
tgaccattct gcctatggat tggttctgac ctttgaaatg tttgctgtcc tttagatcgt 22380
gacagaagga gcctcttctg ggagctgtga agaccccaca gatctcactg gttttcttgc 22440
ttttattgga agagttagca tttgttgaag tttatattta tgtaaaataa caataagtag 22500
attttaaaat ttttctttaa attctgtgat ctaataagaa gagagactct ttctctgtca 22560
ttgggaggct tgatgaggat cggacatacc tgctgagagt atcctgtaat gttttcataa 22620
gattggaaat ggtgaaatga gagcagaaat gtaggcagag gatgccaacg ctgtttccta 22680
tttcctaagt aaaactgagc agggcagaat ctccccagcc ctgccagaac tcccttcctc 22740
cttgggtccg ctgtcactgt catgctggcc ttgacatctg ctacaagtgc acacacatgg 22800
ggaaccacac agggaagtga acacatgtcc tgacgtgtgt gtgtgcctgg tgtggctgct 22860
tccttgatcc aggctttgtt ttgttacgag gctctgccct cctaccttca ggccttgctc 22920
ctcatcatgg gcatgcaagg atggaatcgt taccccagag tacacttttt gacttggatt 22980
acttgtagtt tagtactgga gttcagaact ttaatttccc atcagaaacc tgcctcccgg 23040
acccaggaca ctgaccttga ttgggcacga ttttccagat aagaccttac ctcctcccaa 23100
cagggtttgc cttcccttca gaatacagga aagtacacgt ggttccaaga ggaccatgct 23160
cttactaaga taaaagggag gagggtgact aggtactttc ctctgctgcc atcccttgaa 23220
ggaagggggc ttccttcaat gcctcatcag ttccagggag tatgcttgac ccagcaacac 23280
agaggaagaa gtgacctcat agcaatgagg ggcaagcatg tggatattgc tgggtatttc 23340
ttcctcaaag tctacctggg gacaggtgat gaagacgctt acttctctgc aatacaccgt 23400
gatcaggctt tggtcttcat gacacatttt agccttgcct atgtgtgttg aacagagctg 23460
gtcatcctca gaaataaaag aagagagcaa taagtacagg aaggctttca gtcccagaat 23520
agtgttagga ctaaatgtca gagaacaggg ggactgtagg agtttgggga ccttagcatg 23580
gataccctct caatctgctc ccctgtggta taaacagtaa agcccattgt actaaaaggc 23640
cttgagtgct tgtctctggg gcaggtggag ccagtgatgg gtgccccgag aggaggatgc 23700
tggagagggg acagtgtcta aggcagttgg agaaaaagga caatggctta tgcagtcagg 23760
cctagaagat gcaagggatg tcacagcata gtgtccacag gcatccctag atgtctttca 23820
ttttgtttca ggaagaatat tgacaaaggt agtgatggga gggttatttc aaggatgcta 23880
ttttcatgtg tccaagtaaa cttaagattc ctaagaactt tgacctctaa tgcttttaaa 23940
gaccgtgtac ctcatgccca tatgcacatt cagttagaaa ataaatgtag attctttggt 24000
gaattcgaag atgtgctcat ggagtggcac agcgtgatct cagtgtacac atgaagcatg 24060
ctgatgagag cttcttggat cttgtttctt caggtggact tgcattaaag tgctgttgaa 24120
tctctgcact gggagtggga gcagccatgc gatgggtgcc ttaatccgag tgccatcctg 24180
gctctctcca ggctgcttca tttgctgtga ggggtagggg gaggaggagt ttccaggcaa 24240
tggccttatc tgttctggtg gttgaccaag ggtcgggggt cccaaaggtg gagttccagg 24300

-continued atgagagtgc acccttgggg atggtactta gaaagagtgg ggactaggcc tcagccaggg 24360
aatggtgggc cagggtggag ctcctttgta tcaaggagtt agggccaagg gccatgcagg 24420
tgggcctgca gaaggtgggt ggtgatatgg cctttctggt gataacagac tcgtggcact 24480
gttttcctgg ggctgttggg gttgcatgga gcagattctt actcaggctt actgtcttaa 24540
ggagggaaga atgctttttt atgaatacgc ataggtctgt ggggctgtgg agcctgggga 24600
atccgaggct ggcgtgggag tctggggccc tctagcggtg gtggtgcatc ctcagctcag 24660
tgccactcac tgtccctatt tctctctgtc catttctctc ctcactgcag tgcttcctct 24720
ccttcctaga tttttttctc taagtttgac tattcaccac cccagagact ctgttctatc 24780
ccatgacctc ttgctgtact ttctttcaaa tctaaatttt cttgattatt tttcttaatt 24840
tacagtttca agattagatc tgttgggagc attctgtgct ctacctcagc ccctggttga 24900
gctatggatt ggtgtccccc atggtgacgt ggtctggact ccctttttgtg tgaagagctg 24960
tggcagggca gtgaggtttt gtggaactca gggagcatct ggcactatgt atgaggttgt 25020
gaggtgggag agagctctta aatctaccag ccttgttgat cttgggaact aggagagagt 25080
gctagggaag ccagtgccag caggcctgga gcctcatatt tctttggcat ttgtatgata 25140
ccttctagta cttcgttttt tgacttatat atgaactaac tcaatttaga tgcttagaaa 25200
ataaacggcc actggacctg caagagatta gtagtggtgt tccatagcct tagacatttc 25260
ttacactttt atccacagat aagaaaaaaa tagtgatatt tgatttgttt tgccaaggct 25320
tagaaggatc taatatgtgt tactcgttga gcagcgggaa gcagcagaca tttctagggt 25380
ttctccctgt caccattcag gagacagtgc acacaatccc cttggctctt acctgaacac 25440
tgaccacagg tctgtcattg caggctggga gtcctccgtc agcatcagct ccggctccgg 25500
tgtcctcctt ctctcgcact tctatcacgc catccagcca ggacatctgc aggtaacact 25560
ctgcttcaga tgctgccatg atcagtgtgc agccagaaat aagcattagt gtctgtaggt 25620
tcttgaattt ccatttgctt aatcaatctg cctttggtct aaacagttgg cgagttttat 25680
gtgtggtttg ctcaccaagt tacccatgct agtctcattt cttcactatg atgtctattc 25740
tcttttaaaa ttgtttttac tttctgtgct tttatcccac tgttctgcat gcagttccag 25800
tgcagtgttt tctgagtgtt gtcaccacag ttccgtgcag tctgctgttg tctcgaaagc 25860
tcctcactgc cagagttctc tgacacaagg gctcactgtg acagttatct gtaaggacac 25920
attacaggcg tcaaagagaa attcctttgg ttcagaatgg gcccaggcct tgaagcctgc 25980
taagaatacc aaagccagaa gaacactaaa gttctcaagg tccctcaatg atgtgggtga 26040
gaaggcgcag gatacttcag aaagttttgc ctatgtggaa agaacttgtt ctgaagggaa 26100
attaatactc cctcaagata cgtgtctcag aactaacagg tttcatcata aagaaaaaag 26160
aaccctgaac cacaaacctc ttggcaattc caaacattct tgtgtttcat gcctttctgc 26220
cggtcgctca actgcctcag aggtggaagc tggcaagggg ggcaggcccg gcctgctgct 26280
ggaagagaag gcggatggtg aggccacgtc ccgaagccgg caactgctcc agtacctgtt 26340
ctcactctcg cacggcttga gcgccagcag cctgcacagg ttccatgagc tggagagctg 26400
cgctgctcgc ctgcacactg ccaagtcctc cagcgggctg gcagggagta tgggcttctg 26460
ctctgacgag atgggagacg acgatgtctt tgaggacagc acatctgcaa aactgaagag 26520
tagggttctg cgggcgcccc tctgctccac ggaaaaggac agcgacctgg attgtccttc 26580
tcccttctct gaaaaattac cccccatatc tcccgtgtcc acgtcagggg atgtctgcag 26640

-continued

```
gttggtttgc caggaagtgc cattctagcc atctctgctc gcatcaggaa cctcctcttg  26700
ctttagtatg tgaagtttca ggaaaatgaa gtaataggaa gttgtaacca gttgtgggtt  26760
gatggttttc tccagaagaa tggagtatca atatcgtttg aaaaacttaa tttttatgat  26820
gtgagtccca agatagtttt acaaatgata aaagaggaag aagctggctg ggcgcagtgg  26880
ctcacgcctg taatcccagc actttgggag gctgaggcgg gtggatcacc tgaggtcagg  26940
agtttgagac cagcttggcc aacgtggcga aaccccgtct ctactaaaaa tacaaaaatt  27000
agccgggcgt ggtggcgggc gcctgtaatc ccagctactc aggaggctga ggcaggagaa  27060
ttgcttgaac ccgggaggcg gaggttgcag tgagccaaga ttgcgccatt gcactccagc  27120
ctgggcaaca agagtgaaac tctgtctaaa aaaaaacaaa acaaaacaaa aaaaaaaaga  27180
ggaagaagct acacatatta aaggccaagc tgactcttct aaactaaaaa taagtagact  27240
ttgcataaag aaactggaag aaagaaacta gtatcttcag ttttccagcc tgatggtcca  27300
gattttaagc attgttgcat ctcccagcct ctttttaac ccttgctccc tacctacccc  27360
caaaaggtgt gtggggactg gctgttctcc agtagctcct tccttccttc tttttaactg  27420
aggtgtagcc acctatgtcc catcctaact ctgtttcccc cctttatctt cccttgtgca  27480
gcatccttgt ctggcctcca taattcactt tttgtcatga ctcttgtgcc ctcctcattc  27540
tgacctttct ccagtctccg ctccttagtg ccagctgtca tcatttctaa catttggatc  27600
agagatcccc tcactaaaac agcctgagag cctggctcct tccaggacga gtgccccaac  27660
ctgttctcta gctgctggaa aagacccctc tgtttcttaa aagcctgtta agttccttca  27720
ggctagtagc tacaccttgt tgcatacttc cttggaaata gagagtgctt tcaaattaat  27780
ttctcactta ttgctattag tggtcccaag aaaaagagat gaaattgcag catcttgtaa  27840
tggtgagttt tttaggtcta ggagagaggt actgtcatct ttgtttactt gctgagagac  27900
gacagaaatg tgtagttgtg gggtatgaag gtaaagtcag tgattatagc taaaaagcaa  27960
acgtcattta aggtcactgg tatttttgga tgttggaatg cagcgcttac catccataca  28020
agaacccgct gggagggcca agaccatccc gtgcgcggcg ggaaccgcga catccgccac  28080
tcggatgccc gctggagcgg gcggagaccc acgcgcgcgc caatgtcccg gcgcgcgggc  28140
tgctcaccca gggcagcggc gtagtcgccg ggggcacaag cccgagccgc ccggggcggc  28200
gcgcggagaa ggagcgcaga ccccgtgaac acgccggagg accgtccgcg cggcccgtcg  28260
cgccactgcc tactgccagg ggcggcgggt gacgacaaaa ccctcggtgc gccgcgcctg  28320
gcagtccgcg gcccccgccc ccccagcggc gcgcacccgg gggcgcgggc cgaacccggc  28380
aaggtgagag ggccgtggcg cccgggcgct gaccactatc attctccgcc acacggacga  28440
aggcaggagc accacgggcg gccggcgggc cgcccgctcg ggccaaagag cccgcccgcc  28500
agcggannnn nnnnnnnnnn nnnnnnnnnn nnnnnnnnnn nnnnnnnnnn nnnnnnnnnn  28560
nnnnnnnnnn nnnnnnnnnn nnnnnnnnnn nnnnnnnnnn nnnnnngagg ccgggcgagc  28620
gcaggcgggc ggagagcaga ccacgcggaa gaggccgaga gagaaagcgg ggcacccggc  28680
cggggggtc atttacaagg gacgctgggc acgaaggagg ctggggcgaa gatgagtcca  28740
ggggttgggt tgagagcgct gcgcagccgg gctgagaaga gaagctgacg agtgactccc  28800
gacaagggac gggggagagg gaacctgggg gcaggcagag gcctaggggg tgggctctga  28860
gggcagccac tcccaccggc cctcccccag ccccgcaggc cagccacatg ccccgtgctc  28920
cagacgaccc agctacatgg atggcagcgt cctgaagggg gatgatcggt agggagtggg  28980
tgcggaggct cacgcctgta atcccagtgt tcggggattc ccgagcggga ggatcgcttg  29040
```

-continued agccggggag gtggaagctg cagtgatctg cgccactgaa ctcccgcctg ggcggcagag 29100
tgagaccctg tttcaaaagg caccaggggt gtagggaagg agcgatatcc cccaggcaag 29160
gaaggctgcg gaggggccag gccaggagag aagggccctg agctcagtgg acgggcaggg 29220
tgcctgtgga ggaagggagg gacgtagcag caggaggaag ggtgaggacc caggctgggg 29280
atcgggagaa gtgatggcgg aggaaagaga ggccggaaga ggagggggcc tgctggcctg 29340
gcactggaaa gcaaagcgtg ggtttgtata tgggaagaag accacatccc ctcttatcgt 29400
catcccaact cagaaaccat ttggccccaa gtcaccaaag cactcatagg aaccactttt 29460
cctgtgacac aagtaggatt ctcccacttt taacttccca aatgctaccc gaaagcctct 29520
gaaatccttg gaaatttaaa aaataatccc cttctattaa ctgatgccta taaaacatat 29580
tgactttcat taaattttgt tatgaaatca gggatgtgtc ccattgtaaa ataaatttgt 29640
ttggaaaatg tagggtggta tcccatctaa aaatcagacg aggctagaaa atttcaattt 29700
tatttgctaa ggtagcatca tgttgttaaa aatgcatcat aaaataagac caagagttaa 29760
tacaaagcat gaagtcatgt ttccctcaaa aaaatgattt gttctgtagt caaattaatt 29820
tggaaaacat tgcaaactct tcagcagtgg ttctcaaagt atagcttgcg tcagaatccc 29880
ctggggccct tgctaaaatc tggatggcta cactccccgc ctagagtggg ttaaactcag 29940
tgcccactgg caggaaactg aaacttggct gaagtcaccg aggaggcctt ccccgttaaa 30000
cctctggctg gcgacagctt ggtttcctcg ccgctgcttc tgagtaattc tggcacgcag 30060
ttcctcctag ccacctgctg tacctggaag ggggccagcc ctcctcagca ggctttgctc 30120
ctgccctgca cagcacaact gtggcgtaaa aaatggaaaa gctggtagca gaaggaaaga 30180
gcagggagac agaggttagg tgaacctcaa tggcctcatt aaagcaaatt gagaaagaga 30240
gtttccttcc cagtgaggcg ggacagtgca gaaatgcggc ccgtcctggg agaagtaggg 30300
gcgaggggtg gggggctcac cgggcacatg gccaacagct ggtgcccagc ctgggccaca 30360
gtttggcaca ggagaaagct gaagatgcag gagaaagcta ggtcactgcc cctaggccag 30420
gtgatcaagg tggctgttac ctgcctgtgt ggccttgaaa aagcctggtg ccctctctgg 30480
cttgcagggt ccttcttttt acaaaagcgg gtcttcgaag ccctgaatat tccagttatc 30540
tgtaaggata tagaaatatt ttgcctctag atgacatgta aatatgttcc tcctaactcc 30600
acttcttcct acatctgtgg cttcttctga gaactaccag acccaccctg ttttcagagt 30660
aaacctcctg ttttgaggtc aaacagaccc agctgggtaa ttggtgactc actcctggtt 30720
cctccaaaga acaggggcaa gggaccaccc gggacctcag gtgccccagc acaggacctc 30780
tttctggggc accctctggc actgggccat cttcaggccc tacagggctc tcggggcctg 30840
cgtaggcctc tcatctccca gaaataagtt cttttcccca cccagactga caccagatgc 30900
tacagtgagg tttacccctc cagcttgaca agcattccta gcccagaaca ctcagctgac 30960
gaggggtgct gggggaggaa ggaggcagca aggctgaaag aagcttctct gggtattcca 31020
gtgcctggct gctggtcgta gccatggtga gaccacagca gcctccctgg aagcaagcac 31080
ctgtgtaaaa gcccctcctt ccccacaagg ggctggatcc aagtgaagaa ggtaccagaa 31140
ggactggaag atgatgctgg tattattcga cagctccagg gtgctgtagc actgagcacc 31200
tactgtatgc agcccatcac aaagccagcc acactgccca ggctgtgcca tggcaacttc 31260
cagcagtaca ccctctcggt cacctgcagg ctccttgttc atcctgacac atgaggagaa 31320
aaagacagta ctcacaaagg cctctagcct tgtggcccca ggaccctctc ctgagcatca 31380

-continued

```
tggcctccta ggagacccag ggtagccagg acaaaggaga gaagcatttg ctaagctaag  31440
aaaggatgga aggggattgc tgttctgcct ggatgcaccc ctagacctgg cagggcaggc  31500
aggagagacc cccagtgtct cttgcttatc ctaggagttc ccccctgtgg ttgctccagt  31560
ttgctgcctt catgcatgtt cacagggtga ttcccctgag acaacagagc tgggatgtca  31620
ccaagccctg tgtcccatca gccaggctct ccccagcctc catcctctca ttctgctgga  31680
tcaggaggat gtggggaggt ccctgactcc ccagctttcc ccatgacaag gtgtgtgtct  31740
acagctcaga cccagccatg ctccacctga gaagtgggtc caggcagagc actgggtcct  31800
ggccacctag ggctgcctcc tcaggggtgg gcaggaaggg gagccactgg aggagtgccc  31860
cgggcacagt cccctgcacc aggtgaggtc acctcttagt ccatgaggcg atgctgcatg  31920
agcccctctg gacactagaa ggcctgggct caatgctgag taaagtgcag gcatgactgt  31980
gccctcagca tgcatagggc agcaggcata gattcataca cgtgagtttg cacttaagct  32040
gcagtaagag ctacagagga aatgaacaga gacagcatca ctccagtgag ccctccagat  32100
acaccccatg tgcgcagtaa gagaatggca tagtctattg ggacagccac atcaaaatac  32160
cacagaccag atggcttaaa cggcagatat ttgtctctca caggtccgga ggctagaagt  32220
ccaagattag ggtgccagcc aatccacttg ctggtgaggg ccctcttccc agcttgcaga  32280
tgtctctgtg ttcccacagc atggtcacgt ggcagagaga gggggacagg gcatgaataa  32340
gccctcggtg ccttcctctt cttacgagga tgctaatccc atcacgggta ccccaccctc  32400
gtgacctcgt ctaaccctaa tcacctccca aaggccccat ctcctaatgc catcacactg  32460
ggggtcaggg cttcaacaca tgaatttggg gagcacaatt tagtccacag cagaaaagaa  32520
aggggcacag agcattccag cctgaaggaa acagatgtgc aaaggcccaa ggcaaaggcc  32580
tgagctctga ggggcaacca gagtcaaggc tgaagagtgg gcagtgattg agcactgacg  32640
gtggagaggc aacaggctat cttgttaatc tcagtctttt gtgtgccaga gagagaaact  32700
gaggcacagt gtgtcatggt gaacactggg cagcactccc acgctcctgt cctgcactct  32760
gcagggttat ggaggaagcc tgggaagtct ctcccctctt ttccaccttt cctggaccca  32820
tcccacaccc tgcctcctcc aggaagccct ggggattgct catacactca catctcactc  32880
cttagtacct gcagcctgca ttctgaattt agcaagctct ggccttgggt ttctattttc  32940
ttgtcctgtg cagtgagcat ttggaaactt ctcctcagca ccaaacacgg agccatttag  33000
cagaaaatac atgagttttc aagtcaattg aactgttcat cgccccaaaa gccaggcaac  33060
acggtagagc agctggatct ctgttcgtag aagctttctc agggactggc ccaccgagtg  33120
ggggactgca agtgcccgat gagtgaatga atgaacacat gtgtgaatgg aattcaaggc  33180
actgcaggct attctggagg gtactggcct gtctcttcga caggtgaggt gcagtagaac  33240
agcatcccgt atagatgcca gtttctgacc tggttctgaa aagccagtca cctacctctg  33300
cagagctgcc tggagggggc gggggttgtg aggacccctg agagcttggt gtgaaggggc  33360
tctgcagagg gaggcatggc tagtgtgcgc aaggtgacct ctctcctggt ctgcaggatg  33420
gagaacctgt tcatcaaccg cttcatgcac atgttccagt cttcttggaa tgacttcgcc  33480
gactttgaga aaatctttgt caagatcagc aacactattt ctggtgagtg tgcctctggg  33540
ggcccaagtg gtgctgggga caggggatgc tgctctcctg tctgatactt gccgggaaat  33600
tgacaagggc cttcctgcct gctgcagcat gggggcctcg ctgccaccat gccaccctgg  33660
acagcacccc ctacactcca caccttttac catcactgtg gtcacccttg tgcccagagg  33720
tttctcctcc tcagatattc aagctcgagc accctcaacc tcatttcact atcaaaagtc  33780
```

-continued

```
tcaaaagtat cagaactttt tcttggcaca aatcaatcat ttgtgcttct gaacagagca  33840
aaggcagaac ttggcttgtg ttttaggtat ttacacaaaa gcaactttgg gttcctttgg  33900
actaggatgt gtttgatgag agcactagct tcatagtggc cagtcatggc atgggaagga  33960
cgttaggaag gcaggaatgg ctggacaaga agaggtgctg aaatcaggac atggggaacc  34020
aaacttggca aactgccccc agggactctc ctccacgccc tccttcttcc atcctggaca  34080
ctccatgctg ggctgaagga cctgagtgct ccaggaggct tctgagccac gaagggccag  34140
ctcaggtatg atgagttggt gccacagcct gacccagtga tgggcagggg gcagcagttg  34200
gagctgtgcc catccaggga gcactcggga gaggagacca agcagggact ctgctcttag  34260
gtgaggtcag gagggccatg gccctggctg ccctctactc agagctcagg gtgggcctcg  34320
cttttctcct ggtagagcgg gtcatgaatc actggcagga agacctgatg tttggctacc  34380
agttcctgaa tggctgcaac cctgtgttga tccggcgctg cacagagctg cccgagaagc  34440
tcccggtgac cacggagatg gtagagtgca gcctggagcg gcagctcagc ttggagcagg  34500
aggtccaggt aggggttgat gggctgggga agtggccaag gtcacagtct gtcaggtgga  34560
agccagttcc tcctggccag tgctcatagg ccaccaagac gctaactgca ggcccatctg  34620
gcctacagca gccgcttcct tttcctggca gcagtgtcag ccagggtcct gggcattatg  34680
cagactgtct tgtgcaacat cagaggagga attgcgggga atgtttctcc atgatgctcg  34740
agtctgggaa cataatgtca atattttcac tatcagtatc aataattaca ggagctaccc  34800
ttgattaggg gcctgtggtg ggacaggcat tgtgacaggt gctttacaca caaggtcatc  34860
agttgtcacc caccttgcaa aggggagaac actggagaaa gaagcagacc ttgtgtgaca  34920
atacacaagg ggcacgagga gaacccaaca gaatggttga ttttctcgtt agaaatgctg  34980
ctgcccatgc tcctgtcgca ccctcctccc caccctcacc tgcagactca gctgcctccg  35040
gctgcaaggc tgacctagtc ttgagacaga agaagttcaa accaactcca cctggatctg  35100
gtggggctca gcaacaggcg ctggcccatc agcctgcctc ttccccatgg atccagcgtg  35160
atggggcctc ctgccaccca ggccctgctg cctatcccca ggtgtccagg tggcctctgc  35220
tgcttccagt cttttgagct cagcttaccc tgaggcccta gttggagagg gatggttggt  35280
gccctttaga gataaaccta cagccccagt acctggccca cctgaatcta gagggccacc  35340
cacccagctg aagtccctgg gcaagtctcc tgccccagtg caggcagtgt ttcctaacct  35400
cctcctcctc ctgcacccaa ccaggcccag aacacttcct ggtcatgtga acagctgaca  35460
gttacaatcc cccacacact gagagagcat ctgtgttcct gagtggactg aattgctaga  35520
tgtagtaaca ttgatttggt ggctataggt ttcaaacttc aagtcagaga tcatagaact  35580
ttaagccata tagaatccta gaattggaag actctgagca gccatctctg cacccagcag  35640
ccaaggagtg gccatcctca gcacctggca gggcatcagc ctcccactgg gagtcccggc  35700
cacctccagg gcacgtgggt tatgagtcac ctttcctttg agctgaccca cccctcactg  35760
actagactct taaacacaca ctgccccgtc taatacacac cagcatgatt cttaatcccc  35820
acagtcattc acgctgccca tctggcagca ccttaatgat ctacagcaag cttgtggcct  35880
actaaaaacg cctccattgt tttttaaaat gtgcagttat tttccggatc atgaatagag  35940
aaattgtatc cctgttgttg gtattgattc agtgttccag ctcaagtttg agttcttaga  36000
ctttatattt ggattctttg gtttcaaatc acaaaaatca actccatctg gtttaatcca  36060
agaactctat tggctcaggc aacagtaaaa agcaatgcta actcatttgg gaccaggct  36120
```

-continued

```
cagatcatcc cctgcactgt ctctctctcg ctccatgtct caatcctctg cctctggtga  36180
tttttttcctt aggagggttt ccttatgtgg aggtaaaaaa tgatcaccgg cagcttcaga  36240
tttaccttcc accagcttag caaacaccac ccactcccag caagaaagac cctgtttccc  36300
aatgctccca gcagatgtct taggccatcc tcgggcctca ctgattctgt gagccagtgc  36360
ccacggccag gagaatggaa tacactgacc tagaggggac agggactcta gacaggcaaa  36420
aactccactg tcagaagcag aatcctaaaa tgtcagaact gaaaggtagg cccgcccctc  36480
gttttccaga aatatgaaag ggaggcttgg gataacagag aaatgctgca ggcattggcc  36540
ccaaatctca ggcctcctat tcccagtatc accttcacca gcctgggtgg tctcaagatt  36600
ggattagcag ccattccttc tgggtagagt ctgatggtca cttcagctct caaagtccag  36660
ctatccagcc atagtcctag aaggcaagac atcactgtgc ccgaccaacc caagggtctc  36720
cacctgcccc cctcaacaca aggtgccctg agtgcctccg cggggatagt ccccgtcccc  36780
acccctgctt cccccgccca tcgcgacaga tgctcagagc tcatccctgg tgtcacacca  36840
cataaaggag gagggcggtg gccaggctcc gagctcctgc cgtcctgggt gggtggcttc  36900
tgtcctgcgt gccgccgggc agcccggggg tcctgcgcgc gggcgcggtc ggtggagctg  36960
caggggggcg ctctgggatg tctccaggca gagtagatac tgacccctcc gcagccggga  37020
ccctcaccct ttccttcatc actcaggaaa cagaaaaggc ttcagaagga gcggccatgc  37080
ccccggccta agcgctgcgt tcccggccca gcaggcctac cctgcacctg gcgttcctag  37140
gggcccctct gcgggaccca ctgcgcggct cgcagcggcc gcccgcctcc cacttcaccg  37200
gcacgctcgt tgcgtgtcga ggtgtgttga ctcctacagc aaagggcacg gatccgcggg  37260
tcagcaagcc cgacgaattt acaccaatga cccgccgtgt cgccagtctc agaccagggc  37320
acaacacgcc aaccctgcag accaccccca cctccccagc cactgcagac ccttccccct  37380
ctgcttctgc agcacctgtc ccgaaacacg ctcattcccg cccccgcaga ccttccctac  37440
ctcctggaga cccccctcaa cccctgtaga gtcccctgcc cgtgcagaat cccctccccc  37500
ttcccccgca gccccctac cccacccggc ggacagcccc gctcgcttcc tgttcttctc  37560
ccaagggaga cccctgtcct ggctctgact ggggttgagt tcgccagttt tgacttatgt  37620
gtagagtctt caccacgggc tggaagtacg gtnnnnnnnn nnnnnnnnnn nnnnnnnnnn  37680
nnnnnnnnnn nnnnnnnnnn nnnnnnnnnn nnnnnnnnnn nnnnnnnnnn nnnnnnnnnn  37740
nnnnnnnnnn nngagcgtac ttcagcccgg gtgaagattc cttacacctt atacaaaaat  37800
taattcaagt tggattaaag acttacatgt cagacctaaa accataaaat ccttagaaga  37860
aaacctaggc aataccattc aggacatagg catgggcaag gacttcatgt ctgaaacacc  37920
aaaagcaatg ggaacaaaag ccaaaataga caaatgggat ctaattaaac taaagagctt  37980
ctgcacagca aaagaaacta ccatcagagt gaacaggcaa cccacagaat gggagaaaat  38040
ttttgcacct actcatctga caaagggcta atatccagaa tctacaatga actcaaacaa  38100
atttacaagc aaaaaacaaa caaccccatc aaaaagtagg caaaggatat gaacagacac  38160
ttctcaaaag aagacattta tgcagccaaa aaacacatga aaaaatgctc atcatcactg  38220
gccatcagag aaatgcaaat caaaaccaca gtgagatgcc atctcacacc agttagaatg  38280
gcgatcatta aaaagtcagg aaacaacagg tgctggagag gatgtggaga aataggaaca  38340
cttttacact gttggtggga ctgtaaacta gttcaaccat tgtggaagtc agtgtggcaa  38400
ttcctcaagg atctagaact agaaatacca tttgacccag caatcccatt actgggtata  38460
tacccaaagg actataaatc atgctgctat aaagacacat gcacacgtag gtttattgtg  38520
```

-continued

```
gcactattcc caagagcaaa gacttggaac caacccaaat ttccaacaat gatagactgg  38580
attaagaaaa tgtggcacat atacaccatg gaatactatg cagccataaa aaatgatgag  38640
ttcatgtcct ttgtagggac atggatgaag ctggaaacta tcattctcag caaactattg  38700
caaggacaaa aaaccaaaca cctcatgttc tcactcatag gtgggaattg aacaatgaga  38760
acacatggac acaggaaggg gaacatcaca cactgggcac tgttgtgggg tggggggctg  38820
ggggagggat agcattagga gatataccta atgctaaatg acgagttaat gggtgcagca  38880
caccaacatg gcacatgtat acatatgtaa ctgacctgca cgttgtgcac atgtacccta  38940
aaacttaaag tataataata aaaaaaaata aataaaaata aaaaataaaa gaaaatgaag  39000
aaaatcatgt catttgcagc aacatggatt tggctagagg actttatcct aggcaaacaa  39060
atacagaaac agaaaatcaa ataccacata ttctcactca taagggggag gtaaacactg  39120
ggtactgatg gacataaaga tagcaacaat agacactggg gactattggg gtggtgaagg  39180
agggaaggga gaaagtgttg aaaaactgtt gagtactatt ctcagtatct gggtaatggg  39240
accattcata ccccaaacct caacatcaca caatataccc aggttacaaa cttgcacaag  39300
tgccctctga atctaaaata aaagttgaaa aagcaaaaat aaaacagtaa acaacaacaa  39360
caacaaaaca gcaaaaccct caataaatac ataaataaaa atataaataa atgtctttgc  39420
cagagctttt tgttttttgt gtggctttga gttagtatct ggggtcacgt tgcttttaag  39480
ctgtttgcta tcaactgcat cctatctaat atttcttttt cttaatagta aaccactcaa  39540
tttttgtgag gagatattac attgtggttt tgatttacat ttctctaatg atttcctttc  39600
cagtttggat gctgagcatt ttttcttatg ttttttgccc attcatatat aattttaaaa  39660
gaaatgtcta ttcaaatcct tttgccattt taaaatcata ttatttttaa atattgtgtt  39720
gtagaaatta tttatatatt ctggatatta actctttatc agatatataa tttactaata  39780
ttttcttcca tccacaagtt ttttttaaca ttgttatgtc ctttaatgca taaaagtttt  39840
aaaaagtttg atgtagtccc aattgtctat tttttctttt gttgtctgta cttttggtgt  39900
catattaaaa aataattgcc atatcccctt attctaagag ttttatagtt ttagatcttc  39960
catttaagtt ttaaatccat tttgagttaa ttcttgtata tggcataaga caaagtttca  40020
acttcactct ttcatgtgtg gatatccaag tttcccaaca ctgtttgttg aagagaatgt  40080
tcttccctca ttgagcggat ctggaatgct gtaaatatta tttgaccata tatgtggagt  40140
tttcttttaa tgggttcttt attctattcc attggtctat atgtctctct ttaagccagt  40200
gtcatgctgt tttaattact gtagtcttgt aacatgtttt gagatcacgg agcatgagac  40260
cttcaactca gttagttttc aagattgtct agtcagagta tatatgaata tttagataaa  40320
tttttctctt ttttcaaaaa atgcagctta gattttgata gggattacat ataatttgta  40380
gactgctttg ggttctattg acttttcaaa ttaatacata atgttgtaca gatttgggga  40440
atacatctga tattttggag atcttaacat taaatcttcc aatccatgaa taccaatgtc  40500
tttacattta tttgtgactt ctttcagtac tgttttgtag ttttcagtgt acaagccttt  40560
tatttccctg gctaagttta ttcctaagta ttttactatt tttgatggta ttgtaattaa  40620
attattttct taattacctt tggattgttt atagttaatt tatagaaagg caactgattt  40680
ttgtgtgtcg attttggatc ctgcaacttt ccagaatttg tttaatagtt ccaacagttt  40740
tctggatttt atgcatatat gcatctaaca gttttctaga ttttatgcag gagtctagga  40800
ttttatgcat ataggatcaa gtcatctgtg agcagagata attttacttt tttcttttat  40860
```

-continued

```
tctttggatg tcttttcttg cttaattttt ttttcctaat tggtctgctt ggaaattcaa  40920
atactatatt gaatagaagc gaagagacag agtatacttg tcttgttcct aatccagaag  40980
aaaagtttga atcttttacc attgagtgta agtttacctg tggatttttc atatatggcc  41040
tttattatgt tattttcctt ctattcctag tttgctgagt gttttcgtga taaaaggtgt  41100
taaattttgt taaacatttt ttctacatca atataaatga tcatgctgtt ttgtccttta  41160
ttctattact atagtgtatt acattgattt ttgcatgttg tattattctt tttttttgag  41220
atgaaatctc attctgtcat tctggctgga gtgcagtggc atgacctcag ctcactgcaa  41280
catttgcctc ctgggttcaa gggattctcc tgtctcagcc tcccaaagtg ctgggattac  41340
aggcatgagc cagcacaccc tgccacatgt tctatcattc ttgcattcca ggaataaagc  41400
caacctgatc atcacaaata ttggtctgta gttttctttt catgtaatgt ctttgtttga  41460
ctttgaaatc agggtaatac tggcctcata taatgagctt tgaagtgttt tttatattca  41520
tttttgtaaa tgactttgag aaacattggt tctaattctt ccttaaatgt ttggtagtca  41580
tccggttctg ggctgttgtt tgtttggagg tttttgaacc agtttaatct ccttcgtagt  41640
tataagtctg ttcgtttttt ctacttcttc atgattcact cttattaggt tgtatatttc  41700
tagaaattta tgcacttcta aattatccaa tttgttgaca tataattaac tgttgatggt  41760
attttcttat aatccttttg atttctatgg catgggttct aatgttctct tttttatttc  41820
tgatttatta gttgaatctt ttttccttag ttaatctagc taagcatttg ttaattttgt  41880
tggtgttttc aaaaaccacc tcttagtttt gttgattttt ttctattgtt tttatattct  41940
atatttcatt tatctctgat ttaatctaat ctttaggatt ttcctccttc tgctagcttt  42000
gggtgtagtt ttttttctct cctagtttcc tgaggtataa agttaggttg ttgatttgca  42060
aactttcttc tacttctttt tttttttttc ttaagttgtg gagatggggt cttgctttgt  42120
tgcccaggct ggtctcaaat tcctggcctc cagaagttct cctccctcag cctgtcaaag  42180
tgctgggatt gcaggcatga cccaccatgc ctagccactt tcttcctttt ataatgcaca  42240
tatttatagc tataaaattc tctgttagca ctgcttctgc tgcatcttac acattttggt  42300
acattgtatt tttattttcc tttatctcaa gatattttct aacttccctt gtgatttctt  42360
ttttgaccca ttgcttgttg aaaactgtgt tgtttaattt tcacatattt gtgaattttt  42420
tgttttcctt ctgctactga tgtctagttt tatgtcattt tcatcaaaat agatattttg  42480
tataatttca atcttttaaa atttgttaca agttttttttg tggtataaca tgtgatttat  42540
ctttgggaat attccatgta aacttgagaa aaatactatt ctgattttat tgggtggaat  42600
gttctgcaca tgtttgttag cactatttat agtgttgttc aagtactgta tttccttatc  42660
gattttctgt cttgttgttc tagccattat tgtaagtgag gaattgaagt cgcctaccat  42720
tattatgctg tttatgtttc ctctctgatc tgtcaatgtt tgcttcagat atttaggagc  42780
tctggtatta gaggtatata tatttgtaat tgttatatct ttctgctgaa ttgacttttt  42840
gttatataat atccattttt ttgtcttgtg actatttttg actttaagtc tattttgttg  42900
gatagtagta tagtcacttc tgcttgcttt tatttaccat ttgcatggca tttacttttc  42960
cttttttttca ttttaagcat atttgtttct tagacctaaa tgacaggata aagttggatc  43020
ctttttacaa atccattttc cagtctatat cttttgattc aggagtttaa tccatttaca  43080
tttaaagtaa ttactgatag ggaaggacct acacttgcca ttttgttgtt tcctgtatgt  43140
tttgtaaatt ttgtttttta ttccttctct tactgacctc ttttgggttt tgtcgatttt  43200
tttttgtggt gacattttga ttcccttcct gtttcctttt gtgtgtattc tatagatttt  43260
```

-continued

```
tttatggtta ccataagaat tataaaaaac atcttaaagt gttaacaagc tattttaaac  43320
tgttaagaga ataacttcga ctgtgtacaa aaactatttc ttcaaagctc ctaccctcac  43380
cttaggttac ttatgtcaca agttacatct tcatatgtaa tgtattcatt aacacagttt  43440
tatagttatt tttaagcttt tgtcttgtaa attctataca agaattaaaa gtgcatttat  43500
gtaccaaaac tgcatagtac agtctctata tatgtccata tatttatctt tactggagag  43560
ctttatattt tcataagact tcatgttact atttagcatc cttttgtttc aacttgcaag  43620
atactacagc aggtccagtg gtaatgaact ccccagtttt tgttcatcct ggaaaggctg  43680
atttttcctt tatgtttgaa ggatggtttt gctggatata atatttttgg ttgaaatttt  43740
cttttctttc agctctttga atatattatc cccctgcctt ctggcctgca aggtttctgt  43800
tgataaatcc actgataatt ttataaaggc ttccttttac atgacaagtt actttctttt  43860
gctgctttca agattgtctc tttgtctttg acttttgaga gtttgattat agtgtgtctc  43920
actgtgagtc tctgggtttt ctttaacatt tttttttgt tcatatcttc tgatgatgaa  43980
ttcctttaac ttttatattt gtgaaatgtt ttttcttcat tttcagaagg tatttttagt  44040
gagtgtaaaa ttctacattg acagtttttt tctttcagta ctgtttagtg tttctctact  44100
gtcttcttgc ttgtactgat tgtatagaaa ctctgctgta attcttatct ttgtgtcttt  44160
gtacttaatg tgccttttta ctctgcctgt ttttaagatt ttatttttat tattgatttt  44220
gatcatgtgg cttggtgtga gtttcttcat atttattgtg cttggggttc attgagctta  44280
ttaagtctgt aggtttatat ttttcattac atttagaaaa attgtagcca ttattcattc  44340
aaattttttt ctgttcttct cccatttctc atgcccttat ggggtctaat tatatgtata  44400
ttaggctatt tgaggttgtc ttacagctca cttacagttc ttatgtttat ttttccactt  44460
ctatttcatt tgggcaggtt tattatactt ttccctaatt tgctaatttt tttgcaatgt  44520
ctaatccact gttaatctca tccaatgtat tattaatttc agacattgta gttttcatct  44580
ctagaaattg ttcatctttt tatatcttct ttgtctctat ttgatatgct aagtcttttc  44640
tctagcttct tgagcatatg aaatatagtt atgacaacta ttttatttta ttacaacttt  44700
taccttaggt tcagaggtac atgtgcaggt ttgttatgta ggtaaactcg tgtcacagga  44760
gtttgtttat tatttcatca ctcaggtact aagcctagta cccaatagtt gtttttctgt  44820
tcctctccct tctcctaccc tccaacttca agtaggcccc agtgtttatt gttcctctct  44880
ttgtatcact actattttaa tgtctctact agttctctta tttttgtcat ttctgagttg  44940
attttatttt tctcactatg gccatattct cctacttctt tgaatatctg gtatgcaaat  45000
tatacctagt atggatatta tatcaagacc ctgtcgcaat atggatacct aaaagaaaat  45060
aacaatgttt accagtttgc tctaagcctt tcttagctct tttgcttgtt tctcaagaac  45120
aagcacagag ggtggagctc aaccaagact gaagttaaag atgtagaaag attgagatgg  45180
gaagtaatta agttgaggag ctctgataca atggtatttc tctttttaat catgtaagat  45240
gcaagcccaa gataatatgt tgggaaagtt gaaggcgaat gtcttgagaa atatgaaatg  45300
cacccaaggc tatggctggg tgatagaaat aactaaaaag ttttaaaagg attgttttat  45360
agctggtcct tgctgaggtt aggggatagg cctggaaaaa ttgagcagtg gtattgccca  45420
ggcaggactc ctcatgacat tctccagatc cctaagtttt tccaagtttc caagcatttc  45480
cttggccagc aagtcatctc gcagcacaga tcctactctc tttcagtcag tcattccaca  45540
actctacaaa gcatttttct ccatcaaatg ggaacttttg gggttctgca taatttttca  45600
```

-continued

```
gggttccacc acttttgact ctttctggat accttgtaag gatattataa ctctttaatt  45660
catgtccttg attttctctt ttaactttta atactgttca ttgcctgttt acctctttca  45720
ccctcttctt ttcacttccg ccctctttct tgtgtaagta tataatcatc cttttttttct  45780
tcctcgaatc tcagttctcg ggagtaacat atacaattca ttcttacttc cagtctttta  45840
ttcctaagtt ccttatctct agttctcttg catatttgtg gcaattatta gtttttttcc  45900
aaaaatccat tctccctttt tcctgtacat gtatctttcc agcttgacca catttcccag  45960
cttccctggc agctaggtga agcaatgtaa ctaaactttt gcctgtaaaa tatgagcaga  46020
agttatgtgc acaatatctg cctcacttgc ttaaaataaa ttgtattatt tgagctttct  46080
atattgtccc tttttacaac taaaatgtag aggttatggc aacttttatg gtaaagagaa  46140
tcatcacgta ggagatcaag aatcattgat ttgagaggaa cctaaatcct ttaatgactt  46200
agtggagcaa gactgcccca tcagtctgga agctacccca caacttatgt atatcttcag  46260
attgttgagc aaaagagaaa aaatgaagcc actatatatt taggtctctt catgttaaca  46320
gtttagcttt taacctaaca cacatttatt cctgaatggt agcatattat taacatcaca  46380
ggaagggaat tccttgttca tggatctttt attttgttga aataaaggta atctgcttgg  46440
gcttaatact gccaaggcag aattttttgg aataattatt tctatagatg acccattcat  46500
aatgacaact aacatggttt ctaaaatgga ttcatgtacg tcatcttatt tagtccccgc  46560
aaaaattctg aaggtaggta taattattcc cattctatat attgaaaaat tgggattcag  46620
agagactacg gacttataca agtttctgca gctatttaag aaacagagta aagtctcaaa  46680
gccattaatg aactgtttag tttagtgctg cttagtaaaa ttagaactgt ttgaagtgcg  46740
ttttaatagt aaacccatcg atatttagtc agctctctgc ttgctaacta atatggaaga  46800
aaaaacatac atctacgtac atcctgaatt gggagaaggg aaataaaata ttgccaatcc  46860
cctttcctgt attaggtact gtgataaggc gataaggctt ttcattatta taaatgagtc  46920
ctggagaggt taagcgcagt cacccaaagt cacatgacca gtaactttca gagattttac  46980
cccaggtctg gaaagactct gaagcccatg ttattgcctc cagagcctgg tggagaaccc  47040
ctgaatggga cagagactca gcagacagag tggtcctttc cttccaggga gtcagggaag  47100
gtttggtagg ggagatagag ttagatctgg gtgggatttg gatgaaatga gatcaagcag  47160
ggataaataa gatccaagct gtttatgagg gacagggaga ggccagctct gttagaaaga  47220
gtggtttata cagagaagca tggaaacatt tgctccatgc ctcgccttcc atggatagca  47280
gtccagaaat gctacttgcc tgcctgacag tctttctcca gtccccaggt gtggacacgt  47340
tctgagcacc tgagcctggg tctgccctga cccagattct gtgagctggg acagagaatg  47400
tgtcctgctg tccctcctcc cccacttggg cccacaccct tttctacaca tttggattag  47460
aaatctgaat tggcctttct gtgaacccca atgacaggca agtccccagt aaagaagcac  47520
ttaatttaat tgctccttca gggtccactt agagtaatag ttgtgaacag ctctccctag  47580
tgtctcccac aggcagtgac aaatgttgct aaagataagt cacaaattct tggcaaggcc  47640
atcttaaata tgggaaggaa accttgttca gtcctgaaca gtcctgttca gactgatctt  47700
atcacaggtt gcacactgcc tcaatgtcac catgtttcta ccctcagttg tgcttggcag  47760
agagaggaca gctatacata aagtctgttc actctacaaa ggtgaaatca tttttttttaa  47820
ggtaattatg attgttctga ggatggtgat tgagtgacat ttaaaaaatg ggaaaagttc  47880
tactcataac tctgtctgct taatttgctt atataaaaga cttaatggtt tttgttgagt  47940
tgatccagag tcagtaacat ttgaatatgt gttattacca tttgatcagt aacaaaacaa  48000
```

-continued

```
cagggtaagt gggatgccaa atgtggctga gagtttaggg tttacattcc acaccccagc  48060
cttaaatacg tttgtataaa ttattggttg atttttcttt ttcatggctt ttctttgaca  48120
tttgatgggg ctggatttat ggaggcaacc aacaaattac acagcaatga attctggact  48180
gtagtcccac agccttgagc ctagatacta gctgtgtcac taatactctg tgtgaccagg  48240
gtaagttatt tagatacatt tatgactttc caaatcaata ggttggacaa agttatcttc  48300
aaaatgtctt tcagatttga ccctgaacat atgcgattct ggcatgttct gatttttagt  48360
tttctgttct tgaagcatgt ctacaataga aatgcctacc ttcatataca ataaaaggac  48420
attagattaa tatggtgtct gtgaaaatca ttgaacagct ttagagataa aaataatgaa  48480
atgagtcaag ttctccatta ttaattaaat cttttaaatt ttctgtttat gaaactatga  48540
acaataaatt ggaacaaaga tataatctca ctacaagtaa attgtatttt atgtaaaata  48600
taatttgtct ttagaaaata ctcaatgaaa ttaccttttt aatttcagag attttgagga  48660
ctattattgt tatttcttta aagtgataaa tgtaatccaa gatgcctttt ttcccccttc  48720
agaagcttga gtgcccaagg gtttgataaa tgtggaaaat aaccgctgtt cgaatatcct  48780
gttggcctgc tggtgagatg tcatcgtgtt gtctgaatgc agtatgtgtt taaacttgcc  48840
atttattacc tgaaattgtg ttattttgcc tcataccctt agtaatactc ttgtaatgct  48900
ggctgagaat tgaagcaaat gccctatgaa actcaaggga gcaaggtctt tgttattttt  48960
cagaagaaat gactggctga ggctgtaaag aaatcttgtg gtcattctca tggaaagagg  49020
attggagccc cgattctttg atctcattat tgaccagttg attgagaaga ctgtcctcct  49080
gtccccaccc aatcacaata agtgggtaat tacctgaggg ctaatttgct ccttgaatgt  49140
gaatacattt gtggaaattt ccttgtgctc agcacctgtt caaaacatcc atttgtattg  49200
cagagctatt gtttttctaa tctcattgtg gagctaagag agagattgtg tttaaggttt  49260
ccttcgtaat aggttttctt gctccaggaa ggatgcgtga cagactctgc acactgctgc  49320
ttggtaggtg ttcagtgatg gatgcgtttt ccatctccca ggtacagctg cagctgtgct  49380
gactctggtg cgtttgtaat atgcactgtg gagtgcacca tgatttcatg atggctggag  49440
aaatctggtg gctagaattc tagggaggag gacatgagtc ggaagtgcag aaacctcaca  49500
ctgggacatt gatggagaaa atccaattct gtccctggag ttaaagagga gtcactcact  49560
gggccatcat aagagcaaat aaagttacag ttatttcttc agatccacaa ctcaaactca  49620
gcgaaagtaa ttattcactc tttttgtccc aaacaataat gaaatcagct aaagcatatt  49680
gtatttatta cttccactca agttattgag ctgttctgac accttgttgc tgggaagata  49740
cacagatgga acaccatcat ttccattgat tctgatcata ccccacgcta atatagcctt  49800
attgctctga gtcatagga ttttatgctt gcctattcaa aaaacagttt ttaccttatt  49860
aaaaggtgat atgacctgag ctggagatga tgtttggtca ttttgtgtaa accttttaat  49920
attttagtgg taaatacatt tcttgaatct tgacaaaaac ataattaaaa tgaacatatt  49980
taaaatggac atcttccaaa tgttcatttt taaaacaaac atcttccaaa tgttcatttt  50040
taaaatgaat atcttcgtta acttttttttt ttttttttga gacggagtct cgctctgtca  50100
cccaggctgg agtgcagtgg cgcgatctcg gctcactgca agctccgcct cccgggttca  50160
cgccattctc ctgcctcagc ctccagagta gctaggacta caggcgcccg ccaccacgcc  50220
cggctaattt ttgtattttt agtagagacg ggtttcacc gtgttagcca ggaaggtctc  50280
gatctcctga ccttctgatc caccctccac ggcctcccaa agtgctggga ttacaggcgt  50340
```

-continued

```
gagtcaccac gcccagcctc ttccttaact tttaatgaat aaagagttga aagggaaaaa  50400
ccaaatgtgc actatgctga ttttatcttg agctgtacag aatgtgcagt aacttaagaa  50460
tataagtcat tctgctgtta ttcatactag cctattcttt agcattattt aaacacacat  50520
atttgagtgt ctacacactg cctgctaggc agggggctgg gtgccaagaa gggatgtcca  50580
gagataaacg ggcatatgtg ttaatctttt agggcacagt ccagtaacct gatcaaggag  50640
tgacgtgtat tgtgtactag gatagaagtc agtatcagag gaaacacaaa ggaaagagtg  50700
gtactttctc cccagggaag ggatgctcag aaagaggggg ctgattatgt ccctggttca  50760
tgagaaaaag ggcattcctg gctcagggag tgggaagaac aaaaccaaga aatcctggaa  50820
tggcttggtg catcagccag tctgtgagtg cagggcatgg ctggagttct ggctttaaga  50880
tgagtgggaa gaaaggctgg agaggaggtg gatccaggaa aagttgctgg gagcatttat  50940
tcttttggca atgggaagcc atggaagaac tgttgtaagg aggattctgt gtgatacatc  51000
tgccttttag agaggtcatt ttatagaaaa agtagaaaat acagaccagc aaaaatttaa  51060
aaagtgaaaa caatcactgt tcaagctctg gtctagcact caccagtgtt tttcctacag  51120
gtgcatatac aaacatgctt ttacatttta tttttatttt aaatttttca ctatcctcaa  51180
tatcagtgga aacaaatctg ctttttttaat tttttttttta aaaatgagat cctattgtac  51240
acattatttt aaattttttt tcattctttc cttttttttaa aattaaaaca atttttttttg  51300
agacagtctc actctgtcgc ccaggctaga gtgcagcatc gtggtctcag ctcaccgaaa  51360
ccttgcctcc caggttcaag cgattctcct gcctcagcct tccaagtagc tgggattaca  51420
gacatccacc accaccgtgt caggttaatt tttgtatttt tagtagagaa tggggtttca  51480
ccattttgga caggctggtc ttnnnnnnnn nnnnnnnnnn nnnnnnnnnn nnnnnnnnnn  51540
nnnnnnnnnn nnnnnnnnnn nnnnnnnnnn nnnnnnnnnn nnnnnnnnnn nnnnnnnnnn  51600
nnagcgtatt cgcccgtggt gaagatcgta gtagagtcta ccacctcggc cgtgaacctg  51660
gctcaggggg cgcagccggg gtgggcgacc cagccaggtc tgcggagcgg tgcccggcgg  51720
caaccccctc acggacgctg ggactccccc accccgtccc cattcagcgc tagcggtgga  51780
ggggccaggc ccgccccagg tagtcaggca ggggtcccgg ctcctccccc aggaccaccg  51840
ccccgcgggc gctcacgtcc tgatggcttc ccacaccagg agcccgtcgt cccggtagaa  51900
gtagtagggg atgtcttctt tgctctccat gccccgggcc ttgatggcct cgggaaagca  51960
cagggaggca taggtcaggt ccttcatggc cctctgcacc atctgcacgt gcccaccgcc  52020
ccctgtggcg ttggcctgga gtgggaggta gagtgccctg agcgggtggc tcctcccaca  52080
gctgtccaga cccatccctg aggaaatgtg ccaggggagg cgaggaggcc aggcaggcag  52140
aggtgcaagc ccttgtcctg tgagatgggg gagggatgtt taacgcagag aatgacaagg  52200
gcagccgggt ggagaggtgc tagggaggag cctcccgccc aatccaatgc aagggactga  52260
accgtggggc tgcagagtac aagagggaag ggtgcgctcc cagccacagg agggcagcag  52320
gcgtgggcag gtgtgtgggg gaccccagca ccagcgggcc tgggctgtga agtctgctct  52380
agtgctgagc acacgaccct cagtcattgc tctcagtgac cctcagtttc caggacccat  52440
gcaactctgt tgagggcctg ttgtgtgctc aggtgagggc tggagagacc cacaaggagg  52500
gatcctggtc ctgatcccga tcccggcttc tgagtgatgc agacacactc acaagctcac  52560
tggcacatat gtgtgtccac gtgcacacac acacatgcaa atacacccag ggggctgggc  52620
tgtcggtgcc acagaggttt tgaagaagga cttgggtgct ggggtgccag agattggtcc  52680
acggtgggca ttcagcccaa gcaggaccaa ccagagctgc cccccagcac tttctgttta  52740
```

-continued

```
gatgcggctg ggagataatg gccacatgag aacctgaggt ggagctacta tgatgagctc  52800
ctgtgccctc tcccatgggg gcctgtctgc agcaggagag tgtgatgcca acacaggtga  52860
aagagacaga aagagggagc cagtgtgcat gcaccctggg gcattgcttg agtccctgga  52920
tccatttctg gctgaggccc ccgaccctct attgtgtcca ggtatttgag ataaggcatg  52980
tcttgtccag ctgcagctgg tttgagttgg gttttgtcat ttgcagccca aacagtgtct  53040
caacttcagt ggtcatctgg cctggtcact aatgggctgg ggaaaggagg aaggttgggg  53100
caagggccca tgtgagagtc caagcttggt aaggctacag agggctcaaa acgaggtggg  53160
gtgctacctg agggatgcga gggctgggca gggcctggag tccccgatgc aggagacagt  53220
gggttgggag ggttgggacc cgggaagcag agtgctgggg aggtccaggt cagggtggca  53280
ggggtgtggc agattaagag gcagacacag gttcctggtg cgtaggaggt caggggggcca  53340
taaggagtgt gttccagagg ggggtctaca cccaggtccc agaggctggg agaggggagg  53400
ggtgggagga ggggaccagg agccatcagt gagaaggaag acctggtggt gcgcctggag  53460
gagtgctcct ggctgaatgg cacgggctgg agacatcagg aggatgctgg agccagtgct  53520
ctgagcagac tccagccttc acccttccag gcctcctgaa agggtgtcta gatctcagat  53580
agggagtgaa ggcggccagg ctgggctctt ccaggcaaca agtagggtag gagggcaccc  53640
accttgtcaa agaggccaca ctcgcagatg agctgctcac gggccttggt gttgattgca  53700
atggtgaatc tcacgtgtgc caccagcagc tggggagggg agaggaggag gcctcagagg  53760
gggcccagtc aggtgacctg gtgcctcagg gacccgcagc tcccccaccc aggcctgccc  53820
tataggatga tgctgggcgc agggaggaag tgaaggctgg gtgctgatct ttctgctgaa  53880
taagtgctgg aggcctgcac ccctctgatg cttactaagc atgataatga ttcagagggt  53940
cctggccagc acttgtacaa tgcttacctc tttgctccct gagttcactg tcttaatctg  54000
accatcattc tgtaaggcag ctgtactatt tgacctgttt tactggtgag gaaactgagg  54060
cacatgggta cttttagcat gcagtcaccc cagcagccaa tgcttgtagg attcgagaac  54120
agggacggag agtgatggca ggggcggcca tcagcatcag ccgaggatca ccatgaactc  54180
atttgccttt tccaactcta ctggctggcc agcgaggccc gtgtgtcagg cccatgcccc  54240
agccgcgtgt cctggggaac agcaggctcc tagctgtttt cttcctttag gggcattact  54300
gactctgaga acatctctcc agggctccct ttctgccacc cactcccagc cacaggtccc  54360
cctgtgggat gtcagtgatc cctcccactc cacatctcag atgccctccc atagcaggtg  54420
gggcggtagc tggctgtacc ttgaaaatgg ggtgcacagc aggcagctgg cggtacattg  54480
caatgccaaa aacctcagac accagatgtg ttcgcagaag gtgggtgatg gtctggtgga  54540
cgtggaagtc actggaacgc acccagattt tggccaaaag ccagtcgtat tttgcatccg  54600
aagggaggaa aataggggttc tcatctcccg ggatttggtt gagctgatac attgggggaa  54660
aggaaacaca ctgctatatt tcacttcaga gtatagttgt tggagaactt cgcctcttgg  54720
gaagttccag aagtatctga atttctttaa cagtgacttt ggaatcagaa gagcctggag  54780
ggggtaaagg gccctgcggt ggtatttcct gtcccagcca tattacttac aacctgcatg  54840
actctggatg acacactggg ctttctaagc tccggcttca gcatctgtca tgtggggaca  54900
gtgatcgctc ggctcacagt tactcaggag ctggcagcat ggaaggagcg ggcaggccga  54960
aggcccagca gcggaggggg aggatcgctg tccccctctt ccctccttgc cctgctccct  55020
cttctactgc ctctccttgg tctctcatac tttcctccct ctcctcttcc ctgaaatgct  55080
```

-continued

```
ggagctcccc agggtctgcc atggtgctcc tgtcttcttt tcttgcccta agtcagctcc  55140
tcctgtttaa aggcttgggg ccctcctggt actgagcctc ccagatcagg gtctgcagct  55200
tgagctctgc ctggagccca cacctgtggc caggcacctc ctgtagcaga ggctggacct  55260
gtcttccctt tccagtttcc actccacact gggacaaggt gagttttttt cttttccaaa  55320
atgcaaatca tgtcatgtta actgcctcct caatcacctc ttaatgccag aaaataaaat  55380
ccccaagctc tgtggtgacc tggttgctga tgcctctgta cacacagcct cactttcgtg  55440
cccccacacc agcacccagc cccaggtccc tccatgccag cagccctgca cgttgccccc  55500
ttattgagag cccagcacag cctcagcacc cgacagtgag ttctcacggg agccggcagc  55560
aggtgctggc attgcccatt tttacatgaa gacatggggt attggagggg ttgacagaaa  55620
gaatgaggtg ggtggcaggg ctgcagccaa gagcggccag gaaggggcat ggccagactt  55680
taggtgctgg gaaagaccag tgtcactgca gcacagtggt catggctggg gagggagaac  55740
tgtcccagag cacacagctg tgtcacttgc tataagtatt gtggaaggtg gggtccttgg  55800
gcgtctctcc ctcgaaaaca gtgctgtcca atagacatat aatgctaccc cacacatgga  55860
attgtatata ttcaggaagc catattaata aaaataaaag gaaacaggtg aaatgccggt  55920
gaataatata attttatttt acccaatata tccagaatat tatcacttca acatgaaacc  55980
aatctaaaac tattaaatga gatatttcac attccccacc tccttattct aagtcttaaa  56040
aatcaggtgt gaactttgca cttgcagcag gttttggttt ggacgagcca aatcccaagt  56100
gctccagagc cctggtggcc agtggctcca ccctggtcag agagacccca gaagcctcag  56160
cactccctga ggaccaagga ggggggaggg aggagggaga gcagagtgtg acttgcacat  56220
taggcgtgcc tgtctgttta tacttgagat tagttggctg cttttaaata ccagacagtt  56280
tcacataaaa atttgaatga cctggttttc ttgaaaaatt agaaggtctc agaactctgc  56340
acccaggttc tcacagaact acgctcttgt ccccttttaca gagtcccagc tctcagggtc  56400
cccactgcca cacccgtttg catgagatgc ctgggccact gatacctgat ctgtgcccta  56460
gaatgctggg ctgcctggca tgctctgaga cactttctga catgtcccca catgctctga  56520
catgttcctg atggctctgg gacactgaca tgttcctgat ggctctggga cactgacatg  56580
ttcctgacat cctctggggc cgaggagccc ccctgttgtg tgctaggggc tttacccatg  56640
ctatctcact taatcctcac tttgaccctg caaggcagat attccttgct gtacccattt  56700
tacatggggg gaaactgagg ctccagctgg tttagcagct ctcccaagtc acacagtagg  56760
taaagagctc agccggcaac atgatattga acaggcaaaa attggaagca atccccctaa  56820
aaactggaac aagacaagga tgtccactct cacccctcct attcaataga gtactggaag  56880
tcctagtcag agcaattagg caagagaaag aaataaaagg gatccaaatg aaaaaaaaaa  56940
aaagaggaag tcaaattatc tttgttcatc catgatatga ttctatacct agaaaaccct  57000
gaagattcct ccaaaagact cctagacttg ataaacaact tcagtaaagt ctcaatgtta  57060
taagtaaaat gcttgtttag aaacagaatg cttgttcctc ggtactgcaa ggaaaaatca  57120
gcatttagac aaaaagtttt tttagcaagc caattttact ttctgcagaa agggtgctcc  57180
tcgcagatgg aacaatggcg agagcacacc tgaataatgg agagaagcaa tttttattcc  57240
ttacgcagct tgtccctgct accgtgtcct gtctccattg gctggagcca aacctcacag  57300
tctaaactaa aacccgactg gctaataact taaaactttt ctaaataggt aaaagcagtg  57360
gaaagacaaa ggaaaagagg aagttgctta tgaaaggact tagaaaagta ataacatttc  57420
caaataagga aggggcatgg gctgcaagct gggacatgcc tgtgagcacg tccagcacaa  57480
```

-continued atatcttggt taaagtacaa ggacatagaa tgtactcatt cccttatatc taacagctac 57540
atatgatagg gcttaacaaa aagttattag cacaaagcga aaaggcttaa aaaaagttag 57600
tctttagaaa aaactattat ttctaacaca taatttactc cttaacaaaa aaaaaacttt 57660
tgactttcta cactcaagat acaaaatcag tgtacaaaaa tcagtagcat ttctttttat 57720
ttgagacgga gtctcactat cacccaggct ggagtgcagt ggtgtgatcg cagctcactg 57780
caacctccgc ctcccaggtt caagcaattc tcctgcctca gcctcccaag tagctgggat 57840
tacaggcagg tgttaccaca cctggctaat ttttgtattt ttaattgaga cggggtttca 57900
ccatgttggt caggctggtc tcaaactcct gacctcaggt gatctgccca cctcggcctc 57960
ccaaagtgct gggattacag gcgtgagcca ctgtgcctgg cctaaaaatc agtagcattt 58020
ctatgcacca acaatgttca ggttcaggct gagaaccata tcaggaacgt ggtgatctca 58080
gttacaatag tcccccatac acaaaataaa ataccaaaga atgtatccag ccaaggaggt 58140
gaaagagctc tacagagaga actataaaac actgatgaaa gaaatcatag atgacacaaa 58200
aaaatggaaa aacatcccag ctaatgggtt ggaagaaagc aatctacaga tacaacacaa 58260
ttcctatcaa attatcaaca tcatttttca cagaattaga aaaaaaaatc ctaaaattca 58320
tatggaacca aaaaatagcc gaatagccaa agcaatccta ggcaaaaata caaagctgga 58380
ggcatcacat tacctgactt caaactatac tacaagacta cagtaacaaa aacagcatgg 58440
tatactggta caaaaatagg cacagagatc aatggaacag aacagagaac ccagaaataa 58500
agccatatac ctgcaaccaa ctgatttttg acaaaatcaa caaaaataaa caataaggaa 58560
aggacatcct attcaataaa tagtgttgga aaaactggct acctatatgc agaagaatga 58620
cgctgggccc ctacctctca ccatatacaa aaattacctc tagatggatt acagacttaa 58680
atgtaagact tcaaacttta aacattctag aagaaaacct aggaaaaaat cttatggaca 58740
tttcctaggc aaagaattta tgactagacc tcaaaggcat atgcaacaaa aacaaaaatt 58800
gacaaatgag acttaatcaa attaaagagc ttctgcacag caaaacaaac tatcaacaaa 58860
gtaaacagac aacctacaga atgagagaaa atatttgcaa ctatgcatcc acaaacgact 58920
aatacccaga atctatgagg aacttaagaa aaaacaccac cattaaaaag tgggcaaagg 58980
acaggaacag acacttctca aaagaagaca tacaagtggc caacaaacat atgaaaaaat 59040
gcccaacatc actaatcatc agagaaatgc aaattaaaac cacaaaggga taccagtcag 59100
aatggctatt attaaaaagt aaaaaaatga cagatgttgg caggatgcag acaaaaggga 59160
atgcttacac actgttggtg gcagtgtaaa ttacttccat ccctgtggaa agcagtttgg 59220
agattttgca aagaactgca aatagaatta ccagttgacc caacaacccc attactgtgt 59280
acctacccaa aggaaaagaa attgttttac caaaaggaca taggcacaca tatgtttatt 59340
gcagcactgt tcacaatatc aaaatcatgt aatcaaccta ggtgcccatc aatagtggca 59400
ccagataaag aaaatgtgat acatgtactc caaggaatac tacatagcca taaaaaagaa 59460
tgaaatcgtg ttctttgcag caacatggat gcagcttagg attggcactt aagccataat 59520
cttaagtgaa ttaacccaga aacagaaaat cgaatactgc atgttcttat ttataagtgg 59580
gagctaagca ttgtgtacac atgggcataa aagtgggaac aaaagacact ggggactcca 59640
ggaaggggag ggagggagga aagggttgaa aaactgggta ttgggtacta tgctcagtat 59700
ttgagtgatg ggttcaatag aagcctaacc ccagcattat gcaatataac catgtaacaa 59760
acctgcacat gtacctgaat ctaaaatttt atatattaaa aaaaaaaaaa ctgttctgac 59820

-continued

```
cagtaaaaaa agagctgaat gaggatgggc ccagtgctct gcctatttca gcccatcact  59880
ctcccttctg cttctcttca cctcccggcc tgaccgggcc tcacctgccc atctccttga  59940
gctcttgtac cactgagctg ggccttcccc aacccatcct tcacatcctc ccactcctgt  60000
ccaggatttt ggcctgccat gggatgccag aacttgccct gagcaatttg tgtttcttaa  60060
atttgttttt tgggtaagga agtagctttg cgtttctgat tagaaaagaa tatgtgctta  60120
tcgtaaaaag aaatctgagt catgacagga gagcctgaga aagaaaacat catctcatct  60180
tccagcgccc agggataacc accaaattct ggggagcctc ctttcatagg tctttgcatg  60240
tgtgcacatt tatctgtcca attttccatc aactgaatat gattataatc aacatctgtc  60300
tctttgtttt gctcacctgt cccccactgg gccatcactg tgttcctacc tggtgacact  60360
gcgtccttgt gtccccatgc tggcacagta ggcctgctgc atccttgcat tcattttaca  60420
taagtgagac catgcccatt gccttagcag tttgaaggag ctatttgtat acgacagata  60480
tgtatccttt atcggtccct tgtgtcttgt ttttccactg ttaactcatt gtggagaccc  60540
ctccaggtca gctggaaggg aaccaaagca ttcctttcaa agacgcctca acattttatg  60600
gtgaggacat ggaagggctc actcactcaa tcctcttctg ccttcagact gttttcaatt  60660
tttttcccca tcacaaacta tgctcctgtt gctacccaca cacatttgtg ctttcatttc  60720
tgctgagtgg ctgctagcga aggctgagcc ttgggggttt gggtatgttt tcgagtagac  60780
agtgcctgcc ctactgttcc tcagacagtt tcactctcct ggtgcacacc tgttcagtgc  60840
tactggctgt cagaacactt aaacaataaa gtcccctcca gtgctcctcc aattgagacg  60900
gggcaggggc ctcctcttag ggcactgtag ccccccagcc ccgcaacagg gcatggaaat  60960
gaaggaaaat cccgagttcc ttgaagggaa gttccaggca cctagctagc cctgagaaat  61020
aaatgagcaa cttgacaaac aagagggtaa cagcagccta aaacaacagc caaggaagcc  61080
agagtcctgg gctgtttggt tccctctgga aactaaagag aacccctgaa catgtgtctc  61140
tgagttgttt ttcagaaacc cagaccccca ccaaaccgat ccactggcac agagacctca  61200
gataagacgg aactgaggac tgaactctga gcaggctctt tgttctaaat ttcttcctgg  61260
ggggcctggg ggaagtcccg cccacaagcc acagctaaca ttcctttctg gtaacccaaa  61320
tttttaaatg aaacttctct tccttaacca atttcaaaac aacaaatttt tgaatctacc  61380
tatgacctgg aagcccaccc ccacttcaag atatcccgcc cttttaggcc aaaaccaatg  61440
tgtaccctcc atgtattgat taatgatttt gcctgttaac ttctgcaatt cctgaaattc  61500
actctgcctt taaaaaccct tacctgcaag ccatcaggga gttccggtct taagagtgag  61560
ctgcccaatt ctccttttttt ggtccccgca ataaatgcct tgtgttctcg tagattatat  61620
cccaatctca gtgtttggtt ttgctgcact gggcaagcag atcccagtcc agctcggtaa  61680
cacaactgtc ctcgccacga cagcctcaac cccaggaccc tctgaccgcc cactgcaaca  61740
tgcacctggt acagcaggcg ctgtgggatc tgctccggtg ctggccgaag ctctgacctt  61800
gctccggtgc tggccgaagc tctgaccttg ggctgcccag gcccaccagt tatcccgtga  61860
acactgccag gctgcaacaa ctcatgagca gagcatgggg ctccgtcctt gctggtgtct  61920
gggagttacc cctttgtttt tccaaccagg catgtcagaa atgatatctc attgttaact  61980
ttcatttgca tttctctaac tacaggtgaa gttaggagtt tttccatatg ctggttgccc  62040
atttacattt cttcttttgt gaattgccta ttcatattct ctgctcattt ttccactgga  62100
gtattggtat tttcccgtca atgtaaagga gctacctgtg tatcatagat aggcatctct  62160
tagctgtcac ttctgttatg gttactcacc ctaatctctg ttttgctttt tggctttgtt  62220
```

-continued

```
tatggtttat cactcaagtt ttaaaacatt acataatcaa atatgcttag ctttcccctt  62280
ataacttctt ggtttccttt tccttctaaa agtcttctga gtgtctgcgt aattagtttt  62340
tctaaattcg tttacttttt tcattttaat ttttacttca tctgaatttt ttctttttct  62400
tctaagcaac tcctctacat gatgagattt atttttgtaa atggcatgac agagcagtcc  62460
aatttaattt tcttctcatg caaaggcagt gtgatagcat cattaaaata atatcccttt  62520
ttcactgagt tgaaaaacct ccattgtgat acactgaatt cctctgtggg ggagtccatt  62580
tctggatctt actctatact gtcccccaat tctctctgtt ttcaagcaca gtgtctgctt  62640
aacagtaacc ttacaaatcc agcaaggaaa gtgttccttc tgtgttttct tttacttttt  62700
tttttttttt taaagatagg gtcttactct gttgcccagt gtggagtgca gtggagcgac  62760
catggctcac tgcagcctca aactcctgga ctcaagccat cctcccacct cagcctcctg  62820
agcagttggg attacaggca tgcgccacca tacctaattt tttctattaa tttttttttt  62880
ttttaagaca tgaggtctca cttggttgcc ctgcctctct atgtggtttt aatttttttc  62940
aaaaaatttt tgactatgct agatttcttt ttccatatga atctttcaat tttttaattg  63000
ttttctctcc tttttagttc ctcttcacca ccaccacacc cccaccaaga aagataaaaa  63060
attctggctg aaattttact tggaagtgca ttaagttttt ataatagaat ttggtagaac  63120
tgacattttt acagtttcct ccccaatatc aaatcactgt taagagttca ttgtatatcc  63180
tttaaaataa ctttatagtt ggccgggtgc ggtagctcac gcctgtaatg ccaacacttt  63240
gggaggctga ggcaggcaaa tcacaaggtc aggagttcga gaccagcctg gccaacatgg  63300
tgaaatgccg tctctactaa aaatacaaaa aattagctgg gcgtggtggc aggtgcctgt  63360
aatcccagct actcgggagg ctgaggcagg agaattgctt gaacctggga ggtggaggtt  63420
gcagtgagcc gagatcacgc cactgcactc tagcctgggt gacagtgcga aactccatct  63480
caaataaata aataaataaa taaataaata aataaataaa taactttata gtttttcctt  63540
atatgggcat tatattttat tgttagtatg gagaaaggct attgattttt ttgagaaata  63600
tatttatcta aacactttgc caaatgaatt tattaatcta gtagctttta aaaaaattag  63660
aatctcttgt gttttctagg tctaccatag cattaccaga aaagatcatc ttccctgttc  63720
tttgacaata tgtttattga ttgttttcct gttttatcat gtggtatgac ctctaaaata  63780
atgttgaata aaaacagtga tatcagcatt cttattattt taatggaaat ggcattagag  63840
ttgcaccttt ttgatgttag ctatctttat catataaagt aaggttcctc ctattaattt  63900
ttattagttg tggctattaa atgttattaa attccctttt agtgtgaatt gatataatca  63960
taaactttat ccttatgggt ataataaatt atggtggtag ctctcttgat attgaaatat  64020
ctggaataaa ccctgcttgg ttattacata tagtcattta atacactgct gcactcactt  64080
cgctaatatc acctttagtt ttcttttaaa tctttattta atacttggat tggtcttcag  64140
ccttcttttg aagcctgcct gtatccagtt tcagaactaa gcttacacca gctttatatg  64200
atcaatttgg ggctgataaa gagccctgga aatgtcagct gtctagtggc tgggtgagac  64260
tcagctgctc gctgtgtagg tctgtttcca atcactatat ggaaattggc ctattttcta  64320
caatttcttc taatttatct tttcctaggt ttttatccat ttctctaatt tttcaaattt  64380
ttgccatatt actctcattt aaaaaaatatg taatcataat tactgttctt tttttttttt  64440
aagagacggg gtcttgatat gttgctcagg ctagactgct gtggctattc acaggtgtga  64500
tcatagcaca ctacagcctc aagtgagcct cctgcctcag cctctcaagt agctgggact  64560
```

-continued

```
acagttgtgt accaccatgg tgcctggcta taattactct ttttatgatt cctttttat  64620
tccgaatctt gcattttttt tttctatctc tttttttcca tcagcctcat gaggaggtta  64680
ttattattat tttttggacc tttcaaagaa ccagatcttg gatttactat cctctggctt  64740
tcatttgctt gagtctttat agtttgcaaa gtttccattt tcagaagaag aaagagaccc  64800
aggaacattc tgtggcttgc tcaaggtccc acagcctgct agcaagtggc tgaactggaa  64860
tttaagctag gcccctgact ccaggctgct ccaagagatc tctgagccaa gcttttgaag  64920
gcaccatcag tggtgcctgg gatctccggg gatctcccag caattttgtc ttcttttagg  64980
tcacctgtcc ctttacctgc tgcttcagtt tcttaggcac agggcttctc tctggtaaca  65040
gacaggaagc tcctctgagg ctacgtgccc ctgggagact gtggggaggc tggaatctag  65100
agtcagatga cctggcttga atcctagctc tgtggctggc tgtgggcacc tgtgtctcag  65160
ttttcttatc tgggtaaaat gatcaacatc aatagagccc actacctagg atggttgtgg  65220
tgatgattac acaaataaag ataggttatc taaaacccca gtggtcaaat gtgcttcaga  65280
atccagaatt tttaggattt tagcagtggg tatacttcat tatgtgccat accccctccc  65340
acccccagtc tagggcaaca tactatttta caatcgaaca gagcagtatt tctgcagtga  65400
tccacataca tatcacattg aatggaaaaa gcctctaaat aacctcacct attgcttcaa  65460
agaaggtttg tttacaaaca atgaatttgc tgcacagttt tgaaatatgc agcagttttc  65520
agatttttta gatttagaat cgagggtaag ggattgcgga ctgtgcaggt taacccatag  65580
gatagccttg gcatgtggct ggtgcctgac ctatccagct gctattgtgt ccacagctcc  65640
caaggtccag ttcatggaca ttatttgctg aatgctcatc tgccagtctc ccacggtgtc  65700
ctctgcgcag ttcctcccta ctcccaggga cctatgccca gtccagtcct ggccttggcc  65760
cctgctgtct gcacaccagc tcccagcctg gcagcaggct ggtgccagga acagggggag  65820
acaaagccct gtgcccgcct gcctttcctc cagggtctcc ctcttcctcc tgcctcatct  65880
ccggtggaca taagaactca catcatcatc aaaggtggca taccaggact ggcctggttc  65940
ctgaccccag aacccatggt gcccctcagt ggtcttggtc tccagcttag tccacagctt  66000
cacctgcctg gcccctggca gcaccttgac tgggggccct tggtcagggt gctggggtgg  66060
agagtgcaga atatgatccc agggcaggtc ctccacagtg tgcctcgact ggccaggggc  66120
ttctcaagtg tgccttgggg agtagaaccc tctccgcccc tatggacagc ccacctcagg  66180
gcctgcagga agccctagtg tctttcaaga catagcttcc tcagctggag tgtgaatgga  66240
gccacccagg agccctggat cgcagaggac tgagctgctc agaaaggtgt gccccccagc  66300
agcctacctg gatggcaatg gggacaatct tgttggccag gttcttatac agcaagcaga  66360
tgggagcggc caggaactgg agtgtgcagg ggtctgtttt gttggcatcg atgccatcca  66420
gcagctcaaa gtccacgatg aaaatgttcc cttgctgcag gaggcagaga gatgtgtcca  66480
aatcaggctc agcagacgga ccaaaaatca ggcctgggga aagagtgatg acctctgggc  66540
acccctctcc ctttcctgcg actcagcgga gctcagaatg tgtacttctc tcctctgact  66600
ccaaggctga ttgattcaca tggaaggtgt tcacaggttg tggcagttcg gggtaagatg  66660
aaggaatggc agcagctcat tcggcatttg tggtgtctga aacctgcttg actggcacga  66720
aagatgagag accgacccga gtgtcagttt actaagaaga aagaggttag gtgaaataga  66780
tgtgacgagt taaatgccaa tcttcaccac ggggctgaag gtccgnnnnn nnnnnnnnnn  66840
nnnnnnnnnn nnnnnnnnnn nnnnnnnnnn nnnnnnnnnn nnnnnnnnnn nnnnnnnnnn  66900
nnnnnnnnnn nnnnnnnnnn nnnnnggggt cctcagggac tgggcctcag cccgccggtg  66960
```

-continued gttccaccct aggcttcccc aagtcggtca agagccggga gcagctgtcg gagtacctga 67020
ccgtggtgat cttcaccgcc tccgcccagc acgccgcggt caacttcggc caggtaggca 67080
gggccgggcc cgctgggcag ggctcccttc tcaaggccgc tgcctcctcc cccgccccgg 67140
ttctgcacgc gtactgcacc ctcggacagc ctcggggcct ggcacgggac ttgcaggatg 67200
gattctgccc gctcagccaa gggcgctggc cgcggggaaa gaggatggac ggactgcagg 67260
gcccgctgga gttgggggc acggggagga cggggcccag ggggcagctg ggcagcaggg 67320
cttcgggggt gcccacgctt gctggcggtc gtctccgcag tacgactggt gctcctggat 67380
ccccaatgcg cccccaacca tgcgagcccc gccaccgact gccaagggcg tggtgaccat 67440
tgagcagatc gtggacacgc tgcccgaccg cggccgctcc tgctggcatc tgggtgcagt 67500
gtgggcgctg agccagttcc aggaaaacga ggtgaagctg ggcagggcgg ggcacagccc 67560
caggtcaccc caggttaagc ggttcctcag cctcagggct ttgtgactcg ggccccaagg 67620
ctcacttgga gcaaaggaat cctgacttcc aaggctggaa gggcccagaa ggctgcagcc 67680
gccaccaggt cccccggcct cagcctggac agagctcagg gtgtgcaggg caggagagca 67740
cacagcccag gctttgctca ctgtcaccag agggtcgtgt gtgacgcccc ctccccccag 67800
ctattgacaa agttcttgca catgtgtttt accctggtac tccagaggga atgaccaaga 67860
gtttcctggg ttccttccgg acacgtgcat ctcatttaac ctaacaactg aatccggtgt 67920
gtcttcgtgg atgcacccgc tttggggtag ctcagtactg catagaatgg ccggaccagt 67980
ccaacctgct ccagactgct gggtgtctga gttgttcccg gccaatgtgt tggtccctca 68040
ctggacatcc ttgtttttgt ggctttgcac atgtgttcag tatgaccgca cacattccta 68100
gcagacaaat tccttggtca aagaatattg atactgaatt gccctccaca aactaaattc 68160
aaaatcccat tatcaatagc ctatgtttct tggacctttc cagctcagaa gctttgtgat 68220
cttaatccaa tacagtattt ttttaaaatg atatctagct ctgccccgca gacatctgtg 68280
tgagaatgca aataagcaca ggaccccaac agggcagcca cccctcagg ctccctggcc 68340
cgctttctgc cttcctgggc tggagaggcc agtgctggcc ccagcgcccc tgatgggagg 68400
tgagagtgct gcgcaggggt ggcccaagac agcaggatac catggctgca aacaccagca 68460
gcccccagct tcatctgcat catctcgtaa ccacttggca gcaggcagtt attttcccac 68520
ttatccatga agccccagcc ctggagcctt ccttagagaa gcaggttgga ggcgacgaca 68580
cttgccttcc cgaggccctc ttgtcaggca gcagagggtg aatatgggga ggtgaataga 68640
tgctccctcc ttcatctccc aaacggtggc tggccccttg ggatgagaca ggcctgtcag 68700
tttacacggg tagtggattg acctatgtgt gtgtccatgt ctgggccctc agctgttcct 68760
gggcatgtac ccagaagagc attttatcga gaagcctgtg aaggaagcca tggcccgatt 68820
ccgcaagaac ctcgaggcca ttgtcagcgt gattgctgag cgcaacaaga agaagcagct 68880
gccatattac tacttgtccc cagaccggat tccgaacagt gtggccatct gagcacactg 68940
ccagtctcac tgtgggaagg ccagctgccc cagccagatg gactccagcc tgcctggcag 69000
gctgtctggc caggcctctt ggcagtcaca tctcttcctc cgaggccagt acctttccat 69060
ttattctttg atcttcaggg aactgcatag attgatcaaa gtgtaaacac catagggacc 69120
cattctacac agagcaggac tgcacagcgt cctgtccaca cccagctcag catttccaca 69180
ccaagcagca acagcaaatc acgaccactg atagatgtct attcttgttg gagacatggg 69240
atgattattt tctgttctat ttgtgcttag tccaattcct tgcacatagt aggtacccaa 69300

-continued

```
ttcaattact attgaatgaa ttaagaattg gttgccataa aaataaatca gttcatttaa  69360
aatgggtctt gttccatgtg ttatattcca atcaccccaa acagctcact gccatctccc  69420
acaccaagag aaaaaaaaag ccatagtcac cgtgatttta tcaaggcaaa agcctcccca  69480
cccaagtctg gatagaaggt gctttttccc tcaagcagtg tctactctct ttggaacaca  69540
tcccaaatgt caccacctct gggaaggcat ccttggttcc tgtctctacc ctggatttgt  69600
cagaacctct gttcttgccc cctctgtggt ctctcccttg ggacaggagc ccctggaagg  69660
acagaaaacc cactttattt atgtctgtgc cccagggctg gcataaggca ccagcactca  69720
gctgttctct ccttttcctc ctggaagggc acctagctaa tggatattag gcattgtctt  69780
gggagctggg ggcttatttt ttcctgaggc agggttctta acatgacata aaaaataaaa  69840
atgggcaggg cgcggtggct cacgcctgta atcccagcat tttgggaggc caaggtggga  69900
ggatcatttg aggtcagaat tcaagaccag cctggccaac acggtgaaac cccatctcta  69960
ctgaaaatac aaaaattagc caggcatggt agcaggtacc tgtaatccca gctactcagg  70020
aggctgaggc aggaaaattg catgaacctg ggagacagag gttgcagaga gtggatatcg  70080
caccactgca ctccagcctg ggcaatagag cgagactctg tctcaaatag ttaataaata  70140
aataaattaa attaaataaa aacgcattct ctttccccag ccccaagtag cagagcccgc  70200
tctgagcctg ggcatggtga cccattctcc tcgtgctcac atgcccaact cccagccctc  70260
cagcccctgg cttcggaatc atgtcatcag ggtctcccat gtctctggaa ggtgcttcca  70320
gtgtggcagg ccatcagctc agtgtctggg taaaggcttc tacagggcca gcatggcata  70380
ggggggaggt gtgcatgcgt tcctgaagcc acaaggtctt ctgaggagac ctgactattg  70440
gggtggggac tagagactga ggtccagccc cttaatgccc cagactccct gccatccctc  70500
ggagaatttc ccaccacact tatgaatgat cttcgggaca ggtgacataa acatacagct  70560
atggtagagg cattcagctc catgccactg tgagaatgaa cataccaact tttaggcaac  70620
aaggccatgt ggtcaaggag agaggagaaa cgaataggag taggcagggg tggtgaagca  70680
ggtctgacat tggcaaaagt gacagagaag gattgggttg gaagggcttc agatggcaga  70740
gaacctctga aaaagtctca tgccagctaa tgaagagtcc tcaaagtcac catcacagaa  70800
atcttacatc tggcagaaat gacagcaata gtttggcatg aaccccacag tggatccaaa  70860
cgtgtggcag ctgagatcgt cagttaatta tgttctctgc agctggtcct tctggttccc  70920
tggagctggg tatctgagta gcacagctcc actgctacca caggagaggg agaatcccaa  70980
attctgtgca tagactgtct aaacctctgg atgaccccta agacacatgt acataaggca  71040
aactgcaaac agcccaattt aggataaaac agcctgtctt actctgtttg tgctgctata  71100
ataaaatacc tcagactggg tcatttatat agaacagaaa ttgattcctc acagttctgg  71160
aggctggaag tctaagagga ggcactggca gtttcagtgt ctggtaaggg agggatcagt  71220
gtctgctccc aagaggatgc cctctgtgct gtgtcctcac ccagcagaag agcaaaaaag  71280
ggcgaacatt ctcaaaagcc tcttttataa ggacatcaat ccattcatga gggcagaacc  71340
ctcaagaatt aatcatttct caaaaggccc ctcctcctaa tgccatcacc ttggggttta  71400
agttccaaca catgattttt ggaaggacac atacattcaa atcattgcac aaccaaagtg  71460
atatttgaac tttcaaatag tttgcagttt gagatcaact aagttaattg cttgcttgaa  71520
taaaaacatc acagccgggc acgatggctc acgcctgtaa ttccagcact ttgggaagcc  71580
aaggtgggca gatcacttga ggtcaggagt tcgaaaccag cctgaccaac atggtgaaac  71640
cccatttcta ctaaaaatac aaaaattagc caggcggccg ggcgtggtgg ctcatgcctg  71700
```

-continued

```
taatcccagc tctttgggag gccgaggcgg gtggatcaca aggtcaggag attgagacca  71760
tcctggccaa cacagtgaaa ccctgtctct actaaaaatg caaaaattag ctgttgagac  71820
tactcgggaa gctgaggcag gagaattgct tgagccgaga tcgtgccatc gcactccagc  71880
ctgggggaca agagcaagac ttcgtctcaa aaaaaaaaaa agaaaagaaa ttttctggat  71940
taggataatg ttctatattt ggataagggt ttaggttacc tagatagata catttatcaa  72000
aagtcatcaa atggtacact tcagatgtac gcatgtcact gtatgtaaat attaccccaa  72060
aatcaacaag aaccatgagc aaatactgac ttctagtgaa cgacatgcat actgaaactt  72120
tcgtagtgaa gtataattat ggctgcagtt gactctgaaa tacataaaaa cctaagttga  72180
tgggtgaata cagtgattaa tagatagaaa tctgtggtaa agcatacgga gaaaaatgtt  72240
aattgtagat tctagggttt atatatattc tcactatata attaaacgtt tttatgttta  72300
aaaattttta taatgttgaa aaaccatgaa atcctaccta acgcagtaag acaagaaaaa  72360
gagataaaag gtatatgtac tgggaagtaa gaaataaaac cgtctttgtt agcagatgac  72420
atgctcatct atgtagaaaa tccaaaagaa tggataaaga aactcctgga actaataagt  72480
ggttacagta aggttgtagg atacaaggtt aatatacaaa agtcaatcac tctcttattc  72540
accagtaatg aacaagtgga aattgaaatt caaaacaaaa tactatttac attaatactc  72600
caaaaataca tacttaggtt taaatctaat aaaatacata caagatcttt atgaggaaaa  72660
ctgcaaccct gatgacagaa atcaaagaga aactaaagaa atagacataa gtaaatattc  72720
cccagaaaga ctcaatattg tcaagatgtc agttcttcaa aacttgacct atagattcaa  72780
tgcaatccta atcaaaatct cagcaagtta tgttgtggat actgacaaac ttattctttt  72840
tttttttttt tttttttttg agacggagtt tcgctctgtt gcccaggctg gagtgcagtg  72900
gcgcgatctc gactcactgc aagctccgcc tcccgggttc acgccattct cctgcctcag  72960
cctcccatgt agctgggact acaggcacgc gccaccatgc ccggctaatt tttgtatttt  73020
tagtagagac ggggtttcac cgtgttagcc aggatggtct cgatctcctg acctcgtgat  73080
ccacccgtct cggcctccca aagtgctggg attacaggcg tgagccaccg cgcccggcca  73140
acttattcta aaatttagat agggaagcaa aagacccaga acagctaaca caacaatata  73200
gtaggaaaac aacaaatttg gaaaatggat actacccaac tccaagactt actataaagc  73260
tacagtaatc aagatagtgc cgtattggtg aaagaataga caaatagatc aatggaacag  73320
aatagagagc ctaagaaata gaccttcata aatacagtca actcatcctt gacaaagtag  73380
catagacact acaatggagc aaagattgtc ttttcaacaa gtggtgcagg aacaactgga  73440
tatccacatg caaaaacaaa caaacaagca tgaatctaga tacagacctt atgctcttca  73500
caaaaattaa ctcaaaatgg attatagatc taaatgtaaa attcaaaact ataaaattcc  73560
cataacatag gataaaatct agatgaccta ggtatggcta tgacttttta gacataacac  73620
caaagccatg gtccatgaaa gaaataattg gtaagttgga cttaattaaa attaaaacct  73680
tccgctctgc aaaagaccac actaggagag ggaggaaata tttacaaaga cacatctgat  73740
aaagaattgt tacttaaatt atacaaagcc ttcttaaact taacagtaag gaaacaatct  73800
gattgaaaaa tgggccaaag actttaacaa acaaaagaag atatacaaat ggcaagtaag  73860
tatgtgaaaa gaagctgcac agctgggggg cgtggtggct cacgccttta atcccagcac  73920
tttgggaggt caaggcgggc agatcacctg aggtcaagag accagcctgt ccaacatgga  73980
aaaacctgtc tctactaaaa atataaaatt agctaggcat ggtgatgcat gcctgtcatc  74040
```

-continued

```
ccagctactt gggaagctga ggcaggagaa tcgcttgaac ccggaaggtg gaggttgcag  74100
tgagccaaga tcgcgccatt gcactccagc ctgggcaaca agagtaaaac tctgtctcaa  74160
gaaaaaaaaa aaaaagctgc acattctatg ttatcaggga aatgcaaatt tagaataacg  74220
caataacaag ataccactac atacatatta gaatggccaa aattgagaac actgacagca  74280
ccaaatgtgg aggaggatgt ggagcaacag gaactagaga gaatgcaaaa tggtatagcc  74340
acttaggaag acagcttggc agtttcttac aaaactaaat atactcttac cacacaatcc  74400
agcaatcaca ctccttggta tttacttaca tcccaacaaa aaccctcata tggatgtcta  74460
gagcagcttt gttcataatt gtcaaaactt ggaagcaacc aaagatgccc ttcggtaggt  74520
gagtaaataa ataatatcca gacaatggaa ataccattca gtactaaaga gaaatgagct  74580
atcaagccat gaaaaggcgt ggaagaaact gaagtgtgta tcactaaaag tcaatctgaa  74640
aagggtgcat aagtttccaa agatatgata ttgcagaaaa ggcaaaactg tggagacagt  74700
aaaaagattg ccaggggcta gggcagtggg agggatgaat aggcagggca cagaggattt  74760
tcagggcaat aacactactc tgtatgacac tataatgttg gatacatggc cagatccaca  74820
gaatgtagaa caccaagagt gaaccttgaa ctatggactt tgagtgatga ggatgagtca  74880
gtgtaggctc atggattgta ataaatgcac cactgtgggg gggggggat attgataact  74940
ggggggctgt acatgtgtag ggacaggagt aaatgggaaa tctctacttt tgttaccggt  75000
ggagggtgta ccgcattttg aacaaaaaat tggacaaaac gcacaaagca aggaaagaat  75060
gaagcaacaa aagcagagat ttattgaaaa cgaaagtaca ctccacaggg tgggagcagg  75120
cctaagcagg tggctcaagg gcctgaatac agattttttct ggggtttaaa taccctctag  75180
aggtttccat tggttacttg gtgtataccc tacgcaaatg aagaggatga agggaggtta  75240
caaagttatt tacttggtgt agaaaattag ggtttttccc ttttatttag ttgtaggaag  75300
cccttaggtt acctgcctcc agaccctatt ctcctgcctc attttattcc taattttgtt  75360
gtgaacctaa aattgctcta aaaaatgaaa tcttttaaac aagaaaataa acttataaat  75420
tgcaaatatg tgtcacttac ataaaaacaa agaattagtg tccctacatc aggaaaaaaa  75480
cacctataat tcaatgtaaa aatgcaaaaa agccaagaga aatggccaag ccatggaaat  75540
tcacagaagt agaaataggc agtaaataaa caatgctcaa tttcatttat ctgagaaatg  75600
gagagtaaaa cttcagtgac atacaaagga gtaacaatca ttttaggaac aattttaaaa  75660
ataacacttg tgatgtggct caggaaagat tcatattctc actgtaggaa ggtaagtgaa  75720
tcattttaga ggtcagtttt gcaacttaga agatcaaatg catctaccct ttttctactt  75780
ctagaaatgt atcttcagaa gtgcccctcc ctccctcaca cacccccaag tgtacaaaaa  75840
taaatgacat ggatgtggac tgcagccttg tttctaatac caaaaatcag taaacaacct  75900
aaaaatctgt atccatgagg atttaaagaa atcctgcatg agttagaaag aataaggtag  75960
atgcctgggt tctaacatag aaaatatcaa actggttgtt agatgaaaaa agcaagttgc  76020
aaagtgaggt aatgtgtaaa tgcagtaagc aaaatacatc atatatatag tactttctat  76080
gtatttacct atatgagcgt gatgcctcca actgcatagc tgtggctccg ggagcaggac  76140
cttgtaacag agcctctgcc cctgactgtc ctgaggggcc tttccctggg aaaggaacca  76200
ggtttgattt tcagtctctt ttgttatcac catgctgaca gctttgcttg tcatatgcct  76260
ttccctccgc tgtactgatt ttaccttaca gaagctctcc ttagtgcttc atcagacact  76320
ccctcttttc caaagaaaag acagccgcat tccatggtca tctggttgag ctcgaggtga  76380
gccccaggga tcatgtgcct cccaccaggc tgacacccca gtggtgagga gttgcccctt  76440
```

-continued

```
ggctttttcg aggccaagca actcagaggt gtggcaggat tgcatgtcac agtggcactt  76500
ccaaggccct ggagagtgac tcaacgcctc tgttattaag atgtcacaca ggctgtgcag  76560
caacaactct agggacaccc ttcacactga cagagttggc aagcttttcc tataaagggg  76620
cacacagtga atactgtagg ctttgtaggc catactatct gtcccaacaa ttcaactttg  76680
cccactgtag ctgtgaatca accgtagata atattaagtg aatgtgcact gctgtttgct  76740
aatagtttat tgacaaaaac agctgctttt gagcagtttg ctaccccgac agagactgtg  76800
gggagtccct ggtggcagcg agctacaggc agccagtacc ccatcagtgt ggctggttcc  76860
atcctctcaa gcctgcctgc acccagacac tgtcgagtgt gtcttcagaa aaactcctaa  76920
aattccccaa aagcacagtg gctccccgag agccacctcc ctcaccttct tacaggggca  76980
ggttcctctt ccggttccac cctcctcagc acggagctca ggggccatcc ccacctcctc  77040
ttggccgcaa gcacagacct tcccacacag gctcagcagc tctgcgggcc tgtcccccac  77100
ctggagctgc aggcctccac tcctggggac agctgtgacc atggctctgc aaagcagcct  77160
tgtgcctagc tcccaagtca gctggcagcc cagagtggaa caattctgtg gatcacctct  77220
gagacagcag cacatctggg caagcctggc ttcccacccc tcacctcctg caacctctga  77280
cccttgccat gcatgtggta gggaagctgc aaccaggcct cagcactccc agacctgtgg  77340
gcggtttgct gtctgaggat cgtggcactg ccttccctca gaggccttgc cagagccagg  77400
ggatgcagcg tggcagagct gtcactggca accctgctgg tctccctggt gctttctcag  77460
ctgggctgtg ggtcaggaca aatttctatg gataaggctg gatcataatc tagtgctcca  77520
tggtcatgca gcgacagact cgagtctgcc ttctctcagg gtggtgagct caggtaggaa  77580
cgggatgttt gaagcaagca cacctgtgag aaatgcctgt tttcactccc atcccacaca  77640
ctcgtccaga cactgccagc ccacccccga cacacgtgtc tgagggaggc tgaggaaaac  77700
agacacctcc aggagccgca tactatttcc tgatgtgtaa gccagacaac cctggaaagg  77760
aggtcaggga accggagtgc ctgccaacgt ccccagcctc cctgcagcaa aacactctca  77820
tggcaaaact ccttttttaaa gaaaggcttt attgctgcaa ttagacatcc cagtgtatag  77880
cacaaacccc cctgtacaga gaattattca agtggtaata ctgagaaaca gtgaacacac  77940
acaaaagaat acaaaactag acatttagat cactagaaac tttctaaggt aagaaaaatt  78000
tcaaatgtga agtgcctttt agaaactaca ccacacatgc cagtgtaaat ttggtttaac  78060
aatcaatttc tataaacatt gcatctaact gtgcactgat caactgcaca acttcaacaa  78120
ttacttccaa gacaaagata aatgctttta tttccctatg ttttggtctt tccttgggct  78180
agagacagaa gctgcatgtt tcaaaccaga ttcaaaaggg aaagcacttc aaaacagaaa  78240
gtacttcaat tgtgtatttg ccttcagcca catccagaga cttgtggatc tcacccggtt  78300
ggtcccagcc cttctccaac cctgaagccc acagcagggg tgcagaggca gccccagatc  78360
gtgcagacat cacccgaggc tcccaaactg gcccagctgc ctgaggcctg catgcctgtg  78420
gccaggtagg acacatgtgc aggtttgaaa actaggccta caagactgaa gagtggactg  78480
aagcaaaaag gggagaaaca ttagaggcct acagtaggaa gagacctttt atagagtttt  78540
caggaaattc tcacaataaa cttgggcaca aagaccaaat tgctgaggcc agaagcctgc  78600
ttatggtact gtgacttatg gggagtagag gccaaatcag agagggctgg ctggtgatac  78660
cccagaccac ttgcctcttc cccttccctg gcctacaaat accaggcctc ctggccctga  78720
gacctcattc tgggtttcta tatgggtcaa ccaaatgcca tcctttcact aaacccaggt  78780
```

-continued

```
gcaaaatggg gggggaaggg gggaagctgg ggagtacaca gcacccaaaa gaaccgagag  78840
agcaagtttt ccaaggctac aggaacattg gcagagctgg tggccacacc agatgggagt  78900
accacatccc caccaggctt catgcttcac tgctagatgc agggggctag aagggtctga  78960
tgaatcagga gctgaactag aaccttcaag aaaagaaaag gcaagggggt ggctctgtgc  79020
cccgccagga gaggaaagaa gaatgtgtgt ggattgtcca cagtgaggcc agaaacgatg  79080
agatggtgtt aggcagaaaa gaagggagag ggcttcccat gagaatctgg ctgggcatgg  79140
gagggataca gggctcagtt atcaaggcac ctttgccata gtggggtgcc agctacattg  79200
ggtgggatgc ccaggggctg tccctaccta agcactttct tgtctacagg aagtcttggt  79260
gcttttcaag ttcagcataa ggggttccat atgtgaagtg gggattcaca cttagaaaat  79320
ctatcctggt cttcacctga aacactcatc tactgctggg tggcaggaac aagtatacaa  79380
aaccaggggc cttgcctggg cagttcctaa gggacattgg cagggctgac ctgggattca  79440
gctcccctga gtggacagtc tgtggttgcc tggggtcccc aggctgagaa ggggtatggg  79500
taattgcact tcggggcaca gtgaacacag gcacgggctg gatgtgccct gggagacaga  79560
aaggagaggc tgacctattc tcaggagctg gctatggctg gacagtgcct gcccggccag  79620
aggaaggcca cagcagagcc actccacaga ctaagacctg tgttgccaag gaatcagaca  79680
ctggcttgga ggagacagga ggacaaagcc tgctgctatt aagcccacac cgtagcttag  79740
agatccttca gcctcctggc cttcaaaaca aactccaggg cttccactct gaaaggcaaa  79800
ggaatcacct cgtgtttgct tcatcccctt agcaggatga acgaaacgcc taaggcccaa  79860
aaagactgag ggcaggaccc ccagcatctc ccatctcctc cgtgcaggct gggtgagaga  79920
atggcctgga aaggaagcat ctgcgctaca ttgtgcttca ggcccccccca gcaactttcc  79980
cggaggtaac tatttgcctg gaaaactagg aaactgggtt ttaaaaacag aattttaagc  80040
agacttttta gagggacaag gccatttgat ggtagtgatt ttggttttgt tttatgaaaa  80100
tggtacaggt ggtaatccct gatgacagaa tgcactgaga gtggggccaa gggccctgaa  80160
ggatcctgtc tgttcagtct ggttaaggcg acagctgggc gggcatgtgg ccggggagca  80220
gtggcacagc ggaccctggc agtttgctca cacctggccc tcgtcccaga gccagcccac  80280
ctgcctcttg gccctggtag tgactccaca gaacttcccc gagcagaagc ctcacagtgg  80340
gccagcaccc atcttgcatg caagggagaa cctgcatgca gtgcacacac cccggccagg  80400
gtggcacatg gctgctcttt caatgtgaag ccaacaccaa ctggagagat ttaactataa  80460
aggaatattt tttaaatatt cagttttgtt gtcattactc acttcctttc cttccatttc  80520
gatctcagaa actgttcttt ttcagtgttg acaaaaaaga aatgtatggg ccaggtctac  80580
aaagtaacac cttgtcataa aacaggctca aaagcatagg aatcatgctt taattgccat  80640
ttagcatcca ctaattccca tgagatctgt gattaaaaaa aaagcctctg gcctgcttgt  80700
cctgtcttaa aagtcatgag tctgttttat gaacagaaag aatgccacgc ttcttagcat  80760
atgtaaggca aaatggattt ttgatctctc atgatgtaaa ggagatacaa aggtaaggaa  80820
gggaagattt ctaagtgaga ctttttttga gtgtcaatcc cgctggacac acatattaca  80880
aaataaagat tttcttctgt aaagtgctgt ttgctcagtg aatcatgcgc caccacagag  80940
caccatggct ccacctgctc aagagcatgg aggaggcagc atcggcagag ggcaggcagg  81000
agtctgtgtt tgggggtctg tttcaatacc atctcctggg gttcgccgtg atgcagaggg  81060
aatcttctcg tcatggctag acactcccca atgctctgct ccaggctggg gaccactgca  81120
agctggaggc ggctgggtat cagggcctgg gcacccctgc tcctcctctt cccttgggat  81180
```

-continued

```
tggcatttta ttctctcatt cagctcaaga ccatgggcag gaactctgct ggctccccat  81240
gatgtcatca tggggtcttc cactttccca cagagctgcc aggcagaggc aggacccagg  81300
catgcctggc ccacaggaag gttttctagg agactaagga gggtttagaa aaagagaagc  81360
cactataaat agtcacctgt ccagtctatg ctattaaagg acataagaaa ggtatacaat  81420
tggcagtaaa caatttcctt cagctcttca tggatgtcca ggaaaatgac aacccgcaca  81480
caatcagacg tgaatgattt ctgctccagt gtcttcaggc tctgtgcaac aagaagagtt  81540
tgtgtcggaa tgacagattc catatccatg tttattttca aagttgggct ctgttagtgg  81600
agatttttca aaaatattct ttttgcttgt ttctggacag ttttgaacat agatcactct  81660
attataggcc ttgagtctct tccacaattg cacatacact ttacactgaa catacataaa  81720
aagaagtcct ccggtgaagc cgatggccac aaccaccaat ttagtccaaa agggccattc  81780
taggattcct ggaagggaaa aactcagcct attagatttt atttaagata tgtcttcacc  81840
acggggctga agnnnnnnnn nnnnnnnnnn nnnnnnnnnn nnnnnnnnnn nnnnnnnnnn  81900
nnnnnnnnnn nnnnnnnnnn nnnnnnnnnn nnnnnnnnnn nnnnnnnnnn nnggcggtga  81960
ctgtgacatt gaggttcggc gtcgggggag agggaaaagg agagggagag ggagagggag  82020
agggagaggg agagggagag ggagagccat atgtagttta aagtagtttt tttccaattc  82080
tgagaagaag gtcattggta gcttgatggg gatggcaatg actctataaa ttaccttggg  82140
cagtatggct attttcacga tattgattct tcctacccat gagcatggaa tgttcttcca  82200
tttgtttgta tcctctttta tttccttgag cagtggttta tatttctcct tgaagaggtc  82260
cttcacatcc cttgtaagtt ggattcctag gtattttatt ctctttgaag caattgtgaa  82320
tgggagttca ctcatgattt ggctctctgt ttgtctgtta ttggtgtata agaatgcttg  82380
tgatttttac acattgattt tgtatactga gactctgctg aagttgccta tcagcttaag  82440
gagattttgg gctgagacga tggggttttc taggtataca atcatgtcat ctgcagacag  82500
ggacaatttg acttcctctt ttcctaatcg aatgcccttt atttccttct cttgcctgat  82560
tgccctggct agaacttcca acactatgtt gaataggagt ggtgagagag ggcatccctg  82620
tcttgtgcca gttttcaaag ggaatgcttc cagtttttgc ccatgatgta tgatattggc  82680
tgtgggtttg tcatagatag ctcttattat tttgagatac atctcatcaa tacctaattt  82740
attgagagtt tttagcatga agcgttgctg aattttgtca aaggcctttt ctgcatctat  82800
tgaaataatc atgtggtttt tgtcattggt tctgtttgta tactgggtta catttattga  82860
tttgtgtacg ttgaaccagc ccttgcatcc cagggatgaa gcccacttga tcatggtgga  82920
taagcttttt gatgtgctgc tggattcgtt tgccagtatt tattgaggat ttttgcatcg  82980
atgttcatca aggatattgg tctaaaatgg gtttttttgtt gggtctctgc ccagctttgg  83040
tctcaggatg atgcctcccc tattaaaaga gggagggagg attccctctt tttctattga  83100
ttggaatagt ttcagaagga atggtaccag ctcctccttg tacctctggt agaattcggc  83160
tgtgaatcct tcaggtcctg gactgttttt ggttggtaag gtattaattg ttgcctcaat  83220
ttcagagcct gttattggtc tattcagaga ttcatcttct tcctggttta gtcttgggag  83280
ggtgtatgta tggaggaatt tttccatttc ttctagattt tctagtttat ttgcatagag  83340
gtgtttataa tattctctga tggtagttta tatttctgtg ggatcagtgg cgatatcccc  83400
tttatcattt tttattgcat ctatttgatt cttctgtctt ttcttcttta ttagtcttgc  83460
tagcggtcta tcaattttgt tgatcttttc aaaaaaccag ctcctggatt cattgatttt  83520
```

-continued

```
ctgaagggtt ttttgtgtct ctatttcctt cagttctgct ctgatcttag ttatttcttg  83580
ccttctgcta gcttttgaat gtgtttgctc ttgcttctct atttcttttc attgtgatgt  83640
tagggtgtca attttagatc tttcctgctt tctcatgcgg gcatttagtg ctataaattt  83700
ccttctacat attgctttga atatgtccca gagattctgg tatgttgtgt gtttgttctc  83760
attggtttca aagaatatct ttgtttctgc cttcatttca ttatgtaccc agtagtcatt  83820
caggagcagg ttgttcagtt tccatgtagt tgagtggttt tgagtgagtt tcttagtcct  83880
gagttctagt ttgattgcac tgtggtctga gagatagttt gttacaattt ctgttctttt  83940
acatttgctg aggagagctt tacttccaac tatgtggtca attttggaat aggtgtggtg  84000
tggtgctaaa aaaaatgtat attctgttga tttggggtgg agagttctgt agatgtctat  84060
taggtccgct tggtgcagag ctgagttcaa ttcctgggta tccttgttaa ctttctgtct  84120
cgttgatctg tctaatgttg acagtggggt gttaaagtct cccattatta ttgtgtgggt  84180
gtctaattct ctttgtagat ctctaaggac ttgctttatg aatctgggtg cccctgtact  84240
gggtgcatgt atgtttagta tagttagctc ttcttgttga attgatccct ttaccattgt  84300
gtaatggcct tctttgtctc ttttgatctt tgttggttta aagtctgttt tatcagagac  84360
taggattgca acccctgcct ttgttttcca tttgcttggt agatcttcct ccatcccttt  84420
attttgaacc tatgtgtgtc tctgcatgtg agatgggttt cctgaataca gcacactgat  84480
gggtcttgac tctttatcca gttttccagt ctgtgtcttt taactggaac atttagccca  84540
tttactttta aggttaatat tgttatgtgt gaatttgatc ctgtcattat gatgttagct  84600
ggttattttg ctagttagtt gatgcagttt cttcctagca tcgatggtct ttacaatgtg  84660
gcatgttttt gtggtggctg gtatgggttg ccccttttcca tgtttagtgc ttccttcagg  84720
agctctttta gggcaggcct ggtggtgaca aaatctctca gcatttgctt gtctgtaaag  84780
gattttatgt ctccttcatt tatgaagctt agtttggttg gatatgaaat tctgggttga  84840
aaattctttt ctttaagaat gttgaatatt ggccctcact ctcttctggc ttgtagagtt  84900
tctgccaaga catgagctgt tagtctgatg ggcttccctt tgtgggtaac ctgacctttc  84960
tctctggctg ctctcaacat tttttccttg atttcaactt tggtgaatct gacaattatg  85020
tgtcttggag ttgctcctct cgaggagtat ctttgtggca ttctctgtag ttcctgaatt  85080
tgaatgttgg gctgccttgc tagattgggg aagttctcct ggataatatc ctgcagagtg  85140
ttttccaact tggttccatt ctccccgtct ctttcaggta caccaattag atgtagattt  85200
ggtcttttca catagtccca tgtttcttgg aggctttgtt catttttttt ttctttttc  85260
tctaaacttc tcttcatgct tcatttcatt gatttgattt tccatcccca atacccttc  85320
ttccagttga ttgaatcagc tactgaggct tgtgcattca tcatgtagtt ctcatgccat  85380
ggttttctgc tccatcaggt catttaagga cttctctgca ttggttattc tagttagcca  85440
ttcatctaat tttttttcaa ggtttttaac tgctttgcca tgggttcgga cttcctcctt  85500
tagctcagag tagtttgatc atctgaagcc ttcttctctc aactcgtcaa agtcattctc  85560
catccaggtt tgttctgttg ctggtgagga gccgtgttcc tttggaggag gagaggcact  85620
ctgattttta gagcttccag tttttctgct ctgtttgttc ctcatctttg tggttttatc  85680
tacctttggt ctttgatgat ggtgacgtac agatggggtt ttggtgtgga tgtcctttct  85740
gtttgttagt tttccttcta gaattcagga ccctcagctg caggtctgtt ggagtttact  85800
ggaggtccac tccagaccct gtttgcctgg gtatcagcag cagaggctgc agaacagtgg  85860
atattggtga acagcaaatg ttgctgcctg atcattcctc tggaagtttt gtctgagagg  85920
```

-continued agtacccagc cgtgtgaggt gtcagtctgc ccctactagg gggtgcctcc cagttaggct 85980
attcggggt cagggaccca cttgaggagg cagtctgccc attctcagat gtcaagctgt 86040
gtgctgggag aaccacttct ttcttcaaag ctgtcagaca gggacattta agtctgcagt 86100
ggttattgct gtcttttgtt tgtctgtgcc ctgcccctgg aggtggagtg tacagaggca 86160
tgcaggcctc cttgagctgt ggtgggctcc agccagttca agcttcccgg ctgctttgtt 86220
tacctactca agcctgggca atggcgggca cccctccccc agcctcgctg ccgccttaca 86280
gtttggtctc agactgctgt gctagcaaag agtgaggctc tgtgggtgta gaaccctcca 86340
agctatgtgt gggatataat ctcctggtgt gctgtttatt aagcccattg gaaaagcaca 86400
atattagggc aggagtgacc caattttcca ggtgccatct gtgaatgctt tctttgacta 86460
ggaaagggaa ttccctgacc tcttgccctt cccaggtgag gtgatccctc accctgcttt 86520
gggtcacgca tggtgtgcta cacccactgt cctgcaacca ctgtctggca ctccccagtt 86580
agatgaaccc ggtacctcag ttggaaatgt ggaaatcacc tgtcttttgc atcgctcatg 86640
ctgggagctg tagactggaa ctgttcctat tcagccatct tggctccacg tatatccact 86700
gccacacttc tttagtcata aagtgagtgc cttggtcaga ggcaatgctg tgtggaatac 86760
catgatggtg gataaggcat tctgtgagtc catgaatggt agtcttggca gagcattgtg 86820
ttcagtttag gcaaacccat atccagagta agtgtctgtt tcagtgagga caaacctctg 86880
cccttttcag gatggaagag gtccagtata accaaccttc caccaggtaa cagactgatc 86940
accccgagga atggtgccat attgagggct cagtgttagt ctctgctgct gtcaaattgg 87000
gcactcagct gtagccatag ccaggccagt tttggtgagt ggaagtccat gttgctgagc 87060
ccatgtataa cctccatccc tgccaccatg gccactttgt ttatgggccc attgggtgat 87120
aacaggggtg gctggggaaa gaggctgagt gatgtccaca gaacaggtca tcttatccac 87180
ttgattatta aaatcctcct ctgctgagat cacccattgg tgagcactca catgggatcc 87240
aaatatcttc acaggttttg gccactcaga gaggtccatc cacatacctc ttccccaaat 87300
ttctttgtca ccaattttcc aatcatgctt cttccaagtc cctgaccatc cagccaaacc 87360
attggctaca gcccatgaat caatatataa tcgcacatct ggccatttat ccttccatga 87420
aaagtgcaca accaggtgca ctgcttgaag ttctgcccac tgggaagatt tcccttcacc 87480
actgcccttc agtgatgtcc tagaaagggg ctgtagtgct gcagctgtcc acttttgggt 87540
ggtgcctgca tatcgtgcag aaccatctgt gaaccaggcc ctagtcttct cttcctctgt 87600
caactgatca tagagaactc cccatgaggc catcggtgca ggctggggaa gagaaggtgg 87660
ggtggcagtt gtggagacca tggcatttg agctacttcc ttgtgtaact tacttgtgcc 87720
tttaggacct gctcgagccc aatcacatat atatcacttc catttgatga tggaatgctg 87780
ctgtgcatga cccattttat ggctacatgg gtcagaaagc acccagttca tgatagacag 87840
ttcagttcac atggtgactt gatgacccat aatcaaatgt tcagtttcca ccaaagctca 87900
gtaacaggcc aagagctgtc tttcaaaagc acagtagtta tatgcagaaa atggcagggc 87960
cttgtttcaa aattttagag gcatctgctg tgattcacct gtgggggcct gccaaaggct 88020
ccaaacagca tccctatctg ccactgatgc ctcaagcacc attggatctg ctgagtcata 88080
tggcccaaac agcagagcag gttggacagc agcctggacc tgaggcagag ccttatcctg 88140
ttctggaccc cactcaaaac tggcagcctt ttgagtcact cgataaatgg gcctgagtaa 88200
cacacccaaa tgaggaaagt gttacctcca aaatccaagt aggcccacta catattgtgc 88260

-continued

```
cttttctta gttgtaggag gggccaaatg cagcaactta tccttcatct tacaaggagt  88320
atcttgacag gccccacacc agtggacccc tagaaatgtt actgaggtag aaggtccctg  88380
aattttagtc aaatttattt ctcatcctct ggcacacaaa catctcacaa ataagtccag  88440
tgtgtttgct acttcttgct cactggatcc gatcagcata atgtcatcaa tgtaatggac  88500
cagtgtgata tcttgcagaa gcaaaaagtg gtcaagatct ctccaaataa gattatgatg  88560
caaagccaga gtttatatac tcttgaggta ggagagtaaa gatatattgc tagtcttgcc  88620
agctgaaggc aaattgcttc tagtgggcct tatgaatagg aatggagaaa aaggcatttg  88680
ccaagtcaat ggctgcatac caggtaccag gaaatgtgtt aatttgctca agcaatgaaa  88740
ccgtatctgg tacagcagct gcaattggag tcaccactta gttaagctta tgataatcca  88800
ctgtcattct ccaagatcca tctgtcttat gcacatgcca aatgggagag ttgaatgggg  88860
gtgtgatgaa aatcaccacc cttgcgcctt tcaagtcctt gatcatggca ctaatctctg  88920
caatccctcc agggatgtga tattgttttt gatttaccat ttttctaggt agaggcagct  88980
ctaatgcctt ccatttggcc tttcccacca taataggcct caccctacca gtcagggagc  89040
caatgtgggt gttcttccag ctgctaagta tgtctatgcc aattatgcat tctggcactg  89100
gggaaatgaa cacaggatga gcctggggac ccattggacc cactgtaagt cagacctgag  89160
ctaaaactcc attaattacc tcacctccat aagctcctgc tttaactgga ggaccacaat  89220
gacgttttga gtcccttaga attaacgtca gctcagagct agtgtcctgt aatcccccaa  89280
atgactgata atttcccttt ccccaatgca cagttacctt gataaaaggc tggaggtctc  89340
cttgggaaaa aatgggagaa agattaacag cataaattgt tggtagtgta gtgggctcct  89400
tccttaatgg gacccaactt cccctttatt caaggggttc tgtgtctgta aactggctca  89460
agtcaaaaat tgattgaggg gccatgattc tctattttta taattcaaag tagtgttttg  89520
tccatttgac ctggaagttt tctgcttata taaattaagt aggaaagaag taggcatcct  89580
aacaatttca cttctgggaa cactgtgatt aattagcgaa tgccagaact ctacatgagt  89640
cagactattc tgattgctgc tttgccacta ctgtctgtta tggtagttat gcccaccttg  89700
cctttgatgg ttgagtgcca ccacttggcc tctgccacct tgggatccaa ttattcccat  89760
tgtatttacc tttattagtt gagtgactgt ggttctcacc attggatctg atatgcagag  89820
aattacgggg ctcttcaaag atgcaggtgc taccctcaca gatctatttt gcaaggtatt  89880
ggtcaagggt atatcttctg ggcccttcca tctgggatga gtaggtctaa agtgactaat  89940
ccactccacc atctcaatct ctctaagcct ttggatccct tcctctacat taaaccaaga  90000
gtgatcagac atttccagct ccctcacagt ggccatcttt caatccatat ttcagctaac  90060
taagcaaata aattattaga accttttttt aactccctga gctgcaatat taaatgcaga  90120
gtctctactt agtgggccca aatcaacaaa ttcagcctga tccaactcta tgttccttcc  90180
accattatcc cacaccctta atatccattc tcatgcctgt tctccagatt tctgtttata  90240
taaattagaa aactcaagta gttcttttca agtatagtga acctcctcat gggtttcact  90300
ctcaacctca cctcttgggg cccataagga ctttagtctg gttataggtc tagaagcaga  90360
caggggtgtt gggggtggct cctgaggaga atcaacatta ttttgcctgg caactgctca  90420
gggggggcca tcactgttgc cttaggcagc acagtgttta tctccccaga caaatatgga  90480
aaggctgatg gcagcatggg tcagggagag gatgtcacca ctactgggga tggggaagct  90540
gttttttttc tggcaaaaaa ggtttcctga gactttacaa actcagtgtc cccagcttca  90600
tcagggtcct cccacatgtc ccctttccaa gttgcagggt cccattcttt tccaaacgat  90660
```

-continued

```
gccctcactt taatagtaca tacctggtga ggctgtgcat gcacccttca ttggaagtca  90720
gccacttgca caataagagc tcatatccat tttcccacaa tttcagctct ttctctgcag  90780
gagataatac tttcactcag ggcaatctta gcagatttga ggctcagtat ctgcttctga  90840
agccaggagt tagaatccct aagttcattt tctttcatca ctttgtccat tgaacttagg  90900
agaaaccaac caacttcatt atgtttccac atatggtcaa aggtattatt tatagagtca  90960
ctaaactcct tgcctctcat gagcgctgaa tcaggaatgt caaatgcatt tattttgctt  91020
aactctctaa acagttcata gaaaggaaca ctgaatcagt gttctccata ctatcagaag  91080
tagagtcctt agcatttttg agtctaatca tattaaacag ccactccaga aaccctaaaa  91140
ccaatgaaag aactgcatcc ttaatgttct gttcctctag aaccactcct ggtacaaaaa  91200
tctgtgttag ggttctctag aggggcagaa ctaataggat agagatatat aagaaggaaa  91260
gtttattaag tattaactca catgatcaca aggtcccaca ataggatatc tgcaagctga  91320
ggaacaagga gagccagtcc aagtcctaaa ctgaagaact tcgagtctga tgttcaaggg  91380
cagggagcat ccagtaccag agaaagatgt aggctgggaa gctaggccag tttagtcttt  91440
tcatgttttt ctgccaactt ttcatattct agctgcactg gcagctgatt agatggtgcc  91500
cacccaggtt aagcgtgggt ctgcctttcc cagcccactg actcaaatgt taatctcctt  91560
tggcaacacc ttcacagaca cacctaggat caatactttg catccttcaa tccaatcaag  91620
ttgacactca gtattaacca tcacagaagc attatctact aataccacca tataaaagat  91680
gcggatgtta gcatagttat cacactgttt cctcacacaa tccactaccc atggcttggt  91740
ttctatggac atattattgg atctgagcca gcttattata atgttttaaa taatattcaa  91800
gaattgttac aattgcattt tgaattgtta ttatttaaat ataggtcaat ttctaaatag  91860
attcttgtcc atagtcagat tttacatcat gatttcctca ctcatgacat ttaaaagttt  91920
atttgttaaa tttagccaat atatacaagt ctgcatttgg ggatgggtaa ttgaatgcca  91980
tttttaattt ttgggtaatg gagacttttt ttatgttgcc tttatatttg atccataact  92040
aggctatgta gtacatttct gggtcaaatc tctattgctt taaaactttg tggttttgct  92100
tcattatctc ctagtatcta cagttactga agtgatacgt acaaccagct ttggacatga  92160
tgaatgtttt aggctaaaga cttgggtgtt ctttggtctt tggaagtttt ctttaatact  92220
ctctttaaat ttgtctgatt ccacttcttg gttccctttt caggaacacc aagtattcac  92280
acagtggata gtcatctgtc ctctacttct aaaattttgt tatttaacaa aatgttataa  92340
aagtagaatc acatttatgt aaccttttttg gattgatgtt ttttgctcag cataatttcc  92400
tggcaatcca tccaagttgt tgcatgcatc aatcatccat tcctttacat tgctaagtag  92460
tattccatgc tatgtattta caacagtttg tttacccatt cacctgttga aaaacatctt  92520
ggctgaatct agttcttagc tattaatatt ataaacaaag atgctataaa catttgtttg  92580
acagtttttt gtgtgaagtt tttatttttc tgggataaat gcctgggagt gcaattgctg  92640
ggtcatatga tagttgtgtg tttttctttg agaaactccc aaaatttccc agagtggatg  92700
aagtatttta tgtttctatc agtaatgtat cagtgatccg gtttctacac atccttacca  92760
gcatttggtg gtgtcatgat ttttaatttt agccattctg atagatgagt agtgatagct  92820
tattgttgtt tcaatttgca tttccctaaa acctaataat tttgaacatc ttttcatgtg  92880
attatttgct gtccatgaaa tatctgtgga aacagtgagt agaaggatgc tttccacagt  92940
ctgagaagga cagctgggag aggtggatga agagaggttg gtatatgggt acaaaaatac  93000
```

-continued

```
aattaagacc tctggtccat gctgggcaca gtggctcatg cctgcaatcc cagcactttg  93060
ggaggccaaa gcgggtggat cacctgaggt caggagctta agaccagctt ggccaacatg  93120
gtgaaaccct gtctctactg aacatacaaa aattagccgg gcatggtggt gcgtgcctgt  93180
aatcccagct actcaggagg ctgaggtggg agaatcactt aaacccggga ggcgaagttt  93240
gcagtaagcc gaggtcacac cactgcactc cagcctgggc aacagagcac tccagccggg  93300
gcaacagagc aagactctgt ctcaaaaaaa taaaataaaa taaagtaaaa caaaataaag  93360
agttccaatc cagcagagag tgtggtgaga tggtgcggga ccagctccct gggacttctg  93420
agcctttgcc ctggccagtg gggggagctga gccaggatag gctgtagcct ctgccccgtg  93480
acaccaggac ccttgtggtg gctgccacca ggacccttgg ggtgggtgcc tgggccttga  93540
agatgcagca agcctccctt ccccctacac ctcagtgact gagggtggtg gtggcctttc  93600
ccaggccgca ccctgccggg tatagacgaa gtccccactg agcctggatg cagtgccttt  93660
gggtggtggt gggagtggca ggggcagctt ggtgactatc cgggtgtgag gattgggaag  93720
gtgctcttgg gatgcaggac acgggctcag ccacctcttt aggccatggc gctgccagat  93780
ccgggtcctg gtgaccactc tgtcccagct gggtgagact tacctagtcc tgaggacaac  93840
agacaatggc cttaataggc ctggaaggtg agtggaggca cagaggagga cagtgtggaa  93900
cagttagcag gcattgggct gttggtcttc cttctaccag acctggaagg acctcacatt  93960
tggcctatgg gaaatgcccg ccacactttg ggaagattta ctatctgctt ctagaaggct  94020
gtgtgtatat tatgaaaaag ctattctcaa ctcaccccca accttttaat agataacatc  94080
tgtggggagg ctgacaagat ggctgaatag aaacagctca ggtgtgcagc tcacagtgag  94140
atcaatgcag aaggtgggtg atttctgcat ttccaactga ggtacccggc tcatctcatt  94200
tggactggtt agacagtggg tgcagcccat ggagggtgaa ctgaggcagg gtggggtgtt  94260
gcctcacctg ggaagtgcaa ggggtcagaa aactcccctg ttagccaagg gaagctgtaa  94320
ggagctgtgc catgaggagt ggtgcattcc agcccagata ctatgctttt cccatggtct  94380
ttgcaaccca cagaccagga gattccctcc agtgcttatg ccaccagggt cttgggtttc  94440
aagcacaaaa ctgggtggcc atttgggtag acaccaaggt agctgcagga gtctttttc  94500
ataccccagg gatgcctgga atgtcagcga gacagaacca ttcactcccc tggaaagggg  94560
gccgaagcca gggaaccagg tggtctagct cagtggatcc cacccccatg gagcccagca  94620
agctaagatc cactggcttg aaattcttgc tgccagcaca gtagtctgaa gttgacctgg  94680
gatgctggag cttggtatgg ggaggggcgt ctgccattac tgaggcttga gtaggcagtg  94740
ttcctctcac agtgtaaaca aaactgcaag gaagttccaa ctgggtggaa cacaccacag  94800
cgctgccagg ctgctgtagc aagactgcct ctctagattc ctcctgtctg ggcagggcat  94860
ctctgaaaaa aaggcagaag ccccagtcag ggacttatag ataaaactcc catctctctg  94920
ggacagagca cctgggggaa ggggcagctg tgggtgcagc ttcagcagat tttaacatcc  94980
ctgcctgcca gctctgaaga gagcagtgga tctcccagca cagtgtttga gcagactgcc  95040
acctcaagtg ggtccctgac cccctggcct cctgaccggg agataccttc cagaagaagc  95100
caacagacac ctcacacaag agagctccag ctggcatctg gcaggtgccc ctctgggaca  95160
aagctttcag aggaaggaac aggcagcaat ctttgctgtt ctgcagcctc cactggtgat  95220
acccaggcaa acaaggtctg aagtagatgt ccagcacact ccagcagacc tgcagcagag  95280
aggcctgact gttagaagaa aaactaacaa acagaaagga atagcatcaa catcaacaaa  95340
aaggacatcc actcagaaac cccatccaaa ggtcaccaac atcaaacaca aaaggtaggt  95400
```

-continued

```
aaatccatga agatggggag aaaccagcac aaaaaggctg aaaattccaa aaaccagaat  95460
gcctcttctt ctccaaaaaa tcacaacttc tcaccatcaa gggaacaaaa ctggatggag  95520
aatgaatttg atgaattggc agaagtaggc ttcaaaggtg gataataaca aactcctctg  95580
agctaaagga gaatgttcta acccaacgca aggaagcaaa gaaacttgaa aaaagattag  95640
atgaattgct aactagaata acgagtttag agaagaacat aaatgacctg atggagctga  95700
aaaacacagc acaagaactt agtgaagcat acacacatat caatagctga atcgatcaag  95760
tggaagaaag gatatcagag attgaagatc aacttgcaga aaccctataa gccagaagag  95820
actaggggcc aatattcaac attcttaaag aaaagaattt tcaatgctga atttcatatc  95880
cagccaaact aagcttcata agtgaaggag aaataaaatt ctttacagac aagcaaatgt  95940
gagacatttt gtcgtcacca cgcctgcatt acaagagctc ctgaagggag caataagcat  96000
ggaaaggaaa aaatggtgcc agccactgca aaaacatgcc aaatggtaaa gaccatcaac  96060
gctatgaaga aactgcatca agtaatgggc aaaataacca gctagcatca taatgatagg  96120
atcaaattta cacataacat attaacctta aatgtaaatg ggctaaatgc cccaattaaa  96180
agacacagac tggcaacatg gataaagagt caagacccat cagtgtgcag tattcaggag  96240
acccatctca catgcaaaaa cacacatagg cccaaaataa agggatggag gaatatttac  96300
caagcaaatg gaaagcaaaa aacaaacaaa caaacaaaca aacaaacaaa caggggttgc  96360
aatcatagtc tctgataaaa cagactttaa accaacaaag atcaaaagag aaaaagaaag  96420
ccattacata gtggctaaga agagctaact atcctaaata tacatgcacc caatacagga  96480
gcacccagat tcataaggca agttcttaaa cacctacaag gagacttaga ctcccacaca  96540
ataatagtgg gagattttaa taccccactg tcaatatcag acaggtcaat gagacagaaa  96600
attaacaagg atatctagga attgaactca gctccagact aagcagacct aatagacatc  96660
tatagaactc tccaccccaa atcaacagaa tatacattct tctcagcacc acatcgcact  96720
tattctaaaa ttgaccacat aattggaagt aaaacactcc tcagcaaatg cagaagaatg  96780
gaaatcataa caaacagtct ctcacaccac agcgcaatta aattagaatt cagaattaag  96840
aaactcactc aaaacctcac acttacatgg aaactgaaca acctgctcct gaatgactgc  96900
tggataaata atgaaatgaa gaaggataaa gatgttgttt gaaaacaata agaataatgt  96960
accagaaact ctgggacata tttaaagcag tgtgtagagg aaaatttata gcagtaattg  97020
cctacaaaag aacacaggaa agatctaaaa tcgacaccct aacatcacaa ttaaaagaac  97080
tagagaagca agagcaaaca aattcaaaag ctagcagaaa acaagagata actaagatca  97140
gggcagaact gaaagagata gagacatgaa aaaccccttaa aaatcaatta atcgctctcc  97200
ctctccctct ccctctccct ctccgtctcc ctctccgtct ccctctcccc acggtctccc  97260
tctccctctc tttccacggt ctccctctga tgccgagccg aagctggact gtactgctgc  97320
catctcggct cactgcaacc tccctgcctg attctcctgc ctcagcctgc cgagtgcctg  97380
cgattgcagg tgcgcgccgc cacgcctgac tggttttctc tgcccggcca gccgccccgt  97440
ccgggaggga ggtaggaggt cagccccccg cccggccagc cgccccatcc gggaggtgag  97500
gggtgcctct gcccggccgc ccctactggg aagtgaggag cccctctgcc cagccaccac  97560
cccgtctggg aggtgtaccc aacagctcat tgagaagggg ccatgatgac aatggcggtt  97620
ttgtggaata gaaagggggg aaaggtgggg aaaagattga gaaatcggat ggttgccgtg  97680
tctgtgtaga aagaagtaga catgggagac ttttcatttt gttctgtact aagaaaaatt  97740
```

-continued

```
cttctgccgt gggatcctgt ggatctgtga ccttacccc aaccctgtgc tctctgaaac  97800
atgtgctgtg tccactcatg gttaaatgga ttaagggtgg tgcaagatgt gctttgttaa  97860
acagatgctt gaaggcagca tgctccttaa gagtcatcac cactccctaa tctcaagtac  97920
ccagggacac aaacactgcg gaaggcagca gggtcctctg cttgggaaaa ccagagacct  97980
ttgttcactt gtttatctgc tgaccctccc tccattattg tcctatgacc ctgccaaatc  98040
cccctctgcg agaaacaccc aagaatgatc aataaaaaaa taaataaata aaaataaaaa  98100
taaaataaaa taaaataaaa aaagaaataa acacaaataa aatgttaaaa ttcccattct  98160
acataaaatc atctatagat gtttttaaat atacaacatg attatcaagg acttaatctg  98220
taccacattc ttgtagatgt aaagttaaaa ttcttgtaac catcactctc aaccctaccc  98280
tatcttccag cataaatgag actttcacat gttttctctt gcccagatgg agacactaac  98340
tgtaggcttt ggaaatgtct taaaaaaaaa aaaaaaaaaa agagagccag gcatcttcaa  98400
acagagaaaa gctgtttgaa cacatttatc taagtctatc aaaagctatg attgttagca  98460
agaggtaacc ttgtaatgcc aaggcagaaa actgccacca aaccacaaaa agcttgttca  98520
actgctgaac ctaaaattaa acaatttatc tctcattaaa aaaaaaaaat caattaatcc  98580
aggagctggt tttttttaa agatcaacaa aatagataga ccactagcca gactaataaa  98640
gaggaaaaga gagaagagtc aaatagacat aataaaaaat gataaaggag atatcaccac  98700
tgatcccaca gaaatacaac ctaccatcag agaatattat aaacacctct atgcaaataa  98760
accagaaaat ctagaagaaa tggataaatt cctggacaca tacaccctcc caagactaaa  98820
ccaggaagaa gtcaaatccc tgaataagcc aataacaaac tctgaaattg aggtggtaat  98880
taatagccta ccaaccaaaa aaagtccagg accagacgga ttcacagctg aattctacca  98940
gaggtacaaa aggagctggt accattcctt ctgaaactat tccaaacaat agaaaaagag  99000
agaatctccc taactcattt tacgaggcca gcatcatcct gataccaaag cctggcagag  99060
acacaacaaa aaaagaaaat ttcaggccga aatccctaat gaatattgat gcaaaaatcc  99120
tcagtaaaat tctggcaaac cgaatccagc agcacatcaa aaagcttatc caccatgatc  99180
aagttggctt catccctggg atgcaaggct ggttcaacat atgcaaatta atgaacgtaa  99240
tgcatcacat aaacagaacc aatgacaaaa accatgtgat tatctcaata gatgcagaaa  99300
agaccttcga caaaattcaa cagcccttca cgctaaaaac tctcaataaa ctagatattc  99360
atggaacatg tctcaaaaca atcagagcta tttatgagaa acccacagca gccaatatca  99420
tactgaatgg gcaaaaactg gaagcattcc ctttgaaaac tggcataaga caaggatgcc  99480
ctctctcacc actcctattc aacatagtat tgggagttct ggccagggca atcaggcaac  99540
agaaagaaat gaaggatatt caattaggaa aagaggaagt caaattgtct ctgtttgcag  99600
atgacatgac tgtatattta gaaaacccca tcatctcagc ccaaaatctc cttaagctga  99660
taagcaactt cagcaaagtc ttgggataca aaatcaatgt gcaaaaatca caagcattcc  99720
tatacaccaa taacagacaa accgagagcc aaatcacgag tgaactccca ttcacagttg  99780
ctgcaaagag aataaaatac ttaggaatcc aacttacaag ggatgtgaag gacctcttca  99840
aggagaacta caaatcactg ctcaatgaca tcagagagga cacaaacaaa tggaaaaaca  99900
ttccatgctc atggatagga agaatcaata tcgtgaaaat ggccataata tccaaagtaa  99960
tttatagatt gaatgctatc cccatcaagc taccactgac tttcttcaca gaattggaaa 100020
aaactacttt aaatttcata tagaaccaaa aaagagcctg catagccaag ccaatcttaa 100080
gcaaaaataa caaagctgga ggcatcacac tacctgactt taaactatac tacatggctg 100140
```

-continued

```
cagtaaccaa aacagcatgg tactagtacc aaaacagata tatagaccaa tggaacagaa 100200
cagaggcctc agaaataaca ccacacatct acaactatct gatctttgac aaacctgaca 100260
aaaacaagca atggggaaag gattctctac ttaataaatg gcattgggaa aactggttag 100320
ccatatgcag aaagctgaaa ctagatccct tccttccact gtatacaaaa attaactcaa 100380
gatgggctaa agacttaaat gtaagaccta aaaccataaa aaccctaaaa gaaaacatag 100440
gtaataccat tcaggacata ggcatgggca aagacttcat gactaaaaca caaaaagcaa 100500
tggcaacaaa agccaaaatt gacaaatggg atctaattaa actaaggagc ttctgcacag 100560
cgaaagtaac taccatcaga gtgaacaggc aaccaacaga atgggagaac atttttgcaa 100620
tctatccatc taacaaaggg ctaatatcca gaatctacaa agaacttaaa caaatttaca 100680
agaaaaaaca aacaattcca tcaaaaagtg ggtgaaggat aagaaaagac tcttctcaaa 100740
agaagacatt tatgcagtca acaagcatag gaaaaaaagc tcatcatcac tggtcattag 100800
agaagtgcaa atcaaaaaca caatgagata ccatttcatg ccagttagaa tggccatcat 100860
taaaaagtca agaaacaaca gatactagag agcatgtgga gaaataggac cacttttaca 100920
ctgttggtgg gagtggaaat tagttcaacc attgtggaag acagtgtggt attcctcatc 100980
ttcaccacgg ggtggaggta cgnnnnnnnn nnnnnnnnnn nnnnnnnnnn nnnnnnnnnn 101040
nnnnnnnnnn nnnnnnnnnn nnnnnnnnnn nnnnnnnnnn nnnnnnnnnn nnnnnnnnnn 101100
nnagaaacat agaccctgcc caacgcatat tcctgaaagg gatggcaagg ttttttttaaa 101160
ggttttatgg gtttaggtgt actctaaagg attttaaccc ttctaaaatt atttttgtat 101220
aaaggtgtaa gaaagggatc caacttcact cttttacaaa tgggaagcca gtttttcccg 101280
gccccttttt ttaaaaagga ttccctttcc cattggttgt ttttttcaag gttgtcaaag 101340
atcagaaggt tgtagatgtg ggttggtaat ttttaggggt ttgttttggt cccattggtc 101400
cataggtcgg ttgtggtacc agggccatgt tgttttggtt actgtaagcc tcgtagtatg 101460
gtttgaagtc aggtagcatg atgcctccag ctctgttctt ttggcttagg attgtcttgg 101520
caatgcgggc tctttttttgg gttccatatg aactttaaag tagtttttcc caattctgtg 101580
cagaaagtca ttggtagttt gatggggatg gcattgatct ataaattacc ttgggagtat 101640
ggccattttc atgatattga ttcttcctat ccatgagcat ggaatgttct tccatttgtt 101700
tgtgtcctct tttattttgt tgagcagtgg tttgtagttc tccttgaaga ggtccttcac 101760
atcccttgta agttggattc ctaggtattt tattctcttt gaagcaattg tgaatgggag 101820
ttcactcatg atttggctgt ctgtctgtta ttggtatata agaatgcttg tgatttttgc 101880
acattgattt tgtatcctga gactttgctg aagttcctta tcagcttaag gagattttgg 101940
gctgagacga tggggttttc tagatataaa atcatgtcat ctacaaacag ggacaatttg 102000
acttcctctt ttcctaattg aataccettt atttccttct cctgcctgat tgccctggcc 102060
agaacttcca acactatgtt gaataggagt ggtgagagag ggcatccctg tcttgtgcca 102120
gttttcaaag ggaatgcttc cagtttttgc tccttcagta tgatattggc tgtgggtctg 102180
tcataaatag ctcttattat tttgagatac atcccatcaa tacctaattt attgagagtt 102240
ttcagcatga atggttgttg aattttgtca aaggcctttt ctgcatctat tgagataatc 102300
atgtgttttt tgtcattggt tctgtttata tgctagatta catttattga tttgcgtatg 102360
ttgaaccagc cttccatccc agggatgaag cccacttgat catggtggat aagctttctg 102420
atgtactgct ggattcggtt tgccagtatt ttattgagga ttttcgcatt gatgttcatc 102480
```

-continued

```
agggatattg gtctaaaatt ctctttgttt gttgtgtgtc tgccaggctt tggtatcggg 102540
atgatgctgg cctcatataa tgagttaggg aggattccct ctttttctat tgattggaat 102600
agtttcgcca aactgacatg atttttaaaa ttccctatag ggtcaatgtg cagatttaaa 102660
gatccctaca ctcagtagtc ctgggatagg gtcgggggat ccatatgttt aacaagcagc 102720
ctagagtctc ccgatagcct gggcaagctt taaaaagccc tgcggacatt cggatgaaac 102780
aaaggtgcac agaacctata tctctgccat ttattagctg ggggccttag gcaaggaagg 102840
tagtcaacct ccgtattcct cagttcctca actgtaaaat ggggatgatg actgtggctc 102900
cctcgtgggg ttgtgacgga ggaacagggg acatatgtcc tgggatcagc actggcaatt 102960
tggccattct taccatagca cctgccatct tggtgacagc ctggacacaa agccttcaca 103020
cctttgaagt ggccatagag agcatgagat atggatgggg aggaggcatt ccaactaaag 103080
acccctgctt tgggccaaaa acacatgtat gtctggtgtc tggagtcctc tggttatgcc 103140
tttttaaga taccggttgt cctgcaattg tgcgttgaga atccactcta tggccaacat 103200
atcatcaaag cgtttggctc agctaggctg ttccccccaac ccaaggaccc catgaggaaa 103260
ggagtgaggg ttccaccccc agcaccagcc actggagggg ctgcccagag tccctcagtt 103320
ctcgtaaact tacgctttgg agtaattcag aacaaagtcc actccttttt cactatcaaa 103380
ctggatatca cggggtaaat ccttgtggca tttggcatcg atgctcaagg ggaagccagg 103440
gttccactcc atccatctga gcatgagaaa ggagaagaaa ttgagttaaa tgccagcctt 103500
tggtctgccc cctcagctga gggccgccca cactgtcaga cgatgttaca cagggagatt 103560
gatgtactca aaataaagtc aacacatcat aggctgaccc tgtgtccagt aaggttctgg 103620
gacctcttcc aaagtccagt cgcaccaact ttgctgtgcc ctgagcatca gagtgggaac 103680
cctgagactg ggcttatagt ggtacaggtg tgcaccactg cataaaaagt tctgtaggta 103740
gtctagggag acctcactta ctagaggtga cattgaacag tagaggcctg ccttgccagt 103800
cactggaggt agaaggtatt aaggctgccc agccacgccc aacctggaca tccaccattc 103860
tgccaacttg atcagtgtgt gccctggact gcgtgcatgt cctgcatgtg gcatttgggg 103920
aaatgggaca gttcttctgc cttcacaata ggacgacacg gcagcaggtg gcctgggaga 103980
gggacccagg cacagatggc taaaaggctt ccctctctca cctgctggcc aatagcagct 104040
ttagagatta ttacaatcaa aacagcttcc ccaaagacaa gccacggact gcatccagta 104100
aacatgctca gatcctgaca tccttgaaac gtatcccgtg gcattgggca tttgtgtttt 104160
tgaaaaatgt ttattttgct tttttgttta cttattgagt aaacttaaat tgtgaaaatg 104220
tcagaggtgt ttgaaccaca gcaactccat cttgaatagg ggctgggtaa aataaggctg 104280
agacctactg ggcagcattc ccaggaggtt aggcattcta agtcacagga tgagacagga 104340
cattgatgca agatacaggg cagaaagacc ttgctgataa aatgggttgt ggtaaagaag 104400
ccggccaaaa cccaacaaaa ctaagatggt gatgaaagtg acctctgttc atcctcacca 104460
ctcattatat gctaattata atgcattagc atgctaaaag aaactcccac cagtgccatg 104520
acagtttaca aatgccatag taatgtcagg aagttaccct atatggtcta aaaaagggag 104580
gaaccttcag ttcctggaat tgcccacccc tctcctggaa aactcatgaa taatccactc 104640
attgtttagc acatgatcac gaagtgactg taagtatgct cagtcgagta gcccatgcta 104700
ctgccttgcc tatggagtag cctttcttta ttgctttact ttcctaataa acttgctttc 104760
actttatgga ttcaccctga attctttcct gtggaggtcc aagaactctc tcttggggtc 104820
tggatcagga cccctttctg gtaacaaaaa caaaatgaaa tcctgttagt ttctttgggg 104880
```

-continued agggagaatg attttgtgtt tgtttaaaaa ccagatttta cattttaggg ttttagcttt 104940
ttcatttata ttcctaattc tccttccttt taaaattttc ttttgagagg aaagtaaaat 105000
atcgagattt tgggtcttaa aaaagtcctg agttatttta atatgatctt gtgctttgac 105060
tttccccaaa tcccaactgt cacagtgtcc tcttggccca gtagcctctc cttaggatca 105120
caagaagtga acagggaccg ggtatgatcc ttctgacagc aaaggcattt tgtcaagtgt 105180
tttctgttat gtggcacctt acatttctca ctgttggttt atttagaata ttctacgtcc 105240
tcagatttta agaaaacctt ccatttttgc tgtttgtatt aatgccaatg atagtatatt 105300
aacaaggata aaaatgtgga caagtctaca catttttttgt ttgtttgttt tggaaaatga 105360
ctcaaggcat ctccaatata tatctaaaat tgagccattc agtagcctca ctggtagtaa 105420
tgatcaatta attagctatc attagtcata tcaatttaaa tattactgat gattttctct 105480
ttgcctggac agttcaaggg ctctagttaa ttttaaaagc tcagtggagc tagatgtttt 105540
tcagtatgta aacaatgagc catgcaaggg catctgtgcc agcaaatggc attaatgttt 105600
tcttaagtga atagtccact tggacggatg tggaatactt cttcagcacc aaaaagacct 105660
tcttgcccca tgccctgccc tggtctatgg agggtggcag caccaatggg cagaaatgcc 105720
ccacttgtgt ggttagaaga tgatggcctc acagcacatg gagacaggac agcttgcttg 105780
ctagttcact actgcccccc tgaaaccaaa tgtttatgtc ccttccactg caggtcactg 105840
ctgcttaaga gaccctgaca ggctgacctg cacaggagcc gaaggcctgc atggccacag 105900
acattaactg gtggagatgg aatcccactc cattgaggaa gaccaagtgg aacacccagg 105960
cagaaggaac aaagaagtag aaaggcattt aatttattgg aaaaaaaatg agagagagag 106020
agaaagagag agagagaaag caagagagac agagagacag agagagagag agagagaaag 106080
agagagagag aaagcaagag agacagagag acagagagag agagagagag agagagacag 106140
acagacagag agatcctaag gggatgcagt tagtataatt ggagtgtaaa aagactttct 106200
gtaaccacaa acatgatttc tgaatgaaga cttcaataga gaaacagaca aagagaataa 106260
tcactgtgag atgtttggtc tcttgtatta aaagaaaagc tttagacaaa ttaaatttag 106320
cagtttaatt gagcaaagaa caattcaaga atagggcagc ccctaaacca gagcaggctc 106380
cgagtgactt tgatgctgtc tcatagttgg ataggattta tgggcagaaa aaggaacgtg 106440
atgtacagaa aatggaagtg aggtacagaa acagccagat tggtgatggc tcagcatttg 106500
ccttacttga gcccagtttg aacagctggc cactgtgagt ggctgaagtc tggccgctgt 106560
gattggctga gacttggtta cttgctatga gagtaggtga cagtctgttt acacatccag 106620
ttaggttaca gttcactatg tacagagaaa cttttaggct gaatttaaaa tatgtaagga 106680
gaaaagttta agctaaactc attaacacct agaagagaga aggtgttcat tcgacaacta 106740
attatggagc acctactatg tgccaggaag tgctttgtgc aaaatagaag aacatgtaac 106800
ccaaatacag ggtgaaacta caaagaaatg gaagccataa atgaaactat gagagacata 106860
aaccaaaaat aaaattctaa gcccctgaac tgactgatgg accctcccct tggccaaggg 106920
cattccaaag ttaacctgaa aaattagttc aggccatgat aggaatgggt ggctaaacgt 106980
gcctcattgt actctcctcc tcttggaatt caggcacaac tgatcagcat tcacatcaac 107040
acagagatgt taagcccatt agaacagact ctttaagatt gataagaaac atttacaatt 107100
gattctacct gaagcctgct acctggaggc ttcatctgca tgataaaaaa ctttgtttcc 107160
acaacccctt atcttaacct agacattcca agtttttaga taataattct tttaagcagt 107220

-continued tgccaatcag aaactctttg aatctgccta tgacctggaa gctcccctcc cccaagttgt 107280
cccacctttc caaaaccaaa ccactgtcca tcttacatgt attgactgat gtcttatgtc 107340
tccctaaaat gcacaaaagc aagctgtacc ccaaccacct tgggtgcatg ttctcaggat 107400
ctcctggggc tgcatcatgg gccactggtc actcatattt ggctcagaat aagtcttttc 107460
aaatatttca cagagtgtga ctcttttcat taacagacat gaaagccaga tacagatgta 107520
atatgcaagg agtaaaagct ccaaaaggag agagagtaat atatggagaa gtgaaaaaaa 107580
tcaaagaaat aaaagaagaa ctcctttaag ctgaaaaata cttcaatatc ttaagtctgt 107640
gaaaggaaat taaattttag gaccccaaac tcatttagcc aaagggaaat gtcaagctgg 107700
gaactgtgtc atgcaaacct gcctccccct tttggttcct aaataagatg gctatgatga 107760
aaagctacat gtctccacca tattttgctc acaaggaaat tcctagtgaa ccgttaaaat 107820
ttcaccatgg caatgcaaat tgatagctta tctttacaag tgcagtcacc caccagatac 107880
aaatgcatat ctgattgttc ccctgcctta ctttatctat gttctcttat gtaaaatgca 107940
gactccctgc atttttcctc tgcctcattt gtttatgtca tcttatgtta aaaaaaatgc 108000
agattcactg agccagagaa aggcatgaat aactattttt ccctgccctg ctcttacatg 108060
aaaattgtgt acttctcaat atcccgccct tttcccttta aatttggagc cctcaaaatc 108120
accttcagag aaaggcatag tgctgtctcc cgggcatgcg tccttaactt tcgcaaataa 108180
atttcctaaa atgattgaga cttgtctcgt catttttctc aatgacaagt cctaggtggg 108240
ggggaaaaaa aaaaaggaaa aagatacacc taggtatata ctgaatacat tttaaaatgt 108300
ccaagagaca ggagaaacag agacagagag aaggaaagag atgcagagag tgaacgagag 108360
aggaagaaag tgggggaggg agggagatag aaactctagg aaaagaaaca aactatcatt 108420
agatttctcc tctgtcattc tgaaaatggg aagactgaag tgtatacaca ctttttttag 108480
atcgtcatct aagcctctca tattgtcatc aatgagggca ggggaatttg tttgagggga 108540
tgggtagggg gacaggacga caagcacaga ctcagatctt acactacaca tggaccttct 108600
gaggaaatta attgaacaag ttcagctgaa caaaaattaa attagaatga atcaataaac 108660
tcctaaatac agcaaagaat atgcattata aaactacagc aaatataata gtaaacaaag 108720
aaacaaaaat atgagaggga tgttcatcac tactaccact acttgttttg ggaattccag 108780
acatggaata agaaaagaat atcagtggtg tagataatgg aaagtaagag acaaaattat 108840
taacatttag ataatatgag cacattaact aaccagactc actaacaaca aacaaacaaa 108900
aacaagtgat tagaaccaat gaaagaattc agtaagggac caacacacag taaatgtaag 108960
aaacaagtaa tttacattta tcccagcaat atttttgcaa acagaaaaat atcctactca 109020
gaacagcaaa tgctaaatgt agagtagcta gaaaggtgaa ggacctgcat gaagaaaact 109080
agaaattcta tggaagtacg ttgacacagg atctagagag gtggaaagac acgctgtgtt 109140
cctggatgga aagactgaat ctcagtaaaa tgccaacaca taacacagtt atgtgaagtt 109200
caaagtaatt ctcattatga aaaacttaag aaagaacagt gagatatgta acagacatta 109260
acatttatta gaaagttatg ataaccaaaa gctggtgctg gggtctcgag tagaaaaata 109320
ggctaacaca taaagtgcgg aaacagaccc agagactatg tatacataat acaaaactcg 109380
ccaacactta tccagtgctt tctatgtgcc tactactatt ctctgtgttt tcatggttta 109440
acctattatc tcaaacccct aaaaggaagg cactgttatt tccctcattt tacagatgag 109500
ggaagtgagg cacagacaga ttaaacaact ttcacaggac tggagaaagt gccagtaagt 109560
gtgagttgag cccagacact cgaatccaga gctcatgact gccatcctat gccagcttgt 109620

-continued accgtgggta tcatcatccc tgtcatccaa gtcaggagga aagacatcat ccctgtcatc 109680
caagtcagga acgaatgcta ccgggagagt tccacccagg tatgtatgaa aacacgtggc 109740
aggagtgggg catggtggcg cacgcctgta gccccagcta cttgggaggc tgacgtggga 109800
agatggattg agcctgggtt agtttgaggc agcagtgaac catgatcatg ccactgcact 109860
ccagcctagg aaacagagca agactctgtc tcaaaaaaaa aaaaaaaggt agatgaatga 109920
aagctctaaa ctcaaagggg aaattataaa agtattagac aaaattacgg gggaagtatt 109980
tgtgtaacac tgggatggaa agggttttct taagcaaagg aggaaaccca aaagttatag 110040
atgtaaacaa tacatagtta ataaaataaa gaactaaaat ctcctgtggc aaaagcaaca 110100
gaagacaaat aataaatgct atacatatgt aacaaacgga tactatcctg atatagaaag 110160
agctccttta gattaataat tgaaagaaca atagggaaaa aaagcttata aataggcaat 110220
gcagtgatgc ttattagtgg tcaggggagt gcagactaaa acaaccacaa ggtcttaggg 110280
atttttagac tgtcaaacaa ggtcatcggg tactgacaaa tgtatggatg ggcaaaagta 110340
tcttttcata cacagctggt aggaccgcaa attacgatac aattttgtga aaggattttt 110400
gtcggtattt cttaagatga aaaaatgctg atttgttcca gcaatctgag ttctggaaat 110460
ggatctgcca ttaattaaag caccagtaca tcaagatgtt tgtacaaggt tggttctggc 110520
agcattgttt gtactgcaat acccaaaaca aacaaacaca tctacaaatg ggaaatgaac 110580
tgaacgtcag tgaatagggg aatggctaag taaattatgg tgcattccca gaaggcaaga 110640
aatagtagca gtttaagaag gggaaaatat atgagatact atttcacacg caagaatgaa 110700
aacatctgaa gatgcgaagt gttgatgatg cagggaaaca gtgaatctca gaaacagtta 110760
ctggggtgtc tactggcaga atgcctttgg aaaacaatca gcaatatcta gaaagcttaa 110820
aaacacgtgg tctgcaaccc tgcaactcta cttcttggaa tattccctac agtaactctt 110880
ccatgagagc acagagagat gtgtgagaaa gctcactgtc gcttggtttg caacagctag 110940
aaattaaaga cagcccgcct gcccatcagc aggagagcgg acgagcgcat gggttattca 111000
gatactgata tgccatgaag aagttaactg catgaaccac atctatctgt gtcaaccaga 111060
tcctcttcaa tacttagtga tgagtgaaaa gtgcaggtca cataatgatt agattaaatt 111120
atatcgatta acaaacacct acactttgcc atttactgct gtgtgtgagt gtgcatgtaa 111180
cacagacaga tgtggtcaca gtgggagagc acaagctgtg ggctatgacc tgggtctgct 111240
tctccttctc cctgcgtggc tgagtgagta aggagggcct gcaagaagcg ccagctttct 111300
gacatagtgt ggactattct tagtcattgc tttacttcca aactctgatc tggaagcctg 111360
agaaatcttc tgagaaagag gaactccaag attgtgcaga cagtgcaaag ttcagtgttt 111420
cctgaacgga agcaaaggag ggtttctgaa aaggacagat gagtggaagg aggaagaaaa 111480
aaatgattaa atctaagaaa gggggaaacg atctcaccag aagccccctg ctgcaagatt 111540
atgataatgt taagtagctc ccagataatt gggctagttt gtgttatctt agatgagtag 111600
atagcaaagt ctaattagag ccccactaat tcatactaaa gtgttagtgg cttataacaa 111660
attaaatgaa ttttatgggc attttatctt aacccagatt cacaggccag aagtgctctg 111720
agaactggct gcaggggctt tgccataggt gtctgaaaca gggagggaag ccaaggaaga 111780
agcatagaaa caacagccct ttgggatggg aggcagagct caagcacaac gtgtgcactg 111840
caccaggtat ggaagtctgg aaacacatca tatggtgcct gagctgagag gcttgtgcac 111900
aaatactcta aaacaaatca cacatttata aacccttaac atgacccaca gcacagcagg 111960

-continued

```
ttactctccc acacttgatg ctaatggcat gtaagtttta tttttgattt ttcaattggg 112020
aaatagaata tataaaatat gtatggatat gtatatatgc acacacacac tcacacatgc 112080
agaaaaatgt acaaaacacc tgtacgaaca ccatccaggt aaaaaatcag aacattgtcc 112140
gtaccctcac ccccaccttt cccaatcaac cctccttcca tccccggtaa tgaccatcct 112200
cggctttatg ataatcattt tcttgttatt gtttaaggtt ccgctatgac acacctccct 112260
aaacaatttc attccaaagt tatgaattgg ccagacacgc tcctggcttc tttccttcaa 112320
cactgcgtca gtgaggtttg tccatgttag cagcagtttg ttgattttcc ttgcagtgta 112380
gaattttcct tgacaatttg tctgttctac tgtttgttgg acattgagtt gttgccattt 112440
tttggccatc atgagtaatg ctgttgtgag tatccaggcg cacatgcaca caaatttgga 112500
tcccactata ggatttctgg gtcatagatt ataatgtagc ttcagtttta tgacatattg 112560
ctaaattgtt ttccacggag gtcttaccaa cttgtcctcc tgccggtggt atatgagtgt 112620
tcccagccct ctggatcttc tttaatactc aggtgttgtc agttgttgaa gtgttgccca 112680
tctgggggca tatgtgtggt agtagcagca gttcactgtg atcttctgat ttccccgagt 112740
cctaatgaag ttgaacacct tttgtatact tgctgcttat attttgtaca gtaagtactc 112800
aaacttcttg cccattttct agtgaatgac actccccttc ttaaagattt gtaggtcctt 112860
cacatactag gaataattct cgtcaatcac tccatgactt gccttcactc tctcctggtg 112920
tctttcaatg aacagagtgt ccttatcttg agggaggcaa acttaccaat cttttccttt 112980
gtgtttaata tgttctgagt cttgtttgaa aaatcctttt agcttgagac ctggaagaat 113040
aatcacctgt agtctaaatg tcttacagtt ttgcctttaa cttttaagtc taatcaaccc 113100
caagctgagt ctcctgaatg gcaagaggtg gagtctgatt tcttctcctt ctccttcagc 113160
cctccgtgct ggctggcccc tgtcctcgag atgcatgtcc agtggcccag tgccacccat 113220
cagccgagcc ctccgtagca gacccagtac ccacatacgt gtggctgttt gttgtttctt 113280
tattctgttt caaggaatgt ttttgatgaa aagggggatg aagctaagac agttttgagg 113340
tggggcaatt gtgttcttgg tgtgggattt ctcacccctt gacagcagtg ggtggctggg 113400
catagggggaa gaaggagcta cagggttgag ggatgctgtt gcaacttaga aaaattaaga 113460
aaaatgaaga tattgctcag ttatggcaag tgtttgatga aacagggacc catacatggc 113520
tcgtgaaaac tggttaaaga tttttttttt tttttttttt gagacggagt ctcgctctgt 113580
cgcccaggct ggagtgcagt ggtgcaatct cggctcactg caagctccgc ctcccaggtt 113640
cacgccattc tcttgcctca gcctcccgag cagctgggac tacaggcgcc cgccaccacg 113700
cccggctaat tttttgtatt ttttagtaga gacggggttt caccgtgtta gccaggatgg 113760
tctcgatctc ctgacctggt gatccaccca cctcagcctc ccaaatggtt aaagattttt 113820
gaggagaaat ttgtcaatgt atactaataa cttttactat ttggtaattt catatctggg 113880
catctgtcct aggaaaatac ttaataatgt atacaaattt cacatacaag ggttttcact 113940
ttgcttataa gaatacaaaa attagaaacc tcctaaatgt ccagggaagc tgggtgttta 114000
agtgaatgat gaggcatcca tccaatggaa tagtacatag aaactagaat aatgtttatg 114060
atgagatttt gaaaatatgg gaaaatgatt tttgctacac tgctaaaggg cagcaaggag 114120
gatgcaaagt ggtatatata gcacaatccc aaattttaaa aagtgaataa gacaaagtga 114180
aaacaattaa acatgaattt ttatgaaaaa gttcataaaa ttcataattc atacagaaaa 114240
taggtatttt tctggctcta tattattttc cttcttttac ttttttgagt taaaaaaaca 114300
acccagatat actacatatt ccttgtaaga agttcaacta ttgagggata tgtagaaaag 114360
```

-continued tatcacaata ttggctccca aaggcccctc cacagcccag gtaacttcac tgtccatgta 114420
gaatgattcc ttccactttc ttcccttgga aggaggcaca gactcaaatg tttccagggg 114480
ccaaagcagg aaatgaaatg aaagaaaacc ttgatataga caacagacaa gtgtggactg 114540
gggaagcctg aagaatatct ctgtttactc ataagtcaat aatgatccat caaacacttg 114600
tagaggctgg atacagccca tcagccaccc atttccagag gagcactctg taatgtgtta 114660
ttatcttcca aaaagcttta ctgagataca tttacatacc attaaattca ccccttaaaa 114720
atatgctatc aaaagatttt aatatatttg cagagttgta tgtgtaacca tcattataac 114780
ccaattctga aataatctca tccccagagg acacctcgaa cccattaaca ttcactcctt 114840
gtttcccctc cccaactcct agtgctaggc aactactcac ctactaacct gactctgtgg 114900
gtttgcctat tctggacatt tcatacagat agaatcacac aatatggggt cttccgtaag 114960
tgagttttcc atttagcata tttttgaagt tcattcagtg tttggcatct atctgtagtt 115020
catttctttt cttttctttt ctttttttga aatggagtct tgctctgtca cccaggctgg 115080
agtgcagtgg cgggatctag gctcactgca acctccgcct cccgggttca agtgattctc 115140
ctgccttagc ctcccaagca gctgggatta caggcgtgca ccaacatgcc cggctaattt 115200
ttgtattttt gtagacatgg ggtttcacca tgttggccag gttggtctca aactcctgac 115260
ctcaagtgat ctgcccgtct caacctccca aagtgctagg attacaggtg tgagcctccg 115320
cgcttggcat tcattccttt ttgatgccaa aaaatatccc attgtatgga taaactatat 115380
tttgtttatt cattcctcag ttaatggaat ttaggttgtt tctacttttt gactattgtg 115440
aacaatggtg ctataaatat gtgtgtacaa gttttgtata gacatgtggt ttcaatattc 115500
ttgggtagag gcctaggagt agaattgctg ggtcatattg tagctgggtt tcagattttg 115560
aggaaccact aaactgtttt ctgaagtggc tgcatcatct tacattccgg tagcagcatc 115620
agggttccag tttctccaca tccttggcag cacttgttac tatctgtctt ttttattcta 115680
accattttag tggttagaat tgtatcttgt ggttttgatt tgaaatttcc tgatgattaa 115740
taatgttgag catattttca cgtgcttatt ggagattcac aaattttctc tggagaacta 115800
tttaattaaa tcctttgcta atttttaaac ggggtttttt gtacagaata ttttaaaatt 115860
gagttgtcag agttctttat atattctgga tacaagtccc ttatcagaca tatgatttag 115920
atattttctc cattctgtgg attgtctttt cactttattg atgatgtcct ttgaagcata 115980
gatcttttac attttaatga catctaactt gtctactttc ttttgctgcc tgtgctcttg 116040
gtgccatatc taagagactt tgccgaaccc aagattatga agacttactt gtatgttttc 116100
ttccaagagt gttatgttgt tagcccttac ttttagatct atcatccatt ttgaattaat 116160
ttttaaattt atctagcagc gttattgaaa tataatgcac atactgtaaa atttatccat 116220
ttaaagtgtt caattcaagg atgtttagta ttaattttta cacaatggac aaccatcagt 116280
tttagaacat tttcatcccc ggcaaaagga acactgtatc ctttagctgt cactcccatg 116340
accacttcct cattccctgc ccctaggcaa ccagtaatct actttatatc tgtacagatt 116400
tttcttttcc agaaatttca tataaaagga atcatacaat atatgatctt ttgtgactgg 116460
tttctttcac ttagcataat gtttttgaga ttcatccatg ttgtaacaag tgtcagtatt 116520
tcattcttct ttcatggtca aattatatag atatactata ttttatccat tcatccatta 116580
atggacgttt gggttgtgta cactttttga tagttacagg tcatgctgct ataatcatgc 116640
atgtacaagt ttttgtgtgg gcatatgttt ccatttctgt tgggaatatg cttaagagtg 116700

-continued gaaatgctgt catattgtaa ctctctgttg aacagtcagg agctagcaga ctgtttccca 116760
agcagctgtg ccattttaca ttcccaccag cagtgtatga gggttctgat ttctccacat 116820
ccttgtcaac acttgttctt gtcggatttt tttattctag ccatcctagt atcaagtggt 116880
atctcattgt ggtgttgatt tgcatttcct agatgactaa tgggtccttg gagaaatatc 116940
tattcagatc ctcactcatt tttttcattt tttaattgga ctatttgtct ttattgagtt 117000
gtaagagttc tttataaatt atggatggaa ggcccttatc agatatacaa tttgtaaata 117060
tttcttccat tctgtggttc atcttttcac tttcttgatg gtgtcctttg aaacataaag 117120
gtttgtaaat ttgatgacat cactttatca ctttatctat ttttcttttg ttgctgatgc 117180
ttttggtgtc atatcaagag tcctttgtca aatccaaagt catgaaggtt tactcctgtg 117240
ttttcttaaa agagttttat agttttagct cttacattta ggtaggtatt tgactcattt 117300
tgtgttaatt tatgtatatg gtgtgagcta aggatccaac ttcattcttt tgcatgtggc 117360
tatccagttt tgctaggacc atttgttgaa aagactattc tttctctgtt aaactgtctt 117420
gctgcttctg tcaaaaatta attggccata agtgtaaggg cttatttctg gactctcaag 117480
tctatttcat tgatctatat atctatcctt atgccgatat cacattgtct tgaatactat 117540
agctgtgtag taattttgat attgagaagt gcaagtcctc catctttgtt ttctttttat 117600
caagattgtt ttggctattc tgggtccctt ccatttccat atgaatttgc agaattgaca 117660
gcttgtcaat ttctgcaaag aaatcagcta gaattttgat aagggttgtg ttgaacgtgt 117720
acattaattt gtggggtatt gccattttaa caaaattaag tcctctgatt catgaacatg 117780
aaatgtcttt caacctattt agatcttctt taataatgtt aaacaatgtt ttgtagtttc 117840
attgtacaag tctcagacta ctttgttaaa tttattcata aatgtttact gtttttgatg 117900
ctattgtaaa ttgaactttt tcttactttt atttcacata gttggttgtt aatgtataga 117960
aaaacaattg attatcttgt atcttgcaat cttggtggtt tattagttct aataatttct 118020
tttggtgaat gccttcagat tttctatata taagatcatg ttatttgtaa attgtggtag 118080
ttttacttac tgtactccat tgtgggtgcc tttacttatc tttttattcc ctaactgagc 118140
tggctagacc ctccagtaca atgttgaata gaagtagcaa aagtgaacat ctttatcctg 118200
tttctggatt cagcctttca tcattaagta taatgttaac tgtgaatttt cttttttttgt 118260 gtatgtgggg ggacggagtc ttgcttgtca ccatgctgga gtgcagtggc atgatctcag 118320
ctcactgcaa cctccgcctt ctgggttcaa gtgattctcc tgcctcagcc tcctgagtag 118380
ctgggactac aggcgcatgc caccacacac agctactttt tgtattttag tatagacggg 118440
gtttcaccat gttggccagg atggtctcaa tctcttgaca tcgtgatcca cccgccttgg 118500
cctcccaaag tgctgggatt acaggtgtga accaccacgc ccagcctaat tgtgaatttt 118560
caaaccttta tcaggttgag gacattttct tcaattccta ttttttgagt gttttatcat 118620
gaatgggtgt tggattttgt caaatgcctt ttttgtatgt ctattgaaat gattatgtac 118680
tttgttttgt tttgttattt actctattga tatggtgaat tcaattaatt gatttttgga 118740
tgttaaacca actttgcatt cctgggctaa atcccacatg ttcatattgt ttaatgcctt 118800
ttatatactt ctgggttagg tttgctagta tttcgttgaa aatgtttata tctatattgc 118860
taagggatat tggtttatag ttttcttgtg atgcctttag ttttggtata atatgggtat 118920
gagacaatga attgggaagt gttccttcta tttcttaaaa gagtttatgc aagatcagta 118980
ttaattcttt aaatgtttga tagaattagc cagtgaagct atctgggtct gggcttctat 119040
ttgtgggaaa ttttagaatt agtaattcaa tctctttggt tgtgattgtt ttattcagat 119100

-continued taactatttc ttcatgagtc agttttggca gtttgcgtct ttctaggaat ttgcgcattt 119160
catttaacta gtttgttggc atgcaattgt tcatagtatt ctttttttatt aattttaatt 119220
tctgtattga ttttccctca ttttatgagt ctcatttttc cttttttatt cattttaatt 119280
tctgtattga ttttctctta ttgctcattt taatggtttg aatcctctgg tcagttggct 119340
gaagagttgt caattttatt gctgatcatg tatcactttt ataattgaat tgttataaga 119400
agacataaga agtaagaggc aacccctaca atggagaaca ttaaggtaca ctcaagcttt 119460
tctgcccatt cttcctacat gccaatatgg ttgatccaaa gttattttca ttactctcct 119520
ctccatctct tgtctggagt tgtaggtaag gtgaagtttg gggattgtgc acccacactg 119580
ggagctggtg ccttggtgac tttccagcag tgacaggcca tacactgtgg aaagggttta 119640
tttcatacca tgctcttgag atagaagaaa ccatggcccc gtggccactc gatctgatgt 119700
cataactcac cgatattgtt tttgccgtgt ttccagttct ttacgtcggt gttgcttgag 119760
aatgtgaatt tggtcatctc gggccaactt tgctgtaaag aaagaacaac atgagaggag 119820
cctgaggaag aacaataaca atgcccaatg ccaagtgttc aggcttccct cagatgccct 119880
gcccatgccg agtgctttat gtgcatgacc tcatttgagc ctcagagcac ttccccaatt 119940
aatgatgaag aaactgaggc ttagggaagt tgtgtagctt tgctcttgaa ctttacccaa 120000
ggtcacacac ctaattagtg aattttcttt tttttttttt aattctactt taagttctag 120060
gatacatgtg cacaacgtgc aggtttgtta catatgtata catgtgtcat gttggtgtgc 120120
tgcacccatt aactcgtcat ttacattagt tatatctcct aatgctatcc ctccccctta 120180
cccccacccc atgacagacc ttggtgtgtg atgttcccct tcctgtgtcc aagtgttctc 120240
attgttcaat tcccacctat gagtgagaac atgtagtgtt tgttttttttg tccttgcgat 120300
agtttgctga gaagggtgat ttccagcttc atccatgtcc ctacaaagga catgaattca 120360
tcctttttta tggctgcata gtattccatg gtgtatatgt gccacatttt cttaattcag 120420
tctatcattg atggacattt gggttggttc caagtctttg ctattgtgaa tagtgctgca 120480
ataaacatac gtgtgcatgt gtctttatag cagcatgatt tataatcctt tgggtatata 120540
cccagtaatg ggatggctgg gtcaaatggt atttctagtt ctagatccct gaggaattgc 120600
cacagtgtct tccacaaagg ttgaactagt ttacagtccc accaacagta taaaagtgtt 120660
cccatttctc cacaccctct ccagcacctg ttgtttcctg actttttaat gattgccatt 120720
gtaactggtg tgagatggta tatcattatg gttttgattt gcatttctct gatggccagt 120780
gatgatgagc attttttcat gtgtctgttg gctgcataaa cgtcttcttt tgagaagtgt 120840
ctgttcatat ccttcgccca ctttttgatg gggttgtttg tttttttctt gtaaatttgt 120900
ttgagttgtt tgtagattct ggatattagc cctttgtcag atgagtagat tgcaaaattt 120960
ttttcccatt ctgtaggttg cctgttcact ctgatggtag tttcttttgc tgtgcagaag 121020
ctctttagtt taattagatc ccatttgtcc attttggctt ttgttgccat tgcttttggt 121080
gttttagaca tgaagtcctt gcccatgctt atgtcctgaa tggtattgcc taggttttcc 121140
tctagggttt tgatggtttt aggtctaaca tttaagtctt taatccacct tgaattaatt 121200
tttgtataag gtgtaaggaa gggatccagc ttcagctgtc tacctatggc tagccagttt 121260
tcccagcacc atttattaaa tagggaatcc tttccccatt gcttgttttt gtcaggtttg 121320
tcaaagatca gatggttgta gatgtgtggt gtcatttctg agggctctgt tctgttccat 121380
tggtctatat ctctgttttg gtaccagtac catgctgttt tggttactgt agccttgtag 121440

-continued

```
tatagtttga agtcaggtag catgatgcct ccagctttgt tcttttggct taggattgtc 121500
ttggcaatgc gggctctttt ttggttccat atgaacttta acgtagattt ttccaattct 121560
gagaagaaag tcattggtag tttgatgggg atgacattga atctataaat taccttggga 121620
gtatggccat ttttatgata ttcattcttc ctatccatga gcatgggatg ttcttccatt 121680
tgtttgtgtc ttcctttatt tcgttgagca gtgatttgta gttctccttg aagaggtcct 121740
tcacatccct tgtaagttgg attcttaggt attttattct ctttgtagca attgtgaatg 121800
ggagttcact cctgatttgg ctctctgttt gtctgttatt ggtgtataag aatgcttgtg 121860
attcttgcac attgattttg tatcctgaga ctttgctgaa gttgcctatc agctttaagg 121920
agattttggg ctgagacaat ggggttttct aaatatacaa tcatgtcatc tggaaacagg 121980
gacaatttga cttcctcttt tcctaattaa ataccottta tttctttctc ctgcctgatt 122040
gccctggcca gaacttccaa cactatgttg aataggagtg gtgagagagg gcatccctgt 122100
cttgtgccag ttttcaaagg gaatgcttcc agtttttgcc cattcagtat gatattggtt 122160
gtgggtttgt cataaatagc tcttattatt ttgagatacg tcccatcaat acctaattta 122220
ttgagagttt ttagcatgaa tggttgttga attttgtcaa aggccttttc tgcatctatt 122280
gagataatca tgtggttttt gtctttggtt ctgtttatat gctggattac atttattgat 122340
ttgtgtatgt tgaaccagct ttgcatccca gggatgatgc ccacttgatc ctggtggata 122400
agctttttga tgtgctgctg gattcggttt gccagtattt tattgaggat ttttgcatcg 122460
atgttcatca gggatattgg tctaaaattg ttttttttgt gtgtgtatct gccaggcttt 122520
ggtatcagga tgatgctggc ctcataaaat gagttaggga ggattccctc tttttctatt 122580
gattggaata gtttcagaag gaatggtacc agctcctcct tgtacctctg gtagaattcg 122640
gctgtgaatc catctggtcc tgaacttttc tgggttggta ggctgttaat tattgcctca 122700
atttcagagc ctgttattgg tctattcagg gattcaactt cttcctggtt tagtcttggg 122760
agggtgtatg tgtcgaggaa tttatccatt ttttctagat tttctagtta atttgcttag 122820
agttgtttat agtattctct gatggtagtt tgtatttctg tggaatccgt ggtgatgtcc 122880
cctttatcac tttttattgc gtctaattga ttcttctctt cttttttttt tctttttttt 122940
taattgatca ttcttgggtg tttctcgcag agggggattt ggcagggtca taggacaata 123000
gtggagggaa ggtcagcaga taaacaagtc aacaaaggtc tctggttttc ctaggcagag 123060
gaccctgcgg ccatccgcag tgtttgtgtc cctgggtact tgagattagg gagtggtgat 123120
gactcttaag gagcctgctg ccttcaagca tctgtttaac aaagcacatc ttgcactgcc 123180
cttaatccat ttaaccctga gtggacacag cacatgtttc agagagcaca gggttggggg 123240
taaggtcata gatcaacagg atcccaaggc agaagaattt ttcttagtac agaacaaaat 123300
gaaaagtctc ccatgtctac ctctttctac acagacacag caaccatccg atttctcaat 123360
cttttcccca cctttccccc ttttctattc cacaaaacca ccattgtcat catggcccgt 123420
tctcaatgag ctgttggcta cacctcccag atggggtggt ggccaggcag aggggctcct 123480
cacttcccag taggggtggc caggcagagg cacccctcac ctcccggacg gggcagctgg 123540
ccgggcgggg ggctgacccc cccacctccc tctcggacgg ggcggctggc cgggcggggg 123600
gctgaacccc tcccctcccg gacggggcgg ctggccgggc gggggctga ccgcccccca 123660
cctccctccc ggacagggtg gctgccgggc ggagacgctc ctcacttccc agacggggcg 123720
gctgccgggc ggaggggctc ctcacttctc agaaggggcg gctgccgggc ggaggggctc 123780
ctcacttctc agatggaggg gctcctcact tctcagatgg ggcggctgcc gggcggaggg 123840
```

-continued tctcctcact tctcagacag ggcggccggg cagaggcgct cctcacctcc cagacagggt 123900
ggtggggcag tggtgctccc cacatctcag atgatgggcg gctgggcaga gacgctcctc 123960
acttcatccc agacgatggg cggccaggca gagacgctcc tcacttccta gacaggatgg 124020
cggccgggca gagacgctcc tcactttcca gactgggcag ccaggcagag gggctcctta 124080
catcccagac gatgggtggc caggcagaga cgctcctcac ttcccagacg gggtggcggc 124140
cgggcagagg ctgcaatctc ggcactttgg gaggccaagg caggcggctg ggaggcggag 124200
gttgtagccg agccgagatc acgccactgc accccagcct gggcaccatt gagcactgag 124260
tgaatgagac tccgtctgct atcccggcac ctctgggagg ccgaggctgg cggatcactc 124320
gcggttagga tctggatatt agcctgttct acacagtgaa tctccgtctt taccatttta 124380
ttatgttata ttagttctgc gtggtggtgc gcacctgtct ctctcatgca ctcggctatg 124440
ctgtagcatg acaatccgtc agtgttgttg tttcgactct tgagtcgcct cgacactcag 124500
tcttggtgct ccttatcata tggagatcgt tggtcgtcgt ttcttgtttg ggttttgctt 124560
gtgccttttc tgtttattgt atcgcttatg atcgtgatgt tgtcttagtt gcttgttggt 124620
ctctagtgtg ttttttgtgt tgtatcttgt tcttgcgttg agtgggttgg gcgttggccc 124680
gaggctttct tttggttctg tggtgtctct gacgttttgt tgctctnnnn nnnnnnnnnn 124740
nnnnnnnnnn nnnnnnnnnn nnnnnnnnnn nnnnnnnnnn nnnnnnnnnn nnnnnnnnnn 124800
nnnnnnnnnn nnnnnnnnnn nnnnnntaga tttggacgtt atgttttgag tattttattt 124860
gattgggtat ggttagtagt attgaggggc atgtgggtta attaggtttt gtatagatta 124920
tatttatttt atttattgta ttttaatgat tagatgttgg ttttaacgtg atagatggtg 124980
ggtatagatt atagatgtga gtcggtgagc tatatgggat aggtaggttg ggtgtgtcgt 125040
gcttctcgcg gcctctctca gcagtgtgct tcggcctcga gaccaccaac tcaacatcac 125100
gtccatctca tttcgcgcta cgacacactc atgtctgtac gcacgagtgt atcttctcgc 125160
gagcgcttct gtctggcgtg ctggggggc gtgggggggg ggggcggggc ggggggagat 125220
aggacgtgga agaggagaga tggcagaggg gagatggcag agggagagct gaatcttctc 125280
ttttcttctt tattagtctt gctagcagtc tatcaatttt gttgatcctt tcaaaaaatc 125340
agctcctgga ctcattgatt ttttgaaggg atttttgtgt ctctacctcc ttcagttctg 125400
ctctgatctt aattatttct tgccttctgc tagcttttga atgtgtttgc tcttgcttct 125460
ctagttcttt taactgtgat gttagggtgt caattttaga tcttccctgc tttctcttgt 125520
gggcatgtag tgctataaat ttccctctac acactgcttt aaatgtgtcc cagagattct 125580
ggtatgttgt gtctttgttc tcattggttt caaagaaaat ctttatttct gccttcattt 125640
cgttatgtac ccagtagtca ttcaggtgca ggttgttcag tgtccatgta gttgagaggt 125700
tttgagtgag tttcttaatc ttgagttcta gtttgattgc actgtggtct gagagacagt 125760
ttgttatggt ttctgttctt ttacatttgc taaggagtgc tttacttcca actatgtggt 125820
caatttcaga ataggtgtga tgcagtgctg agaagaatgt acattctgtt gatttggggt 125880
ggagagttct gtagatgtct attagctccg cttgctggag agctgagttc aattcctgga 125940
tatccttgtt aactttctgt ctcattgatc tgtctaatgt tgacagtggg gtgttaaagt 126000
ctctcattat tattgtgtgg gagtctaggt ctctttgtag gtttttaaga acttgcttaa 126060
taaatttggg tgctcctgta ttgggtgcat atacgtttcg gatagttagc tcttcttgtt 126120
gaattgatcc ctttaccatt atgtaatggc cttctttgtc tcttttgatc tttgttggtt 126180

-continued taaagtctgt tttatcagag actaggattg caacccctgc ctttgttttc catttgcttg 126240
gtagatcttc ctccaatccc tttattttga gcttatgtgt gtctccgcac atgagatggg 126300
tttcctgaat acagcacact gatgggtctt gactctttat ccaatttgcc agtctgtgtc 126360
ttttaattgg agcatttagc ccatttacat ttatggttaa tattgttatg tgtgaatttg 126420
atcttgtctt tacgatgtta gatggttatt ttgctcatta gttgatgcag tttcttccta 126480
gcattgatgg tctttacaat gtggcatgtt tttgcagtgg ctggtaccag ttgttcattt 126540
ccatgtttag tgcttccttc aggagttctt ttagggcagg cctggtggtg acaaaatctc 126600
tcagcatttg cttgtctgta aaggatttta tttctccttc acttatgaag cttagtttgg 126660
ctggatatga aattctgggt tgaaaattct tttctttaag aatgttgaat attggccccc 126720
agtctcttct ggcttgtagg gtttctgccg agagatcagc tgttagtctg atgggcttcc 126780
ctttgtgggt aacctgacct ttctctctgg ctgcccttaa catcttttcc ttcatttcaa 126840
ctttggtgaa tctgacaatt atgtgtctcg gagttgctct tctcaaggag tatctttgtg 126900
gtgttctctg tatttcctga atttgaatgt tggcctgcct tgctagggtg agcaagttct 126960
cctgcataat atcctgcaga gtgttttcca acctggttcc attctcccca tcactttcag 127020
gtacaccaat cagatgtaga tttggtcttt tcacatagtc ccatatttct tggaggcttc 127080
gttcatttct ttttattctt ttttctctaa acttatcttc tcgcttcatt tcattcattt 127140
gatcttcagt cactgatacc ctttcttaca gttgatcgaa tcggctactg aagcttgtgc 127200
attcgtcaca tagttctcgt gccatgtttt tcagctccat caggtcattt aaggacttct 127260
ctacattggt tattctagtt agccattcgt ctaatctttt ttcaaggttt ttagcttttt 127320
ttgcgatggg ttccaacttc cttctttagc tgggagaagt ttgatcatct gaagccttct 127380
tctctcaact cgtcaaagtc attctccatc cagctttgtt ccaccactcg cgaggagctg 127440
ccttcctttg gaaggggaga ggcactctga tttgtagaat gttcagcttt tctgctctgt 127500
ttttccccat ctttgtggtt ttatttacct ttggtctttg atgatggtga cgtacagatg 127560
gggttttggt ggtgtggatg tcctttctgt ttgttagttt tccttctaac agtcaggacc 127620
ctcagctgca ggtttgttga tgtttgctag aggtccactc cagaccctgt ttgcccgagt 127680
atcagcagca gaggctgcag aacagcgaat attgctgaac agcaaatgtt gctgcctgat 127740
tgctcctctg gaagctttgt ctcagaggtg tacctggcca tgtggggtgt cagtctgccc 127800
ctactggagg gtgcctccca gttaggctac tctggggtca gggagccact tgagggggca 127860
gtctgtccct tctcagatct caaattccat gttgggtgaa ccactagtca cttcaaagct 127920
gtcagacagg gacatttaag tctgcagagg tttctgctgc cttttgttcg gctatgacct 127980
gcccccagag gtggagtcta cagaggctgg caggccttct gagctgcgat gggctccacc 128040
cagttcgagc ttgctggcaa tgagcaaggc tctgtgggca tgggaccctc cgagccagac 128100
atgggatata atctcctggt atgctgtttg ctaagactgt tggaaaagta cagtattagg 128160
gtgggagtga cccaatttc caggtgctgt ccgtcaccac ttcccttggc taggaaaggg 128220
aattccctga ctccttgcac ttcccaggtg aggtgatgct cacactcaat gggctgcccc 128280
cactgttctg cccccactgt ccaacaatcc ccagtgagat gaacccagtg cctcagttgg 128340
aaatgcagaa atcacccatc ttctgcattg ctcatgttgg gagctgtaga ctggagctgt 128400
tcctattcgg ccatcttgga accagtctga attagtgaat tttcaacata aaactcaact 128460
cctgtgctct tagccactca ctttacaaaa gccaaatcca gttcctcatc ctcttgccca 128520
ctcactcagc aagccttggg gcccctgcct ttcagtgctt agagaatcat gttcagatgc 128580

-continued

```
aagagccagg cttggttctc actgggcttg gcaggcacag tacatgccta actctggcct 128640
gcgtgtgcat ttccacttga ggtcctaacc ttccactcag cccctcaaga ctcttcaggg 128700
acctaagggc ccctggtgca gagctgcctt tttgctccag gagaaaggca tttcgtggcc 128760
cttggtgggt atctttaaat cactgcagaa tagtttactc ctcttctctg aaattcttat 128820
actgagcaaa aacgggagtt cactctgggt tttagtgttg cctgtgagag cagcagttct 128880
cacagctctt atgtttctaa gtccatttca ttgtttcatg gagaaatgtg tgacgatgac 128940
acaacccggt ttcctgtcgt gcctacacag aggattgaga atgagctcca ttctaaaaga 129000
gtgcagtgtc ctagatggct ttagaagaga cacatgtgct tggacttggg ctctgtcact 129060
gaagctgtgt gaccaagagt tgccctgacc ccctcacatg taaaatggag atgataatgc 129120
ctacttctcc gggtcatggt gtgcatttgg ggagagaatg caggaaagcc ctccacacgg 129180
cgcctggcac gcagtaaatg ccaatggatg ggaacaatga tcattatcat tatgcctata 129240
gtcatcactg gcctgagggt tctgctcctc cctctaagcc tagctctgag agcatcttat 129300
ctctcagcct gtcctgctgc cgtctctcac tgcaggagtt ggagcaggta gcaggtagct 129360
aagggcgggg ctgcttctca gagcctttag agcagatgag gtcatatcat gaccactctt 129420
taaactattg cttaaggcca agcctgtgaa cgcagcccat agagctgtga ataggggggag 129480
cccagatctc ctgaaaacag gtcctggaat agtttctcta gctctcgtgg taaagcattg 129540
tgttttaaaa cttacttttc aacacagatt attatatttt tgtaaaatat aataaaaatt 129600
aattactaga aaaatgaaat tttaaaaacc caaagatatt caaaatccaa gtcttttttt 129660
ttcttattag gtgcaaaagt cacaaaattg ttctgttaag ttgctataaa agtttctaaa 129720
acccctcctc tgagtctttg tattttattt tgtatttatt ttatttttat ttttttaag 129780
agacagggtc tccctctgtc tcccaggcta gagtgcagtg gcatgatcat agctccctgc 129840
agccttgaac ttcaggactc aagtgattcc ccaacctcag cctcctaagt agttgggact 129900
ataggcacac accaccacac ctggctaatt tttttttttt ttttgagaca gagtcttgct 129960
ctgttgccca ggctggggta cagtggcatg atctcagctc actgcaagct ccacttccca 130020
ggttcacgcc attctcctgc ctcagcctcc caagtagctg ggactacagt tgcccaccac 130080
cacatccagc taatttttttg tatttttagt agagacgggg ttttactgtg ttagccagga 130140
tggtctcgat ctcctgacct tgtgatccac ccgcctcggc ccctagctaa ttttcaattt 130200
tttttgtaga gatggggtct ctctacattg cccaggcttg tgacaaaatc ctagactcaa 130260
acaatcctcc cgccttagcc acccaaagtg ctggaactat aggcttcaac ctctgtactg 130320
atctaattgc agacctggac gcagttagtt ctcagatgac actcaggcca cattctgagc 130380
tgtccacccg acagcacttc caggctgaga catcttcatc cttgagcttg gaactggggt 130440
ccaaaaagga atattaacgg gatacctctg catcctcccc tggggatgta aagccagcca 130500
ggaggggagg cttgaggcca cagaaggcaa gctgagtatt aatggtgaca ataactgtta 130560
tcattggcta tgggggtaat tctggaggca ctcaacattc atcatctctt atctacctta 130620
aggaaccagc taatctcttg ggcaccttga ctctgaggag ctggatctct tcagtttcac 130680
tggtatgaat aagtcagtac atgcggaatt gcaacatgcc aagtttcaaa aagagaatag 130740
ttctgtctcc cctggtcccg aaggtgtttg aagaatttat ccaatggctg atgaagttct 130800
gggagcacag caggatgaga aagcctggac tgacggcaga agagctcagc agggcaggtt 130860
ccaaggactg acacagtgcc ttaatgaagc tgtcccttca cacagatgct ctggatctgt 130920
```

-continued ggggccacag taatggccct ctgacattca tgttcaccca aggtgtagtg gtgaaatatt 130980
agatttaagg ggtgatcata tggtgagtaa ttgaatcact tgtaggctgg ccccctcat 131040
ttccaggttg ttcaagggat tggttgtttt gccatgtggt ggattaataa ttggccacag 131100
ctggacatgg tagctcatga ctgtaatccc agcactttgg gaggccgagc cgggtggatc 131160
acctgaggtc aggagttcca gactagcctg gccaacatgg caaaaccctt tctctagtaa 131220
aaatacaaaa attagccagg cttggtggct acctggagcc tgtaaaccaa gctccctagg 131280
aggctgaggc aggagaatcg cttgaacctg ggaggcagag gttgcagtgg gctgagatcg 131340
tgccactgcc ctccagcttg ggcaatagag tgagactctg tcccaaaata ataataataa 131400
taataataat aggccacaaa ttctttgaca ttccttccat tgagagatgg gggggtctgc 131460
atccccaccc ccaccccccgg agtctgggtg ggctctgtga ctgcttggac cagtagaata 131520
tgatggaagt tacagtgtgc cagtttccag gcccaagcct gaagagattg gcagcttcca 131580
ctttctgtct cttagaaaac ttgctcttgg aagccagcca tcatgtaaga aatgcaggca 131640
cccagaggac accattctgt gagaagcctt aaagaatgag actccatatg gacagagagg 131700
ccaaggagcc tagaggtgcc agacacatga cagaagaagg cccagccccc ttcagctgat 131760
gctacatggc cacagatgaa ctgcccagtg aagcctttcc taaattcctg acctgcaaga 131820
gcatgaacaa aattaaatgg ctgtttaaag ttaccaagga ggttggtttt acagcagtag 131880
agagaatgga acttgctgga cagcttctct atgctcaccc tccaacctgt gctgtccctg 131940
aaagtgattg gaatgagatg cctcaatggg ttttccactg ggaactctga ccagaaagga 132000
gggaatgtgt agaggaagga gaggccaatc actccccaga acctttctac tgagggccgc 132060
agctcctcca agggtgctgt ctccaggata cttctgcatt actcccacaa ccttccccct 132120
ccccctgcat caggactagt ggtgctgatg gccccgcact ctgcatggtc cctctgcaca 132180
tgggcccaca cctttgtgat gcccctttgt taaaccctca tcctagtgta ccatctgttt 132240
tttgccaaga tgagctgaag ggtctgcagg aagaagggct tcataaccga gaccttgggt 132300
agatgtgcag gagggagttt cagagccagc attttctaac taccagaaaa agagaagtgc 132360
cctgtccaca accttccaca ttctgttgac cacaggaata aatgaacttt gtgatttttt 132420
ttcctgtcat taggtagggg gacaaaaatc ctcttaactc catgttcaga aatattctgg 132480
aaatttggtt tcttaagtca aattccacat cagaaacgat gggatgtggc ctggtagctt 132540
aagaacagca ggtacagaat aacttttttc tcctttgtct cagttttctt agctataaaa 132600
tgggggtaac agtcatctct tcctacctac cccaccaaac ttcgtgaaga acacactagc 132660
tacaggaaac ttggcaaaga gaaagagttt gacgctgtca tggcagaagc agtggctttc 132720
tcttattacg gtggctgcct ggcctttgaa ggcttatctt tccaggttta aactgagagc 132780
aagctgaagg gttatgactc gaagtgaggt aggattttgc caggcacact aggaggctgg 132840
gtatgcaagg tggttcattc agggagcctt ggctgacctt gacgcctgcg tccgtctctg 132900
atgctctgta ccaggtcagc tgtgtgtccc taacaaagaa tggcctccta actggggtct 132960
gcacatctgg gcatcttagt aaggggaaca gatttgaggt tcttctttct ttcagcgaaa 133020
ggtgagactt cgggttgaag aactggtaac tgtgatttgc aggcttgtcc atggctcctc 133080
agagctggca cttggggtgc tccttgtcca ccccttccct ccctaggccc acatggggca 133140
ccctgagctt gcctgagccc tactgtgatc tcacggaggg caggctatga actagaaagt 133200
gatgccacac cctggcaact agagaagtgc ccatccaggg gcatgtccca taggtatctg 133260
cctgtatgga ccctagttac ccactgacaa aaagaggggc acaaccctcc cctgtagaac 133320

-continued

```
tgtagcgcag agtgaggaca tgacgacagt gaggcctggg gccacccgct ccaccctcag 133380
gggcttgtaa gaatcccaag gaaagtcatg cctcctgcag gtgtgtcgag gcacagggca 133440
gagccctccc acttcccgcc cctgcacagc agtgtcattc ctcctatgac tacagtgctt 133500
tgaggacagg aagaactttc ggttcttggg aagcccgggg cagaaggggc ctgagctgct 133560
caccgcgtcc atccctcagg acaacctcga catcgccggt gatccagcgg tagcagggga 133620
actcgatgta gtccccgtgg ggcgtcttca gcgtgatgta cttcaggtac cagtcgtcat 133680
tcagccagta cttgcgcttc tcgattctga ccagctggat ctcgcccagt tcctcgtcca 133740
cagtcacgtc gtatgaatcc acctgggaag gagaacaggc aatcaggcca tgcgtggtct 133800
cctgagcctt tgttctggag gtgttaagaa tttgtcaccc caaggtatgc tgctgtggca 133860
cagggactac gttgaatgaa aagcacttaa aaaaacagca ggtgcaagat actctgacat 133920
tcgtgctgtt tcttagaagc aggagatgaa agtcccctat gaaagatgtc ctcactatac 133980
caaaaggaaa gtaacactct tttcatcaag gttgggaagt tgaagccaaa ggaaatccat 134040
acaaacagat cttgtacaat gaacgcttac ctcccgagtc acttccctgc ccagttacct 134100
gccctagccc aagccccttg gccttatcac atctcacgat gattcattca atgcagtatc 134160
taagggggat tgactctaac tgcttcttgg ggtcttcatc tttttaagag ggctcccatg 134220
ccacgtacaa cttgtattaa agaaatctgt aggctttcgc ccatgaatct gtcttatgcc 134280
gattctcaga cctagctgaa atgggaagag gtggagtttt gcctccacta cagttcatgg 134340
agccaagatt cttcatgaac accttaaatg aactcctgaa ttcatttacc caagacattc 134400
actgaaggcc tgcccctgac aaggctcagt gctacgaccc aggcaggtga aagaaatgga 134460
caaatcctgg gccctgccct tgaggagaga gaatccagtg agccaggatg gtgctgtgct 134520
gctcagaggg caacgcctgc tgactgcact tagctcaggc tggaggatgg ggagatgccc 134580
aggctcatgc ctgcacctgc gaggctgtgc ccagtgaggg tccgcagctg cccccacatg 134640
ggatagcctt gtgggagacc tttacaactg gagatgggct tgctgacagt ggatccccac 134700
aatgactctg ggagtgcagg ggagttacca cccccttccac agatgaagac agcgaggctc 134760
agtgactccc acctctgcca cttgccagca gagctggagt cacaccccag gtctttccat 134820
catagccact tcctctcttt ccagttttca gtggggataa taagtgagtg aaaatggtga 134880
ggcttagata cagggagctt gcatggattc gagtcgtcct gggacatttg cagttcacag 134940
ctgcatggtg atgcccagag aacagtgaga ccaagcagct ctgctgcacc tgtggcatta 135000
ctggtggcag ggtgaggcta gccttgcagc tagaaggcac caccccaggc tgtgtacagc 135060
gcagctgccc aggcctctgg gacaaggctg cttggccccc tccctgccag gctcctgctt 135120
ccaggacaca ggcggctctg aggcaacagc catagcttct ggagggcttt tgtctctgca 135180
gcaatggatg gcagacagga agttgggatg agaggctcag gcattgcatc acgcattctg 135240
atgaccagca ggtttggaaa gccccggact cgatgccctc caaggcatgt tcttttttat 135300
tttgaggtgg agtctcactg tgttgctcag gctggagtgc agtggctcga tctcggctca 135360
ctgcaacctc cacttccagg gttcaagtga ttctcctgcc tcagtctccc aagtagctgg 135420
gactacaggc acctgccacc acatctggtt aagttttgta ttttcagtag agacagggtt 135480
tcaccatgtt ggccaggctg gtctcaaact cctgacctca agtgatccac ctgcctcggt 135540
ctcccaaagt gctgggatta caggcatgag ccactgtgcc tggcccctgc aaggcacttt 135600
ctaagccaga ttcatcaacc cttgaacttt atccctggcg gcagaaccta gagttctcag 135660
```

-continued

```
catgatggca aagtggaagg ggcgaggggt atcatccttt gtgcgagcgc aggcatcccc 135720
attccatgcc ctgcctccaa gctgccagga ggacccctgg agggcttcct aagaggaatg 135780
ggaacttgag tgttttccac aaacctcctg gctctgaata ccgtgagcag tttggggtgg 135840
ctgacgctga ggccagacgc ttgtggtcag aaagcggaag cttcctccct gtgctctgta 135900
gtctaggcca gaggccctag gaacagtttc tgatgacaga ggagccaggc ccatgtggtg 135960
ggatgacatg tcttgggtcc agccacatgt ggaccagcct cggccccacg acaatgcccc 136020
tcctgcaggg agagtatcag cctcatctgc cacctctgag aaagccttcc tgccacagct 136080
tgtcctcagg agagcagggc cacacacaag gcctcgccca tcatggacag ggtgggcagg 136140
ttctgatggg acaggagtct cagcatctca ggggctcggg cccatctgga ggagcagagt 136200
gggggctgag tggcccagga ctggatacgc gtcgggcctg ccccacgcca ggccctgcat 136260
gccacaggga tttacagagg ccttagctgc aggttgtgag ccaagacaga gattcctgat 136320
cccaccgagg agtggggaga gggcagtgag gggtagaagg ctcggtgggc cctggggtct 136380
ggagctctga attcacatcc cagcttcagg caagtagctg gatggcctgg gcacattgct 136440
tcattctctg aagctgtttc ttcatctacc caaaggagat acccctcact tgcaggacca 136500
ttgagaaaat gaaatgacac catcctgggt ggcctccttt ctccagaggc acaggccacc 136560
ggttgtgtgc atcagaacca ccagtgcccc ttcctgaatc caggggggttg cagggcacca 136620
ggccccacac cgcctgtgag ctagcatggg cccctgcgtc acggccactt cgtgactaca 136680
tgtgccaatc cgagtaactg gagcacacat gggaggagga aactgaacct gtgacctcaa 136740
actccttcac tcaaagccca gaaggaactc ctgaaaggct ggagacaggg ctgtgaggac 136800
agagggagag tgggaggcat tctgaatgct ggtggggcag gcagagcaag tctgtgtgcg 136860
gtgaggactg aggggcggcc accagaggcc cgggcctggt ctgagtgtgg ctgctgcagg 136920
ggaagtagct ttcctatggc tctgaggggc tggagaggga ggaaggtgtc cccaggggat 136980
agatgacagg aaagctgggg tggggtggga ggagctaaca gggacactct catgggaggg 137040
aggctcccag taccttggac taagagggga gggagatggg ctgaggaggc attccaggac 137100
tgggcaggtc ccacagggag ggcccgatgt ctacctgggg gtgacgaccc acacgaagag 137160
actgagcagc ttctctgagg gagtggacag tggggtgacc ctccagcaca cctgtggtgc 137220
agtcacaggg gactgggaca ctcctggccc cctgccctac ctacacctgc aggcacctgg 137280
tggagagccc ctgagtttca cttggggtga aatcactagg cagatttaca aggactccat 137340
ctgccatctg acagggactt ccacagcagg agggggccag gcctgcagtc tggctggtct 137400
atggccagcc cagccacttt cctggtgctg gcttcaagcc tgaatatgat aagaggtgaa 137460
caaggggcag agggctccag ccttgaccca actcagggag taaaagacaa agcttgatgg 137520
ctgtggttct aacatcccag gggccactaa tggaagaatg acagataaag gcctccttcc 137580
aggaaaatac cagggtcaca tgtgtcaaac tgcaaaatat cttcggaagg tttgtggaac 137640
tacaatggcc accttcctcc ctcctctctg ggccaagtac actgggctga tgctatattt 137700
gtctatttgc tgtgacacat taaattctca ggtgacacac tgaattatgg tgggcactat 137760
caacagtgga caccccccaa caggccctca ggaagcactg ggcctgggaa tggccgagcg 137820
agtgattatc ctgctttaca gatagaaact gaggctcaga gagcaatggt ggcctcaaga 137880
tcagaaccta cacctgtgtg atggccaagc ccaggttcct cccacagttc cccaaggcca 137940
catcttgaga aaagccctga accggaagct agaaggccca gctttgagcc ctggtttgta 138000
ccctggatgg agtgtaaagg ggcaatgtgg agtggcatgg aaggacaggg aaaagcttca 138060
```

-continued taagagggta tttcaggcag cttttagggg ctgatcagat ttcagagggc agatgagtag 138120
gaggatgggc atgggtagca catttcagat gtggggaact gggagggcag ggtccccggg 138180
ggattcacac gtgggaggag gaaggctgga cacagtttct ggggacagaa gtgggtggcg 138240
tggtggtgca gatgctggag agaaacaagg gaaacctgca actcaccggc ctcatttcac 138300
aaggggccac tttgctgatt ttgcttgttg cttttaactt tttattggat atgtagtttt 138360
aaagcttttg aatatttcgg caaagagtca gttggtcagt tttcatgtga gctttctatc 138420
agcattttag gaaagttttc atctgtcttt catcagatct ctgctgttgc tgggacaggg 138480
agacggatct ctctgcggaa gcaaggatgt gtgccccacc cccagactac ccatcttgga 138540
gggggactaa tgaggggctg tgggaggagg aagctgtaga gcagagagga agattggggg 138600
ccagacaaaa cagagactcg ggatgagaga gggggaggct atggggaaga gctgaggaaa 138660
acaagggacg gagagaggga ttggggtagt ggatagggag accaaggggc agagaagggg 138720
gaaaatgtgg gacagagagc cggagattga gggagcagag aaggggcctc tgagaggtgg 138780
ctggaagaca gagtgtagag gaaaattcag agcaaaaaag aagggagagt tgtagggtag 138840
agagcagaaa cggggggcat ttagggaact gggagcaggg gaaggaagag gaggcagaag 138900
agggggcaga atgtagggaa aagatggctc agagggggag actgggagat gagagacgga 138960
ttgagggtca taccaaagaa atatttatgc tccactaata tattcccatt cacaagaagg 139020
aggtattcta gaattaattt ttcatgaatg taagaatact cactgactta agaagcatga 139080
atcattataa cacttttcta cacttgttga acatattcaa gtatcatata ttaaacacca 139140
cgctattgcc cttagctttc ttaaaagtac cagcacagaa tgaaatgggc caactaagat 139200
ttctcagaaa tcttcagatc tgttacagtt atcgtatccg atctgaatta ctttaaattt 139260
acagagttaa agaaataaat caacttgtta aatttgccta gacttgggtt agcctctgga 139320
aacagggcca ttctgtgtag gatcccggct ttctccagca gacagtgagg agccaaggaa 139380
gacacaaccg tttataggat aatcccacct gcgaaggact tgattcccag tcctgactga 139440
atcactatgc ggaactctga tgagaataac aagggacctg tgactcactt tatcaaggaa 139500
aaaatcagtc ctgtccatta tttgactgaa ctatgccctg gaggaggggg gtgttgacct 139560
gccaataact tggaaatgat taaattgtgt ggaaatacct ttattgttat tgttatcgtt 139620
actactgtta acaatacaga ttttaacact tttccctgta aaatgggata accttgtctt 139680
ctcagcaagt acttcctcta gggtttctct tttaccttta cccaaaaagg atgattgtct 139740
ttacagatac caagctggga gaatgaggaa gtagttctgg gctgggcaag agaaagtgtt 139800
gagtaacttt gcatcaacag gaactttctc aaaagctgat tttttcaagg aaactttcag 139860
ccttagctgg ttccccaccc tgcggtagcc cccaccccca accaccccccc gccccacccc 139920
tgacttatag ccctctcaac ccaatggaaa tgtgacatgc aaatctctcc tgaaatttgc 139980
ccctgggatt ccggctgagg tgtttaatta taatgtcatt tgaatgactt ctcagggtag 140040
gggaagacag accgagagag ggagatagtg gacaaaacag tgccttcact ctttgtccga 140100
agagcccgct atggccacgt tatcatgtcc cctgcaggag gaaagcacac acggggtgcc 140160
cgtgctgtgc agtgtgagca caccaatggc ctgtgcttct agaaccttat gatgtgtgga 140220
ggagaatggg gaggaggaag cacttacaaa ggggaagtag cctgtaccct gtccttctcc 140280
cccaggtgtg gggaatccat gaaataatgg aagtaaatga aggtgcgtca gaaatggcag 140340
agggtgccat caccctaaat ggacgacaca ttaactccag ggcaccgcag tcctcagggt 140400

-continued

```
cagttccccg actggggcaa ctaagcaact gaaggttgct cttgtactca acacctaact 140460
cttcttgaag ggagctcaag ccaggatgct agtgaacttg gctgagggcc atgtcgtgct 140520
acagcgaggg tatgggctcc tggataggaa tcgagcccat ggagagcttg gaatccagaa 140580
aaagagtagt ttttacttac tttaggctct gcacacctaa aacacaaatt ttatccaaga 140640
gtaatcagtt gaaacatgaa cttgccggtt gtatttgtcc attatgagca atttcacaag 140700
gtttgatcaa ataataaact aaatggtgag aaggcagctt ggtaaagtct aaatcttttt 140760
ggtccagtta ggagctgggg tggggtggaa gggaactgat attccctgcg cacctgcagt 140820
atgtctggga ctattaccag tcatttacgg agcgcttcct ctgtgccagg tactggatta 140880
ggcacttcat taaaggctca gtgagaactg cgacctgccc atgctcatgg aaaagagtcg 140940
tggggctgga attcaggtcc agatcagcat taggaactag cttccaaatg ctgagggctc 141000
cctcgcgtcc tcacacctag cgtggaagtg ttccctggtg tacattctgc tgggagggag 141060
tgcagcccct ccatttagga aaagcctctc ctggcctggg ttctgttcct tccctttaat 141120
ttcctctggg gactgtcctg agaatgtaag ctgcccaggt gccgtctgag ccaccagatg 141180
ggcctgggct cacccatgac tcatggacca gactgaagcc aaccctccat tttcagctgg 141240
ggaaactgag gcccagacag acggtagagt gagctggtgg tcatgtctgg acagaactca 141300
ggcctctgga cccgctgacg tgcacccttc cccacggctc acagctggct gctccgaggt 141360
gccctcagag ttctgtgagc atgactcatc tgcctctccc tccctgtgcg acctgcagaa 141420
ggagcctaag gaagaggtgg cacaagaaac gcggcccagt gaagggggct ccggagcctc 141480
ggagcccaga tcttgaagtg gaggggaaac cttgggcctt ctcctcccag ggaagacgcc 141540
ttgcaggcgg cacgcgggaa gtctccgttt ccgacagggg tcgcggccgc cgcgaggggt 141600
cctggacgct tgcccaccag ggtacccacc ggccactggg agcccagggc acgccccacc 141660
gcagttctgc cctccctgac agggtcctgg acaccccccag tcctgtccgg gccgccccga 141720
cgggccctcg gcgcccccgc ccaggcctct gccgtccaaa ccgggtcccg gacgcacctc 141780
agcccgcgct ccacccgtgc cccgcccgcg ctcaccgcgc cacgctcgaa gtcgttgtag 141840
aagggcttgt ccagcaggtg cttctcgctg cagcccgccg agcccacgag gctgaggtag 141900
atgtagtcgt cagtgtcttc accacggggt gaagtacggt ccnnnnnnnn nnnnnnnnnn 141960
nnnnnnnnnn nnnnnnnnnn nnnnnnnnnn nnnnnnnnnn nnnnnnnnnn nnnnnnnnnn 142020
nnnnnnnnnn nnnnnnnnnn nntttttggg ttgttgttgt ctctttgttt ttgcgagcgg 142080
tccttccgcc ccgtggtgaa gacaagtggg cgcctctgcc tggccatccc atctgggagg 142140
tgaggagtgc ctctgcccgg ccaccccgtc tgggaagtga ggagcgtgtc tacccagcca 142200
ccacgtctgg gaggtgagga gcgcttctgc ctggccgccc catctgggaa gtgaggagcg 142260
cctctatctg gccacccctt ctgggaagtg aggagtgcct ctgcccggcc gccaccccgc 142320
ctcggaggcg aggagcacct ctgcccggcc accaccccat ctgagaggca aggaccacct 142380
ctgcctggcc gccatcctgt ctgggaggcg aggagcacct ctgcccagcc gccgccccac 142440
ctaggaggtg aggagcgcct ctggccagcc gccccacctg ggaggcgagg agcgcctctg 142500
cctggccgcc ccatctggga ggtgaggagc gcctctgccc agccaccacc ccatctggga 142560
agtgaggagc gtctctgcca ggccgccccg tctgggaagt gtacccaaca gctccgaaga 142620
gacagcgacc attgagaacg ggccatgatg acgatggcgg ttttgtcaaa aagaaaaggg 142680
ggaaatgtgg ggaaaagaaa gagagatcag attgttactg tgtctgtgta gaaagaaggt 142740
gacataggag acaccatttt gttctgtact aagaaaaatt cttctgcctt gggatgctgt 142800
```

-continued taatgtacaa ccttacccccc aaccccgtgc tcgctgaaac atgtgctgtg tcaactcagg 142860
gttaaatgga ttaagggtgg tgcaagatgt gctttgttaa acagatgctt gaaggcagca 142920
cgctcattaa gagtcatcac cactccctaa tctcaagtac ccagggacac aaacactgct 142980
gaaggctgca gggacctctg cctaggaaaa ccagagacct ttgttcacct gtttatctgc 143040
tgaccttctc tccactatta tactatgact ctgccacatc cccctctctg agaaacaccc 143100
aagaatgatc aataaatact aaaaaaacaa attaattaat taaataaatt tcatatggaa 143160
ccaaaaaaga gcctgcattg ccaagtcaat cttaagccaa aggaacaaag ctggaggcat 143220
cacactacct gacttcaaac tatactacaa ggctacagta accaaaacag cacggtactg 143280
gtaccaaaac agaggtatag accaatggaa cagaacagag ccttcagtaa taatgccaca 143340
tatgtacaac tatctgatct ttgacaaacc tgacaaaaac aagaaatggg gaaaggattc 143400
cctatttcat aaatggtgtt gggaaaactg gctagccaat aaatggtgta gggaaaactg 143460
gctagccata tgtagaaagc tgaaactgga tcccttcctt acatcttata caaaaattaa 143520
ttcaagatgg attaaagact tacatgttag acctaaaacc ataaaaaccc tagaagaaaa 143580
cctaggcaat accattcagg acataggcat gggcaaggac ttcatgccta aaacaccaaa 143640
agcaatggca atgaaagcca aaattgacaa atgggatcta attaaactaa agagcttctg 143700
cacagcaaaa gaaactacca tcagagtgaa caggcaaccc acagaatggg agaaaatttt 143760
tgcaatctac tcatctgaca aagggctaat atccagactc tacaatgaac tcaaacaaat 143820
ttacaagaaa aaaacaaaca accccatcaa aatgtgggcc aaggaaaaga acagacactt 143880
ctcaaaagaa ggcatttatg cagccaaaag acacatgaaa aatgctcat catcactggc 143940
catcagagaa atgcaaatca aaaccacaat gagataccat ctcacaccag ttagaatggt 144000
gatcgttaaa aagtcaggaa acaacaggtg ctggagagga tatggagaaa taggaatact 144060
tttacactgt tggtgggact gtaaactagt tcaaccattg tggaagtcag tgtggcgatt 144120
cctcagggat ctagaactag aaataccatt tgacccagca atcccattac tgggtatata 144180
cccaaagtat tataaatcat gctgctataa agacacatgc acacatatgt ttattgtggc 144240
actattcaca agagcaaaga cttggaacca acccaaatgt ccaacaatga tagactggat 144300
taagaaaatg tggcacttat acaccatgga ataccaagca gccataaaaa atgatgagtt 144360
catgtccttt gtagggacat ggatgaagct agaaaccatc attctcagca aactattgca 144420
aggacaaaaa accaaacact gcatgttctc actcataggt gggaattgaa caatgagaac 144480
acatggacac aggaagggga acatcacaca ctggagcctg ctgtggggtg gggggttggg 144540
ggagggatag cattaggaga tatacctaat gctaaatgac gagttaatgg gtgcagcaca 144600
ccaacatggc acatgtatac atatgtaact aacctgcatg ttgtgcacat gtaccctaaa 144660
acctaaagta taataataaa aaaataagct tataaaatgc ttttaatgct atataacttt 144720
ataactctga aagaataata gatttgtatt atgctgtcag tgagtaggtc tattaagtga 144780
taacattaaa cacaaatacc accatttata aagtatgatt ttgatatcat cggttgtgta 144840
ttttcacccc aaactctgta gatagtaact ttgttttctc atttgaccat gctcaatctt 144900
tagagaccat gctcttctct caaaatgact gtaggttcat ccaagtatgt ttgctaccca 144960
aaatcaatga aacacagtca caactatgtc tgtctaggaa taaagccagc taattagatt 145020
cttattctaa ggaacaagaa gagggcaggt aagaatttga ttatggcaga attctgacca 145080
taatcaataa ctgttttcta ttttttctcc atgttgtcgg gtggttcata cctgactttc 145140

-continued

```
atcatttcca atgattcctg tttgttttgt ttataaattt caaaatcatc atgaaaagtt 145200
tcactgaatg aaaacctgaa aattgggaaa taaacatttt tctgcaaaaa aaaaaaaaca 145260
atgaacactg acttctccta tttctcaaag tcatctcaaa gccatatgag gattaccaca 145320
aacttgcagg tgagaaaatt ctttgcaatg taagaagtgc catgcaaatt agttgatgct 145380
attataatta gtctcaggga tcaaaaatgc ttgaacccta aatctaacac ttcaaaggaa 145440
agcattattt ttcattcatt ttacaagtta cacctccctt cttccccaca tctttgttta 145500
gaatctggac cctgaagtta gaggaccaag attcaaatcc cagcctcatc agtactagct 145560
atgtgatatt gggaatgtta cttgatccct gcttatctta ctttctgcat ttattaaatg 145620
gggatgagaa taatatctac ccaaataagg tgcccaatgc agtgcccaac agcatgaagc 145680
ccaataaagg ttagttaaca tcacatccat aattgacacc tttaggtatt agattttcat 145740
catcccagaa cattttcctt ctttaagcct ttttctttct aagtggcact ttcttggata 145800
ctgattgcac tcctcacaaa cttgaaacgt tcaaacacac aagatgccat ttaggagaca 145860
ttggaacttg ggtttccttc tctgtaaaac tgagtaatga cagtcacctc ccagggctgt 145920
tgtaagaatg aatgagctag agtatgtaaa atatcttagc acagagtgct taagaaatta 145980
ttagttccag ccaagcgtgg tggctcacgc ctgtaatccc agcacttagg gaggccaagg 146040
caggcggctc atctggggtc aggagttcaa gaccacctgg tcaacatggt gaaaccccgt 146100
ctctactaaa aatacaaaaa ttagccaggc gtggtggcat gtgcatgtaa tcccagctac 146160
tcaggaggct gagacaggag aatcacttga acccaggagg tggaggttgc agtgagccga 146220
gatcgtgcca ttgcactcca gcctgggcaa caagagtgaa actctgtctc aaaaaaaaaa 146280
aaaaaaaaaa gaagaagaag aagaaagaag gaaagaaaga gagagagaga aagaaagaaa 146340
gaaagaaaga aagaaagaaa gaaagaaaga aaaagaaaga aagaaaagaa agaaagaagg 146400
aaagagacag aaagaaagaa gggaagaaag aaagaaagaa agaaagaaag aaagaaagaa 146460
agaaagaaag aaagaaagaa gggaagaaag aaagaaagaa agaaaaaaag aaagaaagaa 146520
agaaaaagaa agaaagagag aaagagaaag aaagaaagaa agaaaggaga gacagaacga 146580
aggaaagaag gaaggaatta tttccctttt tcccacccac gcctcaccac aaaccttgtt 146640
gtggggataa catgtaaaag tgaacaaaac tgagaagatc acatcgcata tgcactcagc 146700
ctctagtggg agacacaggc aataaacagg aaaagttaaa aacagtacta ggtagtggtg 146760
agtgcaatta gcctcccgca gcataaaggg aggagaataa ccagtggctc tttcatgcag 146820
agaatcaggg tagacctctg gggagagacc cgcactcaga ctgggatgga attatttatt 146880
ttatgcgtgt tcagttagga gtagaggtgc tctgtcgtga ttatctaatc ttgggaggaa 146940
caatgtcaga cgggtttcaa gatgagtatg agaattggtc ttccttctga aaaaacaaga 147000
attgagttca cactaatcac aaatacatca agcctatttg agtcttgtgt gtgtcatgga 147060
ttgaagtgta tctttccact tagtcaagaa gttccaatga gaagaatgct ccttaacttc 147120
ctaagtgcaa cagagtagtt gaactgagcc atggatggta aatctactta agaaagcaca 147180
tgccatggaa agatagcatt ggctgccctg cctacttctg atggcacagc cttgcaggaa 147240
gggaaagaag ccaagaggca aaagcctggt cttgttctga aaggcacaag gaggtggaag 147300
attaggggaa actcacccaa aaatgactca gctctgaact cagactcaag aagccacaat 147360
aagcaacatg aatggaactg gagggaaata aaccaggcgt agaaacacaa atgttgcata 147420
ttcttactca tgtgggaact aaaaacatgc atttcaagga gaatagaatg atggttatca 147480
gagactggga acagttgtgg gtgggggtgt taagagaggt tgcttaatgg gtacaaacat 147540
```

-continued atagttagat agaaggtata agttctaatg tttgacagca gagtaggaga actatagtta 147600
acagtaatat attgtatact ccaaaatagc tagacaggaa gatttgaaat gttcccaaca 147660
catagaaatg acaaaagctt gaggtaatgg ataccctaaa tatcctgact tgatcattac 147720
acagtctatg cgtgtaacga aataccatat gtaccccata aatatgtaca aatattatgt 147780
atcaataaaa atttttaaaa agaagctgca atcaacattt catcattatc ttttcagcag 147840
catccttaca aagttacaga gacatcttaa gatgtatccc tcttcctctg aatcttcctg 147900
ggatagaaca aatgaaaact aaacaaggag tgggctggga ggagctgtca acatccatcc 147960
taaggaaaag tctgttaggg ctatgagctt cctctgtcct agagtagagc tgggaaaata 148020
gagtcttgac aattgatttc ttattctttc tttctctaaa tccccaatga atatgttttt 148080
ctttttagtg ctcagtggta gacagggctt aattctgttt agttatgcaa acaggccaga 148140
agaaactgaa ataggctata aatgtttgaa gctggccaaa agaagatgta gtcacacaag 148200
ataccctctg gaggaaagtg actgtcagga aagtcacttt cctgaccagc aaaaggacca 148260
gcactatttt gtcctgctga agaagtacat ttgtcctgct gctgtcatgg ggacagtggc 148320
tccagggctt cctgtggaca tgccacaagt tccactccat gagtcaggag atcatgcggt 148380
cagctggggg gaacttaggg ttgctctctt gagcttagcc ttatgctgcg tgtctgcttt 148440
gccaaccaca aaaacgatag tttcatagca agttgcaggc tccctggaaa cttaacctac 148500
ctactaggat acatttacag ctgcttttct cctggcatca ggctggagat caagaaatac 148560
ataaaacata gtccctgccc tcagttagct cagaatatgg tgggggaatg gagacagaag 148620
caaatactgg tgggacaagt gacgatgggc caaaatatgg gcttaaacaa aggttgtggg 148680
agctcagaaa aggagcaact cactctgcct gaaagagtca tggagggctc cacggaaaaa 148740
gcaacatttg tgcaggagga gattagaaca cagaggagaa ggatagcagc actccagatg 148800
aagggaagga aatgtgccaa gatttcatgg gaatgagaag atgtaaactg ctcaggaaaa 148860
accatggttg aagctcttca cagtggctga agcatggtgt gattgtcagt tttgcttgtc 148920
aacttggtca ggctgtagta ctcaactatt caaccaagca ctgatctagg tattgctgtg 148980
aaggtatttt gtagtcgcaa ttaacctcta caatcagttg actctattta aaggacatta 149040
ttctgtacta tctgagtgga cctgatccac ttcatcccaa aggtaaatga ttctccaaca 149100
gtgttctcat ctacatctag ggcttggaag atgaaggtga aggagaatat ggaaaaacaa 149160
caagaaaaaa gtcaatcaat cagaacttcc agccctgtgt ttgttagttc actttatgtt 149220
caaccagtat gtctccactt ttatctgctt ccttgtaaga tttcatctga aaaagggaat 149280
tcactcttca ggtgttggaa atcaattatg agagaagcac ttacagaatg actatctgaa 149340
gagctctgca gacattctcc agagtaaaac aaccataacc ggtgaaaatt aaaaacaaac 149400
aaaataaaaa aatgttagag tattggaaat tgttctaagg gccgacagca aatgaagaaa 149460
tccaagaaag cctaccaatt tcagtgagag gagtgagagt ctatggtgtt gagtctatgg 149520
tgtttaagtt ctgttcattt cctccctctc ctgcaatcag ttcagtgaaa cagaaaccct 149580
gctccagaga tgtgcagcca aaaagacagg gtgccctttc ccctcagctc ccaatctagg 149640
gcagactacc agcatttccc aagcccatct ctggctctat gttgcagaag ttctattcca 149700
agaaagtttg actgagaatc tgaagcttcc ttcttccact cagcctctac tattaaggcg 149760
taagttctat ccccagtgcc acgggccaag aatactgatg ctgaatgtcc ttgctccgct 149820
acactcatag ggcagagatt ccatgggagg agtgaagttt ccattccaga aaaggcagaa 149880

-continued aaacagaaat tactgcccaa tccagtaccc cacccataaa gaaggaaaga catctgagaa 149940
aagcatgaca ctgtccccaa aaccacctgc agagtagtgg cagtagaggc agtagggaga 150000
ctagaggacc tgcctagagg gagaagtagg ccataagaag aaaagtctct agttctccct 150060
aaagggacaa actttatttg caacagaaca tgcggaagtt caagcctaag ggcactgtca 150120
aaaacaatga atattttggt ggtaagcaat taataggtta atggcagctt agtgagagca 150180
acaaactaaa ccataaacca gctagacata tacaataaaa atccaagaaa gagagagcca 150240
agaagggcct tcctgaggtt aaaacaaaca tcaaagtctt gtctgaaaaa ctgctcctgc 150300
aaaggaagca aaatatattt ggatcagact gtggagcaat ttatgcccct aaaaagctgt 150360
caaaaccaaa agagcaatta tctagcaatt gctggaggtt aacagttggg tatgatacca 150420
aaagaggcaa acaactgaac agatcagaga aagaggcagt caaagagagc actgctaaat 150480
gcactgtaat tccaatttga gagaaaatgt gcccagtgct gtgactccct caggaacaac 150540
atcagaggcc acaaattatg gtggaaatag gcttcactat atagtctagc caggcaatta 150600
aacaaataaa caattaaaca acagtaacat agtgaggggg gcagaaatga gtattgcaac 150660
tagctagaac atatttttga acaaaaaaat tatgagtcaa gcagagatat ggaaaagaca 150720
gagccataca ccagaaaaaa ggtaagcaag agaaactgcc tttgtgagtg ccaagatgtc 150780
agacatagca gaaaaaaaac ctcaaagtaa ttattataaa tatgttcaaa aactaaaaga 150840
aaatgtgctt aaaaaataaa agatggtatg ataatttctt gtcaattcaa aaataccaat 150900
aatagattaa aaatattttt tcaaaagtta attaaccaaa tggaaattct ggggtttaaa 150960
agtaaaataa caacaataag aacattttgc tagaggaaat gaacaataga tttgtaccag 151020
aaggaaaaat aatcaaataa acagggattt catcaacacc aaacctgtct tacaagaaat 151080
actaaaggga gttcaatctg aaagaaagaa cattaacaag caacaggaaa tcatctgaag 151140
gtacaaaact cactgtacct tcagatgata ataagtcctc aaaaaacaca gaatattata 151200
acactgtaat tatggtgtgt aagctactta tatcataagt agaaagagga aaagatgaac 151260
tgattaaaaa acaattacaa cagcttttca agacagtata ataagatata taaataacag 151320
aaagcttaaa agcatataaa taaagttaaa atgtagaggt ttttttagtt ttctttttgc 151380
ttgattgtgt atttatttat gcaatcagtg ttgttttcat cagcataaaa taatgggtta 151440
taagatagta tttgcaagcc tcatagtaac ctcaaattta aaaacataca atgtatacac 151500
aaaaagtgaa gagcaagaaa ttaaaacata ccaccaaaaa aaatactttc actaaaaagg 151560
agacaggaag taagaaaaga tgggagagaa gatcacaaaa caaccagaaa ataaataaca 151620
aaatggcaag caagtcctta tttgtcaata ataatattga atgtaaatgg actatactct 151680
ccagtaaaaa gatacagagt ggttgaatgg attaaaaaaa aggacccaat gatctgttac 151740
ctacaagaaa taaacttcac ttataacaat acacagacta aaaataaagt catgggaaat 151800
gatacttcac gacaatggaa accaaaaaag aacaggagta gctatacctt tatcagacta 151860
aatagatttc aagacaaaaa ttgttaagaa aaaccaaata aggtcattat ataatgataa 151920
agagatcagt taagcaagag gatgtaacaa ttgtaaatat atatgcactc aacattggag 151980
cacctagata aataaaacaa atattattag agctaaagaa agatagaccc cctcccccaa 152040
aacaataata gctgtagatt tcaatgctcc actttcagca ttggacagat cttccagaca 152100
gaaaatcagc aaggaaacat cagatgtaat ctgaactata gaccaaatgg gcctaataag 152160
tatttacaga atatttcatc caaaggttac agaagacaca tttttctcct tagcacatac 152220
atcattctca agaacaggcc atatattagg tcatgaatca agtctcaaaa cattcaaaaa 152280

-continued aactgaaata atctcaagca tcttctttga ccacaatgga ataaaactag aaaccaataa 152340
caaggggaat tttggaaact atacaaaaac atggaaatta aacaatatgt tcctaaatga 152400
taagtgggtc aatgaagaaa ttatgaattg aattgaaaat tttctaaaaa caaatgacaa 152460
tggaaacata atgcaccaga acctatggga tacaacaaaa gcagtaccaa gagtgatatt 152520
tccagataag ggcctacatc aaaaaggaag aaaaacttca agtgaataac ctgatgatgc 152580
atcttaaaga attaaaaagg caagagtaaa ccaaacccaa aattagtaga agaaaagaac 152640
taataaagat cacagtagaa ataaataaaa ttggacttct gctccaagat ggcctaatag 152700
aaacagctcc agtctgcagc tcccagcatg attggcacag aagatgggtg atttctgcat 152760
ttccaactga ggtaccaggt tcatctcatt gggactggtt ggacaatgga tgcagcccat 152820
ggagggtgag gtgaagcagg gtgaggagtc acctcacccc ggaagcacaa gtgattgggg 152880
gatttccctt tcctagccaa gggaagccgt gacagactgt acctggaaaa tcggttcact 152940
cccacccaaa tactgtgctt ttcccatagt cttagcaacc ggcagaccag gagattctct 153000
cccaagccta gctcatcagg tcccatgccc acggagcctg gctcactgct agcacagcaa 153060
tctgagatca acctgcgagg ctgcagctgg gtgggggag gggtgtcagc cattgctgag 153120
gactgagtag gtaaacaaag tggccaggaa gctcaaactg ggcagagccc accgcagctc 153180
agcaaggcct actgcctcta tagattccac ctctgtgggc agggcataac tgaacaaaag 153240
gcagcagaca acttctgcag atttaaacgt ccctgcctga cagctctgaa gagagcagtg 153300
gttgccccag catggcatct gagctctgag aacagacaga ctgcctcctc aagtgggtcc 153360
ctaaactcca tgtagcctaa ctgggagaca tctccccata ggggccgaca gacacctcat 153420
acaggtgggt gccactctgg gacaaagctc tcagaggaag gatcaggaag caatatttgc 153480
tcttctgcaa tatttgctgt tctgcagcct ctgctggtga tacccaggca aacagagtct 153540
ggaatggacc tccagcaaac tccagcagac ctgcagctga gggacctgac tgctagaagg 153600
aaaactaaca aacaaaaagg aatagcatca acatcaacaa aaaggacatt cacaccaaaa 153660
cctcatctgt agtcaccaat atcaaagacc aaaggtagat aaaaccacaa agatggggag 153720
aaaccagagc agaaaagctg aaaattctaa aaactgagca ccgcttctcc tccagaggat 153780
tgcaactcct caccggcaac ggaatgaagc tgggtggaga atgactttga caagttggca 153840
gaagtaggct tcagaaggtc ggtaataaca aactactcca aactaaagga gcatgttcta 153900
acccattgca aggaagctaa aaaaccttca aaaaaggtta gacaaatggc taactagaat 153960
aaacagtgta gagaggaact taaatgacct gatggagctg aaaaccgtgg catgaggaca 154020
tcatgatgca tgcacaagct taaatagctg attaaatcaa gtggaagaaa gaatatcagt 154080
gactgaagat caaattaaca aaataaagca agaagataag attagagaaa aaagagtaaa 154140
aagaaatgaa aagcacctcc aagaaatatg ggactatgtg aaaaaaccaa atctacactt 154200
gattggtgta cctgaaagtg atggggagaa ggaaaccaag ttggaaaaca ctcttcagaa 154260
tactatccag gagaacttcc ccaaactagc aaggcaggcc aacattcaaa ttcaagaaat 154320
acagagaaca cccacaaagat attcctcaag aagagcaacc ccaagacaca taattgtcag 154380
cttcaccaag gttgaaatga aggaaaaaaa tgttaagggc agccagagag aaacgttggg 154440
ttaccaacaa agggaagccc atcagactaa aagtagctct ctcagcagac accctgtaag 154500
ccagaagaga gtaggggtca atattcaaca ttcttaaaga aaataatttt caacccagaa 154560
tttcatatcc agccaaacta agcttcataa gtgaaggaga aataaaatcc tttacagaca 154620

-continued agcaaatgct gagagatttt gtcaccatca ggcctgcctt acaagagctc ctgaaggaaa 154680
cactgaacat ggaaaggaac aactgttacc agccactgca aaaacacgcc acattgtaaa 154740
gaccatcgat gacatgaaga aactgcaaca attaactggc aaaataagca gctcacagca 154800
taatgacagg atcaagttca cacataacaa tattaacctt aaatgtaaat gggctaaatg 154860
cctcaattaa agacacagac tggcaaattg catagagtca agacccatca gtgtgcggta 154920
ttcaggagac ccatctcaca tgcaaagaca cacataggga tggaggaaga tccaccaagc 154980
aaatggaaag ccaaaaaaaa aaaaaaaaaa aaaaaaagca ggggttgcaa tcctagtctc 155040
tgataaaaca gagtttaaac caacaaagat ccaaagagac aaagaaagcc attacataat 155100
ggtaaaggga tcaatacaac aagaagaaca aactatccta aatatatatg caaccaatat 155160
gggagcaccc agattcataa agcaagtctg tagagacgta caaagagatg tagacttcca 155220
cacaataata atgggagact ttaacactcc actgtcaata ttagacagat caatgacaca 155280
gaagggtcac aaagatatcc aggacttgaa ttcagctatt caccaagtgg acctaataga 155340
catctacaga actctacacc ccaaatcaac agaatgtaca tacttctcag caccacatca 155400
tacttattct aaaattgacc acataattgg aagtaaaaca ctcctcagca aatgtaaaag 155460
aacagaaatc acaacaaact gtgtctcaga ctacagtgca aacaaattag aactctggat 155520
taataaactc actcaaaatc acacaactac atggaaactg aataacctgc tcctgaatga 155580
ctactgggta cataatgaaa tgaaggcaga aataaagatg ttctttgcaa ccaataagaa 155640
caaagacaca acataccaga ttctccggga cacatttaaa gcagtgtgta cagggaaaat 155700
tatagcacta aatgcccaca agagaaagca ggaaagaact aaaatcaaca acctaacatc 155760
gcaattaaaa gaactagaga agcaagagca aacacattca aaagctagca gaaggcaaga 155820
aataactaag atcagaacag aactgaagga gatagagaca caaaaagcac ttcaaaaaaa 155880
tcaatgaatc caggagctgg tttttaaaaa gatcaacaaa attaatagac cgctagcaag 155940
aataataaag aaaagagaga agaatcaaat tagactcaat aaaaaaagat aaaggggata 156000
tcaccactga tcccatagaa atacaaacta ccatcagaga atactataaa cacctctaca 156060
taaataaact agaaaatcta gaagaagggg gaggagccaa gatggccaaa taggaacagc 156120
tccagtctac agctcccagc gtgagtgaca cagaagacgg gtgatttctg catttccatc 156180
tgaggtaccg ggttcatctc actagggagt gccagacagt gggcacaggt cagtgggtgc 156240
gcgcactgtg tgcgagccaa tgcagggtga ggcgttgcct cactcgggat gtgcaagggg 156300
tcagagagtt ccctttccta gtcaaagaaa ggggtgacag atggcacctg gaaattcggg 156360
tcactcccac ctgaatactg cacttttcca acgggcttaa aaaacggcgc acctggagag 156420
tatatcccgc acctggcttg gagggtccta tgcccacgga gtcttgctga ttgctagcac 156480
agcagtctga gatcaaactg caaggcagcg gcgaggctgg gggaggggcg cctgccattg 156540
cccaggcttg cttaggtaaa caaagcagct gggaacctca aactgggtgg atcccaccac 156600
agctcaagga ggcctgcctg cctctgtagg ctccacctct gggggcaggg cacaggcaaa 156660
caaaaagaca gcagtaacca ctgcagactt aaatgtccct gtctgacagc tttgaagaga 156720
gcagtggttc tcccagcacg cagctggaga tctgagaacg ggcagactgc ctcctcaagt 156780
gggtccctga cccctgaccc ccgagcagcc taactgggag gcatccccga gcagaggcag 156840
actgacacct cacacagccg ggtactccaa cagacctgca gctgagggtc ctgtctgtta 156900
gaaggaaaac taacaaacag aaggacatcc acaccaaaaa cccatctgta catcaccatc 156960
atcaaagacc aaaagtagat aaaaccacaa agatggggaa aaaacagagc agaaaaacta 157020

-continued gaaactctaa aaggcaaagc gcctctcctc ctccaaagga atgcagttcc tcaccaggaa 157080
tggaacaaag ctggacggag aatgactttg acgagctgag agaagaaggc ttcagatgat 157140
caaattactc cgaactacgg gaggacattc aaaccaaagg caaagaagtt gaaaacgttc 157200
aaaaaattta gaagaatgta taactagaat aaccaataca gagaagtgct taaaggagct 157260
gatggagctg aaaaccaagg ctcgagaact acgtgaagac tcaggagccg atgcgatcaa 157320
ctggaagaaa gggtatcagc gatggaagat gaaatgaatg aaatgaagtg agaaggaaag 157380
tttagagaaa aaagaataaa aagaaatgaa caaagcctcc aagaaatatg ggactatgtg 157440
aaaagaccaa atctacatct gattggcgta cctgaaagtg acggggagaa tggaaccaag 157500
ttggaaaaca ctctgcagga tattatccag gagaacttcc ccaatctagc aaggcaggcc 157560
aacattcaga ttcaggaaat acagagaacg ccacaaagat actcctcgag aagagcaaca 157620
ccaagacaca taattgtcag attcaccaaa gttgaaatga agggaacaat gttaagggca 157680
gccagagaga aaggtcgggt taccctcaaa gggaagccca tcagactaac agcggatctc 157740
tcggcagaaa ctctacaagc cagaagagag tggtggccaa tattcaacat tcttaaggaa 157800
aagaattttc aaaccagaat ttcatataca gccaaactaa gcttcataag tgaaggagaa 157860
ataaaatcct ttacagacaa gcaaatgctg agaaattttg tcaccaccag gcctgcccta 157920
aaagagctcc tgaaggaagt gctaaacatg gaaaggaaca accggtacca gccgctgcaa 157980
aatcatgcca aaatgtaaag accatcgagg ctaggaagaa actgcatcaa ctaacgagca 158040
aaacaacctg ctaacatcat aatgacagga tcaaattcac acataacaat attaacttta 158100
catgtaaatg gactaaatgc tgcaattaaa agacacagac tggcaaattg cataaagatt 158160
caagacccat cagtgtgctg tattcaggaa acccatctca cgggcagaga cacacatagg 158220
ctcaaaataa agggatggag gaagacctac caagcaaatg gaaaacaaaa aaaaggcagg 158280
ggttgcaatc ctagtctctg ataaaacaga ctttaaacca acacagatca aaagagacaa 158340
agaaggccat tacttaatgg taaagggatc aattcaacaa gaagagctaa caatcctaaa 158400
tatatatgca cccaatacag gagcacccag attcataaag caagtcctga gtgacctaca 158460
aagagactta gactaccaca cattaataat gggaaacttt aacaccccac tgtcaacatt 158520
agacagatca acaagacaga aagtcaacaa ggatacccag gaattgaact cagctctgca 158580
ccaagcagac ctaatagaca tctacagaac tctccacccc aaatcaacag aatatacatt 158640
tttttcagca ccacaccata cctatttcaa aattgaccac atacttggaa gtaaagctct 158700
cctcagcaaa tgtaaaagaa cagaaattat aacaaactgt ctctctaacc acagtgcaat 158760
caaactacaa ctcaggatga agaaactcac tcaaaactgc tcaactacat ggaaactgaa 158820
caacctgctc ctgaatgact actgggtaca caacgaaatg aaggcagaaa taaagatgtt 158880
ctttgaaacc aatgagaaca aagacacaac ataccagaaa ttctgggatg cattcaaagc 158940
agtgtgtaga gggaaatttg tagcactaaa tgcccacaag agaaagcagg aaagatccaa 159000
aattgacacc ctaacatcac aattaaaaga actagaaaag caagagcaaa cacattcaaa 159060
agctagcaga aggcaagaaa taactaaaat cagagcagaa ctgaaggaaa cagagacaaa 159120
aaaaaccctt caaaaattaa tgaatccagg agctggtttt ttgaaaggat caacaaaatt 159180
gatagaccgc tagcaagaat aataaagaaa aaaagagaga agaatcaaat agatgcaata 159240
aaaaatgata aaggggatat caccaccgat cccacagaaa taaaaactat catcagagaa 159300
tactacaaac acctctatgc aaataaacta gaaaatctag aagaaatgga taaattcctc 159360

-continued gacacataca ctctcccaag actaaaccag gaagaagttg aatctctgaa tagaccaata 159420
acaggagctg aaattgtggc aataatcaat agcttaccaa ccaaaaagag tccaggacca 159480
gatggattca cagccgaatt ttaccagagg tacaaggagg aactggtacc attccttctg 159540
aaactattcc aatcaataga aaaagaggga atcctcccta actcatttta tgaggccagc 159600
atcatcctga taccaaagcc gggcagagac aaaaccaaaa aagaggattt tagaccaata 159660
tccttgagga acattgatgc caaaatcctc aataaaatac tggcaaacca aatccagcag 159720
cacatcaaaa agcttatcca ccatgatcaa gtaggcttca tccctaggat gcaaggcttg 159780
ttcaacatat gcaaatcaat aaatgtaatc cagcatataa acagaaccaa agacaaaaac 159840
cacatgatta tctcaataga tgcagaaaag gcctttgaca aaattcaaca acacttcatg 159900
ttaaaaactc tcaataaatt aggtattgct gggacgtatc tcaaaataat aagagctatc 159960
tatgtcaaac ccacagccaa tatcatactg aatgggcaaa aactggaagc attccctttg 160020
aaaattggca caagacaggg atgccctctc tcaccactcc tattcaacat agtgctggaa 160080
gatctgtcca gggcaatcag gcaggagaag gaaataaagg gtattcaatt aggaaaagag 160140
gaagtcaaat tgtccctgtt tgcagatgac atgattttat atctagaaaa ccccattgtc 160200
tcagcccaaa acctccttaa gctgataagc aacttcagca aagtctcagg atacaaaatc 160260
aatgtacaaa aatcacaagc attcttatac accaacaaca gacaaacaga gagccaaatc 160320
atgagtgaac tcccattcac aattgcttca aagagaataa aatacctagg aatccacctt 160380
acaagggatg tgaagcacct cttcaaggag aactacaaac cactgctcaa cgaaataaaa 160440
gaggatacaa acaaatggaa gaacattcca tgctcatggg taggaagaat caatattgtg 160500
aaaatggcca tactgcccaa ggtaatttac agattcaatg ccatccccat caagctacca 160560
attactttct tcacataatt ggaaaaaact actttaaagt tcatatggaa ccaaaaaaga 160620
gcccgcatca ccaagtcaat cctgagccaa aagaacaagg ctggaggcat cacactacct 160680
gacttcaagc tatactacaa ggctacagta accaaaacag cttggtactg ttaccaaaac 160740
agagatatag atcaatggaa cagaacagag ccctcagaaa taatgctgca tatcgacaac 160800
tgtctgatct ttgacaaacc tgagaaaaac aagaaatggg gaaaggattc cctatttaat 160860
aaatggtgct gggaaaactg gctagccata tgtagaaaga tgaaactgga tcccttcctt 160920
acaccttata caaaaattaa ttcaagatgg attaaagact taaatgtcag acctaaaacc 160980
ataaaaaccc tagaagaaaa cctaggcatt accattcagg acataggcat gggcaaggac 161040
ttcatgtcta aaacaccaaa agcaatggca acaaaagcca aaattgacaa atgggatcta 161100
attaaactaa agagcttctg cacagcaaaa gaaactacca tcagagtgaa taggcaacct 161160
acagaatggg agaaaatttt tgcaatctac tcatctgaca aagggctaat attcagaatc 161220
tacaaagaac ttaaacaaat gttcaagaaa aaaacaaccc catcaaaaag tgggcaaaat 161280
acatgaaaag acacttctca aaagaagaca tttatgcagc caacagacac atgaaaaaat 161340
gctcatcatc actggccatc agagaaatgc aaatcaaaac cacaatgaga taccatctca 161400
caccagttag aatgacgatc attaaagtca ggaaacaaca gatgctggag aggacatgga 161460
gaaataggaa tgcttttaca ctgttggtgg gggtgtaaat tagttcaatc attgttgaag 161520
acagtgtggc aattcctcaa ggatctagaa ctagaaatac catttgaccc agcaatccca 161580
ttactgggta tataccgaaa agattacaaa tggtgcaact ataaagacac atgcacacga 161640
atgtttattg tggcactatt cacaatagca aagacttcta acaaacccag atgtccatca 161700
atgatagact ggattaagaa aatgtggcac atatacacca tggaatacta tgcagccata 161760

-continued aaaaaggatg agttcatgtc cttttcaggg acatggatga agctggaaac catcattctc 161820
agcaaactat gacaaggaca gaaaaccaaa caccgcatgt tctcactcat agatgggaac 161880
tgaacaatga gaacacttgg acacagggca gggaacatca cacaccaggg cctgttgggg 161940
ggtggtggac tgggggagag atagcattag gagaaatacc taatgtaaat gatgagttga 162000
tggatgcagc aaaccaacag ggcacatcta tacctatgta agaaacctgc actttgtgca 162060
caggtaccct agaacttgaa gtataataaa aatgaaaaaa agaaaatgtt actagcaaat 162120
tgtagatggg tatacctaat ataactctgc atgtgcacta tgtgtctgga tacacatgga 162180
aagtattcag gcatacacac caaattgtta aaataaatcc ccttccaaca ttaggagtgg 162240
ctggggagca gatggctttc acttccgcac attccatggt gccagggtaa taccacatca 162300
caatagtaaa tagcaaaaat aacaacctta agtttagatt ttcttatcta aattttaatt 162360
ctgtgaagaa gtttccattt ccctttttca cacaggatag tagaatgcag tttagaaaga 162420
gtgagatcac ttgttagact gtacaatttt taagcatcag cgaagtatac cattaaactt 162480
ctctatcaat ccattctcta aacttcccaa cccaaaaaaa aagaaacaca taaaattgaa 162540
atgaagaaaa caatacaaaa gatcaacaaa aatgaaaggt tggcttttta aagagataaa 162600
caaaattgac aaatgtttag ccagactaag aaaaagagaa ggcccaaata aataaaatca 162660
gagatgaaaa agcagacatt ataactgata ctgcggaaat tcaaaggatc attaatggct 162720
actatgagca actgtatgcc aaacattgga aaatattgaa gaaatagata aattcgtaga 162780
cacacgcaac ctaacaagat tcaaccatga agaaattcaa aatctgaaca gaccaaaaac 162840
aagtaacaag atcaaagcca taattaaaat tttcccagca aagaaaagcc tgagacccaa 162900
tggcttcact gctgaattct atcaaacatt taaagaacta ataccaatcc tactcaaact 162960
attccaaaaa gtagaagagg agggaatatt tccaaactta ttctatgagg ccattactgc 163020
tcctatatca aaaccaagga cacatcaaaa aaagaaaact ataggccaat atctcacatg 163080
aatattgatg aatcctcaaa aaatgctagc aaactgaatt caacatcaca ttaaaaatca 163140
ttcattatga ccaaatggga tttatcccag ggatgcaaat atggttcaac atatacacat 163200
cagtcagtgt aacatatcat atcaacagaa tgaagaagaa aaaccatatg gtcatgttaa 163260
ttgatgctga aaaagtattt gagagaatta aacatctctt catgacaaaa accctcaaaa 163320
acactggaga cagaaggaac atacctcaac acaataaaca gacatatatg acagactcac 163380
agctagaatc atactaaatg gggagaaact gaaagtcatt cctctaagat ctggaacaag 163440
acaaggatgc tcattttcac cagtgttagt ggaacatagt actgaaagtc ctagctagaa 163500
cagactagag acagaaataa ggggcatcca aactgggaag agagaagtca aattaccttt 163560
gttcgcagat ggtatgatct tctgtttgga aaaacctaga ctccataaaa aaatgattag 163620
aactgataaa ttcagtaaag tttcaggata caaaattaac atacaaaaat cagtagcatt 163680
tctatatgtc aatagcaaac aatctgaaaa tgaaatcaag gaagtaatcc catttcccat 163740
ttgcaatagc tataaataaa attaatataa tctcatctct tcaataagtg gtgttgggaa 163800
aactgcatat ccacatacaa aagaataaaa ttagaccctt ttaatataca aaactggacc 163860
caagttaata tacaaaaatt aacttgaaat gaattaaaga cttaaatgta agatctgaaa 163920
ccaaaaactc ctagagagaa acatagggga aaagctcctt gacgttggcc ttggcaataa 163980
ttttttggga tattacacca aaagcacaga cttttgaaaa aataaacaag taggactaca 164040
tcaaactaaa aagcttctgc atggcaaaag aaagtcaaca acatgaaaag gcaacctaca 164100

-continued gaatggaggg aaatatttgc aaaccatata cctgatgaga agttaatatc aaaatataga 164160
aaatatataa ggaactcaca tatctcaata ccaaaaaaat aataacctgt tttataatgg 164220
gcaaaggacc tgaatagaca ttttttcaaa gaagacacac agatggccaa cgagtgcagg 164280
aaaaagcgtt caacatcact aatcatcagg gaaatgcaaa tcaaaaccac aatgagatat 164340
cactccacac ctgttaggaa agctattatg aaaaacacaa gagacaatga atattggcaa 164400
gggcatggag aaaaaagaac ccttgtacac tgttggtaga aatgtaaatt gcaacagcct 164460
ttatggaaaa tagaatggag gttcctcaaa aaataaaaat agaactacca tacaatctag 164520
caattccact tatgagtgta catccaaagg aatcaaatca ctatgtcaaa gagatatctg 164580
tacttccttg tttattgcag ctttactcac agtagccaag ataaggaaaa aatctaaatg 164640
tccatcaacg gataaagaaa atgggggggag gggtgtgcat gtatacatac acaatggact 164700
atttttcagc cataacaaag aaggaaaccc tgccatttgt gacgatatga atgaacccag 164760
aggacattat gttaagtgaa ataagccaga cacagaaata caaatattgt atgatctcat 164820
ttatatgcga atctaaaaat ttcaaacttg aagacgaata agtagaacag tatttatcag 164880
gagctagggg atgtggggaa gaagcaaaat attgggcaaa gagtataaac tttcagttat 164940
gagatgaagg ccaggtgcga tggctcatgt tggtaatccc aatactttgg aaggctgagg 165000
cagagggatt gcttgagacc agcctaggca agaaagtgag acctcatctc tacaaaaaat 165060
aaaaataaaa gaatcagctg ggagtggtgg catacacctg tagtcccagc tagtcaggag 165120
gctgaggggg gaggatcatt tgaaattgga aagtcaaggc tgcagtcagc caagatagtg 165180
ccactgcatt gcagcctggg tgacagagcg aaaccctgtc tcaaaaaaaa aaaaaaaaaa 165240
aagatgaata agttctgggg atcaaatgta cagcatggtg actatagttt ataactgcgt 165300
tattacttga aattggataa gagcagattt taagcatccc cagcaccccc ccaacataca 165360
cacacacaaa tggtaactat aggtggtgat agatatgtta atttgactgt gacaatcagc 165420
attcaatata tacatatatc aaatcatcac attttacccc ttgaaataga aactttgatt 165480
tgtcaatcaa atattttaaa acgaaaataa tcataatatt aatatagcat acaggaaaaa 165540
atttcgtatc tcgactgata cagaaaattt catgataaaa acactttaaa acaaaagaaa 165600
taaaagggaa ctccctcaac ctgataaatg gcatctgtgg aaaccccccag ctagcatcaa 165660 acttaataca gaaaggctgg gtgttcacct cttgaaccag gaacaagaca aagatgcctg 165720
cttttgccac ttccatttga ccttgtactg aggttctggc tagggcaatt atccctgaaa 165780
aagaaataaa aggcttccaa ataaaagaag aagtaaaact atctctactc gctcatgaca 165840
tgatcttgca tatagaaaat gtgcacatgt acacacacac aaaccattag aactaataaa 165900
caagttcagc aagtttgcag aatataaaat gaatgtacaa aaatcaagtg tttttctata 165960
tactagcaat taacaatctc aaaatgaatt aaaattccat ttacaatagt atcaaacata 166020
aattatttag aaataaaaag tgcactgaaa actacaaaat attttgaaat aaatcagaaa 166080
agatttaagt aaatggatca cttgaacctg ggaagcagag gttgcagtgt gccgagattg 166140
taccactgca ctttagcctg ggcaacagag ggagactcca aagagtcgaa aagaaaagaa 166200
aagatttaaa taagctgaaa catattctat ggatcagaag acttaatatt gttaaagtga 166260
caatattccc caaattgatc tacagcttca actcaacccc tatcaaaatc ctagcttgct 166320
ttttggctga aattgacaag ctgattctat aatttatatg gaatctcaaa ggatccagaa 166380
taaccaaaac aatattgaaa aataaagaac agcgttggtg gattaacatt ttccaatttc 166440
aaaacttact atagcactgc ggtaatcaag cagtgtggca ctgtatagca tgtacattac 166500

-continued agatcagtgg actagaatca atgtccagaa ataaaccgtt atgtttataa tgaattactt 166560
tttaataagg tgtcaagaca acgcaatggg aaaagaataa tgaattcaac aaatgatgca 166620
tggacaaccg gacatgcaca tgcaacacaa tgaatttgaa ttcttctatc gctccatgca 166680
taaaaactaa ctcaaaatgg gtcacggatg taaatgaaaa gctaaaacta taataatcct 166740
agaggaaaac ctaggagtaa atctttaaga tgttattgta ggcagtggtt tctcagatag 166800
gaccccaaaa tcacaagcga caaaagaaat tggacttaaa gttaaatact tttgtgcttc 166860
aaacatcatc aagaaagtga aaacacaacc cgcagaagca ataaaaatgt ctgtaagtca 166920
tgtatccgat tagagacttc tatccaggat atataaataa tgcaattcaa tgataaaaaa 166980
gataaatagc ccagttttcc aaagagtcaa gcatctgaat atacatctct ccaaaaatat 167040
acagatatcc aacaagcatg tgaaaagatg ttcaaagcca tttgccaggt gcacaaaccc 167100
aagacagtat gaggagatgc tacagggact ctgctgcttc acagacatga agcgttggtg 167160
agaatgtagg cagccgcctt tggggacttc acatccccgc cgccccacgc acggtgagct 167220
agtgtttaaa cttagccgag atcaatacac gcgactgtgt gcccgtcaga ccctgcgctg 167280
ccggcggggc tgggagaggc gggcgccagg agtgggcggg aacctggggg tcaggcccca 167340
gccgcgggaa gccgcccagg agcgcgcgaa accttctcca cacccttcca ggcatttgcc 167400
cgccgcgatt cagagagccg acccgtgacc cctggcctcc cctagacagc cccgcatgtc 167460
cagatgtgcc gtcccgcctg cctcccgcga ccactggcca tctctgggcc tgggcgcggt 167520
ctcggcgccc gcctgccccc gccaggagcc gcaggtccag ccagtgaaga agcccgcgct 167580
gaaggagcct ctgtgctcca gaatccatcc tcagtatcag cgctggggtg gcctcctcca 167640
ggaagccctt ctgattctct catgggtcgc tcttcctctg cagactcccg gagcacccct 167700
gctccaagta ccgcaagtgg cactgagaac ttggggagag cagaggctgt gcctagattt 167760
gtagggagtc cccgcagctc caccccaggg cctacaggag cctggccttg ggcgaagccg 167820
aggcaggcag gcagggcaaa gggtggaagc aattcaggag agaacgagtg aacgaatgga 167880
tgaggggtgg cagccgaggt tgccccagtc ccctggctgc aggaacagac acctcgctga 167940
ggagagaccc aggagcgagg cccctgcccc gcccgaggcg aggtcccgcc cagtcggcgc 168000
cgcgtgaaga gtgggagaga atactgcggg ggcgggggcg ggggcggggg cgggggcggg 168060
ggccgccggg agcctggagc cagaccgggc ggggccggca ccgggccagg gacagtgggg 168120
gaggaggctg cgggctgagc gaccctgacc ccccccagtc cgcgctggtt ccgg 168174

<210> SEQ ID NO 64
<211> LENGTH: 21
<212> TYPE: DNA
<213> ORGANISM: Homo sapiens

<400> SEQUENCE: 64
aggagcgcgc raaaccttct c 21

<210> SEQ ID NO 65
<211> LENGTH: 18
<212> TYPE: DNA
<213> ORGANISM: Homo sapiens

<400> SEQUENCE: 65
tggacttaaa tacttttg 18

<210> SEQ ID NO 66

-continued

```
<211> LENGTH: 21
<212> TYPE: DNA
<213> ORGANISM: Homo sapiens

<400> SEQUENCE: 66

tcatgtatcc rattagagac t                                              21
```